United States Patent
Brown et al.

(10) Patent No.: US 9,670,183 B2
(45) Date of Patent: Jun. 6, 2017

(54) BICYCLIC AZA COMPOUNDS AS MUSCARINIC M1 RECEPTOR AND/OR M4 RECEPTOR AGONISTS

(71) Applicant: Heptares Therapeutics Limited, Welwyn Garden, Hertfordshire (GB)

(72) Inventors: Giles Albert Brown, Welwyn Garden City (GB); Julie Elaine Cansfield, Welwyn Garden City (GB); Miles Stuart Congreve, Welwyn Garden City (GB); Michael Alistair O'Brien, Welwyn Garden City (GB); Mark Pickworth, Welwyn Garden City (GB); Mark David Rackham, Welwyn Garden City (GB); Benjamin Gerald Tehan, Welwyn Garden City (GB); Barry John Teobald, Welwyn Garden City (GB)

(73) Assignee: Heptares Therapeutics Limited, Welwyn Garden (GB)

( * ) Notice: Subject to any disclaimer, the term of this patent is extended or adjusted under 35 U.S.C. 154(b) by 0 days.

(21) Appl. No.: 15/117,018

(22) PCT Filed: Feb. 6, 2015

(86) PCT No.: PCT/GB2015/050331
§ 371 (c)(1),
(2) Date: Aug. 5, 2016

(87) PCT Pub. No.: WO2015/118342
PCT Pub. Date: Aug. 13, 2015

(65) Prior Publication Data
US 2017/0015650 A1     Jan. 19, 2017

(30) Foreign Application Priority Data

Feb. 6, 2014 (GB) .................................. 1402013.5
Sep. 19, 2014 (GB) .................................. 1416622.7

(51) Int. Cl.
| | | |
|---|---|---|
| *A61K 31/4545* | (2006.01) | |
| *C07D 401/14* | (2006.01) | |
| *C07D 413/14* | (2006.01) | |
| *C07D 417/14* | (2006.01) | |
| *C07D 405/14* | (2006.01) | |
| *C07D 409/14* | (2006.01) | |

(52) U.S. Cl.
CPC ......... *C07D 401/14* (2013.01); *C07D 405/14* (2013.01); *C07D 409/14* (2013.01); *C07D 413/14* (2013.01); *C07D 417/14* (2013.01)

(58) Field of Classification Search
CPC .......................... A61K 31/4545; C07D 401/14
USPC ............................................. 514/278; 546/15
See application file for complete search history.

(56) References Cited

U.S. PATENT DOCUMENTS 9,266,857 B2 * 2/2016 Brown ................. C07D 401/04

FOREIGN PATENT DOCUMENTS

| WO | 2007/100670 A1 | 9/2007 |
| WO | 2013/072705 A1 | 5/2013 |
| WO | 2014/045031 A1 | 3/2014 |

OTHER PUBLICATIONS

International Search Report and Written Opinion issued in PCT/GB2015/050331, mailed Mar. 19, 2015.

* cited by examiner

*Primary Examiner* — Charanjit Aulakh
(74) *Attorney, Agent, or Firm* — McCarter & English, LLP; Steven G. Davis; Mei Bai

(57) ABSTRACT

This invention relates to compounds that are agonists of the muscarinic M1 receptor and/or M4 receptor and which are useful in the treatment of muscarinic M1/M4 receptor mediated diseases. Also provided are pharmaceutical compositions containing the compounds and the therapeutic uses of the compounds. Compounds include those according to formula (1), or a salt thereof, wherein Q, $R^1$, $R^2$, $R^3$ and $R^4$ are as defined herein.

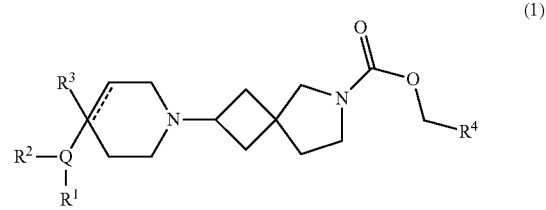

(1)

23 Claims, 2 Drawing Sheets

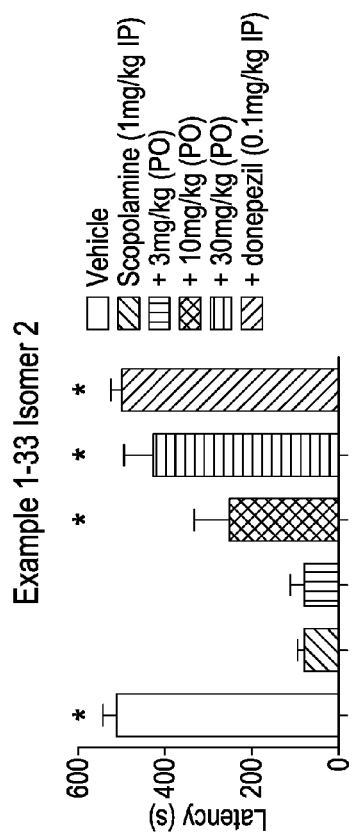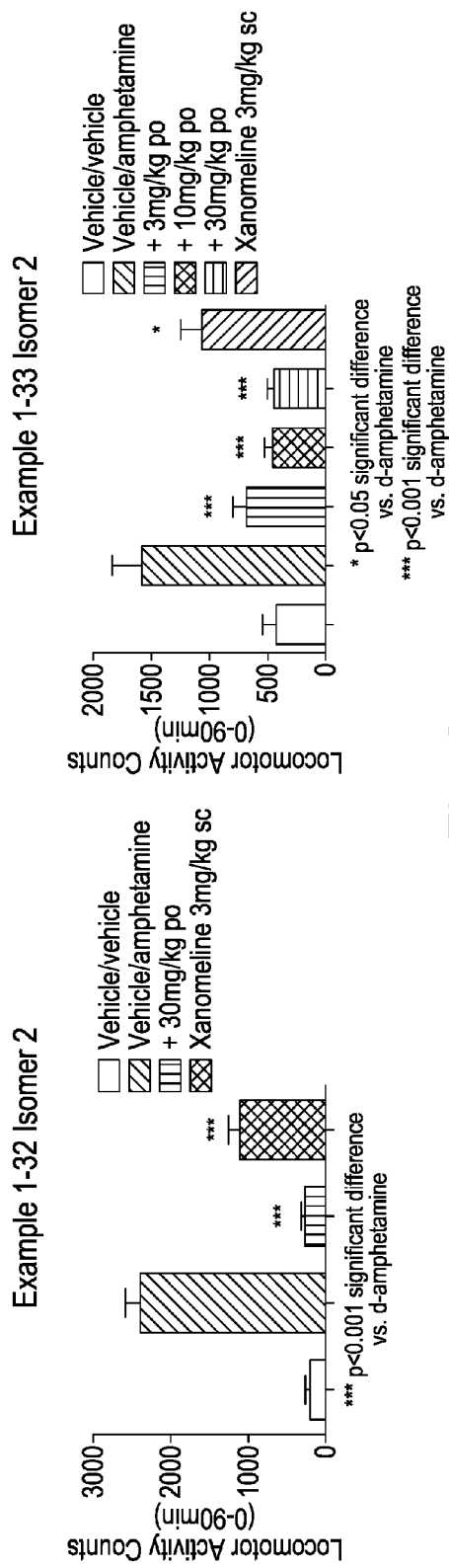

BICYCLIC AZA COMPOUNDS AS MUSCARINIC M1 RECEPTOR AND/OR M4 RECEPTOR AGONISTS

RELATED APPLICATION INFORMATION

This application is a 371 of International Application No. PCT/GB2015/050331, filed Feb. 6, 2015, which claims priority to GB Application No. 1402013.5, filed Feb. 6, 2014, and to GB Application No. 1416622.7, filed Sep. 19, 2014, all of which are herein incorporated by reference.

This invention relates to compounds that are agonists of the muscarinic M1 receptor and/or M4 receptor and which are useful in the treatment of muscarinic M1/M4 receptor mediated diseases. Also provided are pharmaceutical compositions containing the compounds and the therapeutic uses of the compounds.

BACKGROUND OF THE INVENTION

Muscarinic acetylcholine receptors (mAChRs) are members of the G protein-coupled receptor superfamily which mediate the actions of the neurotransmitter acetylcholine in both the central and peripheral nervous system. Five mAChR subtypes have been cloned, $M_1$ to $M_5$. The $M_1$ mAChR is predominantly expressed post-synaptically in the cortex, hippocampus, striatum and thalamus; $M_2$ mAChRs are located predominantly in the brainstem and thalamus, though also in the cortex, hippocampus and striatum where they reside on cholinergic synaptic terminals (Langmead et al., 2008 *Br J Pharmacol*). However, $M_2$ mAChRs are also expressed peripherally on cardiac tissue (where they mediate the vagal innervation of the heart) and in smooth muscle and exocrine glands. $M_3$ mAChRs are expressed at relatively low level in the CNS but are widely expressed in smooth muscle and glandular tissues such as sweat and salivary glands (Langmead et al., 2008 *Br J Pharmacol*).

Muscarinic receptors in the central nervous system, especially the $M_1$ mAChR, play a critical role in mediating higher cognitive processing. Diseases associated with cognitive impairments, such as Alzheimer's disease, are accompanied by loss of cholinergic neurons in the basal forebrain (Whitehouse et al., 1982 *Science*). In schizophrenia, which also has cognitive impairment as an important component of the clinical picture, mAChR density is reduced in the pre-frontal cortex, hippocampus and caudate putamen of schizophrenic subjects (Dean et al., 2002 *Mol Psychiatry*). Furthermore, in animal models, blockade or damage to central cholinergic pathways results in profound cognitive deficits and non-selective mAChR antagonists have been shown to induce psychotomimetic effects in psychiatric patients. Cholinergic replacement therapy has largely been based on the use of acetylcholinesterase inhibitors to prevent the breakdown of endogenous acetylcholine. These compounds have shown efficacy versus symptomatic cognitive decline in the clinic, but give rise to dose-limiting adverse events resulting from stimulation of peripheral $M_2$ and $M_3$ mAChRs including disturbed gastrointestinal motility, bradycardia, nausea and vomiting (http://www.drugs.com/pro/donepezil.html; http://www.drugs.com/pro/rivastigmine.html).

Further discovery efforts have targeted the identification of direct $M_1$ mAChR agonists with the aim of inducing selective improvements in cognitive function with a favourable adverse effect profile. Such efforts resulted in the identification of a range of agonists, exemplified by compounds such as xanomeline, AF267B, sabcomeline, milameline and cevimeline. Many of these compounds have been shown to be highly effective in pre-clinical models of cognition in both rodents and/or non-human primates. Milameline has shown efficacy versus scopolamine-induced deficits in working and spatial memory in rodents; sabcomeline displayed efficacy in a visual object discrimination task in marmosets and xanomeline reversed mAChR antagonist-induced deficits in cognitive performance in a passive avoidance paradigm.

Alzheimer's disease (AD) is the most common neurodegenerative disorder (26.6 million people worldwide in 2006) that affects the elderly, resulting in profound memory loss and cognitive dysfunction. The aetiology of the disease is complex, but is characterised by two hallmark brain pathologies: aggregates of amyloid plaques, largely composed of amyloid-β peptide (Aβ), and neurofibrillary tangles, formed by hyperphosphorylated tau proteins. The accumulation of Aβ is thought to be the central feature in the progression of AD and, as such, many putative therapies for the treatment of AD are currently targeting inhibition of Aβ production. Aβ is derived from proteolytic cleavage of the membrane bound amyloid precursor protein (APP). APP is processed by two routes, nonamyloidgenic and amyloidgenic. Cleavage of APP by γ-secretase is common to both pathways, but in the former APP is cleaved by an α-secretase to yield soluble APPα. However, in the amyloidgenic route, APP is cleaved by β-secretase to yield soluble APPβ and also Aβ. In vitro studies have shown that mAChR agonists can promote the processing of APP toward the soluble, non-amyloidogenic pathway. In vivo studies showed that the mAChR agonist, AF267B, altered disease-like pathology in the 3xTgAD transgenic mouse, a model of the different components of Alzheimer's disease (Caccamo et al., 2006 *Neuron*). The mAChR agonist cevimeline has been shown to give a small, but significant, reduction in cerebrospinal fluid levels of Aβ in Alzheimer's patients, thus demonstrating potential disease modifying efficacy (Nitsch et al., 2000 *Neurol*).

Preclinical studies have suggested that mAChR agonists display an atypical antipsychotic-like profile in a range of pre-clinical paradigms. The mAChR agonist, xanomeline, reverses a number of dopamine mediated behaviours, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile (Mirza et al., 1999 *CNS Drug Rev*). Muscarinic receptors have also been implicated in the neurobiology of addiction. The reinforcing effects of cocaine and other addictive substances are mediated by the mesolimbic dopamine system where behavioral and neurochemical studies have shown that the cholinergic muscarinic receptor subtypes play important roles in regulation of dopaminergic neurotransmission. For example M(4) (−/−) mice demonstrated significantly enhanced reward driven behaviour as result of exposure to cocaine (Schmidt et al Psychopharmacology (2011) August; 216(3): 367-78). Furthermore xanomeline has been demonstrated to block the effects of cocaine in these models.

Muscarinic receptors are also involved in the control of movement and potentially represent novel treatments for movement disorders such as Parkinson's disease, ADHD, Huntingdon's disease, tourette's syndrome and other syndromes associated with dopaminergic dysfunction as an underlying pathogenetic factor driving disease.

Xanomeline, sabcomeline, milameline and cevimeline have all progressed into various stages of clinical development for the treatment of Alzheimer's disease and/or schizophrenia. Phase II clinical studies with xanomeline demonstrated its efficacy versus various cognitive symptom domains, including behavioural disturbances and hallucinations associated with Alzheimer's disease (Bodick et al., 1997 Arch Neurol). This compound was also assessed in a small Phase II study of schizophrenics and gave a significant reduction in positive and negative symptoms when compared to placebo control (Shekhar et al., 2008 Am J Psych). However, in all clinical studies xanomeline and other related mAChR agonists have displayed an unacceptable safety margin with respect to cholinergic adverse events, including nausea, gastrointestinal pain, diahorrhea, diaphoresis (excessive sweating), hypersalivation (excessive salivation), syncope and bradycardia.

Muscarinic receptors are involved in central and peripheral pain. Pain can be divided into three different types: acute, inflammatory, and neuropathic. Acute pain serves an important protective function in keeping the organism safe from stimuli that may produce tissue damage; however management of post-surgical pain is required. Inflammatory pain may occur for many reasons including tissue damage, autoimmune response, and pathogen invasion and is triggered by the action of inflammatory mediators such as neuropeptides and prostaglandins which result in neuronal inflammation and pain. Neuropathic pain is associated with abnormal painful sensations to non-painful stimuli. Neuropathic pain is associated with a number of different diseases/traumas such as spinal cord injury, multiple sclerosis, diabetes (diabetic neuropathy), viral infection (such as HIV or Herpes). It is also common in cancer both as a result of the disease or a side effect of chemotherapy. Activation of muscarinic receptors has been shown to be analgesic across a number of pain states through the activation of receptors in the spinal cord and higher pain centres in the brain. Increasing endogenous levels of acetylcholine through acetylcholinesterase inhibitors, direct activation of muscarinic receptors with agonists or allosteric modulators has been shown to have analgesic activity. In contrast blockade of muscarinic receptors with antagonists or using knockout mice increases pain sensitivity. Evidence for the role of the M1 receptor in pain is reviewed by D. F. Fiorino and M. Garcia-Guzman, 2012.

More recently, a small number of compounds have been identified which display improved selectivity for the $M_1$ mAChR subtype over the peripherally expressed mAChR subtypes (Bridges et al., 2008 Bioorg Med Chem Lett; Johnson et al., 2010 Bioorg Med Chem Lett; Budzik et al., 2010 ACS Med Chem Lett). Despite increased levels of selectivity versus the $M_3$ mAChR subtype, some of these compounds retain significant agonist activity at both this subtype and the $M_2$ mAChR subtype. Herein we describe a series of compounds which unexpectedly display high levels of selectivity for the $M_1$ and/or $M_4$ mAChR over the $M_2$ and $M_3$ receptor subtypes.

DESCRIPTION OF FIGURES

Description of the figures can be found in experimental sections B and C.

FIG. 1 shows that Example 1-33 Isomer 2 was found to reverse scopolamine-induced amnesia in a dose-dependent manner, with an approximate $ED_{50}$ of ca. 10 mg/kg (po). The effect of 30 mg/kg was similar to that produced by the cholinesterase inhibitor donepezil (0.1 mg/kg, ip) which served as a positive control.

THE INVENTION

Figure 2:
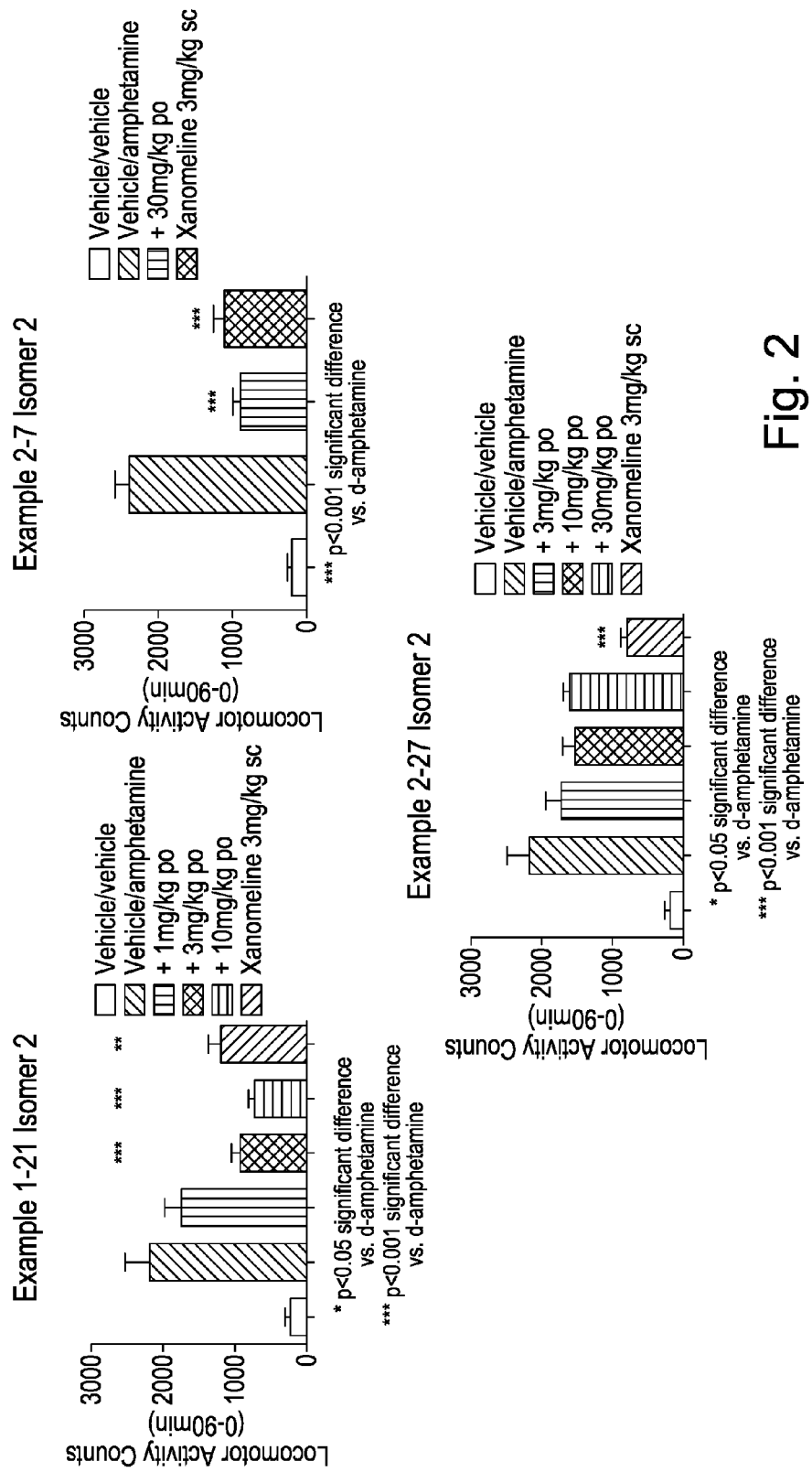
FIG. 2 shows the effect of novel test compounds on d-amphetamine induced hyperactivity in rats. Antipsychotic-like behaviour was assessed in rats by the inhibition of hyperactivity (or hyperlocomotion) elicited by d-amphetamine. Data for Examples 1-21 Isomer 2, 1-32 Isomer 2, 1-33 Isomer 2, 2-7 Isomer 2 and 2-17 Isomer 2 is shown.

The present invention provides compounds having activity as muscarinic M1 and/or M4 receptor agonists. More particularly, the invention provides compounds that exhibit selectivity for the M1 receptor and/or the M4 receptor relative to the M2 and M3 receptor subtypes.

Accordingly, in one embodiment (Embodiment 1.1), the invention provides a compound of the formula (1):

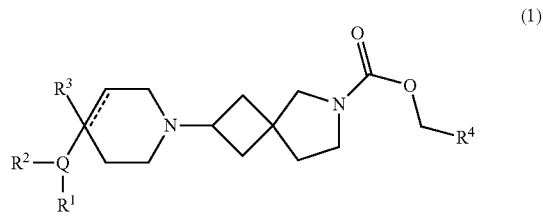

or a salt thereof, wherein

Q is a five or six membered monocyclic heterocyclic ring containing 1, 2, 3 or 4 heteroatom ring members selected from N, O and S; $R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

$R^2$ is selected from hydrogen; fluorine; chlorine; bromine; cyano; hydroxy; methoxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-6}$ non-aromatic hydrocarbon group; or $R^1$ and $R^2$ can be joined together to form a 6 membered fused aromatic ring;

$R^3$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$, $R^6$ and $R^7$ are the same or different and each is independently selected from hydrogen, a non-aromatic $C_{1-4}$ hydrocarbon group optionally substituted with one or more fluorine atoms; or a group of formula $CH_2N(R^a)COOR^b$;

$R^a$ is selected from hydrogen and a non-aromatic $C_{1-4}$ hydrocarbon group;

$R^b$ is a non-aromatic $C_{1-4}$ hydrocarbon group which is optionally substituted with one or more groups selected from fluorine; chlorine; bromine; cyano; hydroxy; methoxy; amino; or a cycloalkyl, heterocycloalkyl, aryl or heteroaryl group;

and the dotted line indicates an optional second carbon-carbon bond, provided that when a second carbon-carbon bond is present, then $R^3$ is absent.

Accordingly, in one embodiment (Embodiment 1.1a), the invention provides a compound of the formula (1a):

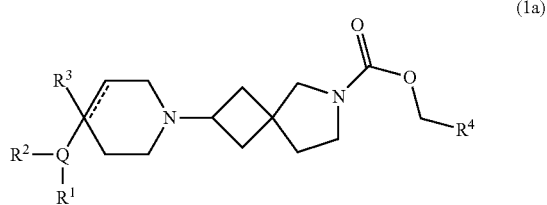

(1a)

or a salt thereof, wherein

Q is a five or six or seven membered monocyclic heterocyclic ring containing 1, 2, 3 or 4 heteroatom ring members selected from N, O and S;

$R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

$R^2$ is selected from hydrogen; fluorine; chlorine; bromine; cyano; hydroxy; methoxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-6}$ non-aromatic hydrocarbon group; or $R^1$ and $R^2$ can be joined together to form a 6 membered fused aromatic ring;

$R^3$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$, $R^6$ and $R^7$ are the same or different and each is independently selected from hydrogen, a non-aromatic $C_{1-4}$ hydrocarbon group optionally substituted with one or more fluorine atoms; or a group of formula $CH_2N(R^a)COOR^b$;

$R^a$ is selected from hydrogen and a non-aromatic $C_{1-4}$ hydrocarbon group;

$R^b$ is a non-aromatic $C_{1-4}$ hydrocarbon group which is optionally substituted with one or more groups selected from fluorine; chlorine; bromine; cyano; hydroxy; methoxy; amino; or a cycloalkyl, heterocycloalkyl, aryl or heteroaryl group;

and the dotted line indicates an optional second carbon-carbon bond, provided that when a second carbon-carbon bond is present, then $R^3$ is absent.

Accordingly, in one embodiment (Embodiment 1.1b), the invention provides a compound of the formula (1b):

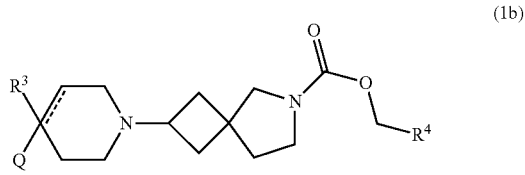

(1b)

or a salt thereof, wherein

Q is an optionally substituted five or six or seven membered heterocyclic ring containing 1, 2, 3 or 4 heteroatom ring members selected from N, O and S;

$R^3$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

and the dotted line indicates an optional second carbon-carbon bond, provided that when a second carbon-carbon bond is present, then $R^3$ is absent.

Particular compounds of the formula (1), (1a) or (1b) are as defined in the Embodiments 1.2 to 1.180 set out below.

1.2 A compound according to Embodiment 1.1 wherein Q is an aromatic or unsaturated heterocyclic ring.

1.3 A compound according to Embodiment 12 wherein Q is an aromatic heterocyclic ring.

1.4 A compound according to Embodiment 1.3 wherein Q is an aromatic heterocyclic ring containing a nitrogen ring member and optionally one or two further ring members selected from O, N and S.

1.5 A compound according to Embodiment 1.4 wherein Q is an aromatic heterocyclic ring containing a nitrogen ring member and optionally one further ring member selected from O, N and S.

1.6 A compound according to Embodiment 1.5 wherein Q is an aromatic heterocyclic ring containing one or two nitrogen ring members.

1.7 A compound according to any one of Embodiments 1.1 to 1.6 wherein Q is a five membered heterocyclic ring linked to the adjacent six-membered ring by a carbon atom of the said five membered heterocyclic ring.

1.8 A compound according to any one of Embodiments 1.1 to 1.6 wherein Q is a five membered heterocyclic ring linked to the adjacent six-membered ring by a nitrogen atom of the said five membered heterocylic ring.

1.9 A compound according to Embodiment 1.1 wherein Q is selected from 1-pyrrolyl, 2-imidazolyl, 1-pyrazolyl, 3-pyrazolyl, 5-pyrazolyl, 2-thiazolyl, 2-oxazolyl, triazolyl, tetrazolyl, thiadiazolyl, oxadiazolyl, and tautomeric forms thereof.

1.10 A compound according to Embodiment 1.6 wherein Q is a pyrrole ring.

1.11 A compound according to Embodiment 1.6 wherein Q is an imidazole ring 1.12 A compound according to Embodiment 1.6 wherein Q is a pyrazole ring.

1.13 A compound according to Embodiment 1.6 wherein Q is selected from 1-pyrazolyl, 3-pyrazolyl, 5-pyrazolyl and tautomeric forms thereof.

1.14 A compound according to Embodiment 1.1 wherein Q is a 6 membered ring containing one or more nitrogen atoms.

1.15 A compound according to Embodiment 1.14 wherein Q is pyridyl, pyrazyl or a 2-oxo-3N (3-piperidin-2-one) ring continuing 0-2 C—C unsaturated bonds.

1.16 A compound according to Embodiment 1.1 wherein Q is a 5, 6 or 7 membered unsaturated heterocyclic ring.

1.17 A compound according to Embodiment 1.16 wherein Q is 5-pyrollidinyl.

1.18 A compound according to Embodiment 1.1 wherein Q is bicyclic; having a further ring attached to Q.

1.19 A compound according to Embodiment 1.1b wherein Q has one or more substituents, for example one, two or three substituents, which may be selected from one $R^1$ and/or $R^2$ wherein $R^1$ and $R^2$ may be the same or different. Further substituents for Q may include (L)-$R^{10}$, (L)-$R^{11}$ and (L)-$R^{12}$, where L is a bond or a $CH_2$ group; $R^{10}$, $R^{11}$ and $R^{12}$ are independently selected from hydrogen; fluorine; chlorine; bromine; cyano; oxo; hydroxy; $OR^{15}$; $NR^{15}R^{16}$; $COR^{15}$; $CSR^{15}$; $COOR^{15}$; $COSR^{15}$; $OCOR^{15}$; $NR^{17}COR^{15}$; $CONR^{15}R^{16}$; $CSNR^{15}R^{16}$; $NR^{17}CONR^{15}R^{16}$; $R^{17}COOR^{15}$; $OCONR^{15}R^{15}$; $SR^{15}$; $SOR^{15}$ and $SO_2R^{15}$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;
wherein the optional substituents for the optionally substituted 5- or 6-membered ring are selected from a group $R^8$ consisting of hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;
wherein $R^{15}$, $R^{16}$ and $R^{17}$ are the same or different, or may be joined together to form a ring, and each is independently selected from hydrogen, a non-aromatic $C_{1-6}$ hydrocarbon group optionally substituted with one or more fluorine atoms and wherein one or two, but not all, carbon atoms of the hydrocarbon group may optionally be replaced by a heteroatom selected from O, N and S and oxidized forms thereof; or a group of formula $CH_2N(R^a)COOR^b$; or a group of formula (L)-$R^{18}$ where L is a bond or a $CH_2$ group and $R^{18}$ is an optionally substituted 5- or 6-membered ring containing 0, 1, 2 or 3 heteroatoms selected from O, N and S and oxidized forms thereof;

wherein the optional substituents for the optionally substituted 5- or 6-membered ring are selected from a group $R^8$.

1.20 A compound according to any one of Embodiments 1.1 to 1.19 wherein $R^1$ is selected from hydrogen; fluorine; chlorine; bromine; cyano; oxo; hydroxy; $OR^5$; $NR^5R^6$; $COR^5$, $COOR^5$; $OCOR^5$; $NR^7COR^5$; $CONR^5R^6$; $NR^7CONR^5R^8$; $NR^7COOR^5$; $OCONR^5R^8$; $SR^5$; $SOR^5$ and $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;
wherein the optional substituents for the optionally substituted 5- or 6-membered ring are selected from a group $R^8$ consisting of hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^8$; $NR^7COOR^5$; $OCONR^5R^8$; $SR^5$; $SOR^5$ and $SO_2R^5$; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.21 A compound according to Embodiment 1.20 wherein $R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^8$; $NR^7COOR^5$; $OCONR^5R^6$; $SR^5$; $SOR^5$ and $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1 or 2 heteroatoms selected from O, N and S and oxidized forms thereof;
wherein the optional substituents for the optionally substituted 5- or 6-membered ring are selected from a group $R^8$ consisting of fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.22 A compound according to Embodiment 1.21 wherein $R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered aryl or heteroaryl ring containing 0, 1 or 2 heteroatoms selected from O, N and S and oxidized forms thereof;
wherein the optional substituents for the optionally substituted 5- or 6-membered aryl or heteroaryl ring are selected from a group $R^8$ consisting of fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.23 A compound according to any one of Embodiments 1.1 to 1.19 wherein $R^1$ is selected from hydrogen; fluorine; chlorine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SO_2R^5$; a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof, wherein the optional substituents for the optionally substituted 5- or 6-membered ring are selected from a group $R^8$ consisting of fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.24 A compound according to Embodiment 1.23 wherein $R^1$ is selected from hydrogen; fluorine; chlorine; cyano; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SO_2R^5$; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.25 A compound according to Embodiment 1.24 wherein $R^1$ is selected from hydrogen; fluorine; chlorine; cyano; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $SO_2R^5$; and a $C_{1-4}$ non-aromatic hydrocarbon group which is optionally substituted with one to six fluorine atoms.

1.26 A compound according to Embodiment 1.25 wherein $R^1$ is selected from hydrogen; fluorine; chlorine; cyano; $NR^5R^6$; $COR^5$; $COOR^5$ and a $C_{1-6}$ non-aromatic hydrocarbon group which is optionally substituted with one to six fluorine atoms.

1.27 A compound according to Embodiment 1.26 wherein $R^1$ is selected from hydrogen; fluorine; chlorine; cyano; $NH_2$, $COR^5$; $COOR^5$ and a $C_{1-4}$ saturated non-aromatic hydrocarbon group which is optionally substituted with one to six fluorine atoms.

1.28 A compound according to Embodiment 1.27 wherein $R^1$ is selected from hydrogen; $COR^5$; $COOR^5$; $CONR^5R^6$ and a $C_{1-4}$ alkyl group.

1.29 A compound according to Embodiment 1.28 wherein $R^1$ is selected from hydrogen; $COR^5$; $COOR^5$ and a $C_{1-3}$ alkyl group.

1.30 A compound according to Embodiment 1.29 wherein $R^1$ is selected from hydrogen; methyl; ethyl and $COOR^5$.

1.31 A compound according to Embodiment 1.30 wherein $R^1$ is hydrogen.

1.32 A compound according to Embodiment 1.30 wherein $R^1$ is methyl or ethyl.

1.33 A compound according to Embodiment 1.20 to 1.30 wherein $R^1$ is COOMe; COOEt; COMe; COEt; $CONH_2$; $CF_3$; CONHMe; $CON(Me)_2$; $COCF_3$; CO-cyclopropyl; CO-cyclobutyl; CONHEt; COH; $NH_2$; OMe;

1.34 A compound according to any one of the Embodiments 1.1 to 1.33 wherein $R^2$ is selected from hydrogen; fluorine; chlorine; bromine; cyano; hydroxy; methoxy; and a $C_{1-6}$ non-aromatic hydrocarbon group; or is joined together with $R^1$ to form a 6 membered fused aromatic ring.

1.35 A compound according to Embodiment 1.34 wherein $R^2$ is selected from hydrogen; fluorine; hydroxy; methoxy; and a $C_{1-6}$ non-aromatic hydrocarbon group.

1.36 A compound according to Embodiment 1.35 wherein $R^2$ is selected from hydrogen; fluorine; methoxy; and a $C_{1-4}$ saturated hydrocarbon group.

1.37 A compound according to Embodiment 1.36 wherein $R^2$ is selected from hydrogen; fluorine; methoxy; and a $C_{1-4}$alkyl group.

1.38 A compound according to Embodiment 1.37 wherein $R^2$ is selected from hydrogen and a $C_{1-3}$ alkyl group.

1.39 A compound according to Embodiment 1.38 wherein $R^2$ is selected from hydrogen and methyl.

1.40 A compound according to Embodiment 1.34 wherein $R^2$ is joined together with $R^1$ to form a 6 membered fused aromatic ring which may be aryl or heteroaryl.

1.41 A compound according to any one of Embodiments 1.1 to 1.40 wherein the dotted line represents a second carbon-carbon bond and $R^3$ is absent.

1.42 A compound according to any one of Embodiments 1.1 to 1.40 wherein $R^3$ is present and the optional second carbon-carbon bond is absent.

1.43 A compound according to Embodiment 1.42 wherein $R^3$ is selected from hydrogen; fluorine; cyano; hydroxy; amino; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.44 A compound according to Embodiment 1.43 wherein $R^3$ is selected from hydrogen; fluorine; cyano; hydroxy; amino; and a $C_{1-6}$ non-aromatic hydrocarbon group which is optionally substituted with one to six fluorine atoms and wherein one, but not all, carbon atoms of the hydrocarbon group may optionally be replaced by a heteroatom selected from O, N and S and oxidized forms thereof.

1.45 A compound according to Embodiment 1.44 wherein $R^3$ is selected from hydrogen; fluorine; cyano; hydroxy; amino; $C_{1-4}$ alkyl and $C_{1-4}$ alkoxy, wherein the $C_{1-4}$ alkyl and $C_{1-4}$ alkoxy are each optionally substituted with one to six fluorine atoms.

1.46 A compound according to Embodiment 1.45 wherein $R^3$ is selected from hydrogen; fluorine; hydroxy and methoxy.

1.47 A compound according to Embodiment 1.46 wherein $R^3$ is hydrogen.

1.48 A compound according to any one of Embodiments 1.1 to 1.47 wherein $R^4$ is hydrogen or an acyclic $C_{1-6}$ hydrocarbon group.

1.49 A compound according to Embodiment 1.48 wherein $R^4$ is hydrogen or an acyclic $C_{1-3}$ hydrocarbon group.

1.50 A compound according to Embodiment 1.49 wherein $R^4$ is hydrogen or a $C_{1-3}$ alkyl group or a $C_{2-3}$ alkynyl group.

1.51 A compound according to Embodiment 1.50 wherein R⁴ is selected from hydrogen, methyl, ethyl, ethynyl and 1-propynyl.

1.52 A compound according to Embodiment 1.51 wherein R⁴ is selected from hydrogen and methyl.

1.53 A compound according to Embodiment 1.52 wherein R⁴ is methyl.

1.54 A compound according to any one of the preceding Embodiments wherein R⁵, when present, is a non-aromatic $C_{1-4}$ hydrocarbon group optionally substituted with one or more fluorine atoms; or a group of formula $CH_2N(R^a)COOR^b$.

1.55 A compound according to Embodiment 1.54 wherein the non-aromatic $C_{1-4}$ hydrocarbon group is a saturated $C_{1-4}$ hydrocarbon group.

1.56 A compound according to any one of Embodiments 1.1 to 1.53 wherein R⁵, when present, is hydrogen.

1.57 A compound according to any one of Embodiments 1.1 to 1.53 wherein R⁵, when present, is selected from hydrogen and a saturated $C_{1-4}$ hydrocarbon group.

1.58 A compound according to Embodiment 1.55 or Embodiment 1.56 wherein the saturated $C_{1-4}$ hydrocarbon group is a $C_{1-4}$ alkyl group.

1.59 A compound according to Embodiment 1.58 wherein the saturated $C_{1-4}$ hydrocarbon group is a $C_{1-3}$ alkyl group.

1.60 A compound according to Embodiment 1.59 wherein the $C_{1-3}$ alkyl group is selected from methyl, ethyl and isopropyl.

1.61 A compound according to Embodiment 1.60 wherein the $C_{1-3}$ alkyl group is ethyl.

1.62 A compound according to any one of the preceding Embodiments wherein R⁶, when present, is a non-aromatic $C_{1-4}$ hydrocarbon group.

1.63 A compound according to Embodiment 1.62 wherein the non-aromatic $C_{1-4}$ hydrocarbon group is a saturated $C_{1-4}$ hydrocarbon group.

1.64 A compound according to any one of Embodiments 1.1 to 1.61 wherein $R^a$, when present, is hydrogen.

1.65 A compound according to Embodiment 1.63 wherein the saturated $C_{1-4}$ hydrocarbon group is a $C_{1-3}$ alkyl group.

1.66 A compound according to Embodiment 1.65 wherein the $C_{1-3}$ alkyl group is selected from methyl, ethyl and isopropyl.

1.67 A compound according to any one of the preceding Embodiments wherein R⁷, when present, is a non-aromatic $C_{1-4}$ hydrocarbon group.

1.68 A compound according to Embodiment 1.67 wherein the non-aromatic $C_{1-4}$ hydrocarbon group is a saturated $C_{1-4}$ hydrocarbon group.

1.69 A compound according to any one of Embodiments 1.1 to 1.66 wherein R⁷, when present, is hydrogen.

1.70 A compound according to any one of Embodiments 1.1 to 1.66 wherein R⁷, when present, is selected from hydrogen and a saturated $C_{1-4}$ hydrocarbon group.

1.71 A compound according to Embodiment 1.68 or Embodiment 1.70 wherein the saturated $C_{1-4}$ hydrocarbon group is a $C_{1-4}$ alkyl group.

1.72 A compound according to Embodiment 1.71 wherein the saturated $C_{1-4}$ hydrocarbon group is a $C_{1-3}$ alkyl group.

1.73 A compound according to Embodiment 1.72 wherein the $C_{1-3}$ alkyl group is selected from methyl, ethyl and isopropyl.

1.74 A compound according to any one of the preceding Embodiments wherein, when R¹ is an optionally substituted 5- or 6-membered ring, it is selected from aromatic rings containing 0, 1 or 2 or 3 heteroatoms selected from O, N and S and oxidized forms thereof.

1.75 A compound according to Embodiment 1.74 wherein the aromatic ring is carbocyclic.

1.76 A compound according to Embodiment 1.74 wherein the aromatic ring is heterocyclic.

1.77 A compound according to any one of Embodiments 1.1 to 1.73 wherein, when R¹ is an optionally substituted 5- or 6-membered ring, it is selected from non-aromatic rings containing 0, 1 or 2 or 3 heteroatoms selected from O, N and S and oxidized forms thereof.

1.78 A compound according to Embodiment 1.77 wherein the non-aromatic ring is carbocyclic.

1.79 A compound according to Embodiment 1.77 wherein the non-aromatic ring is heterocyclic.

1.80 A compound according to any one of Embodiments 1.74 to 1.79 wherein the ring is a 5-membered ring.

1.81 A compound according to any one of Embodiments 1.74 to 1.79 wherein the ring is a 6-membered ring.

1.82 A compound according to any one of the preceding Embodiments wherein, when R¹ is an optionally substituted 5- or 6-membered ring, it is substituted with 0, 1, 2 or 3 substituents R⁸.

1.83 A compound according to Embodiment 1.82 wherein there are 0, 1 or 2 substituents R⁸ present.

1.84 A compound according to Embodiment 1.83 wherein there are 0 substituents R⁸ present.

1.85 A compound according to Embodiment 1.82 wherein there is 1 substituent R⁸ present.

1.86 A compound according to Embodiment 1.82 wherein there are 2 substituents R⁸ present.

1.87 A compound according to any one of Embodiments 1.81, 1.82, 1.83, 1.85 and 1.86 wherein R⁸ when present is selected from fluorine; cyano; oxo; hydroxy; OR⁵; NR⁵R⁶; COR⁵; COOR⁵; OCOR⁵; NR⁷COR⁵; CONR⁵R⁸; SR⁵; SOR⁵ and SO₂R⁵; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.88 A compound according to Embodiment 1.87 wherein R⁸ is selected from fluorine; cyano; oxo; hydroxy; OR⁵; NR⁵R⁶; COR⁵; COOR⁵; OCOR⁵ and SO₂R⁵; and a $C_{1-4}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof.

1.89 A compound according to Embodiment 1.88 wherein R⁸ is selected from fluorine; cyano; oxo; hydroxy; OR⁵; NR⁵R⁶; and a $C_{1-4}$ non-aromatic hydrocarbon group which is optionally substituted with one to six fluorine atoms.

1.90 A compound according to Embodiment 1.89 wherein R⁸ is selected from cyano; oxo; hydroxy; OR⁵; NR⁵R⁶; and $C_{1-4}$ alkyl.

1.91 A compound according to any one of Embodiments 1.1 to 1.40 and 1.42 to 1.53 wherein the moiety:

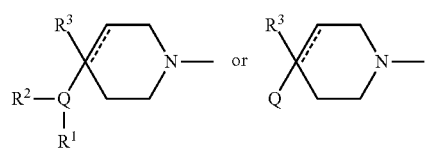

is selected from groups AAA to ACB below:
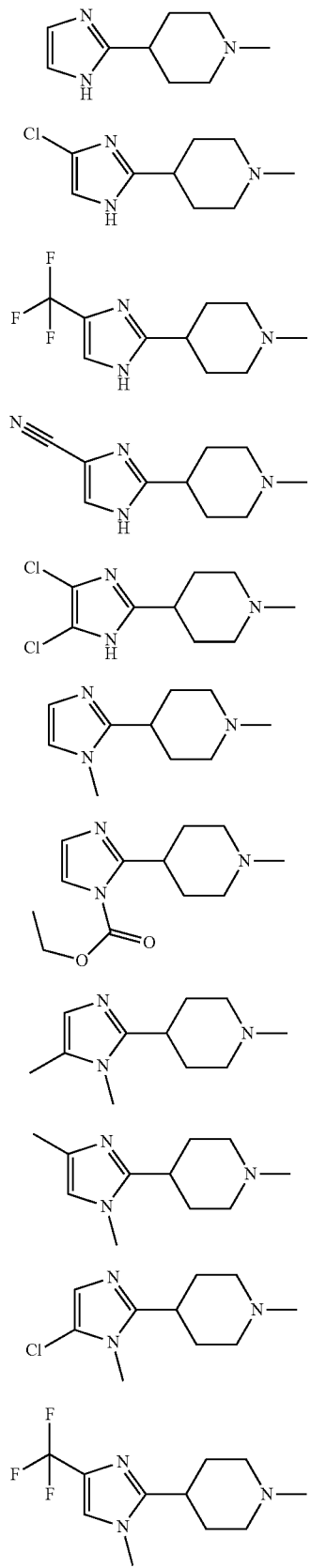
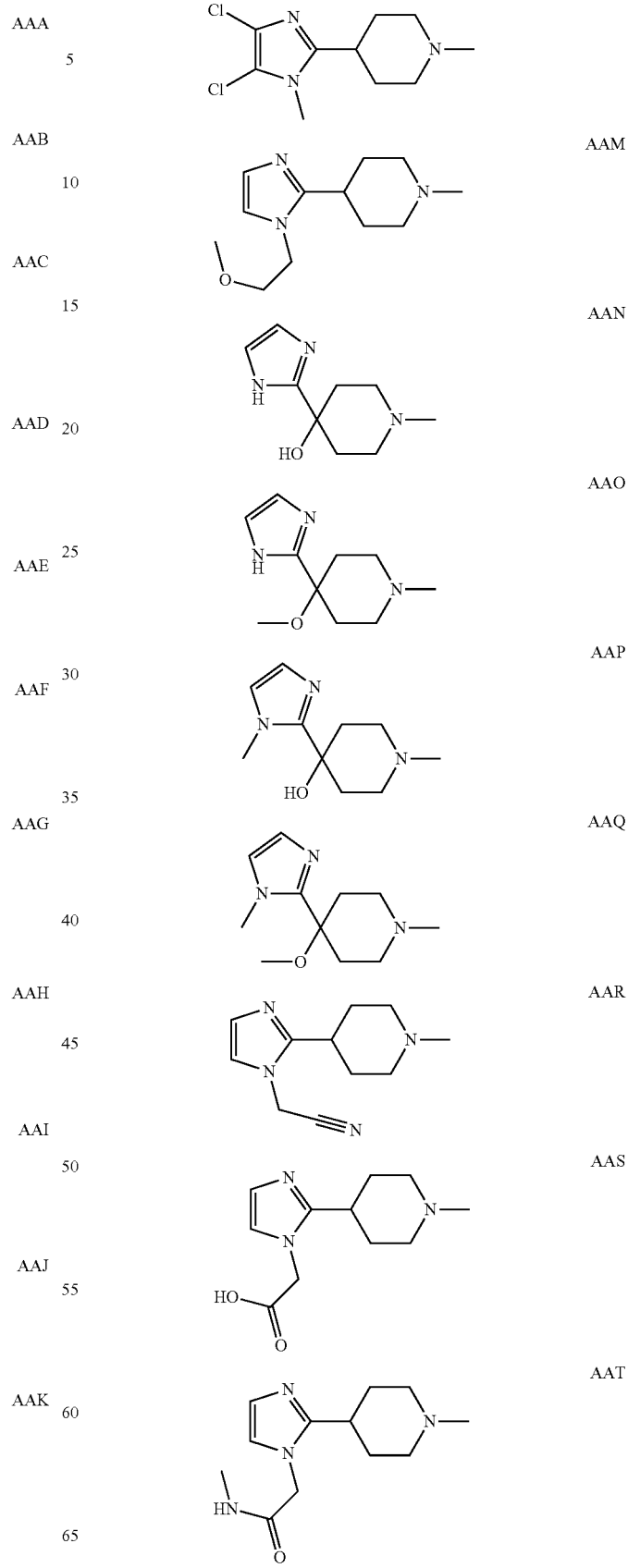

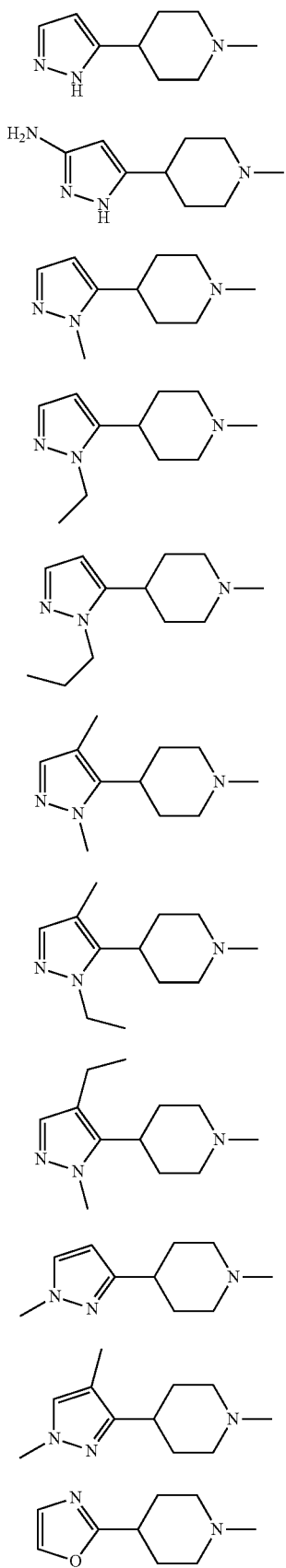
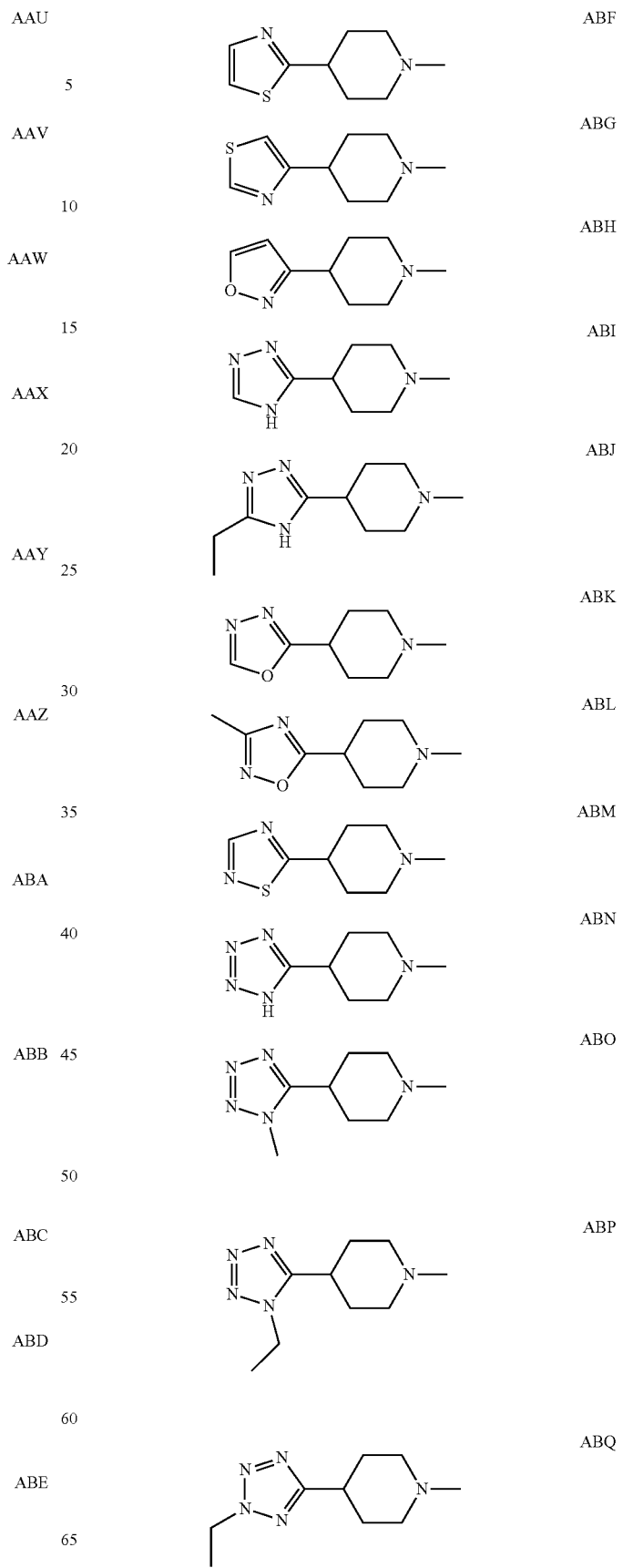

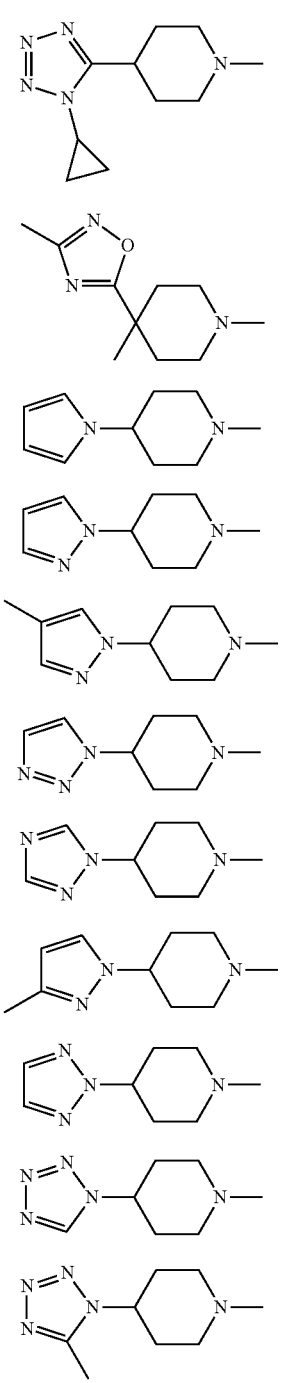

1.92 A compound according to having the formula (2) or formula 2a:

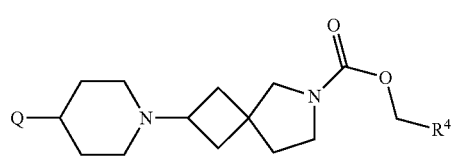
(2)

wherein Q is an optionally substituted 5 or 6 membered heterocyclic or heteraryl ring have one or more nitrogen atoms, and $R^4$ is as defined in any one of Embodiments 1.48 to 1.53; or

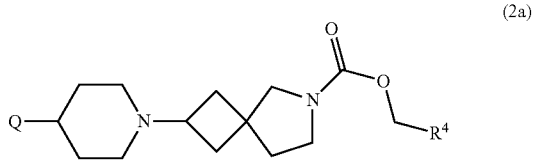
(2a)

wherein Q is an optionally substituted 5, 6 or 7 membered heterocyclic or heteraryl ring have one or more nitrogen atoms, and $R^4$ is as defined in any one of Embodiments 1.48 to 1.53.

1.93 A compound according to formula (2) or formula (2a) wherein Q has one or more substituents, for example one, two or three substituents which are selected from (L)-$R^{10}$, (L)-$R^{11}$ and (L)-$R^{12}$, where L is a bond or a $CH_2$ group; $R^{10}$, $R^{11}$ and $R^{12}$ are independently selected from hydrogen; fluorine; chlorine; bromine; cyano; oxo; hydroxy; $OR^{15}$; $NR^{15}R^{16}$; $COR^{15}$; $CSR^{15}$; $COOR^{15}$; $COSR^{15}$; $OCOR^{15}$; $NR^{17}COR^{15}$; $CONR^{15}R^{16}$; $CSNR^{15}R^{16}$; $NR^{17}CONR^{15}R^{16}$; $R^{17}COOR^{15}$; $OCONR^{15}R^{16}$; $SR^{15}$; $SOR^{15}$ and $SO_2R^{15}$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

wherein the optional substituents for the optionally substituted 5- or 6-membered ring are selected from a group $R^8$ consisting of hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

wherein $R^{15}$, $R^{16}$ and $R^{17}$ are the same or different, or may be joined together to form a ring, and each is independently selected from hydrogen, a non-aromatic $C_{1-6}$ hydrocarbon group optionally substituted with one or more fluorine atoms and wherein one or two, but not all, carbon atoms of the hydrocarbon group may optionally be replaced by a heteroatom selected from O, N and S and oxidized forms thereof; or a group of formula $CH_2N(R^a)COOR^b$; or a group of formula (L)-$R^{18}$ where L is a bond or a $CH_2$ group and $R^{18}$ is an optionally substituted 5- or 6-membered ring containing 0, 1, 2 or 3 heteroatoms selected from O, N and S and oxidized forms thereof;

wherein the optional substituents for the optionally substituted 5- or 6-membered ring are selected from a group $R^8$.

1.94 A compound according to Embodiments 1.1 to 1.93 having the formula (3):

(3)

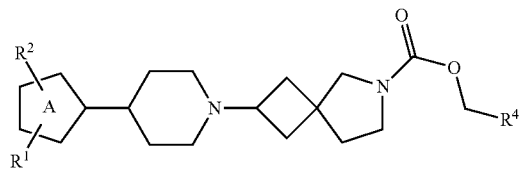

wherein R¹, R² and R⁴ are as defined in any one of Embodiments 1.1 to 1.40 and 1.42 to 1.90 and the ring A is a five membered heterocyclic or heteroaryl ring containing one or two nitrogen ring members.

1.95 A compound according to Embodiment 1.94 wherein the ring A is a five membered heteroaryl ring containing two nitrogen ring members.

1.96 A compound according to Embodiment 1.95 wherein the ring A is an imidazole ring.

1.97 A compound according to Embodiment 1.96 having the formula (4):

(4)

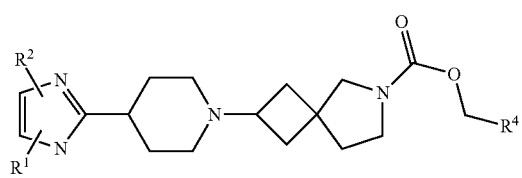

wherein R¹, R² and R⁴ are as defined in any one of Embodiments 1.1 to 1.40 and 1.42 to 1.90.

1.98 A compound according to Embodiment 1.95 wherein the ring A is a pyrazole ring.

1.99 A compound according to Embodiment 1.98 having the formula (5):

(5)

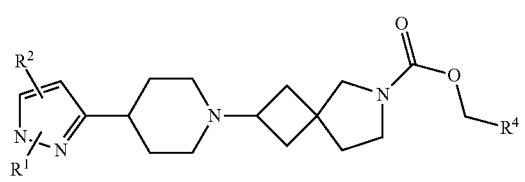

wherein R¹, R² and R⁴ are as defined in any one of Embodiments 1.1 to 1.40 and 1.42 to 1.90.

1.100 A compound according to Embodiment 1.98 having the formula (6):

(6)

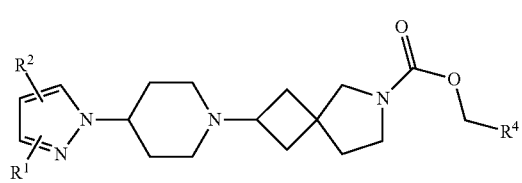

wherein R¹, R² and R⁴ are as defined in any one of Embodiments 1.1 to 1.40 and 1.42 to 1.90.

1.101 A compound according to Embodiment 1.94 wherein ring A is a 5 membered heterocyclic ring containing one nitrogen atom.

1.102 A compound according to Embodiment 1.101 having the formula (7):

(7)

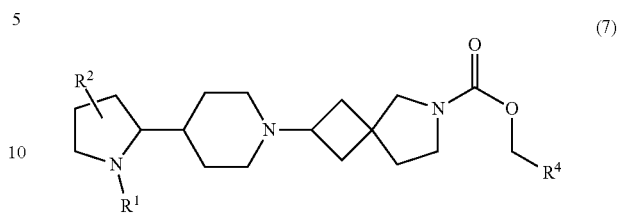

wherein R¹, R² and R⁴ are as defined in any one of Embodiments 1.1 to 1.40 and 1.42 to 1.90.

1.103 A compound according to embodiment 1.101 wherein moiety:

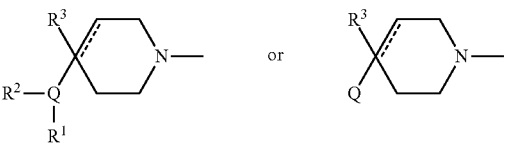

is selected from groups BAA to BCZ below:

BAA

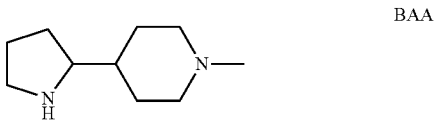

BAB

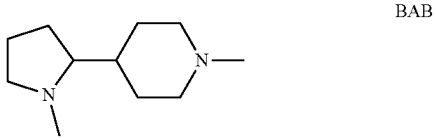

BAC

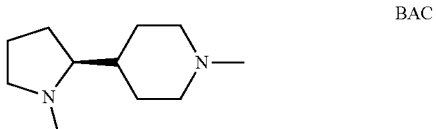

BAD

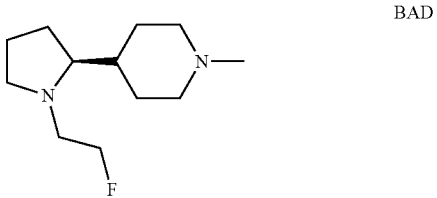

BAE

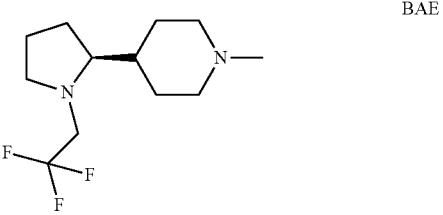

| | |
|---|---|
| 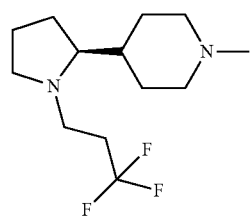 BAF | 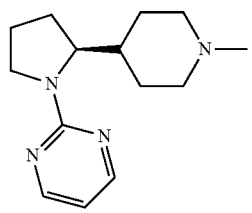 BAM |
| 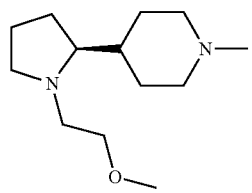 BAG | 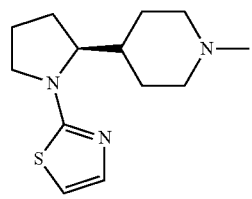 BAN |
| 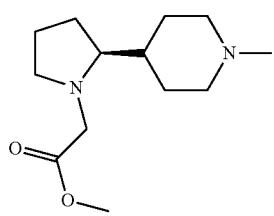 BAH | 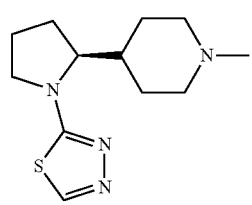 BAO |
| 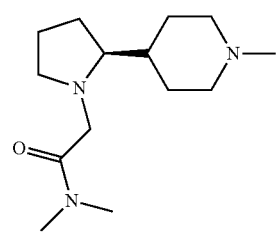 BAI | 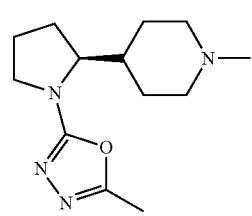 BAP |
| 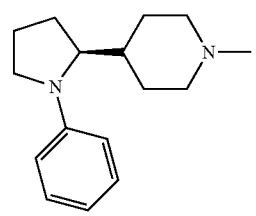 BAJ | 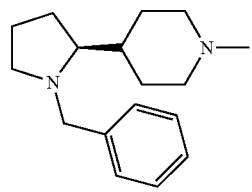 BAQ |
| 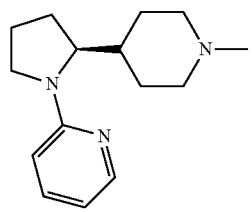 BAK | 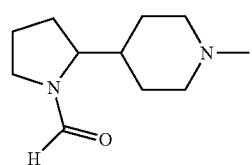 BAR |
| | 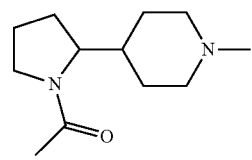 BAS |
| 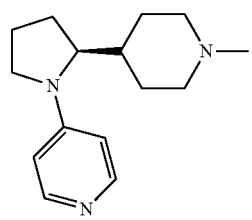 BAL | 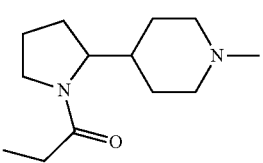 BAT |

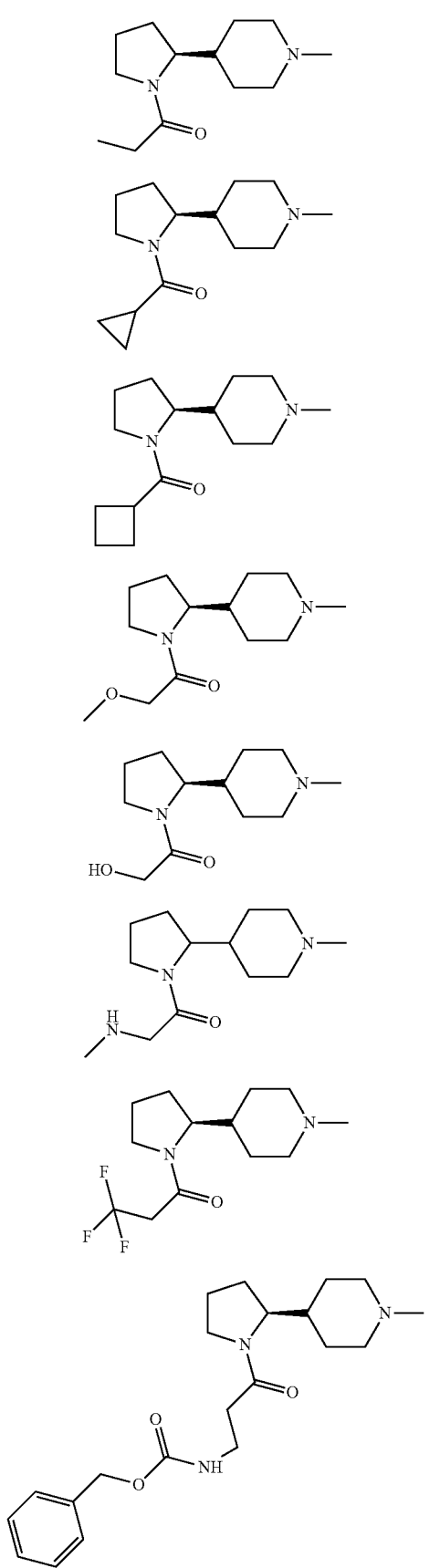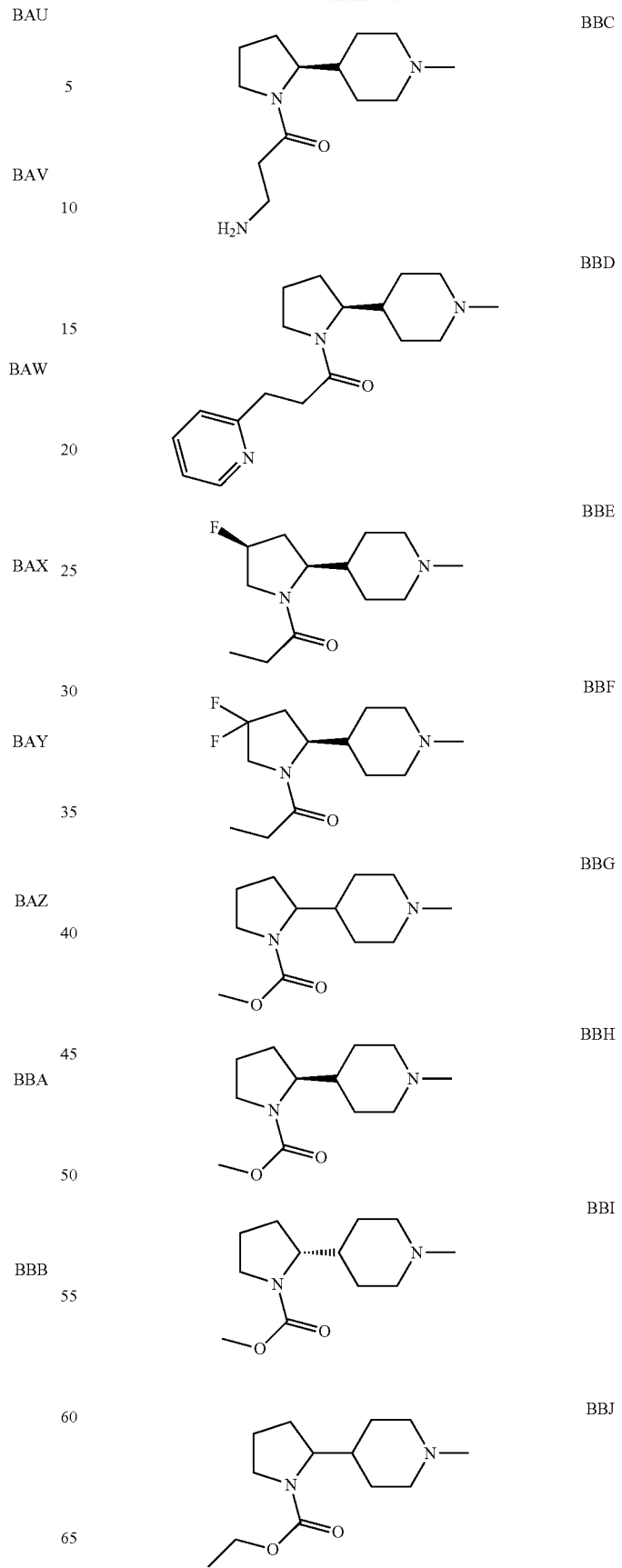

| | |
|---|---|
| 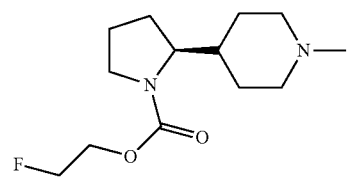 BBK | 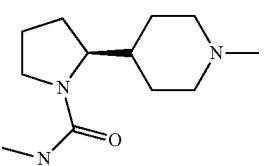 BBS |
| 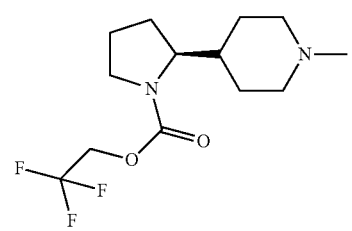 BBL | 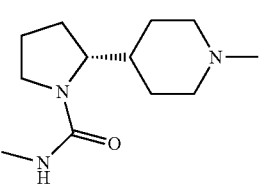 BBT |
| 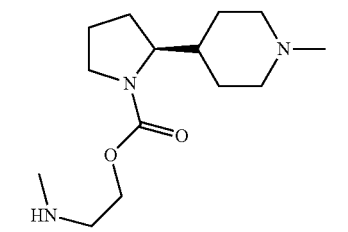 BBM | 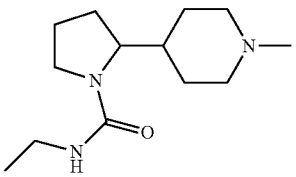 BBU |
| 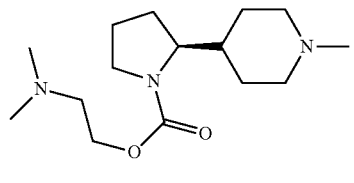 BBN | 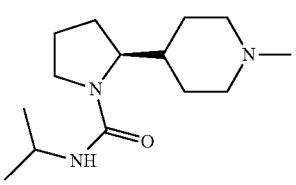 BBV |
| 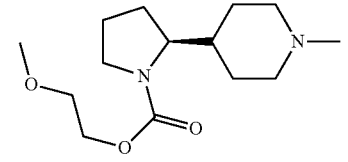 BBO | 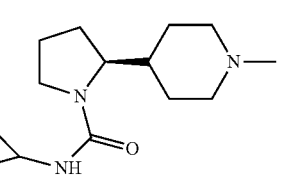 BBW |
| 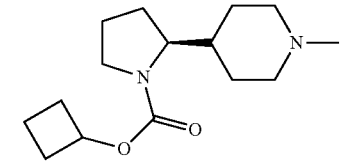 BBP | 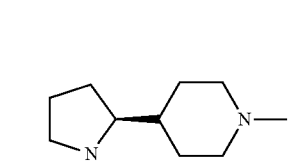 BBX |
| 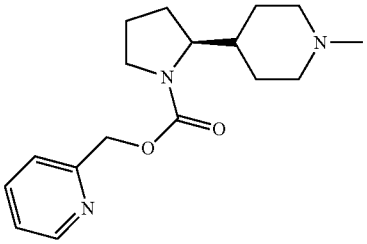 BBQ | 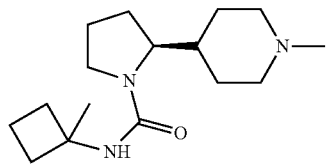 BBY |
| 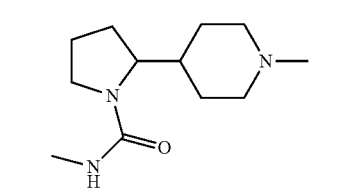 BBR | 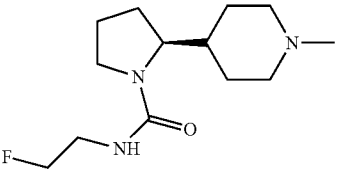 BBZ |

| | |
|---|---|
| BCA | BCJ |
| BCB | BCK |
| BCD | BCL |
| BCE | BCM |
| BCF | BCN |
| BCG | BCO |
| BCH | BCP |
| BCI | |

-continued
BCQ 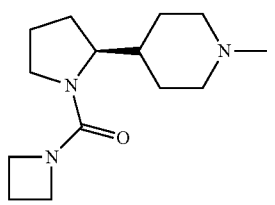
BCR 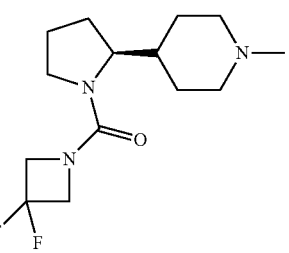
BCS 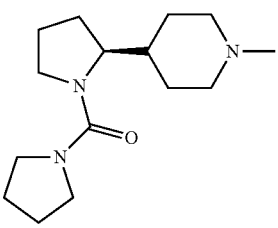
BCT 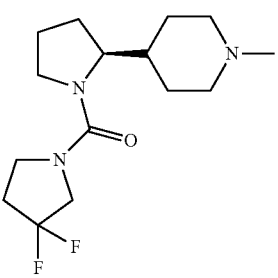
BCU 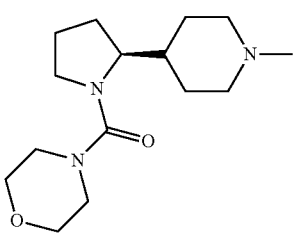
BCV 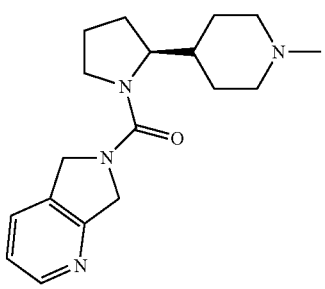
-continued
BCW 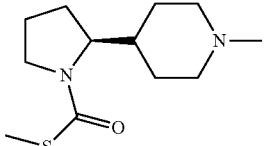
BCX 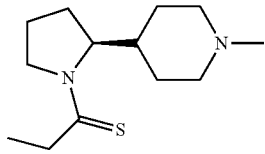
BCY 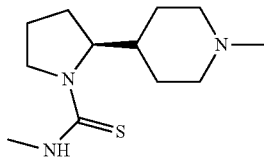
BCZ 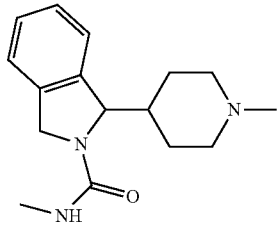
1.104 A compound according to Embodiment 1.101 having the formula (8):
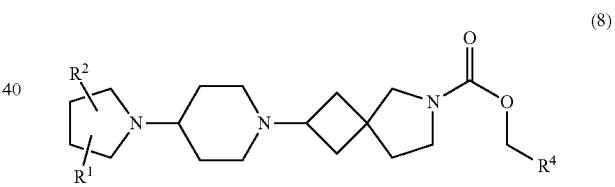
(8)
wherein $R^1$, $R^2$ and $R^4$ are as defined in any one of Embodiments 1.1 to 1.40 and 1.42 to 1.90.
1.105 A compound according to embodiment 1.101 wherein moiety:
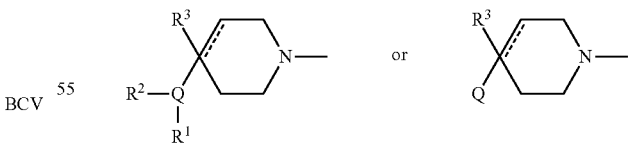
is selected from groups CAA to CBX below:
CAA 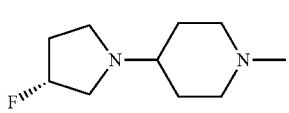

| | |
|---|---|
| CAB | CAL |
| CAC | CAM |
| CAD | CAN |
| CAE | CAO |
| CAF | CAP |
| CAG | CAQ |
| CAH | CAR |
| CAI | CAS |
| CAJ | |
| CAK | |

CAT 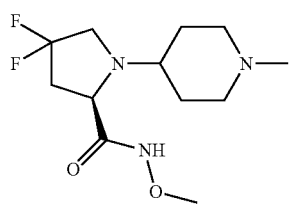
CAU 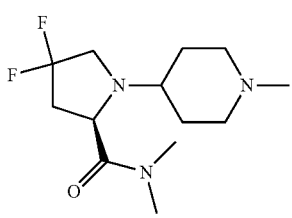
CAV 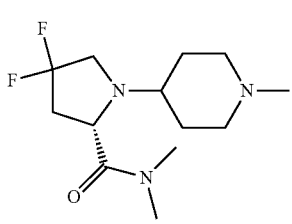
CAW 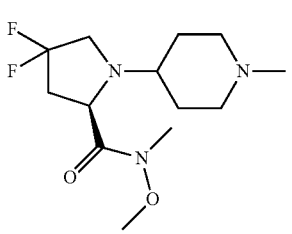
CAX 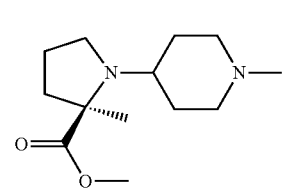
CAY 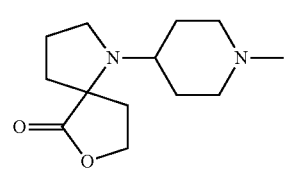
CAZ 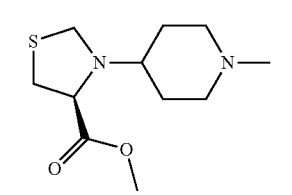
CBA 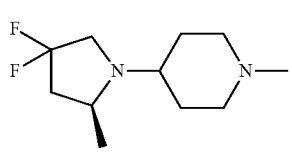
CBB 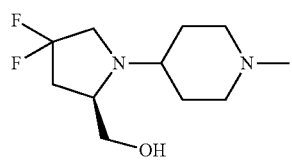
CBC 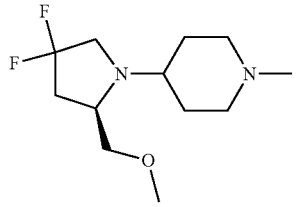
CBD 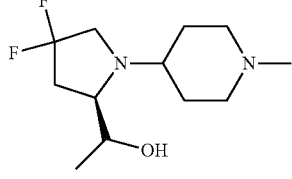
CBE 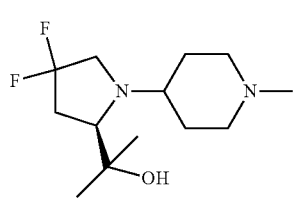
CBF 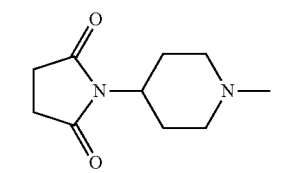
CBG 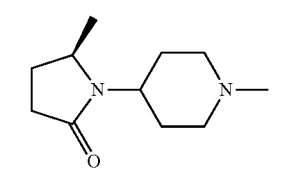
CBH 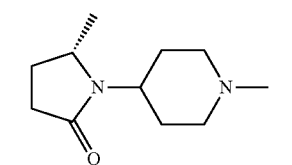
CBI 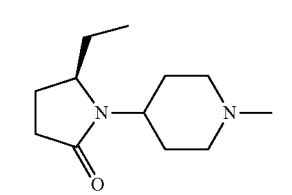

| | | |
|---|---|---|
| CBJ | 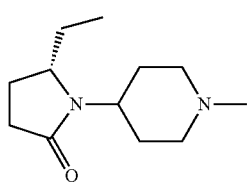 | CBS 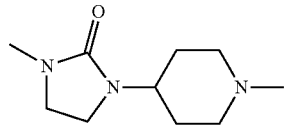 |
| CBK | 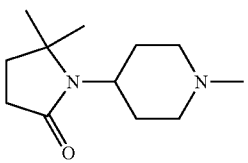 | CBT 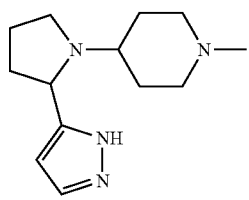 |
| CBL | 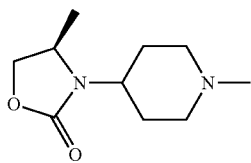 | CBU 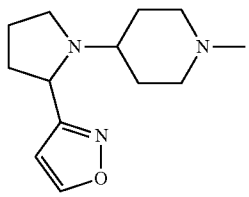 |
| CBM | 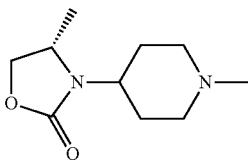 | CBV 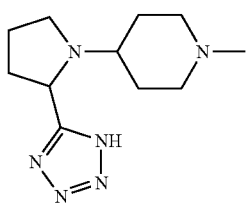 |
| CBN | 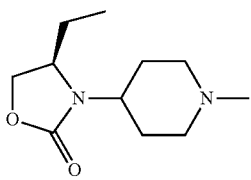 | CBW 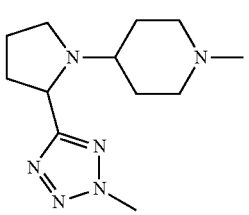 |
| CBO | 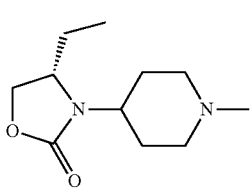 | CBX 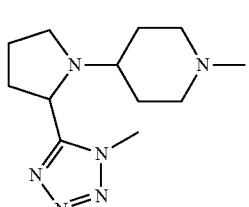 |
| CBP | 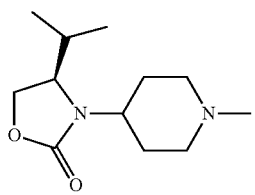 | CBY 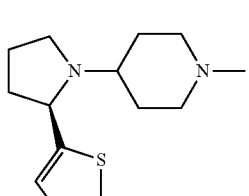 |
| CBQ | 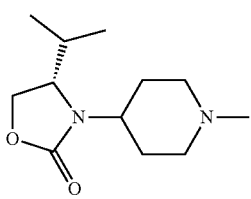 | CBX 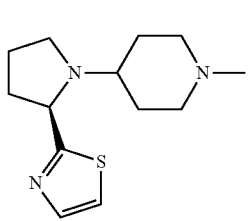 |
| CBR | 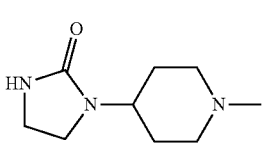 | |

1.106 A compound according to embodiment 1.1 wherein Q is a six membered monocyclic heterocyclic ring containing 1, 2, 3 or 4 heteroatom ring members selected from N, O and S.
1.107 A compound according to Embodiment 1.106 wherein the moiety:
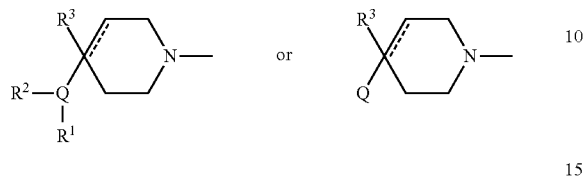
is selected from groups DAA to DBG below:
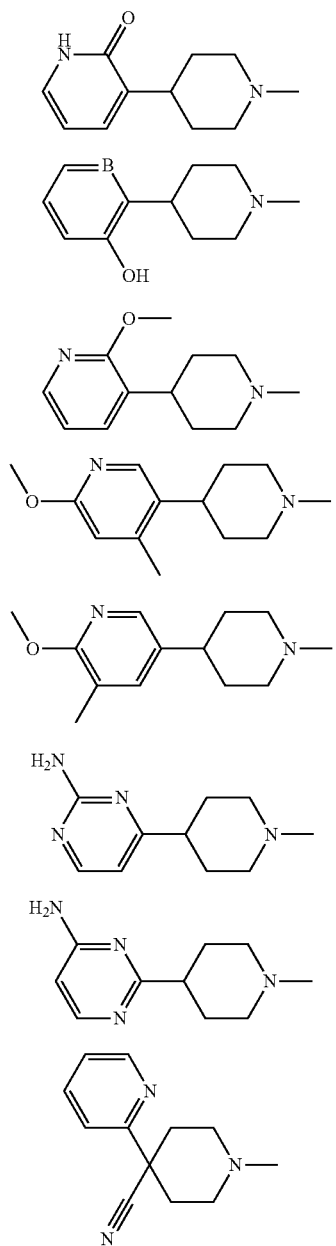
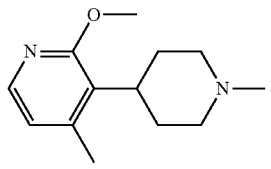
DAI
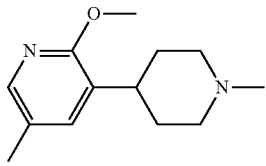
DAJ
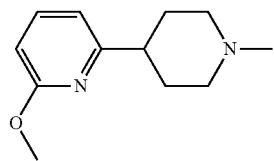
DAK
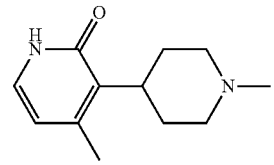
DAL
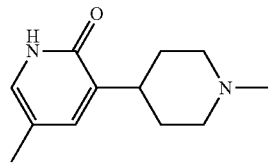
DAM
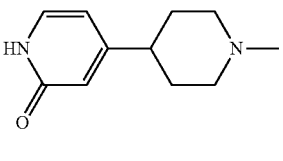
DAN
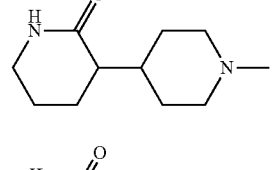
DAO
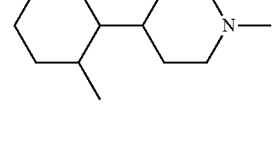
DAP
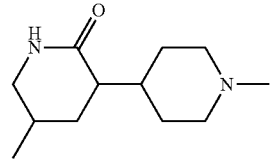
DAQ

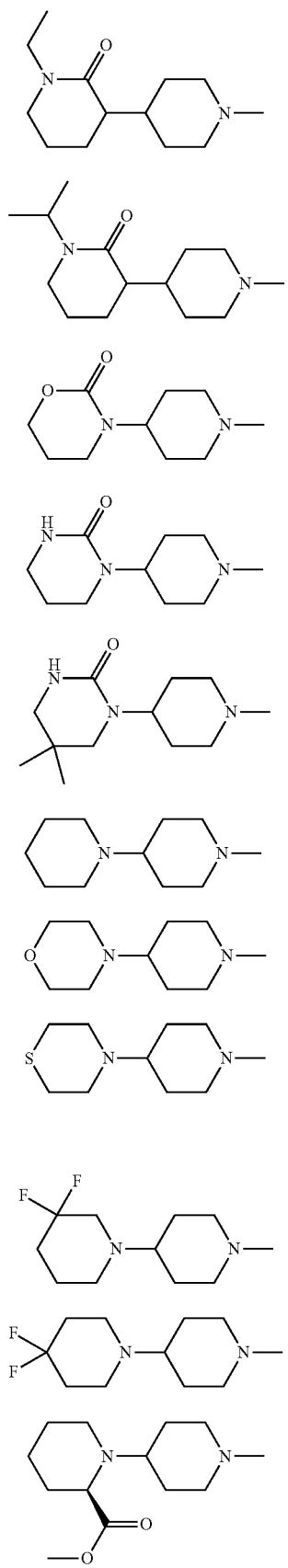
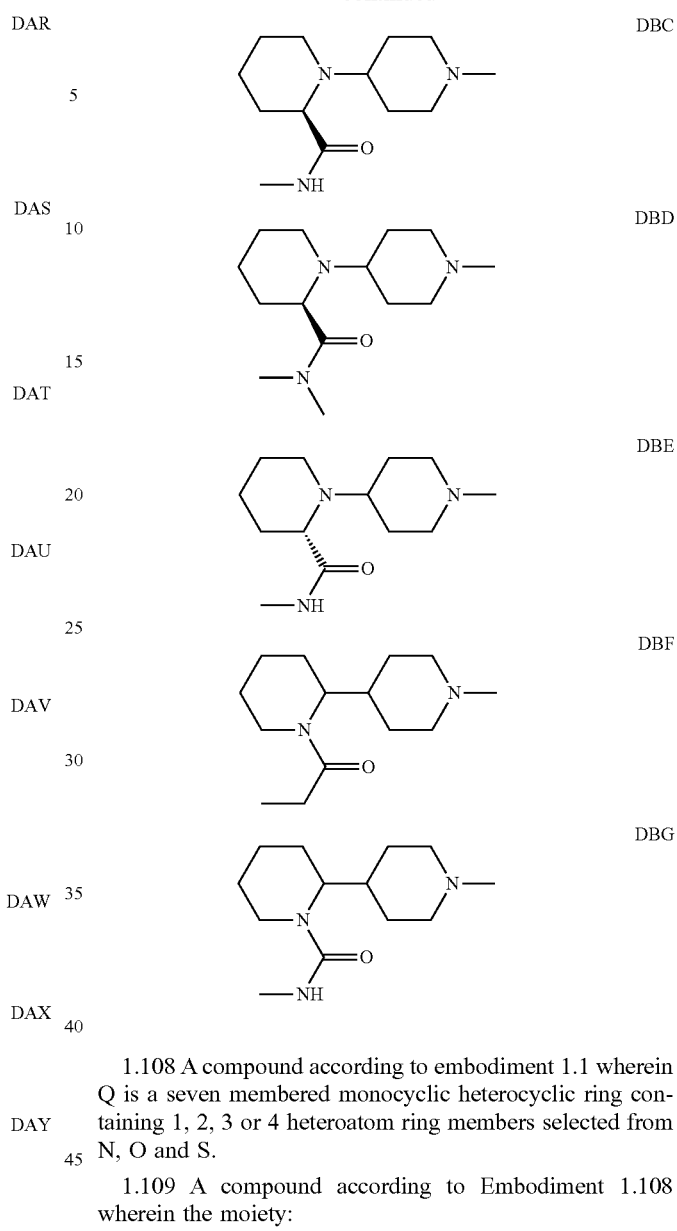
1.108 A compound according to embodiment 1.1 wherein Q is a seven membered monocyclic heterocyclic ring containing 1, 2, 3 or 4 heteroatom ring members selected from N, O and S.
1.109 A compound according to Embodiment 1.108 wherein the moiety:
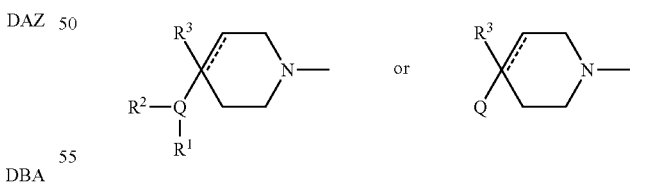
is selected from groups EAA to EAB below:
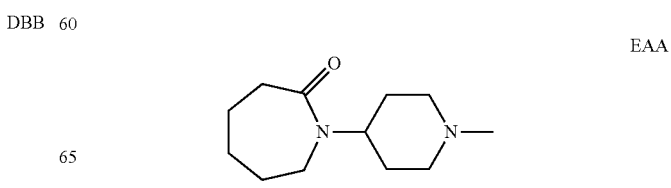

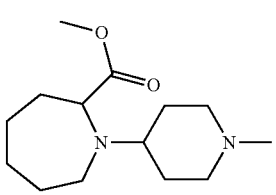

EAB 1.110 A compound according to Embodiment 1.1 which is as defined in any one of Examples 1-1 to 1-73, 2-1 to 2-138, 3-1 to 3-16, 4-1 to 4-20 or 5-1 to 5-2.

1.111 A compound according to any one of Embodiments 1.1 to 1.110 having a molecular weight of less than 550.

1.112 A compound according to Embodiment 1.111 having a molecular weight of less than 500.

1.113 A compound according to Embodiment 1.112 having a molecular weight of, or less than 450.

1.114 A compound according to any one of Embodiments 1.1 to 1.113 which is in the form of a salt.

1.115 A compound according to Embodiment 1.114 wherein the salt is an acid addition salt.

1.116 A compound according to Embodiment 1.115 or Embodiment 1.115 wherein the salt is a pharmaceutically acceptable salt.

DEFINITIONS

In this application, the following definitions apply, unless indicated otherwise.

The term "treatment", in relation to the uses of the compounds of the formula (1), (1a) or (1b), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" as in "$C_{1-10}$ non-aromatic hydrocarbon group" or "acyclic $C_{1-5}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The terms "alkyl", "alkenyl", "alkynyl", "cycloalkyl" aryl, heteroaryl and "cycloalkenyl" are used in their conventional sense (e.g. as defined in the IUPAC Gold Book) unless indicated otherwise.

The term "saturated hydrocarbon group" as in "$C_{1-4}$ saturated hydrocarbon group" refers to a hydrocarbon group containing no carbon-carbon double bonds or triple bonds. The saturated hydrocarbon group can therefore be an alkyl group, a cycloalkyl group, a cycloalkylalkyl group, an alkylcycloalkyl group or a alkylcycloalkylalkyl group. Examples of $C_{1-4}$ saturated hydrocarbon groups include $C_{1-4}$ alkyl groups, cyclopropyl, cyclobutyl and cyclopropylmethyl.

The term "cycloalkyl" as used herein, where the specified number of carbon atoms permits, includes both monocyclic cycloalkyl groups such as cyclopropyl, cyclobutyl, cyclopentyl, cyclohexyl and cycloheptyl, and bicyclic and tricyclic groups. Bicyclic cycloalkyl groups include bridged ring systems such as bicycloheptane, bicyclooctane and adamantane.

In the definitions of $R^1$, $R^2$, $R^3$ and $R^4$ above, where stated, one or two but not all, carbon atoms of the non-aromatic hydrocarbon group may optionally be replaced by a heteroatom selected from O, N and S and (in the case of $R^1$ and $R^4$) oxidised forms thereof. It will be appreciated that when a carbon atom is replaced by a heteroatom, the lower valencies of the heteroatoms compared to carbon means that fewer atoms will be bonded to the heteroatoms than would have been bonded to the carbon atom that has been replaced. Thus, for example, replacement of a carbon atom (valency of four) in a $CH_2$ group by oxygen (valency of two) will mean that the resulting molecule will contain two less hydrogen atoms and replacement of a carbon atom (valency of four) in a $CH_2$ group by nitrogen (valency of three) will mean that the resulting molecule will contain one less hydrogen atom.

Examples of a heteroatom replacements for carbon atoms include replacement of a carbon atom in a —$CH_2$—$CH_2$—$CH_2$— chain with oxygen or sulfur to give an ether —$CH_2$—O—$CH_2$— or thioether —$CH_2$—S—$CH_2$—, replacement of a carbon atom in a group $CH_2$—C≡C—H with nitrogen to give a nitrile (cyano) group $CH_2$—C≡N, replacement of a carbon atom in a group —$CH_2$—$CH_2$—$CH_2$— with C=O to give a ketone —$CH_2$—C(O)—$CH_2$—, replacement of a carbon atom in a group —$CH_2$—$CH_2$—$CH_2$— with S=O or $SO_2$ to give a sulfoxide —$CH_2$—S(O)—$CH_2$— or sulfone —$CH_2$—S(O)$_2$—$CH_2$—, replacement of a carbon atom in a —$CH_2$—$CH_2$—$CH_2$— chain with C(O)NH to give an amide —$CH_2$—$CH_2$—C(O)—NH—, replacement of a carbon atom in a —$CH_2$—$CH_2$—$CH_2$— chain with nitrogen to give an amine —$CH_2$—NH—$CH_2$—, and replacement of a carbon atom in a —$CH_2$—$CH_2$—$CH_2$— chain with C(O)O to give an ester (or carboxylic acid) —$CH_2$—$CH_2$—C(O)—O—. In each such replacement, at least one carbon atom of the hydrocarbon group must remain.

Salts

Many compounds of the formula (1), (1a) or (1b) can exist in the form of salts, for example acid addition salts or, in certain cases salts of organic and inorganic bases such as carboxylate, sulfonate and phosphate salts. All such salts are within the scope of this invention, and references to compounds of the formula (1), (1a) or (1b) include the salt forms of the compounds as defined in Embodiments 1.114 to 1.116.

The salts are typically acid addition salts.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (as defined in Embodiment 1.120) may be formed with a wide variety of acids, both inorganic and organic. Examples of acid addition salts falling within Embodiment 1.120 include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

Where the compounds of the formula (1), (1a) or (1b) contain an amine function, these may form quaternary ammonium salts, for example by reaction with an alkylating agent according to methods well known to the skilled person. Such quaternary ammonium compounds are within the scope of formula (1), (1a) or (1b).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Stereoisomers

Stereoisomers are isomeric molecules that have the same molecular formula and sequence of bonded atoms but which differ only in the three-dimensional orientations of their atoms in space. The stereoisomers can be, for example, geometric isomers or optical isomers.

Geometric Isomers

With geometric isomers, the isomerism is due to the different orientations of an atom or group about a double bond, as in cis and trans (Z and E) isomerism about a carbon-carbon double bond, or cis and trans isomers about an amide bond, or syn and anti isomerism about a carbon nitrogen double bond (e.g. in an oxime), or rotational isomerism about a bond where there is restricted rotation, or cis and trans isomerism about a ring such as a cycloalkane ring.

Accordingly, in another embodiment (Embodiment 1.121), the invention provides a geometric isomer of a compound according to any one of Embodiments 1.1 to 1.116.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

Accordingly, in another embodiment (Embodiment 1.132) the invention provides a compound according to any one of Embodiments 1.1 to 1.121 which contains a chiral centre.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.,* 1966, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, in another embodiment (Embodiment 1.133), the invention provides compositions containing a compound according to Embodiment 1.132 having one or more chiral centres, wherein at least 55% (e.g. at least 60%, 65%, 70%, 75%, 80%, 85%, 90% or 95%) of the compound of Embodiment 1.108 is present as a single optical isomer (e.g. enantiomer or diastereoisomer).

In one general embodiment (Embodiment 1.134), 99% or more (e.g. substantially all) of the total amount of the compound (or compound for use) of Embodiment 1.132 is present as a single optical isomer.

For example, in one embodiment (Embodiment 1.135) the compound is present as a single enantiomer.

In another embodiment (Embodiment 1.136), the compound is present as a single diastereoisomer.

The invention also provides mixtures of optical isomers, which may be racemic or non-racemic. Thus, the invention provides:

1.137 A compound according to Embodiment 1.132 which is in the form of a racemic mixture of optical isomers.

1.138 A compound according to Embodiment 1.132 which is in the form of a non-racemic mixture of optical isomers.

Isotopes

The compounds of the invention as defined in any one of Embodiments 1.1 to 1.138 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention (Embodiment 1.140), the compound of any one of Embodiments 1.1 to 1.138 contains no radioactive isotopes. Such compounds are preferred for therapeutic use. In another embodiment (Embodiment 1.141), however, the compound of any one of Embodiments 1.1 to 1.138 may contain one or more radioisotopes. Compounds containing such radioisotopes may be useful in a diagnostic context.

Solvates

Compounds of the formula (1), (1a) or (1b) as defined in any one of Embodiments 1.1 to 1.141 may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography. The solvates can be stoichiometric or non-stoichiometric solvates. Particularly preferred solvates are hydrates, and examples of hydrates include hemihydrates, monohydrates and dihydrates.

Accordingly, in further embodiments 1.150 and 1.151, the invention provides:

1.151 A compound according to any one of Embodiments 1.1 to 1.141 in the form of a solvate.

1.152 A compound according to Embodiment 1.151 wherein the solvate is a hydrate.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment (Embodiment 1.153), the invention provides a compound as defined in any one of Embodiments 1.1 to 1.141 in an anhydrous form (e.g. anhydrous crystalline form).

Crystalline and Amorphous Forms

The compounds of any one of Embodiments 1.1 to 1.153 may exist in a crystalline or non-crystalline (e.g. amorphous) state. Whether or not a compound exists in a crystalline state can readily be determined by standard techniques such as X-ray powder diffraction (XRPD). Crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can be analysed by gravimetric vapour sorption studies and also by XRPD. Determination of the crystal structure of a compound can be performed by X-ray crystallography which can be carried out according to conventional methods such as those described herein and as described in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of single crystal. In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

Accordingly, in further embodiments, the invention provides:

1.160 A compound according to any one of Embodiments 1.1 to 1.153 in a crystalline form.

1.161 A compound according to any one of Embodiments 1.1 to 1.153 which is:

(a) from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

1.162 A compound according to any one of Embodiments 1.1 to 1.153 which is in an amorphous form.

Prodrugs

The compounds of the formula (1), (1a) or (1b) as defined in any one of Embodiments 1.1 to 1.162 may be presented in the form of a pro-drug. By "prodrugs" is meant for example any compound that is converted in vivo into a biologically active compound of the formula (1), (1a) or (1b), as defined in any one of Embodiments 1.1 to 1.162.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Accordingly, in another embodiment (Embodiment 1.170), the invention provides a pro-drug of a compound as defined in any one of Embodiments 1.1 to 1.170 wherein the compound contains a functional group which is convertable under physiological conditions to form a hydroxyl group or amino group.

Complexes and Clathrates

Also encompassed by formula (1), (1a) or (1b) in Embodiments 1.1 to 1.170 are complexes (e.g. inclusion complexes or clathrates with compounds such as cyclodextrins, or complexes with metals) of the compounds of Embodiments 1.1 to 1.170.

Accordingly, in another embodiment (Embodiment 1.180), the invention provides a compound according to any one of Embodiments 1.1 to 1.170 in the form of a complex or clathrate.

Biological Activity and Therapeutic Uses

The compounds of the present invention have activity as muscarinic M1 receptor agonists. The muscarinic activity of the compounds can be determined using the Phospho-ERK1/2 assay described in Example A below.

A significant advantage of compounds of the invention is that they are highly selective for the M1 receptor relative to the M2 and M3 receptor subtypes. Compounds of the invention are not agonists of the M2 and M3 receptor subtypes. For example, whereas compounds of the invention typically have $pEC_{50}$ values of at least 6 (preferably at least 6.5) and $E_{max}$ values of greater than 80 (preferably greater than 95) against the M1 receptor in the functional assay described in Example A, they may have $pEC_{50}$ values of less than 5 and $E_{max}$ values of less than 20% when tested against the M2 and M3 subtypes in the functional assay of Example A.

Some compounds of the invention are also highly selective for the M4 receptor relative to the M1 receptor. Examples of such compounds include the compound of Example 1-6, 1-9, 1-21 and 2-17.

Other compounds of the invention have activity at both the M1 and M4 receptors. Examples of such compounds include compounds of Examples 1-1 to 1-4 and 1-8 to 1-10 and 2-116.

Accordingly, in Embodiments 2.1 to 2.9, the invention provides:

2.1 A compound according to any one of Embodiments 1.1 to 1.180 for use in medicine.

2.2 A compound according to any one of Embodiments 1.1 to 1.180 for use as a muscarinic M1 and/or M4 receptor agonist.

2.3 A compound according to any one of Embodiments 1.1 to 1.180 which is a muscarinic M1 receptor agonist having a $pEC_{50}$ in the range from 6.0 to 8.1 and an $E_{max}$ of at least 90 against the M1 receptor in the assay of Example A herein or an assay substantially similar thereto.

2.4 A compound according to Embodiment 2.3 which is a muscarinic M1 receptor agonist having a $pEC_{50}$ in the range from 6.5 to 7.5.

2.5 A compound according to Embodiment 2.3 or Embodiment 2.4 having an $E_{max}$ of at least 95 against the M1 receptor.

2.6 A compound according to any one of Embodiments 1.1 to 1.180 which is a muscarinic M4 receptor agonist having a $pEC_{50}$ in the range from 6.0 to 9.0 and an $E_{max}$ of at least 90 against the M4 receptor in the assay of Example A herein or an assay substantially similar thereto.

2.7 A compound according to Embodiment 2.6 which is a muscarinic M4 receptor agonist having a $pEC_{50}$ in the range from 6.5 to 9.0.

2.8 A compound according to Embodiment 2.6 or Embodiment 2.7 having an $E_{max}$ of at least 95 against the M4 receptor.

2.9 A compound according to any one of Embodiments 2.3 to 2.8 which is selective for the M1 and/or M4 receptor compared to the muscarinic M2 and M3 receptors.

2.10 A compound according to Embodiment 2.9 which is selective for the M1 receptor compared to the muscarinic M2 and M3 receptors.

2.11 A compound according to Embodiment 2.9 which is selective for the M4 receptor compared to the muscarinic M2 and M3 receptors.

2.12 A compound according to any one of Embodiments 2.3 to 2.5 which is selective for the M1 receptor compared to the muscarinic M2, M3 and M4 receptors.

2.13 A compound according to any one of Embodiments 2.6 to 2.8 which is selective for the M4 receptor compared to the muscarinic M1, M2 and M3 receptors.

2.14 A compound according to any one of Embodiments 2.3 to 2.8 which is selective for the M1 and M4 receptor compared to the muscarinic M2 and M3 receptors.

2.15 A compound according to any one of Embodiments 2.3 to 2.14 which has a $pEC_{50}$ of less than 5 and an $E_{max}$ of less than 50 against the muscarinic M2 and M3 receptor subtypes.

2.16 A compound according to Embodiment 2.15 which has a $pEC_{50}$ of less than 4.5 and/or an $E_{max}$ of less than 30 against the muscarinic M2 and M3 receptor subtypes.

2.17 A compound according to any one of Embodiments 1.1 to 1.180 and Embodiments 2.3 to 2.16 for use in the treatment of a disease or condition mediated by the muscarinic M1 receptor.

By virtue of their muscarinic M1 and/or M4 receptor agonist activity, compounds of the invention can be used in the treatment of Alzheimer's disease, schizophrenia and other psychotic disorders, cognitive disorders and other diseases mediated by the muscarinic M1 and for M4 receptor, and can also be used in the treatment of various types of pain.

Accordingly, in Embodiments 2.18 to 2.34, the invention provides:

2.18 A compound according to any one of Embodiments 1.1 to 1.180 for use in the treatment of a cognitive disorder or psychotic disorder.

2.19 A compound for use in according to Embodiment 2.18 wherein the cognitive disorder or psychotic disorder comprises, arises from or is associated with a condition selected from cognitive impairment, Mild Cognitive Impairment, frontotemporal dementia, vascular dementia, dementia with Lewy bodies, presenile dementia, senile dementia, Friederich's ataxia, Down's syndrome, Huntington's chorea, hyperkinesia, mania, Tourette's syndrome, Alzheimer's disease, progressive supranuclear palsy, impairment of cognitive functions including attention, orientation, learning disorders, memory (i.e. memory disorders, amnesia, amnesic disorders, transient global amnesia syndrome and age-associated memory impairment) and language function; cognitive impairment as a result of stroke, Huntington's disease, Pick disease, Aids-related dementia or other dementia states such as Multiinfarct dementia, alcoholic dementia, hypotiroidism-related dementia, and dementia associated to other degenerative disorders such as cerebellar atrophy and amyotropic lateral sclerosis; other acute or sub-acute conditions that may cause cognitive decline such as delirium or depression (pseudodementia states) trauma, head trauma, age related cognitive decline, stroke, neurodegeneration, drug-induced states, neurotoxic agents, age related cognitive impairment, autism related cognitive impairment, Down's syndrome, cognitive deficit related to psychosis, and post-electroconvulsive treatment related cognitive disorders; cognitive disorders due to drug abuse or drug withdrawal including nicotine, cannabis, amphetamine, cocaine, Attention Deficit Hyperactivity Disorder (ADHD) and dyskinetic disorders such as Parkinson's disease, neuroleptic-induced parkinsonism, and tardive dyskinesias, schizophrenia, schizophreniform diseases, psychotic depression, mania, acute mania, paranoid, hallucinogenic and delusional disorders, personality disorders, obsessive compulsive disorders, schizotypal disorders, delusional disorders, psychosis due to malignancy, metabolic disorder, endocrine disease or narcolepsy, psychosis due to drug abuse or drug withdrawal, bipolar disorders, epilepsy and schizo-affective disorder.

2.20 A compound according to any one of Embodiments 1.1 to 1.180 for use in the treatment of Alzheimer's disease.

2.21 A compound according to any one of Embodiments 1.1 to 1.180 for use in the treatment of Schizophrenia.

2.22 A method of treatment of a cognitive disorder in a subject (e.g. a mammalian patient such as a human, e.g. a human in need of such treatment), which method comprises the administration of a therapeutically effective dose of a compound according to any one of Embodiments 1.1 to 1.180.

2.23 A method according to Embodiment 2.20 wherein the cognitive disorder comprises, arises from or is associated with a condition as defined in Embodiment 2.19.

2.24 A method according to Embodiment 2.23 wherein the cognitive disorder arises from or is associated with Alzheimer's disease.

2.25 A method according to Embodiment 2.24 wherein the cognitive disorder is Schizophrenia.

2.26 The use of a compound according to any one of Embodiments 1.1 to 1.180 for the manufacture of a medicament for the treatment of a cognitive disorder.

2.27 The use according to Embodiment 2.26 wherein the cognitive disorder comprises, arises from or is associated with a condition as defined in Embodiment 2.11.

2.28 The use according to Embodiment 2.27 wherein the cognitive disorder arises from or is associated with Alzheimer's disease.

2.29 The use according to Embodiment 2.29 wherein the cognitive disorder is Schizophrenia.

2.30 A compound according to any one of Embodiments 1.1 to 1.180 for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain.

2.31 A method of treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain, which method comprises the administration of a therapeutically effective dose of a compound according to any one of Embodiments 1.1 to 1.180.

2.32 A compound according to any one of Embodiments 1.1 to 1.180 for the treatment of peripheral disorders such as reduction of intra ocular pressure in Glaucoma and treatment of dry eyes and dry mouth including Sjogren's Syndrome.

2.33 A method of treatment of peripheral disorders such as reduction of intra ocular pressure in Glaucoma and treatment of dry eyes and dry mouth including Sjogren's Syndrome, which method comprises the administration of a therapeutically effective dose of a compound according to any one of Embodiments 1.1 to 1.180.

2.34 The use of a compound according to any one of Embodiments 1.1 to 1.180 for the manufacture of a medicament for the treatment or lessening the severity of acute, chronic, neuropathic, or inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica, back pain, head or neck pain, severe or intractable pain, nociceptive pain, breakthrough pain, post-surgical pain, or cancer pain or for the treatment of peripheral disorders such as reduction of intra ocular pressure in Glaucoma and treatment of dry eyes and dry mouth including Sjogren's Syndrome.

2.35 The use of a compound according to any one of Embodiments 1.1 to 1.180 for the treatment of addiction.

2.36 The use of a compound according to any one of Embodiments 1.1 to 1.180 for the treatment of movement disorders such as Parkinson's disease, ADHD, Huntingdon's disease, tourette's syndrome and other syndromes associated with dopaminergic dysfunction as an underlying pathogenetic factor driving disease.

Methods for the Preparation of Compounds of the Formula (1), (1a) or (1b)

Compounds of the formula (1), (1a) or (1b) can be prepared in accordance with synthetic methods well known to the skilled person and as described herein.

Accordingly, in another embodiment (Embodiment 3.1), the invention provides a process for the preparation of a compound as defined in any one of Embodiments 1.1 to 1.180, which process comprises:

(A) the reaction of a compound of the formula (10)

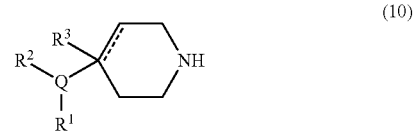

with a compound of the formula (11):

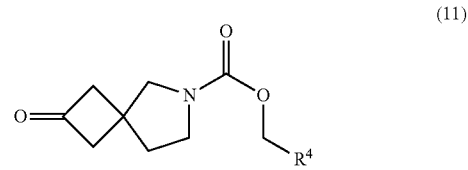

under reductive amination conditions; wherein $R^1$, $R^2$, $R^3$, $R^4$ and Q are as defined in any one of Embodiments 1.1 to 1.180; or (B) the reaction of a compound of the formula (12):

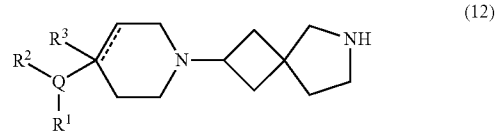

with a compound of the formula Cl—C(=O)—CH$_2$—R$^4$, in the presence of a base; or (C) the reaction of a compound of the formula (10)

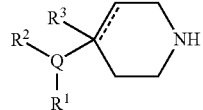

(10)

with a compound of the formula (13):

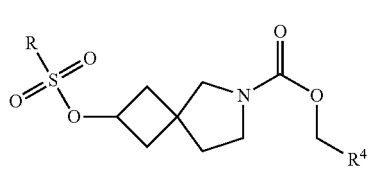

(13)

under nucleophilic substitution conditions; wherein R$^1$, R$^2$, R$^3$, R$^4$ and Q are as defined in any one of Embodiments 1.1 to 1.180; and optionally:

(D) converting one compound of the formula (1), (1a) or (1b) to another compound of the formula (1), (1a) or (1b).

In process variant (A), the piperidine heterocycle (10) is reacted with the substituted ketone (11) under reductive amination conditions. The reductive amination reaction is typically carried out at ambient temperature using a borohydride reducing agent such as sodium triacetoxy-borohydride in a solvent such as dichloromethane or dichloroethane containing acetic acid.

In process variant (C), the piperidine heterocycle (10) is reacted with the sulfonic ester (13, R=methyl, trifluoromethyl or 4-methylphenyl) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide.

Intermediate compounds of the formula (12) can be prepared by the series of reactions shown in Scheme 1 below.

Scheme 1

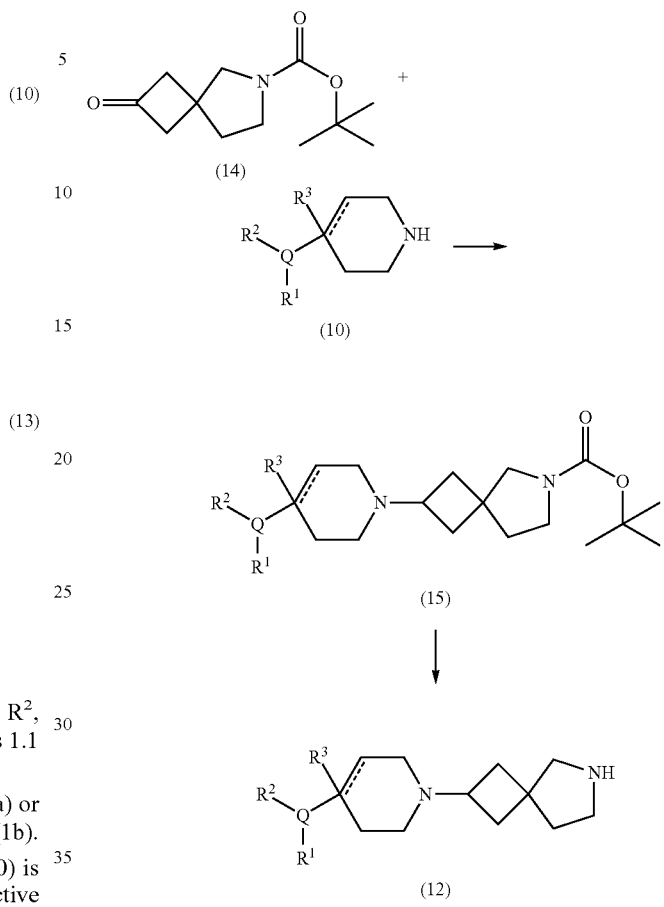

In reaction Scheme 1, the piperidine heterocycle (10) is reacted with the Boc-protected spiroketone (14) under reductive amination conditions. The reductive amination reaction is typically carried out with mild heating (e.g. to a temperature of from about 40° C. to about 70° C.) in the presence of either sodium cyanoborohydride in combination with zinc chloride or sodium triacetoxyborohydride in combination with titanium isopropoxide in a solvent such as dichloromethane or dichloroethane containing acetic acid to give an intermediate piperidine compound (15) which is then deprotected by removal of the Boc group by treatment with acid (e.g. trifluoroacetic acid in dichloromethane) to give the compound (12).

Compounds of the formula (12) can also be prepared by the sequence of reactions shown in Scheme 2 below.

Scheme 2

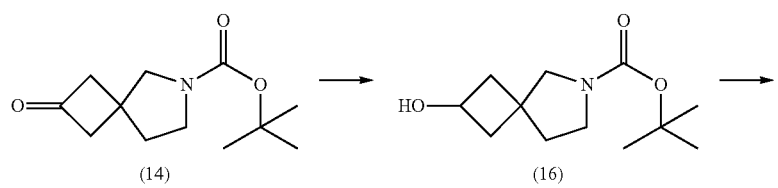

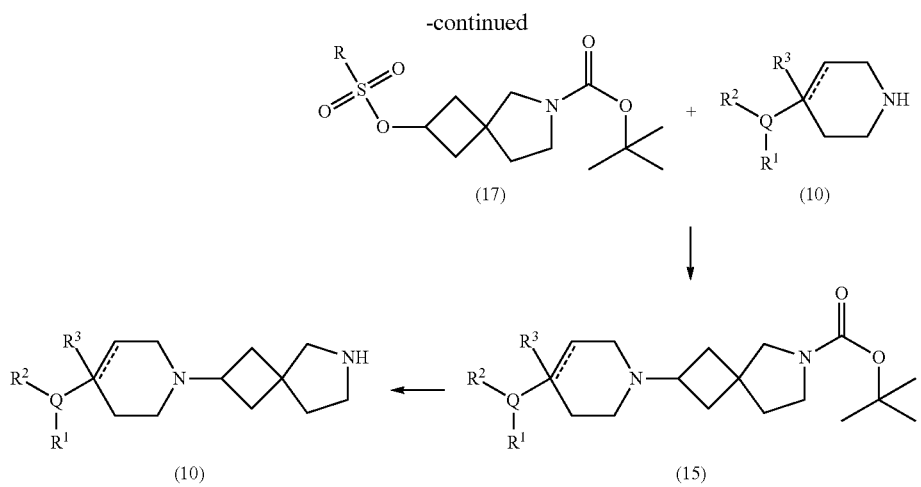

In Scheme 2, the Boc-protected spiroketone (14) is reduced to the alcohol (16) using sodium borohydride in methanol. The alcohol (16) is then activated as the sulfonic ester (17, R=methyl, trifluoromethyl or 4-methylphenyl) using the corresponding sulfonyl chloride in dichloromethane in the presence of a tertiary amine such as triethylamine or N,N-diisopropylethylamine. The sulfonic ester (17) is reacted with the piperidine heterocycle (10) in a nucleophilic substitution reaction which is typically carried out with mild heating (e.g. to a temperature of from about 40° C. to about 70° C.) either neat, with no solvent, or in a suitable solvent such as tetrahydrofuran, acetonitrile or dimethylacetamide to give compound (15) which is then deprotected by removal of the Boc group by treatment with acid (e.g. trifluoroacetic acid in dichloromethane) to give the compound (12).

Once formed, one compound of the formula (1), (1a) or (1b), or a protected derivative thereof, can be converted into another compound of the formula (1), (1a) or (1b) by methods well known to the skilled person. Examples of synthetic procedures for converting one functional group into another functional group are set out in standard texts such as *Advanced Organic Chemistry and Organic Syntheses* (see references above) or *Fiesers' Reagents for Organic Synthesis*, Volumes 1-17, John Wiley, edited by Mary Fieser (ISBN: 0-471-58283-2). Examples of these transformations include amide bond formation, urea formation, carbamate formation, alkylation reactions, N-arylation reaction and C—C bond coupling reactions.

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Greene and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1), (1a) or (1b) as defined in any one of Embodiments 1.1 to 1.180 together with at least one pharmaceutically acceptable excipient.

In one embodiment (Embodiment 4.2), the composition is a tablet composition.

In another embodiment (Embodiment 4.3), the composition is a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1), (1a) or (1b) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1), (12) or (1b) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 5-2

The compounds of Examples 1-1 to 5-2 shown in Table 1 below have been prepared. Their NMR and LCMS properties and the methods used to prepare them are set out in Table 3.

TABLE 1

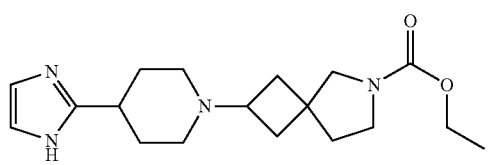 [SMILES: CCOC(=O)N1CCC2(CC(N3CCC(c4ncc[nH]4)CC3)C2)C1]

Example 1-1

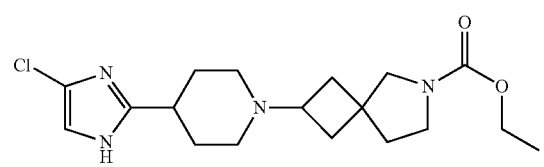 [SMILES: CCOC(=O)N1CCC2(CC(N3CCC(c4nc(Cl)c[nH]4)CC3)C2)C1]

Example 1-2

TABLE 1-continued
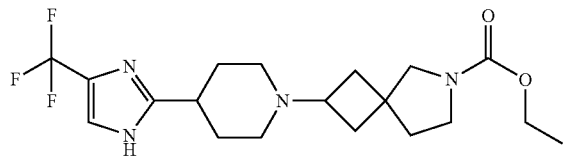 [SMILES: CCOC(=O)N1CCC2(CC(N3CCC(c4nc(C(F)(F)F)c[nH]4)CC3)C2)C1] Example 1-3
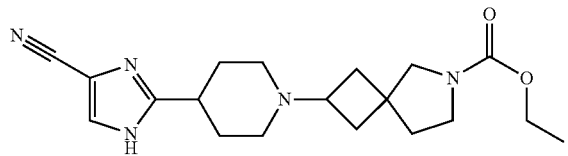 [SMILES: CCOC(=O)N1CCC2(CC(N3CCC(c4nc(C#N)c[nH]4)CC3)C2)C1] Example 1-4
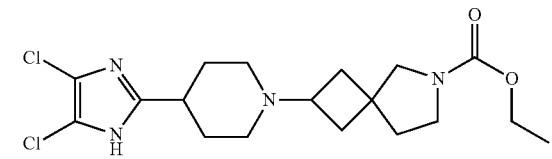 [SMILES: CCOC(=O)N1CCC2(CC(N3CCC(c4nc(Cl)c(Cl)[nH]4)CC3)C2)C1] Example 1-5
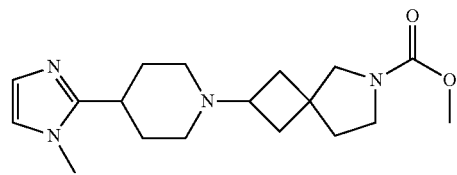 [SMILES: COC(=O)N1CCC2(CC(N3CCC(c4nccn4C)CC3)C2)C1] Example 1-6
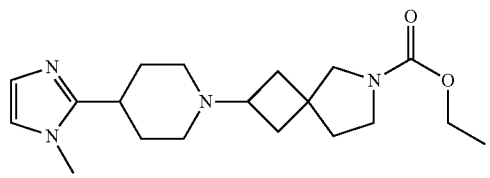 [SMILES: CCOC(=O)N1CCC2(CC(N3CCC(c4nccn4C)CC3)C2)C1] Example 1-7
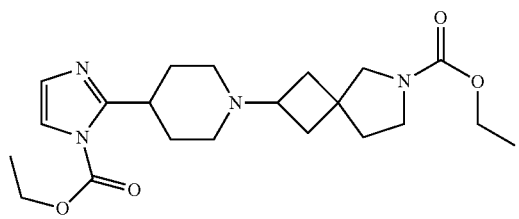 [SMILES: CCOC(=O)N1CCC2(CC(N3CCC(c4nccn4C(=O)OCC)CC3)C2)C1] Example 1-8
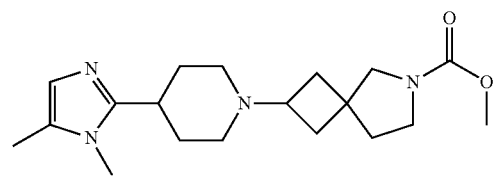 Example 1-9
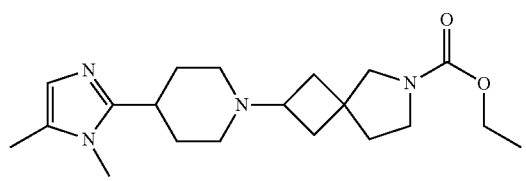 [SMILES: CCOC(=O)N1CCC2(CC(N3CCC(c4ncc(C)n4C)CC3)C2)C1] Example 1-10
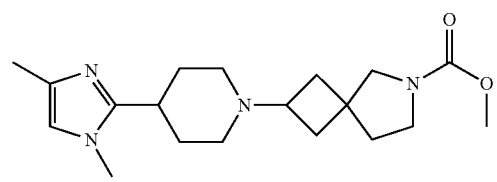 Example 1-11

TABLE 1-continued
| | |
|---|---|
| 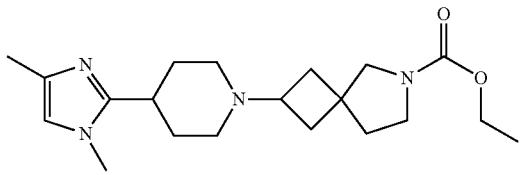 | Example 1-12 |
| 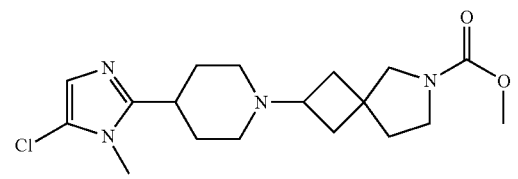 | Example 1-13 |
| 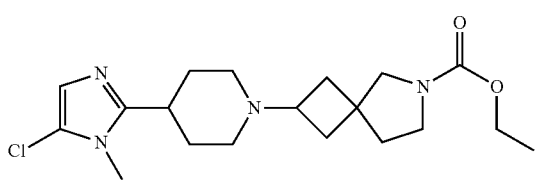 | Example 1-14 |
| 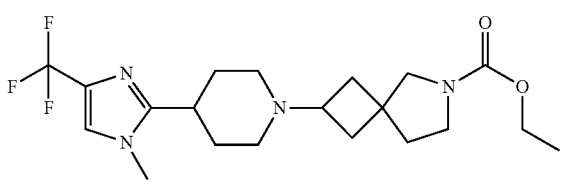 | Example 1-15 |
| 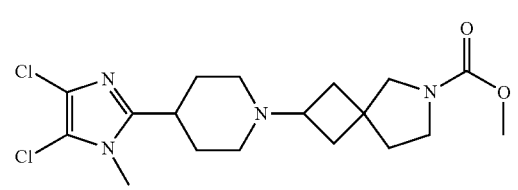 | Example 1-16 |
| 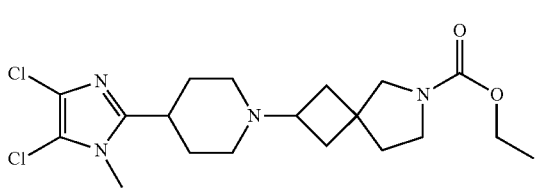 | Example 1-17 |
| 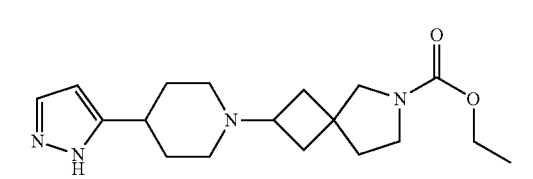 | Example 1-18 |
| 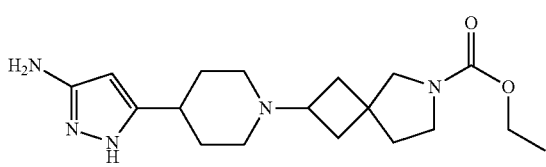 | Example 1-19 |
| 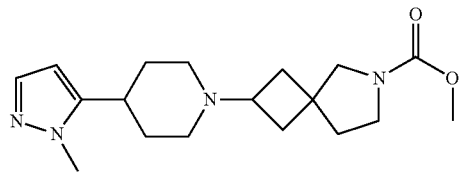 | Example 1-20 |

TABLE 1-continued
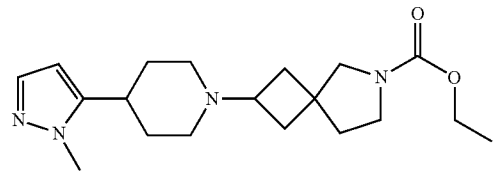 [SMILES: CCOC(=O)N1CCC2(CC(N3CCC(c4ccnn4C)CC3)C2)C1] Example 1-21
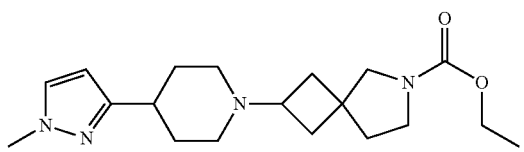 Example 1-22
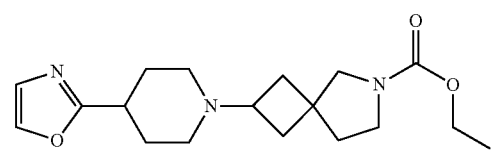 Example 1-23
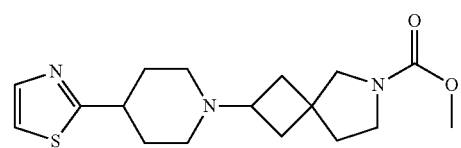 Example 1-24
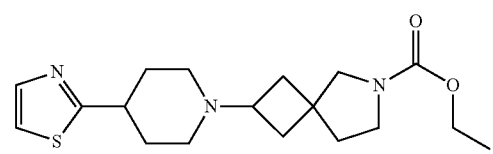 [SMILES: CCOC(=O)N1CCC2(CC(N3CCC(c4ncco4)CC3)C2)C1] Example 1-25
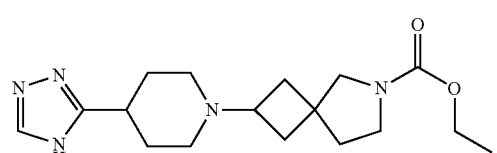 Example 1-26
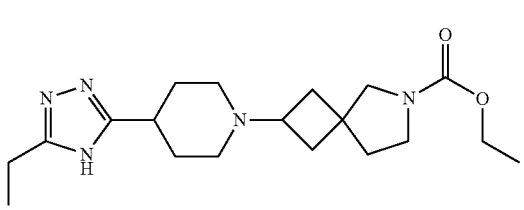 [SMILES: CCOC(=O)N1CCC2(CC(N3CCC(c4nnc(CC)[nH]4)CC3)C2)C1] Example 1-27
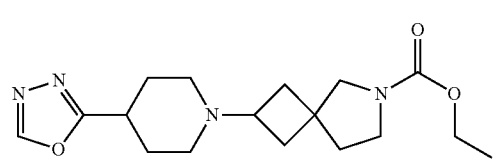 Example 1-28
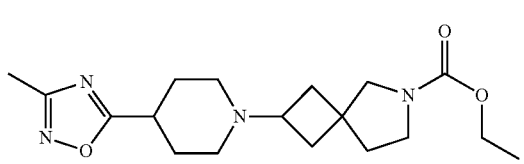 [SMILES: CCOC(=O)N1CCC2(CC(N3CCC(c4nc(C)no4)CC3)C2)C1] Example 1-29

TABLE 1-continued
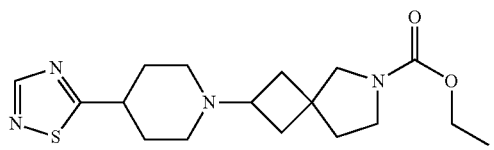 Example 1-30
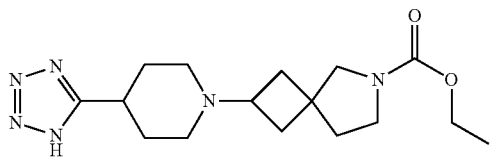 [SMILES: CCOC(=O)N1CCC2(CC(N3CCC(c4nnn[nH]4)CC3)C2)C1] Example 1-31
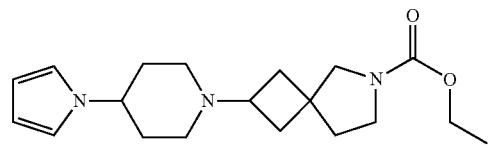 [SMILES: CCOC(=O)N1CCC2(CC(N3CCC(n4cccc4)CC3)C2)C1] Example 1-32
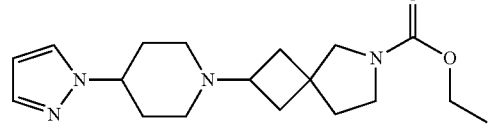 Example 1-33
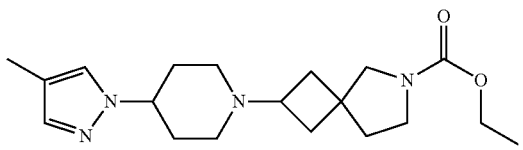 [SMILES: CCOC(=O)N1CCC2(CC(N3CCC(n4cc(C)cn4)CC3)C2)C1] Example 1-34
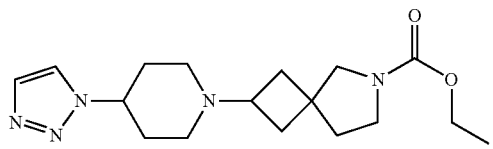 [SMILES: CCOC(=O)N1CCC2(CC(N3CCC(n4ccnn4)CC3)C2)C1] Example 1-35
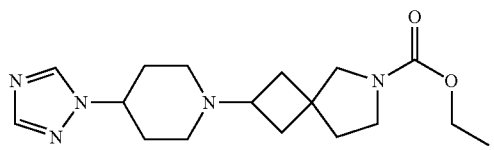 Example 1-36
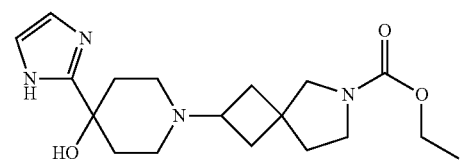 [SMILES: CCOC(=O)N1CCC2(CC(N3CCC(O)(c4ncc[nH]4)CC3)C2)C1] Example 1-37
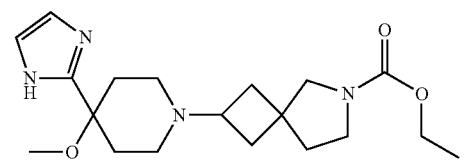 [SMILES: CCOC(=O)N1CCC2(CC(N3CCC(OC)(c4ncc[nH]4)CC3)C2)C1] Example 1-38
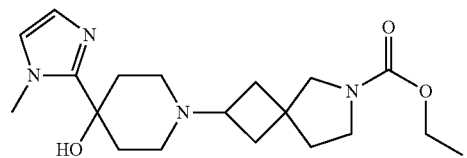 [SMILES: CCOC(=O)N1CCC2(CC(N3CCC(O)(c4nccn4C)CC3)C2)C1] Example 1-39

TABLE 1-continued
| | |
|---|---|
| 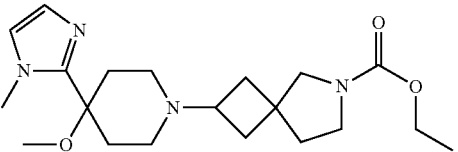 | Example 1-40 |
| 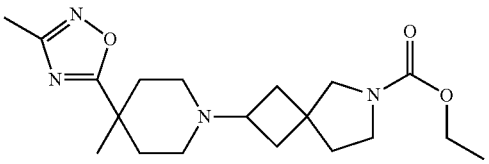 | Example 1-41 |
| 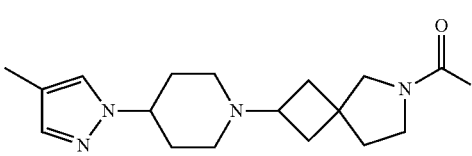 | Example 1-42 |
| 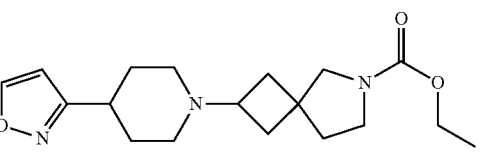 | Example 1-43 |
| 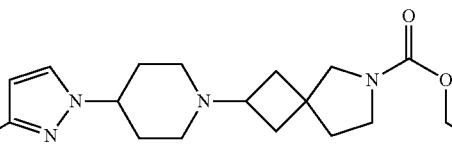 | Example 1-44 |
| 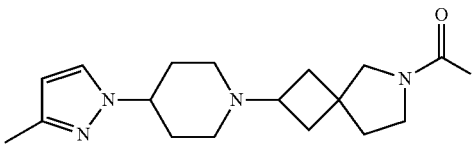 | Example 1-45 |
| 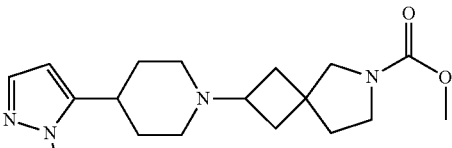 | Example 1-46 |
| 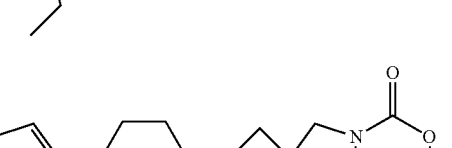 | Example 1-47 |
|  | Example 1-48 |

TABLE 1-continued
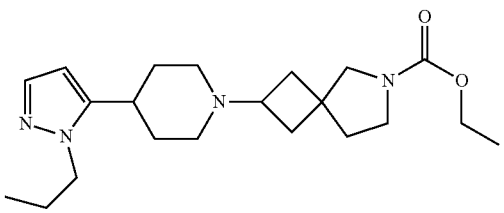 [SMILES: CCCn1nccc1C1CCN(C2CC3(CCN(C(=O)OCC)C3)C2)CC1] Example 1-49
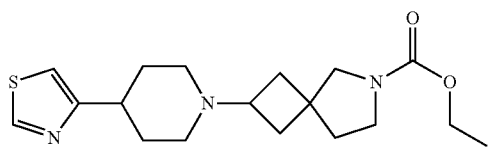 [SMILES: CCOC(=O)N1CCC2(CC(N3CCC(c4cscn4)CC3)C2)C1] Example 1-50
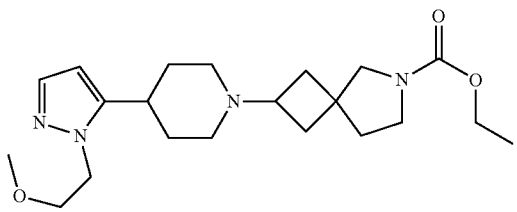 [SMILES: CCOC(=O)N1CCC2(CC(N3CCC(c4ccnn4CCOC)CC3)C2)C1] Example 1-51
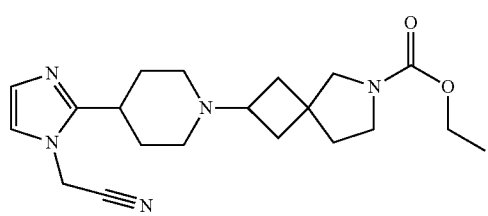 [SMILES: CCOC(=O)N1CCC2(CC(N3CCC(c4nccn4CC#N)CC3)C2)C1] Example 1-52
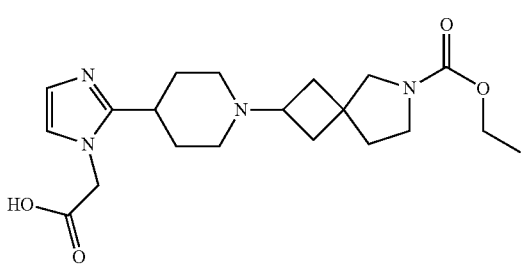 [SMILES: CCOC(=O)N1CCC2(CC(N3CCC(c4nccn4CC(=O)NC)CC3)C2)C1] Example 1-53
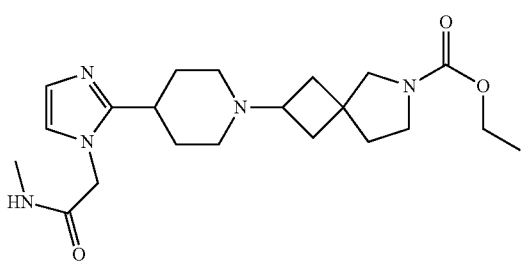 Example 1-54
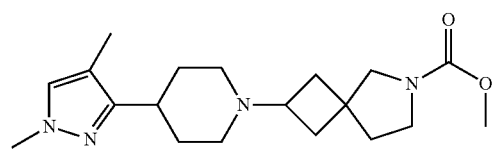 Example 1-55
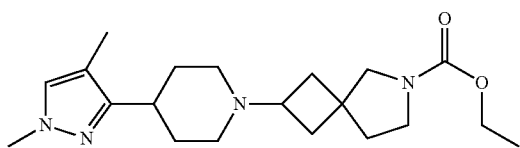 [SMILES: CCOC(=O)N1CCC2(CC(N3CCC(c4nn(C)cc4C)CC3)C2)C1] Example 1-56

TABLE 1-continued
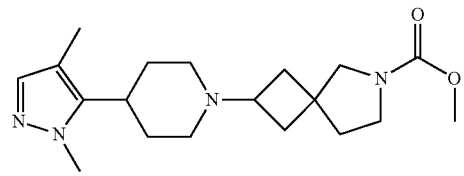 [SMILES: COC(=O)N1CCC2(CC(N3CCC(c4c(C)cnn4C)CC3)C2)C1] Example 1-57
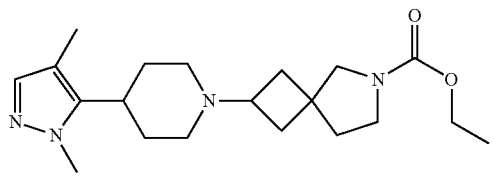 [SMILES: CCOC(=O)N1CCC2(CC(N3CCC(c4c(C)cnn4C)CC3)C2)C1] Example 1-58
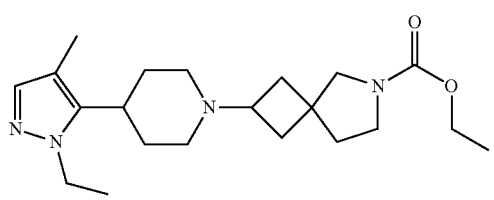 [SMILES: CCOC(=O)N1CCC2(CC(N3CCC(c4c(C)cnn4CC)CC3)C2)C1] Example 1-59
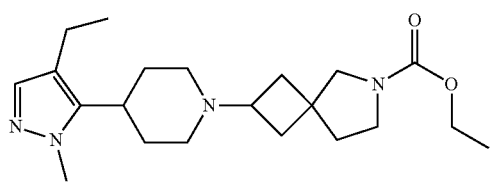 [SMILES: CCOC(=O)N1CCC2(CC(N3CCC(c4c(CC)cnn4C)CC3)C2)C1] Example 1-60
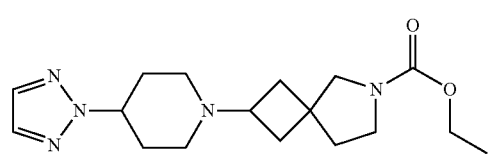 [SMILES: CCOC(=O)N1CCC2(CC(N3CCC(n4nccn4)CC3)C2)C1] Example 1-61
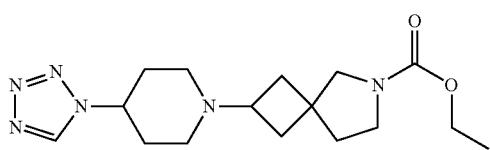 Example 1-62
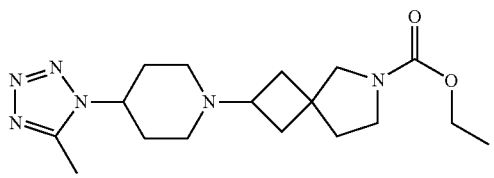 [SMILES: CCOC(=O)N1CCC2(CC(N3CCC(n4nnnc4C)CC3)C2)C1] Example 1-63
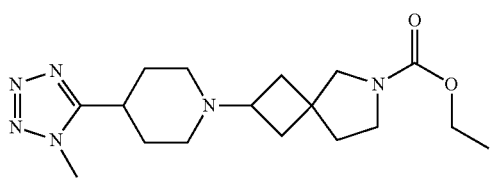 [SMILES: CCOC(=O)N1CCC2(CC(N3CCC(c4nnnn4C)CC3)C2)C1] Example 1-64

TABLE 1-continued
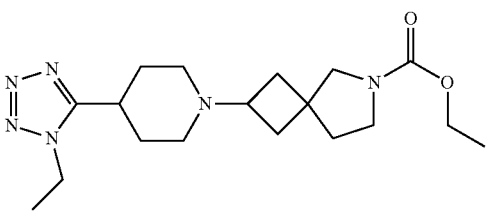 [SMILES: CCOC(=O)N1CCC2(CC(N3CCC(c4nnnn4CC)CC3)C2)C1] Example 1-65
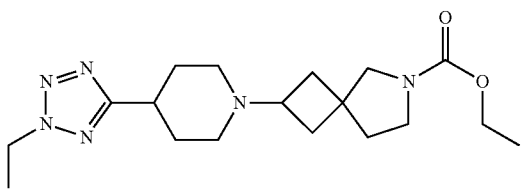 [SMILES: CCOC(=O)N1CCC2(CC(N3CCC(c4nnn(CC)n4)CC3)C2)C1] Example 1-66
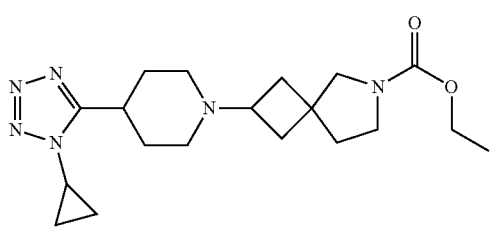 [SMILES: CCOC(=O)N1CCC2(CC(N3CCC(c4nnnn4C4CC4)CC3)C2)C1] Example 1-67
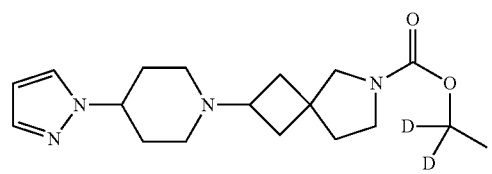 [SMILES: [2H]C([2H])(C)OC(=O)N1CCC2(CC(N3CCC(n4cccn4)CC3)C2)C1] Example 1-68
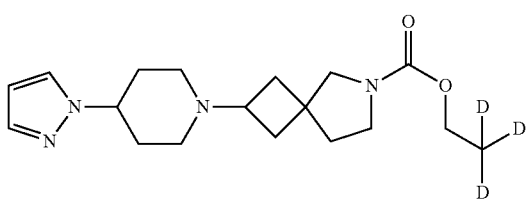 [SMILES: [2H]C([2H])([2H])COC(=O)N1CCC2(CC(N3CCC(n4cccn4)CC3)C2)C1] Example 1-69
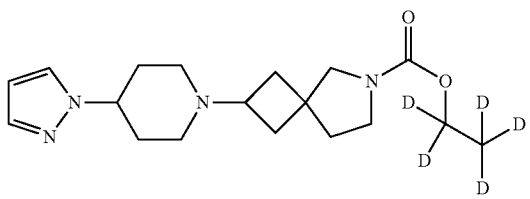 [SMILES: [2H]C([2H])([2H])C([2H])([2H])OC(=O)N1CCC2(CC(N3CCC(n4cccn4)CC3)C2)C1] Example 1-70
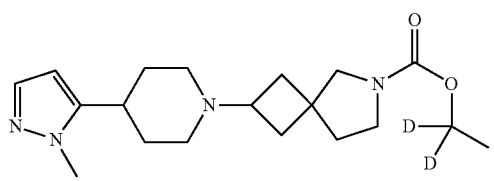 [SMILES: [2H]C([2H])(C)OC(=O)N1CCC2(CC(N3CCC(c4ccnn4C)CC3)C2)C1] Example 1-71
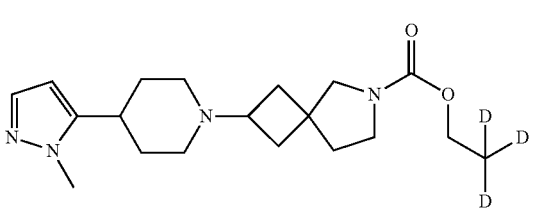 [SMILES: [2H]C([2H])([2H])COC(=O)N1CCC2(CC(N3CCC(c4ccnn4C)CC3)C2)C1] Example 1-72

TABLE 1-continued
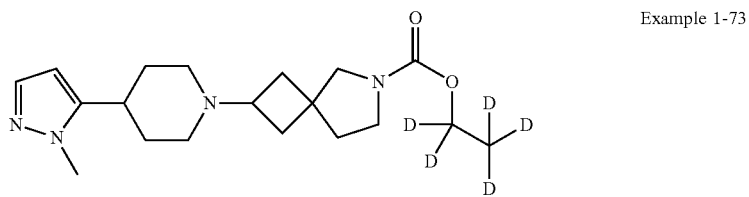 Example 1-73
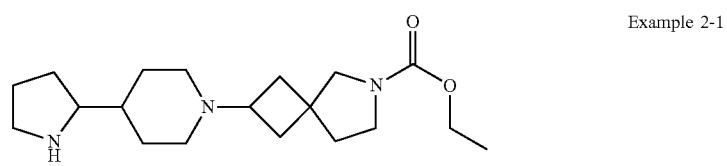 Example 2-1
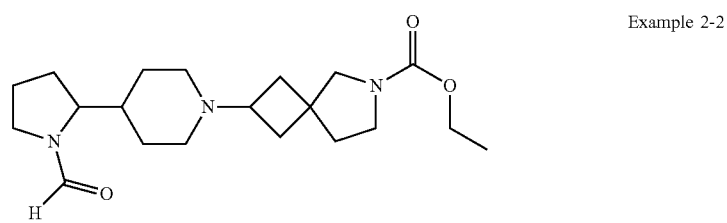 Example 2-2
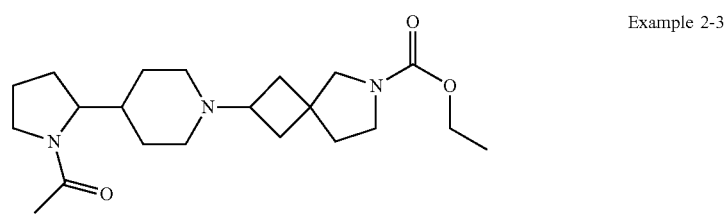 Example 2-3
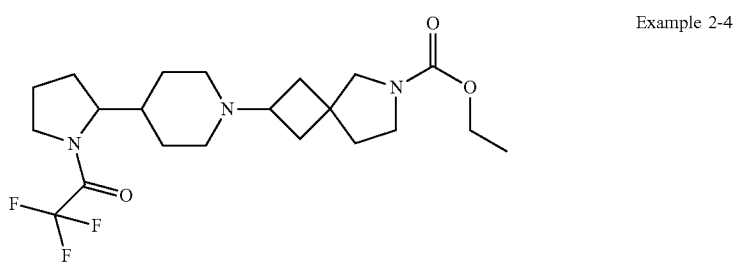 Example 2-4
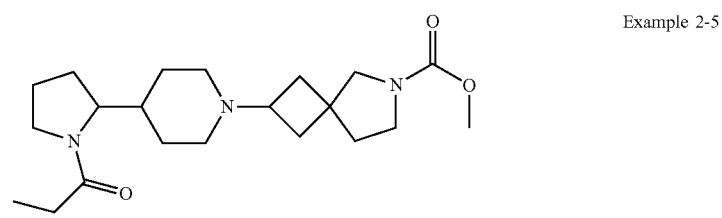 Example 2-5
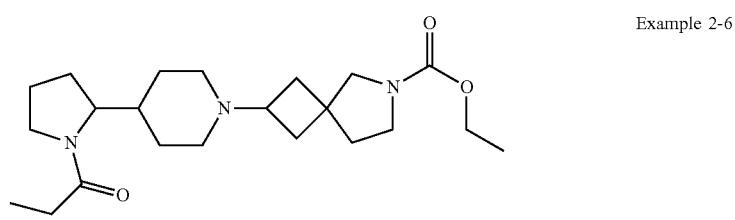 Example 2-6

US 9,670,183 B2
TABLE 1-continued
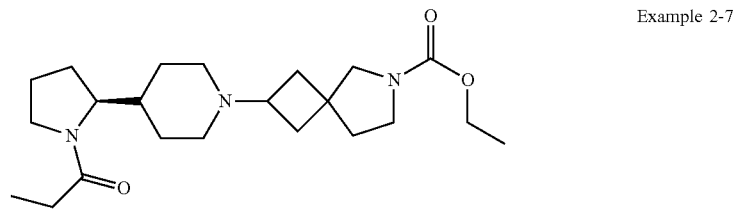
Example 2-7
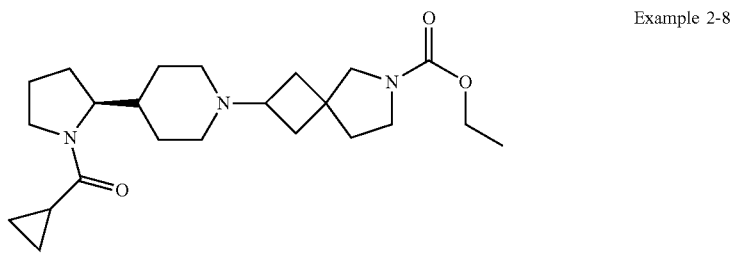
Example 2-8
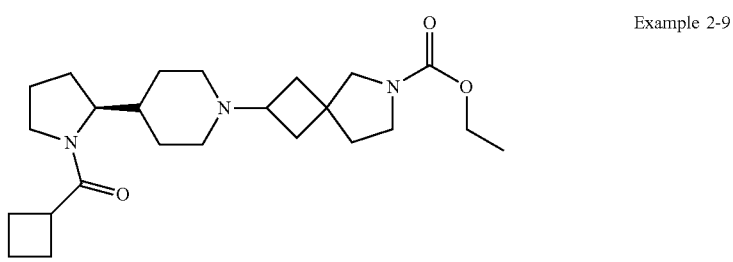
Example 2-9
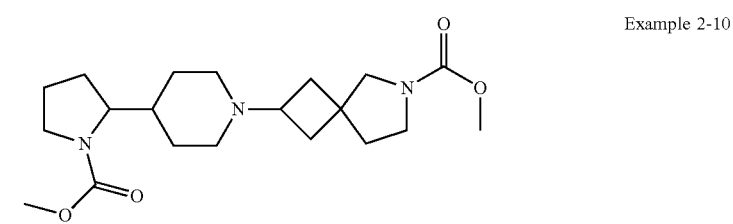
Example 2-10
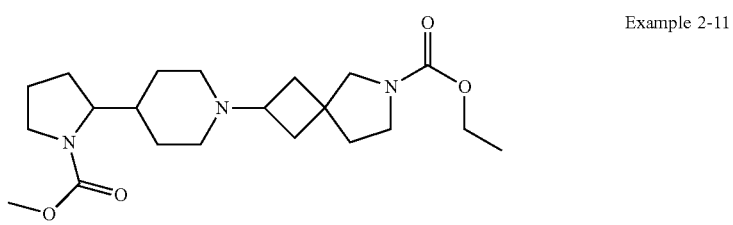
Example 2-11
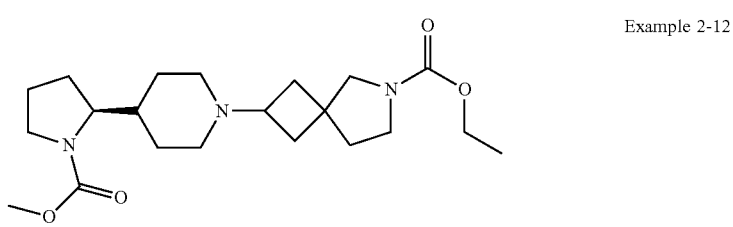
Example 2-12
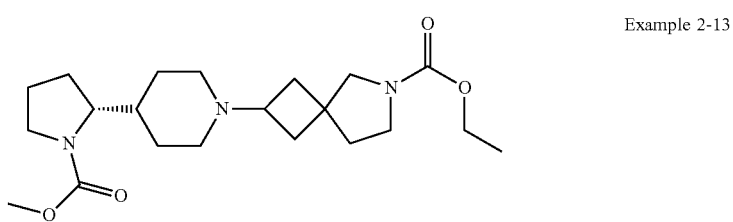
Example 2-13

TABLE 1-continued
| | |
|---|---|
| 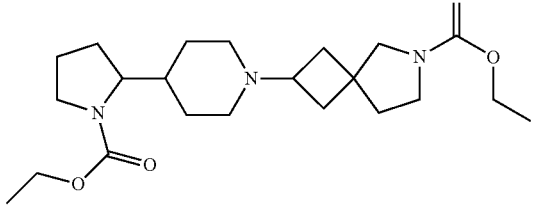 | Example 2-14 |
| 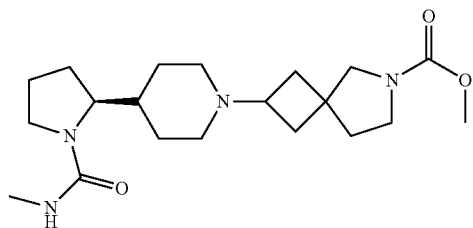 | Example 2-15 |
| 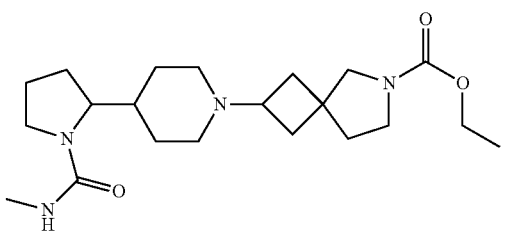 | Example 2-16 |
| 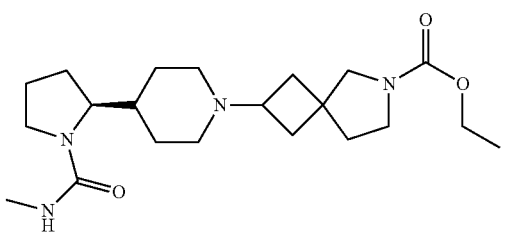 | Example 2-17 |
| 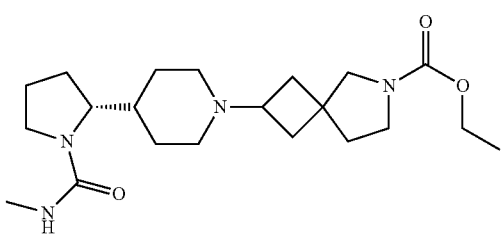 | Example 2-18 |
| 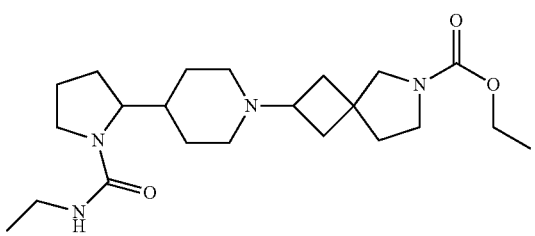 | Example 2-19 |

TABLE 1-continued
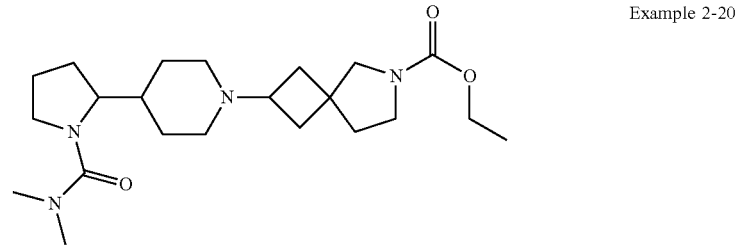 Example 2-20
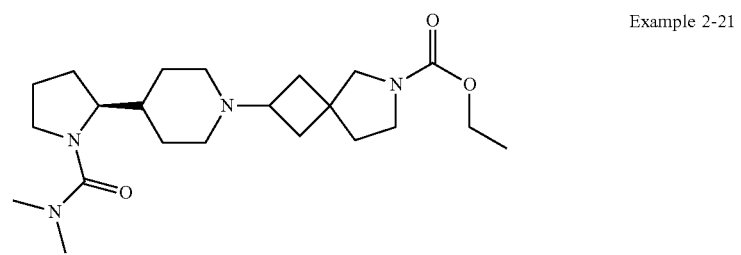 Example 2-21
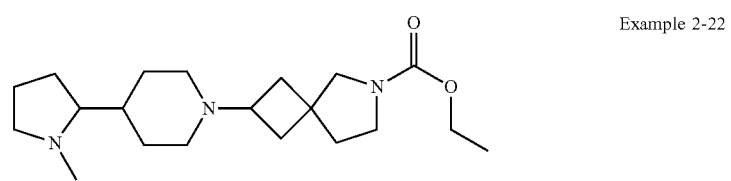 Example 2-22
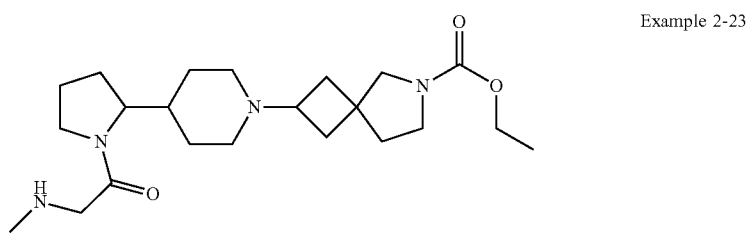 Example 2-23
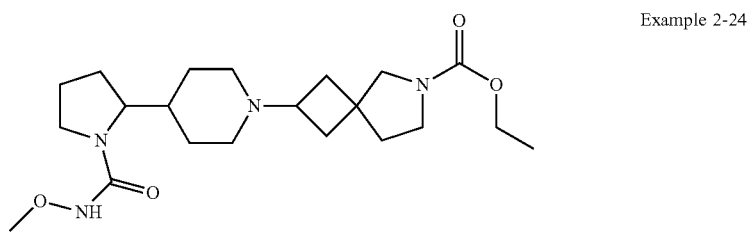 Example 2-24
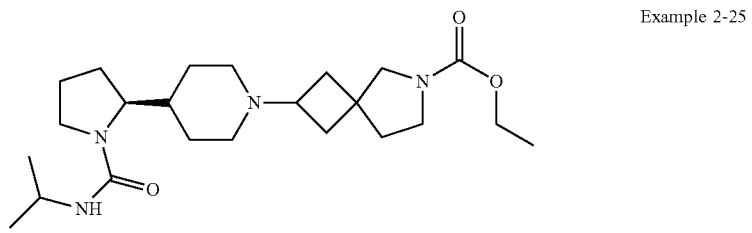 Example 2-25

TABLE 1-continued
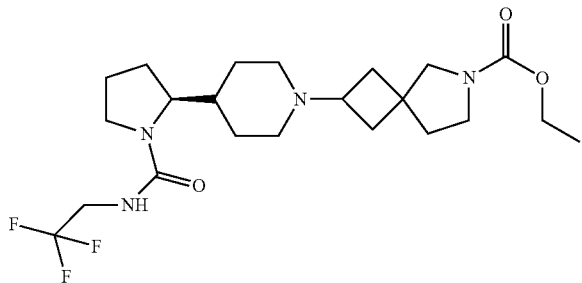 [SMILES: CCOC(=O)N1CCC2(CC(N3CCC([C@@H]4CCCN4C(=O)NCC(F)(F)F)CC3)C2)C1]
Example 2-26
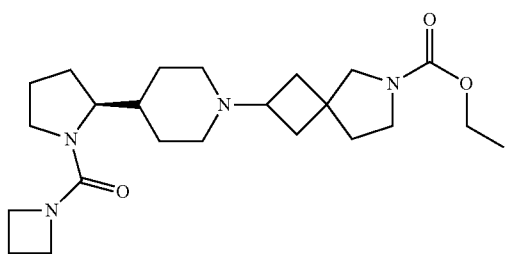
Example 2-27
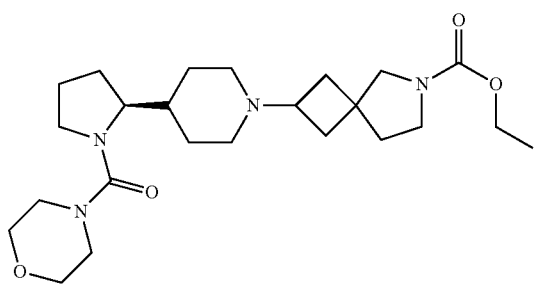 [SMILES: CCOC(=O)N1CCC2(CC(N3CCC([C@@H]4CCCN4C(=O)N4CCOCC4)CC3)C2)C1]
Example 2-28
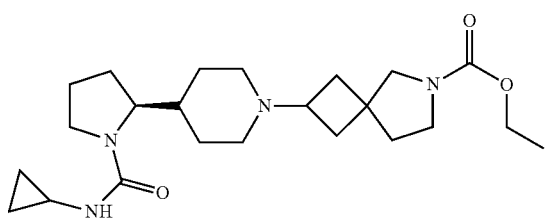 [SMILES: CCOC(=O)N1CCC2(CC(N3CCC([C@@H]4CCCN4C(=O)NC4CC4)CC3)C2)C1]
Example 2-29
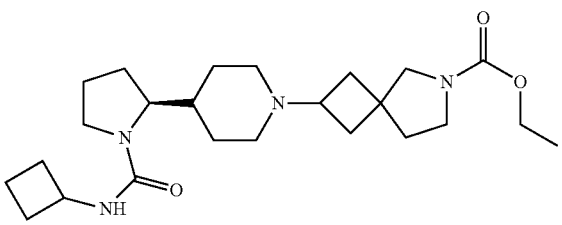 [SMILES: CCOC(=O)N1CCC2(CC(N3CCC([C@@H]4CCCN4C(=O)NC4CCC4)CC3)C2)C1]
Example 2-30
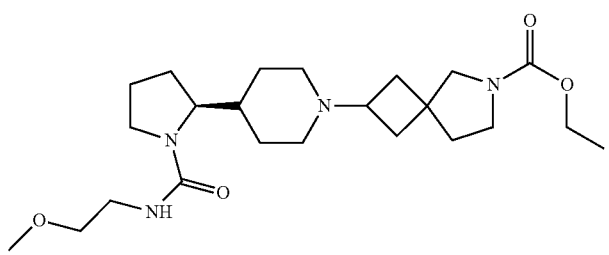 [SMILES: CCOC(=O)N1CCC2(CC(N3CCC([C@@H]4CCCN4C(=O)NCCOC)CC3)C2)C1]
Example 2-31

TABLE 1-continued
| | |
|---|---|
| 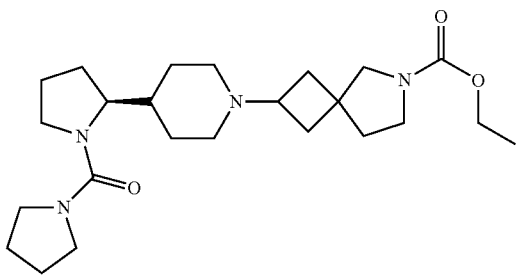 [SMILES: CCOC(=O)N1CCC2(CC(N3CCC([C@@H]4CCCN4C(=O)N4CCCC4)CC3)C2)C1] | Example 2-32 |
| 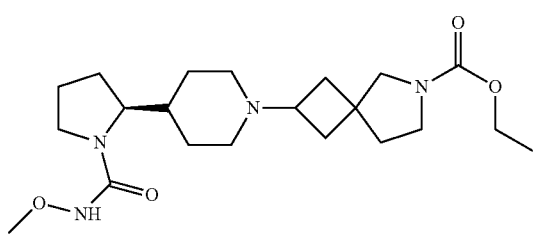 [SMILES: CCOC(=O)N1CCC2(CC(N3CCC([C@@H]4CCCN4C(=O)NOC)CC3)C2)C1] | Example 2-33 |
| 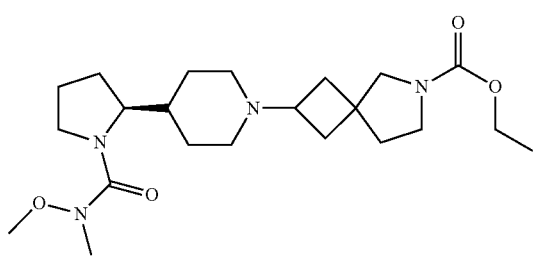 [SMILES: CCOC(=O)N1CCC2(CC(N3CCC([C@@H]4CCCN4C(=O)N(C)OC)CC3)C2)C1] | Example 2-34 |
| 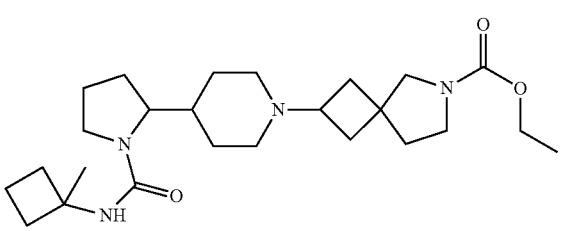 [SMILES: CCOC(=O)N1CCC2(CC(N3CCC(C4CCCN4C(=O)NC4(C)CCC4)CC3)C2)C1] | Example 2-35 |
| 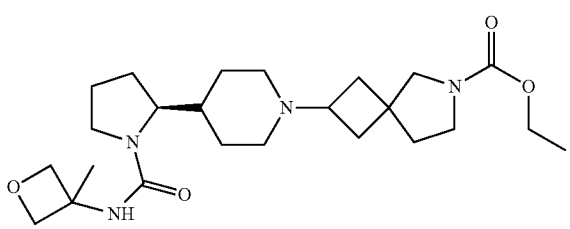 [SMILES: CCOC(=O)N1CCC2(CC(N3CCC([C@@H]4CCCN4C(=O)NC4(C)COC4)CC3)C2)C1] | Example 2-36 |
| 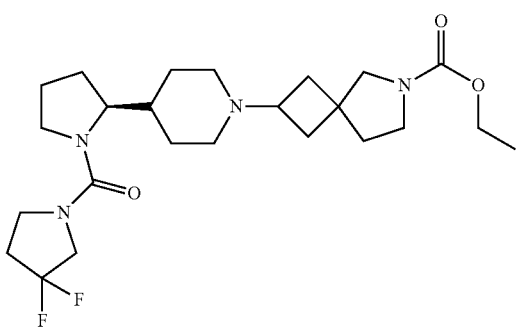 [SMILES: CCOC(=O)N1CCC2(CC(N3CCC([C@@H]4CCCN4C(=O)N4CCC(F)(F)C4)CC3)C2)C1] | Example 2-37 |

TABLE 1-continued
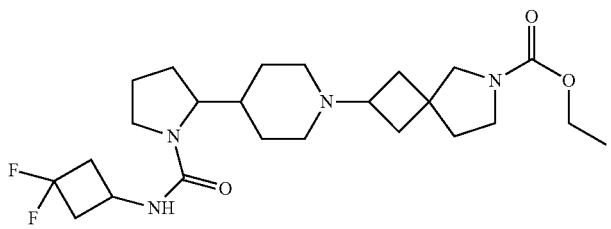 [SMILES: CCOC(=O)N1CCC2(CC(N3CCC(C4CCCN4C(=O)NC4CC(F)(F)C4)CC3)C2)C1]
Example 2-38
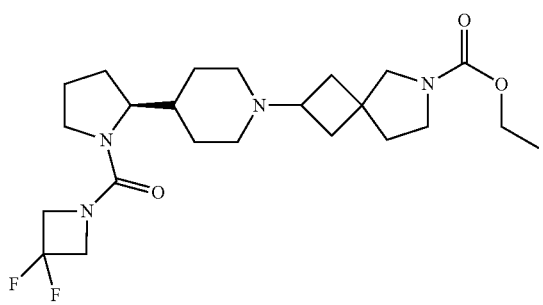 [SMILES: CCOC(=O)N1CCC2(CC(N3CCC([C@@H]4CCCN4C(=O)N4CC(F)(F)C4)CC3)C2)C1]
Example 2-39
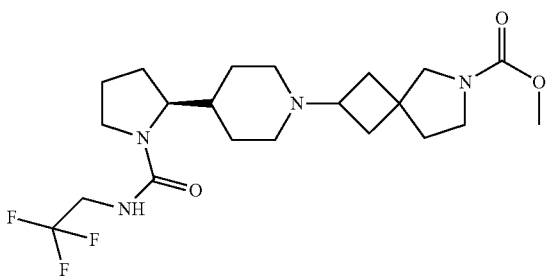 [SMILES: COC(=O)N1CCC2(CC(N3CCC([C@@H]4CCCN4C(=O)NCC(F)(F)F)CC3)C2)C1]
Example 2-40
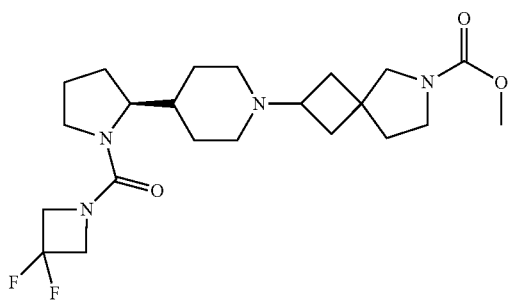 [SMILES: COC(=O)N1CCC2(CC(N3CCC([C@@H]4CCCN4C(=O)N4CC(F)(F)C4)CC3)C2)C1]
Example 2-41
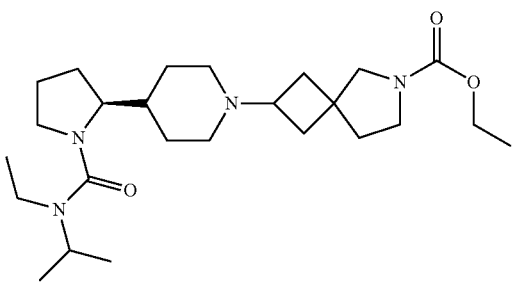 [SMILES: CCOC(=O)N1CCC2(CC(N3CCC([C@@H]4CCCN4C(=O)N(CC)C(C)C)CC3)C2)C1]
Example 2-42
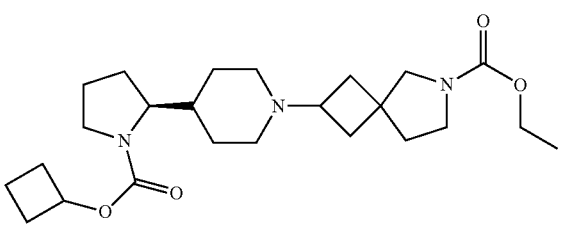 [SMILES: CCOC(=O)N1CCC2(CC(N3CCC([C@@H]4CCCN4C(=O)OC4CCC4)CC3)C2)C1]
Example 2-43

TABLE 1-continued
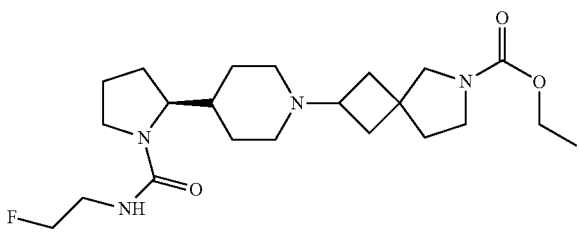 [SMILES: CCOC(=O)N1CCC2(CC(N3CCC([C@@H]4CCCN4C(=O)NCCF)CC3)C2)C1] Example 2-44
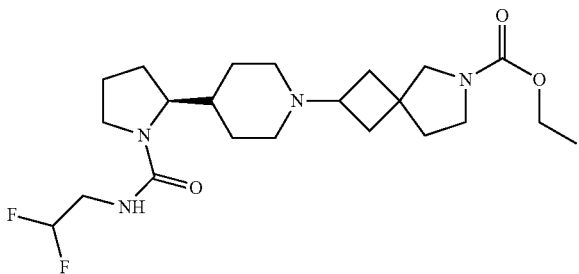 [SMILES: CCOC(=O)N1CCC2(CC(N3CCC([C@@H]4CCCN4C(=O)NCC(F)F)CC3)C2)C1] Example 2-45
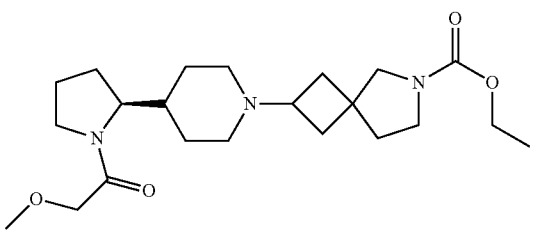 [SMILES: CCOC(=O)N1CCC2(CC(N3CCC([C@@H]4CCCN4C(=O)COC)CC3)C2)C1] Example 2-46
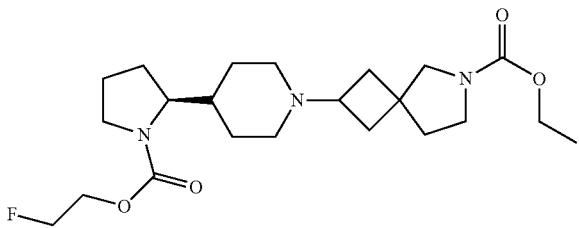 [SMILES: CCOC(=O)N1CCC2(CC(N3CCC([C@@H]4CCCN4C(=O)OCCF)CC3)C2)C1] Example 2-47
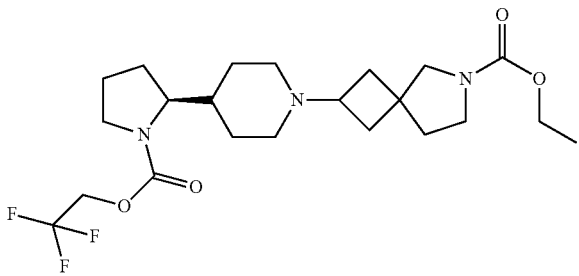 [SMILES: CCOC(=O)N1CCC2(CC(N3CCC([C@@H]4CCCN4C(=O)OCC(F)(F)F)CC3)C2)C1] Example 2-48
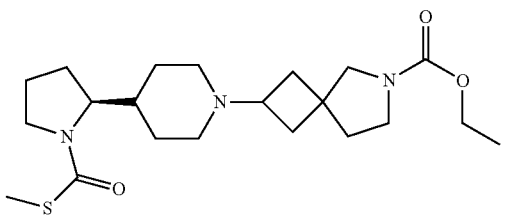 Example 2-49

TABLE 1-continued
| | |
|---|---|
| 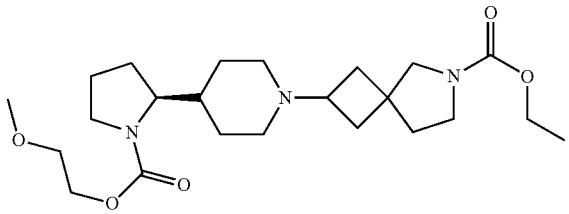 [SMILES: CCOC(=O)N1CCC2(CC(N3CCC([C@@H]4CCCN4C(=O)OCCOC)CC3)C2)C1] | Example 2-50 |
| 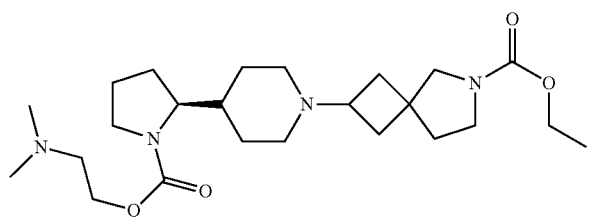 [SMILES: CCOC(=O)N1CCC2(CC(N3CCC([C@@H]4CCCN4C(=O)OCCN(C)C)CC3)C2)C1] | Example 2-51 |
| 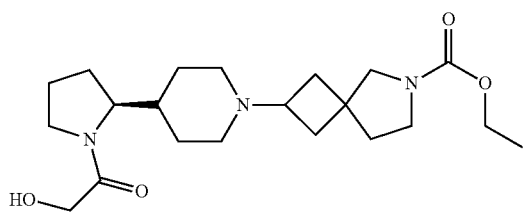 [SMILES: CCOC(=O)N1CCC2(CC(N3CCC([C@@H]4CCCN4C(=O)CO)CC3)C2)C1] | Example 2-52 |
| 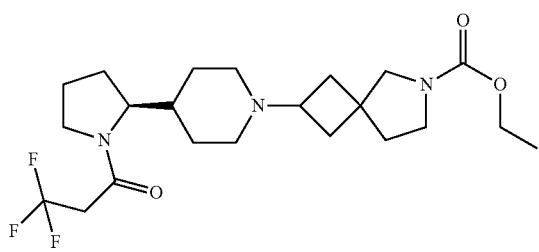 [SMILES: CCOC(=O)N1CCC2(CC(N3CCC([C@@H]4CCCN4C(=O)CC(F)(F)F)CC3)C2)C1] | Example 2-53 |
| 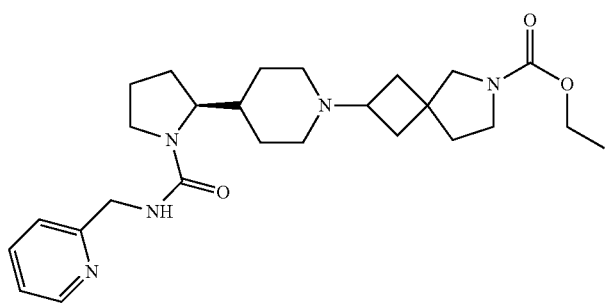 [SMILES: CCOC(=O)N1CCC2(CC(N3CCC([C@@H]4CCCN4C(=O)NCc4ccccn4)CC3)C2)C1] | Example 2-54 |
| 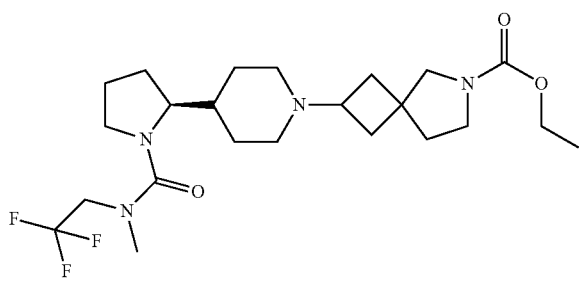 [SMILES: CCOC(=O)N1CCC2(CC(N3CCC([C@@H]4CCCN4C(=O)N(C)CC(F)(F)F)CC3)C2)C1] | Example 2-55 |

TABLE 1-continued

| | |
|---|---|
| (structure) | Example 2-56 |
| (structure) | Example 2-57 |
| (structure) | Example 2-58 |
| (structure) | Example 2-59 |
| (structure) | Example 2-60 |
| (structure) | Example 2-61 |
| (structure) | Example 2-62 |

TABLE 1-continued
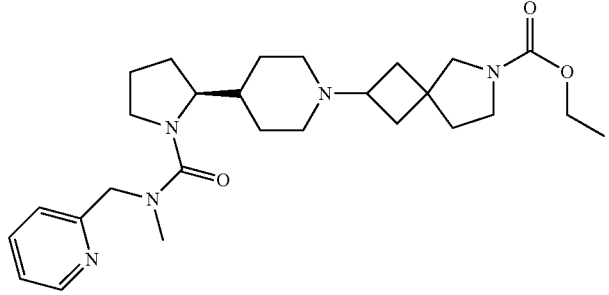 [SMILES: CCOC(=O)N1CCC2(CC(N3CCC([C@@H]4CCCN4C(=O)N(C)Cc4ccccn4)CC3)C2)C1]
Example 2-63
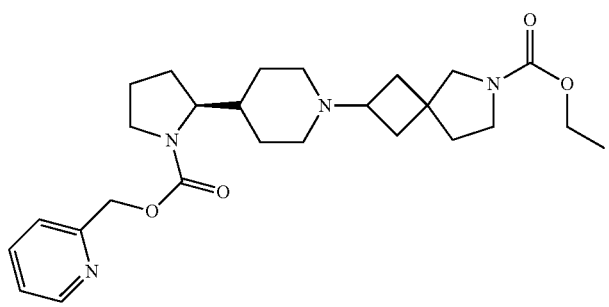 [SMILES: CCOC(=O)N1CCC2(CC(N3CCC([C@@H]4CCCN4C(=O)OCc4ccccn4)CC3)C2)C1]
Example 2-64
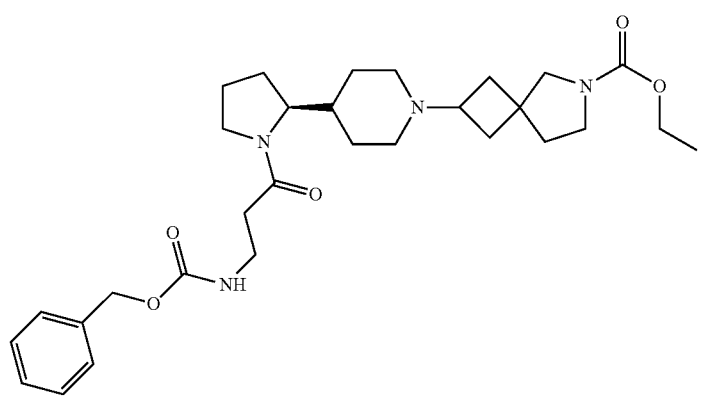 [SMILES: CCOC(=O)N1CCC2(CC(N3CCC([C@@H]4CCCN4C(=O)CCNC(=O)OCc4ccccc4)CC3)C2)C1]
Example 2-65
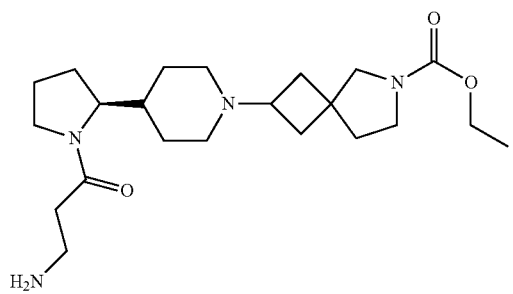 [SMILES: CCOC(=O)N1CCC2(CC(N3CCC([C@@H]4CCCN4C(=O)CCN)CC3)C2)C1]
Example 2-66
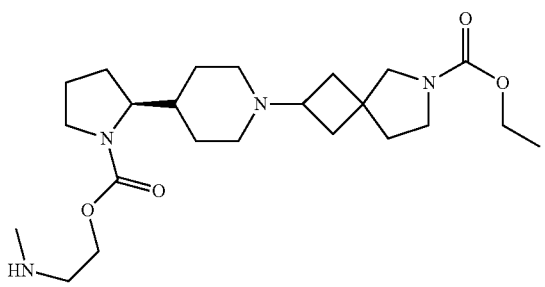 [SMILES: CCOC(=O)N1CCC2(CC(N3CCC([C@@H]4CCCN4C(=O)OCCNC)CC3)C2)C1]
Example 2-67

TABLE 1-continued
| | |
|---|---|
| 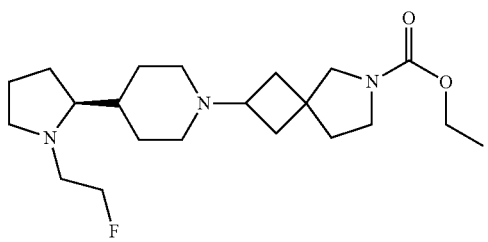 [SMILES: CCOC(=O)N1CCC2(CC(N3CCC([C@@H]4CCCN4CCF)CC3)C2)C1] | Example 2-68 |
| 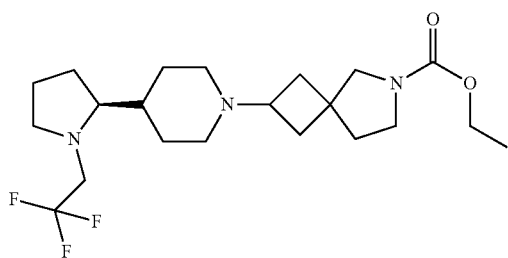 [SMILES: CCOC(=O)N1CCC2(CC(N3CCC([C@@H]4CCCN4CC(F)(F)F)CC3)C2)C1] | Example 2-69 |
| 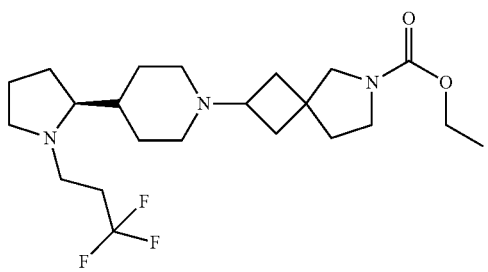 [SMILES: CCOC(=O)N1CCC2(CC(N3CCC([C@@H]4CCCN4CCC(F)(F)F)CC3)C2)C1] | Example 2-70 |
| 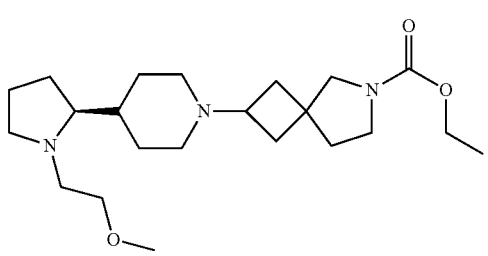 [SMILES: CCOC(=O)N1CCC2(CC(N3CCC([C@@H]4CCCN4CCOC)CC3)C2)C1] | Example 2-71 |
| 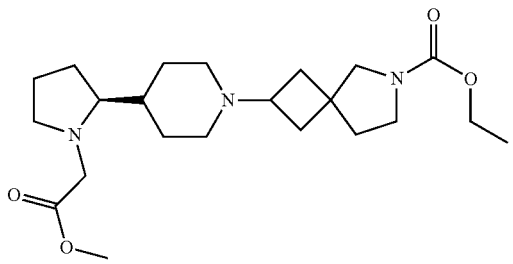 [SMILES: CCOC(=O)N1CCC2(CC(N3CCC([C@@H]4CCCN4CC(=O)OC)CC3)C2)C1] | Example 2-72 |
| 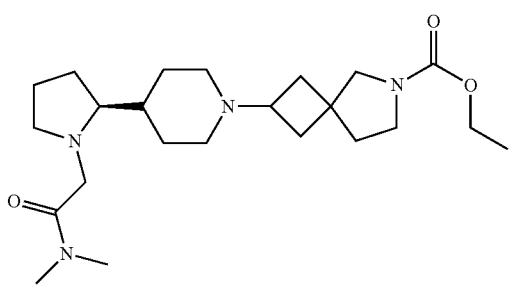 [SMILES: CCOC(=O)N1CCC2(CC(N3CCC([C@@H]4CCCN4CC(=O)N(C)C)CC3)C2)C1] | Example 2-73 |

TABLE 1-continued
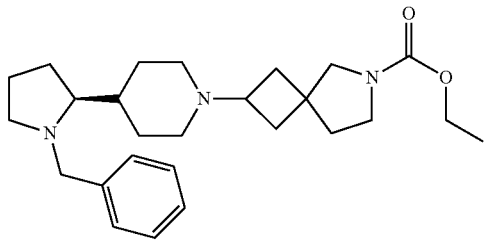 [SMILES: CCOC(=O)N1CCC2(CC(N3CCC([C@@H]4CCCN4Cc4ccccc4)CC3)C2)C1] Example 2-74
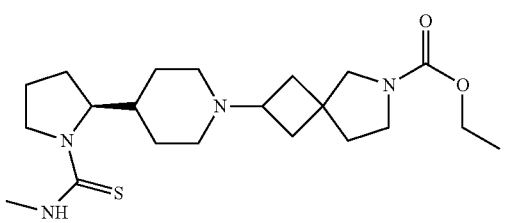 [SMILES: CCOC(=O)N1CCC2(CC(N3CCC([C@@H]4CCCN4C(=S)NC)CC3)C2)C1] Example 2-75
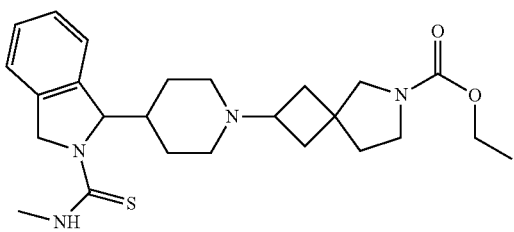 [SMILES: CCOC(=O)N1CCC2(CC(N3CCC(C4c5ccccc5CN4C(=S)NC)CC3)C2)C1] Example 2-76
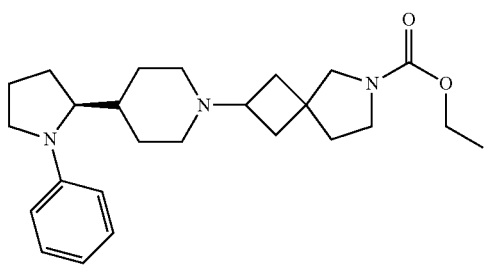 [SMILES: CCOC(=O)N1CCC2(CC(N3CCC([C@@H]4CCCN4c4ccccc4)CC3)C2)C1] Example 2-77
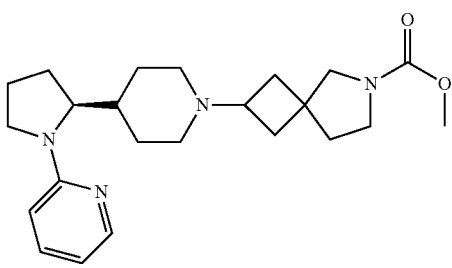 [SMILES: COC(=O)N1CCC2(CC(N3CCC([C@@H]4CCCN4c4ccccn4)CC3)C2)C1] Example 2-78
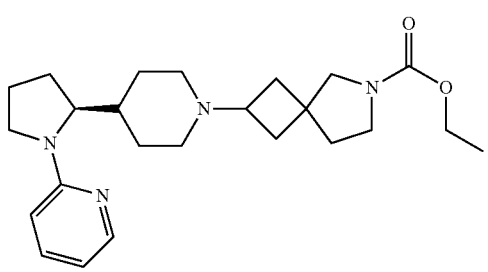 [SMILES: CCOC(=O)N1CCC2(CC(N3CCC([C@@H]4CCCN4c4ccccn4)CC3)C2)C1] Example 2-79

TABLE 1-continued
| | |
|---|---|
| 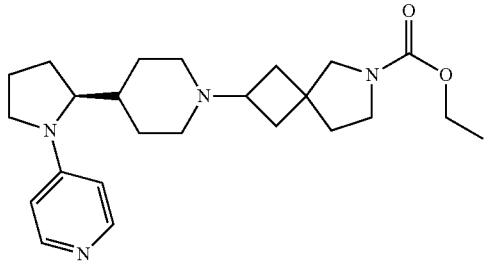 [SMILES: CCOC(=O)N1CCC2(CC(N3CCC([C@@H]4CCCN4c4ccncc4)CC3)C2)C1] | Example 2-80 |
| 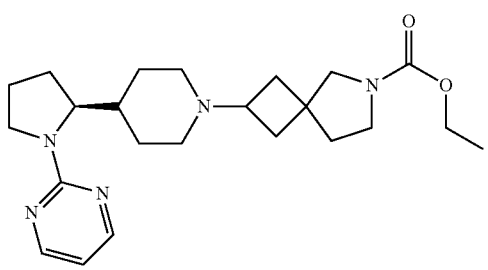 [SMILES: CCOC(=O)N1CCC2(CC(N3CCC([C@@H]4CCCN4c4ncccn4)CC3)C2)C1] | Example 2-81 |
| 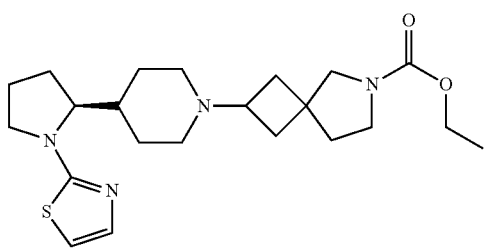 [SMILES: CCOC(=O)N1CCC2(CC(N3CCC([C@@H]4CCCN4c4nccs4)CC3)C2)C1] | Example 2-82 |
| 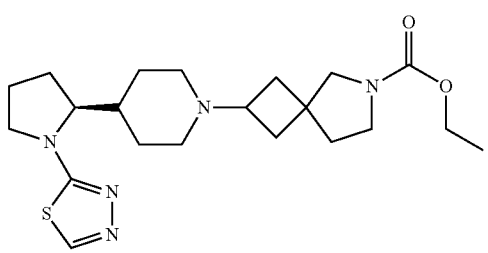 [SMILES: CCOC(=O)N1CCC2(CC(N3CCC([C@@H]4CCCN4c4nncs4)CC3)C2)C1] | Example 2-83 |
| 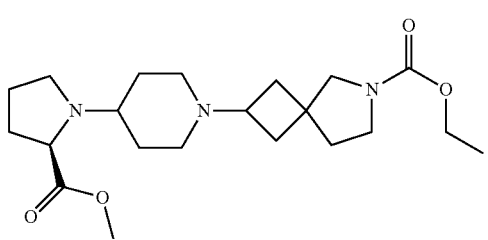 [SMILES: CCOC(=O)N1CCC2(CC(N3CCC(N4CCC[C@@H]4C(=O)OC)CC3)C2)C1] | Example 2-84 |
| 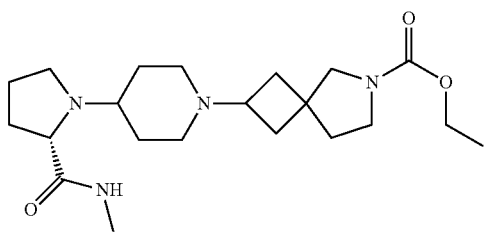 [SMILES: CCOC(=O)N1CCC2(CC(N3CCC(N4CCC[C@H]4C(=O)NC)CC3)C2)C1] | Example 2-85 |

TABLE 1-continued
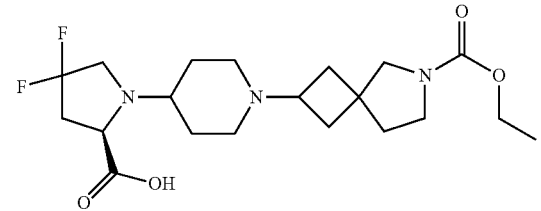 [SMILES: CCOC(=O)N1CCC2(CC(N3CCC(N4CC(F)(F)C[C@@H]4C(=O)O)CC3)C2)C1] Example 2-86
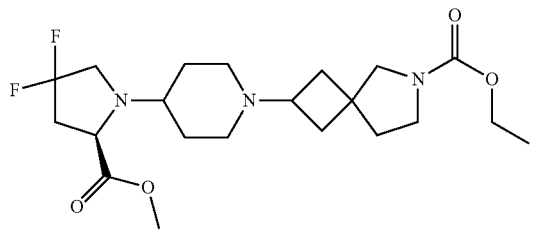 [SMILES: CCOC(=O)N1CCC2(CC(N3CCC(N4CC(F)(F)C[C@@H]4C(=O)OC)CC3)C2)C1] Example 2-87
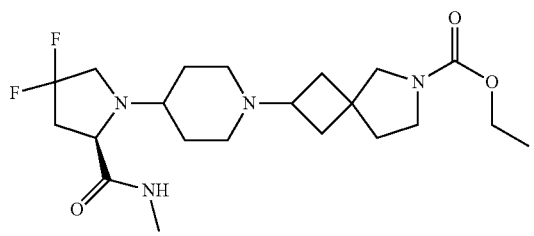 [SMILES: CCOC(=O)N1CCC2(CC(N3CCC(N4CC(F)(F)C[C@@H]4C(=O)NC)CC3)C2)C1] Example 2-88
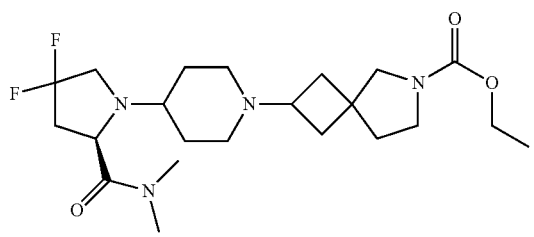 [SMILES: CCOC(=O)N1CCC2(CC(N3CCC(N4CC(F)(F)C[C@@H]4C(=O)N(C)C)CC3)C2)C1] Example 2-89
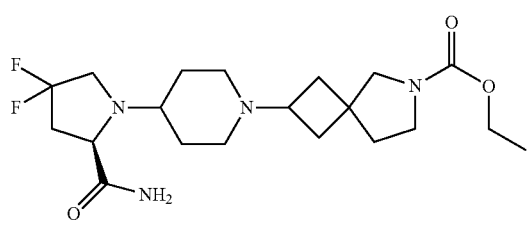 [SMILES: CCOC(=O)N1CCC2(CC(N3CCC(N4CC(F)(F)C[C@@H]4C(N)=O)CC3)C2)C1] Example 2-90
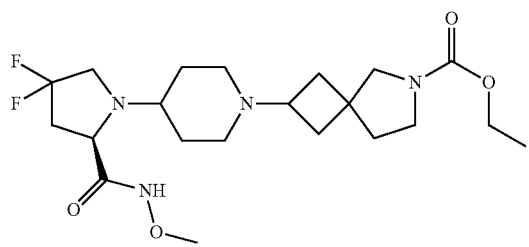 [SMILES: CCOC(=O)N1CCC2(CC(N3CCC(N4CC(F)(F)C[C@@H]4C(=O)NOC)CC3)C2)C1] Example 2-91

TABLE 1-continued
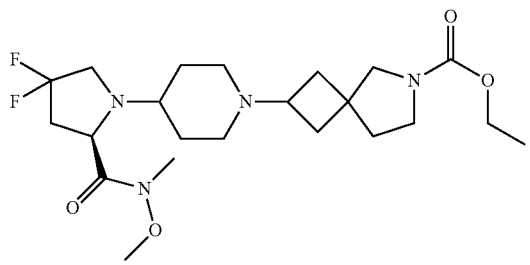 [SMILES: CCOC(=O)N1CCC2(CC(N3CCC(N4CC(F)(F)C[C@@H]4C(=O)N(C)OC)CC3)C2)C1]
Example 2-92
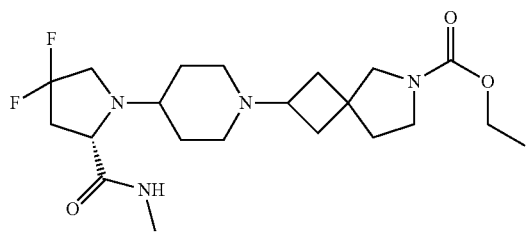 [SMILES: CCOC(=O)N1CCC2(CC(N3CCC(N4CC(F)(F)C[C@H]4C(=O)NC)CC3)C2)C1]
Example 2-93
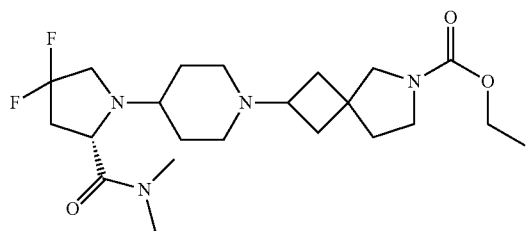 [SMILES: CCOC(=O)N1CCC2(CC(N3CCC(N4CC(F)(F)C[C@H]4C(=O)N(C)C)CC3)C2)C1]
Example 2-94
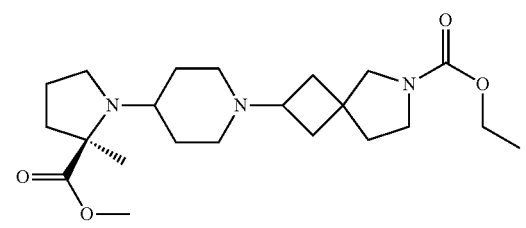 [SMILES: CCOC(=O)N1CCC2(CC(N3CCC(N4CCC[C@]4(C)C(=O)OC)CC3)C2)C1]
Example 2-95
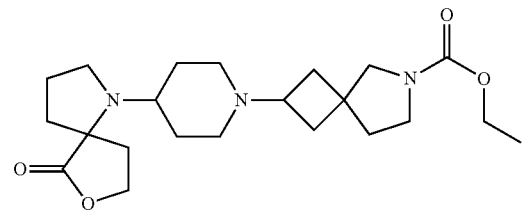 [SMILES: CCOC(=O)N1CCC2(CC(N3CCC(N4CCCC45CCOC5=O)CC3)C2)C1]
Example 2-96
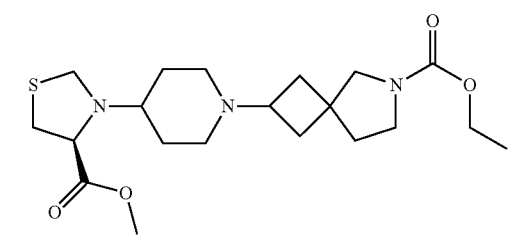 [SMILES: CCOC(=O)N1CCC2(CC(N3CCC(N4CSC[C@@H]4C(=O)OC)CC3)C2)C1]
Example 2-97
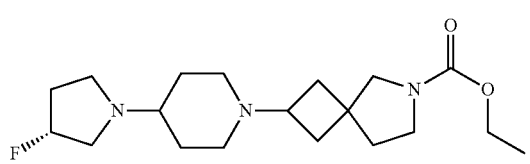 [SMILES: CCOC(=O)N1CCC2(CC(N3CCC(N4CC[C@@H](F)C4)CC3)C2)C1]
Example 2-98

TABLE 1-continued
| | |
|---|---|
| 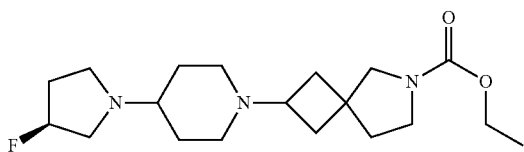 [SMILES: CCOC(=O)N1CCC2(CC(N3CCC(N4CC[C@H](F)C4)CC3)C2)C1] | Example 2-99 |
| 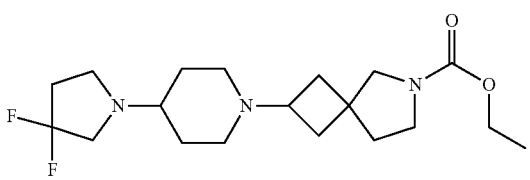 [SMILES: CCOC(=O)N1CCC2(CC(N3CCC(N4CCC(F)(F)C4)CC3)C2)C1] | Example 2-100 |
| 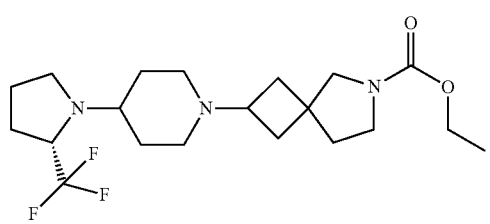 [SMILES: CCOC(=O)N1CCC2(CC(N3CCC(N4CCC[C@H]4C(F)(F)F)CC3)C2)C1] | Example 2-101 |
| 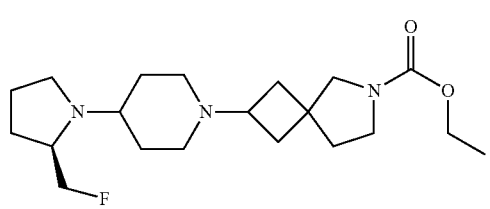 [SMILES: CCOC(=O)N1CCC2(CC(N3CCC(N4CCC[C@@H]4CF)CC3)C2)C1] | Example 2-102 |
| 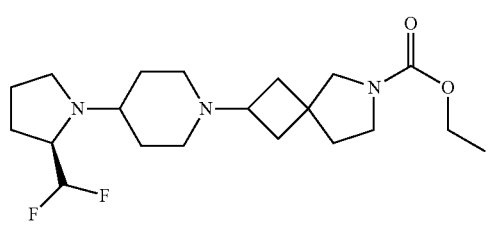 [SMILES: CCOC(=O)N1CCC2(CC(N3CCC(N4CCC[C@@H]4C(F)F)CC3)C2)C1] | Example 2-103 |
| 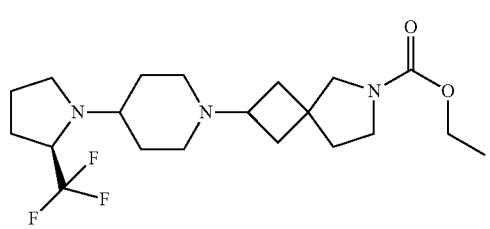 [SMILES: CCOC(=O)N1CCC2(CC(N3CCC(N4CCC[C@@H]4C(F)(F)F)CC3)C2)C1] | Example 2-104 |
| 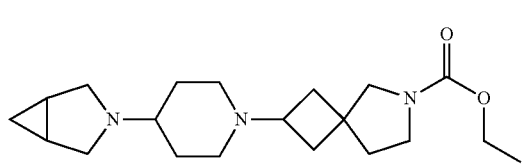 [SMILES: CCOC(=O)N1CCC2(CC(N3CCC(N4CC5CC5C4)CC3)C2)C1] | Example 2-105 |
| 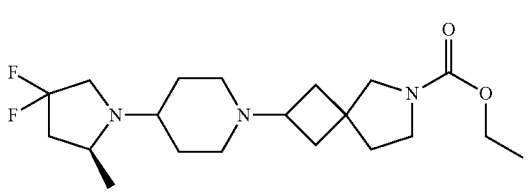 [SMILES: CCOC(=O)N1CCC2(CC(N3CCC(N4CC(F)(F)C[C@@H]4C)CC3)C2)C1] | Example 2-106 |

TABLE 1-continued
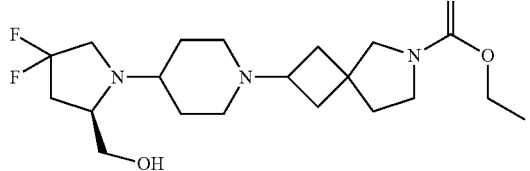 Example 2-107
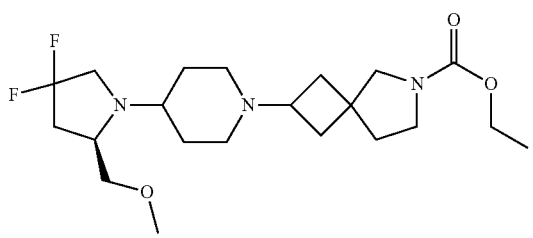 [SMILES: CCOC(=O)N1CCC2(CC(N3CCC(N4CC(F)(F)C[C@@H]4COC)CC3)C2)C1] Example 2-108
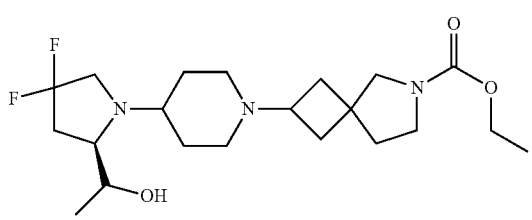 [SMILES: CCOC(=O)N1CCC2(CC(N3CCC(N4CC(F)(F)C[C@@H]4C(C)O)CC3)C2)C1] Example 2-109
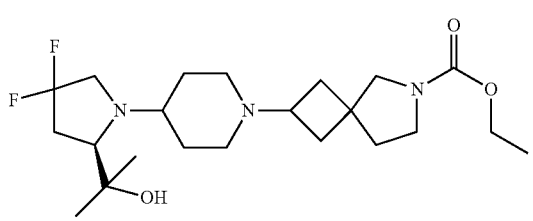 [SMILES: CCOC(=O)N1CCC2(CC(N3CCC(N4CC(F)(F)C[C@@H]4C(C)(C)O)CC3)C2)C1] Example 2-110
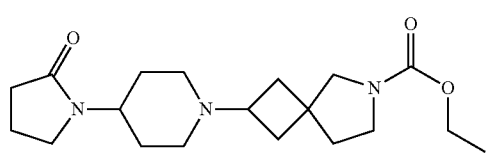 [SMILES: CCOC(=O)N1CCC2(CC(N3CCC(N4CCCC4=O)CC3)C2)C1] Example 2-111
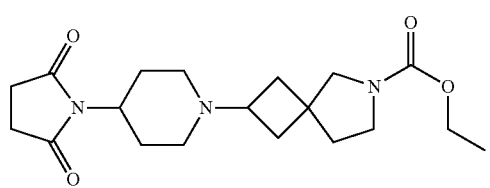 [SMILES: CCOC(=O)N1CCC2(CC(N3CCC(N4C(=O)CCC4=O)CC3)C2)C1] Example 2-112
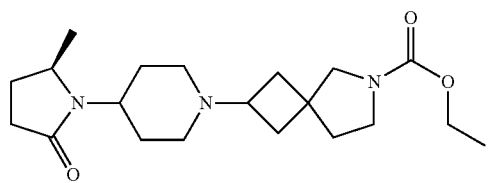 [SMILES: CCOC(=O)N1CCC2(CC(N3CCC(N4C(=O)CC[C@H]4C)CC3)C2)C1] Example 2-113
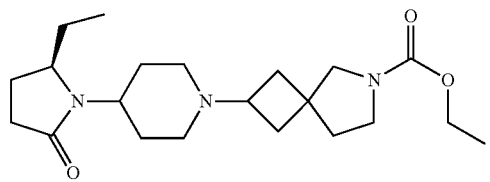 [SMILES: CCOC(=O)N1CCC2(CC(N3CCC(N4C(=O)CC[C@H]4CC)CC3)C2)C1] Example 2-114

TABLE 1-continued
| | |
|---|---|
| 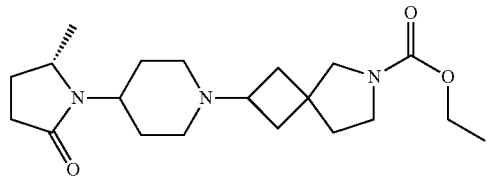 [SMILES: CCOC(=O)N1CCC2(CC(N3CCC(N4C(=O)CC[C@@H]4C)CC3)C2)C1] | Example 2-115 |
| 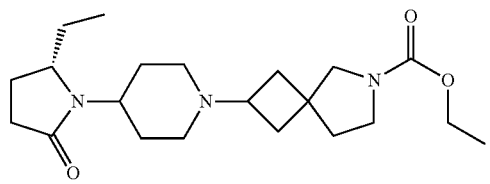 [SMILES: CCOC(=O)N1CCC2(CC(N3CCC(N4C(=O)CC[C@@H]4CC)CC3)C2)C1] | Example 2-116 |
| 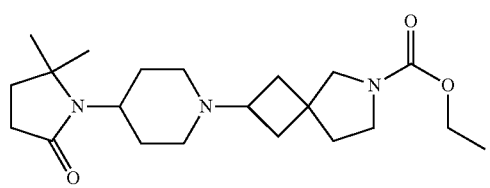 [SMILES: CCOC(=O)N1CCC2(CC(N3CCC(N4C(=O)CCC4(C)C)CC3)C2)C1] | Example 2-117 |
| 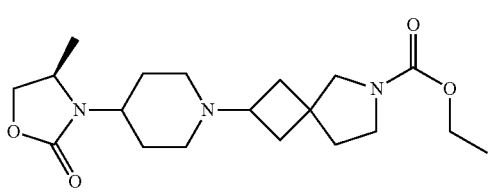 [SMILES: CCOC(=O)N1CCC2(CC(N3CCC(N4C(=O)OC[C@H]4C)CC3)C2)C1] | Example 2-118 |
| 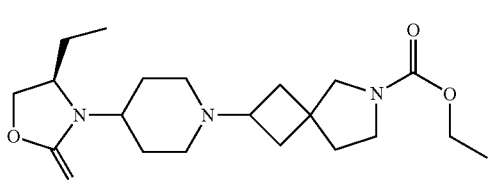 | Example 2-119 |
| 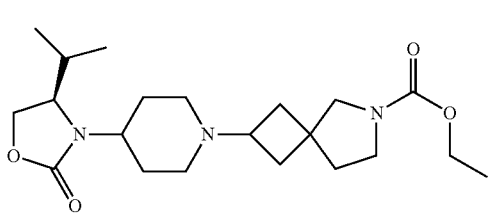 [SMILES: CCOC(=O)N1CCC2(CC(N3CCC(N4C(=O)OC[C@H]4C(C)C)CC3)C2)C1] | Example 2-120 |
| 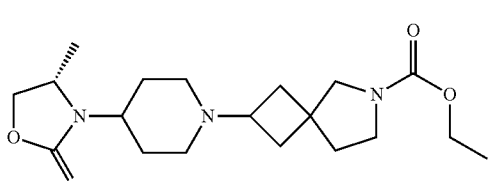 | Example 2-121 |
| 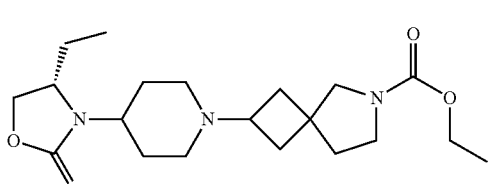 | Example 2-122 |

TABLE 1-continued
| | |
|---|---|
| 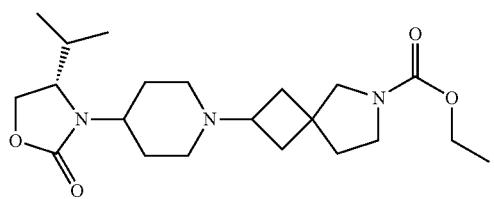 [SMILES: CCOC(=O)N1CCC2(CC(N3CCC(N4C(=O)OC[C@@H]4C(C)C)CC3)C2)C1] | Example 2-123 |
| 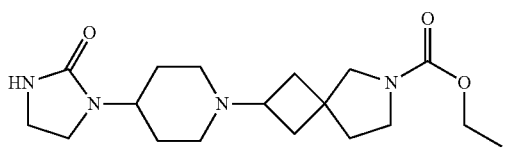 [SMILES: CCOC(=O)N1CCC2(CC(N3CCC(N4CCNC4=O)CC3)C2)C1] | Example 2-124 |
| 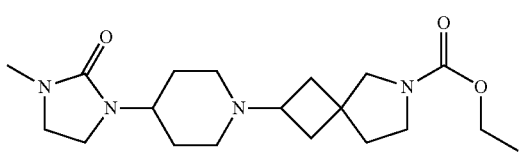 [SMILES: CCOC(=O)N1CCC2(CC(N3CCC(N4CCN(C)C4=O)CC3)C2)C1] | Example 2-125 |
| 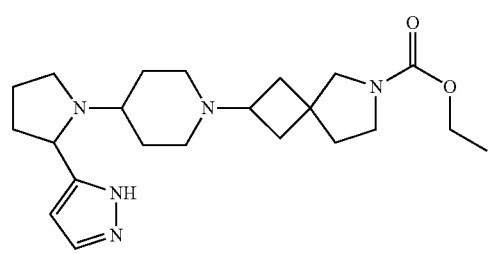 [SMILES: CCOC(=O)N1CCC2(CC(N3CCC(N4CCCC4c4ccn[nH]4)CC3)C2)C1] | Example 2-126 |
| 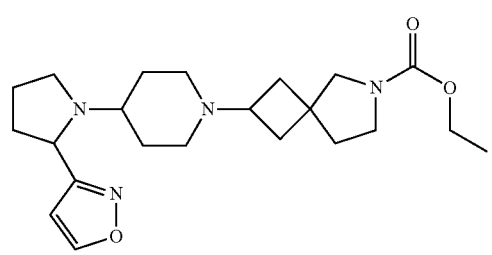 [SMILES: CCOC(=O)N1CCC2(CC(N3CCC(N4CCCC4c4ccon4)CC3)C2)C1] | Example 2-127 |
| 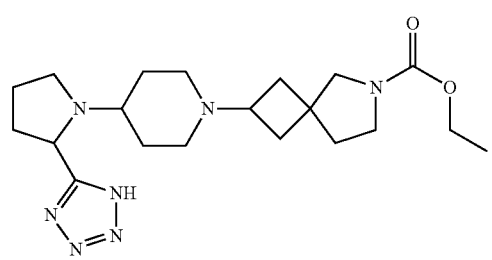 [SMILES: CCOC(=O)N1CCC2(CC(N3CCC(N4CCCC4c4nnn[nH]4)CC3)C2)C1] | Example 2-128 |
| 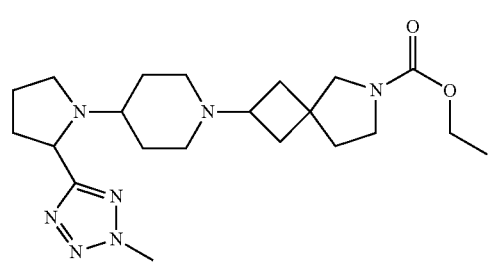 [SMILES: CCOC(=O)N1CCC2(CC(N3CCC(N4CCCC4c4nnn(C)n4)CC3)C2)C1] | Example 2-129 |

TABLE 1-continued
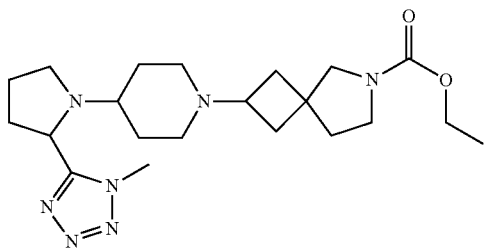 [SMILES: CCOC(=O)N1CCC2(CC(N3CCC(N4CCCC4c4nnnn4C)CC3)C2)C1]
Example 2-130
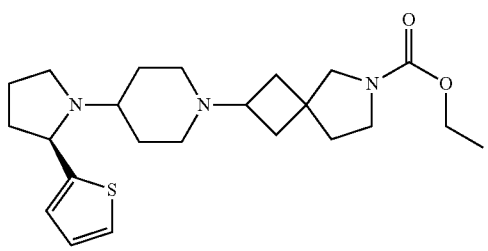 [SMILES: CCOC(=O)N1CCC2(CC(N3CCC(N4CCC[C@@H]4c4cccs4)CC3)C2)C1]
Example 2-131
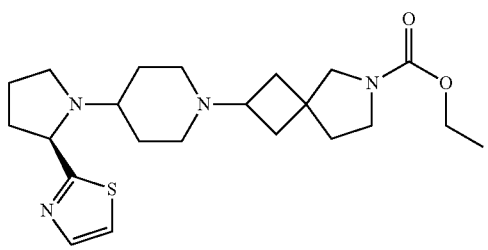 [SMILES: CCOC(=O)N1CCC2(CC(N3CCC(N4CCC[C@@H]4c4nccs4)CC3)C2)C1]
Example 2-132
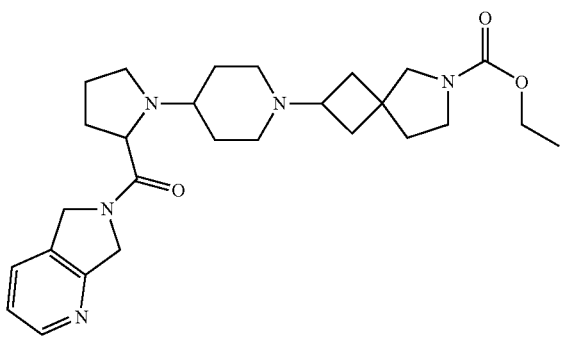 [SMILES: CCOC(=O)N1CCC2(CC(N3CCC(N4CCCC4C(=O)N4Cc5cccnc5C4)CC3)C2)C1]
Example 2-133
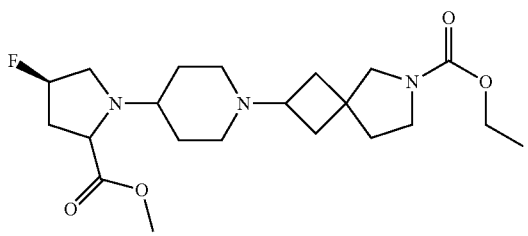 [SMILES: CCOC(=O)N1CCC2(CC(N3CCC(N4C[C@H](F)CC4C(=O)OC)CC3)C2)C1]
Example 2-134
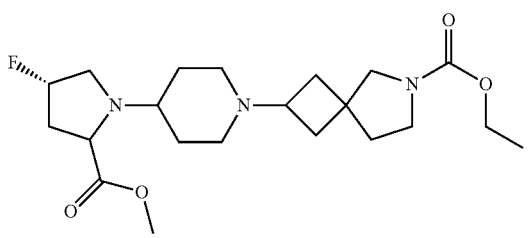 [SMILES: CCOC(=O)N1CCC2(CC(N3CCC(N4C[C@@H](F)CC4C(=O)OC)CC3)C2)C1]
Example 2-135

TABLE 1-continued
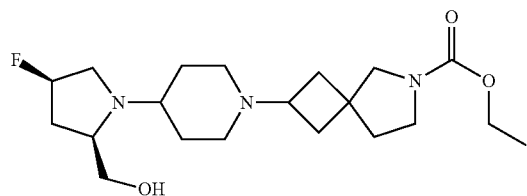 [SMILES: CCOC(=O)N1CCC2(CC(N3CCC(N4C[C@H](F)C[C@@H]4CO)CC3)C2)C1]
Example 2-136
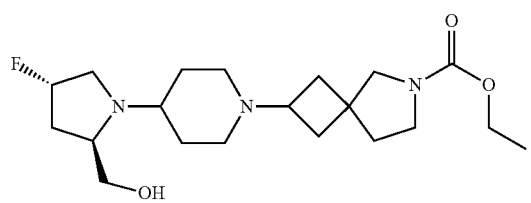 [SMILES: CCOC(=O)N1CCC2(CC(N3CCC(N4C[C@@H](F)C[C@@H]4CO)CC3)C2)C1]
Example 2-137
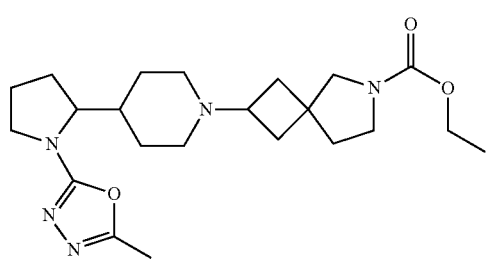 [SMILES: CCOC(=O)N1CCC2(CC(N3CCC(C4CCCN4c4nnc(C)o4)CC3)C2)C1]
Example 2-138
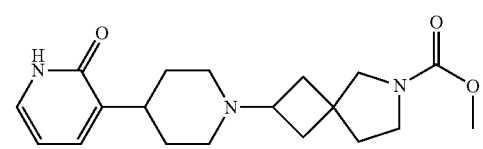 [SMILES: COC(=O)N1CCC2(CC(N3CCC(c4ccc[nH]c4=O)CC3)C2)C1]
Example 3-1
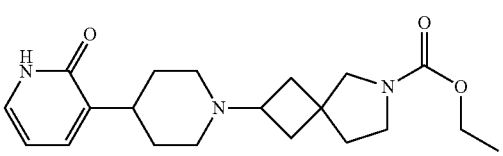 [SMILES: CCOC(=O)N1CCC2(CC(N3CCC(c4ccc[nH]c4=O)CC3)C2)C1]
Example 3-2
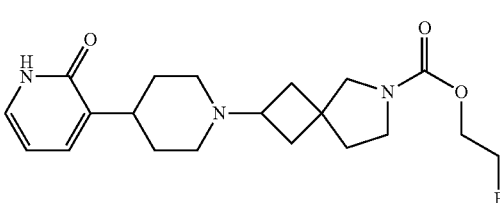 [SMILES: O=C(OCCF)N1CCC2(CC(N3CCC(c4ccc[nH]c4=O)CC3)C2)C1]
Example 3-3
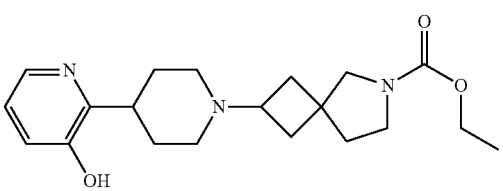 [SMILES: CCOC(=O)N1CCC2(CC(N3CCC(c4ncccc4O)CC3)C2)C1]
Example 3-4
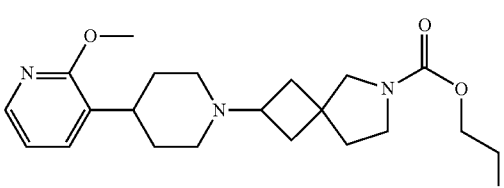
Example 3-5

TABLE 1-continued
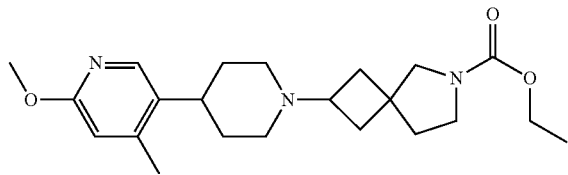 [SMILES: CCOC(=O)N1CCC2(CC(N3CCC(c4cnc(OC)cc4C)CC3)C2)C1]
Example 3-6
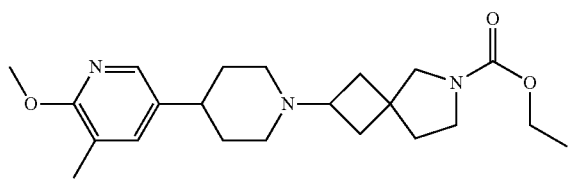
Example 3-7
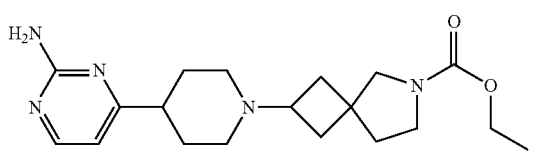 [SMILES: CCOC(=O)N1CCC2(CC(N3CCC(c4ccnc(N)n4)CC3)C2)C1]
Example 3-8
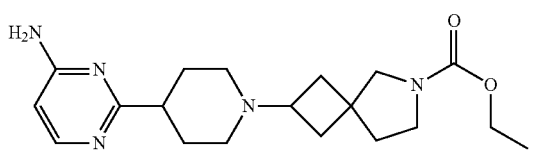 [SMILES: CCOC(=O)N1CCC2(CC(N3CCC(c4nccc(N)n4)CC3)C2)C1]
Example 3-9
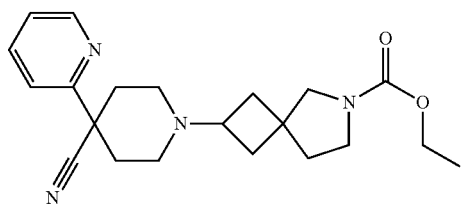 [SMILES: CCOC(=O)N1CCC2(CC(N3CCC(C#N)(c4ccccn4)CC3)C2)C1]
Example 3-10
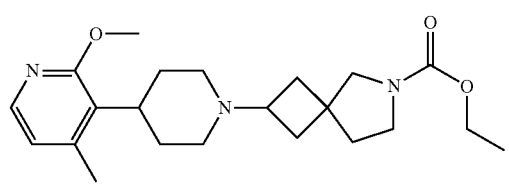 [SMILES: CCOC(=O)N1CCC2(CC(N3CCC(c4c(C)ccnc4OC)CC3)C2)C1]
Example 3-11
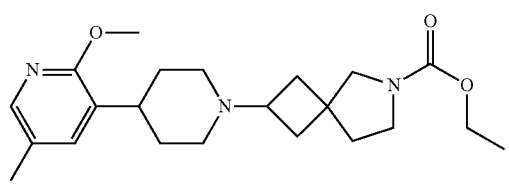 [SMILES: CCOC(=O)N1CCC2(CC(N3CCC(c4cc(C)cnc4OC)CC3)C2)C1]
Example 3-12
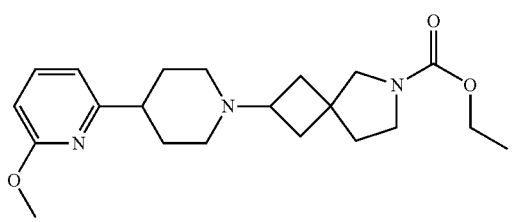 [SMILES: CCOC(=O)N1CCC2(CC(N3CCC(c4cccc(OC)n4)CC3)C2)C1]
Example 3-13

TABLE 1-continued
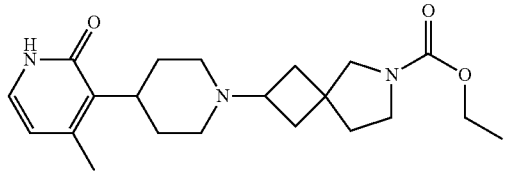 [SMILES: CCOC(=O)N1CCC2(CC(N3CCC(c4c(C)cc[nH]c4=O)CC3)C2)C1]  Example 3-14
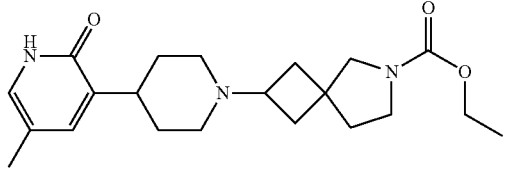 [SMILES: CCOC(=O)N1CCC2(CC(N3CCC(c4cc(C)c[nH]c4=O)CC3)C2)C1]  Example 3-15
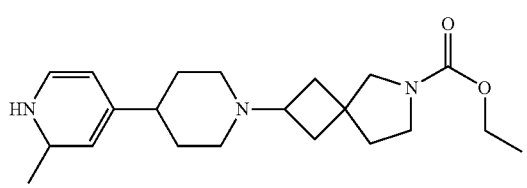 [SMILES: CCOC(=O)N1CCC2(CC(N3CCC(C4=CC(C)NC=C4)CC3)C2)C1]  Example 3-16
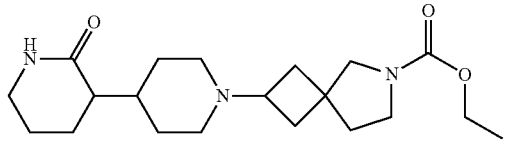  Example 4-1
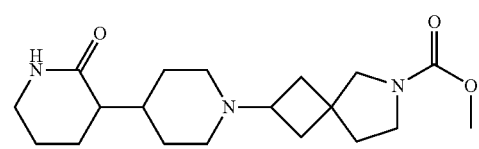 [SMILES: COC(=O)N1CCC2(CC(N3CCC(C4CCCNC4=O)CC3)C2)C1]  Example 4-2
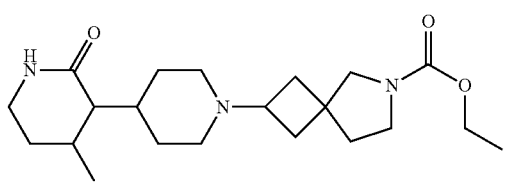 [SMILES: CCOC(=O)N1CCC2(CC(N3CCC(C4C(=O)NCCC4C)CC3)C2)C1]  Example 4-3
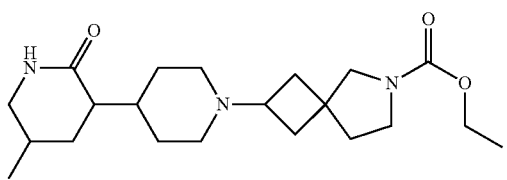 [SMILES: CCOC(=O)N1CCC2(CC(N3CCC(C4CC(C)CNC4=O)CC3)C2)C1]  Example 4-4
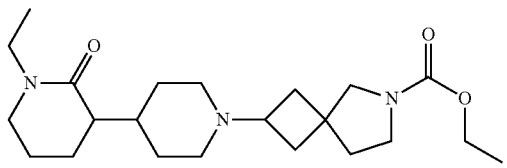 [SMILES: CCOC(=O)N1CCC2(CC(N3CCC(C4CCCN(CC)C4=O)CC3)C2)C1]  Example 4-5
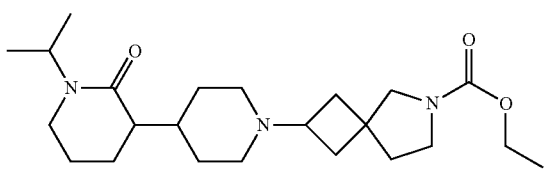 [SMILES: CCOC(=O)N1CCC2(CC(N3CCC(C4CCCN(C(C)C)C4=O)CC3)C2)C1]  Example 4-6

US 9,670,183 B2
TABLE 1-continued
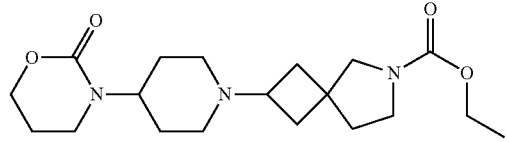 [SMILES: CCOC(=O)N1CCC2(CC(N3CCC(N4CCCOC4=O)CC3)C2)C1] Example 4-7
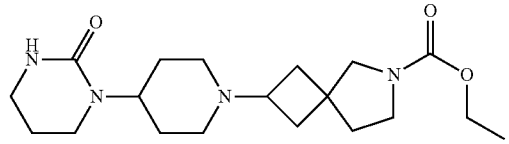 Example 4-8
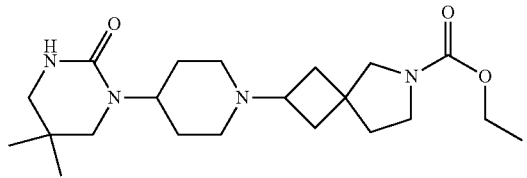 [SMILES: CCOC(=O)N1CCC2(CC(N3CCC(N4CC(C)(C)CNC4=O)CC3)C2)C1] Example 4-9
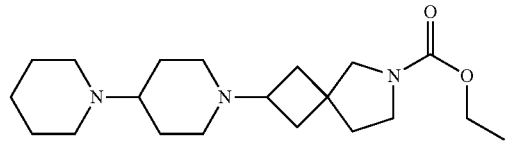 [SMILES: CCOC(=O)N1CCC2(CC(N3CCC(N4CCCCC4)CC3)C2)C1] Example 4-10
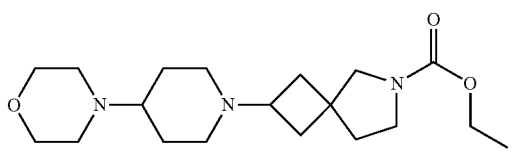 [SMILES: CCOC(=O)N1CCC2(CC(N3CCC(N4CCOCC4)CC3)C2)C1] Example 4-11
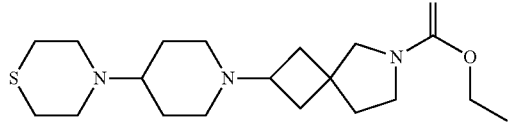 Example 4-12
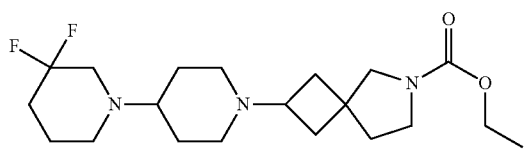 [SMILES: CCOC(=O)N1CCC2(CC(N3CCC(N4CCCC(F)(F)C4)CC3)C2)C1] Example 4-13
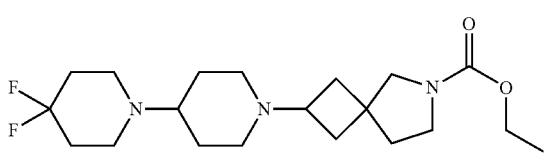 [SMILES: CCOC(=O)N1CCC2(CC(N3CCC(N4CCC(F)(F)CC4)CC3)C2)C1] Example 4-14
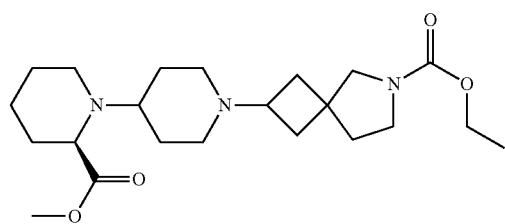 [SMILES: CCOC(=O)N1CCC2(CC(N3CCC(N4CCCC[C@@H]4C(=O)OC)CC3)C2)C1] Example 4-15

TABLE 1-continued

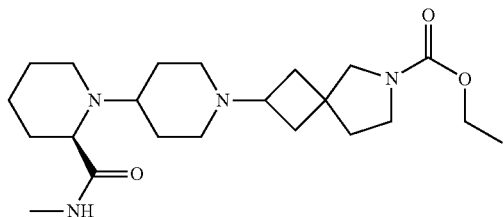 [SMILES: CCOC(=O)N1CCC2(CC(N3CCC(N4CCCC[C@@H]4C(=O)NC)CC3)C2)C1]

Example 4-16

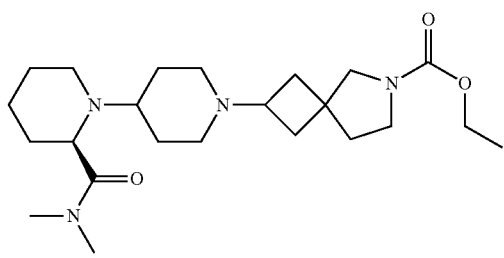 [SMILES: CCOC(=O)N1CCC2(CC(N3CCC(N4CCCC[C@@H]4C(=O)N(C)C)CC3)C2)C1]

Example 4-17

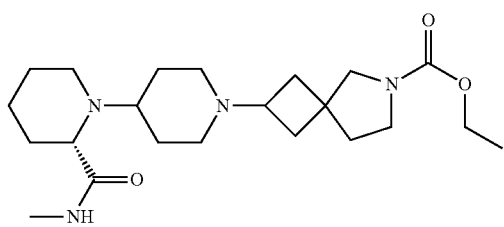 [SMILES: CCOC(=O)N1CCC2(CC(N3CCC(N4CCCC[C@H]4C(=O)NC)CC3)C2)C1]

Example 4-18

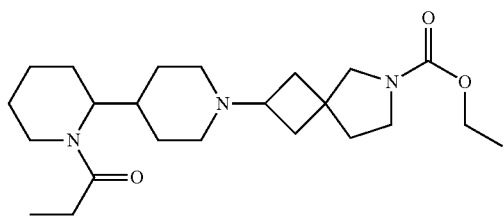 [SMILES: CCOC(=O)N1CCC2(CC(N3CCC(C4CCCCN4C(=O)CC)CC3)C2)C1]

Example 4-19

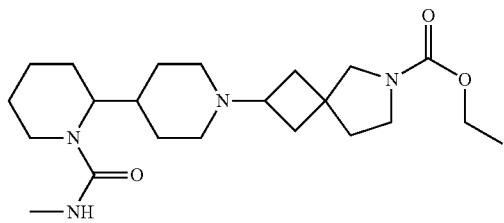 [SMILES: CCOC(=O)N1CCC2(CC(N3CCC(C4CCCCN4C(=O)NC)CC3)C2)C1]

Example 4-20

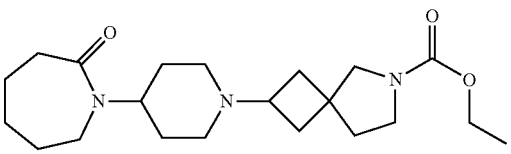 [SMILES: CCOC(=O)N1CCC2(CC(N3CCC(N4CCCCCC4=O)CC3)C2)C1]

Example 5-1

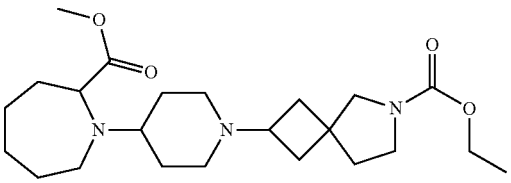 [SMILES: CCOC(=O)N1CCC2(CC(N3CCC(N4CCCCCC4C(=O)OC)CC3)C2)C1]

Example 5-2

General Procedures

Where no preparative routes are included, the relevant intermediate is commercially available. Commercial reagents were utilized without further purification. Room temperature (rt) refers to approximately 20-27° C. $^1$H NMR spectra were recorded at 400 MHz on either a Bruker or Jeol instrument. Chemical shift values are expressed in parts per million (ppm), i.e. (δ:)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. TLC for monitoring reactions refers to TLC run using the specified mobile phase and Silica gel F254 (Merck) as a stationary phase. Microwave-mediated reactions were performed in Biotage Initiator or CEM Discover microwave reactors.

LCMS experiments were typically carried out using electrospray conditions as specified for each compound under the following conditions:

LCMS Methods A and B

Instruments: Waters Alliance 2795, Waters 2996 PDA detector, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method A: 0.00/2, 0.10/2, 2.50/95, 3.50/95, 3.55/2, 4.00/2 or Method B: 0.00/2, 0.10/2, 8.40/95, 9.40/95, 9.50/2, 10.00/2; Solvents: solvent C=2.5 L $H_2O$+2.5 mL ammonia solution; solvent D=2.5 L MeCN+135 mL $H_2O$+2.5 mL ammonia solution); Injection volume 3 μL; UV detection 230 to 400 nM; column temperature 45° C.; Flow rate 1.5 mL/min.

LCMS Method C

Instruments: Agilent 1260 Infinity LC with Diode Array Detector, Agilent 6120B Single Quadrupole MS with API-ES Source; Column: Phenomenex Gemini-NX C-18, 3 micron, 2.0×30 mm; Gradient [time (min)/solvent B in A (%)]: Method: 0.00/5, 2.00/95, 2.50/95, 2.60/5, 3.00/5; Solvents: solvent A=2.5 L $H_2O$+2.5 mL of (28% NH3 in $H_2O$); solvent B=2.5 L MeCN+129 mL $H_2O$+2.7 mL of (28% NH3 in $H_2O$); Injection volume 0.5 μL; UV detection 190 to 400 nM; column temperature 40° C.; Flow rate 1.5 mL/min.

LCMS Methods D and E

Instruments: HP 1100 with G1315A DAD, Micromass ZQ; Column: Waters X-Bridge C-18, 2.5 micron, 2.1×20 mm or Phenomenex Gemini-NX C-18, 3 micron, 2.0×30 mm; Gradient [time (min)/solvent D in C (%)]: Method D: 0.00/2, 0.10/2, 2.50/95, 3.50/95, 3.55/2, 4.00/2 or Method E: 0.00/2, 0.10/2, 8.40/95, 9.40/95, 9.50/2, 10.00/2; Solvents: solvent C=2.5 L $H_2O$+2.5 mL 28% ammonia in $H_2O$ solution; solvent D=2.5 L MeCN+135 mL $H_2O$+2.5 mL 28% ammonia in $H_2O$ solution); Injection volume 1 μL; UV detection 230 to 400 nM; Mass detection 130 to 800 AMU (+ve and −ve electrospray); column temperature 45° C.; Flow rate 1.5 mL/min.

LCMS Method F:

Instruments: Waters Acquity H Class, Photo Diode Array, SQ Detector; Column: BEH C18, 1.7 micron, 2.1×50 mm; Gradient [time (min)/solvent B in A (%)]: 0.00/5, 0.40/5, 0.8/35, 1.20/55, 2.50/100, 3.30/100 4.00/5; Solvents: solvent A=5 mM ammonium acetate and 0.1% formic acid in $H_2O$; solvent B=0.1% formic acid in MeCN; Injection volume 2 μL; UV detection 200 to 400 nM; Mass detection 100 to 1200 AMU (+ve electrospray); column at ambient temperature; Flow rate 0.5 mL/min.

LCMS Method G:

Instruments: Waters 2695, Photo Diode Array, ZQ-2000 Detector; Column: X-Bridge C18, 5 micron, 150×4.6 mm; Gradient [time (min)/solvent B in A (%)]: 0.00/10, 5.00/90, 7.00/100, 11.00/100, 11.01/10 12.00/10; Solvents: solvent A=0.1% ammonia in $H_2O$; solvent B=0.1% ammonia in MeCN; Injection volume 10 μL; UV detection 200 to 400 nM; Mass detection 60 to 1000 AMU (+ve electrospray); column at ambient temperature; Flow rate 1.0 mL/min.

LCMS Method H:

Instruments: Waters 2695, Photo Diode Array, ZQ-2000 Detector; Column: X-Bridge C18, 5 micron, 150×4.6 mm; Gradient [time (min)/solvent B in A (%)]: 0.00/100, 7.00/50, 9.00/0, 11.00/0, 11.01/100, 12.00/100; Solvents: solvent A=0.1% ammonia in $H_2O$; solvent B=0.1% ammonia in MeCN; Injection volume 10 μL; UV detection 200 to 400 nM; Mass detection 60 to 1000 AMU (+ve electrospray); column at ambient temperature; Flow rate 1.0 mL/min.

LCMS Method I:

Instruments: Waters 2695, Photo Diode Array, ZQ-2000 Detector; Column: X-Bridge C18, 3.5 micron, 150×4.6 mm; Gradient [time (min)/solvent B in A (%)]: 0.00/5, 5.00/90, 5.80/95, 10/95; Solvents: solvent A=0.1% ammonia in $H_2O$; solvent B=0.1% ammonia in MeCN; Injection volume 10 μL; UV detection 200 to 400 nM; Mass detection 60 to 1000 AMU (+ve electrospray); column at ambient temperature; Flow rate 1.0 mL/min.

LCMS Method J:

Instruments: Waters 2695, Photo Diode Array, ZQ-2000 Detector; Column: X-Bridge C18, 5 micron, 150×4.6 mm; Gradient [time (min)/solvent B in A (%)]: 0.01/10, 5.00/90, 7.00/100, 11.00/100, 11.01/10, 12.00110; Solvents: solvent A=20 mM ammonium acetate in $H_2O$; solvent B=MeOH; Injection volume 10 μL; UV detection 200 to 400 nM; Mass detection 60 to 1000 AMU (+ve electrospray); column at ambient temperature; Flow rate 1.0 mL/min.

LCMS Method K:

Instruments: Waters 2695, Photo Diode Array, ZQ-2000 Detector; Column: X-Bridge C18, 3.5 micron, 50×4.6 mm; Gradient [time (min)/solvent B in A (%)]: 0.01/0, 0.20/0, 5.00/90, 5.80/95, 7.20/95, 7.21/100, 10.00/100; Solvents: solvent A=0.1% ammonia in $H_2O$; solvent B=0.1% ammonia in MeCN; Injection volume 10 μL; UV detection 200 to 400 nM; Mass detection 60 to 1000 AMU (+ve electrospray); column at ambient temperature; Flow rate 1.0 mL/min.

LCMS Method L

Instruments: Waters Acquity UPLC, Waters 3100 PDA Detector, SQD; Column: Acquity BEH C-18, 1.7 micron, 2.1×100 mm; Gradient [time (min)/solvent B in A (%)]: 0.00/2, 2.00/2, 7.00/50, 8.50/80, 9.50/2, 10.0/2; Solvents: solvent A=5 mM ammonium acetate in water; solvent B=acetonitrile; Injection volume 14; Detection wavelength 214 nm; Column temperature 30° C.; Flow rate 0.3 mL per min.

LCMS Method M

Instruments: Agilent 1260 Infinity series UHPLC; ELSD: Agilent 1260 infinity; Column: Acquity C-18, 1.7 micron, 2.1×50 mm; Gradient [time (min)/solvent B in A (%)]: 0.00/10, 1.00/10, 2.00/15, 4.50/55, 6.00/90, 8.00/90, 9.00/10, 10.00/10; Solvents: A=5 mM ammonium acetate in water, B=acetonitrile; Injection volume: 1 μL; Detection by ELSD; Column temperature: 40° C.; Flow rate: 0.6 mL per/min.

LCMS Method N

Instruments: Waters Acquity UPLC, Waters 3100 PDA Detector, SQD; Column: Acquity BEH C-18, 1.7 micron, 2.1×100 mm; Gradient [time (min)/solvent B in A (%)]: 0.00/2, 0.50/2, 1.50/20, 4.00/92, 5.00/92, 5.50/50, 6.00/2; Solvents: solvent A=5 mM ammonium acetate in water;

solvent B=acetonitrile; Injection volume 1 μL; Detection wavelength 214 nm; Column temperature 35° C.; Flow rate 0.6 mL per min.

LCMS Method O

Instruments: Waters Acquity UPLC, Waters 3100 PDA Detector, SQD; Column: Acquity HSS-T3, 1.8 micron, 2.1×100 mm; Gradient [time (min)/solvent B in A (%)]: 0.00/10, 1.00/10, 2.00/15, 4.50/55, 6.00/90, 8.00/90, 9.00/10, 10.00/10; Solvents: solvent A=0.1% trifluoroacetic acid in water; solvent B=acetonitrile; Injection volume 14; Detection wavelength 214 nm; Column temperature 30° C.; Flow rate 0.3 mL per min.

LCMS data in the experimental section are given in the format: Mass ion, retention time, UV activity.

ABBREVIATIONS

AcOH=acetic acid
CDI=1,1'-Carbonyldiimidazole
d=day(s)
DAST=diethylaminosulfur trifluoride
DCE=dichloroethane
DCM=dichloromethane
DIPEA=diisopropylethylamine
DIAD=diisopropyl azodicarboxylate
DMF=dimethylformamide
DMP=Dess-Martin periodinane
DMSO=dimethylsulfoxide
ES=electro spray ionisation
EtOAc=ethyl acetate
h=hour(s)
HATU=1-[Bis(dimethylamino)methylene]-1H-1,2,3-triazolo[4,5-b]pyridinium 3-oxide hexafluorophosphate
HPLC=high performance liquid chromatography
LC=liquid chromatography
LiAlH$_4$/LAH=Lithium aluminium hydride
MeCN=acetonitrile
MeOH=methanol
min=minute(s)
MS=mass spectrometry
Et$_3$N=triethylamine
NMR=nuclear magnetic resonance
rt=room temperature
sat.=saturated
sol.=solution
STAB=sodium triacetoxyborohydride
THF=tetrahydrofuran
TLC=thin layer chromatography
Prefixes n-, s-, i-, t- and tert- have their usual meanings: normal, secondary, iso, and tertiary.

Synthesis of Intermediates

Procedure for the Preparation of Intermediate 2, ethyl 2-oxo-6-azaspiro[3.4]octane-6-carboxylate

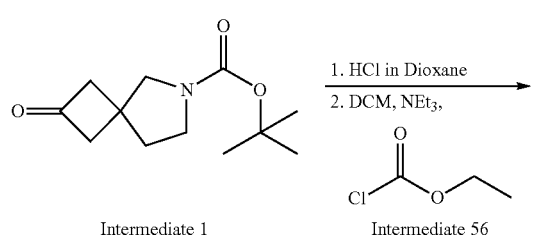

Intermediate 1

Intermediate 56

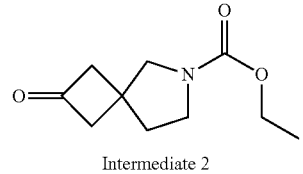

Intermediate 2

6-Boc-2-oxo-6-azaspiro[3.4]octane (3.37 g, 15 mmol) was added portionwise to hydrogen chloride (4 M dioxane solution, 50 mL, 210 mmol). Caution: effervescence. After 24 h, the reaction was concentrated in vacuo and the residual solid was dissolved in a mixture of Et$_3$N (4.18 ml, 30 mmol) and DCM (66 mL). On completion of dissolution, the solution was immediately cooled to 0° C., then ethyl chloroformate (1.57 mL, 16.5 mmol) was added dropwise. After 18 h, the mixture was poured into dichloromethane (100 mL) and NaHCO$_3$ (aq) (100 mL) and extracted (2×100 mL). The organic layers were collected, washed with brine (20 mL), dried over MgSO$_4$, then the residue after evaporation was purified by column chromatography (normal phase, [Biotage SNAP cartridge KP-sil 100 g, 40-63 μm, 60 Å, 50 mL per min, gradient 0% to 4% MeOH in DCM]) to give Intermediate 2, ethyl 2-oxo-6-azaspiro[3.4]octane-6-carboxylate as a colourless oil (2.47 g, 83%). The data for the title compound are in Table 2.

Procedure for the Preparation of Intermediate 3, methyl 2-oxo-6-azaspiro[3.4]octane-6-carboxylate

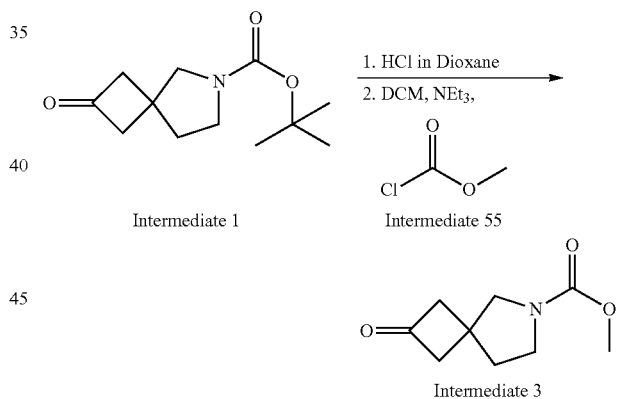

Intermediate 1

Intermediate 55

Intermediate 3

6-Boc-2-oxo-6-azaspiro[3.4]octane (5.00 g, 22.2 mmol) was added portionwise to hydrogen chloride (4 M dioxane solution, 45 mL, 180 mmol) in dichloromethane (5 mL). Caution: effervescence. After 2 h, the reaction was concentrated in vacuo and 1.29 g of the residual solid dissolved in a mixture of triethylamine (2.23 ml, 16.0 mmol) and dichloromethane (10 mL). On completion of dissolution, the solution was immediately cooled to 0° C., then methyl chloroformate (0.68 mL, 8.83 mmol) was added dropwise. After 3 h, the mixture was poured into dichloromethane (50 mL), washed with NaHCO$_3$ (aq) (2×50 mL) and extracted with DCM (50 mL). The organic layers were combined, washed with brine (50 mL), passed through a Biotage Phase Separator, the solvent was removed in vacuo and the residue was purified by column chromatography (normal phase, [Biotage SNAP cartridge KP-sil 50 g, 40-63 μm, 60 Å, 40 mL per min, gradient 0% to 10% MeOH in DCM]) to give Intermediate 3, methyl 2-oxo-6-azaspiro[3.4]octane-6-carboxylate as an orange oil (0.93 g, 66%). The data for the title compound are in Table 2.

Procedure for the Preparation of Intermediate 4, 2-fluoroethyl 2-oxo-6-azaspiro[3.4]octane-6-carboxylate

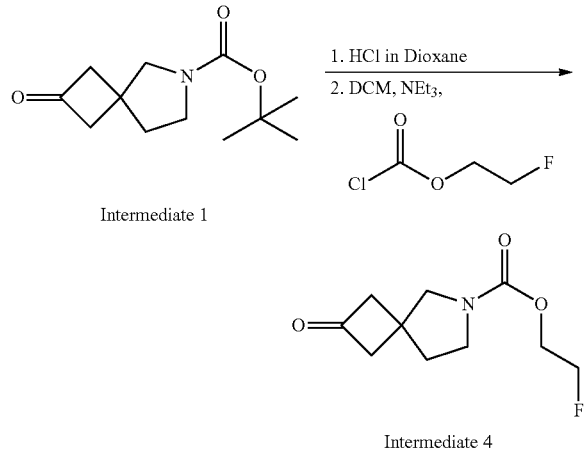

Intermediate 1

Intermediate 4 tert-Butyl 2-oxo-6-azaspiro[3.4]octane-6-carboxylate (5 g, 22.19 mmol) was stirred in HCl in 1,4-dioxane (25 mL) solution for 10 h at rt. The reaction mixture was was concentrated in vacuo and triturated with acetone (3×50 mL) to give 6-azaspiro[3.4]octan-2-one (2.77 g, 55.4%) as a brown gum. The residue was dissolved in dry DCM (20 mL) and Et₃N (0.7 mL, 4.8 mmol) was added. The reaction mixture was cooled to 0° C. and 2-fluoroethyl carbonochloridate (0.45 g, 3.6 mmol) was added. The reaction mixture to stir at 30° C. for 5 h then diluted with water (50 mL), extracted with DCM (2×100 mL), organic layers were combined, dried (Na₂SO₄), and the solvent was removed in vacuo. The residue was purified by column chromatography (normal phase, 60-120 mesh silica, 0 to 10% EtOAc in Hexane) to give Intermediate 4, 2-fluoroethyl 2-oxo-6-azaspiro[3.4]octane-6-carboxylate (0.2 g, 38.8%) as a brown gum. The data for the title compound are in Table 2.

Procedure for the Preparation of Intermediates 20 and 21, 4-(5-chloro-1-methyl-1H-imidazol-2-yl)piperidine trifluoroacetate and 4-(4,5-dichloro-1-methyl-1H-imidazol-2-yl)piperidine trifluoroacetate Respectively

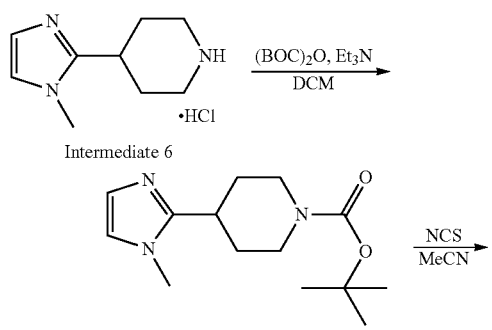

Intermediate 6

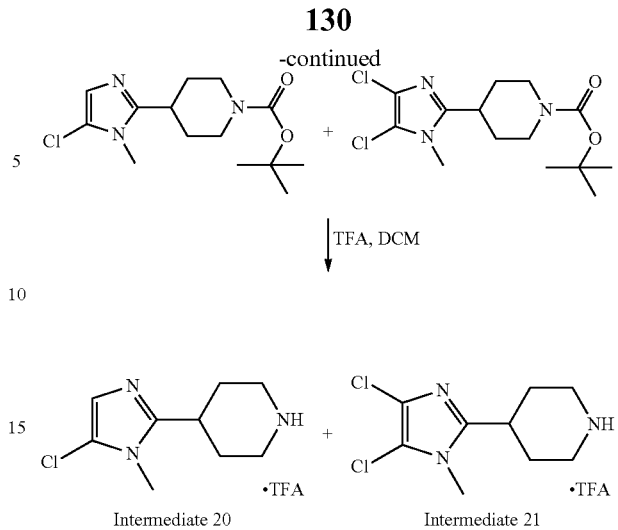

Intermediate 20          Intermediate 21

4-(1-Methylimidazol-2-yl)piperidine hydrochloride (1 g, 4.96 mmol) was suspended in a mixture of anhydrous DCM (20 mL) and Et₃N (2.1 mL, 15.1 mmol) and cooled in an ice-water bath. (BOC)₂O (1.19 g, 5.45 mmol) was added portion wise over 5 mins, the mixture was warmed to rt and stirred for 48 h. The mixture was diluted with DCM, washed with saturated aqueous NaHCO₃ (×2) and brine (×1), then passed through a phase separator and concentrated in vacuo to give tert-butyl 4-(1-methyl-1H-imidazol-2-yl)piperidine-1-carboxylate (1.34 g, quant.) as a solid.

LCMS (Method C): m/z 266 (M+H)⁺ (ES⁺), at 1.43 min, UV active.

tert-Butyl 4-(1-methyl-1H-imidazol-2-yl)piperidine-1-carboxylate (0.250 g, 0.942 mmol) was dissolved in MeCN (7.5 mL), treated with NCS (0.314 g, 2.35 mmol) and stirred at rt overnight. The reaction mixture was concentrated onto flash silica (~15 mL) in vacuo. The resulting powder was purified by column chromatography (normal phase, [Biotage SNAP cartridge KP-sil 50 g, 40-63 μm, 60 Å, 40 mL per min, gradient 2% to 10% Solvent A in DCM over 15 column volumes, where solvent A is 10% of (7 M NH₃/MeOH) in MeOH]) to give a mixture containing tert-butyl 4-(5-chloro-1-methyl-1H-imidazol-2-yl)piperidine-1-carboxylate and tert-butyl 4-(4,5-dichloro-1-methyl-1H-imidazol-2-yl)piperidine-1-carboxylate and succinimide (0.495 g).

LCMS (Method C): monochloro: m/z 300/302 (M+H)⁺ (ES⁺), at 1.68 min, UV active; dichloro: m/z 334/336/338 (M+H)⁺ (ES⁺), at 1.87 min, UV active. Ratio of monochloro: dichloro ~16:1 by LC-UV.

The mixture containing tert-butyl 4-(5-chloro-1-methyl-1H-imidazol-2-yl)piperidine-1-carboxylate and tert-butyl 4-(4,5-dichloro-1-methyl-1H-imidazol-2-yl)piperidine-1-carboxylate and succinimide (0.495 g) was dissolved in DCM (5 mL), treated with TFA (5 mL) and stirred at rt for 6 h. The reaction mixture was concentrated in vacuo and the residue azeotroped with toluene (×2) to afford a crude mixture of Intermediate 20, 4-(5-chloro-1-methyl-1H-imidazol-2-yl)piperidine trifluoroacetate and Intermediate 21, 4-(4,5-dichloro-1-methyl-1H-imidazol-2-yl)piperidine trifluoroacetate mixed with succinimide. Assumed quantitative yield. Used with no further purification. The data for the title compounds are in Table 2.

Procedure for the Preparation of Intermediates 22 and 25, 4-(5-chloro-1H-imidazol-2-yl)piperidine dihydrobromide and 4-(4,5-dichloro-1H-imidazol-2-yl)piperidine dihydrobromide Respectively

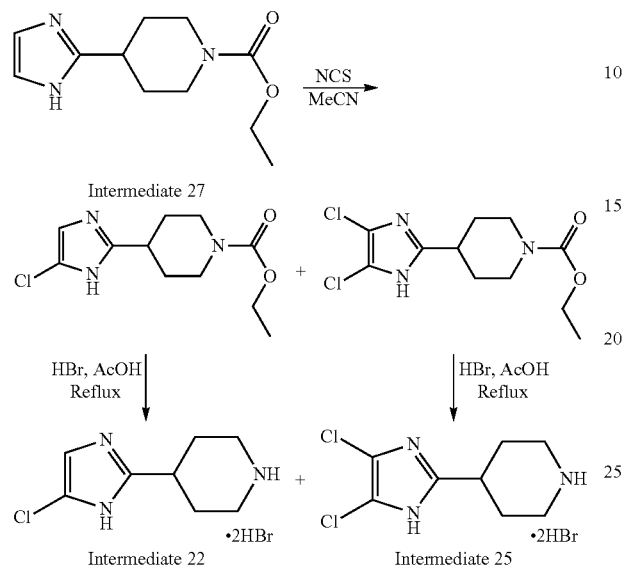

Ethyl 4-(1H-imidazol-2-yl)piperidine-1-carboxylate (0.40 g, 1.79 mmol) was dissolved in MeCN (12 mL), treated with NCS (0.360 g, 2.70 mmol) and stirred at rt for 5.5 h. The reaction mixture was concentrated onto flash silica (~10 mL) in vacuo. The resulting powder was purified by column chromatography (normal phase, [Biotage SNAP cartridge KP-sil 50 g, 40-63 μm, 60 Å, 40 mL per min, gradient 0% to 5% Solvent A in DCM over 15 column volumes, then 5% Solvent A in DCM over 5 column volumes, where solvent A is 10% of (7 M $NH_3$/MeOH) in MeOH]) to give the separated ethyl 4-(5-chloro-1H-imidazol-2-yl)piperidine-1-carboxylate and ethyl 4-(4,5-dichloro-1H-imidazol-2-yl)piperidine-1-carboxylate, both mixed with succinimide. Each was dissolved in DCM, washed with $H_2O$ (×3), passed through a phase separator and concentrated in vacuo to remove succinimide.

Ethyl 4-(5-chloro-1H-imidazol-2-yl)piperidine-1-carboxylate (0.12 g, 26%), LCMS (Method C): m/z 258/260 $(M+H)^+$ $(ES^+)$, at 1.34 min, UV active.

Ethyl 4-(4,5-dichloro-1H-imidazol-2-yl)piperidine-1-carboxylate (0.24 g, 45%), LCMS (Method C): m/z 292/294/296 $(M+H)^+$ $(ES^+)$, at 1.24 min, UV active.

Ethyl 4-(5-chloro-1H-imidazol-2-yl)piperidine-1-carboxylate (0.12 g, 0.47 mmol) was dissolved in AcOH (2 mL), treated with 48% aqueous HBr (2 mL) and heated at reflux at ~120° for 2 h. The reaction mixture was concentrated in vacuo, the residue was azeotroped with toluene (×1) and concentrated in vacuo to afford a solid. Assumed to be Intermediate 22, 4-(5-chloro-1H-imidazol-2-yl)piperidine dihydrobromide salt in quantitative yield. Used immediately.

Ethyl 4-(4,5-dichloro-1H-imidazol-2-yl)piperidine-1-carboxylate (0.24 g, 0.82 mmol) was dissolved in AcOH (2 mL), treated with 48% aqueous HBr (2 mL) and heated ~120° C. for 2 h. The reaction mixture was concentrated in vacuo, the residue was azeotroped with toluene (×1) and concentrated in vacuo to afford a solid. Assumed to be Intermediate 25, 4-(4,5-Dichloro-1H-imidazol-2-yl)piperidine dihydrobromide in quantitative yield. Used immediately. The data for the title compounds are in Table 2.

Procedure for the Preparation of Intermediate 46, tert-butyl 4-(4-(trifluoromethyl)-1H-imidazol-2-yl)piperidine-1-carboxylate and Intermediate 33, 4-[4-(trifluoromethyl)-1H-imidazol-2-yl]piperidine

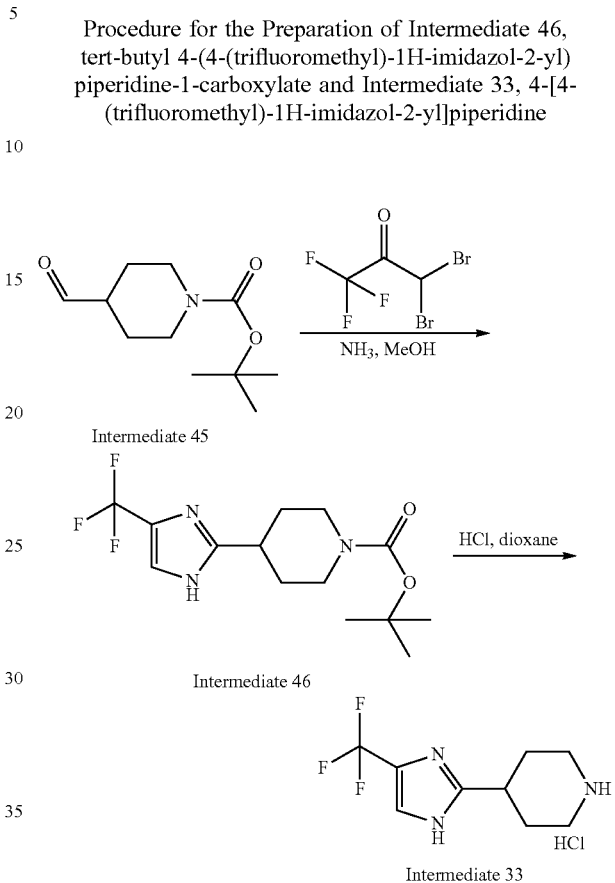

tert-Butyl 4-formylpiperidine-1-carboxylate (2.0 g, 9.4 mmol) was dissolved in MeOH (10 mL) and followed by addition of 7M methanolic ammonia cooled at 0° C. for 30 mins followed by portion wise addition of 3,3-dibromo-1,1,1-trifluoropropan-2-one (5.07 g, 18.5 mmol). The resulting reaction mixture was stirred at 25° C. for 2 h, solvents were removed in vacuo and the residue was partitioned between $H_2O$ (80 mL) and EtOAc (50 mL), the aqueous layer was extracted with EtOAc (2×50 mL), organic layers were combined, dried ($Na_2SO_4$), solvent was removed in vacuo and residue was purified by column chromatography (Activated basic Alumina at 0.5% MeOH in DCM) to give Intermediate 46, tert-butyl 4-(4-(trifluoromethyl)-1H-imidazol-2-yl)piperidine-1-carboxylate (1.80 g, 60%) as a white solid.

The data for the subtitle compound are in Table 2.

tert-Butyl 4-(4-(trifluoromethyl)-1H-imidazol-2-yl)piperidine-1-carboxylate (1 g, 3.13 mmol) was dissolved in 1,4-dioxane (5 mL) and followed by dropwise addition of HCl in 1,4-dioxane (20 mL, 3M solu.). The resulting reaction mixture was stirred at 30° C. for 16 h, the solvents were removed in vacuo and the residue was purified by triturating with diethyl ether (3×5 mL) to give Intermediate 33, 4-(4-(trifluoromethyl)-1H-imidazol-2-yl)piperidine hydrochloride (650 mg, 95%) as a white solid. The data for the title compound are in Table 2.

Procedure for the Preparation of Intermediate 37, 4-[1-methyl-4-(trifluoromethyl)-1H-imidazol-2-yl]piperidine hydrochloride salt

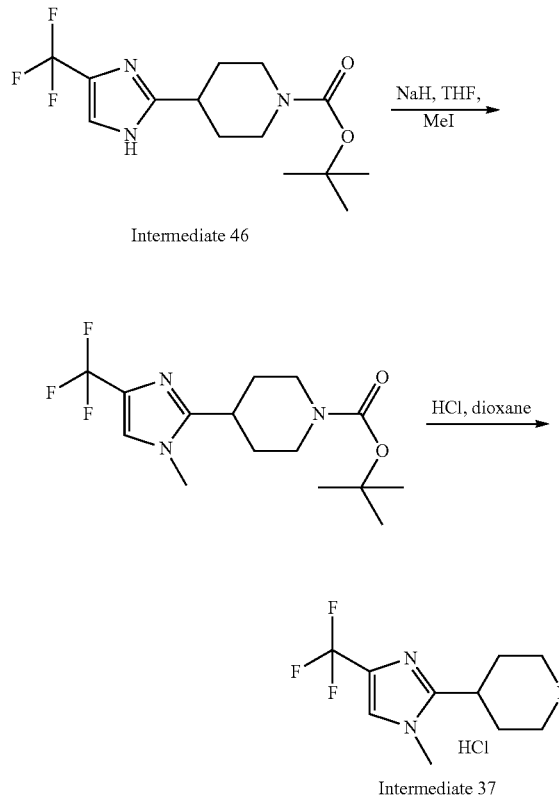

Intermediate 37 tert-Butyl 4-(4-(trifluoromethyl)-1H-imidazol-2-yl)piperidine-1-carboxylate (200 mg, 0.63 mmol) was dissolved in THF (5 mL) and 60% sodium hydride (74 mg, 1.88 mmol) added at 0° C. The reaction mixture was stirred at 0° C. for 10 mins, then methyl iodide (0.06 mL, 0.96 mmol) was added and the resulting reaction mixture was stirred at 25° C. for 2 h. The reaction mixture was partitioned between H$_2$O (60 mL) and EtOAc (45 mL), the aqueous layer was further extracted with EtOAc (2×45 mL), the organic layers were combined, dried (Na$_2$SO$_4$) and the solvents were removed in vacuo. The residue was purified by column chromatography (Normal silica, mesh size: 60-120, 0% to 2.0% to 3.5% MeOH in DCM) to give tert-butyl 4-(1-methyl-4-(trifluoromethyl)-1H-imidazol-2-yl)piperidine-1-carboxylate (190 mg, 91%) as a yellow gum.

LCMS (Method F): m/z 334 (M+H)$^+$ (ES$^+$), at 2.31 min, UV active tert-Butyl 4-(1-methyl-4-(trifluoromethyl)-1H-imidazol-2-yl)piperidine-1-carboxylate (200 mg, 0.6 mmol) was dissolved in 1,4-dioxane (5 mL) and followed by dropwise addition of HCl in 1,4-dioxane (20 mL, 4M solu.). The resulting reaction mixture was stirred at 30° C. for 16 h, the solvents were removed in vacuo and the residue was purified by triturating with diethyl ether (3×5 mL) to give Intermediate 37, 4-[1-methyl-4-(trifluoromethyl)-1H-imidazol-2-yl] piperidine hydrochloride salt (140 mg, 86.8%) as a white solid. The data for the title compound are in Table 2

Procedure for the Preparation of Intermediate 43, 4-(1,3,4-oxadiazol-2-yl)piperidine

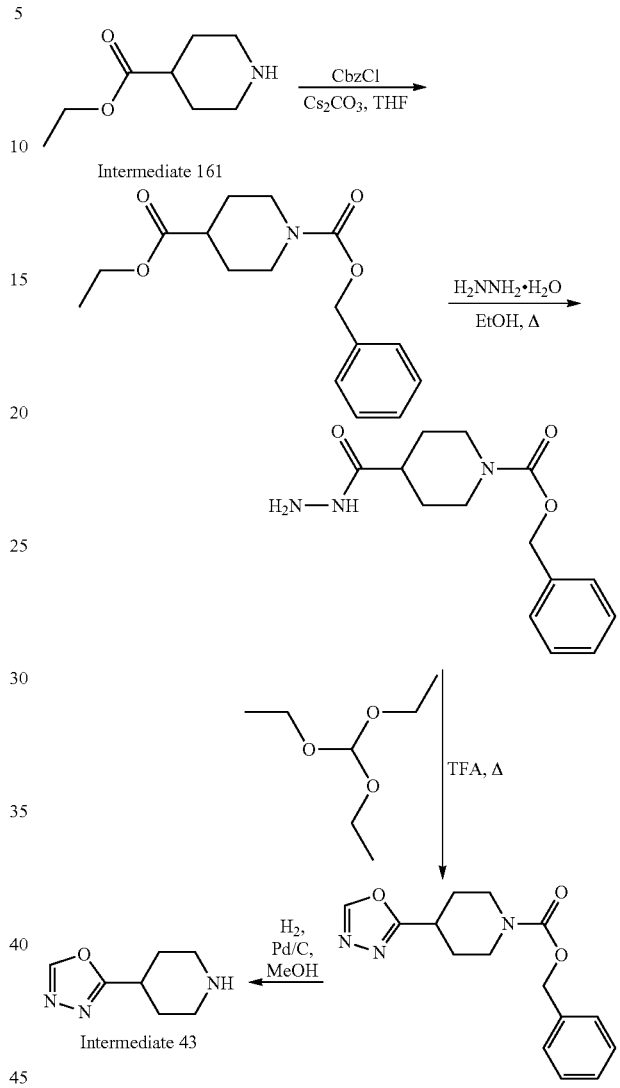

Intermediate 43

Ethyl piperidine-4-carboxylate (3.0 g, 19.1 mmol) was dissolved in THF (15 mL) and Cs$_2$CO$_3$ (7.4 g, 22.9 mmol) added at 0° C. The resulting reaction mixture was stirred at 0-5° C. for 10 mins, then benzyl chloroformate (3.2 g, 19.1 mmol) was added dropwise, and the reaction mixture was stirred at room temperature for 18 h. The reaction mixture was partitioned between H$_2$O (100 mL) and EtOAc (200 mL), the aqueous layer was extracted with EtOAc (2×200 mL), the organic layers were combined, dried (Na$_2$SO$_4$) and the solvent was removed in vacuo. The residue was purified by column chromatography (Normal silica, mesh size: 60-120, 0% to 10% EtOAc in Hexane) to give 1-benzyl 4-ethyl piperidine-1,4-dicarboxylate (4.2 g, 76.4%) as a yellow solid.

LCMS (Method F): m/z 292 (M+H)$^+$ (ES$^+$), at 2.35 min, UV active

1-Benzyl 4-ethyl piperidine-1,4-dicarboxylate (4.2 g, 14.43 mmol) was dissolved in EtOH (10 mL), hydrazine monohydrate (10 mL, 5.41 mmol) was added and the resulting reaction mixture was stirred at 90° C. overnight.

The solvents were removed in vacuo and the crude product was triturated with pentane and hexane to give benzyl 4-(hydrazinylcarbonyl)piperidine-1-carboxylate (3.8 g, 95%) as a white solid.

LCMS (Method H): m/z 278 (M+H)+ (ES+), at 1.76 min, UV active

Benzyl 4-(hydrazinylcarbonyl)piperidine-1-carboxylate (0.5 g, 1.79 mmol), was dissolved in triethylorthoformate (8 mL) and then TFA (0.1 mL) was added. The resulting reaction mixture was stirred at 80° C. overnight. The reaction mixture was partitioned between $H_2O$ (50 mL) and EtOAc (100 mL), the aqueous layer was extracted with EtOAc (2×100 mL), the organic layers were combined, dried ($Na_2SO_4$) and the solvent was removed in vacuo. The residue was purified by column chromatography (Normal silica, mesh size: 60-120, 50% to 60% EtOAc in Hexane) to give benzyl 4-(1,3,4-oxadiazol-2-yl)piperidine-1-carboxylate (0.19 g, 38%) as a yellow solid.

LCMS (Method H): m/z 288 (M+H)+ (ES+), at 2.03 min, UV active

Benzyl 4-(1,3,4-oxadiazol-2-yl)piperidine-1-carboxylate (0.15 g, 0.52 mmol) was dissolved in MeOH (10 mL). Dry 10% Pd on carbon catalyst (20 mg) was added and the reaction mixture was purged with $H_2$ gas at room temperature. The reaction mixture was stirred at room temperature for 12 h under the $H_2$ atmosphere. The reaction mass was filtered through Celite and the was solvent removed in vacuo to give Intermediate 43, 4-(1,3,4-oxadiazol-2-yl)piperidine (0.078 g, 99%) as a colorless gum. The data for the title compound are in Table 2.

Procedure for the Preparation of Intermediate 44,
4-(3-methyl-1,2,4-oxadiazol-5-yl)piperidine

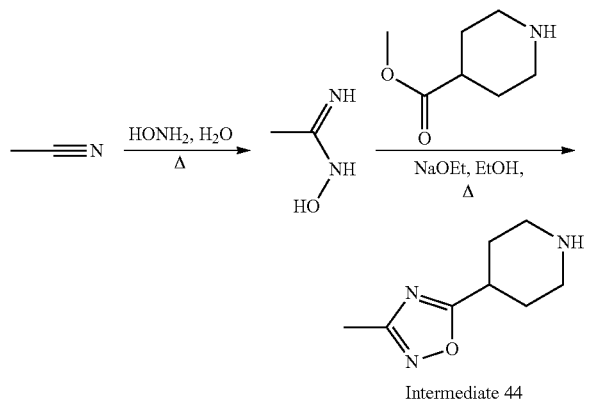

Intermediate 44

Acetonitrile (40.0 mL) and 50% hydroxylamine in water (4.20 mL) were heated at reflux at 90° C. for 24 h. The reaction mixture was cooled to 0° C. and filtered. The residue was dried to give (Z)-N-hydroxyethanimidamide (2.1 g, >100%) as a white crystalline solid.

LCMS (Method H): m/z 74 (M+H)+ (ES+), at 1.86 min, UV inactive (Z)-N-hydroxyethanimidamide (0.50 g, 6.75 mmol) and methyl piperidine-4-carboxylate (1.17 g, 7.42 mmol) were dissolved in ethanol (20 mL). 21% Sodium ethoxide solution in ethanol (0.92 mL, 13.4 mmol) was added dropwise and the reaction mixture was stirred for 30 min at it and then at 100° C. for 16 h. The solvents were removed in vacuo and the residue was purified by column chromatography (nor-mal-Phase Silica, 0 to 12% methanol in DCM) to give Intermediate 44, 4-(3-methyl-1,2,4-oxadiazol-5-yl)piperidine (380 mg, 34%) as a yellow gum. The data for the title compound are in Table 2.

Procedure for the Preparation of Intermediate 47,
4-(1H-imidazol-2-yl)piperidin-4-ol hydrochloride

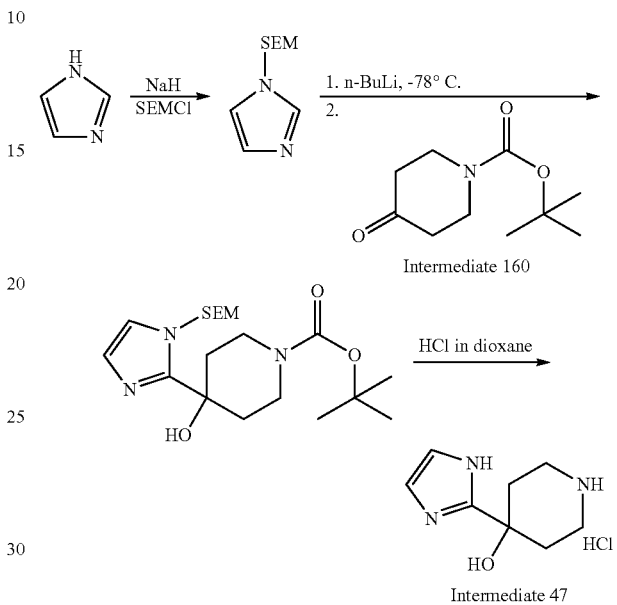

Intermediate 47

1H-Imidazole (8.0 g, 117.5 mmol) was dissolved in DMF (100 mL), sodium hydride (4.7 g, 117.5 mmol, 60% in oil) was added at room temperature. The reaction mixture was stirred at it for 2 h. 2-(trimethylsilyl) ethoxymethyl chloride (20.5 g, 123.38 mmol) was added dropwise to the reaction mixture at rt, after addition the reaction mixture was stirred at it for 16 h Reaction mixture was poured onto ice cold water (1000 mL) and extracted with EtOAc (500 mL), the aqueous layer was further extracted with EtOAc (2×500 mL), organic layers were combined, dried ($Na_2SO_4$) and the solvent were removed in vacuo. The residue was purified by column chromatography (normal phase silica, 0 to 1% methanol in DCM) to give 1-((2-(trimethylsilyl) ethoxy) methyl)-1H-imidazole (16.2 g, 68.6%) as light green gum.

LCMS (Method F): m/z 199 (M+H)+ (ES+), at 1.73 min, UV active 1-((2-(trimethylsilyl)ethoxy)methyl)-1H-imidazole (5.0 g, 25.0 mmol) was dissolved in THF (50 mL) and cooled to −78° C. n-BuLi (19.0 mL, 30 mmol, 1.6M in hexane) was added dropwise at −78° C., the reaction mixture was then stirred at −78° C. for 1 h. A solution of tert-butyl 4-oxopiperidine-1-carboxylate (5.53 g, 27 mmol) in THF (10 mL) was added dropwise at −78° C. to the reaction mixture. The reaction mixture was allowed to warm to it over 2 h. The reaction mixture was quenched with saturated $NH_4Cl$ solution (100 mL), extracted with EtOAc (50 mL), aqueous layer was further extracted with EtOAc (2×50 mL), the organic layers were combined, dried ($Na_2SO_4$), and the solvents were removed in vacuo. The residue was purified by column chromatography (normal phase silica, 0 to 20% EtOAc in hexane) to give tert-butyl 4-hydroxy-4-(1-((2-(trimethylsilyl)ethoxy)methyl)-1H-imidazol-2-yl)piperidine-1-carboxylate (8 g, 80.0%) as light yellow gum.

LCMS (Method F): m/z 398 (M+H)+ (ES+), at 2.16 min, UV active tert-Butyl 4-hydroxy-4-(1-((2-(trimethylsilyl)ethoxy)methyl)-1H-imidazol-2-yl)piperidine-1-carboxylate (2.0 g, 5.0 mmol) was dissolved in 4M HCl in 1,4-Dioxane (20 mL), the reaction mixture was stirred at it for 10 h. The solvents were removed in vacuo, and the residue was triturated with acetone (3×20 mL) to give Intermediate 47, 4-(1H-imidazol-2-yl)piperidin-4-ol (0.5 g, 60.2%) as brown gum. The data for the title compound are in Table 2.

Procedure for the Preparation of Intermediate 48, 4-(1H-imidazol-2-yl)-4-methoxypiperidine hydrochloride salt

Intermediate 48 tert-Butyl 4-hydroxy-4-(1-((2-(trimethylsilyl)ethoxy)methyl)-1H-imidazol-2-yl)piperidine-1-carboxylate (2.0 g, 5.0 mmol) was dissolved in DMF (20 mL). The solution was cooled to 0° C. under N₂ and NaH (0.24 g, 10.0 mmol) was added. The reaction mixture was stirred at 0° C. for 30 min then methyl iodide (1.07 g, 7.5 mmol) was added and the reaction mixture was stirred at it for 2 h. The reaction mixture partitioned between water (50 mL) and EtOAc (50 mL), the aqueous layer was further extracted with EtOAc (3×100 mL), the organic layers were combined, dried (Na₂SO₄), and the solvents were removed in vacuo. The residue was purified by column chromatography (normal phase, 60-120 mesh silica, 0 to 10% EtOAc in Hexane) to give tert-butyl 4-methoxy-4-(1-((2-(trimethylsilyl)ethoxy)methyl)-1H-imidazol-2-yl)piperidine-1-carboxylate (1.5 g, 75.0%) as yellow gum.

tert-butyl 4-methoxy-4-(1-((2-(trimethylsilyl)ethoxy)methyl)-1H-imidazol-2-yl)piperidine-1-carboxylate (1.5 g, 3.6 mmol) was dissolved in 4M HCl in 1,4-Dioxane (20 mL), the reaction mixture was stirred at it for 10 h. The solvents were removed in vacuo, and the residue was triturated with acetone (3×20 mL) to give Intermediate 48, 4-(1H-imidazol-2-yl)-4-methoxypiperidine (0.5 g, 76.0%) as brown solid. The data for the title compound are in Table 2.

Procedure for the Preparation of Intermediate 49, 4-(1-methyl-1H-imidazol-2-yl)piperidin-4-ol hydrochloride salt

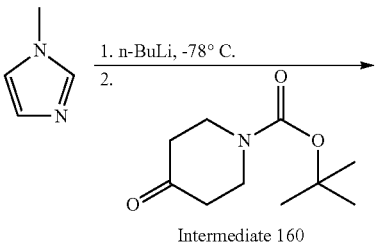

Intermediate 160

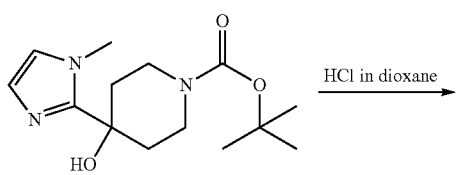

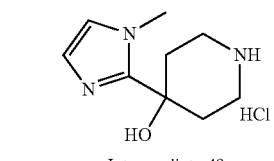

Intermediate 49

1-Methyl imidazole (6.0 g, 73.0 mmol) was dissolved in THF (100 mL) at it and the reaction mixture was cooled to −78° C. under nitrogen, n-BuLi in hexane (45.4 mL, 73.0 mmol) was slowly added. The reaction mixture was gradually warmed to 40° C. and stirred for 4 h, then cooled to −78° C. tert-Butyl 4-oxopiperidine-1-carboxylate (14.56 g, 73.0 mmol) in THF (100 mL) was added. The reaction mixture was gradually warmed to 40° C. and stirred for 10 h, then quenched with water (50 mL). The reaction mixture was partitioned between EtOAc (200 mL) and water (150 mL), the aqueous layer was extracted with EtOAc (2×200 mL) and the organic layers were combined and dried (Na₂SO₄). The solvents were removed in vacuo, and the residue was washed with Methanol to give tert-butyl 4-hydroxy-4-(1-methyl-1H-imidazol-2-yl)piperidine-1-carboxylate (14.0 g, 68.1%) as a solid which was used crude in the subsequent reaction.

LCMS (Method F): m/z 282 (M+H)+ (ES+), at 2.05 min, UV active tert-butyl 4-hydroxy-4-(1-methyl-1H-pyrrol-2-yl)piperidine-1-carboxylate (0.5 g, 1.7 mmol) was dissolved in 1,4 dioxane (30 mL) at rt and the reaction mixture was cooled to 0° C. under nitrogen, HCl in dioxane (15 mL, 4M sol.) was slowly added. The reaction mixture was stirred at it for 6 h, the solvents were removed in vacuo and the residue purified by trituration from pentane (10 mL) and diethyl ether (10 mL) to give Intermediate 49, 4-(1-methyl-1H-imidazol-2-yl)piperidin-4-ol (0.2 g, 62.5%) as brown solid. The data for the title compound are in Table 2.

Procedure for the Preparation of Intermediate 50, 4-methoxy-4-(1-methyl-1H-imidazol-2-yl)piperidine hydrochloride salt

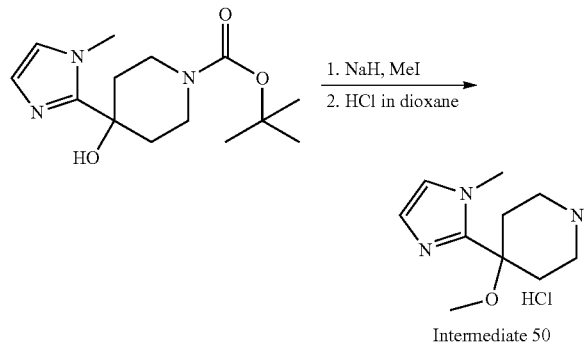

Intermediate 50 tert-Butyl 4-hydroxy-4-(1-methyl-1H-imidazol-2-yl)piperidine-1-carboxylate (3.0 g, 10.6 mmol) was dissolved in DMF (50 mL) at it and the reaction mixture was cooled to 0° C. under nitrogen, NaH (0.64 g, 16.0 mmol, 60% dispersion in oil) was added. The reaction mixture was stirred at 0° C. for 1 hr and then methyliodide (1.8 g, 128 mmol) was added dropwise. The reaction mixture was warmed rt and stirred for 10 h, then quenched with water (50 mL). The reaction mixture was extracted with EtOAc (3×200 mL), and the organic layers were combined and dried ($Na_2SO_4$). The solvents were removed in vacuo, and the residue was purified by column chromatography (normal phase, silica, 60-120 mesh, gradient 0% to 50% EtOAc in Hexane) to give tert-butyl 4-methoxy-4-(1-methyl-1H-imidazol-2-yl)piperidine-1-carboxylate (1.3 g, 41.3%) as an pale yellow solid.

LCMS (Method F): m/z 296 $(M+H)^+$ $(ES^+)$, at 2.36 min, UV active tert-Butyl 4-methoxy-4-(1-methyl-1H-imidazol-2-yl)piperidine-1-carboxylate (1.3 g, 3.3 mmol) was dissolved in 1,4 dioxane (30 mL) at it and the reaction mixture was cooled to 0° C. under nitrogen, HCl in dioxane (15 mL, 4M sol.) was slowly added. The reaction mixture was stirred at it for 6 h, the solvents were removed in vacuo, and the residue purified by trituration from pentane (10 mL) and diethyl ether (10 mL) to give Intermediate 50, 4-methoxy-4-(1-methyl-1H-imidazol-2-yl)piperidine (0.80 g, 94.1%) as an off white solid. The data for the title compound are in Table 2.

Procedure for the Preparation of Intermediate 111, benzyl 4-[(2S,4R)-1-(tert-butoxycarbonyl)-4-hydroxypyrrolidin-2-yl]piperidine-1-carboxylate

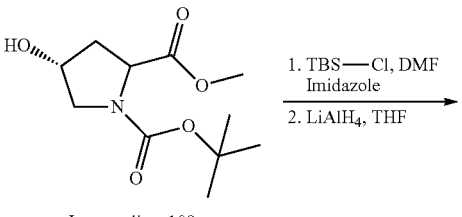

Intermediate 108

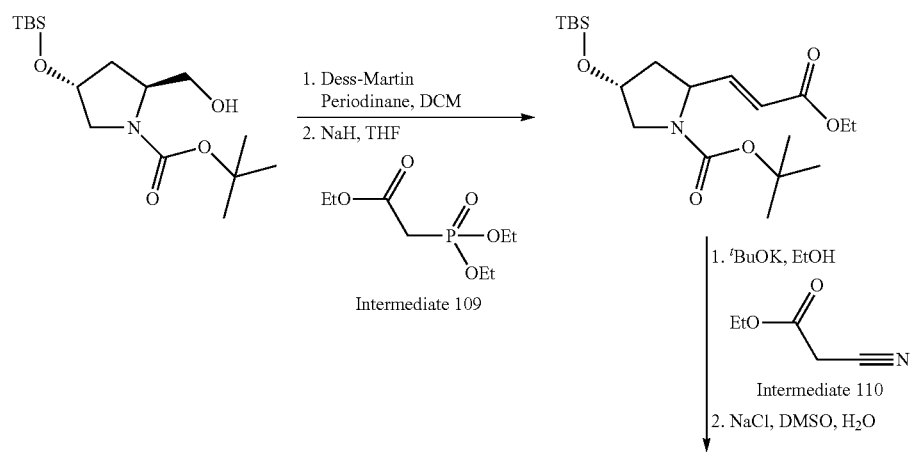

Intermediate 109

Intermediate 110

-continued

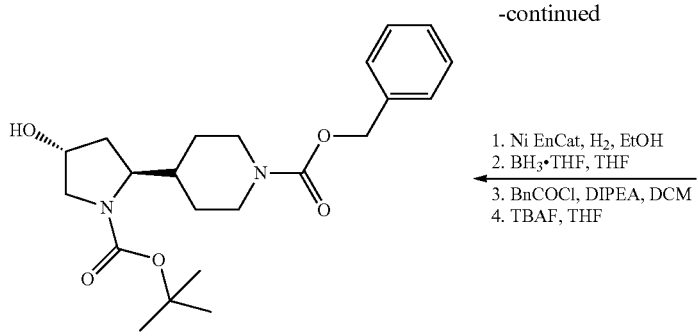

Intermediate 111

1. Ni EnCat, H₂, EtOH
2. BH₃·THF, THF
3. BnCOCl, DIPEA, DCM
4. TBAF, THF

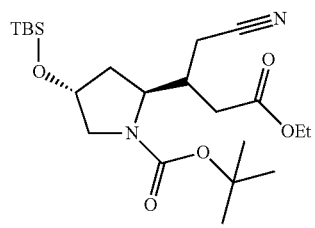

(2S,4R)-1-Boc-4-hydroxy pyrrolidine-2-carboxylic acid methyl ester (25 g, 101.93 mmol) and imidazole (34.687 g, 509.5 mmol) were dissolved in DMF (100 mL) and reaction cooled to 0° C. tert-Butyldimethylsilyl chloride was then added (36.86 g, 244.56 mmol), reaction warmed to RT and stirred for 18 h. Volatiles removed on rotavap and reaction mixture diluted with DCM (250 mL). Mixture washed with H₂O (2×250 mL), combined aqueous layers washed with DCM (250 mL), combined organic layers washed with saturated NH₄Cl$_{(aq)}$ (250 mL) and brine (250 mL) and passed through Biotage Phase separator. Volatiles removed under vacuum to give (2S,4R)-1-Boc-4-tert-butyldimethylsilyl ether-pyrrolidine-2-carboxylic acid methyl ester (35.812 g, 99%).

LCMS (Method D): m/z 260 (M+H-Boc)⁺ (ES+), at 2.64 min, UV inactive (2S,4R)-1-Boc-4-tert-butyldimethylsilyl ether-pyrrolidine-2-carboxylic acid methyl ester (42.7 g, 118.76 mmol) was dissolved in THF (100 mL) and reaction cooled to 0° C. Lithium aluminium hydride was then added (120 mL of 1.0M solution in THF, 120.0 mmol) and reaction stirred at 0° C. for 1 h. Reaction quenched with H₂O (4.5 mL), 15% NaOH solution (4.5 mL) and H₂O (13.5 mL) and filtered through a celite plug. Volatiles removed under vacuum to give (2S,4R)-1-Boc-4-tert-butyldimethylsilylether-pyrrolidine-2-hydroxy methyl (30.320 g, 77%).

LCMS (Method D): m/z 232 (M+H-Boc)⁺ (ES+), at 2.00 min, UV inactive (2S,4R)-1-Boc-4-tert-butyldimethylsilyl ether-pyrrolidine-2-hydroxy methyl (10.050 g, 30.362 mmol) was dissolved in DCM (100 mL) and Dess-Martin Periodinane (15.371 g, 36.253 mmol) was added. Reaction was stirred at it for 2 hours, then volatiles removed on rotavap and crude product loaded directly onto Biotage SNAP column (100 g) for purification (10% to 50% EtOAc in n-hexane gradient) yielding (2S,4R)-1-Boc-4-tert-butyldimethylsilyl ether-pyrrolidine-2-carbaldehyde (2.150 g, 22%).

To a suspension of sodium hydride (135 mg of 60% dispersion in oil, 3.338 mmol) in THF (8 mL) at 0° C. was added triethylphosphono acetate (0.665 mL, 3.338 mmol). After 10 mins, (2S,4R)-1-Boc-4-tert-butyldimethylsilyl ether-pyrrolidine-2-carbaldehyde (1.002 g, 3.034 mmol) in THF (2 mL) was added and reaction stirred at 0° C. for 30 mins. Volatiles removed on rotavap and reaction mixture diluted with DCM (20 mL). Mixture washed with H₂O (2×20 mL), combined aqueous layers washed with DCM (20 mL), combined organic layers washed with brine (20 mL) and passed through Biotage Phase separator. Volatiles removed under vacuum and crude mixture loaded onto Biotage SNAP column (100 g) and purified by column chromatography (0 to 30% EtOAc in Hexane) yielding tert-butyl(2S,4R)-4-{[tert-butyl(dimethyl)silyl]oxy}-2-[(1E)-3-ethoxy-3-oxoprop-1-en-1-yl]pyrrolidine-1-carboxylate as a colourless oil (545 mg, 45%).

LCMS (Method D): m/z 300 (M+H-Boc)⁺ (ES+), at 2.85 min, UV inactive.

To a solution of potassium tert-butoxide (421 mg, 3.753 mmol) and ethyl cyanoacetate (0.399 mL, 3.753 mmol) in EtOH (5 mL) was added tert-butyl(2S,4R)-4-{[tert-butyl(dimethyl)silyl]oxy}-2-[(1E)-3-ethoxy-3-oxoprop-1-en-1-yl]pyrrolidine-1-carboxylate (500 mg, 1.251 mmol) and reaction stirred at 78° C. for 18 h. AcOH was added (0.200 mL) and volatiles removed on rotavap. Reaction mixture diluted with DCM (50 mL) and washed with H₂O (2×50 mL), combined aqueous layers washed with DCM (50 mL), combined organic layers washed with brine (50 mL) and passed through Biotage Phase separator. Volatiles removed under vacuum and crude mixture loaded onto Biotage SNAP column (100 g) and purified by column chromatography (0 to 30% EtOAc in Hexane) yielding diethyl 3-[(4R)-1-(tert-butoxycarbonyl)-4-{[tert-butyl(dimethyl)silyl]oxy}pyrrolidin-2-yl]-2-cyanopentanedioate as a yellow oil (567 mg, 89%).

To a solution of sodium chloride (71 mg, 1.212 mmol) and DMSO (0.040 mL, 2.204 mmol) in H₂O (3 mL) was added diethyl 3-[(4R)-1-(tert-butoxycarbonyl)-4-{[tert-butyl(dimethyl)silyl]oxy}pyrrolidin-2-yl]-2-cyanopentanedioate (565 mg, 1.102 mmol) and reaction stirred at 145° C. for 2 h. Ice water was added was added (50 mL) followed by EtOAc (50 mL) and organic layer washed with H₂O (2×50 mL). Combined organic layers washed with brine (50 mL) and passed through Biotage Phase separator. Volatiles removed under vacuum and crude mixture loaded onto Biotage SNAP column (50 g) and purified by column chromatography (0 to 30% EtOAc in Hexane) yielding tert-butyl(4R)-4-{[tert-butyl(dimethyl)silyl]oxy}-2-(1-cyano-4-ethoxy-4-oxobutan-2-yl)pyrrolidine-1-carboxylate as a yellow oil (351 mg, 72%).

LCMS (Method D): m/z 341 (M+H-Boc)⁺ (ES+), at 2.77 min, UV inactive

To a flask containing NiEnCat™ (65 g wet beads, ~0.25 equiv.) was added tert-butyl(4R)-4-{[tert-butyl(dimethyl)silyl]oxy}-2-(1-cyano-4-ethoxy-4-oxobutan-2-yl)pyrrolidine-1-carboxylate (8.700 g, 19.7 mmol) in EtOH (75 mL) and reaction stirred at 78° C. under a hydrogen balloon atmosphere for 96 h. Reaction mixture filtered over a celite plug and volatiles removed under vacuum, the crude mixture was loaded onto Biotage SNAP column (340 g) and purified by column chromatography (2.5 to 10% MeOH in DCM) yielding tert-butyl(4R)-4-{[tert-butyl(dimethyl)silyl]oxy}-2-(2-oxopiperidin-4-yl)pyrrolidine-1-carboxylate as a yellow oil (4.665 g, 59%).

LCMS (Method D): m/z 399 (M+H)⁺ (ES+), at 1.90 min, UV inactive

To a solution of tert-butyl(4R)-4-{[tert-butyl(dimethyl) silyl]oxy}-2-(2-oxopiperidin-4-yl)pyrrolidine-1-carboxylate (1.850 g, 4.648 mmol) THF (30 mL) was added borane: tetrahydrofuran (9.3 mL of 1.0M solution in THF, 9.300 mmol) at 0° C. and reaction stirred at 60° C. for 30 mins. Reaction cooled to rt and quenched with MeOH (13 mL) and volatiles removed on rotavap. Reaction mixture diluted with DCM (100 mL) and washed with 1M NaOH$_{(aq)}$ (2×100 mL), combined aqueous layers washed with DCM (100 mL), combined organic layers washed with brine (250 mL) and passed through Biotage Phase separator. Volatiles removed under vacuum yielding tert-butyl(2S,4R)-4-{[tert-butyl(dimethyl)silyl]oxy}-2-(piperidin-4-yl)pyrrolidine-1-carboxylate as a yellow oil (1.830 g, >99%).

LCMS (Method D): m/z 285 (M+H-Boc)⁺ (ES+), at 3.00 min, UV inactive

To a solution of tert-butyl(2S,4R)-4-{[tert-butyl(dimethyl)silyl]oxy}-2-(piperidin-4-yl)pyrrolidine-1-carboxylate (1.830 g, 4.766 mmol) in DCM (20 mL) was added diisopropylethylamine (1.814 mL, 10.484 mmol) and benzyl chloroformate (0.816 mL, 5.719 mmol) at 0° C. Reaction warmed to rt and stirred for 18 h. Reaction mixture diluted with DCM (100 mL) and washed with 1M NaOH$_{(aq)}$ (2×100 mL), combined aqueous layers washed with DCM (100 mL), combined organic layers washed with brine (250 mL) and passed through Biotage Phase separator. Volatiles removed under vacuum and crude mixture loaded onto Biotage SNAP column (100 g) and purified by column chromatography (10 to 40% EtOAc in Hexane) yielding benzyl 4-[(2S,4-(tert-butoxycarbonyl)-4-{[tert-butyl(dimethyl)silyl]oxy]pyrrolidin-2-yl}piperidine-1-carboxylate as a colourless oil (700 mg, 28%).

To a solution of benzyl 4-[(2S,4R)-1-(tert-butoxycarbonyl)-4-{[tert-butyl(dimethyl)silyl]oxy}pyrrolidin-2-yl]piperidine-1-carboxylate (0.780 g, 1.504 mmol) in THF (5 mL) was added tetrabutylammonium fluoride (1.800 mL of 1.0 M THF solution, 1.800 mmol) and reaction stirred at it for 1 h. Reaction mixture diluted with DCM (100 mL) and washed with H₂O (2×100 mL), combined aqueous layers washed with DCM (100 mL), combined organic layers washed with brine (250 mL) and passed through Biotage Phase separator. Volatiles removed under vacuum yielding Intermediate 111, benzyl 4-[(2S,4R)-1-(tert-butoxycarbonyl)-4-hydroxypyrrolidin-2-yl]piperidine-1-carboxylate, as a colourless oil (500 mg, 82%). The data for the title compound are in Table 2.

Procedure for the Preparation of Intermediate 112, tert-butyl(2S,4S)-4-fluoro-2-(piperidin-4-yl)pyrrolidine-1-carboxylate

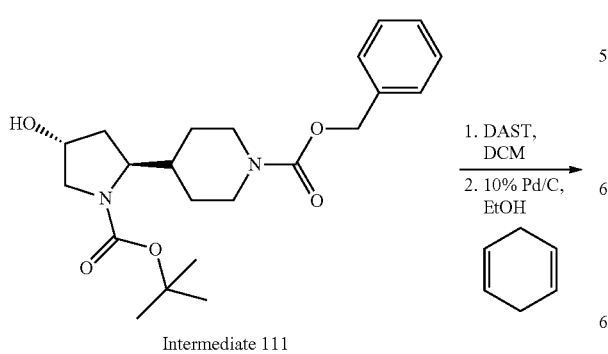

Intermediate 111

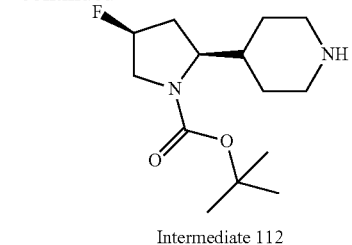

Intermediate 112

Benzyl 4-[(2S,4R)-1-(tert-butoxycarbonyl)-4-hydroxypyrrolidin-2-yl]piperidine-1-carboxylate (100 mg, 0.247 mmol) was dissolved in DCM (1 mL) at −40° C. and DAST was added (0.049 mL, 0.371 mmol). Reaction warmed to rt and stirred for 2 h. Reaction mixture diluted with DCM (25 mL) and washed with saturated NaHCO$_{3(aq)}$ (2×25 mL), combined aqueous layers washed with DCM (25 mL), combined organic layers washed with brine (25 mL) and passed through Biotage Phase separator. Volatiles removed under vacuum to yield benzyl 4-[(2S,4S)-1-(tert-butoxycarbonyl)-4-fluoropyrrolidin-2-yl]piperidine-1-carboxylate (0.090 g, 90%).

LCMS (Method D): m/z 307 (M+H-Boc)⁺ (ES+), at 2.31 min, UV inactive

To a solution of benzyl 4-[(2S,4S)-1-(tert-butoxycarbonyl)-4-fluoropyrrolidin-2-yl]piperidine-1-carboxylate (0.090 g, 0.221 mmol) dissolved in EtOH (2 mL) was added 10% Pd/C (10 mg) and 1,4 cyclohexadiene (0.147 mL, 1.530 mmol) and reaction stirred at 70° C. for 1 h. Reaction filtered through a celite plug and volatiles removed under vacuum to yield Intermediate 112, tert-butyl(2S,4S)-4-fluoro-2-(piperidin-4-yl)pyrrolidine-1-carboxylate (55 mg, 92%). The data for the title compound are in Table 2.

Procedure for the Preparation of Intermediate 113, tert-butyl(2S)-4,4-difluoro-2-(piperidin-4-yl)pyrrolidine-1-carboxylate

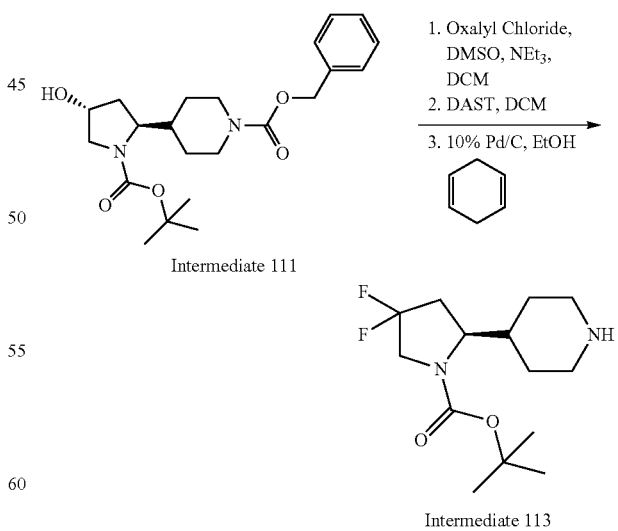

Intermediate 111

Intermediate 113

Oxalyl chloride (0.065 mL, 0.741 mmol) was dissolved in DCM (1 mL) at −78° C. and DMSO was added (0.100 mL). After 5 minutes at −78° C., benzyl 4-[(2S,4R)-1-(tert-butoxycarbonyl)-4-hydroxypyrrolidin-2-yl]piperidine-1-carboxylate (200 mg, 0.494 mmol) was added in DCM (2 mL) followed by triethylamine (0.345 mL, 2.47 mmol) after a further 5 mins at −78° C. Reaction warmed to it and stirred for 30 mins. Reaction mixture diluted with DCM (25 mL) and washed with saturated NaHCO$_{3(aq)}$ (2×25 mL), combined aqueous layers washed with DCM (25 mL), combined organic layers washed with brine (25 mL) and passed through Biotage Phase separator. Volatiles removed under vacuum to yield benzyl 4-[(2S)-1-(tert-butoxycarbonyl)-4-oxopyrrolidin-2-yl]piperidine-1-carboxylate (0.170 g, 85%).

LCMS (Method D): m/z 303 (M+H-Boc)$^+$ (ES+), at 2.15 min, UV inactive benzyl 4-[(2S)-1-(tert-butoxycarbonyl)-4-oxopyrrolidin-2-yl]piperidine-1-carboxylate (170 mg, 0.422 mmol) was dissolved in DCM (1 mL) at −78° C. and DAST was added (0.167 mL, 1.267 mmol). Reaction warmed to it and stirred for 18 h. Reaction mixture diluted with DCM (25 mL) and washed with saturated NaHCO$_{3(aq)}$ (2×25 mL), combined aqueous layers washed with DCM (25 mL), combined organic layers washed with brine (25 mL) and passed through Biotage Phase separator. Volatiles removed under vacuum to yield benzyl 4-[(2S)-1-(tert-butoxycarbonyl)-4,4-difluoropyrrolidin-2-yl]piperidine-1-carboxylate (0.070 g, 39%).

LCMS (Method D): m/z 325 (M+H-Boc)$^+$ (ES+), at 2.41 min, UV inactive

To a solution of benzyl 4-[(2S)-1-(tert-butoxycarbonyl)-4,4-difluoropyrrolidin-2-yl]piperidine-1-carboxylate (0.067 g, 0.158 mmol) dissolved in EtOH (2 mL) was added 10% Pd/C (10 mg) and 1,4 cyclohexadiene (0.105 mL, 1.105 mmol) and reaction stirred at 70° C. for 1 h. Reaction filtered through a celite plug and volatiles removed under vacuum to yield Intermediate 113, tert-butyl(2S)-4,4-difluoro-2-(piperidin-4-yl)pyrrolidine-1-carboxylate (30 mg, 65%). The data for the title compound are in Table 2.

Procedure for the Preparation of Intermediate 125, tert-butyl(2S)-4,4-difluoro-2-methylpyrrolidine-1-carboxylate

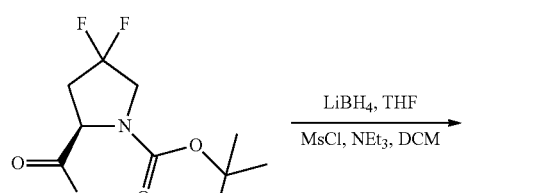

Intermediate 257

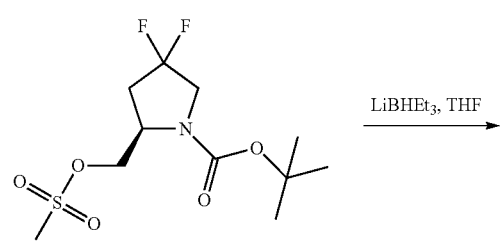

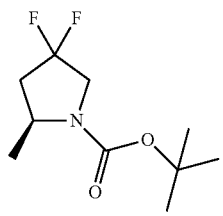

Intermediate 125

To 1-tert-butyl 2-methyl(2R)-4,4-difluoropyrrolidine-1,2-dicarboxylate (2 g, 7.5 mmol) in THF (20 mL) was added lithium borohydride solution in THF (2.0 M, 7.5 mL, 15 mmol) at 0° C. and the reaction was warmed to RT and stirred for 2 h. The reaction was quenched by the portion-wise addition of saturated aqueous NaHCO$_3$, and once effervescence had ceased, the mixture was concentrated to remove THF. The aqueous mixture was partitioned between saturated aqueous NaHCO$_3$ and DCM (×2), the organic phases were passed through a phase separator and concentrated to afford the crude tert-butyl(2R)-4,4-difluoro-2-(hydroxymethyl)pyrrolidine-1-carboxylate (1.98 g, >100%) as an oil.

LCMS (Method C): m/z 260 (M+Na)$^+$ (ES$^+$), at 1.09 min, UV inactive.

To a solution of tert-butyl(2R)-4,4-difluoro-2-(hydroxymethyl)pyrrolidine-1-carboxylate (1 g, 4.2 mmol) in DCM (10 mL) and triethylamine (1.5 mL, 11 mmol) at 0° C. was added MsCl (0.42 mL, 5.4 mmol) portion-wise. The mixture was stirred at 0° C. for 100 min, then partitioned between ice cold saturated aqueous NaHCO$_3$ and ice cold DCM (×2), the organic phases were passed through a phase separator and concentrated to afford the crude tert-butyl(2R)-4,4-difluoro-2-{[(methylsulfonyl)oxy]methyl}pyrrolidine-1-carboxylate (1.55 g, >100%) as an oil.

LCMS (Method C): m/z 338 (M+Na)$^+$ (ES$^+$), at 1.28 min, UV inactive.

To a solution of tert-butyl(2R)-4,4-difluoro-2-{[(methylsulfonyl)oxy]methyl}pyrrolidine-1-carboxylate (1.55 g, 4.9 mmol) in THF (15 mL) at 0° C. was added LiBHEt$_3$ solution in THF (1.0 M, 9.8 mL, 9.8 mmol), portion-wise over 10 min. The mixture was then stirred for 3 days, allowing the cooling bath to expire. The mixture was cooled back to 0° C., quenched by the addition of H$_2$O, then concentrated to remove THF. The aqueous mixture was partitioned between saturated aqueous NaHCO$_3$ and DCM (×2), the organic phases were passed through a phase separator and concentrated to afford the crude Intermediate 125, tert-butyl(2S)-4,4-difluoro-2-methylpyrrolidine-1-carboxylate (0.89 g, 82%) as an oil. The data for the title compound are in Table 2.

Procedure for the Preparation of Intermediate 126, tert-butyl(2R)-4,4-difluoro-2-(hydroxymethyl)pyrrolidine-1-carboxylate

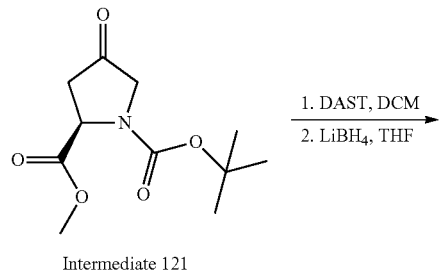

Intermediate 121

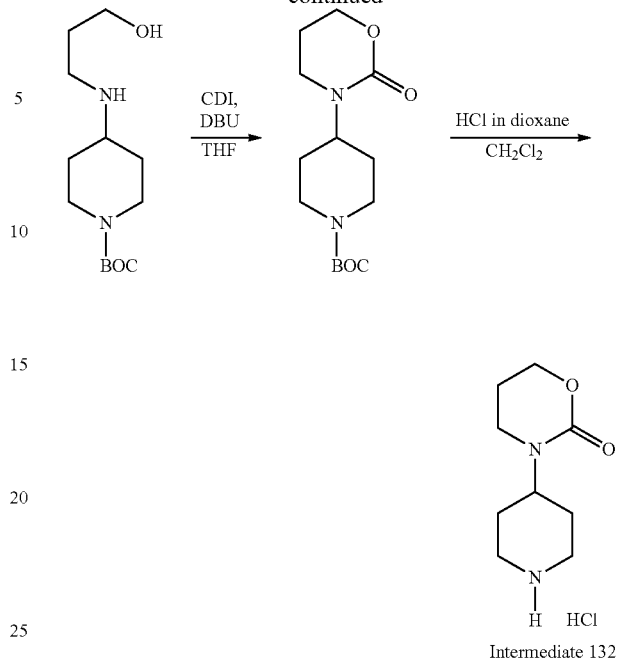

(R)-1-tert-Butyl 2-methyl 4-oxopyrrolidine-1,2-dicarboxylate (1.00 g, 4.111 mmol) was dissolved in DCM (10 mL) at −78° C. and DAST was added (1.629 mL, 12.332 mmol). Reaction warmed to rt and stirred for 2 h. Reaction mixture diluted with DCM (100 mL) and washed with saturated NaHCO$_{3(aq)}$ (2×100 mL), combined aqueous layers washed with DCM (100 mL), combined organic layers washed with brine (25 mL) and passed through Biotage Phase separator. Solvent were removed in vacuo to give an orange oil (0.957 g, 90%).

To (R)-1-tert-Butyl 2-methyl 4,4-difluoropyrrolidine-1,2-dicarboxylate (500 mg, 1.885 mmol) in THF (5 mL) was added lithium borohydride as a 2.0M solution in THF (1.90 mL, 3.80 mmol) at 0° C. and the reaction was warmed to RT and stirred for 1 h. The solvents were removed in vacuo, and the reaction mixture diluted with DCM (50 mL) and washed with saturated NaHCO$_{3(aq)}$ (2×50 mL), combined aqueous layers washed with DCM (50 mL), combined organic layers washed with brine (50 mL) and passed through Biotage Phase separator. Volatiles removed under vacuum yielding Intermediate 126, tert-butyl(2R)-4,4-difluoro-2-(hydroxymethyl)pyrrolidine-1-carboxylate (452 mg, 92%).

Procedure for the Preparation of Intermediate 132, 3-(piperidin-4-yl)-1,3-oxazinan-2-one hydrochloride

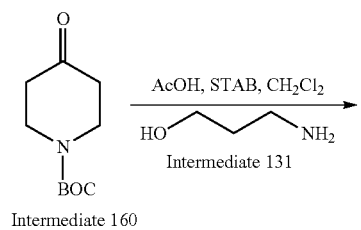

Intermediate 160 tert-Butyl 4-oxopiperidine-1-carboxylate (0.796 g, 4.00 mmol) and 3-aminopropan-1-ol (0.330 g, 4.4 mmol) were mixed in CH$_2$Cl$_2$ (20 mL) at rt, AcOH (0.68 mL, 12.0 mmol) was added and stirred for 3 h. STAB (2.34 g, 10.0 mmol) was added and the reaction mixture was stirred under nitrogen at rt overnight. The reaction mixture was quenched with the addition of NaHCO$_3$ (sat aq.) (40 mL) extracted with CH$_2$Cl$_2$ (4×45 mL) and the combined organic layers were washed with brine, then dried over MgSO$_4$ and filtered. The solvents were removed in vacuo to give crude tert-butyl 4[(3-hydroxypropyl)amino]piperidine-1-carboxylate (1.03 g, 4.00 mmol) which was used without purification.

LCMS (Method B): m/z 259 (M+H)$^+$ (ES+), at 0.24 min, UV inactive.

tert-Butyl 4[(3-hydroxypropyl)amino]piperidine-1-carboxylate (1.03 g, 4.00 mmol), CDI (1.36 g, 8.4 mmol) and DBU (0.24 mL, 1.60 mmol) were dissolved in THF (40 mL), the mixture heated to reflux and maintained for 72 h. The solvents were removed in vacuo and the residue purified by column chromatography [Biotage SNAP cartridge KP-sil 25 g, 40-63 μm, 60 Å, 50 mL per min, gradient 0% to 10% MeOH in DCM]) to give tert-butyl 4-(2-oxo-1,3-oxazinan-3-yl)piperidine-1-carboxylate (0.60 g, 53%) as a colourless oil.

LCMS (Method B): m/z 307 (M+Na)$^+$ (ES+), at 0.16 min, UV inactive.

tert-Butyl 4-(2-oxo-1,3-oxazinan-3-yl)piperidine-1-carboxylate (0.60 g, 2.11 mmol) was dissolved in CH$_2$Cl$_2$ (21 mL), 4 M hydrogen chloride in dioxane (2.64 mL, 10.5 mmol) added and the reaction mixture stirred at it overnight. The precipitate was collected by filtration, washed with CH$_2$Cl$_2$ (2×20 mL) and dried to give Intermediate 132, 3-(piperidin-4-yl)-1,3-oxazinan-2-one hydrochloride (0.352 g, 76%) as a colourless solid. The data for the title compound are in Table 2.

Procedure for the Preparation of Intermediate 151, ethyl 2-(4-oxopiperidin-1-yl)-6-azaspiro[3.4]octane-6-carboxylate hydrochloride

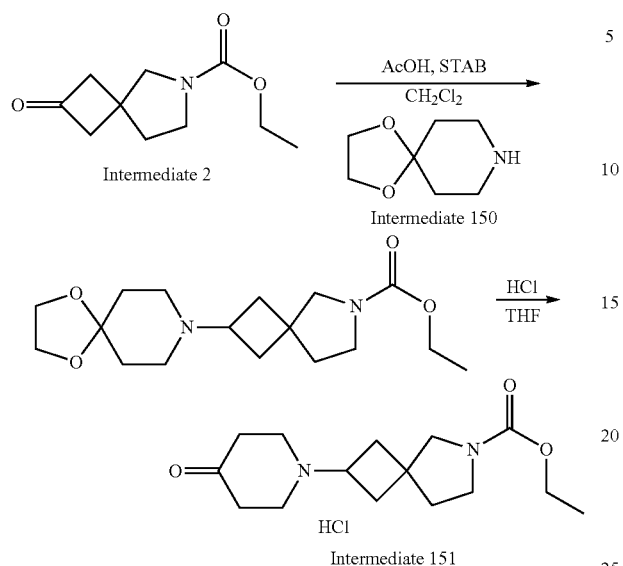

Ethyl 2-oxo-6-azaspiro[3.4]octane-6-carboxylate (0.985 g, 5.00 mmol) and 1,4-dioxa-8-azaspiro[4.5]decane (0.715 g, 5.00 mmol) were mixed in CH$_2$Cl$_2$ (50 mL) at rt, AcOH (0.31 mL, 5.50 mmol) was added and stirred for 3 h. STAB (2.65 g, 12.5 mmol) was added and the reaction mixture was stirred under nitrogen at it overnight. The reaction mixture was quenched with the addition of NaHCO$_3$ (sat aq.) (40 mL) extracted with CH$_2$Cl$_2$ (4×45 mL) and the combined organic layers were washed with brine, then dried over MgSO$_4$ and filtered. The solvents were removed in vacuo to give crude ethyl 2-(1,4-dioxa-8-azaspiro[4.5]dec-8-yl)-6-azaspiro[3.4]octane-6-carboxylate as a mixture of diastereomers which was used without further purification.

LCMS (Method D): m/z 325 (M+H)$^+$ (ES+), at 1.11 min and 1.16 min, UV inactive.

Crude ethyl 2-(1,4-dioxa-8-azaspiro[4.5]dec-8-yl)-6-azaspiro[3.4]octane-6-carboxylate (1.62 g, 5.00 mmol) was dissolved in THF (10 mL), water (10 mL) and concentrated hydrochloric acid (10 mL) were added and the mixture stirred at rt overnight. The solvents were removed in vacuo and the residue tritiated from Et$_2$O to give Intermediate 151, ethyl 2-(4-oxopiperidin-1-yl)-6-azaspiro[3.4]octane-6-carboxylate hydrochloride (1.30 g, 82%) as a colourless solid. The data for the title compound are in Table 2.

Procedure for the Preparation of Intermediate 164, 4-(1,3-thiazol-4-yl)piperidine hydrobromide

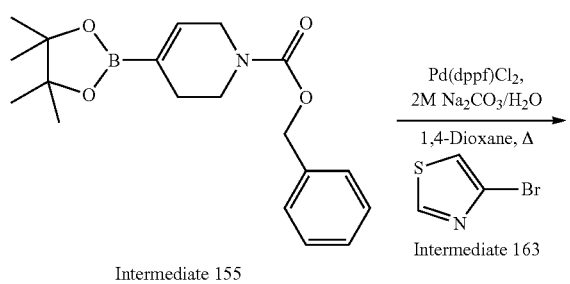

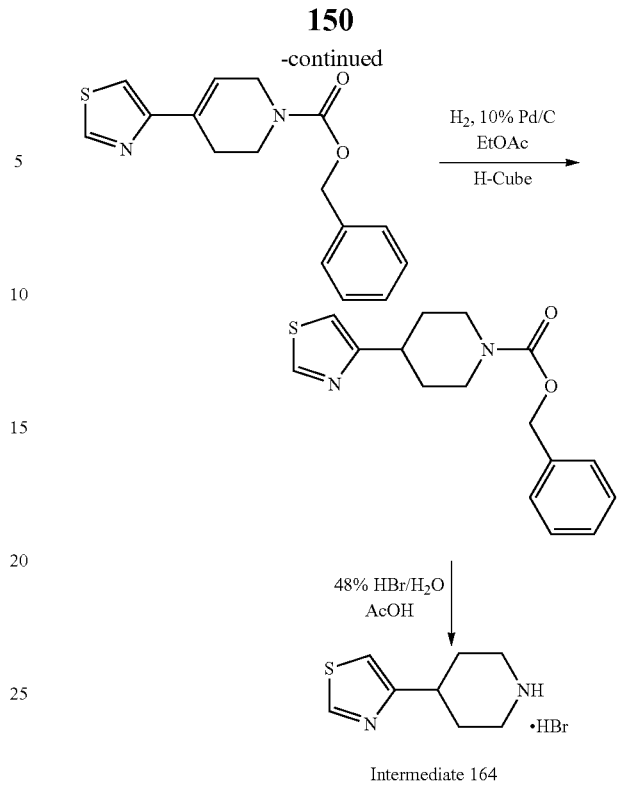

Aqueous sodium carbonate solution (2M) and 1,4-dioxane were both degassed by passing a stream of nitrogen through a fritted glass tube into the liquids for 15 min. Benzyl 4-(4,4,5,5-tetramethyl-1, 3,2-dioxaborolan-2-yl)-3, 6-dihydropyridine-1(2H)-carboxylate (250 mg, 0.73 mmol), 4-bromo-1,3-thiazole (119 mg, 0.73 mmol), [1,1'-Bis(diphenylphosphino)ferrocene]dichloropalladium(II) (32 mg, 0.044 mmol), degassed aqueous sodium carbonate solution (2M, 1.1 mL, 2.2 mmol) and degassed 1,4-dioxane (3 mL) were placed into a nitrogen flushed tube, sealed and heated under pressure at 90° C. for 2.5 h. The cooled reaction mixture was diluted with H$_2$O and extracted with EtOAc. The organic phase was passed through a phase separator and concentrated onto flash silica (15 mL). The resulting powder was purified by column chromatography (normal phase, [Biotage SNAP cartridge KP-sil 50 g, 40-63 µm, 60 A], 40 mL per min, 65% Et$_2$O in isohexane isochratic) to give benzyl 4-(1,3-thiazol-4-yl)-3,6-dihydropyridine-1(2H)-carboxylate (173 mg, 79%).

LCMS (Method C): m/z 301 (M+H)$^+$ (ES$^+$), at 1.46 min, UV active.

A solution of benzyl 4-(1,3-thiazol-4-yl)-3,6-dihydropyridine-1(2H)-carboxylate (150 mg, 0.50 mmol) in EtOAc (10 mL) was hydrogenated over 10% palladium on carbon catalyst at 100 bar pressure and at 50° C. at a flow rate of 1 mL/min using a H-Cube apparatus. The solution was concentrated to give benzyl 4-(1,3-thiazol-4-yl)piperidine-1-carboxylate (143 mg, 95%).

LCMS (Method A): m/z 303 (M+H)$^4$ (ES$^+$), at 1.92 min, UV active.

A solution of benzyl 4-(1,3-thiazol-4-yl)piperidine-1-carboxylate (127 mg, 0.42 mmol) in AcOH (1 mL) and 48% aqueous HBr (1 mL) was stirred at RT overnight. The mixture was then concentrated and the residue azeotroped with toluene to give Intermediate 164, 4-(1,3-thiazol-4-yl)piperidine hydrobromide (160 mg, >100%). The data for the title compound is in Table 2.

Procedure for the Preparation of Intermediate 172, (1R,5S)-3-phenyl-2,4-dioxa-3-borabicyclo[3.3.1]nonan-7-one

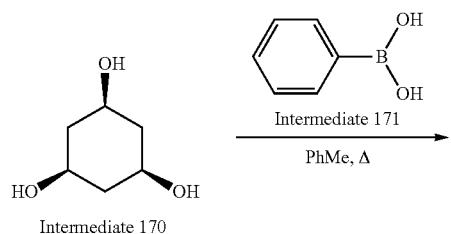

(1.43 g, 87%) as a solid, which was used immediately. (1R,5S,7R)-3-phenyl-2,4-dioxa-3-borabicyclo[3.3.1]nonan-7-ol (1.4 g, 6.4 mmol) was dissolved in DCM (50 mL). Sodium acetate (1.31 g, 16 mmol) and pyridinium chlorochromate (12.9 g, 11 mmol) were added and the reaction mixture was stirred for 16 h. The reaction mixture was filtered through Celite, and the filtrate was concentrated to give the crude product which was recrystallization from DCM:hexane (1:4) to give Intermediate 172, (1R,5S)-3-phenyl-2,4-dioxa-3-borabicyclo[3.3.1]nonan-7-one (0.65 g, 38%) as a solid. The data for the title compound are in Table 2.

Procedure for the Preparation of Intermediate 174, 4-[(2R)-4,4-difluoro-2-(methoxymethyl)pyrrolidin-1-yl]piperidine trifluoroacetate salt

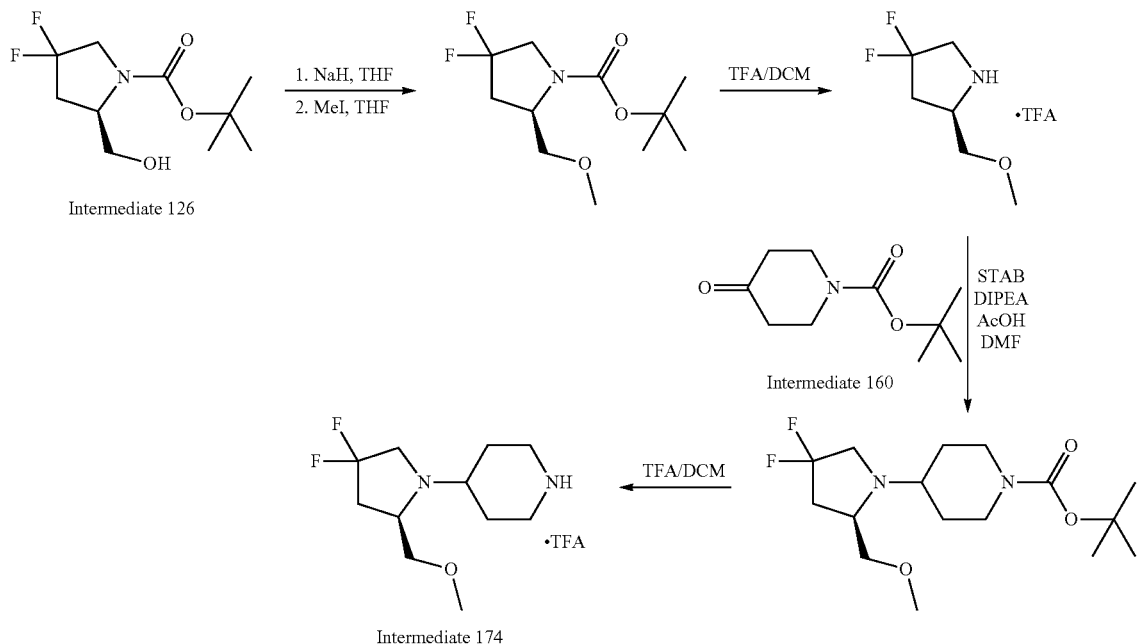

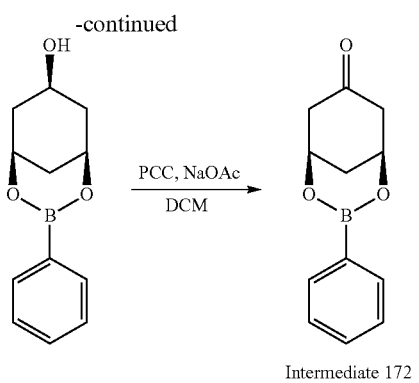

(1S,3S,5S)-Cyclohexane-1,3,5-triol (1.0 g, 6.0 mmol) and phenylboronic acid (0.72 g, 6.0 mmol) were dissolved in toluene (35 mL) and heated at reflux at 120° C. for 16 h. The reaction mixture was concentrated to give the crude (1R, 5S,7R)-3-phenyl-2,4-dioxa-3-borabicyclo[3.3.1]nonan-7-ol A solution of tert-butyl(2R)-4,4-difluoro-2-(hydroxymethyl)pyrrolidine-1-carboxylate (150 mg, 0.63 mmol) in THF (5 mL) was cooled in ice water and treated with 60% sodium hydride suspension in mineral oil (30 mg, 0.75 mmol). The mixture was stirred in ice for 30 min then at RT for 1.5 h before adding methyl iodide (0.118 mL, 1.9 mmol) and stirring at RT overnight. The mixture was quenched with a drop of $H_2O$ then concentrated to remove THF. The residue was partitioned between sat. aqueous $NaHCO_3$ and DCM (×2), the organic phase was passed through a phase separator and concentrated to give the crude tert-butyl(2R)-4,4-difluoro-2-(methoxymethyl)pyrrolidine-1-carboxylate (110 mg, 69%) as an oil.

LCMS (Method C): m/z 274 (M+Na)$^+$ (ES$^+$), at 1.35 min, UV inactive.

A solution of the crude tert-butyl(2R)-4,4-difluoro-2-(methoxymethyl)pyrrolidine-1-carboxylate (110 mg, 0.44 mmol) in DCM (2 mL) and TFA (2 mL) was stirred at RT for 40 min then diluted with toluene and concentrated. The residue was azeotroped with toluene (×2) to give the crude (2R)-4,4-difluoro-2-(methoxymethyl)pyrrolidine trifluoroacetate salt as an oil (172 mg, >100%).

LCMS (Method C): m/z 152 (M+H)⁺ (ES⁺), at 0.73 min, UV inactive.

The crude (2R)-4,4-difluoro-2-(methoxymethyl)pyrrolidine trifluoroacetate salt (172 mg, assumed 0.44 mmol) was dissolved in DMF (5 mL). To the solution was added DIPEA (0.38 mL, 2.2 mmol), AcOH (0.038 mL, 0.66 mmol), tert-butyl 4-oxopiperidine-1-carboxylate (0.087 g, 0.44 mmol) and STAB (0.278 g, 1.3 mmol) in that order. The mixture was stirred at RT for 2 days, then concentrated to remove DMF. The residue was partitioned between sat. aqueous NaHCO₃ and DCM (×2) and the organic phase was passed through a phase separator and concentrated to give the crude tert-butyl 4-[(2R)-4,4-difluoro-2-(methoxymethyl)pyrrolidin-1-yl]piperidine-1-carboxylate (0.241 g, >100%) as an oil.

LCMS (Method C): m/z 335 (M+H)⁺ (ES⁺), at 1.43 min, UV inactive.

A solution of the crude tert-butyl 4-[(2R)-4,4-difluoro-2-(methoxymethyl)pyrrolidin-1-yl]piperidine-1-carboxylate (0.241 g, assumed 0.44 mmol) in DCM (2 mL) and TFA (2 mL) was stirred at RT for 45 min then diluted with toluene and concentrated. The residue was azeotroped with toluene (×2) to give the crude Intermediate 174, 4-[(2R)-4,4-difluoro-2-(methoxymethyl)pyrrolidin-1-yl]piperidine trifluoroacetate salt as an oil.

The data for the title compound is in Table 2.

Procedure for the Preparation of Intermediate 179, 1-[(2R)-4,4-difluoro-1-(piperidin-4-yl)pyrrolidin-2-yl]ethanol trifluoroacetate salt separated and the aqueous was re-extracted with EtOAc. The combined organic phases were passed through a phase separator and concentrated to give the crude aldehyde, which was immediately dissolved in THF (5 mL), cooled to −78° C. and treated with methylmagnesium bromide in ether (3M, 0.42 mL, 1.3 mmol). The mixture was removed from the cooling bath, stirred for 2.75 h and then quenched by the addition of sat. aqueous NH₄Cl. The mixture was concentrated to remove THF and then partitioned between sat. NH₄Cl and DCM (×2). The organic phase was passed through a phase separator and concentrated onto flash silica (10 mL). The resulting powder was purified by column chromatography (normal phase, [Biotage SNAP cartridge KP-sil 25 g, 40-63 μm, 60 Å], 30 mL per min, 20 to 50% EtOAc in isohexane, to give tert-butyl(2R)-4,4-difluoro-2-(1-hydroxyethyl)pyrrolidine-1-carboxylate (0.106 g, 67%) as an oil.

LCMS (Method C): m/z 152 (M−BOC+H)⁺, 196 (M−tBu+H)⁺ (ES⁺), at 1.24 min, UV inactive.

A solution of the tert-butyl(2R)-4,4-difluoro-2-(1-hydroxyethyl)pyrrolidine-1-carboxylate (102 mg, 0.41 mmol) in DCM (2 mL) and TFA (2 mL) was stirred at RT for 30 min then diluted with toluene and concentrated. The residue was azeotroped with toluene to give the crude 1-[(2R)-4,4-difluoropyrrolidin-2-yl]ethanol trifluoroacetate salt as a gum. Used immediately.

LCMS (Method C): m/z 152 (M+H)⁺ (ES⁺), at 0.27 min, UV inactive.

The crude 1-[(2R)-4,4-difluoropyrrolidin-2-yl]ethanol trifluoroacetate salt from above (assumed 0.41 mmol) was

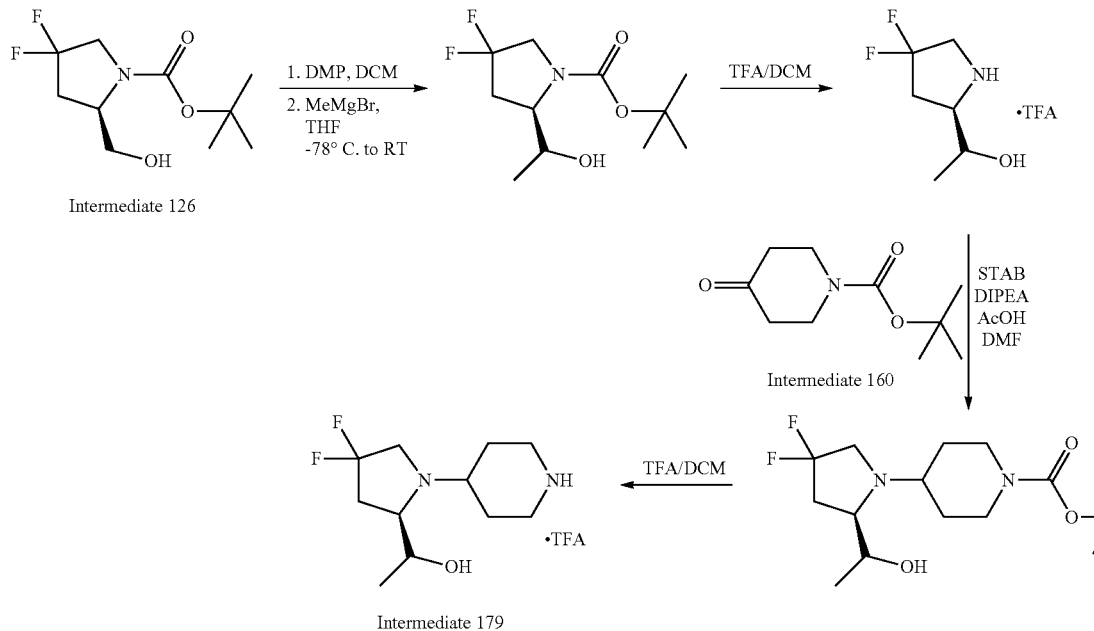

Intermediate 179

A solution of tert-butyl(2R)-4,4-difluoro-2-(hydroxymethyl)pyrrolidine-1-carboxylate (150 mg, 0.63 mmol) in DCM (5 mL) was cooled in ice water and treated with Dess-Martin Periodinane (402 mg, 0.95 mmol). The cooling bath was removed and the mixture was stirred at RT for 3 h. Sat. aqueous NaHCO₃ (5 mL), sat. aqueous sodium thiosulphate (5 mL) and EtOAc (10 mL) were added and the mixture was stirred vigorously for 30 min. The phases were dissolved in DMF (5 mL). To the solution was added DIPEA (0.38 mLm, 2.0 mmol), AcOH (0.035 mL, 0.61 mmol), tert-butyl 4-oxopiperidine-1-carboxylate (0.081 g, 0.41 mmol) and STAB (0.258 g, 1.2 mmol) in that order. The mixture was stirred at RT for 3 days, then concentrated to remove DMF. The residue was azeotroped with toluene, dissolved in MeOH and concentrated onto flash silica (5 mL). The resulting powder was purified by column chromatography (normal phase, [Biotage SNAP cartridge KP-sil 25 g, 40-63 µm, 60 Å], 30 mL per min, 0 to 15% Solvent A in DCM, where Solvent A is 10% of (7 M NH3/MeOH) in MeOH) to give tert-butyl 4-[(2R)-4,4-difluoro-2-(1-hydroxyethyl)pyrrolidin-1-yl]piperidine-1-carboxylate (0.301 g, >100%) as an oil.

LCMS (Method C): m/z 335 (M+H)⁺ (ES⁺), at 1.41 min, UV inactive.

A solution of tert-butyl 4-[(2R)-4,4-difluoro-2-(1-hydroxyethyl)pyrrolidin-1-yl]piperidine-1-carboxylate (0.301 g, assumed 0.41 mmol) in DCM (2 mL) and TFA (2 mL) was stirred at RT for 30 min then diluted with toluene and concentrated. The residue was azeotroped with toluene to give the crude Intermediate 179, 1-[(2R)-4,4-difluoro-1-(piperidin-4-yl)pyrrolidin-2-yl]ethanol trifluoroacetate salt as an oil (0.553 g, >100%). The data for the title compound are in Table 2.

Procedure for the Preparation of Intermediate 215, 4-(1H-tetrazol-1-yl)piperidine hydrochloride salt

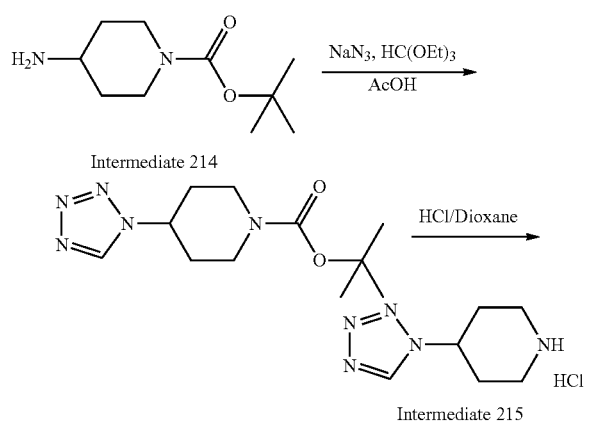

Intermediate 215

Triethylorthoformate (3.5 g, 23 mmol), tert-butyl 4-aminopiperidine-1-carboxylate (0.80 g, 3.9 mmol) and sodium azide (1.52 g, 23 mmol) were dissolved in acetic acid (50 mL). The resulting reaction mixture was stirred at 100° C. for 6 h, then cooled to RT. The volatiles were removed by concentration and the residue was partitioned between H₂O (100 mL) and ethyl acetate (150 mL). The aqueous layer was further extracted with ethyl acetate (2×100 mL), the combined organic layers were dried (Na₂SO₄), and the solvent was removed by concentration to give the crude product, which was triturated with diethyl ether to give tert-butyl 4-(1H-tetrazol-1-yl) piperidine-1-carboxylate (0.51 g, 9%) as a solid.

LCMS (Method F): m/z 254 (M+H)⁺ (ES⁺), at 1.92 min, weakly UV active.

tert-Butyl 4-(1H-tetrazol-1-yl) piperidine-1-carboxylate (0.51 g, 2.0 mmol) was dissolved in 1, 4-dioxane (10 mL). A solution of HCl in 1, 4-dioxane (4M, 5 mL, 20 mmol) was added dropwise and the resulting mixture was stirred at RT for 16 h. The solvents were removed by concentration and the residue was purified by triturating with diethyl ether (3×10 mL) to give Intermediate 215, 4-(1H-tetrazol-1-yl) piperidine hydrochloride (0.30 g, 97%) as a solid. The data for the title compound are in Table 2.

Procedure for the Preparation of Intermediate 218, 4-(1-cyclopropyl-1H-tetrazol-5-yl)piperidine hydrochloride salt

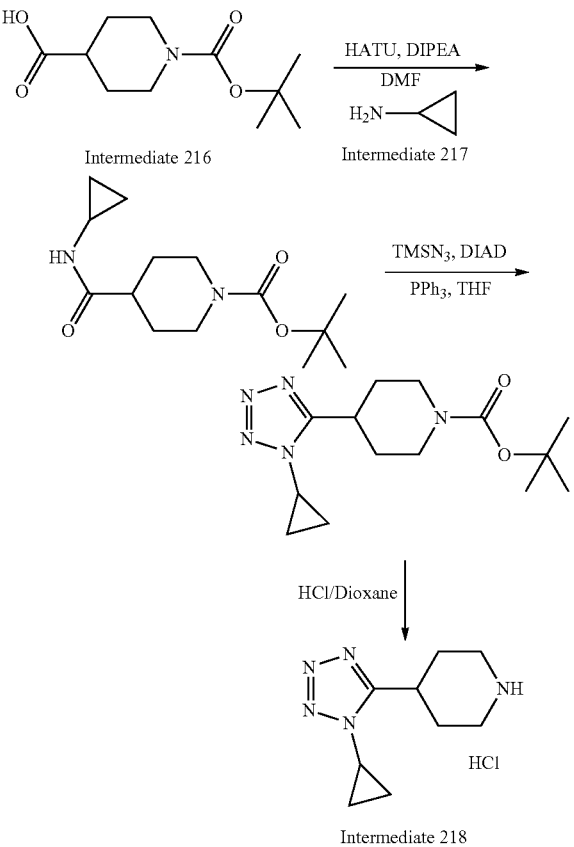

Intermediate 218

1-(tert-Butoxycarbonyl) piperidine-4-carboxylic acid (2.0 g, 8.7 mmol) and cyclopropylamine (0.6 mL, 8.7 mL) were dissolved in DMF (45 mL). HATU (3.3 g, 8.7 mmol) was added at room temperature followed by DIPEA (3.1 mL, 17 mmol). The reaction mixture was stirred at room temperature for 3 h. The reaction mixture was diluted with cold water (250 mL) and extracted with EtOAc (3×100 mL). The combined organic layers were dried (Na₂SO₄) and concentrated to give the crude product, which was purified by column chromatography (Normal phase, Neutral silica gel, 60-120 mesh, 0 to 35% EtOAC in hexanes) to give tert-butyl 4-(cyclopropylcarbamoyl)piperidine-1-carboxylate (1.5 g, 64%) as a solid.

LCMS (Method F): m/z 269 (M+H)⁺ (ES⁺), at 1.80 min, weakly UV active.

tert-Butyl 4-(cyclopropylcarbannoyl)piperidine-1-carboxylate (1.5 g, 5.6 mmol) and triphenyl phosphine (2.9 g, 11 mmol) were dissolved in THF (160 mL). DIAD (2.26 g, 11 mmol) was added at room temperature over 15 min. Trimethylsilyl azide (1.3 g, 11 mmol) was added and the reaction mixture was allowed to stir at room temperature for 24 h. The reaction mixture was diluted with water (250 mL) and extracted with EtOAc (3×100 mL). The combined organic layers were dried (Na₂SO₄) and concentrated to give the crude product, which was purified by column chromatography (Normal phase, Neutral silica gel, 60-120 mesh, 0 to 30% EtOAC in hexane) to give tert-butyl 4-(1-cyclopropyl-1H-tetrazol-5-yl)piperidine-1-carboxylate (400 mg, 24%) as a solid.

LCMS (Method F): m/z 294 (M+H)+ (ES+), at 1.96 min, weakly UV active.

tert-Butyl 4-(1-cyclopropyl-1H-tetrazol-5-yl)piperidine-1-carboxylate (400 mg, 1.4 mmol) was dissolved in dioxane (5 mL). A solution of HCl in dioxane (4M, 5 mL, 20 mmol) was added at 0° C. and the mixture was stirred at room temperature for 5 h. The solvent was removed by concentration and the residue was triturated with diethyl ether (10 mL) to give Intermediate 218 4-(1-cyclopropyl-1H-tetrazol-5-yl)piperidine hydrochloride (260 mg, 98%) as a solid. The data for the title compound are in Table 2.

Procedure for the Preparation of Intermediate 193, 1-(piperidin-4-yl)pyrrolidine-2,5-dione trifluoroacetate salt

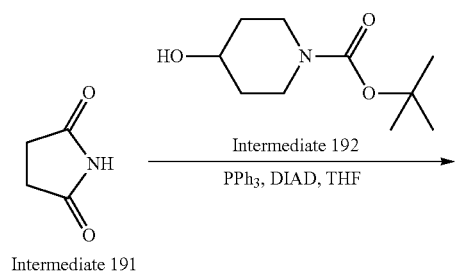

Succinimide (0.099 g, 1.0 mmol), tert-butyl 4-hydroxypiperidine-1-carboxylate (0.221 g, 1.10 mmol) and triphenylphosphine (0.314 g, 1.20 mmol) were dissolved in THF (5 mL) then treated with diisopropyl azodicarboxylate (0.236 mL, 1.20 mmol) and stirred at RT overnight. The reaction mixture was concentrated onto flash silica (5 mL). The resulting powder was purified by column chromatography (normal phase, [Biotage SNAP cartridge KP-sil 25 g, 40-63 µm, 60 Å], 30 mL per min, 20% to 100% EtOAc in isohexane) to give tert-butyl 4-(2,5-dioxopyrrolidin-1-yl)piperidine-1-carboxylate (0.253 g, 90%) as a solid.

LCMS (Method C): m/z 305 (M+Na)+ (ES+), at 1.11 min, UV inactive

A solution of tert-butyl 4-(2,5-dioxopyrrolidin-1-yl)piperidine-1-carboxylate (0.141 g, 0.50 mmol) in DCM (3 mL) and TFA (3 mL) was stirred at RT for 30 min then diluted with toluene and concentrated. The residue was azeotroped with toluene to give Intermediate 193, 1-(piperidin-4-yl)pyrrolidine-2,5-dione trifluoroacetate salt as a gum. Used immediately. The data for the title compound are in Table 2.

Procedure for the Preparation of Intermediate 229, ethyl 2-([2,4'-bipiperidin]-1'-yl)-6-azaspiro[3.4]octane-6-carboxylate

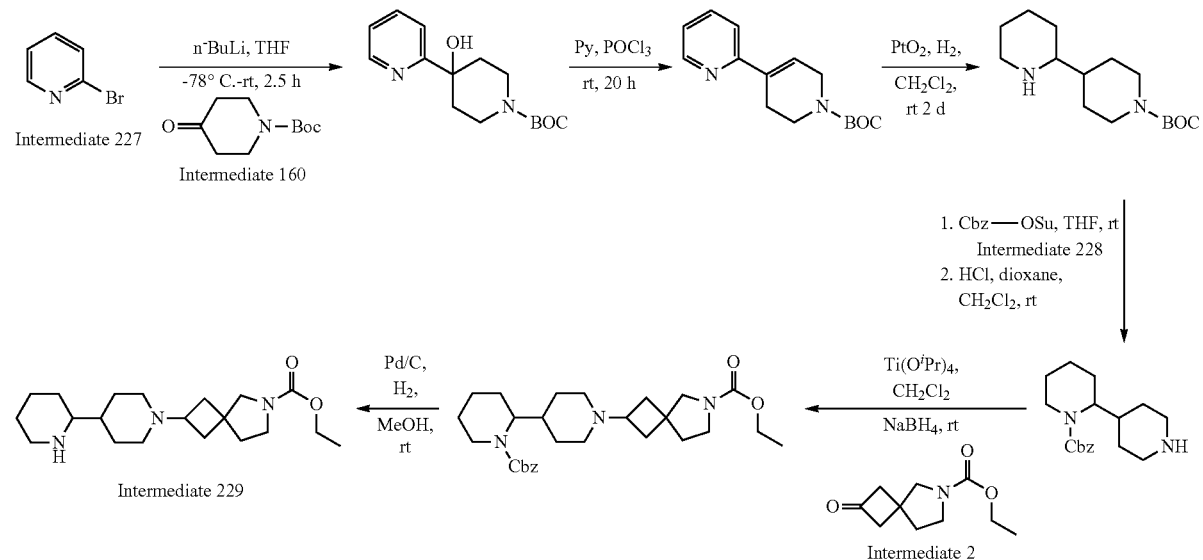

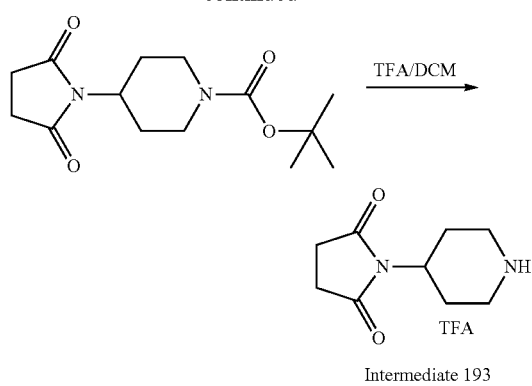

To a solution of 2-bromopyridine (10.0 g, 63.3 mmol) in dry THF (60 mL), n-BuLi (79.1 mL, 2.5 M in hexane, 126 mmol) was slowly added at −78° C. After stirring at this temperature for 30 min, tert-butyl 4-oxopiperidine-1-carboxylate (13.8 g, 69.6 mmol) in THF (40 mL) was slowly added. The reaction temperature was gradually brought to room temperature and stirred for 2 h. After cooling to 0° C., the reaction mixture was carefully quenched with ice cold water (50 mL). After removal of the volatiles, the aq layer was extracted with ethyl acetate (3×50 mL). The organic layers were combined and washed with brine, dried (Na$_2$SO$_4$), filtered and concentrated in vacuo. The residue was purified by flash column chromatography [normal phase, silica gel (100-200 mesh), gradient 0% to 30% ethyl acetate in hexane] to give tert-butyl 4-hydroxy-4-(pyridin-2-yl)piperidine-1-carboxylate (11.4 g, 65%) as a yellow oil.

$^1$H-NMR (400 MHz; CDCl$_3$) δ: 1.48 (s, 9H), 1.56-1.63 (m, 2H), 1.90-2.0 (m, 2H), 3.25-3.46 (m, 2H), 4.05-4.22 (m,

2H), 5.29 (br.s., 1H), 7.20-7.25 (m, 1H), 7.32 (d, J=8.0, Hz, 1H), 7.73 (dt, J=1.6, 8.4 Hz, 1H), 8.53 (d, J=4.8 Hz, 1H).

To a solution of tert-butyl 4-hydroxy-4-(pyridin-2-yl)piperidine-1-carboxylate (11.4 g, 41.0 mmol) in pyridine (100 mL), POCl$_3$ (5.7 mL, 61.5 mmol) was added and stirred at room temperature for 20 h. After removal of pyridine in vacua, the reaction mixture was quenched with aq NaOH (10%, 30 mL) and extracted with chloroform (2×30 mL). The organic layers were combined, dried (Na$_2$SO$_4$), filtered and concentrated in vacuo. The residue was purified by flash column chromatography [normal phase, silica gel (100-200 mesh), gradient 0% to 30% ethyl acetate in hexane] to give tert-butyl 3',6'-dihydro-[2,4'-bipyridine]-1'(2'H)-carboxylate (2.3 g, 21%) as a yellow oil.

$^1$H-NMR (400 MHz; CDCl$_3$) δ: 1.48 (s, 9H), 2.61-2.70 (m, 2H), 3.60-3.70 (m, 2H), 4.10-4.19 (m, 2H), 6.58-6.62 (m, 1H), 7.11-7.19 (m, 1H), 7.36 (d, J=7.88 Hz, 1H), 7.62-7.66 (m, 1H), 8.55 (d, J=4.4 Hz, 1H).

To a solution of tert-butyl 3',6'-dihydro-[2,4'-bipyridine]-1'(2'H)-carboxylate (2.3 g, 8.84 mmol) in CH$_2$Cl$_2$ (20 mL), PtO$_2$ (200 mg, 0.88 mmol) was added and the reaction mixture was stirred at room temperature for 2 d under H$_2$ atmosphere. The reaction mixture was filtered through a pad of celite, washed with MeOH and concentrated in vacuo. The residue was purified by flash column chromatography [normal phase, silica gel (100-200 mesh), gradient 0% to 15% MeOH in DCM having 0.1% aq ammonia] to give tert-butyl[2,4'-bipiperidine]-1-carboxylate (1.05 g, 44%) as a colorless oil.

$^1$H-NMR (400 MHz; CDCl$_3$) δ: 1.30-1.40 (m, 1H), 1.48 (s, 9H), 1.60-1.91 (m, 8H), 2.45-2.55 (m, 2H), 2.58-2.75 (m, 4H), 3.24-3.31 (m, 1H), 4.14-4.24 (m, 2H).

To a solution of tert-butyl[2,4'-bipiperidine]-1'-carboxylate (1.05 g, 3.91 mmol) in THF (5 mL), Cbz-OSu (975 mg, 3.91 mmol) in THF (5 mL) was added and stirred at room temperature for 2 h. The reaction mixture was quenched with water (20 mL) and the aq layer was extracted with ethyl acetate (2×20 mL). The organic layers were combined and washed with brine, dried (Na$_2$SO$_4$), filtered and concentrated in vacuo. The residue was purified by flash column chromatography [normal phase, silica gel (100-200 mesh), gradient 0% to 20% ethyl acetate in hexane] to give 1-benzyl 1'-(tert-butyl) [2,4'-bipiperidine]-1,1'-dicarboxylate (840 mg, 53%) as a colorless oil.

$^1$H-NMR (400 MHz; CDCl$_3$) δ: 1.44 (s, 9H), 1.50-1.63 (m, 2H), 1.68-1.92 (m, 4H), 1.95-2.14 (m, 2H), 2.55-2.80 (m, 2H), 2.81-2.95 (m, 2H), 2.98-3.10 (m, 1H), 3.75-4.24 (m, 3H), 5.11 (s, 2H), 7.34-7.37 (m, 5H).]

To a solution of 1-benzyl 1'-(tert-butyl) [2,4'-bipiperidine]-1,1'-dicarboxylate (840 mg, 2.1 mmol) in CH$_2$Cl$_2$ (10 mL), HCl in dioxane (10 mL, 4 M) was slowly added at 0° C. and the reaction mixture was stirred at room temperature for 2 h. The reaction mixture was quenched with saturated NaHCO$_3$ (20 mL) and the aq layer was extracted with CH$_2$Cl$_2$ (2×20 mL). The organic layers were combined, dried (Na$_2$SO$_4$), filtered and concentrated in vacuo. The residue was purified by flash column chromatography [normal phase, silica gel (100-200 mesh), gradient 0% to 15% MeOH in DCM having 0.1% aq ammonia] to give benzyl [2,4'-bipiperidine]-1-carboxylate (570 mg, 90%) as a colorless sticky solid.

$^1$H-NMR (400 MHz; CDCl$_3$) δ: 1.35-1.70 (m, 6H), 1.71-1.98 (m, 4H), 2.46-2.63 (m, 2H), 2.68-2.73 (m, 1H), 3.03-3.18 (m, 1H), 3.65-3.80 (m, 2H), 3.86-4.16 (m, 2H), 5.11 (s, 2H), 7.34-7.37 (m, 5H).

To a solution of benzyl[2,4'-bipiperidine]-1-carboxylate (520 mg, 1.72 mmol) and ethyl 2-oxo-6-azaspiro[3.4]octane-6-carboxylate (305 mg, 1.55 mmol) in CH$_2$Cl$_2$ (15 mL), Ti(O$^i$Pr)$_4$ (1.6 mL, 5.16 mmol) was added and stirred at 0° C. for 40 min. To this reaction mixture NaBH$_4$ (1.1 g, 5.16 mmol) was added and stirring continued at this temperature for 2 h. The reaction mixture was quenched with water (20 mL) and the aq layer was extracted with CH$_2$Cl$_2$ (2×20 mL). The organic layers were combined, dried (Na$_2$SO$_4$), filtered and concentrated in vacuo. The residue was purified by prep-HPLC (reverse phase, X BRIDGE, C-18, 19×250 mm, 5µ, gradient 68% to 90% ACN in water containing 0.1% NH$_4$OH, 214 nm, RT: 7.45 min for Isomer-1 and 8.37 min for Isomer-2) to give ethyl 2-oxo-6-azaspiro[3.4]octane-6-carboxylate Isomer 1, (120 mg, 15%) and ethyl 2-oxo-6-azaspiro[3.4]octane-6-carboxylate Isomer-2, (160 mg, 19%) as colorless sticky solids.

Isomer-1:

LCMS (Method L): m/z 484 (M+H)$^+$ (ES+), at 5.70 min, UV active.

$^1$H-NMR (400 MHz; CDCl$_3$) δ: 1.10-1.32 (m, 6H), 1.36-1.95 (m, 14H), 2.00-2.18 (m, 2H), 2.52-3.05 (m, 4H), 3.20-3.45 (m, 4H), 3.87-4.18 (m, 4H), 5.11 (s, 2H), 7.30-7.35 (m, 5H).

Isomer-2:

LCMS (Method L): m/z 484 (M+H)$^+$ (ES+), at 5.81 min, UV active.

$^1$H-NMR (400 MHz; CDCl$_3$) δ: 1.10-1.32 (m, 6H), 1.35-1.53 (m, 5H), 1.62-1.80 (m, 5H), 1.81-1.97 (m, 4H), 2.00-2.18 (m, 2H), 2.52-3.00 (m, 4H), 3.18-3.52 (m, 4H), 3.88-4.20 (m, 4H), 5.11 (s, 2H), 7.32-7.37 (m, 5H).

To a solution of a mixture of isomers of ethyl 2-oxo-6-azaspiro[3.4]octane-6-carboxylate (1.0 g, 2.06 mmol) in MeOH (20 mL), 10% Pd on charcoal (320 mg, 50% wet) was added and the reaction mixture was stirred at rt for 16 h under H$_2$ atmosphere. The reaction mixture was filtered through a pad of celite, washed with MeOH and concentrated in vacuo, and triturated with pentane to give Intermediate 229, ethyl 2-([2,4'-bipiperidin]-1'-yl)-6-azaspiro [3.4]octane-6-carboxylate (445 mg, 92%) as a colorless liquid. The data for the title compound are in Table 2.

Procedure for the Preparation of Intermediate 243, tert-butyl 1-(piperidin-4-yl)-1,3-dihydro-2H-isoindole-2-carboxylate

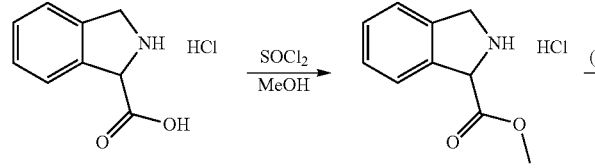

Intermediate 240

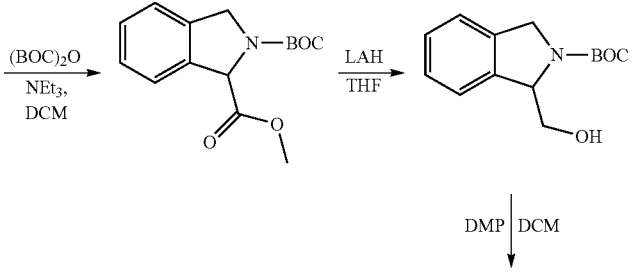

DMP | DCM

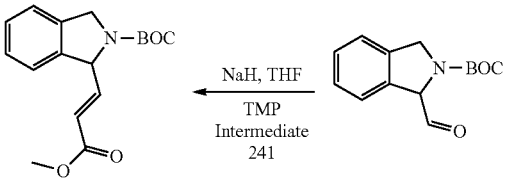

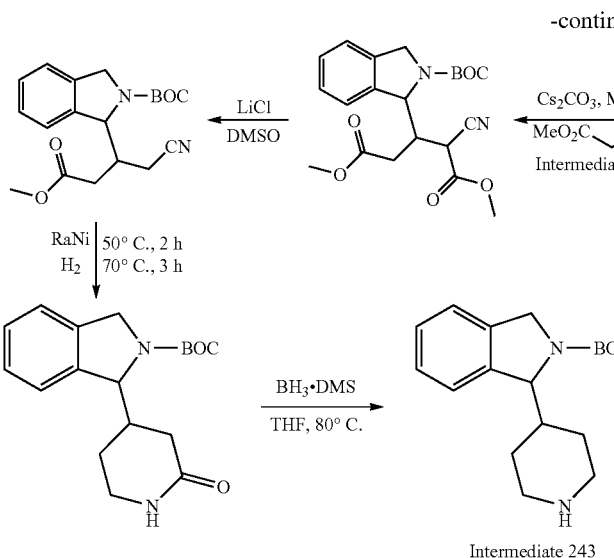

Intermediate 243

To a solution of isoindoline-1-carboxylic acid hydrochloride (5.0 g, 25.0 mmol) in methanol (60 mL), SOCl$_2$ (2.7 mL, 37.5 mmol) was slowly added at 0° C. and the reaction mixture was stirred at room temperature for 16 h. After completion, the reaction mixture was concentrated in vacuo. The residue was triturated with diethyl ether to give methyl isoindoline-1-carboxylate hydrochloride (4.9 g, 92%) as an off white solid. The residue was used for the next step without further purification.

$^1$H-NMR (400 MHz; DMSO-d$_6$) δ: 3.81 (s, 3H), 4.52-4.63 (m, 2H), 5.70 (s, 1H), 7.44-7.50 (m, 4H), 9.77 (br.s., 2H).

To a solution of methyl isoindoline-1-carboxylate hydrochloride (4.9 g, 23.0 mmol) in DCM (50 mL), Et$_3$N (9.9 mL, 69.0 mmol) and (Boc)$_2$O (8.0 mL, 34.0 mmol) were sequentially added at 0° C. The reaction mixture was stirred at room temperature for 12 h. The reaction mixture was quenched with water (20 mL). After separating the organic layer, the aq layer was extracted with CH$_2$Cl$_2$ (3×15 mL). The organic layers were combined and washed with brine, dried (Na$_2$SO$_4$), filtered and concentrated in vacuo. The crude residue was purified by flash column chromatography [normal phase, silica gel (100-200 mesh), gradient 10% to 30% ethyl acetate in hexane] to give 2-(tert-butyl) 1-methyl isoindoline-1,2-dicarboxylate (6.5 g, 90%) as a colorless liquid.

$^1$H-NMR (400 MHz; CDCl$_3$) δ: 1.52 (s, 9H), 3.75 (s, 3H), 4.65-4.85 (m, 2H), 5.45 (s, 1H), 7.25-7.43 (m, 4H).

To a solution 2-(tert-butyl) 1-methyl isoindoline-1,2-dicarboxylate (6.5 g, 23.0 mmol) in THF (60 mL), LAH (2M, 11.5 mL, 23.0 mmol) was slowly added at 0° C. and stirred for 30 min. After completion, the reaction mixture was quenched with sat aq Na$_2$SO$_4$ (20 mL). The reaction mixture was filtered through a pad of celite and washed with ethyl acetate (100 mL), dried (Na$_2$SO$_4$) and concentrated in vacuo to give tert-butyl 1-(hydroxymethyl)isoindoline-2-carboxylate (5.2 g, 91%) as an off white solid. The crude residue was used for the next step without further purification.

$^1$H-NMR (400 MHz; CDCl$_3$) δ: 1.52 (s, 9H), 3.70-3.78 (m, 1H), 3.98-4.03 (m, 1H), 4.60-4.69 (m, 1H), 4.70-4.85 (m, 2H), 5.22 (br.s., 1H), 7.25-7.40 (m, 4H).

To a solution of tert-butyl 1-(hydroxymethyl)isoindoline-2-carboxylate (5.2 g, 20.0 mmol) in DCM (100 mL), Dess-Mertin periodinane (27 g, 62.0 mmol) was added portion wise at 0° C. and stirred at room temperature for 48 h. After completion, the reaction mixture was filtered through a pad of celite and washed with diethyl ether (3×20 mL). The filtrate was washed with sat aq NaHCO$_3$ solution, brine, dried (Na$_2$SO$_4$) and concentrated in vacuo to give tert-butyl 1-formylisoindoline-2-carboxylate (4.5 g, 88%) as a brown liquid. The crude residue was used for the next step without further purification.

$^1$H-NMR (400 MHz; CDCl$_3$) & 1.48 (s, 9H), 4.65-4.90 (m, 2H), 5.29-5.35 (s, 1H), 7.25-7.35 (m, 4H), 9.51 (s, 1H).

To a solution of NaH (874 mg, 18.2 mmol) in THF, trimethylphosphonoacetate (3.3 mL, 18.2 mmol) was added at −78° C. After stirring for 1 h at −78° C., tert-butyl 1-formylisoindoline-2-carboxylate (4.5 g, 18.2 mmol) was slowly added and the reaction mixture was allowed to 0° C. After completion, the reaction mixture was quenched with sat aq NH$_4$Cl solution (10 mL) and the aqueous layer was extracted with ethyl acetate (3×20 mL). The organic layers were combined, dried (Na$_2$SO$_4$) and concentrated in vacuo to give tert-butyl(E)-1-(3-methoxy-3-oxoprop-1-en-1-yl)isoindoline-2-carboxylate (5.2 g, 92%) as a brown liquid. The residue was used for the next step without further purification.

MS (ESI +ve): 304

To a solution of tert-butyl(E)-1-(3-methoxy-3-oxoprop-1-en-1-yl)isoindoline-2-carboxylate (5.2 g, 17.2 mmol) in MeCN (20 mL), Cs$_2$CO$_3$ (11.1 g, 34.4 mmol) was added portion wise at room temperature. After stirring for 20 min, methyl cyanoacetate (3.0 mL, 34.4 mmol) was slowly added and the reaction mixture was stirred at 70° C. for 16 h. After completion, the reaction mixture was filtered through a pad of celite and thoroughly washed with hexane (3×20 mL). The filtrate was concentrated in vacuo to give dimethyl 3-(2-(tert-butoxycarbonyl)isoindolin-1-yl)-2-cyanopentanedioate) (5.5 g, cr) as a brown sticky solid. The crude residue was used for the next step without further purification.

MS (ESI +ve): 403

To a solution of dimethyl 3-(2-(tert-butoxycarbonyl)isoindolin-1-yl)-2-cyanopentanedioate) (1.6 g, crude) in DMSO (15 mL), LiCl (500 mg, 11.7 mmol) was added followed by addition of water (0.1 mL, cat.) and the reaction mixture was stirred at 135° C. for 16 h. After completion, the reaction mixture was quenched with water (20 mL) and the aq layer was extracted with diethyl ether (3×20 mL). The organic layers were combined, dried (Na₂SO₄) and concentrated in vacuo to give tert-butyl 1-(1-cyano-4-methoxy-4-oxobutan-2-yl)isoindoline-2-carboxylate (1.5 g, cr) as a brown semisolid. The crude residue was used for the next step without further purification.

MS (ESI +ve): 345

To a solution of tert-butyl 1-(1-cyano-4-methoxy-4-oxobutan-2-yl)isoindoline-2-carboxylate (300 mg, 0.8 mmol) in MeOH (30 mL), Raney-Ni (0.30 g, wet) was added and the reaction mixture was heated to 50° C. for 2 h under H₂ atmosphere at 50 psi. Then the reaction temperature was increased to 70° C. and stirred for 3 h. After completion, the reaction mixture was filtered through a pad of celite, washed with MeOH (25 mL) and concentrated in vacuo. The residue was triturated with diethyl ether (30 mL) to give tert-butyl 1-(2-oxopiperidin-4-yl)isoindoline-2-carboxylate (0.21 g, 76%) as a brown solid.

MS (ESI +ve): 317

To a solution of tert-butyl 1-(2-oxopiperidin-4-yl)isoindoline-2-carboxylate (210 mg, 0.60 mmol) in THF (5 mL), BH₃-DMS (0.5 mL, 6.60 mmol) was slowly added at 0° C. and the reaction mixture was stirred at 78° C. for 8 h. After cooling at 0° C., the reaction mass was quenched with methanol (0.5 mL) followed by water (1 mL). To the crude reaction mass 5% MeOH/DCM (30 mL) was added and filtered. The filtrate was concentrated in vacuo. The residue was triturated with diethyl ether (20 mL) to give tert-butyl 1-(piperidin-4-yl)isoindoline-2-carboxylate, Intermediate 243 (200 mg, 99%) as a brown solid. The data for the title compound are in Table 2.

Procedure for the Preparation of Intermediate 247, 4-(2H-1,2,3-triazol-2-yl)piperidine

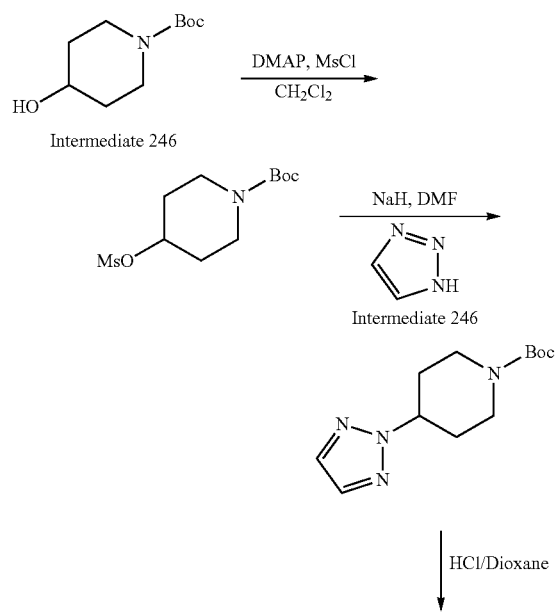

Intermediate 247 tert-Butyl 4-hydroxypiperidine-1-carboxylate (0.500 g, 2.4 mmol) was dissolved in CH₂Cl₂ then DMAP (0.302 g, 2.4 mmol) and methane sulfonyl chloride (0.284 g, 2.48 mmol) added dropwise at 0° C. The resulting reaction mixture was stirred at RT for 6 h then partitioned between H₂O (70 mL) and CH₂Cl₂ (70 mL), the aqueous layer was further extracted with CH₂Cl₂ (2×70 mL), the organic layers were combined, dried (Na₂SO₄), filtered and the solvent removed in vacuo to give crude tert-butyl 4-((methylsulfonyl)oxy) piperidine-1-carboxylate (0.520 g, 75.0%) as a white solid which was used directly without any further purification.

¹H-NMR (400 MHz; DMSO) δ: 1.23 (d, J=9.38 Hz, 2H) 1.54-1.69 (m, 4H) 1.86-1.96 (m, 2H) 2.35 (s, 1H) 2.85-3.00 (m, 2H) 3.18 (d, J=5.42 Hz, 5H) 3.54-3.67 (m, 4H) 4.83 (s, 1H). 1H-1,2,3-Triazole (0.098 g, 1.4 mmol) was dissolved in DMF (5 mL), NaH (0.037 g, 1.5 mmol) was added and stirred at 0° C. for 30 min. tert-Butyl 4-((methylsulfonyl)oxy)piperidine-1-carboxylate (0.400 g, 1.4 mmol) was added and stirred at 150° C. for 1 h. The reaction mixture was partitioned between H₂O (50 mL) and EtOAc (50 mL), the aqueous layer was further extracted with EtOAc (2×50 mL), the organic layers were combined, dried (Na₂SO₄), filtered and the solvent was removed in vacuo to give crude tert-butyl 4-(2H-1,2,3-triazol-2-yl) piperidine-1-carboxylate (0.350 g, 97.0%) as a colorless gum which was used directly without any further purification.

LCMS (Method F): m/z 253 (M+H)⁺ (ES+), at 1.95 min, UV active.

tert-Butyl 4-(2H-1,2,3-triazol-2-yl)piperidine-1-carboxylate (0.500 g, 1.9 mmol) was dissolved in 1,4-dioxane (10 mL) followed by drop wise addition of HCl in 1,4-dioxane (5 mL, 4M). The resulting reaction mixture was stirred at 25° C. for 16 h, the solvents were removed in vacuo and the residue was purified by triturating with diethyl ether (3×10 mL) to give 4-(2H-1,2,3-triazol-2-yl)piperidine hydrochloride, Intermediate 247, (0.290 g, 96.3%) as a light white solid. The data for the title compound are in Table 2.

Procedure for the Preparation of Intermediate 255, 4-(5-methyl-1H-tetrazol-1-yl)piperidine hydrochloride

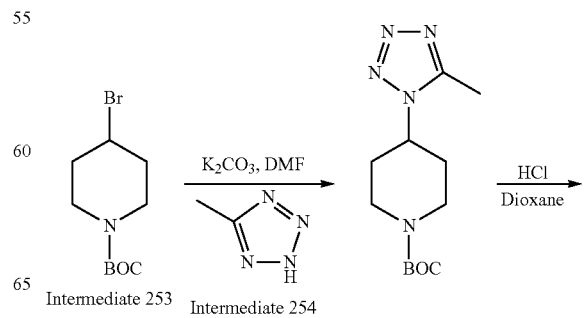

Intermediate 253  Intermediate 254

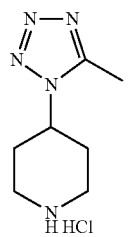
Intermediate 255

5-Methyl-2H-tetrazole (0.500 g, 5.9 mmol) and tert-butyl 4-bromopiperidine-1-carboxylate (1.29 g, 4.8 mmol) were dissolved in DMF. K$_2$CO$_3$ (1.64 g, 11.8 mmol) was added, the resulting reaction mixture was stirred at 100° C. for 6 h then partitioned between H$_2$O (100 mL) and ethyl acetate (150 mL). The aqueous layer was further extracted with ethyl acetate (2×100 mL), the organic layers were combined, dried (Na$_2$SO$_4$), filtered and the solvent was removed in vacuo. The residue was purified by combi-flash column chromatography (normal phase, neutral silica gel, 60-120 mesh, 10 to 20% EtOAc in hexane) to give tert-butyl 4-(5-methyl-1H-tetrazol-1-yl)piperidine-1-carboxylate (0.280 g, 34.6%) as a white solid.

$^1$H-NMR (400 MHz, DMSO) δ: 1.43 (s, 9H), 1.73-1.88 (m, 2H), 2.01 (br. s., 2H), 2.68-2.75 (m, 3H), 2.88-2.91 (m, 2H), 4.03-4.10 (m, 2H), 4.60-4.70 (m, 1H).

tert-Butyl 4-(5-methyl-1H-tetrazol-1-yl) piperidine-1-carboxylate (0.280 g, 1.04 mmol) was dissolved in 1, 4-dioxane (10 mL) followed by drop wise addition of HCl in 1, 4-dioxane (5 mL, 4M). The resulting reaction mixture was stirred at 25° C. for 16 h, the solvents were removed in vacuo and the residue was purified by triturating with diethyl ether (3×10 mL) to give 4-(5-methyl-1H-tetrazol-1-yl)piperidine hydrochloride, Intermediate 255 (0.170 g, 97.6%) as a white solid. The data for the title compound are in Table 2.

Procedure for the Preparation of Intermediate 258, give (R)-2-(4,4-difluoro-1-(piperidin-4-yl)pyrrolidin-2-yl)propan-2-ol hydrochloride To a solution of 1-(tert-butyl) 2-methyl (R)-4,4-difluoro-pyrrolidine-1,2-dicarboxylate (500 mg, 1.89 mmol) in dioxane (15 mL), HCl in dioxane (4 M, 15 mL) was slowly added at 0° C. and stirred at room temperature for 3 h. The reaction mixture was concentrated in vacuo and the residue was triturated with hexane (10 mL). This residue was basified with aq sat NaHCO$_3$ (10 mL) and concentrated. To the crude reaction mass CDM (30 mL) was added and filtered. The filtrate was concentrated in vacuo to give methyl (R)-4,4-difluoropyrrolidine-2-carboxylate (2, 320 mg, 84%) as a brown liquid. This crude residue was used for the next step without further purification.

$^1$H-NMR (400 MHz, CDCl$_3$) δ: 1.40-1.51 (m, 1H), 2.58-2.84 (m, 3H), 3.52-3.62 (m, 1H), 3.84 (s, 3H), 4.40-4.52 (m, 1H).

To a solution of methyl (R)-4,4-difluoropyrrolidine-2-carboxylate (200 mg, 1.21 mmol) and tort-butyl 4-oxopiperidine-1-carboxylate (240 mg, 1.21 mmol) in methanol (20 mL), 10% palladium on carbon (300 mg, 50% wet) was added and the reaction mixture was stirred under H$_2$ (1 atm) at room temperature for 24 h. After completion, the reaction mixture was filtered through a pad of celite, thoroughly washed with methanol and concentrated in vacuo to give tert-butyl (R)-4-(4,4-difluoro-2-(methoxycarbonyl)pyrrolidin-1-yl)piperidine-1-carboxylate (400 mg, 95%) as a colourless liquid.

$^1$H-NMR (400 MHz, CDCl$_3$) δ: 1.32-1.45 (m, 1H), 1.45 (s, 9H), 1.61-1.80 (m, 4H), 2.39-2.49 (m, 1H), 2.50-2.83 (m, 2H), 3.19 (s, 3H), 3.35-3.49 (m, 2H), 3.61-3.82 (m, 3H), 3.94-4.05 (m, 1H).

To a solution tert-butyl (R)-4-(4,4-difluoro-2-(methoxy-carbonyl)pyrrolidin-1-yl)piperidine-1-carboxylate (375 mg, 1.07 mmol) in THF (10 mL), MeMgBr (3M, 1.07 mL, 3.21 mmol) was slowly added at 0° C. and stirred for 4 h at room temperature. After completion, the reaction mixture was quenched with sat aq NH$_4$Cl solution (10 mL) and the aqueous layer was extracted with ethyl acetate (3×10 mL). The organic layers were combined, dried (Na$_2$SO$_4$), filtered and concentrated in vacua. The crude residue was purified by flash column chromatography [normal phase, silica gel (100-200 mesh), gradient 10% to 30% ethyl acetate in hexane] to give tert-butyl (R)-4-(4,4-difluoro-2-(2-hydroxy-

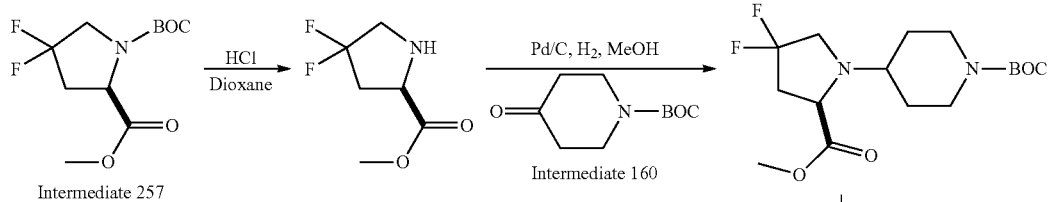

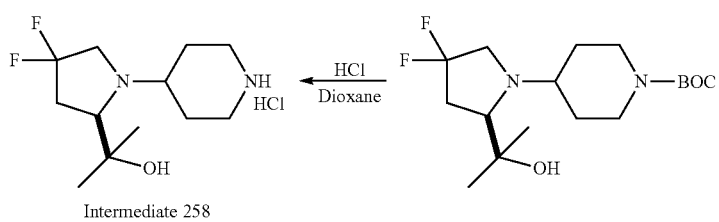

Intermediate 258 propan-2-yl)pyrrolidin-1-yl)piperidine-1-carboxylate (240 mg, 64%) as a colorless liquid.

¹H-NMR (400 MHz, CDCl₃) δ: 1.11 (s, 3H), 1.21 (s, 3H), 1.21-1.40 (m, 2H), 1.46 (s, 9H), 1.61-1.80 (m, 2H), 2.15-2.30 (m, 3H), 2.50-2.83 (m, 3H), 3.02-3.23 (m, 2H), 4.09-4.30 (m, 2H). O—H not observed.

To a solution of (R)-4-(4,4-difluoro-2-(2-hydroxypropan-2-yl)pyrrolidin-1-yl)piperidine-1-carboxylate (240 mg, 0.69 mmol) in dioxane (10 mL), HCl in dioxane (4 M, 10 mL) was slowly added at 0° C. and stirred at room temperature for 2 h. The reaction mixture was concentrated in vacuo and the residue triturated with hexane (10 mL). To the crude reaction mass CH₂Cl₂ (30 mL) was added and filtered. The filtrate was concentrated in vacuo to give (R)-2-(4,4-difluoro-1-(piperidin-4-yl)pyrrolidin-2-yl)propan-2-ol hydrochloride, Intermediate 258 (150 mg, 87%) as a brown liquid. The data for the title compound are in Table 2.

Procedure for the Preparation of Intermediate 282, tert-butyl(2R)-2-(dimethylcarbamoyl)piperidine-1-carboxylate

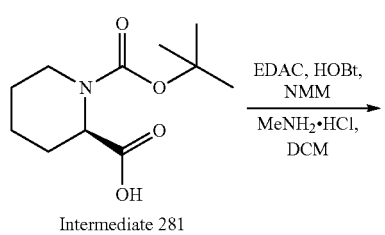

Intermediate 281

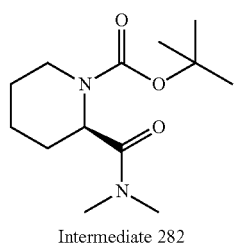

Intermediate 282

(R)-(tert-butoxycarbonyl)piperidine-2-carboxylic acid (0.500 g, 2.18 mmol) was dissolved in anhydrous DCM (8 mL) and the reaction mixture was cooled to 0° C. under nitrogen. 1-ethyl-3-(3-dimethylaminopropyl)-carbodiimide HCl (0.628 g, 3.275 mmol), hydroxybenzotriazole (0.334 g, 2.183 mmol), N-methylmorpholine (1.104 g, 10.915 mmol) and dimethylamine hydrochloride (0.356 g, 4.36 mmol) was added and the reaction mixture was stirred at rt under nitrogen overnight. The reaction mixture was diluted with DCM (20 mL) and washed with sat. NaHCO₃ (aq) (20 mL) and sat. NaCl (aq) (20 mL). The organic layer was passed through a Biotage Phase Separator Cartridge and the solvents were removed in vacuo. The residue was purified by column chromatography (normal phase, [Biotage SNAP cartridge KP-sil 25 g 40-63 μm, 60 Å, 25 mL per min, gradient 0% to 10% MeOH/DCM]) to give tert-butyl(2R)-2-(dimethylcarbamoyl)piperidine-1-carboxylate, Intermediate 282, (0.241 g, 43%) as an amber oil. The data for the title compound are in Table 2

Procedure for the Preparation of Intermediate 295, tert-butyl(2R)-2-(fluoromethyl)pyrrolidine-1-carboxylate

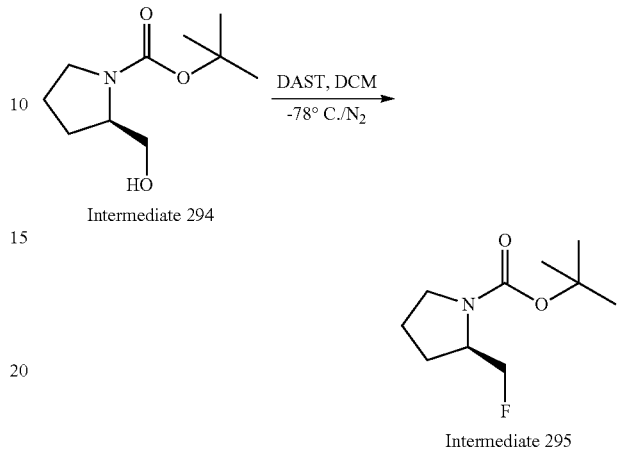

(2R)-(+)-1-Boc-2-pyrolidinemethanol (0.300 g, 1.49 mmol) was dissolved in DCM (8 mL) and cooled under nitrogen to −78° C. N,N-Diethylaminosulfur trifluoride (0.360 g 2.24 mmol) was added to the reaction mixture dropwise, the reaction mixture was stirred at −78° C. under nitrogen for 4 h and then warmed to rt overnight. The reaction mixture was quenched by addition of sat. NaHCO₃ (aq) (20 mL) and extracted with DCM (2×15 mL), the organic layers were combined and dried by passing through a Biotage Phase Separator Cartridge and the solvents were removed in vacuo. The residue was purified by column chromatography (normal phase, [Biotage SNAP cartridge KP-sil 10 g 40-63 μm, 60 Å, 12 mL per min, gradient 0% to 4% MeOH/DCM]) to give tert-butyl(2R)-2-(fluoromethyl)pyrrolidine-1-carboxylate, Intermediate 295, (0.104 g, 34%), as an amber oil. The data for the title compound are in Table 2

Procedure for the Preparation of Intermediate 285, methyl(4S)-1,3-thiazolidine-4-carboxylate hydrochloride

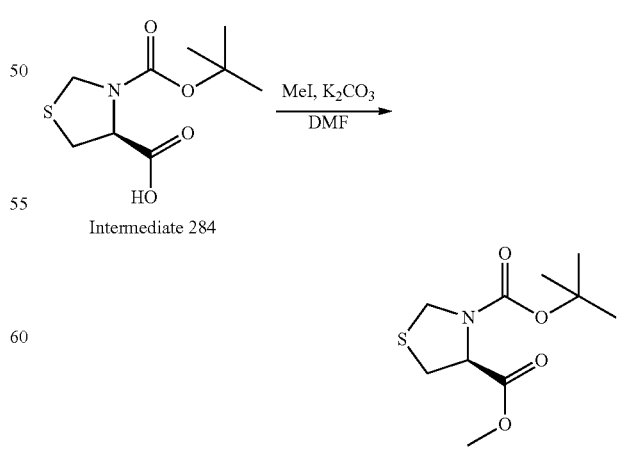

(S)-3-Boc-thiazolidine-4-carboxylic acid (1.00 g, 4.29 mmol) was dissolved in anhydrous DMF (4 mL), potassium carbonate (2.372 g, 17.16 mmol) and iodomethane (0.730 g, 5.14 mmol) were added. The reaction mixture was stirred at rt under nitrogen overnight. The solvents were removed in vacuo and the residue was dissolved in EtOAc (40 mL) and washed with water (3×20 mL) and sat. NaCl (aq) (20 mL), dried (MgSO$_4$). The solvents were removed in vacuo give 3-tert-butyl-4-methyl(4S)-1,3-thiazolidine-3,4-dicarboxylate, Intermediate 285, (0.812 g, 77%) as a pale yellow oil. The data for the title compound are in Table 2

Procedure for the Preparation of Intermediate 297, tert-butyl(2R)-2-(difluoromethyl)pyrrolidine-1-carboxylate

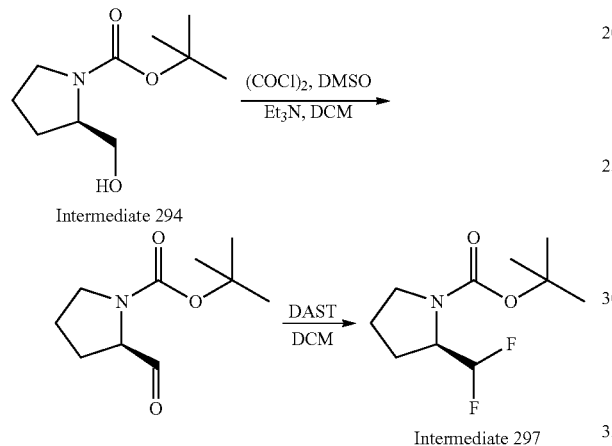

Intermediate 294

Intermediate 297

DMSO (0.698 g, 8.94 mmol) was added dropwise to a solution of oxalyl chloride (0.566 g, 2.93 mmol) in anhydrous DCM (12 mL) at −78° C. under nitrogen. The reaction mixture was stirred at −78° C. under nitrogen for 15 min then a solution of (2R)-(+)-1-Boc-2-pyrrolidinemethanol (0.600 g, 2.98 mmol) in anhydrous DCM (4 mL) was added dropwise. The reaction mixture was stirred at −78° C. under nitrogen for 15 min then Et$_3$N (1.06 g, 11.92 mmol) was added and the reaction mixture was stirred at 0° C. under nitrogen for 1 h. The reaction mixture was quenched with sat. NaHCO$_3$ (aq) (20 mL) and extracted with DCM (2×20 mL), the organic layers were combined and dried by passing through a Biotage Phase Separator Cartridge and the solvents were removed in vacuo. The residue was purified by column chromatography (normal phase, [Biotage SNAP cartridge KP-sil 10 g 40-63 μm, 60 Å, 12 mL per min, gradient 0% to 4% MeOH/DCM]) to give tert-butyl(2R)-2-formylpyrrolidine-1-carboxylate (0.435 g, 73%).

tert-butyl(2R)-2-formylpyrrolidine-1-carboxylate (0.435 g, 2.19 mmol) was dissolved in anhydrous DCM (8 mL) and cooled under nitrogen to −78° C. N,N-Diethylaminosulfur trifluoride (0.528 g, 3.28 mmol) was added to the reaction mixture dropwise, the reaction mixture was stirred at −78° C. under nitrogen for 3 h and then warmed to rt overnight. The reaction mixture was quenched by addition of sat. NaHCO$_3$ (aq) (20 mL) and extracted with DCM (2×15 mL), the organic layers were combined and dried by passing through a Biotage Phase Separator Cartridge and the solvents were removed in vacuo. The residue was purified by column chromatography (normal phase, [Biotage SNAP cartridge KP-sil 10 g 40-63 μm, 60 Å, 12 mL per min, gradient 0% to 4% MeOH/DCM]) to give tert-butyl(2R)-2-(difluoromethyl)pyrrolidine-1-carboxylate, Intermediate 297, (0.217 g, 45%) as an amber oil. The data for the title compound are in Table 2

General Synthetic Procedures for Intermediates

Route 1

Typical Procedure for the Preparation of Piperidines Via Suzuki Reaction, Hydrogenation and Boc-Deprotection as Exemplified by the Preparation of Intermediate 30, 5-(piperidin-4-yl)-1,2,4-thiadiazole

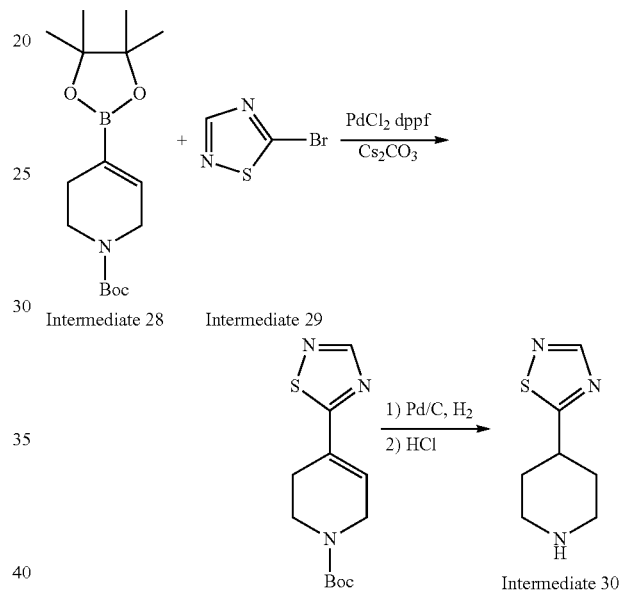

Intermediate 28    Intermediate 29

Intermediate 30

2-5-Bromo-1,2,4-thiadiazole (108 mg, 0.65 mmol), tert-butyl 4-(4,4,5,5-tetramethyl-1,3,2-dioxaborolan-2-yl)-3,6-dihydropyridine-1(2H)-carboxylate (200 mg, 0.65 mmol) and Cs$_2$CO$_3$ (632 mg, 1.94 mmol) were dissolved in Dioxane:water (10:2 mL). The reaction mixture was degassed for 30 mins followed by addition of PdCl$_2$dppf (24 mg, 0.03 mmol) then stirred for 16 h at 90° C. The reaction mixture was partitioned between H$_2$O (80 mL) and EtOAc (50 mL), the aqueous layer was further extracted with EtOAc (2×50 mL), the organic layers were combined, dried (Na$_2$SO$_4$), solvents were removed in vacuo and the residue was purified by column chromatography (normal phase silica, mesh size: 60-120, 16% to 20% EtOAc in Hexane) to give tert-butyl 4-(1,2,4-thiadiazol-5-yl)-3,6-dihydropyridine-1(2H)-carboxylate (158 mg, 92.0%) as an off white solid.

LCMS (Method F): m/z 212 (M+H-56)[4] (ES+), at 2.37 min, UV active tert-Butyl 4-(1,2,4-thiadiazol-5-yl)-3,6-dihydropyridine-1(2H)-carboxylate (200 mg, 0.74 mmol) was dissolved in MeOH (15 mL) and 10% Pd/C (20 mg) was added. The reaction mixture was purged with H$_2$ gas and stirred at 25° C. for 8 h under H$_2$ pressure. The reaction mixture was filtered through celite, the residue was washed with MeOH, and the solvents were removed in vacuo and the residue was purified by column chromatography (normal phase silica, mesh size: 60-120, 20% to 24% EtOAc in Hexane) to give tert-butyl 4-(1,2,4-thiadiazol-5-yl)piperidine-1-carboxylate (150 mg, 74.6%) as a dark green gum.

LCMS (Method F): m/z 214 (M+H)+ (ES+), at 2.14 min, UV active tert-Butyl 4-(1,2,4-thiadiazol-5-yl)piperidine-1-carboxylate (150 mg, 0.56 mmol) was dissolved in 1,4-dioxane (5 mL), HCl in dioxane (10 mL, 3.0M solu.) was added dropwise and the reaction was stirred at 30° C. for 16 h. Solvents were removed in vacuo and the residue was purified by triturating with diethyl ether (3×3 mL) to give Intermediate 30, 5-(piperidin-4-yl)-1,2,4-thiadiazole (102 mg, 89.5%) as a dark green gum. The data for the title compound are in Table 2.

Route 2

Procedure for the Preparation of Intermediate 34, 4-(1,5-dimethyl-1H-imidazol-2-yl)-1,2,3,6-tetrahydropyridine

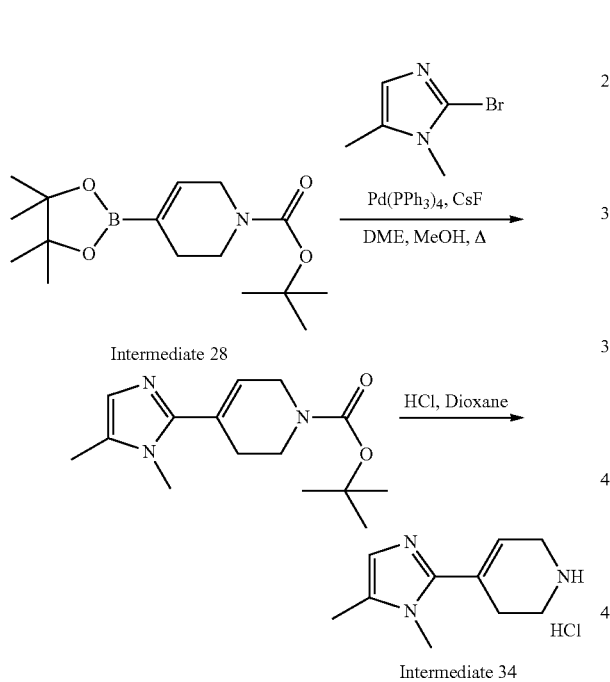

Intermediate 34 tert-Butyl 4-(4,4,5,5-tetramethyl-1,3,2-dioxaborolan-2-yl)-3,6-dihydropyridine-1(2H)-carboxylate (2.0 g, 6.55 mmol), 2-bromo-1,5-dimethyl-1H-imidazole (1.13 g, 6.45 mmol) and CsF (2.9 g, 1.85 mmol) were dissolved in DME: MeOH (2:1, 30 mL). The reaction mixture was degassed for 5 mins, then Pd(PPh3)4 (73 mg, 0.064 mmol) was added and the resulting reaction mixture was stirred for 5 h at 100° C. The reaction mixture was partitioned between H2O (100 mL) and EtOAc (100 mL), the aqueous layer was further extracted with EtOAc (2×100 mL), the organic layers were combined, dried (Na2SO4) and the solvents were removed in vacuo. The residue was purified by column chromatography (normal silica, mesh size: 60-120, 13% to 17% Ethyl acetate in Hexane) to give tert-butyl 4-(1,5-dimethyl-1H-imidazol-2-yl)-3,6-dihydropyridine-1(2H)-carboxylate (1 g, 55%) as a yellow gum.

LCMS (Method F): m/z 278 (M−H)+ (ES+), at 1.70 min, UV active tert-Butyl 4-(1,5-dimethyl-1H-imidazol-2-yl)-3,6-dihydropyridine-1(2H)-carboxylate (1.0 g, 3.61 mmol) was dissolved in 1,4-dioxane (20 mL) followed by dropwise addition of HCl in 1,4-dioxane (20 mL, 3M solu.). The resulting reaction mixture was stirred at 30° C. for 16 h, the solvents were removed in vacuo and the residue was purified by triturating with diethyl ether (3×5 mL) to give Intermediate 34, 4-(1,5-dimethyl-1H-imidazol-2-yl)-1,2,3,6-tetrahydropyridine hydrochloride (0.5 g, 65%) as a white solid. The data for the title compound are in Table 2.

Route 3

Typical Procedure for the Preparation of Piperidines Via Suzuki Reaction, Hydrogenation and Boc-Deprotection as Exemplified by the Preparation of Intermediate 65, 3-(piperidin-4-yl)pyridin-2(1H)-one hydrochloride

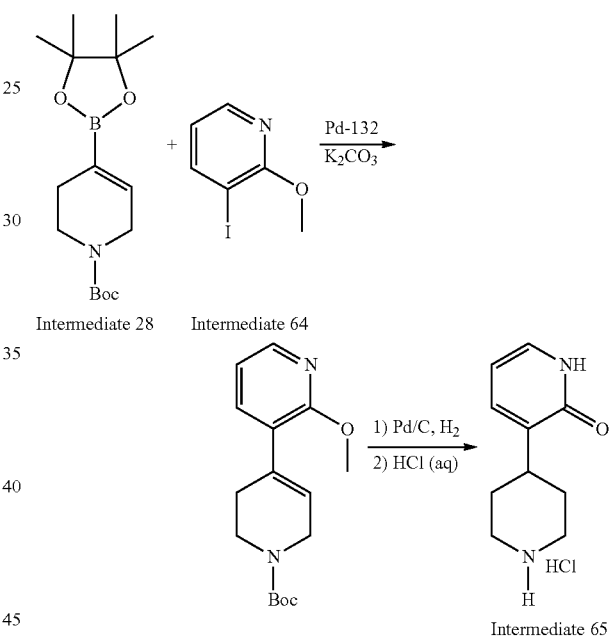

tert-Butyl 4-(4,4,5,5-tetramethyl-1,3,2-dioxaborolan-2-yl)-3,6-dihydropyridine-1(2H)-carboxylate (2.5 g, 10.0 mmol), 3-iodo-2-methoxypyridine (8.21 g, 26.0 mmol) and K2CO3 (4.3 g, 31.8 mmol) were dissolved in 1-4 dioxane (10 mL) and water (5 mL). The reaction mixture was degassed using N2 for 15 min; Pd-132 (0.376 g, 0.53 mmol) was added and the reaction mixture was stirred at 80° C. for 2 h. The reaction mixture was diluted with water (50 mL), extracted with EtOAc (2×100 mL), the organic layers were combined, dried (Na2SO4), solvent was removed in vacuo and crude product was purified by column chromatography (Normal phase, 60-120 mesh silica, 0 to 20% EtOAc in Hexane) to give tert-butyl 2-methoxy-3',6'-dihydro-[3,4'-bipyridine]-1'(2'H)-carboxylate (2.0 g, 69.0%) as off white solid.

LCMS (Method F): m/z 291 (M+H)+ (ES+), at 2.39 min, UV active tert-Butyl 2-methoxy-3',6'-dihydro-[3,4'-bipyridine]-1' (2'H)-carboxylate (1.89 g, 6.51 mmol) was dissolved in MeOH (10 mL) and 10% Pd/C (0.2 g) was added. The reaction mixture was purged with H₂ gas and stirred at rt for 12 h under H₂. The reaction mixture was filtered through celite and solvents were removed in vacuo to give tert-butyl 4-(2-methoxypyridin-3-yl) piperidine-1-carboxylate (0.91 g, 47.9%) as a colorless gum.

LCMS (Method F): m/z 293 (M+H)⁺ (ES+), at 2.50 min, UV active tert-Butyl 4-(2-methoxypyridin-3-yl) piperidine-1-carboxylate (0.200 g, 0.6 mmol) was dissolved in 1,4-dioxane (4.0 mL) and water (2.0 mL) and conc. HCl was added, the reaction mixture was stirred for 10 h at 100° C. The solvents were removed in vacuo and the residue was triturated with acetone (3×10 mL) to give Intermediate 65, 3-(piperidin-4-yl)pyridin-2(1H)-one hydrochloride (0.100 g, 82.6%) as a brown solid. The data for the title compound are in Table 2.

Route 4

Typical Procedure for the Preparation of Piperidines Via Suzuki Reaction, Hydrogenation and Boc-Deprotection as Exemplified by the Preparation of Intermediate 66, 2-methoxy-3-(piperidin-4-yl)pyridine hydrochloride

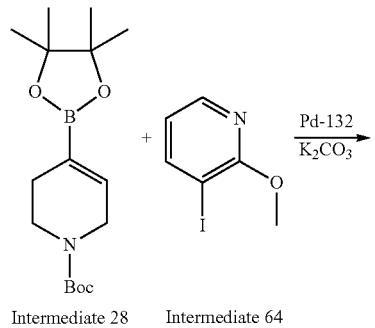

Intermediate 28    Intermediate 64

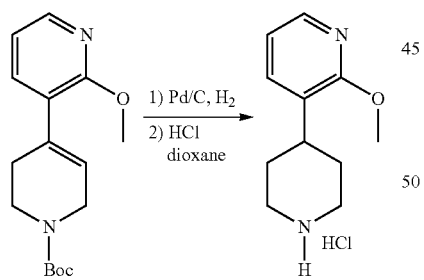

Intermediate 66 tert-Butyl 4-(4,4,5,5-tetramethyl-1,3,2-dioxaborolan-2-yl)-3,6-dihydropyridine-1(2H)-carboxylate (2.5 g, 10.0 mmol), 3-iodo-2-methoxypyridine (8.21 g, 26.0 mmol) and K₂CO₃ (4.3 g, 31.8 mmol) were dissolved in 1-4 dioxane (10 mL) and water (5 mL). The reaction mixture was degassed using N₂ for 15 min; Pd-132 (0.376 g, 0.53 mmol) was added and the reaction mixture was stirred at 80° C. for 2 h.

The reaction mixture was diluted with water (50 mL), extracted with EtOAc (2×100 mL), the organic layers were combined, dried (Na₂SO₄), solvent was removed in vacuo and crude product was purified by column chromatography (Normal phase, 60-120 mesh silica, 0 to 20% EtOAc in Hexane) to give tert-butyl 2-methoxy-3',6'-dihydro-[3,4'-bipyridine]-1'(2'H)-carboxylate (2.0 g, 69.0%) as off white solid.

LCMS (Method F): m/z 291 (M+H)⁺ (ES+), at 2.39 min, UV active tert-Butyl 2-methoxy-3',6'-dihydro-[3,4'-bipyridine]-1' (2'H)-carboxylate (1.89 g, 6.51 mmol) was dissolved in MeOH (10 mL) and 10% Pd/C (0.2 g) was added. The reaction mixture was purged with H₂ gas and stirred at it for 12 h under H₂. The reaction mixture was filtered through celite and solvents were removed in vacuo to give tert-butyl 4-(2-methoxypyridin-3-yl) piperidine-1-carboxylate (0.91 g, 47.9%) as a colorless gum.

LCMS (Method F): m/z 293 (M+H)⁺ (ES+), at 2.50 min, UV active tert-Butyl 4-(2-methoxypyridin-3-yl)piperidine-1-carboxylate (0.8 g, 2.7 mmol) was stirred in HCl in 1,4-dioxane (4.0 mL, 4.0M solu.) for 10 h at rt. The solvents were removed in vacuo and the residue was triturated by acetone (3×10 mL) to give Intermediate 66, 2-methoxy-3-(piperidin-4-yl)pyridine hydrochloride (0.135 g, 25.7%) as white solid. The data for the title compound are in Table 2.

Route 5

Typical Procedure for the Preparation of Piperidines Via Hydrogenation as Exemplified by the Preparation of Intermediate 69, 3,4'-bipiperidin-2-one

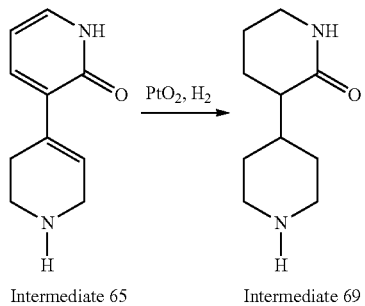 [SMILES: O=c1[nH]cccc1C1=CCNCC1 ; O=C1NCCCC1C1CCNCC1]

Intermediate 65    Intermediate 69

3-(Piperidin-4-yl)-1,6-dihydropyridin-2-ol (0.5 g, 2.8 mmol) was dissolved in MeOH (10 mL) and PtO₂ (0.2 g) was added. The reaction mixture was purged with H₂ gas and stirred at it for 12 h under H₂ gas. The reaction mixture was filtered through celite and the solvents were removed in vacuo to give Intermediate 69, 3,4'-bipiperidin-2-one (0.4 g, 78.3%) as a brown gum. The data for the title compound are in Table 2.

Route 6

Typical Procedure for the Preparation of Pyrrolidines Via Via Reductive Amination and Boc-Deprotection as Exemplified by the Preparation of Intermediate 127, Mixture of Diastereomers of ethyl 2-{4-[(2S)-pyrrolidin-2-yl]piperidin-1-yl}-6-azaspiro[3.4]octane-6-carboxylate

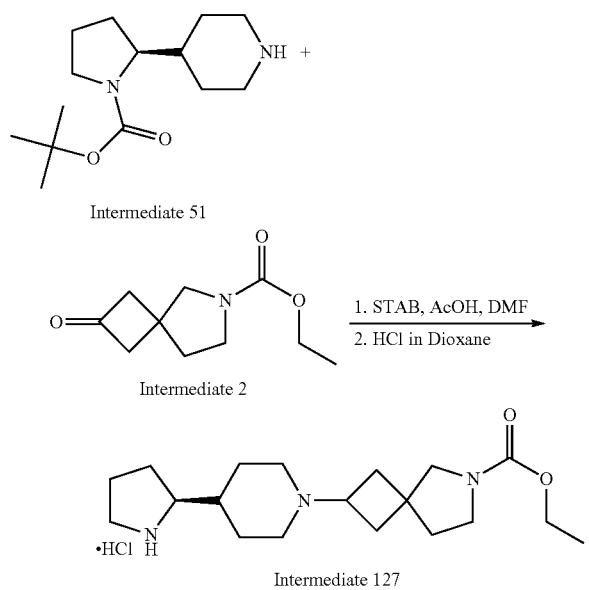

(S)-tert-Butyl 2-(piperidin-4-yl)pyrrolidine-1-carboxylate (1.24 g, 6.29 mmol) and ethyl 2-oxo-6-azaspiro[3.4]octane-6-carboxylate (1.60 g, 6.29 mmol) were dissolved in DMF (15 mL) at it and acetic acid (0.54 mL, 9.44 mmol) was added. The reaction mixture was stirred at rt for 3 h. STAB (2.67 g, 12.6 mmol) was then added and the reaction mixture was stirred overnight under nitrogen at rt. The solvents were removed in vacuo, and the residue was purified by column chromatography (normal phase, [Biotage SNAP cartridge KP-sil 340 g, 40-63 µm, 60 Å, 80 mL per min, gradient 0% to 10% 7N $NH_3$ in MeOH in DCM]) to give an inseparable mixture of isomers of ethyl 2-{4-[(2S)-1-(tert-butoxycarbonyl)pyrrolidin-2-yl]piperidin-1-yl}-6-azaspiro[3.4]octane-6-carboxylate (2.46 g, 90%) as a yellow solid.

LCMS (Method D): m/z 436 (M+H)$^+$ (ES$^+$), at 2.36 min, UV inactive.

A mixture of diastereomers of ethyl 2-{4-[(2S)-1-(tert-butoxycarbonyl)pyrrolidin-2-yl]piperidin-1-yl}-6-azaspiro[3.4]octane-6-carboxylate (0.6 g, 1.4 mmol) was dissolved in 1,4-dioxane (10 mL) and treated dropwise with HCl in 1,4-dioxane (4M, 15 mL, 60 mmol). The resulting reaction mixture was stirred at 25° C. for 16 h, the solvents were removed and the residue was purified by triturating with diethyl ether (3×10 mL) to give a mixture of diastereomers of ethyl 2-{4-[(2S)-pyrrolidin-2-yl]piperidin-1-yl}-6-azaspiro[3.4]octane-6-carboxylate, Intermediate 127 as a solid (0.45 g, 97%). The data for the title compound are in Table 2.

Route 7

Typical Procedure for the Preparation of Piperidines Via Reductive Amination, Boc-Deprotection, Urea Formation, and Hydrogenolysis as Exemplified by the Preparation of Intermediate 137, 1-(piperidin-4-yl)tetrahydropyrimidin-2(1H)-one

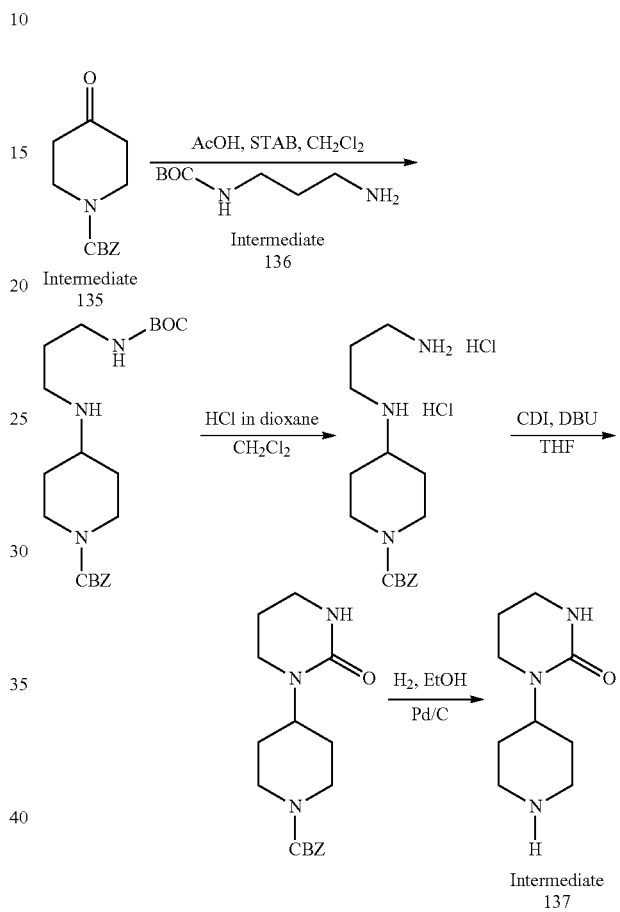

Benzyl 4-oxopiperidine-1-carboxylate (0.932 g, 4.00 mmol) and tert-butyl(3-aminopropyl)carbamate (0.766 g, 4.4 mmol) were mixed in $CH_2Cl_2$ (20 mL) at rt, AcOH (0.68 mL, 12.0 mmol) was added and stirred for 3 h. STAB (2.59 g, 12.0 mmol) was added and the reaction mixture was stirred under nitrogen at rt overnight. The reaction mixture was quenched with the addition of $NaHCO_3$ (sat aq.) (40 mL) extracted with $CH_2Cl_2$ (4×45 mL) and the combined organic layers were washed with brine, then dried over $MgSO_4$ and filtered. The solvents were removed in vacuo and the residue purified by column chromatography [Biotage SNAP cartridge KP-sil 25 g, 40-63 µm, 60 Å, 50 mL per min, gradient 0% to 10% MeOH in DCM]) to give benzyl 4-({3-[(tert-butoxycarbonyl)amino]propyl}amino)piperidine-1-carboxylate (1.54 g, 98%) as a colourless oil.

LCMS (Method B): m/z 392 (M+H)$^+$ (ES+), at 1.73 min, UV active.

Benzyl 4-({3-[(tert-butoxycarbonyl)amino]propyl}amino)piperidine-1-carboxylate (1.54 g, 3.92 mmol) was dissolved in $CH_2Cl_2$ (19.5 mL), 4 M hydrogen chloride in dioxane (4.90 mL, 19.6 mmol) added and the reaction mixture stirred at rt overnight. The solvents were removed in vacuo, the residue washed with CH₂Cl₂ (2×20 mL) and dried to give crude benzyl 4-[(3-aminopropyl)amino]piperidine-1-carboxylate dihydrochloride (1.41 g, 99%) as an off-white solid.

LCMS (Method B): m/z 292 (M+H)⁺ (ES+), at 1.46 min, UV active.

Crude benzyl 4-[(3-aminopropyl)amino]piperidine-1-carboxylate dihydrochloride (1.41 g, 3.88 mmol), CDI (0.778 g, 4.80 mmol) and pyridine (0.24 mL, 12.0 mmol) were dissolved in THF (39 mL), the mixture heated to reflux and maintained for 18 h. The solvents were removed in vacuo and the residue purified by column chromatography [Biotage SNAP cartridge KP-sil 50 g, 40-63 μm, 60 Å, 50 mL per min, gradient 0% to 10% MeOH in DCM]) to give benzyl 4-(2-oxotetrahydropyrimidin-1(2H)-yl)piperidine-1-carboxylate (0.82 g, 65%) as a colourless solid.

LCMS (Method B): m/z 318 (M+H)⁺ (ES+), at 2.62 min, UV active.

Benzyl 4-(2-oxotetrahydropyrimidin-1(2H)-yl)piperidine-1-carboxylate (0.82 g, 2.59 mmol) was dissolved in EtOH (100 mL) and passed through a 10% Pd/C cartridge using a H-Cube set at 50° C., 40 Bar H₂ at 1 mL/min. The eluted solution was concentrated in vacuo to give Intermediate 137, 1-(piperidin-4-yl)tetrahydropyrimidin-2(1H)-one (0.470 g, 99%) as a colourless solid. The data for the title compound are in Table 2.

Route 8

Typical Procedure for the Preparation of Piperidines Via Reductive Amination, and Boc-Deprotection as Exemplified by the Preparation of Intermediate 139, (2S)—N-methyl-1-(piperidin-4-yl)pyrrolidine-2-carboxamide

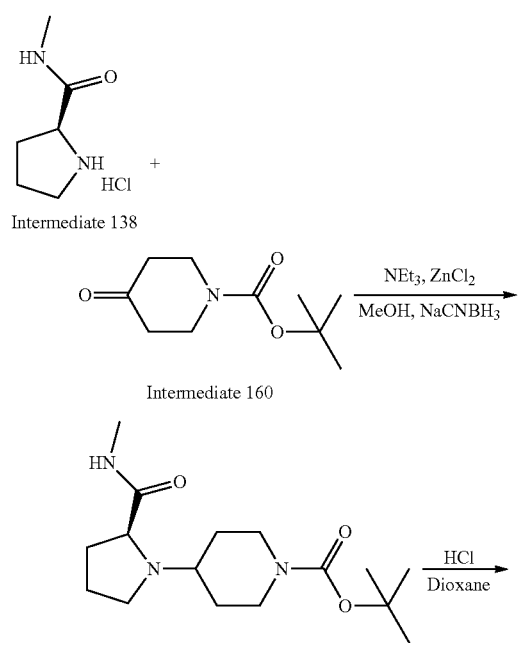

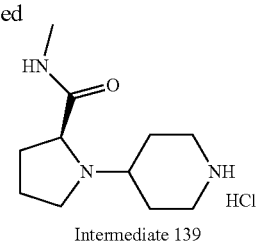

Intermediate 139

(S)-N-methylpyrrolidine-2-carboxamide (0.5 g, 3.8 mmol), NEt₃ (1.5 mL, 11.0 mmol), tert-butyl 4-oxopiperidine-1-carboxylate (0.38 g, 3.9 mmol) and ZnCl₂ (0.15 g, 4.5 mmol) were dissolved in MeOH (15 mL) under nitrogen and stirred for 1 h at 50-60° C. NaCNBH₃ (0.16 g, 0.67 mmol) was added portion wise at 0-10° C. and the mixture stirred for 3 hrs at room temperature. The reaction mixture was partitioned between EtOAc (2×100 mL) and water (50 mL), the organic layers were combined, dried (Na₂SO₄), filtered, the solvent was removed in vacuo and the crude product was purified by column chromatography (normal phase silica, 0 to 20% EtOAc in hexane) to give tert-butyl (S)-4-(2-(methylcarbamoyl) pyrrolidin-1-yl) piperidine-1-carboxylate (0.3 g, 25.0%) as a light brown liquid.

TLC observation: RF value: 0.5 (EA:Hex, 5:5).

LCMS (Method G): m/z 312 (M+H)⁺ (ES+), at 1.61 min, UV inactive.

tert-Butyl(S)-4-(2-(methylcarbamoyl) pyrrolidin-1-yl) piperidine-1-carboxylate (0.3 g, 0.96 mmol) was stirred in HCl in 1,4-dioxane (5.00 mL) solution for 10 hrs at room temperature. The reaction mixture was concentrated under high vacuum and triturated by acetone (3×10 mL) to give Intermediate 139, (S)-N-methyl-1-(piperidin-4-yl)pyrrolidine-2-carboxamide dihydrochloride (0.135 g, 67.16%) as a colourless solid. The data for the title compound are in Table 2.

Route 9

General Procedure for the Preparation of Piperidines Carrying a N-Linked Cyclic Amine at the 4-Position Via Reductive Alkylation and Deprotection as Exemplified by the Preparation of Intermediate 181, 4-[2-(1H-pyrazol-5-yl)pyrrolidin-1-yl] piperidine trifluoroacetate salt

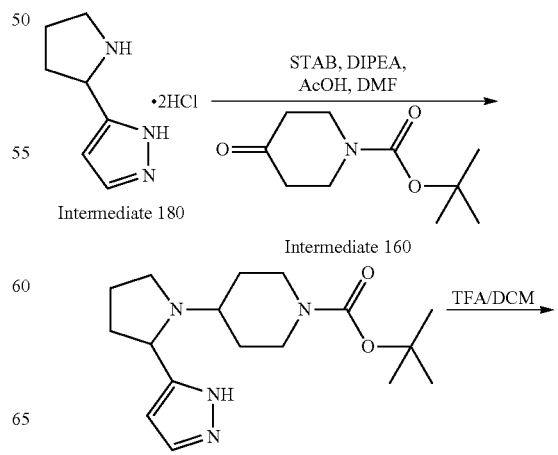

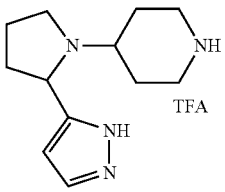

Intermediate 181

5-(Pyrrolidin-2-yl)-1H-pyrazole dihydrochloride (0.105 g, 0.50 mmol) was dissolved in DMF (5 mL). To the solution was added DIPEA (0.435 mL, 2.5 mmol), AcOH (0.043 mL, 0.75 mmol), tert-butyl 4-oxopiperidine-1-carboxylate (0.100 g, 0.50 mmol) and STAB (0.318 g, 1.50 mmol) in that order. The mixture was stirred at it for 2 days, then concentrated to remove DMF. The residue was partitioned between sat. aqueous NaHCO₃ and DCM (×2) and the organic phase was passed through a phase separator and concentrated to give the crude tert-butyl 4-[2-(1H-pyrazol-5-yl)pyrrolidin-1-yl] piperidine-1-carboxylate (0.271 g, >100%) as an oil.

LCMS (Method C): m/z 321 (M+H)⁺ (ES⁺), at 1.18 min, UV active

A solution of the crude tert-butyl 4-[2-(1H-pyrazol-5-yl)pyrrolidin-1-yl]piperidine-1-carboxylate (0.271 g, assumed 0.50 mmol) in DCM (3 mL) and TFA (3 mL) was stirred at RT for 110 min then diluted with toluene and concentrated. The residue was azeotroped with toluene to give the crude Intermediate 181, 4-[2-(1H-pyrazol-5-yl)pyrrolidin-1-yl]piperidine trifluoroacetate salt (0.598 g, >100%) as an oil. Used immediately. The data for the title compound are in Table 2.

Route 10

General Procedure for the Preparation of Pyrrolidinone or Oxadiazolone Containing Piperidines Via Copper Catalyzed Coupling to Pyridine Followed by Hydrogenation as Exemplified by the Preparation of Intermediate 184, 5-methyl-1-(piperidin-4-yl)pyrrolidin-2-one acetate salt

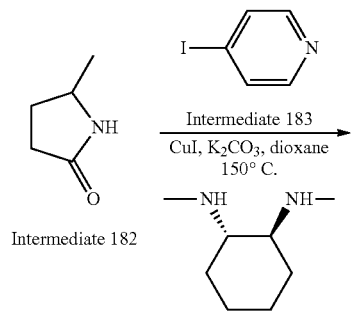

Intermediate 182

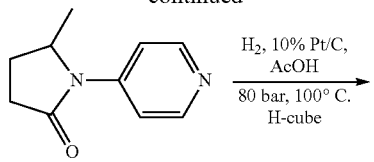

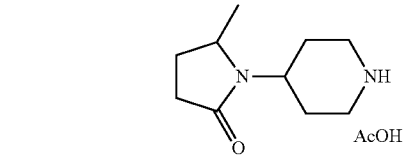

Intermediate 184

A mixture of 5-methylpyrrolidin-2-one (0.050 g, 0.50 mmol), 4-iodopyridine (0.103 g, 0.50 mmol), (trans)-N,N'-dimethylcyclohexane-1,2-diamine (0.016 mL, 0.10 mmol), CuI (0.019 g, 0.10 mmol) and K₂CO₃ (0.209 g, 1.5 mmol) in dioxane (2 mL) was sealed in a nitrogen flushed glass tube and heated with stirring at 150° C. overnight. The cooled reaction mixture was concentrated onto flash silica (5 mL). The resulting powder was purified by column chromatography (normal phase, [Biotage SNAP cartridge KP-sil 25 g, 40-63 µm, 60 Å], 30 mL per min, 0 to 5% Solvent A in DCM, where Solvent A is 10% of (7 M NH₃/MeOH) in MeOH) to give 5-methyl-1-(pyridin-4-yl)pyrrolidin-2-one (0.088 g, 99%) as an oil.

LCMS (Method C): m/z 177 (M+H)⁺ (ES⁺), at 0.69 min, UV active

The 5-methyl-1-(pyridin-4-yl)pyrrolidin-2-one (0.080 g, 0.45 mmol) was dissolved in AcOH (8 mL) and hydrogenated over 10% Pt/C catalyst at 80 bar pressure and 100° C. at a flow-rate of 1 mL/min using a H-Cube. The solution was then concentrated and the residue azeotroped with toluene (×2) to afford the crude Intermediate 184, 5-methyl-1-(piperidin-4-yl)pyrrolidin-2-one acetate salt (0.166 g, >100%) as an oil. The data for the title compound are in Table 2.

Route 11

Typical Procedure for the Preparation of Piperidines Via Copper Catalyzed Coupling to Pyridine Followed by Hydrogenation as Exemplified by the Preparation of Intermediate 199, (5R)-5-methyl-1-(piperidin-4-yl)pyrrolidin-2-one acetate salt and Intermediate 200, (5R)-5-ethyl-1-(piperidin-4-yl)pyrrolidin-2-one acetate salt

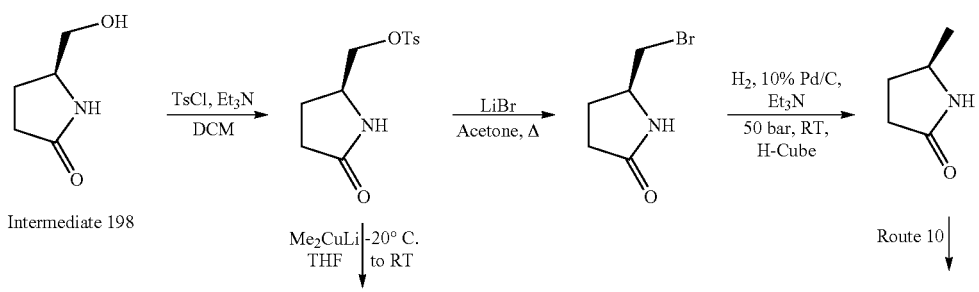

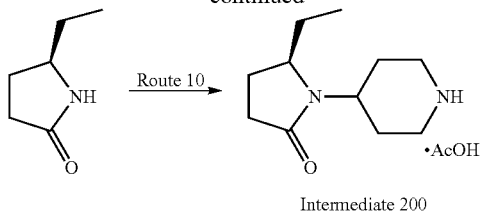
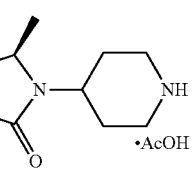

Intermediate 200    Intermediate 199

Intermediate 199, (5R)-5-methyl-1-(piperidin-4-yl)pyrrolidin-2-one acetate salt

To a solution of (5S)-5-(hydroxymethyl)pyrrolidin-2-one (2.0 g, 17 mmol) and 4-methylbenzenesulfonyl chloride (5.3 g, 28 mmol) in DCM (24 mL) was added triethylamine (12 mL, 86 mmol). The resulting mixture was stirred at RT overnight then concentrated. The residue was dissolved in DCM and washed with 1 M aqueous HCl (×3) and brine (×1), then passed through a phase separator and concentrated to give a brown solid. The solid was recrystallized from DCM/isohexane to give a tan solid that was removed by filtration, washed with DCM/isohexane mixture and dried in air to give [(2S)-5-oxopyrrolidin-2-yl]methyl 4-methylbenzenesulfonate (3.13 g, 67%).

LCMS (Method C): m/z 270 (M+H)$^+$ (ES$^+$), at 0.97 min, UV active

A mixture of [(2S)-5-oxopyrrolidin-2-yl]methyl 4-methylbenzenesulfonate (0.50 g, 1.9 mmol) and lithium bromide (0.484 g, 5.6 mmol) in acetone (5 mL) was heated at reflux under N$_2$ overnight, then allowed to cool. The solvent was removed by concentration, the residue was distributed between DCM and H$_2$O and the phases were separated. The aqueous phase was extracted with DCM (×3), then the organic phases were passed through a phase separator and concentrated to give (5S)-5-(bromomethyl)pyrrolidin-2-one (0.284 g, 86%) as a gum.

LCMS (Method C): m/z 178/180 (M+H)$^+$ (ES$^+$), at 0.37 min, weakly UV active

A solution of (5S)-5-(bromomethyl)pyrrolidin-2-one (0.284 g, 1.6 mmol) in triethylamine (0.267 mL, 1.9 mmol) and ethanol (32 mL) was hydrogenated over 10% Pd/C catalyst at 50 bar pressure and at RT at a flow-rate of 1 mL/min using a H-Cube. The solution was concentrated to give the crude (5R)-5-methylpyrrolidin-2-one (0.445 g, >100%) as a sticky solid.

LCMS (Method C): m/z 100 (M+H)$^+$ (ES$^+$), at 0.34 min, weakly UV active

The crude (5R)-5-methylpyrrolidin-2-one (0.445 g, assumed 1.5 mmol) was reacted according to Route 10 (coupling with Intermediate 183) to give the crude Intermediate 199, (5R)-5-methyl-1-(piperidin-4-yl)pyrrolidin-2-one acetate salt (0.125 g, 46%) as an oil. The data for the title compound are in Table 2.

Intermediate 200, (5R)-5-ethyl-1-(piperidin-4-yl)pyrrolidin-2-one acetate salt

Methyllithium (1.5 M in ether, 7.4 mL, 11 mmol) was added quickly with stirring to a suspension of copper iodide (1.06 g, 5.6 mmol) in THF (6 mL), pre-cooled in ice-water under N$_2$. The pale brown solution was stirred in ice-water for 45 min, then cooled to −20° C. A solution of [(2S)-5-oxopyrrolidin-2-yl]methyl 4-methylbenzenesulfonate (0.50 g, 1.9 mmol) in THF (6 mL) was added portion-wise over 2 min and the resulting solution was stirred at −20° C. for 45 min, then in ice-water overnight, allowing the cooling bath to slowly expire. The mixture was quenched with saturated aqueous NH$_4$Cl (15 mL) and stirred for several hours. The two-phase mixture was extracted with ether (×3), the organic phases were washed with brine, passed through a phase separator and concentrated to give the crude (5R)-5-ethylpyrrolidin-2-one (0.124 g, 59%) as an oil.

LCMS (Method C): m/z 114 (M+H)$^+$ (ES$^+$), at 0.50 min, weakly UV active

The crude (5R)-5-ethylpyrrolidin-2-one (0.124 g, 1.10 mmol) was reacted according to Route 10 (coupling with Intermediate 183) to give the crude Intermediate 200, (5R)-5-ethyl-1-(piperidin-4-yl)pyrrolidin-2-one acetate salt (0.156 g, 72%) as a gum. The data for the title compound are in Table 2.

Route 12

Typical Procedure for the Preparation of Piperidines Via Carbamate Formation, Copper Catalyzed Coupling to Pyridine Followed by Hydrogenation as Exemplified by the Preparation of Intermediate 205, (4R)-4-methyl-3-(piperidin-4-yl)-1,3-oxazolidin-2-one acetate salt

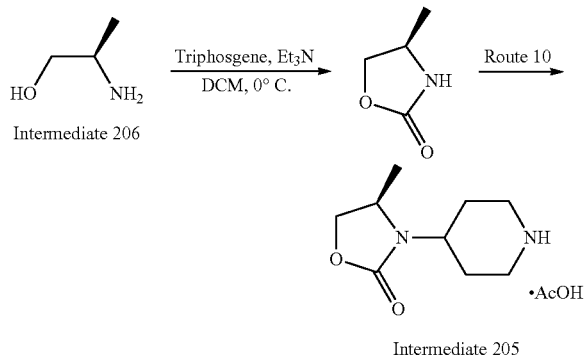

Intermediate 205

A solution of triphosgene (0.297 g, 1.0 mmol) in DCM (5 mL) was added portion-wise over 1 h to a solution of (2R)-2-aminopropan-1-ol (0.156 mL, 2.0 mmol) and triethylamine (0.56 mL, 4.0 mmol) in DCM (5 mL), precooled in ice-water. The mixture was stirred in ice-water for a further 2 h, then ether (6 mL) was added. The thick suspension was filtered through a sinter, washing the solid with more ether (6 mL). The filtrate was concentrated onto flash silica (5 mL) and the resulting powder was purified by column chromatography (normal phase, [Biotage SNAP cartridge KP-sil 25 g, 40-63 µm, 60 A], 30 mL per min, 100% EtOAc) to give (4R)-4-methyl-1,3-oxazolidin-2-one (192 mg, 95%) as a solid.

LCMS (Method C): m/z 102 (M+H)+ (ES+), at 0.14 min, UV inactive (4R)-4-Methyl-1,3-oxazolidin-2-one (0.188 g, 1.9 mmol) was reacted according to Route 10 (coupling with Intermediate 183) to give the crude Intermediate 205, (4R)-4-methyl-3-(piperidin-4-yl)-1,3-oxazolidin-2-one acetate salt (0.343 g, 100%) as a solid. The data for the title compound are in Table 2.

Route 13

Typical Procedure for the Preparation of Piperidines Via Reductive Aminations, as Exemplified by the Preparation of Intermediate 159, tert-butyl 4-[(2R)-2-(methoxycarbonyl)pyrrolidin-1-yl]piperidine-1-carboxylate

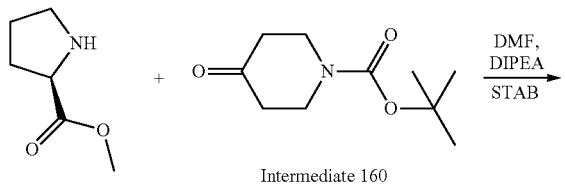

Intermediate 115

Intermediate 160

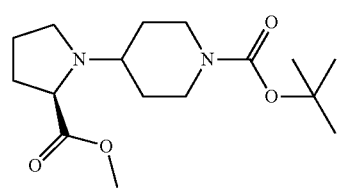

Intermediate 159

D-Proline methyl ester hydrochloride (0.200 g, 1.208 mmol) and 1-Boc-4-piperidinone (0.24 g, 1.208 mmol) were dissolved in DMF (2 mL) at rt and diisopropylethylamine (0.209 mL, 1.208 mmol) was added. The reaction mixture was stirred at rt for 3 h. STAB (0.512 g, 2.416 mmol) was then added and the reaction mixture was stirred overnight under nitrogen at rt. The solvents were removed in vacuo, and residue was partitioned between H$_2$O (15 mL) and EtOAc (25 mL), aqueous layer was extracted with EtOAc (2×25 mL), organic layers were combined, dried over Na$_2$SO$_4$ and solvent was removed in vacuo to give tert-butyl 4-[(2R)-2-(methoxycarbonyl)pyrrolidin-1-yl]piperidine-1-carboxylate, Intermediate 159, as a white solid (393 mg, >99%). The data for the title compound areas in Table 2

Route 14

Typical Procedure for the Preparation of Piperidines Via Reductive Aminations, as Exemplified by the Preparation of Intermediate 271, tert-butyl 3,3-difluoro-1,4'-bipiperidine-1'-carboxylate

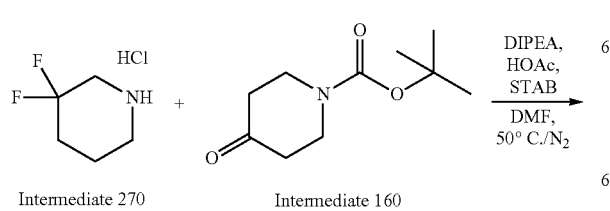

Intermediate 270    Intermediate 160

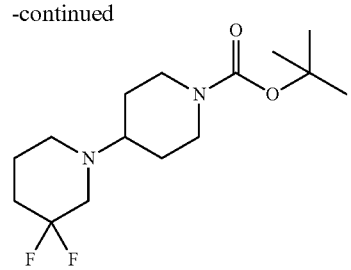

Intermediate 271

3,3-difluoropiperidine. HCl (0.30 g, 1.90 mmol) and 1-Boc-4-piperidinone (0.379 g, 1.90 mmol) were dissolved in DMF (8 mL) at it and diisopropylethylamine (0.246 g, 1.90 mmol) was added. The reaction mixture was stirred at 50° C. under nitrogen for 2 h. The reaction mixture was cooled to rt, glacial acetic acid (0.114 g, 1.90 mmol) and STAB (1.01 g, 4.76 mmol) was then added and the reaction mixture was stirred overnight at 50° C. under nitrogen. Water (2 mL) was added to the cooled reaction mixture and the solvents were removed in vacuo. The residue was diluted with sat. NaHCO$_3$ (aq) (10 mL) and extracted with DCM (2×10 mL) The combined organic layers were passed through a Biotage Phase Separator Cartridge to dry and the solvents were removed in vacuo. The residue was purified by column chromatography (normal phase, [Biotage SNAP cartridge KP-sil 25 g 40-63 μm, 60 Å, 25 mL per min, gradient 0% to 10% MeOH/DCM]) to give tert-butyl 3,3-difluoro-1,4'-bipiperidine-1'-carboxylate, Intermediate 271, (0.347 g, 60%) as an amber oil. The data for the title compound are in Table 2

Route 15

Typical Procedure for the Preparation of Piperidines Via Tetrazole Formation, Followed by Alkylation as Exemplified by the Preparation of Intermediate 195, 4-(1-methyl-1H-tetrazol-5-yl)piperidine hydrochloride salt

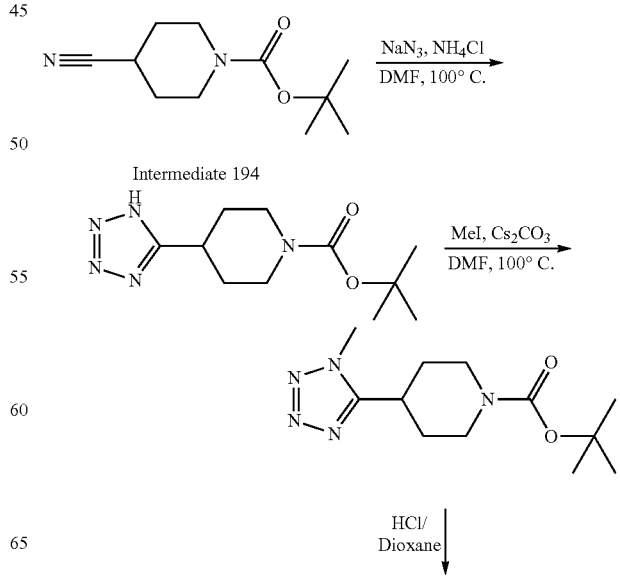

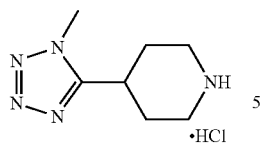

Intermediate 195

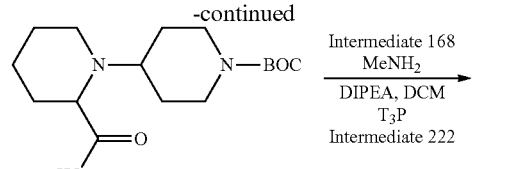

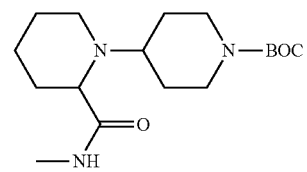

tert-Butyl 4-cyanopiperidine-1-carboxylate (2.1 g, 10 mmol), sodium azide (1.95 g, 30 mmol) and ammonium chloride (1.6 g, 30 mmol) were dissolved in DMF (20 mL). The reaction mixture was stirred at 100° C. for 24 h, then diluted with water (250 mL) and extracted with EtOAc (3×100 mL). The combined organic layers were dried (Na$_2$SO$_4$) and concentrated to give the crude product, which was purified by column chromatography (Normal phase, Neutral silica gel, 60-120 mesh, 0 to 5% MeOH in DCM) to give tert-butyl 4-(1H-tetrazol-5-yl)piperidine-1-carboxylate (1.25 g, 50%) as a solid.

LCMS (Method F): m/z 198 (M-tBu+H)$^+$ (ES$^+$), at 1.69 min, UV inactive tert-Butyl 4-(1H-tetrazol-5-yl)piperidine-1-carboxylate (1.2 g, 4.7 mmol), iodomethane (2.0 g, 14 mmol) and Cs$_2$CO$_3$ (9.6 g, 28 mmol) were dissolved in dry DMF (36 mL). The reaction mixture was stirred at 100° C. for 2 h, then diluted with water (250 mL) and extracted with EtOAc (3×100 mL). The combined organic layers were dried (Na$_2$SO$_4$) and concentrated to give the crude product, which was purified by column chromatography (Normal phase, Neutral silica gel, 60-120 mesh, 0 to 35% EtOAc in hexane and then 45 to 60% EtOAc in hexane to separate the two regioisomers. The required regioisomer, tert-butyl 4-(1-methyl-1H-tetrazol-5-yl)piperidine-1-carboxylate (0.160 g, 13%), was the second to elute from the column and was obtained as a solid.

LCMS (Method F): m/z 212 (M-tBu+H)$^+$ (ES$^+$), at 1.79 min, UV inactive tert-Butyl 4-(1-methyl-1H-tetrazol-5-yl)piperidine-1-carboxylate (0.160 g, 0.60 mmol) was dissolved in dioxane (3 mL). HCl in dioxane (4M, 3 mL, 12 mmol) was added at 0° C. and the mixture was stirred at room temperature for 5 h. The solvent was removed and the mixture was triturated with diethyl ether (5 mL) to give 4-(1-methyl-1H-tetrazol-5-yl)piperidine hydrochloride salt, Intermediate 195, (0.130 g, >100%) as solid. The data for the title compound are in Table 2.

Route 16

Typical Procedure for the Preparation of Piperidines Via Reductive Amination, Amide Formation and Boc-Deprotection as Exemplified by the Preparation of Intermediate 223, (2R)-N-methyl-1,4'-bipiperidine-2-carboxamide

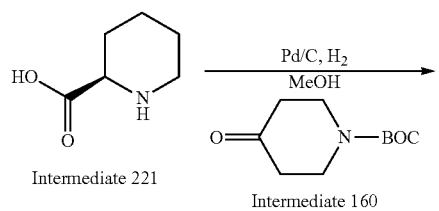

To a solution of R-pipecolinic acid (1 g, 7.75 mmol) and tert-butyl 4-oxopiperidine-1-carboxylate (2.31 g, 11.6 mmol) in MeOH (40 mL), 10% Pd on charcoal (1 g, 50% wet) was added and the reaction mixture was stirred at room temperature under H$_2$ (1 atm) for 48 h. The reaction mixture was filtered through a celite bed and the filtrate was evaporated in vacuo. This crude residue was triturated in DCM (50 mL) to give (R)-1'-(tert-butoxycarbonyl)-[1,4'-bipiperidine]-2-carboxylic acid (1.2 g, 50%) as a white solid. This crude residue was used for the next step without further purification.

$^1$H-NMR (400 MHz; CDCl$_3$) δ: 1.46 (s, 9H), 1.50-1.59 (m, 1H), 1.75-1.91 (m, 4H), 1.93-2.05 (m, 2H), 2.10-2.19 (m, 2H), 2.35-2.41 (m, 1H), 2.51-2.69 (m, 3H), 3.41-3.49 (m, 1H), 3.55-3.61 (m, 1H), 3.70-3.79 (m, 1H), 4.25-4.36 (m, 2H).

To a solution of (R)-1'-(tert-butoxycarbonyl)-[1,4'-bipiperidine]-2-carboxylic acid (1.0 g, 3.20 mmol) and MeNH$_2$ (2 M in THF, 3.2 mL, 6.41 mmol) in DCM (20 mL), DIPEA (1.75 mL, 9.60 mmol) was added at 0° C. After stirring for 10 min, 1-propane phosphonic anhydride [50% solution in ethyl acetate (4.07 mL, 6.41 mmol)] was added and stirred at room temperature for 3 h. After completion, the reaction mixture was quenched with saturated aq NaHCO$_3$ and extracted with DCM (3×30 mL). The organic layers were combined and washed with brine, dried (Na$_2$SO$_4$) and concentrated in vacuo to give tert-butyl (R)-2-(methylcarbamoyl)-[1,4'-bipiperidine]-1'-carboxylate (4, 1 g, 97%) as a colorless gummy liquid. This crude residue was used for the next step without further purification.

$^1$H-NMR (400 MHz, DMSO) δ: 1.46 (s, 9H), 1.61-1.80 (m, 4H), 1.91-2.08 (m, 4H), 2.25-2.33 (m, 2H), 2.61-2.71 (m, 4H), 2.82 (d, J=4.8 Hz, 3H), 3.32-3.45 (m, 2H), 4.25-4.36 (m, 2H), 6.85 (br.s., 1H).

To a solution of tert-butyl (R)-2-(methylcarbamoyl)-[1,4'-bipiperidine]-1'-carboxylate (700 mg, 2.15 mmol) in dioxane (10 mL), HCl in dioxane (4 M, 10 mL) was slowly added at 0° C. and stirred at room temperature for 3 h. The reaction mixture was concentrated in vacuo. This was basified with aq sat NaHCO$_3$ (10 mL) and concentrated. To the crude reaction mass 5% MeOH/DCM (30 mL) was added, stirred for 10 min and filtered. The filtrate was concentrated in vacuo to give Intermediate 223, (R)-N-methyl-[1,4'-bipiperidine]-2-carboxamide (400 mg, 83%) as a brown gummy liquid. The data for the title compound are in Table 2.

Route 17

Typical Procedure for the Preparation of Iodo Pyrazoles Via Sandmeyer Reaction as Exemplified by the Preparation of Intermediate 250, 4-ethyl-5-iodo-1-methyl-1H-pyrazole

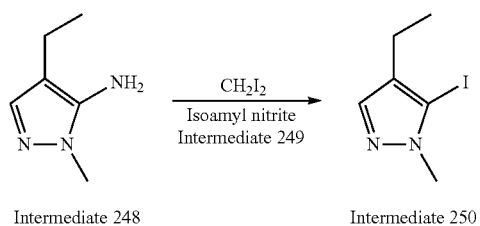

Intermediate 248        Intermediate 250

1-Ethyl4-methyl-1H pyrazole amine (0.5 g, 3.932 mmol), was dissolved in di iodo methane (9.0 mL) at 0-5° c. under nitrogen atmosphere followed by the dropwise addition of isoamyl nitrite and the mixture was stirred for 2 h at 80° C. then 2 h at room temperature. The reaction mixture was partitioned between $H_2O$ (100 mL) and EtOAc (250 mL), the aqueous layer was further extracted with EtOAc (2×250 mL), the combined organic layers were dried ($Na_2SO_4$), filtered and the solvent was removed in vacuo. The residue was purified by column chromatography (normal phase, neutral silica gel, 60-120 mesh, 30 to 50% ethyl acetate in hexane) to give 4-ethyl-5-iodo-1-methyl-1H-pyrazole Intermediate 250 (0.5 g, 53.23%) as a light yellowish gum. The data for the title compound are in Table 2.

Route 18

Typical Procedure for the Preparation of Activated Carbamates Via Deprotection, Carbamate Formation Followed by Reductive Amination as Exemplified by the Preparation of Intermediate 302, tert-butyl(2R)-2-(difluoromethyl)pyrrolidine-1-carboxylate

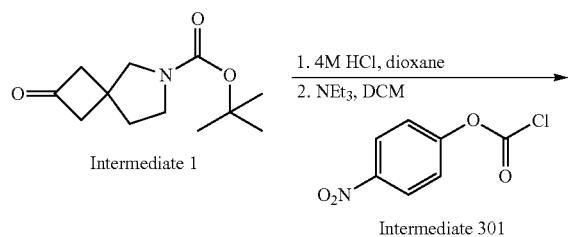

Intermediate 1

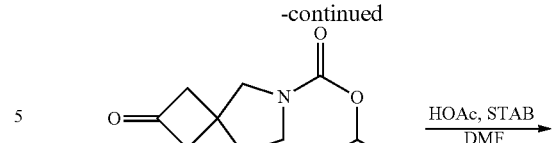

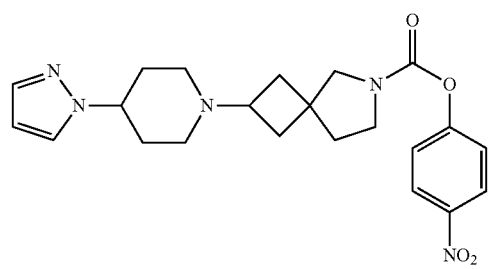

Intermediate 302

6-Boc-2-oxo-6-aza-spiro[3.4]octane (4.00 g, 0.017 mol) was dissolved in 4M HCl in dioxane (25 mL) and stirred at rt under nitrogen overnight. The solvents were removed in vacuo to give an off white solid which was suspended in DCM (40 mL), reaction mixture was cooled under nitrogen to 0° C. $Et_3N$ (3.60 g, 0.036 mol) and 4-nitrophenyl chloroformate (3.767 g, 0.0187 mol) were added and the reaction mixture was and stirred at rt overnight. The reaction mixture was quenched with sat. $NaHCO_3$ (aq) (30 mL) and extracted with DCM (3×20 mL). The organic layers were combined and dried by passing through a Biotage Phase Separator Cartridge and the solvents were removed in vacuo. The residue was purified by column chromatography (normal phase, [Biotage SNAP cartridge KP-sil 50 g 40-63 µm, 60 Å, 50 mL per min, gradient 0% to 6% MeOH/DCM]) to give 4-nitrophenyl 2-oxo-6-azaspiro[3.4]octane-6-carboxylate as a yellow solid (1.40 g, 27%).

LCMS (Method C): m/z 291 (M+H)+ (ES+) at 1.167 min 4-nitrophenyl 2-oxo-6-azaspiro[3.4]octane-6-carboxylate (0.700 g, 2.41 mmol) was dissolved in DMF (15 mL). 4-(1H-pyrazole-1-yl)piperidine (0.365 g, 2.41 mmol), glacial acetic acid (0.144 g, 2.41 mmol) and STAB (1.535 g, 7.24 mmol) were added, the reaction mixture was stirred at 50° C. under nitrogen overnight. Reaction mixture quenched with water (2 mL) and the solvents were removed in vacuo. The residue was partitioned between DCM (20 mL) and sat. $NaHCO_3$ (aq) (20 mL), aqueous layer was extracted with DCM (2×20 mL), the organic layers were combined and dried by passing through a Biotage Phase Separator Cartridge and the solvents were removed in vacuo. The residue was purified by column chromatography (normal phase, [Biotage SNAP cartridge KP-sil 25 g 40-63 µm, BOA, 25 mL per min, gradient 0% to 10% MeOH/DCM]) to give 4-nitrophenyl 2-[4-(1H-pyrazol-1-yl)piperidin-1-yl]-6-azaspiro[3.4]octane-6-carboxylate, Intermediate 302, (0.738 g, 72%). The data for the title compound are in Table 2

General Synthetic Procedures for Examples

Route a

Typical Procedure for the Preparation of Piperidines Via Sodium Triacetoxyborohydride reductive amination as exemplified by the Preparation of Example 1-1, ethyl 2-[4-(1H-imidazol-2-yl)piperidin-1-yl]-6-azaspiro[3.4]octane-6-carboxylate Route b Typical Procedure for the Preparation of Piperidines Via Sodium Cyanoborohydride and Zinc Chloride Reductive Amination as Exemplified by the Preparation of Example 1-3, Ethyl 2-(4-(4-(trifluoromethyl)-1H-imidazol-2-yl)piperidin-1-yl)-6-azaspiro[3.4]octane-6-carboxylate

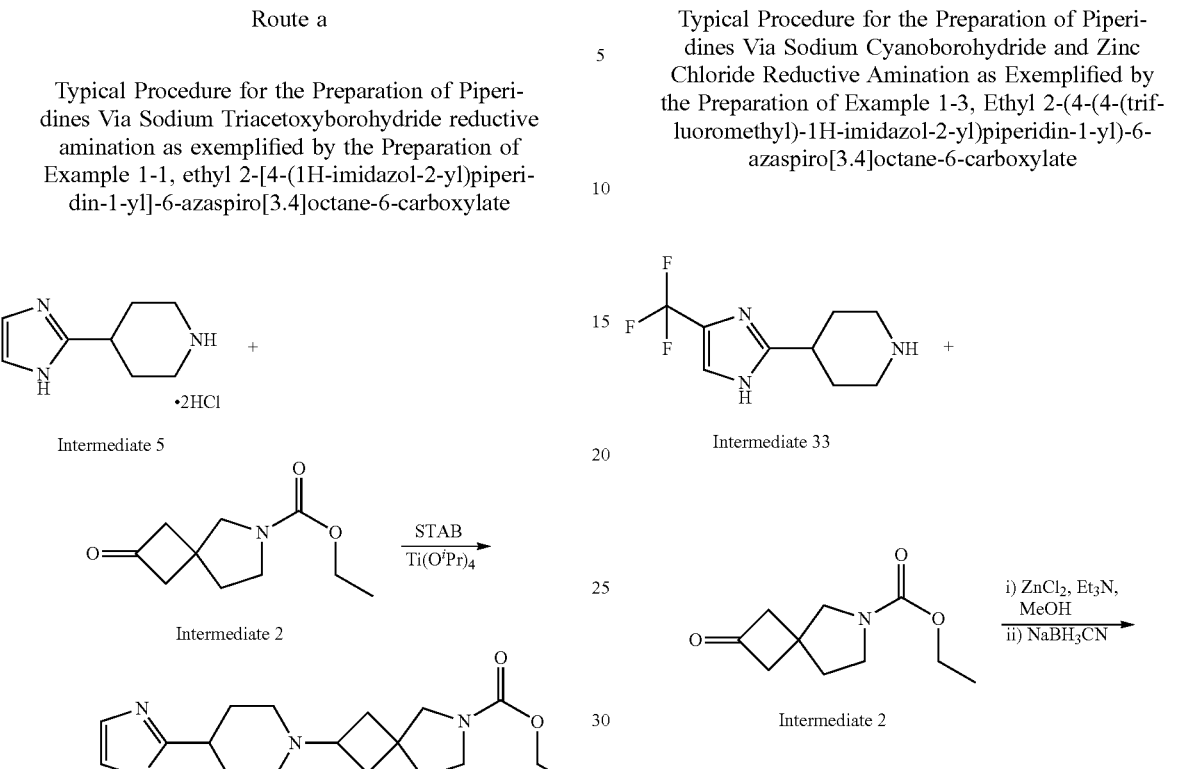

4-(1H-Imidazol-2-yl)piperidine dihydrochloride (1.43 g, 7.1 mmol) and ethyl 2-oxo-6-azaspiro[3.4]octane-6-carboxylate (1.60 g, 7.1 mmol) were dissolved in DCM (60 mL) at rt and titanium isopropoxide (2.31 mL, 7.81 mmol) was added. The reaction mixture was stirred at it for 1 h. The reaction mixture was cooled to −5° C., then STAB (3.01 g, 14.2 mmol) and acetic acid (350 μL, 4.26 mmol) were added and the reaction mixture was stirred overnight under nitrogen while warming to rt. The reaction mixture was quenched with the addition of NaHCO$_3$ (sat aq.) (10 mL) and diluted with DCM then filtered through a pad of celite. The layers were separated and the aqueous layer was extracted with DCM. The combined DCM layers were washed with brine, then dried over MgSO$_4$. The solvents were removed in vacuo, and the residue was purified by column chromatography (normal phase, [Biotage SNAP cartridge KP-sil 50 g, 40-63 μm, 60 Å, 50 mL per min, gradient 1% to 10% MeOH in DCM with 0.5% NEt$_3$]) to give an inseparable mixture of diastereomers of ethyl 2-[4-(1H-imidazol-2-yl)piperidine]-6-azaspiro[3.4]octane-6-carboxylate (2.645 g, 98.3%) as a white solid. Preparative HPLC was used to separate the diastereomers, using a Phenomenex Gemini-N C18 column, 150×21 mm, eluting with 28 to 38% MeCN/H$_2$O at 18 ml/min and collecting fractions by monitoring at 218 nm to give isomer 1 ethyl 2-[4-(1H-imidazol-2-yl)piperidine]-6-azaspiro[3.4]octane-6-carboxylate (0.338 g, 14%) as a colourless solid and isomer 2 ethyl 2-[4-(1H-imidazol-2-yl)piperidine]-6-azaspiro[3.4]octane-6-carboxylate (0.369 g, 16%) as a colourless solid. The data for Isomer 2 are in Table 3.

4-(4-(Trifluoromethyl)-1H-imidazol-2-yl)piperidine (100 mg, 0.46 mmol), ethyl 2-oxo-6-azaspiro[3.4]octane-6-carboxylate (89 mg, 0.46 mmol), ZnCl2 (2 mg, 0.01 mmol) and triethylamine (0.3 mL, 2.28 mmol) were dissolved in MeOH (5 mL) and the reaction mixture was stirred at 50° C. for 2 h. The reaction mixture was cooled down to 0° C., and NaBH$_3$CN (114 mg, 1.83 mmol) was added portion wise. The resulting reaction mixture was stirred at 25° C. for 7 h and the solvents were removed in vacuo. The residue was partitioned between H$_2$O (50 mL) and EtOAc (35 mL), the aqueous layer was extracted with EtOAc (2×35 mL), the organic layers were combined, dried (Na$_2$SO$_4$) and the solvent was removed in vacuo. The residue was purified by Prep HPLC [reverse phase (X-BRIDGE, C-18, 250×19 mm, 5 um, 18 mL per min, gradient 28.0% (over 40.0 mins), 100% (over 3.0 mins) then 28.0% (over 5.0 min), 0.1% NH$_3$ in MeCN/water] to give ethyl 2-(4-(4-(trifluoromethyl)-1H-imidazol-2-yl)piperidin-1-yl)-6-azaspiro[3.4]octane-6-carboxylate Example 1-3 Isomer 1, (15 mg, 8.24%) as a yellow solid and ethyl 2-(4-(4-(trifluoromethyl)-1H-imidazol-2-yl)piperidin-1-yl)-6-azaspiro[3.4]octane-6-carboxylate Example 1-3 Isomer 2, (12 mg, 6.6%) as a yellow solid. The data for Isomer 2 are in Table 3

Route c

Typical Procedure for the Conversion of Trifluoromethyl Substituted Imidazoles to Cyano Substituted Imidazoles as Exemplified by the Preparation of Example 1-4, ethyl 2-[4-(4-cyano-1H-imidazol-2-yl)piperidin-1-yl]-6-azaspiro[3.4]octane-6-carboxylate

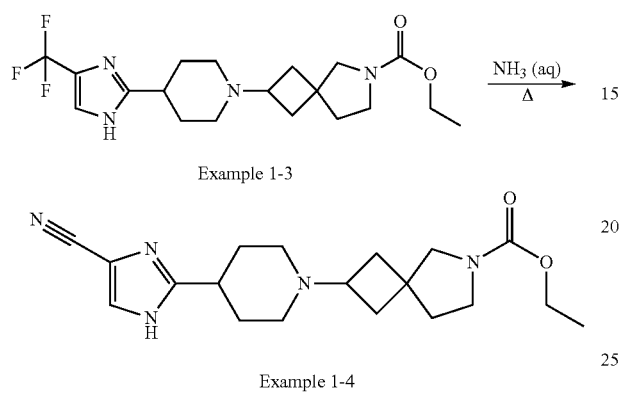

Example 1-3

Example 1-4

Ethyl 2-(4-(4-(trifluoromethyl)-1H-imidazol-2-yl)piperidin-1-yl)-6-azaspiro[3.4]octane-6-carboxylate (200 mg, 0.50 mmol) was dissolved in $NH_3$ solution (20 mL) and stirred at 60° C. for 8 h. The solvents were removed in vacuo and the residue was partitioned between $H_2O$ (60 mL) and EtOAc (40 mL), aqueous layer was extracted with EtOAc (2×40 mL), organic layers were combined, dried ($Na_2SO_4$). The solvent was removed in vacuo and the residue was purified by Prep HPLC [reverse phase (DURASHELL, C-18, 250×21.2 mm, 5 um, 22 mL per min, gradient 25.0% (over 30.0 mins), 100% (over 3.0 mins) then 25.0% (over 7.0 min), 0.1% NH3 in MeCN/water] to give ethyl 2-(4-(4-cyano-1H-imidazol-2-yl)piperidin-1-yl)-6-azaspiro[3.4]octane-6-carboxylate, Example 1-4 Isomer 1, (26 mg, 14.6%) as a yellow solid and ethyl 2-[4-(4-cyano-1H-imidazol-2-yl)piperidin-1-yl]-6-azaspiro[3.4]octane-6-carboxylate, Example 1-4 Isomer 2, (25 mg, 14.06%) as a yellow solid. The data for Isomer 2 are in Table 3.

Route d

Typical Procedure for the Preparation of Piperidines Via Sodium Triacetoxyborohydride Reductive Amination, Boc-Deprotection and Ethylcarbamate Formation as Exemplified by the Preparation of Example 1-7, ethyl 2-[4-(1-methyl-1H-imidazol-2-yl)piperidin-1-yl]-6-azaspiro[3.4]octane-6-carboxylate

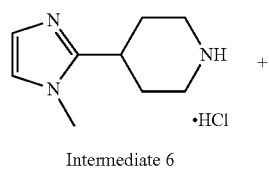

Intermediate 6

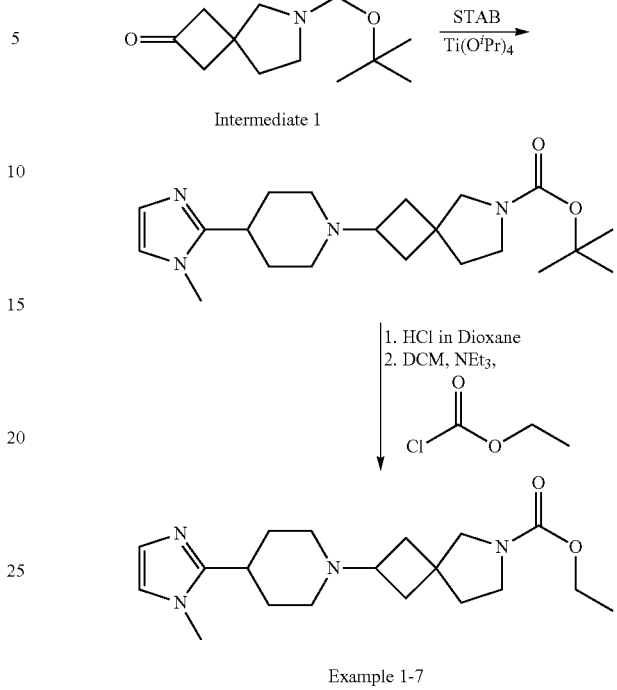

Intermediate 1

Example 1-7

4-(1-Methylimidazol-2-yl)piperidine hydrochloride (0.244 g, 1.21 mmol) and 6-Boc-2-oxo-6-azaspiro[3,4]octane (0.273 g, 1.21 mmol) were dissolved in DCM (10 mL) at it and titanium isopropoxide (0.4 mL, 2.42 mmol) was added. The reaction mixture was stirred at it for 1 h. The reaction mixture was cooled to −5° C., then STAB (0.513 g, 2.42 mmol) and acetic acid (27 µL, 480 µmol) were added and the reaction mixture was stirred overnight under nitrogen while warming to rt. The reaction mixture was quenched with the addition of $NaHCO_3$ (sat aq.) (10 mL) and diluted with DCM then filtered through a pad of celite. The layers were separated and the aqueous layer was extracted with DCM. The combined DCM layers were washed with brine, then dried over $MgSO_4$. The solvents were removed in vacuo, and the residue was purified by column chromatography (normal phase, [Biotage SNAP cartridge KP-sil 25 g, 40-63 µm, 60 Å, 50 mL per min, gradient 1% to 10% MeOH in DCM]) to give an inseparable mixture of isomers of tert-butyl 2-[4-(1-methyl-1H-imidazol-2-yl)piperidine]-6-azaspiro[3.4]octane-6-carboxylate (0.330 g, 72%) as a yellow gum.

LCMS (Method A): m/z 374 (M+H)$^+$ (ES$^+$), at 1.68 min, UV inactive.

Tert-butyl 2-[4-(1-methyl-1H-imidazol-2-yl)piperidine]-6-azaspiro[3.4]octane-6-carboxylate (0.326 g, 0.87 mmol) was dissolved in 4 M hydrogen chloride in dioxane (1.2 mL, 5.2 mmol). The reaction mixture was stirred at it for 18 h. The volatiles were then removed in vacuo and the residue dissolved DCM (17 mL) and triethylamine (0.49 mL, 3.49 mmol). Ethyl chloroformate (125 µL. 1.31 mmol) was added dropwise and the solution stirred at rt for 18 h. The mixture was then poured into $NaHCO_3$ (aq) (75 mL) and DCM (75 mL), extracted (2×75 mL), and the combined DCM extracts washed with brine (20 mL) then dried over $MgSO_4$. After concentration, the residue was purified by column chromatography (normal phase, [Biotage SNAP cartridge KP-sil 25 g, 40-63 µm, 60 Å, 50 mL per min, gradient 1% to 10% MeOH in DCM]) to provide ethyl 2-[4-(1-methyl-1H-imidazol-2-yl)piperidine]-6-azaspiro[3.4]octane-6-carboxylate as a brown oil as a mixture of diastereomers (0.25 g, 83%). Preparative HPLC was used to separate the diastereomers, using a Phenomenex Gemini-N C18 column, 150×21 mm, eluting with 38 to 48% MeCN/H₂O at 18 ml/min and collecting fractions by monitoring at 218 nm to give ethyl 2-[4-(1-methyl-1H-imidazol-2-yl)piperidine]-6-azaspiro[3.4]octane-6-carboxylate, Example 1-7 Isomer 1, (0.044 g, 15%) as a colourless oil and ethyl 2-[4-(1-methyl-1H-imidazol-2-yl)piperidine]-6-azaspiro[3.4]octane-6-carboxylate, Example 1-7 Isomer 2, (0.031 g, 10%) as a colourless oil. The data for Isomer 2 are in Table 3

Route e

Typical Procedure for the Hydrogenation of Compounds Containing 3,6-dihydropyridin-1(2H)-yl to Give Compounds Containing Piperidinyl as Exemplified by the Preparation of Example 1-9, methyl 2-[4-(1,5-dimethyl-1H-imidazol-2-yl)piperidin-1-yl]-6-azaspiro[3.4]octane-6-carboxylate

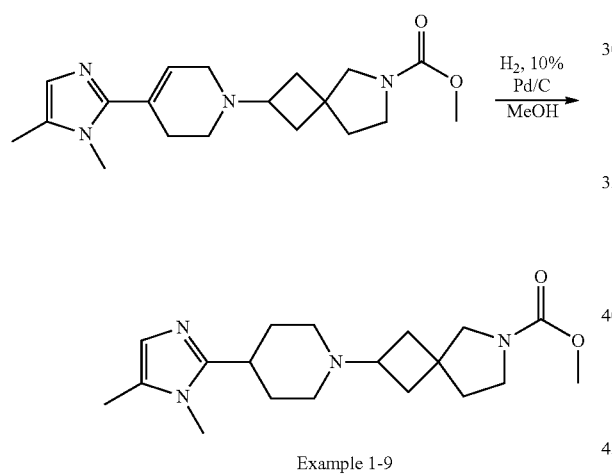

Example 1-9

Methyl 2-(4-(1,5-dimethyl-1H-imidazol-2-yl)-3,6-dihydropyridin-1(2H)-yl)-6-azaspiro[3.4]octane-6-carboxylate (102 mg, 0.29 mmol) [synthesized via route d and intermediates 3 and 34] was dissolved in MeOH (10 mL) and 10% Pd/C (25 mg) was added. The reaction mixture was purged with H₂ gas then stirred at 25° C. for 20 h under a balloon of H₂. The reaction mixture was filtered through celite and wash with MeOH, the solvents from the filtrate were removed in vacuo, and the residue was purified by preperative HPLC (X Bridge, C-18, 150×30 mm, 5um, 40 mL per min, gradient 30% (over 12.00 mins), 100% (over 14.00 mins), then 30% (over 14.01 mins), 0.1% Ammonia in Acetonitrile/water] to give methyl 2-[4-(1,5-dimethyl-1H-imidazol-2-yl)piperidin-1-yl]-6-azaspiro[3.4]octane-6-carboxylate, Example 1-9 Isomer 1, (5.6 mg, 5.8%) as a colourless gum and methyl 2-[4-(1,5-dimethyl-1H-imidazol-2-yl)piperidin-1-yl]-6-azaspiro[3.4]octane-6-carboxylate, Example 1-9 Isomer 2, (11.6 mg, 11.7%) as a colourless gum. The data for Isomer 2 are in Table 3.

Route f

Typical Procedure for the Preparation of Piperidines Via Sodium Triacetoxyborohydride Reductive Amination, Boc-Deprotection and Ethylcarbamate Formation as Exemplified by the Preparation of Example 1-36, ethyl 2-[4-(1H-1,2,4-triazol-1-yl)piperidin-1-yl]-6-azaspiro[3.4]octane-6-carboxylate

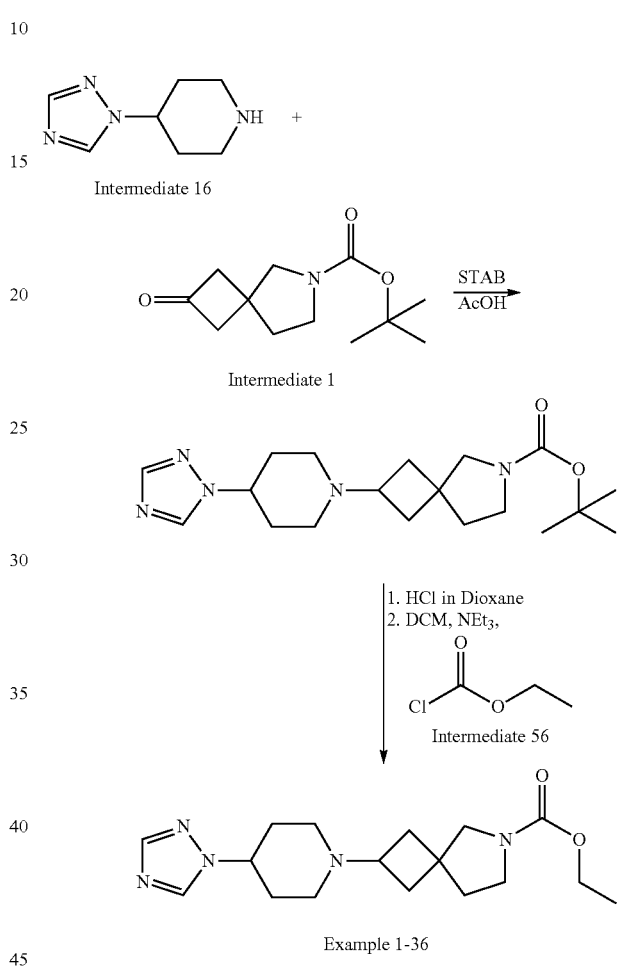

Example 1-36

4-(1H-1,2,4-Triazol-1-yl)piperidine (0.152 g, 1.0 mmol) and 6-Boc-2-oxo-6-azaspiro[3,4]octane (0.222 g, 1.05 mmol) were dissolved in DCM (10 mL) under N₂ at rt and acetic acid (0.13 mL, 2.22 mmol) was added. The reaction mixture was stirred at it for 2 h, STAB (0.53 g, 2.50 mmol) added and the reaction mixture stirred overnight at rt. The reaction mixture was quenched with the addition of NaHCO₃ (sat aq.) (30 mL), extracted with DCM (4×25 mL) and the combined DCM layers passed through a Biotage phase separator. The solvents were removed in vacuo, to give a crude mixture of diastereomers of tert-butyl 2-[4-(1H-1,2,4-triazol-1-yl)piperidin-1-yl]-6-azaspiro[3.4]octane-6-carboxylate which was used without purification.

LCMS (Method C): m/z 362 (M+H)⁺ (ES⁺), at 1.58 min and 1.61 min, UV inactive.

Crude tert-butyl 2-[4-(1H-1,2,4-triazol-1-yl)piperidin-1-yl]-6-azaspiro[3.4]octane-6-carboxylate (assumed 1.0 mmol) was dissolved in 4 M hydrogen chloride in dioxane (1.2 mL, 5.2 mmol) and the reaction mixture stirred overnight at it overnight. The volatiles were removed in vacuo and the residue dissolved in DCM (10 mL) and NEt₃ (0.70 mL, 5.0 mmol) added. Ethyl chloroformate (0.14 mL, 1.5 mmol) was added dropwise and the solution stirred at it overnight. The mixture was poured into NaHCO$_3$ (aq) (40 mL) extracted with DCM (4×40 mL), and the combined DCM layers passed through a Biotage phase separator. The solvents were removed in vacuo, and the residue was purified by column chromatography (normal phase, [Biotage SNAP cartridge KP-sil 25 g, 40-63 μm, 60 Å, 40 mL per min, gradient 0% to 10% MeOH in DCM) to give an inseparable mixture of diastereomers of ethyl 2-[4-(1H-1,2,4-triazol-1-yl)piperidin-1-yl]-6-azaspiro[3.4]octane-6-carboxylate. Preparative HPLC was used to separate the diastereomers, using a Phenomenex Gemini-NX 5 μm C18 110A Axia column, 100×30 mm, eluting with 25 to 55% MeCN/Solvent B over 14.4 at 30 mL/min [where Solvent B is 0.2% of (28% NH$_3$/H$_2$O) in H$_2$O] and collecting fractions by monitoring at 210 nm to give ethyl 2-[4-(1H-1,2,4-triazol-1-yl)piperidin-1-yl]-6-azaspiro[3.4]octane-6-carboxylate, Example 1-36 Isomer 1, (0.026 g, 8%) as a colourless solid and ethyl 2-[4-(1H-1,2,4-triazol-1-yl)piperidin-1-yl]-6-azaspiro[3.4]octane-6-carboxylate, Example 1-36 Isomer 2, (0.026 g, 8%) as a colourless solid. The data for Isomer 2 are in Table 3.

Route g

Typical Procedure for the Alkylation of Imidazole Containing Compounds Using Sodium Hydride in DMF as Exemplified by the Preparation of Example 1-51, ethyl 2-{4-[1-(2-methoxyethyl)-1H-imidazol-2-yl]piperidin-1-yl}-6-azaspiro[3.4]octane-6-carboxylate

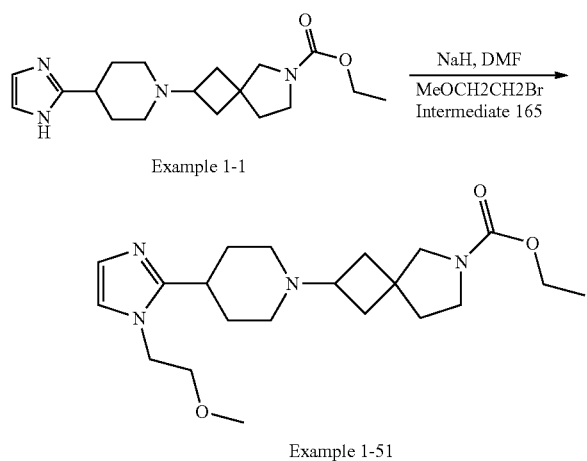

Example 1-1

Example 1-51

Mixture of diastereomers of ethyl 2-[4-(1H-imidazol-2-yl)piperidin-1-yl]-6-azaspiro[3.4]octane-6-carboxylate (150 mg, 0.45 mmol) was dissolved in anhydrous DMF (3 mL), treated with a 60% suspension of sodium hydride in mineral oil (27 mg, 0.68 mmol) and stirred at RT for 2 h. 2-Bromoethyl methyl ether (0.051 mL, 0.54 mmol) was added and the mixture was stirred at RT overnight. The mixture was concentrated to remove DMF. The residue was dissolved in MeOH and concentrated onto flash silica (5 mL). The resulting powder was purified by column chromatography (normal phase, [Biotage SNAP cartridge KP-sil 25 g, 40-63 μm, 60 Å], 30 mL per min, 0 to 20% Solvent A in DCM, where Solvent A is 10% of (7 M NH3/MeOH) in MeOH) to give a mixture of diastereomers of ethyl 2-{4-[1-(2-methoxyethyl)-1H-imidazol-2-yl]piperidin-1-yl}-6-azaspiro[3.4]octane-6-carboxylate (159 mg, 90%). This mixture was dissolved in MeOH and the solution was purified by preparative reversed phase HPLC using a Phenomenex Gemini-NX 5 μm C18 110A Axia column, 100×30 mm, eluted with 15 to 45% MeCN/Solvent B over 14.4 min at 30 mL/min [where solvent B is 0.2% of (28% NH$_3$/H$_2$O) in H$_2$O] and collecting fractions by monitoring at 210 nm to give ethyl 2-{4-[1-(2-methoxyethyl)-1H-imidazol-2-yl]piperidin-1-yl}-6-azaspiro[3.4]octane-6-carboxylate, Example 1-51 Isomer 1, (54 mg, 31%) and ethyl 2-{4-[1-(2-methoxyethyl)-1H-imidazol-2-yl]piperidin-1-yl}-6-azaspiro[3.4]octane-6-carboxylate, Example 1-51 Isomer 2, (27 mg, 15%).

The data for Isomer 2 are in Table 3

Route h

Typical Procedure for the Alkylation of Imidazole Containing Compounds Using Potassium Carbonate in DMF as Exemplified by the Preparation of Example 1-52, ethyl 2-{4-[1-(cyanomethyl)-1H-imidazol-2-yl]piperidin-1-yl}-6-azaspiro[3.4]octane-6-carboxylate

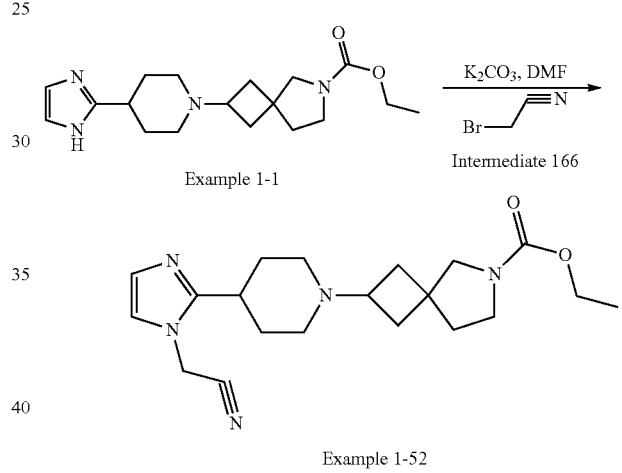

Example 1-1

Example 1-52

Mixture of diastereomers of ethyl 2-[4-(1H-imidazol-2-yl)piperidin-1-yl]-6-azaspiro[3.4]octane-6-carboxylate (150 mg, 0.45 mmol) was dissolved in anhydrous DMF (3 mL). Potassium carbonate (187 mg, 1.4 mmol) and bromoacetonitrile (0.114 mL, 1.6 mmol) were added and the mixture was stirred at RT over two nights. The mixture was concentrated to remove DMF. The residue was dissolved in MeOH and concentrated onto flash silica (5 mL). The resulting powder was purified by column chromatography (normal phase, [Biotage SNAP cartridge KP-sil 25 g, 40-63 μm, 60 Å], 30 mL per min, 0 to 20% Solvent A in DCM, where Solvent A is 10% of (7 M NH3/MeOH) in MeOH) to give a mixture of diastereomers of ethyl 2-{4-[1-(cyanomethyl)-1H-imidazol-2-yl]piperidin-1-yl}-6-azaspiro[3.4]octane-6-carboxylate (91 mg, 54%). This mixture was dissolved in MeOH and the solution was purified by preparative reversed phase HPLC using a Phenomenex Gemini-NX 5 μm C18 110A Axia column, 100×30 mm, eluted with 15 to 45% MeCN/Solvent B over 14.4 min at 30 mL/min [where solvent B is 0.2% of (28% NH$_3$/H$_2$O) in H$_2$O] and collecting fractions by monitoring at 210 nm to give ethyl 2-{4-[1-(cyanomethyl)-1H-imidazol-2-yl]piperidin-1-yl}-6-azaspiro[3.4]octane-6-carboxylate, Example 1-52 Isomer 1, (8 mg, 5%) and ethyl 2-{4-[1-(cyanomethyl)-1H-imidazol-2-yl]piperidin-1-yl}-6-azaspiro[3.4]octane-6-carboxylate, Example 1-52 Isomer 2, (5 mg, 3%). The data for Isomer 2 are in Table 3

Route i

Procedure for the Preparation of Example 1-53, (2-{1-[6-(ethoxycarbonyl)-6-azaspiro[3.4]oct-2-yl]piperidin-4-yl}-1H-imidazol-1-yl)acetic acid and Example 1-54, ethyl 2-(4-{1-[2-(methylamino)-2-oxoethyl]-1H-imidazol-2-yl}piperidin-1-yl)-6-azaspiro[3.4]octane-6-carboxylate

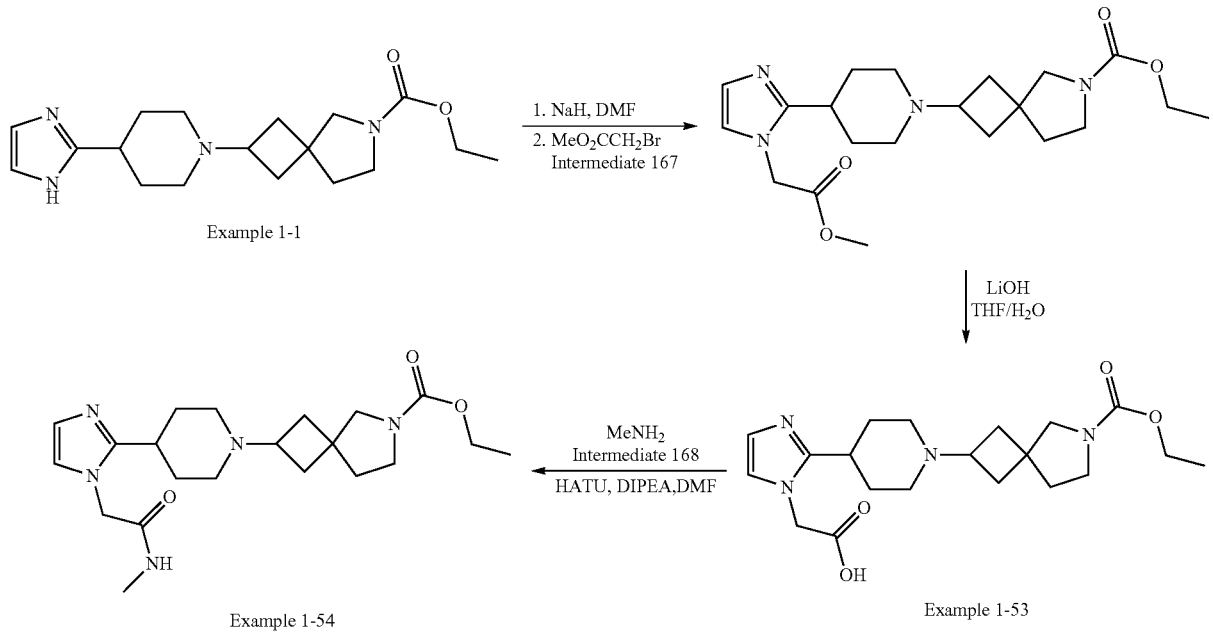

Example 1-1

Example 1-54

Example 1-53

Mixture of diastereomers of ethyl 2-[4-(1H-imidazol-2-yl)piperidin-1-yl]-6-azaspiro[3.4]octane-6-carboxylate (500 mg, 1.5 mmol) was reacted with 60% dispersion of sodium hydride in mineral oil (90 mg, 2.3 mmol) and methyl bromoacetate (0.171 mL, 1.8 mmol) in DMF (10 mL) using the method of Route g to give a mixture of diastereomers of ethyl 2-{4-[1-(2-methoxy-2-oxoethyl)-1H-imidazol-2-yl]piperidin-1-yl}-6-azaspiro[3.4]octane-6-carboxylate (393 mg, 65%).

LCMS (Method C): m/z 405 (M+H)⁺ (ES⁺), at 1.12 & 1.17 min, weakly UV active.

The mixture of diastereomers of ethyl 2-{4-[1-(2-methoxy-2-oxoethyl)-1H-imidazol-2-yl]piperidin-1-yl}-6-azaspiro[3.4]octane-6-carboxylate (180 mg, 0.45 mmol) was stirred with lithium hydroxide monohydrate (75 mg, 1.8 mmol) in THF (4 mL) and H$_2$O (1 mL) at it for 5 days. The mixture was concentrated to remove THF, acidified with 1M aqueous HCl and concentrated to afford the crude mixture of diastereomers of (2-{1-[6-(ethoxycarbonyl)-6-azaspiro[3.4]oct-2-yl]piperidin-4-yl}-1H-imidazol-1-yl)acetic acid (0.4 g, >100%). Approximately 0.2 g of this mixture was dissolved in MeOH and the solution was purified by preparative reversed phase HPLC using a Phenomenex Gemini-NX 5 μm C18 110A Axia column, 100×30 mm, eluted with 5 to 15% MeCN/Solvent B over 14.4 min at 30 mL/min [where solvent B is 0.2% of (28% NH$_3$/H$_2$O) in H$_2$O] and collecting fractions by monitoring at 210 nm to give (2-{1-[6-(ethoxycarbonyl)-6-azaspiro[3.4]oct-2-yl]piperidin-4-yl}-1H-imidazol-1-yl)acetic acid, Example 1-53 Isomer 1, (30 mg, 17%) and (2-{1-[6-(ethoxycarbonyl)-6-azaspiro[3.4]oct-2-yl]piperidin-4-yl}-1H-imidazol-1-yl)acetic acid, Example 1-53 Isomer 2, (22 mg, 13%).

The data for Isomer 2 are in Table 3.

The remaining crude mixture of diastereomers of (2-{1-[6-(ethoxycarbonyl)-6-azaspiro[3.4]oct-2-yl]piperidin-4-yl}-1H-imidazol-1-yl)acetic acid, Example 1-53, (0.2 g, assumed 0.22 mmol) was dissolved in DMF (3 mL) and treated with diisopropylethylamine (0.155 mL, 0.89 mmol) and a solution of methylamine in methanol (2M, 0.33 mL, 0.66 mmol). HATU (0.127 g, 0.33 mmol) was then added and the mixture was stirred at RT overnight. The mixture was concentrated to remove DMF, the residue was dissolved in a mixture of DCM and MeOH and concentrated onto flash silica (10 mL). The resulting powder was purified by column chromatography (normal phase, [Biotage SNAP cartridge KP-sil 25 g, 40-63 μm, 60 Å], 30 mL per min, 0 to 20% Solvent A in DCM, where Solvent A is 10% of (7 M NH3/MeOH) in MeOH) to give a mixture of diastereomers of ethyl 2-(4-{1-[2-(methylamino)-2-oxoethyl]-1H-imidazol-2-yl}piperidin-1-yl)-6-azaspiro[3.4]octane-6-carboxylate. This mixture was dissolved in MeOH and the solution was purified by preparative reversed phase HPLC using a Phenomenex Gemini-NX 5 μm C18 110A Axia column, 100×30 mm, eluted with 15 to 45% MeCN/Solvent B over 14.4 min at 30 mL/min [where solvent B is 0.2% of (28% NH$_3$/H$_2$O) in H$_2$O] and collecting fractions by monitoring at 210 nm to give ethyl 2-(4-{1-[2-(methylamino)-2-oxoethyl]-1H-imidazol-2-yl}piperidin-1-yl)-6-azaspiro[3.4]octane-6-carboxylate, Example 1-54 Isomer 1, (9 mg, 4%) and ethyl 2-(4-{1-[2-(methylamino)-2-oxoethyl]-1H-imidazol- 2-yl}piperidin-1-yl)-6-azaspiro[3.4]octane-6-carboxylate, Example 1-54 Isomer 2, (6 mg, 3%). The data for Isomer 2 are in Table 3

Route j

Typical Procedure for the Preparation of Piperidines Via Carbamate Formation, as Exemplified by the Preparation of Example 1-70, ethyl 2-{4-[(2R)-4,4-difluoro-2-(methylcarbamoyl)pyrrolidin-1-yl]piperidin-1-yl}-6-azaspiro[3.4]octane-6-carboxylate

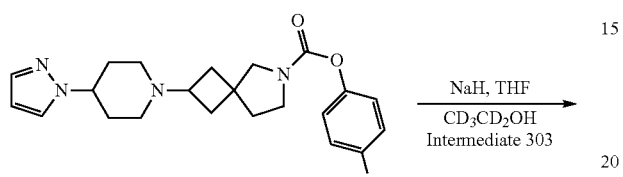

Intermediate 302

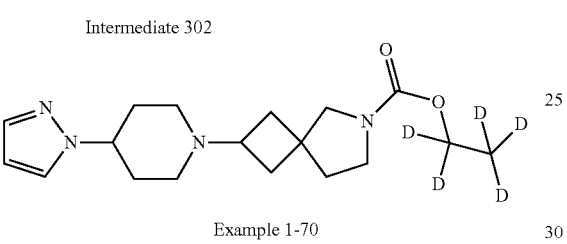

Example 1-70 were removed in vacuo, and the residue was purified by column chromatography (normal phase, [Biotage SNAP cartridge KP-sil 10 g 40-63 ⌊m, 60 Å, 12 mL per min, gradient 0% to 10% MeOH/DCM]). The residue was further purified by preparative reversed phase HPLC (Phenomenex Gemini-NX 5 µm C18 110A Axia column, 100×30 mm, eluting with 20 to 50% MeCN/Solvent B over 14.4 min at 30 mL/min [where solvent B is 0.2% of (28% NH$_3$/H$_2$O) in H$_2$O] and collecting fractions by monitoring at 210 nm) to give ($^2$H$_5$)ethyl 2-[4-(1H-pyrazol-1-yl)piperidin-1-yl]-6-azaspiro[3.4]octane-6-carboxylate, Example 1-70 Isomer 1, (0.017 g, 17%) as a white solid and ($^2$H$_5$)ethyl 2-[4-(1H-pyrazol-1-yl)piperidin-1-yl]-6-azaspiro[3.4]octane-6-carboxylate, Example 1-70 Isomer 2, (0.013 g, 13%) as a white solid. The data for Isomer 2 are in Table 3.

Route k

Typical Procedure for the Preparation of Piperidines Via Formamide Formation as Exemplified by the Preparation of Example 2-2, ethyl 2-[4-(1-formylpyrrolidin-2-yl)piperidin-1-yl]-6-azaspiro[3.4]octane-6-carboxylate

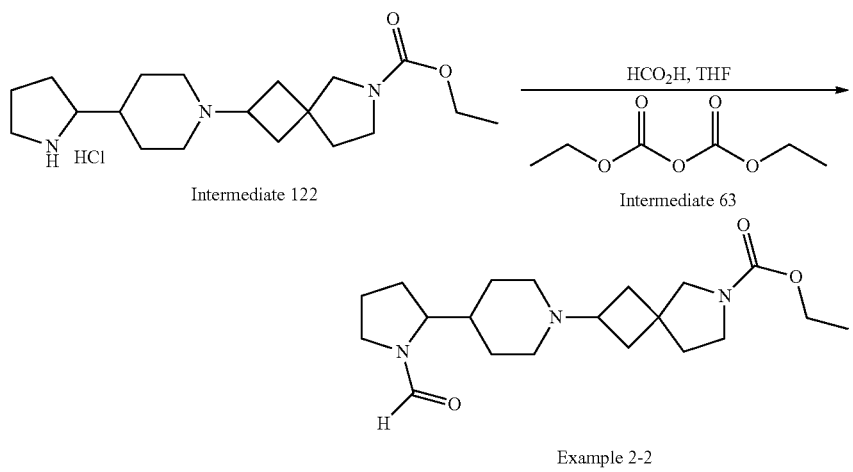

Example 2-2

4-nitrophenyl 2-[4-(1H-pyrazol-1-yl)piperidin-1-yl]-6-azaspiro[3.4]octane-6-carboxylate (0.125 g, 0.294 mmol) was suspended in anhydrous THF (4 mL) and sonicated to cause dissolution. Sodium hydride, 60% dispersion in mineral oil, (0.026 g, 0.647 mmol) was added and the reaction mixture was stirred at rt under nitrogen for 10 mins. Ethanol-1,1-2,2,2-d5 (0.150 g, 2.94 mmol) was added and the reaction mixture was stirred at rt under nitrogen overnight. Water (1 mL) was added to the reaction mixture and the solvents were removed in vacuo. The residue was partitioned between DCM (20 mL) and sat. NaHCO$_3$ (aq) (10 mL), aqueous layer was extracted with DCM (2×10 mL). The organic layers were combined and dried by passing through a Biotage Phase Separator Cartridge. The solvents A mixture of formic acid (2 mL) and acetic anhydride (0.1 mL, 1.43 mmol) were stirred at 60° C. for 1 h, then the reaction was cooled to 0° C., and a mixture of diastereomers of ethyl 2-(4-(pyrrolidin-2-yl)piperidin-1-yl)-6-azaspiro[3.4]octane-6-carboxylate.HCl (100 mg, 0.30 mmol) in THF (2 mL) was added dropwise. The resulting reaction mixture was stirred at 60° C. for 8 h, adjusted to basic pH then the reaction mixture was partitioned between H$_2$O (40 mL) and EtOAc (25 mL). The aqueous layer was further extracted with EtOAc (2×25 mL) and the organic layers were combined and dried over Na$_2$SO$_4$. Solvents were removed in vacuo and the residue was purified by preperative HPLC (X Bridge, C-18, 150×30 mm, 5um, 40 mL per min, gradient 30% (over 12.00 mins), 100% (over 14.00 mins), then 30%

(over 14.01 mins), 0.1% Ammonia in Acetonitrile/water] to give ethyl 2-[4-(1-formylpyrrolidin-2-yl)piperidin-1-yl]-6-azaspiro[3.4]octane-6-carboxylate Example 2-2 isomer 1 (14.6 mg, 13.0%) as a yellow gum and ethyl 2-[4-(1-formylpyrrolidin-2-yl)piperidin-1-yl]-6-azaspiro[3.4]octane-6-carboxylate Example 2-2 isomer 2 (12.5 mg, 11.1%) as a yellow gum. The data for Isomer 2 are in Table 3

Route L

Typical Procedure for the Preparation of Piperidines Via Amide Formation as Exemplified by the Preparation of Example 2-4, ethyl 2-{4-[1-(trifluoroacetyl)pyrrolidin-2-yl]piperidin-1-yl}-6-azaspiro[3.4]octane-6-carboxylate

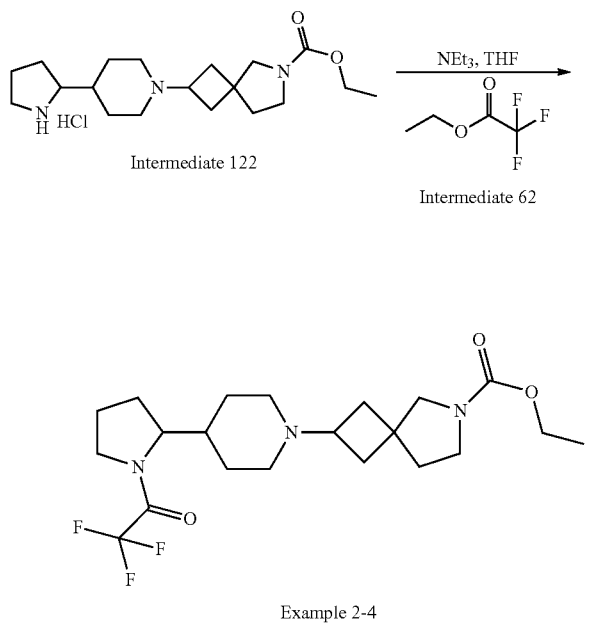

Ethyl 2-(4-(pyrrolidin-2-yl)piperidin-1-yl)-6-azaspiro[3.4]octane-6-carboxylate (50 mg, 0.15 mmol) and NEt₃ (0.06 mL, 0.45 mmol) were dissolved in THF (3 mL) at rt. Ethyl 2,2,2-trifluoroacetate (0.03 mg, 0.22 mmol) was added dropwise, and the resulting reaction mixture was stirred at it for 8 h. The reaction mixture was partitioned between $H_2O$ (40 mL) and EtOAc (25 mL), the aqueous layer was further extracted with EtOAc (2×25 mL), the organic layers were combined and dried over $Na_2SO_4$. Solvents were removed in vacuo and residue was purified by preperative HPLC (X Bridge, C-18, 150×30 mm, 5 um, 40 mL per min, gradient 30% (over 12.00 mins), 100% (over 14.00 mins), then 30% (over 14.01 mins), 0.1% Ammonia in Acetonitrile/water] to give ethyl 2-{4-[1-(trifluoroacetyl)pyrrolidin-2-yl]piperidin-1-yl}-6-azaspiro[3.4]octane-6-carboxylate Example 2-4 isomer-1 (5.5 mg, 8.0%) as a yellow gum and ethyl 2-{4-[1-(trifluoroacetyl)pyrrolidin-2-yl]piperidin-1-yl}-6-azaspiro[3.4]octane-6-carboxylate, Example 2-4 isomer-2 (6.2 mg, 9.7%) as a yellow gum. The data for Isomer 2 are in Table 3

Route m

Typical Procedure for the Preparation of Piperidines Via Amide/Carbamate/Urea Formation as Exemplified by the Preparation of Example 2-17, ethyl 2-{4-[(2S)-1-(methylcarbamoyl)pyrrolidin-2-yl]piperidin-1-yl}-6-azaspiro[3.4]octane-6-carboxylate

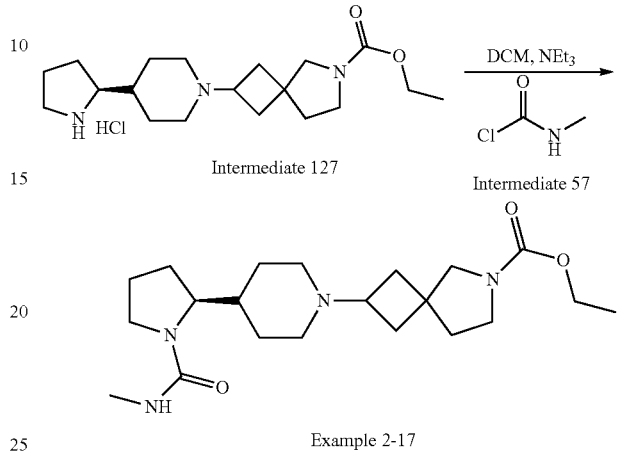

A mixture of diastereomers of ethyl 2-{4-[(2S)-pyrrolidin-2-yl]piperidin-1-yl}-6-azaspiro[3.4]octane-6-carboxylate.HCl (2.10 g, 5.65 mmol) was dissolved DCM (20 mL) and triethylamine (1.54 mL, 11.1 mmol). Methylaminoformyl chloride (620 mg, 6.63 mmol) was added and the solution stirred at it for 2 h. The mixture was then poured into 1M NaOH (aq) (50 mL), extracted with DCM (2×50 mL), and the combined DCM extracts washed with brine (50 mL) then passed through a Biotage phase separator and concentrated in vacuo, to provide ethyl 2-{4-[(2S)-1-(methylcarbamoyl)pyrrolidin-2-yl]piperidin-1-yl}-6-azaspiro[3.4]octane-6-carboxylate as a yellow solid and as a mixture of diastereomers (1.79 g, 82%). Preparative HPLC was used to separate the diastereomers, using a Phenomenex Gemini-NX C18 column, 100×30 mm, eluting with 25 to 35% MeCN/0.2% ammonia in $H_2O$ (v/v) at 18 ml/min and collecting fractions by monitoring at 210 nm to give Example 2-17 Isomer 1, ethyl 2-{4-[(2S)-1-(methylcarbamoyl)pyrrolidin-2-yl]piperidin-1-yl}-6-azaspiro[3.4]octane-6-carboxylate (0.78 g, 36%) as a colourless oil and Example 2-17 Isomer 2, ethyl 2-{4-[(2S)-1-(methylcarbamoyl)pyrrolidin-2-yl]piperidin-1-yl}-6-azaspiro[3.4]octane-6-carboxylate (0.67 g, 31%) as a colourless oil. The data for Isomer 2 are in Table 3

Route n

Typical Procedure for the Preparation of Piperidines Via Urea/Carbamate Formation as Exemplified by the Preparation of Example 2-19, ethyl 2-{4-[1-(ethylcarbamoyl)pyrrolidin-2-yl]piperidin-1-yl}-6-azaspiro[3.4]octane-6-carboxylate

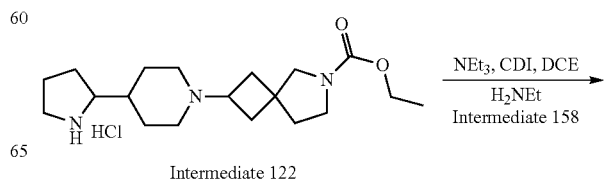

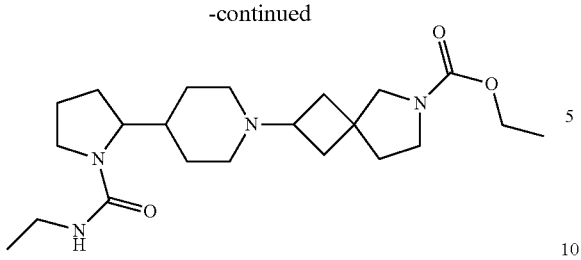

Example 2-19

A mixture of diastereomers of ethyl 2-(4-(pyrrolidin-2-yl)piperidin-1-yl)-6-azaspiro[3.4]octane-6-carboxylate.HCl (100 mg, 0.30 mmol), diethyl amine (0.3 mL, 0.60 mmol) and NEt$_2$ (0.1 mL, 0.90 mmol) were dissolved in DCE (5 mL) at rt. CDI (145 mg, 0.60 mmol) was added and the reaction mixture was stirred at it for 15 h. The reaction mixture was partitioned between H$_2$O (40 mL) and EtOAc (25 mL), the aqueous layer was further extracted with EtOAc (2×25 mL), the organic layers were combined, dried (Na$_2$SO$_4$), the solvents were removed in vacuo and residue was purified by Prep HPLC [reverse phase HPLC (X-BRIDGE, C-18, 250×19 mm, 5 um, 15 mL per min, gradient 30.0% to 38.0% (over 25.0 mins), 100.0% (over 3.0 mins) then 30.0% (over 2.0 mins), 0.1% NH$_3$ in MeCN/water] to give ethyl 2-(4-(1-(ethylcarbamoyl)pyrrolidin-2-yl)piperidin-1-yl)-6-azaspiro[3.4]octane-6-carboxylate, Example 2 19 isomer-1, (7.5 mg, 6.20%) as a yellow gum and ethyl 2-(4-(1-(ethylcarbamoyl)pyrrolidin-2-yl)piperidin-1-yl)-6-azaspiro[3.4]octane-6-carboxylate, Example 2-19 isomer 2, (8.1 mg, 6.60%) as a yellow gum. The data for Isomer 2 are in Table 3

Route o

Typical Procedure for the Preparation of Piperidines Via Alkylation as Exemplified by the Preparation of Example 2-22, ethyl 2-[4-(1-methylpyrrolidin-2-yl)piperidin-1-yl]-6-azaspiro[3.4]octane-6-carboxylate Example 2-22

A mixture of diastereomers of ethyl 2-(4-(pyrrolidin-2-yl)piperidin-1-yl)-6-azaspiro[3.4]octane-6-carboxylate.HCl (200 mg, 0.60 mmol) and formaldehyde (40% soln, 1.01 mL, 3.60 mmol) were dissolved in H$_2$O (2 mL) at 25° C. Formic acid (0.303 mL, 0.90 mmol) was added dropwise and the resulting mixture was stirred at 70° C. for 14 h. The reaction mixture was quenched with NaHCO$_3$ solution (5 mL), then the reaction mixture was partitioned between H$_2$O (50 mL) and EtOAc (35 mL). The aqueous layer was further extracted with EtOAc (2×35 mL), organic layers were combined and dried over Na$_2$SO$_4$. Solvents were removed in vacuo and the residue was purified by Prep HPLC [reverse phase HPLC (X-Bridge, C-18, 250×19.0 mm, 5 um, 14 mL per min, gradient 37% (over 28.0 mins), 100% (over 4.0 mins) then 37% (over 3.0 mins), 0.1% NH3 in MeCN/water] to give ethyl 2-(4-(1-methylpyrrolidin-2-yl)piperidin-1-yl)-6-azaspiro[3.4]octane-6-carboxylate, Example 2-22 isomer 1 (12 mg, 5.80%) as a yellow gum and ethyl 2-(4-(1-methylpyrrolidin-2-yl)piperidin-1-yl)-6-azaspiro[3.4]octane-6-carboxylate, Example 2-22 isomer 2 (11 mg, 5.30%) as a yellow gum. The data for Isomer 2 are in Table 3

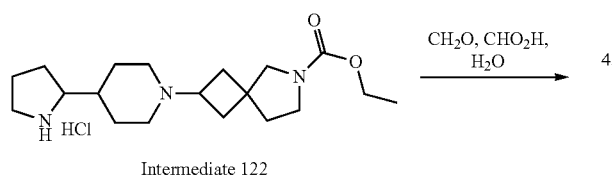

Intermediate 122

Route p

Typical Procedure for the Preparation of Piperidines Via Amide Formation as Exemplified by the Preparation of Example 2-23, ethyl 2-{4-[1-(N-methylglycyl)pyrrolidin-2-yl]piperidin-1-yl}-6-azaspiro[3.4]octane-6-carboxylate

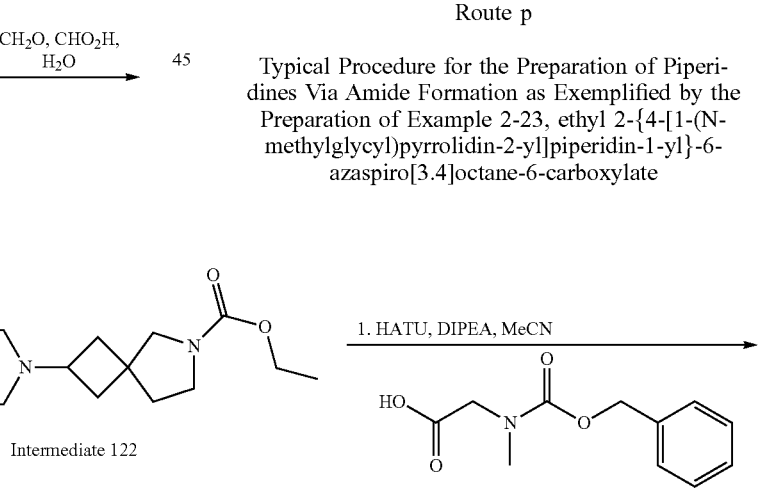

Intermediate 122

Intermediate 75

2. H$_2$, 10% Pd/C, MeOH

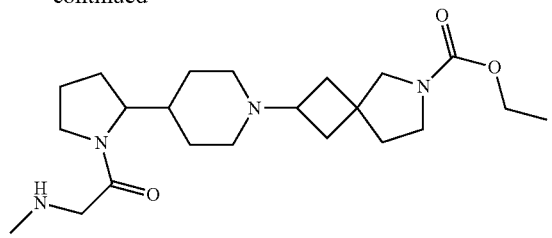

Example 2-23

N-[(benzyloxy)carbonyl]-N-methylglycine (73 mg, 0.33 mmol) was dissolved in acetonitrile (5 mL) followed by addition of HATU (170 mg, 0.45 mmol) and DIPEA (0.2 mL, 0.90 mmol). The reaction mixture was stirred at 0° C. for 10 minutes, followed by addition of a mixture of diastereomers of ethyl 2-(4-(pyrrolidin-2-yl)piperidin-1-yl)-6-azaspiro[3.4]octane-6-carboxylate.HCl (100 mg, 0.30 mmol) and resulting reaction mixture was stirred at 25° C. for 3 h. The reaction mixture was partitioned between H₂O (50 mL) and EtOAc (35 mL), the aqueous layer was further extracted with EtOAc (2×35 mL), the organic layers were combined, dried over Na₂SO₄ and solvents were removed in vacuo. Finally, the residue was purified by column chromatography (normal basic alumina, activated, 0.5% to 1.0% MeOH in DCM) to give ethyl 2-(4-(1-(N-((benzyloxy)carbonyl)-N-methylglycyl) pyrrolidin-2-yl)piperidin-1-yl)-6-azaspiro[3.4]octane-6-carboxylate (130 mg, 80.74%) as a brown gum. Ethyl 2-(4-(1-(N-((benzyloxy)carbonyl)-N-methylglycyl)pyrrolidin-2-yl)piperidin-1-yl)-6-azaspiro[3.4]octane-6-carboxylate (130 mg, 0.24 mmol) was dissolved in MeOH (10 mL) followed by addition of Pd/C (dry basis, 13 mg). The reaction was then purged with H₂ gas and resulting reaction mixture was stirred at 25° C. for 10 h. The reaction mixture was filtered through a celite plug and washed with methanol, then the filtrate dried over Na₂SO₄ and solvents were removed in vacuo. The residue was purified by Prep HPLC [reverse phase HPLC (X-BRIDGE, C-18, 250×19 mm, 5 um, 15 mL per min, gradient 20.0% to 35.0% (over 30.0 mins), 100.0% (over 3.0 mins) then 20.0% (over 2.0 mins), 0.1% NH3 in MeCN/water] to give ethyl 2-(4-(1-(methylglycyl)pyrrolidin-2-yl)piperidin-1-yl)-6-azaspiro[3.4]octane-6-carboxylate Example 2-23 isomer 1, (9.0 mg, 9.27%) as a yellow gum and ethyl 2-(4-(1-(ethyl-carbamoyl)pyrrolidin-2-yl)piperidin-1-yl)-6-azaspiro[3.4]octane-6-carboxylate, Example 2-23 isomer 2, (8.0 mg, 8.50%) as a yellow gum. The data for Isomer 2 are in Table 3

Route q

Typical Procedure for the Preparation of Piperidines Via Urea Formation as Exemplified by the Preparation of Example 2-27, ethyl 2-{4-[(2S)-1-(azetidin-1-ylcarbonyl)pyrrolidin-2-yl]piperidin-1-yl}-6-azaspiro[3.4]octane-6-carboxylate

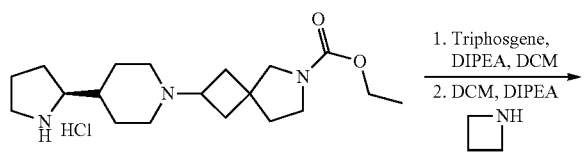

Intermediate 127

1. Triphosgene, DIPEA, DCM
2. DCM, DIPEA

Intermediate 79

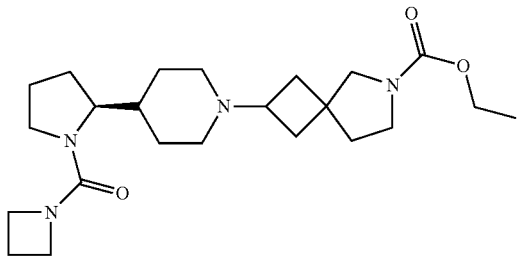

Example 2-27

A mixture of diastereomers of ethyl 2-{4-[(2S)-pyrrolidin-2-yl]piperidin-1-yl}-6-azaspiro[3.4]octane-6-carboxylate.HCl (100 mg, 0.291 mmol) were dissolved DCM (5 mL) and diisopropylethylamine (0.099 mL, 0.58 mmol). Triphosgene (88 mg, 0.291 mmol) was added at 0° C. and the solution warmed to rt and stirred for 1 h. The mixture was then diluted with DCM (50 mL) and washed with H₂O (70 mL). The aqueous layer was extracted with DCM (2×50 mL), and the combined DCM extracts dried with Na₂SO₄ and concentrated in vacuo. The residue was dissolved in DCM (5 mL) and azetidine (0.020 mL, 0.291 mmol) and diisopropylethylamine (0.256 mL, 1.48 mmol) were added. The reaction was stirred at rt for 1 h. The mixture was then diluted with DCM (50 mL) and washed with H₂O (70 mL). The aqueous layer was extracted with DCM (2×50 mL), and the combined DCM extracts dried with Na₂SO₄ and concentrated in vacuo, to provide ethyl 2-{4-[(2S)-1-(azetidin-1-ylcarbonyl)pyrrolidin-2-yl]piperidin-1-yl}-6-azaspiro[3.4]octane-6-carboxylate as a yellow solid and as a mixture of diastereomers. The residue was purified by Prep HPLC [reverse phase HPLC (CHIRALPAK AD-H, C-18, 250×20 mm, 5 um, 18.0 mL per min, gradient 0% to 50% (over 15.0 mins), 0.1% Ammonia in acetonitrile and 0.1% ammonia in H₂O to give ethyl(S)-2-(4-(1-(azetidine-1-carbonyl)pyrrolidin-2-yl)piperidin-1-yl)-6-azaspiro[3.4]octane-6-carboxylate Example 2-27 isomer 1 (20 mg, 16.12%) as a colorless gum, and Example 2-27 isomer 2 (20 mg, 16.12%) as a colorless gum. The data for Isomer 2 are in Table 3

Route r

Typical Procedure for the Preparation of Piperidines Via Urea Formation and Dehydration as Exemplified by the Preparation of Example 2-42, ethyl 2-(4-{(2S)-1-[ethyl(propan-2-yl)carbamoyl]pyrrolidin-2-yl}piperidin-1-yl)-6-azaspiro[3.4]octane-6-carboxylate and Example 2-138, ethyl 2-{4-[(2S)-1-(5-methyl-1,3,4-oxadiazol-2-yl)pyrrolidin-2-yl]piperidin-1-yl}-6-azaspiro[3.4]octane-6-carboxylate

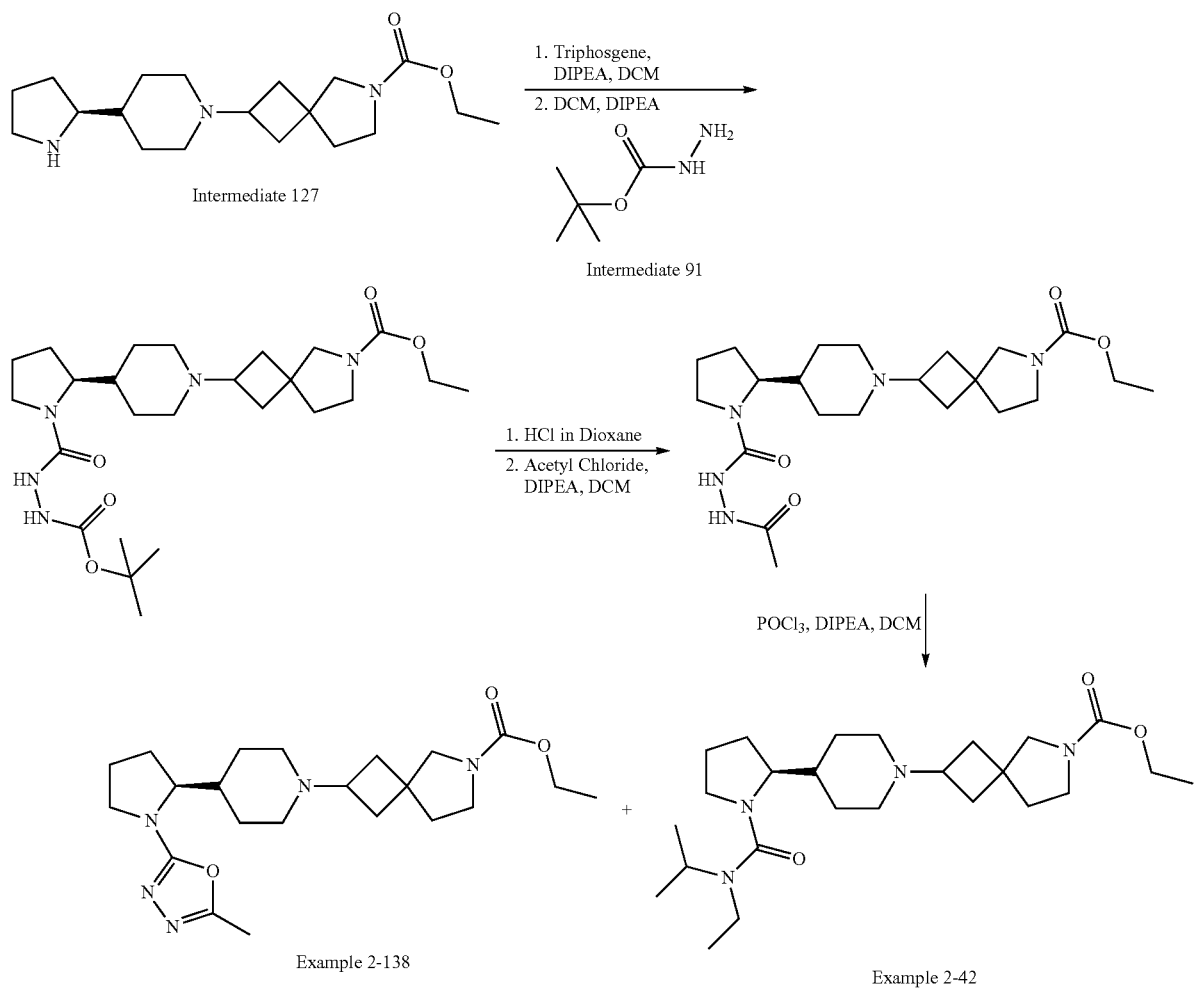

A mixture of diastereomers of ethyl 2-{4-[(2S)-pyrrolidin-2-yl]piperidin-1-yl}-6-azaspiro[3.4]octane-6-carboxylate.HCl (164 mg, 0.403 mmol) was dissolved in DCM (2 mL) and diisopropylethylamine (0.209 mL, 1.21 mmol). Triphosgene (43 mg, 0.145 mmol) was added at 0° C. and the solution warmed to rt and stirred for 18 h. To this mixture was added tert-butyl carbazate (108 mg, 0.82 mmol) and diisopropylethylamine (0.142 mL, 0.82 mmol) and the reaction was stirred at rt for 18 h. The mixture was then diluted with DCM (20 mL) and washed with saturated NaHCO₃ (aq) (2×20 mL). The aqueous layers were extracted with DCM (20 mL), and the combined DCM extracts washed with brine (50 mL) then passed through a Biotage phase separator and concentrated in vacuo, to provide ethyl 2-{4-[(2S)-1-(tert-butyl carbazoyl)pyrrolidin-2-yl]piperidin-1-yl}-6-azaspiro[3.4]octane-6-carboxylate as a yellow oil and as a mixture of diastereomers (192 mg, 97%).

LCMS (Method D): m/z 494 (M+H)⁺ (ES⁺), at 1.83 and 1.87 min, UV inactive.

The crude product was dissolved in 4 M hydrogen chloride in dioxane (2.0 mL, 8.0 mmol) and DCM (1 mL). The reaction mixture was stirred at it for 1 h. The volatiles were then removed in vacuo, before the reaction mixture was redissolved in DCM (2 mL) and diisopropylethylamine (0.142 mL, 0.82 mmol). Acetyl chloride (0.031 mL, 0.428 mmol) was added at 0° C., and the solution warmed to it and stirred for 2 h. The volatiles were removed in vacuo and carried through to next step without further purification. The residue was dissolved in toluene (2 mL) and diisopropylethylamine (0.135 mL, 0.78 mmol) and cooled to 0° C. Phosphorus oxychloride was added (0.182 mL, 1.945 mmol) and reaction stirred at 110° C. for 30 minutes, before the reaction was cooled to rt and quenched with ice water (20 mL). The mixture was then diluted with DCM (20 mL) and washed with 1M NaOH$_{(aq)}$ (2×20 mL). The aqueous layers were extracted with DCM (3×20 mL), and the combined DCM extracts washed with brine (50 mL) then passed through a Biotage phase separator and concentrated in vacuo. The residue was purified by preparative HPLC, using a Phenomenex Gemini-NX C18 column, 100×30 mm, eluting with 25 to 45% MeCN/0.2% ammonia in H$_2$O (v/v) at 18 mL/min and collecting fractions by monitoring at 210 nm to give Example 2-42 Isomer 1, ethyl 2-(4-{(2S)-1-[ethyl(propan-2-yl)carbamoyl]pyrrolidin-2-yl}piperidin-1-yl)-6-azaspiro[3.4]octane-6-carboxylate (1.7 mg, 1%) as a colourless oil, Example 2-42 Isomer 2, ethyl 2-(4-{(2S)-1-[ethyl(propan-2-yl)carbamoyl]pyrrolidin-2-yl}piperidin-1-yl)-6-azaspiro[3.4]octane-6-carboxylate (1.6 mg, 1%) as a colourless oil, Example 2-138 Isomer 1, ethyl 2-{4-[(2S)-1-(5-methyl-1,3,4-oxadiazol-2-yl)pyrrolidin-2-yl]piperidin-1-yl}-6-azaspiro[3.4]octane-6-carboxylate (3.9 mg, 2.5%) as a colourless oil and Example 2-138 Isomer 2, ethyl 2-{4-[(2S)-1-(5-methyl-1,3,4-oxadiazol-2-yl)pyrrolidin-2-yl]piperidin-1-yl}-6-azaspiro[3.4]octane-6-carboxylate (3.0 mg, 2%) as a colourless oil. The data for Isomers 2 are in Table 3

Route s

Typical Procedure for the Preparation of Piperidines Via Carbamate Formation as Exemplified by the Preparation of Example 2-47, ethyl 2-(4-{(2S)-1-[(2-fluoroethoxy)carbonyl]pyrrolidin-2-yl}piperidin-1-yl)-6-azaspiro[3.4]octane-6-carboxylate

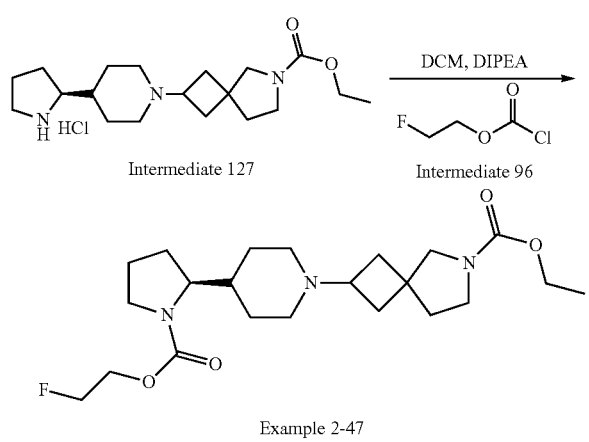

A mixture of diastereomers of ethyl 2-{4-[(2S)-pyrrolidin-2-yl]piperidin-1-yl}-6-azaspiro[3.4]octane-6-carboxylate.HCl (0.15 g, 0.44 mmol) and diisopropylethylamine (0.152 mL, 0.89 mmol) were dissolved in DCM (5 mL), then reaction mixture was cooled to 0° C. 2-fluoroethyl chloroformate (0.062 g, 0.492 mmol) was added and the resulting reaction mixture was stirred at 25° C. for 16 h. The reaction mixture was partitioned between H$_2$O (70 mL) and DCM (50 mL), aqueous layer was further extracted with DCM (2×50 mL), organic layers were combined, dried over Na$_2$SO$_4$, and solvent was removed in vacuo. The residue was purified by Prep HPLC [reverse phase HPLC (CHIRALPAK AD-H, C-18, 250×20 mm, 5 um, 18.0 mL per min, gradient 0% to 35% (over 52 mins), 0.1% ammonia in acetonitrile and 0.1% ammonia in Water to give ethyl 2-(4-{(2S)-1-[(2-fluoroethoxy)carbonyl]pyrrolidin-2-yl}piperidin-1-yl)-6-azaspiro[3.4]octane-6-carboxylate Example 2-47 isomer-1 (17 mg, 8.9%) as a yellow gum, and ethyl 2-(4-{(2S)-1-[(2-fluoroethoxy)carbonyl]pyrrolidin-2-yl}piperidin-1-yl)-6-azaspiro[3.4]octane-6-carboxylate Example 2-47 isomer-2 (19 mg, 10%) as a yellow gum. The data for Isomer 2 are in Table 3

Route t

Typical Procedure for the Preparation of Piperidines Via Amide Formation as Exemplified by the Preparation of Example 2-52, ethyl 2-{4-[(2S)-1-(hydroxyacetyl)pyrrolidin-2-yl]piperidin-1-yl}-6-azaspiro[3.4]octane-6-carboxylate

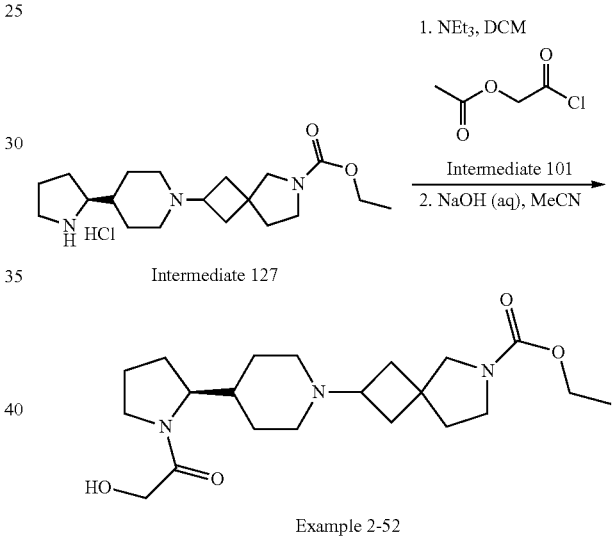

A mixture of diastereomers of ethyl 2-{4-[(2S)-pyrrolidin-2-yl]piperidin-1-yl}-6-azaspiro[3.4]octane-6-carboxylate.HCl (0.2 g, 0.541 mmol) and triethylamine (0.152 mL, 1.1 mmol) were dissolved in DCM (5 mL), then reaction mixture was cooled to 0° C. and acetoxy acetyl chloride (0.080 g, 0.591 mmol) was added. The reaction mixture was stirred at room temperature for 2 h. The volatiles were removed in vacuo, then the residue was dissolved in acetonitrile (25 mL) and 20% NaOH solution in water (10 mL) and stirred it at room temperature for 1 h. The reaction mixture was partitioned between H$_2$O (70 mL) and DCM (50 mL), aqueous layer was further extracted with DCM (2×50 mL), the organic layers were combined, dried over Na$_2$SO$_4$, the solvent was removed under vacuum and residue was purified by Prep HPLC [reverse phase HPLC (CHIRALPAK AD-H, C-18, 250×20 mm, 5 um, 18.0 mL per min, gradient 0% to 30% (over 35.0 mins), 0.1% Ammonia in Acetonitrile and 0.1% Ammonia in Water to give ethyl(S)-2-(4-(1-(2-hydroxyacetyl)pyrrolidin-2-yl)piperidin-1-yl)-6-azaspiro[3.4]octane-6-carboxylate Example 2-52 isomer 1 (8 mg, 8.3%) as a colorless gum, and ethyl(S)-2-(4-(1-(2-hydroxyacetyl)

pyrrolidin-2-yl)piperidin-1-yl)-6-azaspiro[3.4]octane-6-carboxylate Example 2-52 isomer 2 (12 mg, 12.24%) as a colorless gum. The data for Isomer 2 are in Table 3

Route u

Typical Procedure for the Preparation of Piperidines Via Amide Formation as Exemplified by the Preparation of Example 2-53, ethyl 2-{4-[(2S)-1-(3,3,3-trifluoropropanoyl)pyrrolidin-2-yl]piperidin-1-yl}-6-azaspiro[3.4]octane-6-carboxylate

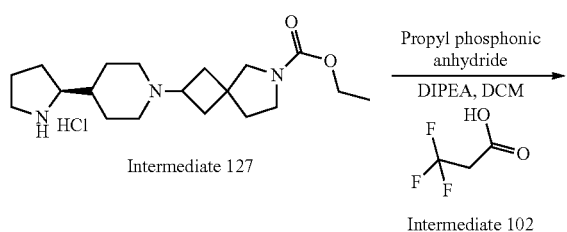

Intermediate 127

Intermediate 102

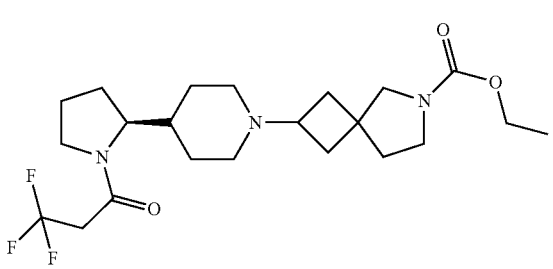

Example 2-53

(A mixture of diastereomers of ethyl 2-{4-[(2S)-pyrrolidin-2-yl]piperidin-1-yl}-6-azaspiro[3.4]octane-6-carboxylate.HCl (0.12 g, 0.36 mmol) and diisopropylethylamine (0.123 mL, 0.71 mmol) were dissolved in DCM (10 mL) followed by the addition of trifluoropropanioic acid (0.045 g, 0.394 mmol). The reaction mixture was cooled to 0° C., and propyl phosphonic anhydride was added (0.140 g, 0.462 mmol 50% EtOAc solution) was added and the resulting reaction mixture was stirred at 25° C. for 2 h. The reaction mixture was partitioned between H₂O (20 mL) and DCM (50 mL), aqueous layer was further extracted with DCM (2×50 mL), organic layers were combined, dried over Na₂SO₄, and solvent was removed in vacuo. The residue was purified by Prep HPLC [reverse phase HPLC (CHIRALPAK AD-H, C-18, 250×20 mm, 5 um, 18.0 mL per min, gradient 0% to 30% (over 27.0 mins), 0.1% Ammonia in Acetonitrile and 0.1% Ammonia in Water to ethyl(S)-2-(4-(1-(3,3,3-trifluoropropanoyl)pyrrolidin-2-yl)piperidin-1-yl)-6-azaspiro[3.4]octane-6-carboxylate Example 2-53 isomer 1 (9 mg, 6.0%) as a colorless gum, and ethyl(S)-2-(4-(1-(3,3,3-trifluoropropanoyl)pyrrolidin-2-yl)piperidin-1-yl)-6-azaspiro[3.4]octane-6-carboxylate Example 2-53 isomer 2 (9 mg, 6.0%) as a colorless gum. The data for Isomer 2 are in Table 3

Route v

Typical Procedure for the Preparation of Thioamides Via Lawesson Reagent as Exemplified by the Preparation of Example 2-58, ethyl 2-{4-[(2S)-1-propanethioylpyrrolidin-2-yl]piperidin-1-yl}-6-azaspiro[3.4]octane-6-carboxylate Example 2-7

Example 2-58

Ethyl 2-{4-[(2S)-1-propanoylpyrrolidin-2-yl]piperidin-1-yl}-6-azaspiro[3.4]octane-6-carboxylate (0.341 g, 0.87 mmol) was dissolved in THF (4 mL) followed by the addition of Lawesson Reagent (0.265 g, 0.65 mmol). The reaction mixture was stirred at 70° C. for 24 hours. The volatiles were removed in vacuo, and the reaction mixture was partitioned between 1M NaOH$_{(aq)}$ (50 mL) and DCM (30 mL), aqueous layer was further extracted with DCM (2×50 mL), organic layers were combined, washed with 5% sodium metabisulfite$_{(aq)}$, dried over Na₂SO₄, and solvents were removed in vacuo. The residue was purified by Preparative HPLC, using a Phenomenex Gemini-NX C18 column, 100×30 mm, eluting with 25 to 45% MeCN/0.2% ammonia in H₂O (v/v) at 18 mL/min and collecting fractions by monitoring at 210 nm to give Example 2-58 Isomer 1 ethyl 2-{4-[(2S)-1-propanethioylpyrrolidin-2-yl]piperidin-1-yl}-6-azaspiro[3.4]octane-6-carboxylate (14.1 mg, 4%) as a yellow oil and Example 2-58 Isomer 2, ethyl 2-{4-[(2S)-1-propanethioylpyrrolidin-2-yl]piperidin-1-yl}-6-azaspiro [3.4]octane-6-carboxylate (7.6 mg, 2%) as a yellow oil. The data for Isomer 2 are in Table 3

Route w

Typical Procedure for the Preparation of Piperidines Via Alkylation as Exemplified by the Preparation of Example 2-61, ethyl 2-{4-[(2S)-1-ethylpyrrolidin-2-yl]piperidin-1-yl}-6-azaspiro[3.4] octane-6-carboxylate Intermediate 127

Intermediate 114

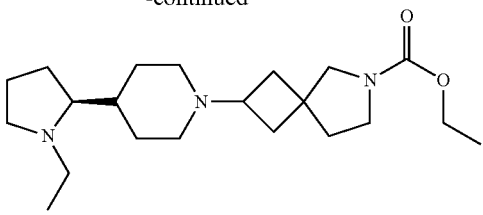

Example 2-61

A mixture of diastereomers of ethyl 2-{4-[(2S)-pyrrolidin-2-yl]piperidin-1-yl}-6-azaspiro[3.4]octane-6-carboxylate.HCl (0.100 g, 0.29 mmol) and potassium carbonate (0.123 mg, 0.89 mmol) were dissolved in DMF (5 mL) and the reaction mixture was stirred at 60° C. for 2 hours. Iodoethane was then added (0.049 g, 0.31 mmol and the reaction mixture was stirred at 100° C. for 62 hours. The reaction mixture was partitioned between H$_2$O (70 mL) and EtOAc (50 mL), aqueous layer was further extracted with EtOAc (2×50 mL), organic layers were combined, dried over Na$_2$SO$_4$, and solvent was removed in vacuo. The residue was purified by Prep HPLC (X Bridge, C-18, 150×19 mm, Sum, 20 mL per min, gradient 35% (over 0.01 mins). 100% (over 25.01 mins), then 35% (over 30.00 mins), 0.1% ammonia in acetonitrile/water] to give ethyl(S)-2-(4-(1-ethylpyrrolidin-2-yl)piperidin-1-yl)-6-azaspiro[3.4]octane-6-carboxylate Example 2-61 isomer 1 (43 mg, 38.8%) as a colourless gum, and ethyl(S)-2-(4-(1-ethylpyrrolidin-2-yl)piperidin-1-yl)-6-azaspiro[3.4]octane-6-carboxylate Example 2-61 isomer 2 (26 mg, 23.1%) as a colourless gum. The data for Isomer 2 are in Table 3

Route x

Typical Procedure for the Preparation of Piperidines Via s Amide Formation as Exemplified by the Preparation of Example 2-62, ethyl 2-(4-{(2S)-1-[3-(pyridin-2-yl)propanoyl]pyrrolidin-2-yl}piperidin-1-yl)-6-azaspiro[3.4]octane-6-carboxylate To a solution of oxalyl chloride (0.065 mL, 0.768 mmol) in DCM (2 mL) at 0° C. was added 2-pyridinepropionic acid (106 mg, 0.704 mmol) and DMF (1 drop). A mixture of diastereomers of ethyl 2-{4-[(2S)-pyrrolidin-2-yl]piperidin-1-yl}-6-azaspiro[3.4]octane-6-carboxylate.HCl (262 mg, 0.640 mmol) was dissolved in DCM (1 mL) and diisopropylethylamine (0.355 mL, 2.049 mmol) and added to the solution, which was stirred at it for 2 h. The mixture was then poured into 1M NaOH (aq) (50 mL), extracted with DCM (2×50 mL), and the combined DCM extracts washed with brine (50 mL) then passed through a Biotage phase separator and concentrated in vacuo, to provide ethyl 2-(4-{(2S)-1-[3-(pyridin-2-yl)propanoyl]pyrrolidin-2-yl}piperidin-1-yl)-6-azaspiro[3.4]octane-6-carboxylate as a black oil and as a mixture of diastereomers (0.245 g, 82%). Preparative HPLC was used to separate the diastereomers, using a Phenomenex Gemini-NX C18 column, 100×30 mm, eluting with 25 to 45% MeCN/0.2% ammonia in H$_2$O (v/v) at 18 mL/min and collecting fractions by monitoring at 210 nm to give Example 2-62 Isomer 1, ethyl 2-(4-{(2S)-1-[3-(pyridin-2-yl)propanoyl]pyrrolidin-2-yl}piperidin-1-yl)-6-azaspiro[3.4]octane-6-carboxylate (0.042 g, 14%) as a colourless oil and Example 2-62 Isomer 2, ethyl 2-(4-{(2S)-1-[3-(pyridin-2-yl)propanoyl]pyrrolidin-2-yl}piperidin-1-yl)-6-azaspiro[3.4]octane-6-carboxylate (0.030 g, 10%) as a colourless oil. The data for 2 are in Table 3

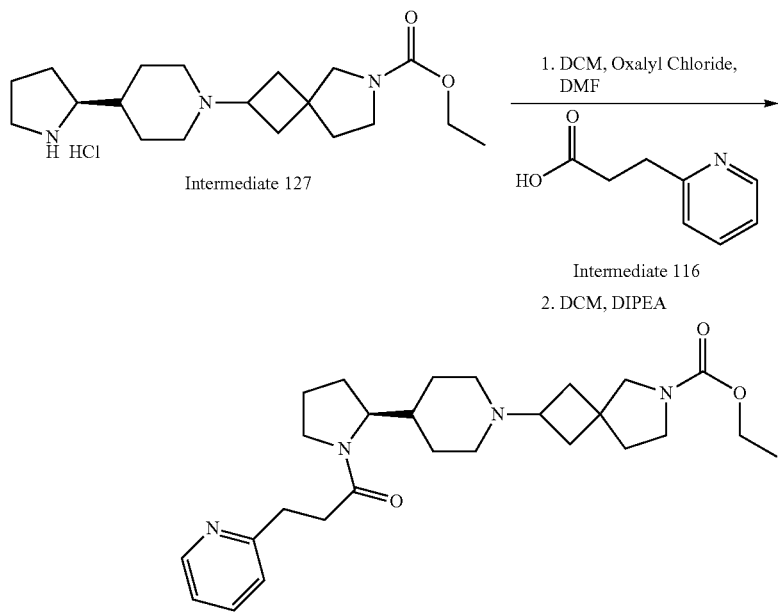

Example 2-62

Route y

Typical Procedure for the Preparation of Piperidines Via Amide Formation and CBZ-Deprotection as Exemplified by the Preparation of Example 2-65, ethyl 2-{4-[(2S)-1-{N-[(benzyloxy)carbonyl]-β-alanyl}pyrrolidin-2-yl]piperidin-1-yl}-6-azaspiro[3.4]octane-6-carboxylate and Example 2-66, ethyl 2-{4-[(2S)-1-(β-alanyl)pyrrolidin-2-yl]piperidin-1-yl}-6-azaspiro[3.4]octane-6-carboxylate

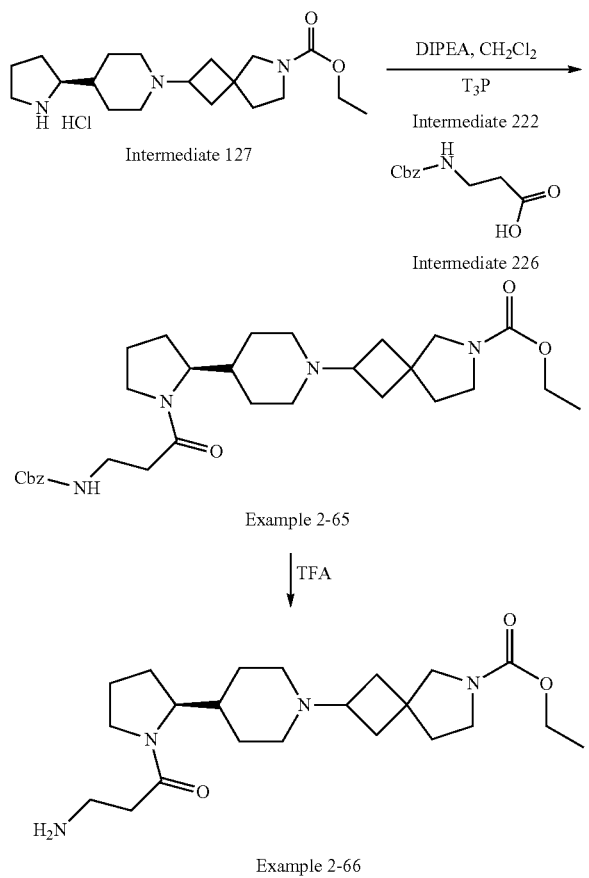

A mixture of diastereomers of ethyl 2-{4-[(2S)-pyrrolidin-2-yl]piperidin-1-yl}-6-azaspiro[3.4]octane-6-carboxylate.HCl (100 mg, 0.298 mmol) and DIPEA (0.102 mL, 0.597 mmol) were dissolved in $CH_2Cl_2$ (5 mL), cooled to 0° C. and Z-β-ala-OH (0.066 g, 0.298 mmol) added followed by propane phosphonic anhydride (0.123 g, 0.388 mmol, 50% In ethyl acetate). The resulting reaction mixture was stirred at 25° C. for 3 h, partitioned between $H_2O$ (70 mL) and $CH_2Cl_2$ (50 mL) and the aqueous layer further extracted with $CH_2Cl_2$ (2×50 mL). The combined organic layers were dried ($Na_2SO_4$), filtered and the solvent removed in vacuo to give ethyl 2-{4-[(2S)-1-{N-[(benzyloxy)carbonyl]-β-alanyl}pyrrolidin-2-yl]piperidin-1-yl}-6-azaspiro[3.4]octane-6-carboxylate (100 mg, 71.4%) as a colorless gum which was used directly without purification for the synthesis of Example 2-66.

LCMS (Method I): m/z 541 (M+H)$^+$ (ES+) at 4.38 and 4.51 min, UV inactive.

The residue could be purified by Prep HPLC [reverse phase HPLC (CHIRALPAK AD-H, C-18, 250×20 mm, 5 um, 18.0 mL per min, gradient 0% to 50% (over 15.0 mins), 0.1% ammonia in acetonitrile and 0.1% ammonia in water to give ethyl 2-{4-[(2S)-1-{N-[(benzyloxy)carbonyl]-β-alanyl}pyrrolidin-2-yl]piperidin-1-yl}-6-azaspiro[3.4]octane-6-carboxylate Example 2-65 Isomer 1 (20 mg, 12.5%) as a colourless gum, and ethyl 2-{4-[(2S)-1-{N-[(benzyloxy)carbonyl]-β-alanyl}pyrrolidin-2-yl]piperidin-1-yl}-6-azaspiro[3.4]octane-6-carboxylate Example 2-65 Isomer 2 (20 mg, 12.5%) as a colourless gum. The data for Isomer 2 are in Table 3.

A mixture of diastereomers of ethyl 2-{4-[(2S)-1-{N-[(benzyloxy)carbonyl]-β-alanyl}pyrrolidin-2-yl]piperidin-1-yl}-6-azaspiro[3.4]octane-6-carboxylate (100 mg, 0.185 mmol) was dissolved in TFA (2.0 mL). The resulting solution was stirred at 80° C. for 3 h, concentrated in vacuo and the residue purified by Prep HPLC [reverse phase HPLC (CHIRALPAK AD-H, C-18, 250×19 mm, 5 um, 13.0 mL per min, gradient 0% to 30% (over 30.0 mins), 0.1% ammonia in acetonitrile and 0.1% ammonia in water to give ethyl(S)-2-(4-(1-(3-aminopropanoyl)pyrrolidin-2-yl)piperidin-1-yl)-6-azaspiro[3.4]octane-6-carboxylate Example 2-66 Isomer 1 (2 mg, 2.63%) as a colorless gum and ethyl(S)-2-(4-(1-(3-aminopropanoyl)pyrrolidin-2-yl)piperidin-1-yl)-6-azaspiro[3.4]octane-6-carboxylate Example 2-66 Isomer 2 (3 mg, 4.0%) as a colorless gum. The data for Isomer 2 are in Table 3.

Route z

Typical Procedure for the Preparation of Piperidines Via Alkylation as Exemplified by the Preparation of Example 2-68, ethyl 2-{4-[(2S)-1-(2-fluoroethyl)pyrrolidin-2-yl]piperidin-1-yl}-6-azaspiro[3.4]octane-6-carboxylate

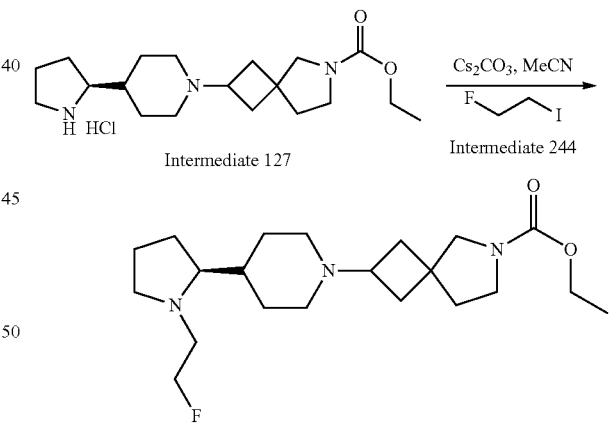

A mixture of diastereomers of ethyl 2-{4-[(2S)-pyrrolidin-2-yl]piperidin-1-yl}-6-azaspiro[3.4]octane-6-carboxylate.HCl (100 mg, 0.27 mmol) was dissolved in MeCN (5 mL), $CS_2CO_3$ (290 mg, 0.89 mmol) was added followed by the addition of 2-iodo-1-fluoroethane (56 mg g, 0.32 mmol) and the reaction mixture was stirred at 50° C. for 16 h. The reaction mixture was partitioned between $H_2O$ (70 mL) and ethyl acetate (50 mL), the aqueous layer was further extracted with ethyl acetate (2×50 mL), the organic layers were combined, dried ($Na_2SO_4$), filtered and the solvent was removed in vacuo. The residue was purified by prep HPLC

[reverse phase HPLC (CHIRALPAK AD-H, C-18, 250×19 mm, 5 um, 15.0 mL per min, gradient 0% to 40% (over 19.0 mins), 0.1% ammonia in acetonitrile and 0.1% ammonia in water] to give ethyl(S)-2-(4-(1-(2-fluoroethyl)pyrrolidin-2-yl)piperidin-1-yl)-6-azaspiro[3.4]octane-6-carboxylate Example 2-68 Isomer 1 (25 mg, 25%) as a yellowish gum and ethyl(S)-2-(4-(1-(2-fluoroethyl)pyrrolidin-2-yl)piperidin-1-yl)-6-azaspiro[3.4]octane-6-carboxylate Example 2-68 Isomer 2 (20 mg, 20.3%) as a yellowish gum. The data for Isomer 2 are in Table 3.

Route aa

Typical Procedure for the Preparation of Piperidines Via Alkylation as Exemplified by the Preparation of Example 2-69, ethyl 2-{4-[(2S)-1-(2,2,2-trifluoroethyl)pyrrolidin-2-yl]piperidin-1-yl}-6-azaspiro[3.4]octane-6-carboxylate Route ab Typical Procedure for the Preparation of Piperidines Via Alkylation as Exemplified by the Preparation of Example 2-70, ethyl 2-{4-[(2S)-1-(3,3,3-trifluoropropyl)pyrrolidin-2-yl]piperidin-1-yl}-6-azaspiro[3.4]octane-6-carboxylate

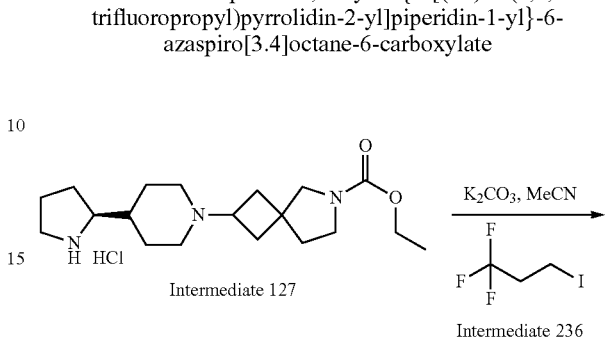

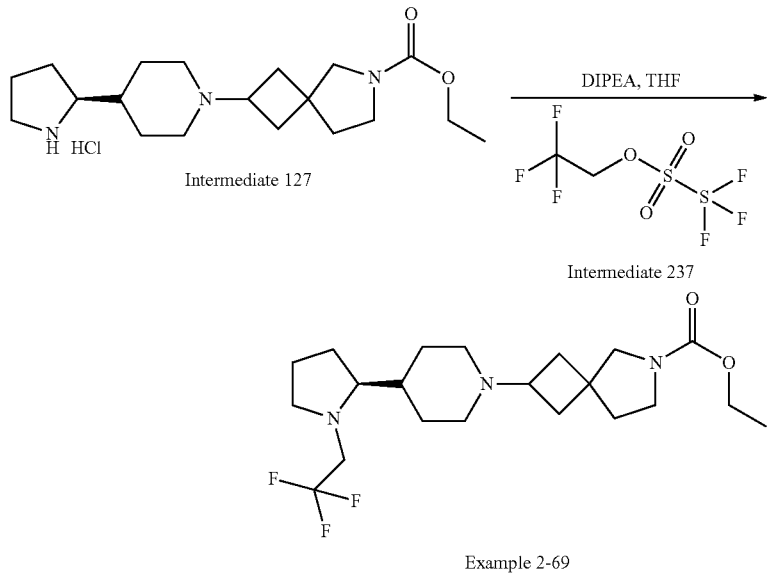

A mixture of diastereomers of ethyl 2-{4-[(2S)-pyrrolidin-2-yl]piperidin-1-yl}-6-azaspiro[3.4]octane-6-carboxylate.HCl (0.100 g, 0.29 mmol) and DIPEA (0.112 g, 0.87 mmol) were dissolved in THF (5 mL) and stirred at 60° C. for 2 hrs. 2,2,2-Trifluoroethyl trifluoromethanesulfonate (0.067 g, 0.29 mmol) was added dropwise at 0° C. and the resulting reaction mixture was stirred at room temperature for 24 h. The reaction mixture was partitioned between H₂O (70 mL) and EtOAc (50 mL), the aqueous layer was further extracted with EtOAc (2×50 mL), the organic layers were combined, dried (Na₂SO₄), filtered and concentrated in vacuo. The residue was purified by prep HPLC (X Bridge, C-18, 250×19 mm, 5 um, 12 mL per min, gradient 45% (over 0.01 mins), 100% (over 30.00 mins), then 45% (over 32.00 mins), 0.1% ammonia in acetonitrile/water to give ethyl(S)-2-(4-(1-(2,2,2-trifluoroethyl)pyrrolidin-2-yl)piperidin-1-yl)-6-azaspiro[3.4]octane-6-carboxylate Example 2-69 Isomer 1 (0.003 g, 2.4%) as a colorless gum and ethyl(S)-2-(4-(1-(2,2,2-trifluoroethyl)pyrrolidin-2-yl)piperidin-1-yl)-6-azaspiro[3.4]octane-6-carboxylate Example 2-69 Isomer 2 (0.002 mg, 1.6%) as a colorless gum. The data for Isomer 2 are in Table 3.

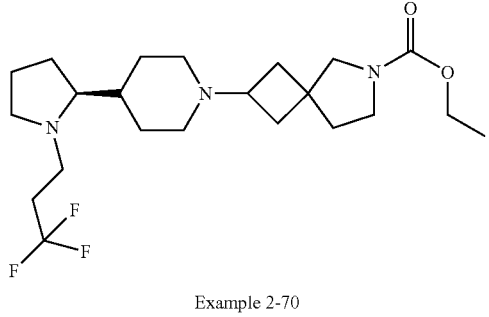

Example 2-70

A mixture of diastereomers of ethyl 2-{4-[(2S)-pyrrolidin-2-yl]piperidin-1-yl}-6-azaspiro[3.4]octane-6-carboxylate.HCl (0.100 g, 0.29 mmol) and K₂CO₃ (0.123 g, 0.89 mmol) were dissolved in MeCN (5 mL) and reaction mixture was stirred at 60° C. for 2 hrs. 1,1,1-Trifluoro-3-iodopropane (0.066 g, 0.29 mmol) was added dropwise at 0° C. and the resulting mixture was stirred at room temperature for 8 h. The reaction mixture was partitioned between H₂O (70 mL) and EtOAc (50 mL), the aqueous layer was further extracted with EtOAc (2×50 mL), the organic layers were combined, dried (Na₂SO₄), filtered and the solvent was removed in vacuo. The residue was purified by prep HPLC (X Bridge, C-18, 250×19 mm, 5 um, 15 mL per min, gradient 60% (over 0.01 mins), 100% (over 14.01 mins), then 60% (over 23.00 mins), 0.1% ammonia in acetonitrile/water to give ethyl(S)-2-(4-(1-(3,3,3-trifluoropropyl)pyrrolidin-2-yl)piperidin-1-yl)-6-azaspiro[3.4]octane-6-carboxylate Example 2-70 Isomer 1 (0.005 g, 3.9%) as a colorless gum, and ethyl(S)-2-(4-(1-(3,3,3-trifluoropropyl)pyrrolidin-2-yl)piperidin-1-yl)-6-azaspiro[3.4]octane-6-carboxylate Example 2-70 Isomer 2 (0.005 mg, 3.9%) as a colorless gum. The data for Isomer 1 and Isomer 2 are in Table 3.

Route ac

Typical Procedure for the Preparation of Piperidines Via Alkylation as Exemplified by the Preparation of Example 2-72, ethyl(S)-2-(4-(1-(2-methoxy-2-oxoethyl)pyrrolidin-2-yl)piperidin-1-yl)-6-azaspiro[3.4]octane-6-carboxylate

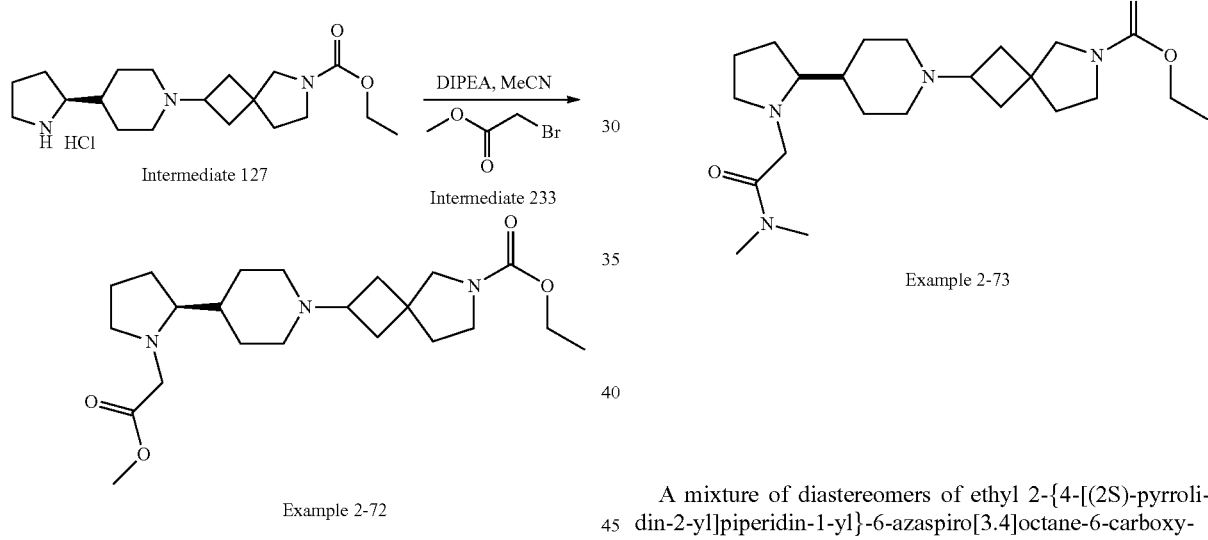

Example 2-72

A mixture of diastereomers of ethyl 2-{4-[(2S)-pyrrolidin-2-yl]piperidin-1-yl}-6-azaspiro[3.4]octane-6-carboxylate.HCl (0.100 g, 0.29 mmol) and DIPEA (0.14 mL, 0.87 mmol) were dissolved in MeCN (5 mL) and reaction mixture was stirred at RT for 1 h. Methyl bromoacetate (0.044 g, 0.29 mmol) was added dropwise and the resulting reaction mixture was stirred at 100° C. for 3 h. The reaction mixture was partitioned between H₂O (70 mL) and EtOAc (50 mL), aqueous layer was further extracted with EtOAc (2×50 mL), the organic layers were combined, dried (Na₂SO₄), filtered and the solvent was removed in vacuo. The residue was purified by prep HPLC (X Bridge, C-18, 250×19 mm, 5 um, 15 mL per min, gradient 48% (over 0.01 mins), 100% (over 11.1 mins), 48% (over 48.00 mins), 0.1% ammonia in acetonitrile/water] to give ethyl(S)-2-(4-(1-(2-methoxy-2-oxoethyl)pyrrolidin-2-yl)piperidin-1-yl)-6-azaspiro[3.4]octane-6-carboxylate Example 2-72 Isomer 1 (0.012 g, 9.9%) as a colorless gum, and ethyl(S)-2-(4-(1-(2-methoxy-2-oxoethyl)pyrrolidin-2-yl)piperidin-1-yl)-6-azaspiro[3.4]octane-6-carboxylate Example 2-72 Isomer 2 (0.013 mg, 10.7%) as a colorless gum. The data for Isomer 2 are in Table 3.

Route ad

Typical Procedure for the Preparation of Piperidines Via Alkylation as Exemplified by the Preparation of Example 2-72, ethyl 2-(4-{(2S)-1-[2-(dimethylamino)-2-oxoethyl]pyrrolidin-2-yl}piperidin-1-yl)-6-azaspiro[3.4]octane-6-carboxylate

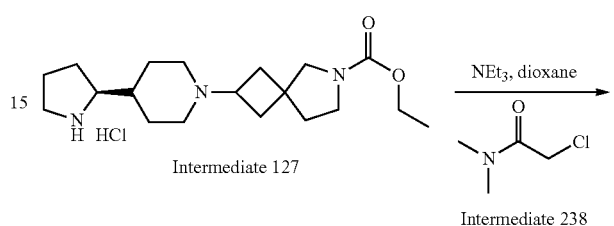

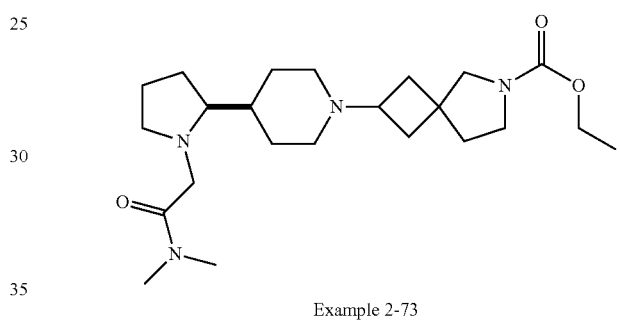

Example 2-73

A mixture of diastereomers of ethyl 2-{4-[(2S)-pyrrolidin-2-yl]piperidin-1-yl}-6-azaspiro[3.4]octane-6-carboxylate.HCl (0.100 g, 0.29 mmol) and NEt₃ (0.087 g, 0.85 mmol) were dissolved in dioxane (5 mL) and the reaction mixture was stirred at 60° C. for 30 min. 2-Chloro-N,N-dimethylacetamide (0.036 g, 0.29 mmol) was added dropwise at 0° C. and the resulting mixture was stirred at room temperature for 12 h. The reaction mixture was partitioned between H₂O (70 mL) and EtOAc (50 mL), the aqueous layer was further extracted with EtOAc (2×50 mL), the organic layers were combined, dried (Na₂SO₄), filtered and concentrated in vacuo. The residue was purified by prep HPLC (X Bridge, C-18, 250×19 mm, 5 um, 14 mL per min, gradient 20% (over 0.01 mins), 40% (over 36.00 mins), 100% (over 44.00 mins), then 20% (over 52.00 mins), 0.1% ammonia in acetonitrile/water] to give ethyl(S)-2-(4-(1-(2-(dimethylamino)-2-oxoethyl)pyrrolidin-2-yl)piperidin-1-yl)-6-azaspiro[3.4]octane-6-carboxylate Example 2-72 Isomer 1 (0.002 g, 1.6%) as a yellow gum and ethyl(S)-2-(4-(1-(2-(dimethylamino)-2-oxoethyl)pyrrolidin-2-yl) piperidin-1-yl)-6-azaspiro[3.4]octane-6-carboxylate Example 2-72 Isomer 2 (0.002 mg, 1.6%) as a yellow gum. The data for Isomer 2 are in Table 3.

Route ae

Typical Procedure for the Preparation of Piperidines Via Reductive Amination, Boc-Deprotection and Urea/Amide Formation as Exemplified by the Preparation of Example 2-76, ethyl 2-{4-[2-(methylcarbamoyl)-2,3-dihydro-1H-isoindol-1-yl]piperidin-1-yl}-6-azaspiro[3.4]octane-6-carboxylate

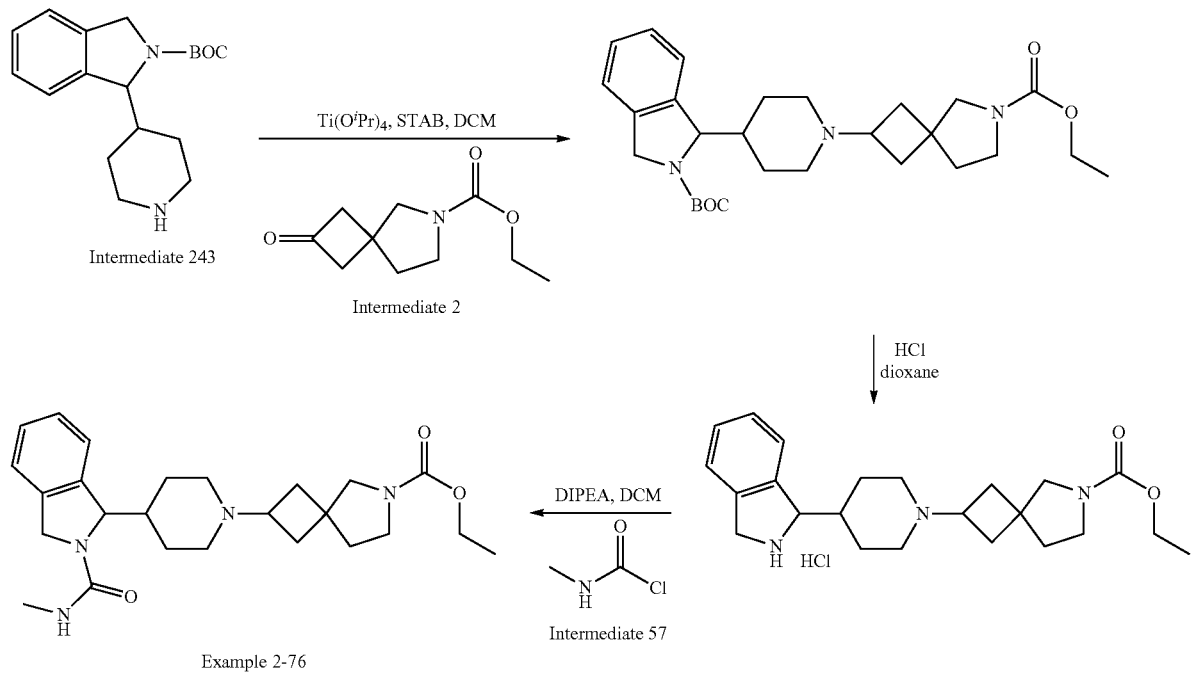

To a solution of tert-butyl 1-(piperidin-4-yl)isoindoline-2-carboxylate (135 mg, 0.45 mmol) and ethyl 3-oxo-8-azabicyclo[3.2.1]octane-8-carboxylate (88 mg, 0.890 mmol) in DCM (5 mL), Ti(O$^i$Pr)$_4$ (0.40 mL, 1.34 mmol) was added at 0° C. and the reaction mixture was stirred for 1 h. Na(OAc)$_3$BH (283 mg, 1.34 mmol) was added portion wise to the reaction mixture and stirred at 0° C. for 2 h. After completion, the reaction mixture was quenched with aq sat NaHCO$_3$ and extracted with DCM (3×30 mL). The organic layers were combined and washed with brine, dried (Na$_2$SO$_4$) and concentrated in vacuo. The residue was purified by flash column chromatography [normal phase, silica gel (100-200 mesh), gradient 5% to 10% methanol in DCM] to give tert-butyl 1-(1-(6-(ethoxycarbonyl)-6-azaspiro[3.4]octan-2-yl)piperidin-4-yl)isoindoline-2-carboxylate (35 mg, 75%) as a colourless liquid.

MS (ESI +ve): 484

To a solution of tert-butyl 1-(1-(6-(ethoxycarbonyl)-6-azaspiro[3.4]octan-2-yl)piperidin-4-yl)isoindoline-2-carboxylate (290 mg, 0.61 mmol) in 1,4-dioxane (10 mL), HCl in dioxane (4 M, 5 mL) was slowly added at 0° C. and the mixture was stirred at room temperature for 5 h. The solvent was evaporated in vacuo. The solid residue was triturated with diethyl ether to give ethyl 2-(4-(isoindolin-1-yl)piperidin-1-yl)-6-azaspiro[3.4]octane-6-carboxylate hydrochloride (250 mg, cr) as an off white solid.

MS (ESI +ve): 384

$^1$H-NMR (400 MHz; DMSO-d$_6$) δ: 1.15 (t, J=6.9 Hz, 3H), 1.16-1.26 (m, 1H), 1.70-1.90 (m, 5H), 1.95-2.28 (m, 5H), 3.49-3.72 (m, 4H), 3.60-3.72 (m, 4H), 3.98-4.15 (m, 2H), 4.13 (q, J=6.9 Hz, 2H), 4.45-4.59 (m, 2H), 7.37-7.49 (m, 5H), 9.54, 10.19 (2br.s., 2H).

To a solution of ethyl 2-(4-(isoindolin-1-yl)piperidin-1-yl)-6-azaspiro[3.4]octane-6-carboxylate hydrochloride (240 mg, 0.40 mmol) in DCM (5 mL), DIPEA (0.43 mL, 2.38 mmol) was added at 0° C. To this reaction mixture methylcarbamic chloride (67 mg, 0.72 mmol) was added and stirred at room temperature for 16 h. The reaction mixture was quenched with water (10 mL) and the aq layer was extracted with DCM (2×20 mL). The organic layers were combined, dried (Na$_2$SO$_4$) and concentrated in vacuo. The residue was purified by flash column chromatography [normal phase, silica gel (100-200 mesh), gradient 5% to 10% methanol in DCM] to give ethyl 2-(4-(2-(methylcarbamoyl)-isoindolin-1-yl)piperidin-1-yl)-6-azaspiro[3.4]octane-6-carboxylate as a mixture of diastereomers (130 mg, 48%) as a gummy liquid.

LCMS (Method M): m/z 441 (M+H)$^+$ (ES+), at 1.97 and 1.99 min, UV active.

$^1$H-NMR (400 MHz; DMSO-d$_3$): δ: 1.15 (t, J=6.9 Hz, 3H), 1.16-1.26 (m, 4H), 1.49-1.90 (m, 5H), 1.91-2.01 (m, 2H), 2.62 (d, J=3.9 Hz, 3H), 2.70-2.90 (m, 2H), 3.09-3.25 (m, 4H), 3.97 (q, J=6.8 Hz, 2H), 4.45-4.59 (m, 2H), 5.01-5.09 (m, 1H), 6.27 (br.s., 1H), 7.22-7.32 (m, 4H).

Separation of diastereomers using prep HPLC (73.0 mg submitted, Gilson Semi Preparative HPLC system—including Dual Piston Pumps 331 and 332, a 171 Diode Array Detector and a GX-271 Liquid Handler, solvents:

aqueous=water+0.2% ammonia (28% ammonia solution) and organic=acetonitrile, gradient: 20-50% organic in aqueous, flow Rate: 30 ml/min, column: Gemini-NX, C18, 5µ, 100×30 mm) gave ethyl 2-(4-(2-(methylcarbamoyl)-isoindolin-1-yl)piperidin-1-yl)-6-azaspiro[3.4]octane-6-carboxylate Example 2-76 Isomer 1 (8.99 mg, 12.3%) as a colourless gum and ethyl 2-(4-(2-(methylcarbamoyl)-isoindolin-1-yl)piperidin-1-yl)-6-azaspiro[3.4]octane-6-carboxylate Example 2-76 Isomer 2 (10.9 mg, 14.9%) as a colourless gum. The data for Isomer 1 and Isomer 2 are in Table 3.

Route af

Typical Procedure for the Arylation of Pyrrolidine as Exemplified by the Preparation of Example 2-77, ethyl 2-{4-[(2S)-1-phenylpyrrolidin-2-yl]piperidin-1-yl}-6-azaspiro[3.4]octane-6-carboxylate Route ag Typical Procedure for the Arylation of Pyrrolidine Containing Compounds with Heterocycles Using Cesium Carbonate and Copper Iodide in DMF as Exemplified by the Preparation of Example 2-78, methyl 2-{4-[(2S)-1-(pyridin-2-yl)pyrrolidin-2-yl]piperidin-1-yl}-6-azaspiro[3.4]octane-6-carboxylate

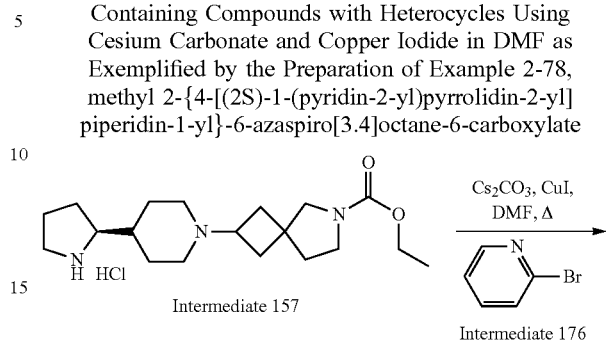

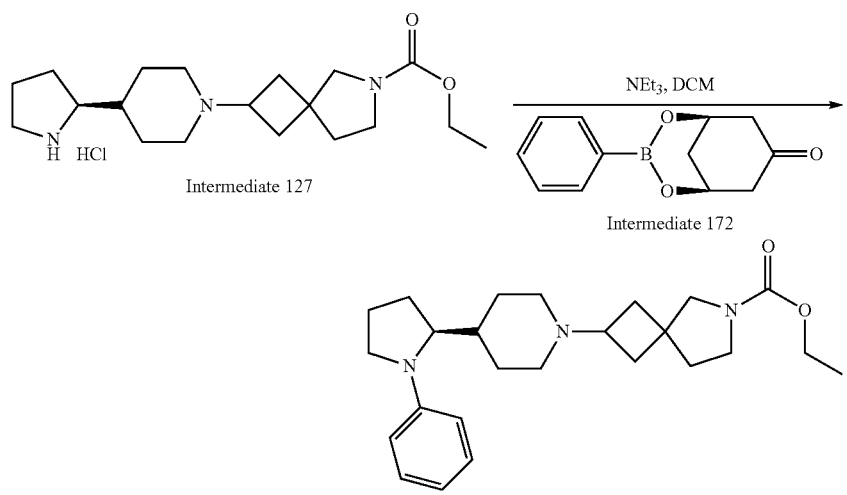

A mixture of diastereomers of ethyl 2-{4-[(2S)-pyrrolidin-2-yl]piperidin-1-yl}-6-azaspiro[3.4]octane-6-carboxylate.HCl (0.100 g, 0.27 mmol) was dissolved in DCM (5 mL), and triethylamine (54 mg, 0.54 mmol) was added followed by (1R,5S)-3-phenyl-2,4-dioxa-3-borabicyclo[3.3.1]nonan-7-one (see J. Luo at al. Tetrahedron Letters 54 (2013), 4505-4508, 58 mg, 0.53 mmol). The reaction mixture was stirred at room temperature for 16 h, then partitioned between H₂O (70 mL) and DCM (100 mL). The aqueous layer was further extracted with DCM (2×50 mL), and the organic layers were combined, dried (Na₂SO₄), the solvent was removed and the residue was purified by Prep HPLC [reverse phase HPLC (CHIRALPAK AD-H, C-18, 250×19 mm, 5 um, 15.0 mL per min, gradient 0% to 30% (over 21.0 mins), 0.1% Ammonia in Acetonitrile and 0.1% Ammonia in Water to give ethyl 2-{4-[(2S)-1-phenylpyrrolidin-2-yl]piperidin-1-yl}-6-azaspiro[3.4]octane-6-carboxylate, Example 2-77 Isomer 1 (10 mg, 13%) as a gum, and ethyl 2-{4-[(2S)-1-phenylpyrrolidin-2-yl]piperidin-1-yl}-6-azaspiro[3.4]octane-6-carboxylate, Example 2-77 Isomer 2 (10 mg, 13%) as a gum. The data for Isomer 2 are in Table 3.

-continued

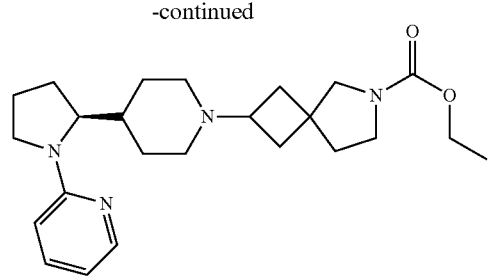

Example 2-78

A mixture of diastereomers of methyl 2-{4-[(2S)-pyrrolidin-2-yl]piperidin-1-yl}-6-azaspiro[3.4]octane-6-carboxylate.HCl (0.120 g, 0.37 mmol), Cs₂CO₃ (0.361 g, 1.1 mmol) and CuI (0.105 g, 0.50 mmol) were dissolved in DMF (5 mL) and stirred at RT for 30 min. 2-Bromopyridine (0.058 g, 0.37 mmol) was then added and the resulting mixture was stirred at 100° C. for 18 h. The reaction mixture was partitioned between H₂O (70 mL) and EtOAc (50 mL). The aqueous layer was further extracted with EtOAc (2×50 mL). The organic layers were combined, dried (Na₂SO₄), the solvent was removed by concentration and the residue was purified Prep HPLC (X Bridge, C-18, 150×19 mm, 5 um, 13 mL per min, gradient 40% to 100% (over 20 mins), 0.1% Ammonia in Acetonitrile/water] to give methyl 2-{4-[(2S)-1-(pyridin-2-yl)pyrrolidin-2-yl]piperidin-1-yl}-6-azaspiro[3.4]octane-6-carboxylate Example 2-78 Isomer 1 (0.011 g, 2%) as a gum, and methyl 2-{4-[(2S)-1-(pyridin-2-yl)pyrrolidin-2-yl]piperidin-1-yl}-6-azaspiro[3.4]octane-6-carboxylate Example 2-78 Isomer 2 (0.09 mg, 2%) as a gum. The data for Isomer 2 are in Table 3.

Route ah

Typical Procedure for the Arylation of Pyrrolidine Containing Compounds with Heterocycles Using Sodium Carbonate in Ethanol as Exemplified by the Preparation of Example 2-81, ethyl 2-{4-[(2S)-1-(pyrimidin-2-yl)pyrrolidin-2-yl]piperidin-1-yl}-6-azaspiro[3.4]octane-6-carboxylate

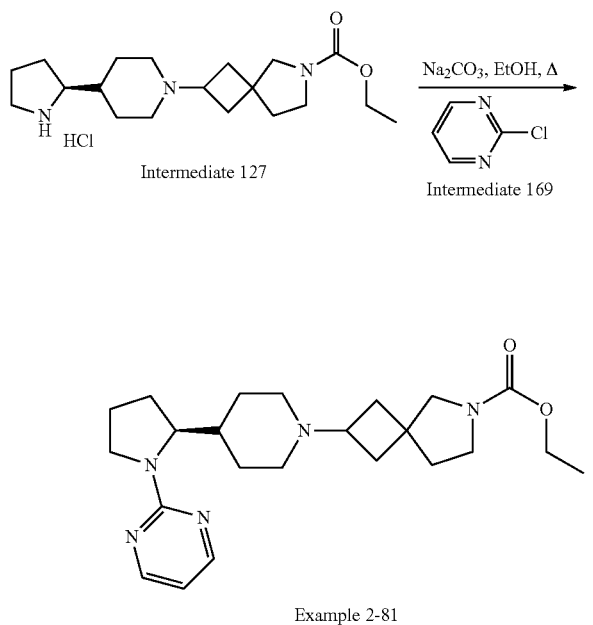

Example 2-81

A mixture of diastereomers of ethyl 2-{4-[(2S)-pyrrolidin-2-yl]piperidin-1-yl}-6-azaspiro[3.4]octane-6-carboxylate.HCl (0.100 g, 0.29 mmol) and Na₂CO₃ (0.092 g, 0.87 mmol) were dissolved in ethanol (10 mL) and stirred at RT for 30 min. 2-Chloropyrimidine (0.034 g, 0.29 mmol) was then added at 0° C. The resulting reaction mixture was stirred at 80° C. for 6 h. The reaction mixture was concentrated and dichloromethane was added. The mixture was filtered, and the filtrate was concentrated and purified by Prep HPLC (X Bridge, C-18, 150×19 mm, 5 um, 15 mL per min, gradient 38% (over 0.01 mins), 42% (over 15.00 mins), 100% (over 19.00 mins), then 38% (over 23.00 mins), 0.1% Ammonia in Acetonitrile/water] to give ethyl 2-{4-[(2S)-1-(pyrimidin-2-yl)pyrrolidin-2-yl]piperidin-1-yl}-6-azaspiro[3.4]octane-6-carboxylate, Example 2-81 Isomer 1 (0.031 g, 25%) as a gum, and ethyl 2-{4-[(2S)-1-(pyrimidin-2-yl)pyrrolidin-2-yl]piperidin-1-yl}-6-azaspiro[3.4]octane-6-carboxylate, Example 2-81 Isomer 2 (0.017 mg, 14%) as a gum. The data for Isomer 2 are in Table 3.

Route ai

Typical Procedure for the Arylation of Pyrrolidine Containing Compounds with Heterocycles Using Cesium Carbonate in DMF as Exemplified by the Preparation of Example 2-82, ethyl 2-{4-[(2S)-1-(1,3-thiazol-2-yl)pyrrolidin-2-yl]piperidin-1-yl}-6-azaspiro[3.4]octane-6-carboxylate

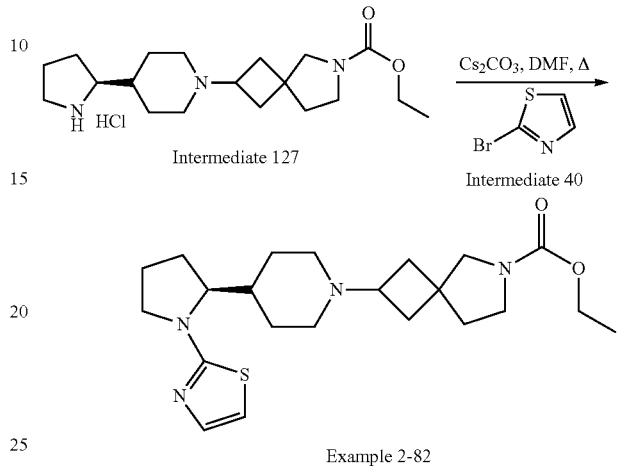

Example 2-82

The mixture of diastereomers of ethyl 2-{4-[(2S)-pyrrolidin-2-yl]piperidin-1-yl}-6-azaspiro[3.4]octane-6-carboxylate.HCl, Intermediate 127, (100 mg, 0.27 mmol) was dissolved in DMF (5 mL) and CS₂CO₃ (260 mg, 0.81 mmol) was added to it, followed by the addition of 2-bromothiazole (58 mg, 0.29 mmol). The reaction mixture was stirred at 90° C. for 16 h. The reaction mixture was partitioned between H₂O (70 mL) and EtOAc (50 mL). The aqueous layer was further extracted with EtOAc (2×50 mL). The organic layers were combined, dried (Na₂SO₄), the solvent was removed by concentration and the residue was purified by Prep HPLC [reverse phase HPLC (CHIRALPAK AD-H, C-18, 250×19 mm, 5 um, 15.0 mL per min, gradient 0% to 30% (over 21.0 mins), 0.1% Ammonia in Acetonitrile and 0.1% Ammonia in Water to give ethyl 2-{4-[(2S)-1-(1,3-thiazol-2-yl)pyrrolidin-2-yl]piperidin-1-yl}-6-azaspiro[3.4]octane-6-carboxylate, Example 2-82 Isomer 1 (20 mg, 18%) as a colorless gum, and ethyl 2-{4-[(2S)-1-(1,3-thiazol-2-yl)pyrrolidin-2-yl]piperidin-1-yl}-6-azaspiro[3.4]octane-6-carboxylate, Example 2-82 Isomer 2 (6 mg, 6%) as a colorless gum. The data for Isomer 1 and Isomer 2 are in Table 3.

Route aj

Typical Procedure for the Preparation of Piperidines Via Deprotection and Reductive Aminations, as Exemplified by the Preparation of Example 2-84, ethyl 2-{4-[(2R)-2-(methoxycarbonyl)pyrrolidin-1-yl]piperidin-1-yl}-6-azaspiro[3.4]octane-6-carboxylate

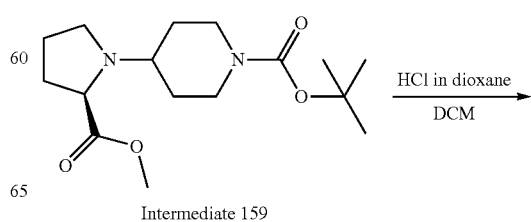

Intermediate 159

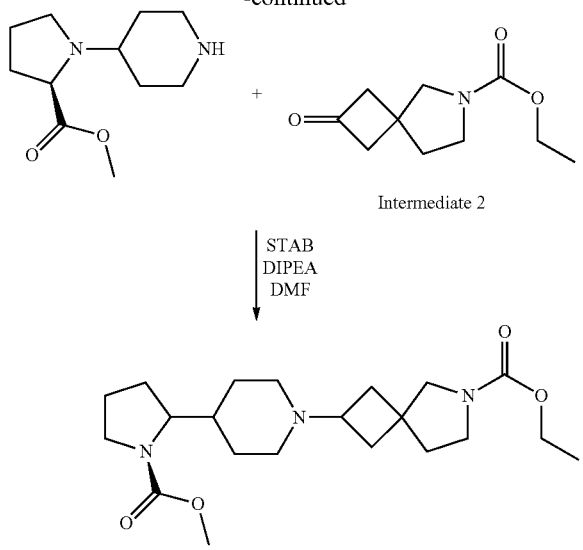

Example 2-84

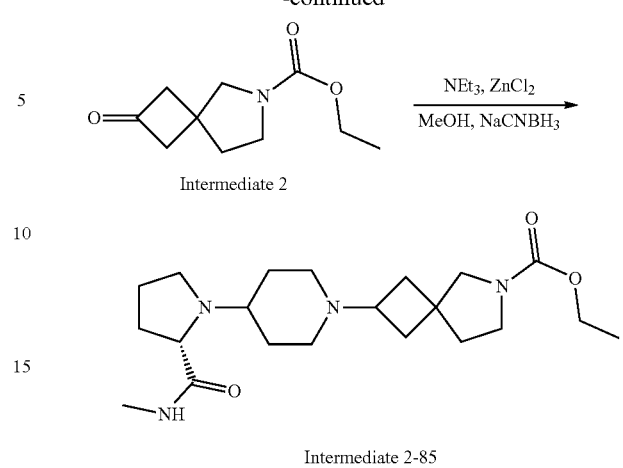

Intermediate 2-85 tert-Butyl 4-[(2R)-2-(methoxycarbonyl)pyrrolidin-1-yl]piperidine-1-carboxylate (0.396 g, 1.26 mmol) was dissolved in DCM (1 mL), followed by the dropwise addition of HCl in dioxane (3 mL, 4.0 M solu.). The resulting reaction mixture was stirred at rt for 1 h, the solvents were removed in vacuo and the residue was carried on to the next step without further purification.

Methyl 1-piperidin-4-yl-D-prolinate.HCl (0.358 g, 1.26 mmol) and ethyl 2-oxo-6-azaspiro[3.4]octane-6-carboxylate (0.266 g, 1.26 mmol) were dissolved in DMF (4 mL) at rt and DIPEA (0.435 mL, 2.510 mmol) was added. The reaction mixture was stirred at it for 3 h. STAB (0.533 g, 2.518 mmol) was then added and the reaction mixture was stirred overnight under nitrogen at rt. The solvents were removed in vacuo, and Preparative HPLC was used to separate the diastereomers, using a Phenomenex Gemini-NX C18 column, 100×30 mm, eluting with 25 to 45% MeCN/0.2% ammonia in H₂O (v/v) at 18 mL/min and collecting fractions by monitoring at 210 nm to give Example 2-84 Isomer 1 ethyl 2-{4-[(2R)-2-(methoxycarbonyl)pyrrolidin-1-yl]piperidin-1-yl}-6-azaspiro[3.4]octane-6-carboxylate (18.4 mg, 4%) as a colourless oil and Example 2-84 Isomer 2, ethyl 2-{4-[(2R)-2-(methoxycarbonyl)pyrrolidin-1-yl]piperidin-1-yl}-6-azaspiro[3.4]octane-6-carboxylate (13.9 mg, 3%) as a colourless oil. The data for Isomer 2 are in Table 3

Route ak

Typical Procedure for the Preparation of Piperidines Via Reductive Amination as Exemplified by the Preparation of Example 2-85, ethyl 2-{4-[(2S)-2-(methylcarbamoyl)pyrrolidin-1-yl]piperidin-1-yl}-6-azaspiro[3.4]octane-6-carboxylate

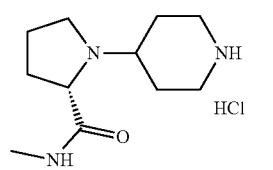

Intermediate 139

(S)-N-methyl-1-(piperidin-4-yl)pyrrolidine-2-carboxamide dihydrochloride (0.2 g, 0.94 mmol), NEt₃ (0.75 mL, 5.0 mmol), 6-(ethoxycarbonyl)-2-oxo-6-azaspiro[3.4]octan-8-ylium (0.188 g, 0.93 mmol) and ZnCl₂ (30 mg, 0.02 mmol) were dissolved in MeOH (15.00 mL) under nitrogen and stirred for 1 h at 50-60° C. NaCNBH₃ (0.069 g, 1.0 mmol) was added portion wise at 0-10° C. and the reaction mixture stirred for 3 h at room temperature. The reaction mixture was partitioned between EtOAc (2×50 mL) and water (30 mL), the organic layers were combined, dried (Na₂SO₄), filtered and the solvent was removed in vacuo and the crude product was purified by PREP-HPLC [reverse phase HPLC (X-Bridge PREP C18, 250×19 mm, 5um, 15 mL per min, gradient 30% to 100% (over 22 min), then 100% (2 min), 0.1% NH₃ in Acetonitrile to give Example 2-85 Isomer 1, ethyl(S)-2-(4-(2-(methylcarbamoyl)pyrrolidin-1-yl)piperidin-1-yl)-6-azaspiro[3.4]octane-6-carboxylate (0.09 g, 24.32%) as a white solid and Example 2-85 Isomer 2, ethyl(S)-2-(4-(2-(methylcarbamoyl)pyrrolidin-1-yl)piperidin-1-yl)-6-azaspiro[3.4]octane-6-carboxylate (0.089 g, 24.10%) as a white solid. The data for Isomer 2 are in Table 3.

Route ap

Typical Procedure for the Preparation of Piperidines Via Deprotection and Sodium Triacetoxyborohydride Reductive Amination, as Exemplified by the Preparation of Example 2-87, ethyl 2-{4-[(2R)-4,4-difluoro-2-(methoxycarbonyl)pyrrolidin-1-yl]-6-azaspiro[3.4]octane-6-carboxylate

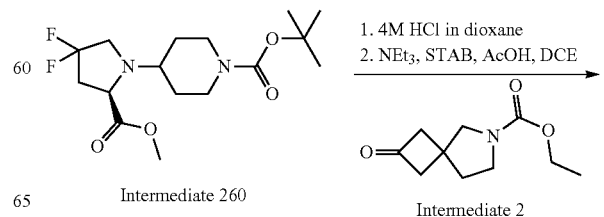

Intermediate 260      Intermediate 2

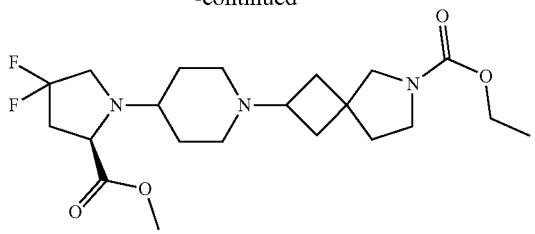

Example 2-87

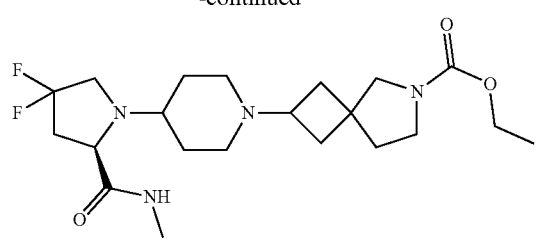

Example 2-88 tert-butyl 4-[(2R)-4,4-difluoro-2-(methoxycarbonyl)pyrrolidin-1-yl]piperidine-1-carboxylate (0.36 g, 1.03 mmol) was dissolved in 4.0M HCl in dioxane (10 mL) and the reaction mixture was stirred at rt for 6 h. The solvents were removed in vacuo and the residue was used in the next step without further purification. The crude reaction mixture and ethyl 2-oxo-6-azaspiro[3.4]octane-6-carboxylate (0.243 g, 1.233 mmol) were dissolved in DCE (10 mL) at it and Et$_3$N (0.249 g, 2.47 mmol) was added. The reaction mixture was stirred at 50° C. under nitrogen for 2 h. The reaction mixture was cooled to rt, glacial acetic acid (0.114 g, 1.90 mmol) and STAB (0.784 g, 3.69 mmol) were added and the reaction mixture was stirred overnight at 50° C. under nitrogen. Water (2 mL) was added to the cooled reaction mixture and the solvents were removed in vacuo. The residue was partitioned between DCM (15 mL) and sat. NaHCO$_3$ (aq) (15 mL), the aqueous layer was washed with DCM (2×15 mL). The organic layers were combined and dried by passing through a Biotage Phase Separator Cartridge. The solvents were removed in vacuo, and the residue was purified by column chromatography (normal phase, [Biotage SNAP cartridge KP-sil 10 g 40-63 µm, 60 Å, 12 mL per min, gradient 1% to 10% MeOH/DCM]). The residue was further purified by preparative reversed phase HPLC (Phenomenex Gemini-NX 5 µm C18 110A Axia column, 100×30 mm, eluting with 20 to 50% MeCN/Solvent B over 14.4 min at 30 mL/min [where solvent B is 0.2% of (28% NH$_3$/H$_2$O) in H$_2$O] and collecting fractions by monitoring at 210 nm) to give ethyl 2-{4-[(2R)-4,4-difluoro-2-(methoxycarbonyl)pyrrolidin-1-yl}-6-azaspiro[3.4]octane-6-carboxylate, Example 2-87 Isomer 1 (0.020 g, 4.5%) and ethyl 2-{4-[(2R)-4,4-difluoro-2-(methoxycarbonyl)pyrrolidin-1-yl}-6-azaspiro[3.4]octane-6-carboxylate, Example 2-87 Isomer 2 (0.020 g, 4.5%). The data for Isomer 2 are in Table 3.

Route am

Typical Procedure for the Preparation of Piperidines Via Deprotection and Amide Formation, as Exemplified by the Preparation of Example 2-88, ethyl 2-{4-[(2R)-4,4-difluoro-2-(methylcarbamoyl)pyrrolidin-1-yl]piperidin-1-yl}-6-azaspiro[3.4]octane-6-carboxylate

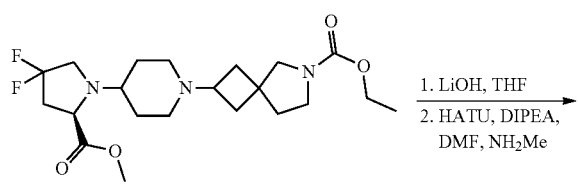

Example 2-87

1. LiOH, THF
2. HATU, DIPEA, DMF, NH$_2$Me

A mixture of diastereomers of ethyl 2-{4-[(2R)-4,4-difluoro-2-(methoxycarbonyl)pyrrolidin-1-yl]piperidin-1-yl}-6-azaspiro[3.4]octane-6-carboxylate, Example 2-87, (0.400 g, 0.932 mmol) was dissolved in THF (8 mL) and 1M LION (aq) (1.9 mL) was added, the reaction mixture was stirred at rt overnight. The reaction mixture was neutralised using 2.0M HCl solution and solvents were removed in vacuo. The residue was azeotroped with toluene to give 1-{1-[6-(ethoxycarbonyl)-6-azaspiro[3.4]oct-2-yl]piperidin-4-yl}-4,4-difluoro-D-proline (0.440 g, 100%) as a yellow glass.

LCMS (Method C): m/z 416 (M+H)+ (ES+) at 0.71 min, UV inactive

1-{1-[6-(ethoxycarbonyl)-6-azaspiro[3.4]oct-2-yl]piperidin-4-yl}-4,4-difluoro-D-proline (0.193 g, 0.466 mmol), was dissolved in anhydrous DMF (5 mL) and HATU (0.533 g, 1.398 mmol), 2.0M methylamine solution in THF (2.3 mL, 2.33 mmol) and DIPEA (0.301 g, 2.33 mmol) were added, the reaction mixture was stirred overnight at 11. The solvents were removed in vacuo, and the residue was partitioned between DCM (20 mL) and sat. NaHCO$_3$ (aq) (20 mL), aqueous layer was extracted with DCM (2×15 mL). The organic layers were combined, washed with brine (20 mL) and dried by passing through a Biotage Phase Separator Cartridge. The solvents were removed in vacuo, and the residue was purified by column chromatography (normal phase, [Biotage SNAP cartridge KP-sil 10 g 40-63 µm, 60 Å, 12 mL per min, gradient 0% to 10% MeOH/DCM]). The residue was further purified by preparative reversed phase HPLC (Phenomenex Gemini-NX 5 µm C18 110A Axia column, 100×30 mm, eluting with 20 to 50% MeCN/Solvent B over 14.4 min at 30 mL/min [where solvent B is 0.2% of (28% NH$_3$/H$_2$O) in H$_2$O] and collecting fractions by monitoring at 210 nm) to give ethyl 2-{4-[(2R)-4,4-difluoro-2-(methylcarbamoyl)pyrrolidin-1-yl]piperidin-1-yl}-6-azaspiro[3.4]octane-6-carboxylate, Example 2-88 Isomer 1, (0.038 g, 18%) as a colourless oil and ethyl 2-{4-[(2R)-4,4-difluoro-2-(methylcarbamoyl)pyrrolidin-1-yl]piperidin-1-yl}-6-azaspiro[3.4]octane-6-carboxylate, Example 2-88 Isomer 2, (0.037 g, 18%) as a colourless oil. The data for Isomer 2 are in Table 3.

Route an

Typical Procedure for the Preparation of Piperidines Via Amide Formation, as Exemplified by the Preparation of Example 2-90, ethyl 2-{4-[(2R)-2-carbamoyl-4,4-difluoropyrrolidin-1-yl]piperidin-1-yl}-6-azaspiro[3.4]octane-6-carboxylate

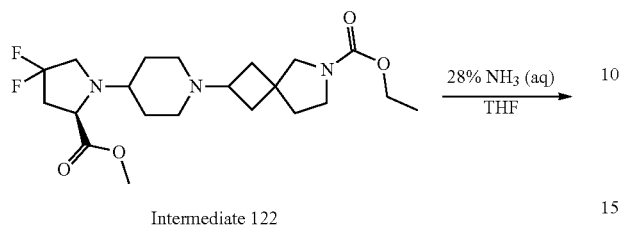

Intermediate 122

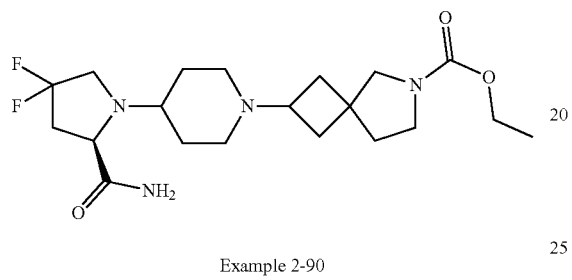

Example 2-90

Mixture of diastereomers of ethyl 2-{4-[(2R)-2-methoxycarbonyl-4,4-difluoropyrrolidin-1-yl]piperidin-1-yl}-6-azaspiro[3.4]octane-6-carboxylate (456 mg, 1.062 mmol) was dissolved in THF (1 mL) and 28% NH$_3$ solution (9 mL) at 60° C. and reaction stirred for 18 h. Reaction mixture neutralized with 1M HCl$_{(aq)}$ diluted with DCM (25 mL) and washed with H$_2$O (2×25 mL), combined aqueous layers washed with DCM (25 mL), combined organic layers washed with brine (25 mL) and passed through Biotage Phase separator. Volatiles removed under vacuum to yield an orange oil (0.290 g, 65%). Preparative HPLC was used to separate the diastereomers, using a Phenomenex Gemini-NX C18 column, 100×30 mm, eluting with 20 to 45% MeCN/0.2% ammonia in H$_2$O (v/v) at 18 mL/min and collecting fractions by monitoring at 210 nm to give Example 2-90 Isomer 1 ethyl 2-{4-[(2R)-2-carbamoyl-4,4-difluoropyrrolidin-1-yl]piperidin-1-yl}-6-azaspiro[3.4]octane-6-carboxylate (16.8 mg, 4%) as a colourless oil and Example 2-90 Isomer 2, ethyl 2-{4-[(2R)-2-carbamoyl-4,4-difluoropyrrolidin-1-yl]piperidin-1-yl}-6-azaspiro[3.4]octane-6-carboxylate (12.4 mg, 3%) as a colourless oil. The data for Isomer 2 are in Table 3

Route ao

Typical Procedure for the Preparation of Piperidines Via Hydrolysis and Amide Formation, as Exemplified by the Preparation of Example 2-91, ethyl 2-{4-[(2R)-4,4-difluoro-2-(methoxycarbamoyl)pyrrolidin-1-yl]piperidin-1-yl}-6-azaspiro[3.4]octane-6-carboxylate

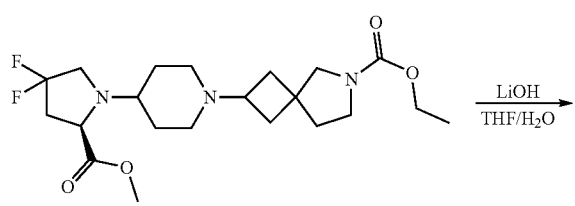

Example 2-87

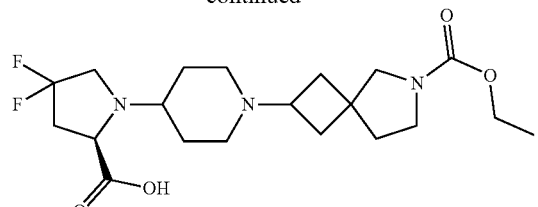

Example 2-86

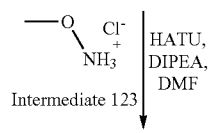

Intermediate 123

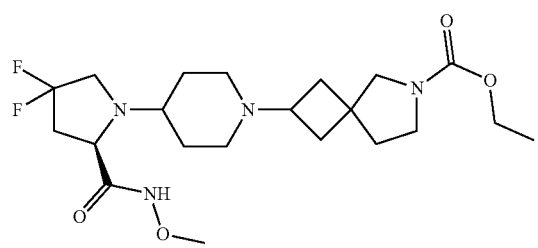

Example 2-91

Mixture of diastereomers of ethyl 2-{4-[(2R)-2-methoxycarbonyl-4,4-difluoropyrrolidin-1-yl]piperidin-1-yl}-6-azaspiro[3.4]octane-6-carboxylate (230 mg, 0.536 mmol) was dissolved in THF (6.5 mL) and 1.0M LiOH solution (1.1 mL, 1.1 mmol) at rt and reaction stirred for 18 h. Volatiles removed under vacuum and compound carried through without further purification. 1-{1-[6-(ethoxycarbonyl)-6-azaspiro[3.4]oct-2-yl]piperidin-4-yl}-4,4-difluoro-D-proline (125 mg, 0.300 mmol) was dissolved in DMF (1 mL) followed by addition of HATU (228 mg, 0.60 mmol) and DIPEA (0.260 mL, 1.50 mmol). The reaction mixture was stirred at 0° C. for 10 minutes, followed by addition of methoxyamine hydrochloride (25 mg, 0.30 mmol) and resulting reaction mixture was stirred at it for 18 h. The reaction mixture was concentrated in vacuo, then was partitioned between saturated NaHCO$_{3(aq)}$ (50 mL) and DCM (50 mL), the aqueous layer was further extracted with DCM (2×50 mL), the organic layers were combined, washed with brine (50 mL) and passed through Biotage Phase separator. Volatiles removed under vacuum to yield an orange oil (0.102 g, 77%). Preparative HPLC was used to separate the diastereomers, using a Phenomenex Gemini-NX C18 column, 100×30 mm, eluting with 20 to 50% MeCN/0.2% ammonia in H$_2$O (v/v) at 18 mL/min and collecting fractions by monitoring at 210 nm to give Example 2-91 Isomer 1 ethyl 2-{4-[(2R)-4,4-difluoro-2-(methoxycarbamoyl)pyrrolidin-1-yl]piperidin-1-yl}-6-azaspiro[3.4]octane-6-carboxylate (12.2 mg, 4%) as a colourless oil and Example 2-91 Isomer 2, ethyl 2-{4-[(2R)-4,4-difluoro-2-(methoxycarbamoyl)pyrrolidin-1-yl]piperidin-1-yl}-6-azaspiro[3.4]octane-6-carboxylate (7.2 mg, 3%) as a colourless oil. The data for Isomer 2 are in Table 3

Route ap

Typical Procedure for the Preparation of Piperidines Via Deprotection and Sodium Triacetoxyborohydride Reductive Amination, as Exemplified by the Preparation of Example 2-111, ethyl 2-[4-(2-oxopyrrolidin-1-yl)piperidin-1-yl]-6-azaspiro[3.4]octane-6-carboxylate

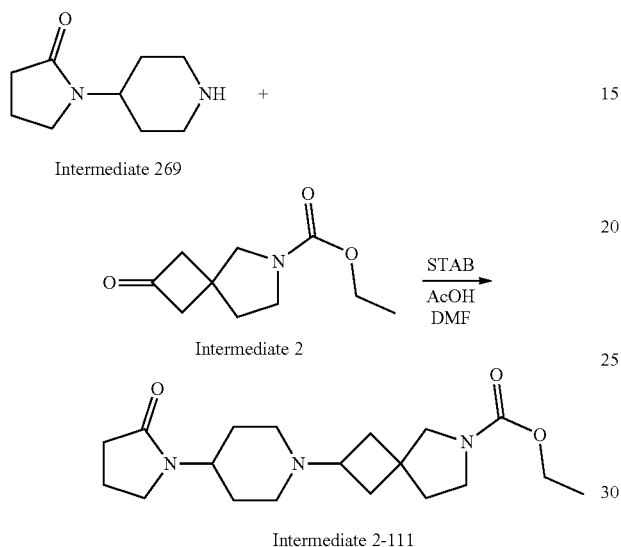

Intermediate 2-111

1-Piperidin-4-yl pyrrolidine-2-one (0.200 g, 1.19 mmol) and ethyl 2-oxo-6-azaspiro[3.4]octane-6-carboxylate (0.212 g, 1.14 mmol) were dissolved in DMF (6 mL) at it, the reaction mixture was stirred at 40° C. under nitrogen for 3 h. The reaction mixture was cooled to rt, STAB (0.630 g, 2.97 mmol) and glacial acetic acid (0.071 g, 1.189 mmol) were added and the reaction mixture was stirred overnight at 40° C. under nitrogen. Water (2 mL) was added to the cooled reaction mixture and the solvents were removed in vacuo. The residue was partitioned between DCM (15 mL) and sat. NaHCO₃ (aq) (15 mL), the aqueous layer was washed with DCM (2×15 mL). The organic layers were combined and dried by passing through a Biotage Phase Separator Cartridge. The solvents were removed in vacuo, and the residue was purified by column chromatography (normal phase, [Biotage SNAP cartridge KP-sil 10 g 40-63 µm, 60 Å, 12 mL per min, gradient 1% to 10% MeOH/DCM]). The residue was further purified by preparative reversed phase HPLC (Phenomenex Gemini-NX 5 µm C18 110A Axia column, 100×30 mm, eluting with 20 to 35% MeCN/Solvent B over 14.4 min at 30 mL/min [where solvent B is 0.2% of (28% NH₃/H₂O) in H₂O] and collecting fractions by monitoring at 210 nm) to give ethyl 2-[4-(2-oxopyrrolidin-1-yl)piperidin-1-yl]-6-azaspiro[3.4]octane-6-carboxylate, Example 2-111 Isomer 1, (0.008 g, 2%) as a colourless oil and ethyl 2-[4-(2-oxopyrrolidin-1-yl)piperidin-1-yl]-6-azaspiro[3.4]octane-6-carboxylate, Example 2-111 Isomer 2, (0.009 g, 2%) as a colourless oil. The data for Isomer 2 are in Table 3.

If amine used in the reductive amination contains a second amine group which is protected (with standard amine protecting groups such as BOC or Cbz). Then standard methods for deprotection can be used to remove these protecting groups once the reductive amination has been performed to allow further functionalization of the target.

Route aq

Typical Procedure for the Preparation of Piperidines Via Reductive Amination, Boc Deprotection and Urea Formation as Exemplified by the Preparation of Example 2-124, ethyl 2-[4-(2-oxo-1,2-dihydropyridin-4-yl)piperidin-1-yl]-6-azaspiro[3.4]octane-6-carboxylate

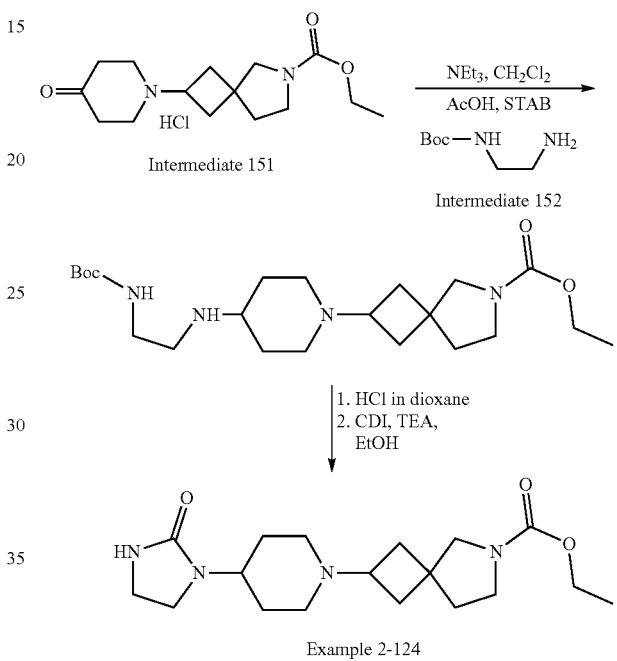

Example 2-124

Ethyl 2-(4-oxopiperidin-1-yl)-6-azaspiro[3.4]octane-6-carboxylate hydrochloride (0.316 g, 1.00 mmol) and tert-butyl(2-aminoethyl)carbamate (0.320 g, 2.00 mmol) were dissolved in DCM (10 mL) under N₂ at rt, NEt₃ (0.15 mL, 1.10 mmol) was added and the reaction mixture was stirred at it for 0.5 h. Acetic acid (0.13 mL, 2.20 mmol) was added, the reaction mixture stirred at rt for 2 h, STAB (0.530 g, 2.50 mmol) was added and the reaction mixture stirred overnight. The reaction mixture was quenched with the addition of NaHCO₃ (sat aq.) (30 mL), extracted with DCM (4×25 mL), the combined DCM layers were passed through a Biotage phase separator and concentrated in vacuo to give crude ethyl 2-[4-({2-[(tert-butoxycarbonyl)amino]ethyl}amino)piperidin-1-yl]-6-azaspiro[3.4]octane-6-carboxylate as a mixture of diastereomers which was used without any further purification.

LCMS (Method D): m/z 425 (M+H)⁺ (ES+), at 1.30 and 1.35 min, UV inactive.

Crude ethyl 2-[4-({2-[(tert-butoxycarbonyl)amino]ethyl}amino)piperidin-1-yl]-6-azaspiro[3.4]octane-6-carboxylate (0.424 g, 1.00 mmol) was dissolved in CH₂Cl₂ (10 mL), 4 M hydrogen chloride in dioxane (1.25 mL, 5.0 mmol) added and the reaction mixture stirred at rt overnight. The volatiles were removed in vacuo, the residue dissolved in EtOH (10 mL), NEt₃ (1.40 mL, 10.0 mmol) and CDI (0.244 g, 1.50 mmol) added and the mixture heated to reflux and maintained overnight. The solvent was removed in vacuo, the residue partitioned between CH$_2$Cl$_2$ (20 mL) and water (20 mL) and the aqueous layer extracted with CH$_2$Cl$_2$ (4×20 mL). The combined organics were concentrated in vacuo to give crude ethyl 2-[4-(2-oxoimidazolidin-1-yl)piperidin-1-yl]-6-azaspiro[3.4]octane-6-carboxylate as a mixture of diastereomers. Preparative HPLC was used to separate the diastereomers, using a Phenomenex Gemini-N C18 column, 150×21 mm, eluting with 25 to 45% MeCN in 0.2% NH$_3$/H$_2$O at 18 mL/min and collecting fractions by monitoring at 210 nm to give ethyl 2-[4-(2-oxo-1,2-dihydropyridin-4-yl)piperidin-1-yl]-6-azaspiro[3.4]octane-6-carboxylate, Example 2-124 Isomer 1, (0.008 g, 2.3%) as a colourless solid and ethyl 2-[4-(2-oxo-1,2-dihydropyridin-4-yl)piperidin-1-yl]-6-azaspiro[3.4]octane-6-carboxylate Example 2-124 Isomer 2, (0.008 g, 2.3%) as a colourless solid. The data for Isomer 2 are in Table 3.

Route ar

Typical Procedure for the Preparation of Piperidines Via Ester Reduction, as Exemplified by the Preparation of Example 2-136, ethyl 2-{4-[(2R,4R)-4-fluoro-2-(hydroxymethyl)pyrrolidin-1-yl]piperidin-1-yl}-6-azaspiro[3.4]octane-6-carboxylate

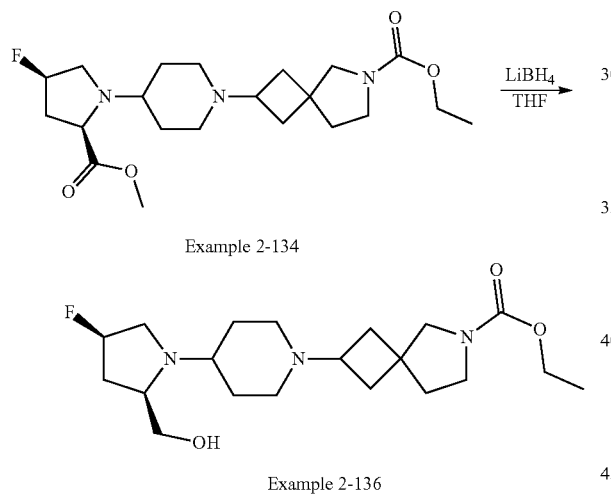

Example 2-134

Example 2-136

A mixture of diastereomers of ethyl 2-{4-[(2R,4R)-4-fluoro-2-(methoxycarbonyl) pyrrolidin-1-yl]piperidin-1-yl}-6-azaspiro[3.4]octane-6-carboxylate (0.140 g, 0.341 mmol) was dissolved in anhydrous THF (10 mL) and cooled to 0° C. under nitrogen. 2.0M Lithium borohydride solution in THF (1.02 mL, 1.023 mmol) was added dropwise to the reaction mixture and then the reaction mixture was allowed to warm to rt overnight. The reaction mixture was quenched with sat. NaHCO$_3$ (aq) (15 mL) and then extracted with EtOAc (2×15 mL), the organic layers were combined and dried (MgSO$_4$). The solvents were removed in vacuo, and the residue was purified by column chromatography (normal phase, [Biotage SNAP cartridge KP-sil 10 g 40-63 μm, 60 Å, 12 mL per min, gradient 0% to 10% MeOH/DCM]). The residue was further purified by preparative reversed phase HPLC (Phenomenex Gemini-NX 5 μm C18 110A Axia column, 100×30 mm, eluting with 20 to 50% MeCN/Solvent B over 14.4 min at 30 mL/min [where solvent B is 0.2% of (28% NH$_3$/H$_2$O) in H$_2$O] and collecting fractions by monitoring at 210 nm) to give ethyl 2-{4-[(2R,4R)-4-fluoro-2-(hydroxymethyl)pyrrolidin-1-yl]piperidin-1-yl}-6-azaspiro[3.4]octane-6-carboxylate, Example 2-136 Isomer 1, (2.99 mg, 0.23%) as a white solid and ethyl 2-{4-[(2R,4R)-4-fluoro-2-(hydroxymethyl)pyrrolidin-1-yl]piperidin-1-yl}-6-azaspiro[3.4]octane-6-carboxylate, Example 2-136 Isomer 2, (3.10 mg, 0.24%) as a white solid. The data for Isomer 2 are in Table 3.

Route as

Typical Procedure for the Preparation of Piperidines Via Sodium Triacetoxyborohydride Reductive Amination in DMF as Exemplified by the Preparation of Example 3-4, ethyl 2-[4-(3-hydroxypyridin-2-yl)piperidin-1-yl]-6-azaspiro[3.4]octane-6-carboxylate

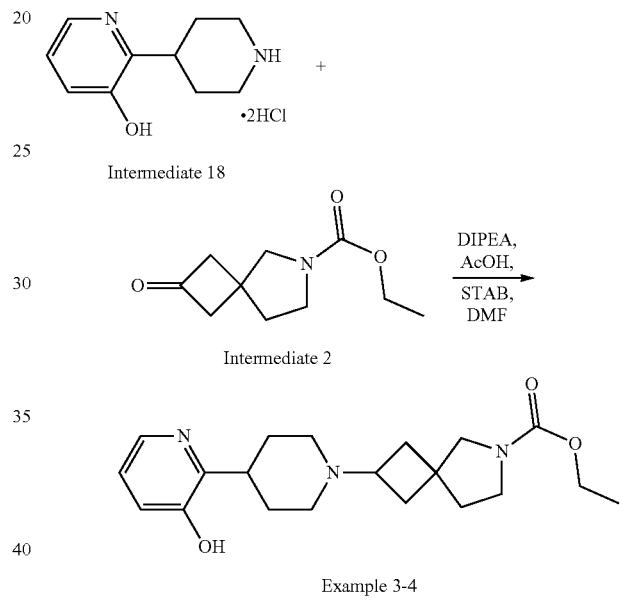

Intermediate 18

Intermediate 2

Example 3-4

2-(Piperidin-4-yl)pyridin-3-ol dihydrochloride (0.20 g, 0.8 mmol) and ethyl 2-oxo-6-azaspiro[3.4]octane-6-carboxylate (0.157 g, 0.8 mmol) were mixed in DMF (8 mL) at rt. DIPEA (0.28 mL, 1.6 mmol) and AcOH (0.07 mL, 1.2 mmol) were added, followed by STAB (0.34 g, 1.6 mmol). The reaction mixture was stirred under nitrogen at rt overnight, then quenched with the addition of a small quantity of MeOH, and concentrated in vacuo to remove all the solvents. The residue was dissolved in a mixture of MeOH and DCM and concentrated onto flash silica (~10 mL) in vacuo. The resulting powder was purified by column chromatography (normal phase, [Biotage SNAP cartridge KP-sil 25 g, 40-63 μm, 60 Å, 30 mL per min, gradient 0% to 15% Solvent A in DCM over 15 column volumes, where solvent A is 10% of (7 M NH$_3$/MeOH) in MeOH]) to give a crude mixture of diastereomers (0.258 g). This mixture was dissolved in MeOH, a small quantity of 28% NH$_3$/H$_2$O was added (~0.1 mL), and the solution was purified by preparative reversed phase HPLC using a Phenomenex Gemini-NX 5 vim C18 110A Axia column, 100×30 mm, eluted with 15 to 25% MeCN/Solvent B over 14.4 min at 30 mL/min [where solvent B is 0.2% of (28% NH$_3$/H$_2$O) in H$_2$O] and collecting fractions by monitoring at 230 nm to give ethyl 2-[4-(3-hydroxypyridin-2-yl)piperidin-1-yl]-6-azaspiro[3.4]octane- 6-carboxylate, Example 3-4 Isomer 1, (0.034 g, 12%) and ethyl 2-[4-(3-hydroxypyridin-2-yl)piperidin-1-yl]-6-azaspiro[3.4]octane-6-carboxylate, Example 3-4 Isomer 2, (0.052 g, 18%). The data for Isomer 2 are in Table 3.

Route at

Typical Procedure for the Preparation of Piperidines Via Sodium Triacetoxyborohydride Reductive Amination as Exemplified by the Preparation of Example 3-10, ethyl 2-[4-cyano-(pyridine-2-yl)piperidin-1-yl]-6-azaspiro[3.4]octane-6-carboxylate

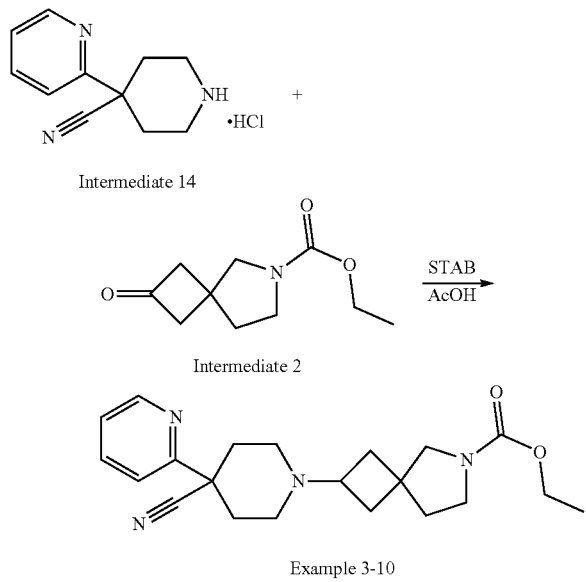

Intermediate 14

Intermediate 2

Example 3-10

4-(Pyridin-2-yl)piperidine-4-carbonitrile hydrochloride (0.187 g, 1.0 mmol) and ethyl 2-oxo-6-azaspiro[3.4]octane-6-carboxylate (0.197 g, 1.0 mmol) were dissolved in DCM (10 mL) under $N_2$ at rt and $NEt_3$ (0.15 mL, 1.1 mmol) was added. The reaction mixture was stirred at rt for 1 h, acetic acid (0.13 mL, 2.2 mmol) was added and the reaction mixture stirred at rt for 3 h. STAB (0.636 g, 3.0 mmol) was added and the reaction mixture stirred overnight. The reaction mixture was quenched with the addition of $NaHCO_3$ (sat aq.) (30 mL), extracted with DCM (4×25 mL) and the combined DCM layers passed through a Biotage phase separator. The solvents were removed in vacuo, and the residue was purified by column chromatography (normal phase, [Biotage SNAP cartridge KP-sil 25 g, 40-63 μm, 60 Å, 40 mL per min, gradient 0% to 10% MeOH in DCM) to give an inseparable mixture of diastereomers of ethyl 2-[4-cyano-(pyridine-2-yl)piperidin-1-yl]-6-azaspiro[3.4]octane-6-carboxylate. Preparative HPLC was used to separate the diastereomers, using a Phenomenex Gemini-N C18 column, 150×21 mm, eluting with 25 to 65% MeOH/$H_2O$ at 18 mL/min and collecting fractions by monitoring at 210 nm to give ethyl 2-[4-cyano-(pyridine-2-yl)piperidin-1-yl]-6-azaspiro[3.4]octane-6-carboxylate, Example 3-10 Isomer 1, (0.012 g, 3%) as a colourless solid and ethyl 2-[4-cyano-(pyridine-2-yl)piperidin-1-yl]-6-azaspiro[3.4]octane-6-carboxylate, Example 3-10 Isomer 2, (0.014 g, 4%) as a colourless solid. The data for both Isomers are in Table 3.

Route au

Typical Procedure for the Preparation of Piperidines Via Alkylation as Exemplified by the Preparation of Example 4-5, ethyl 2-(1-ethyl-2-oxo-3,4'-bipiperidin-1'-yl)-6-azaspiro[3.4]octane-6-carboxylate

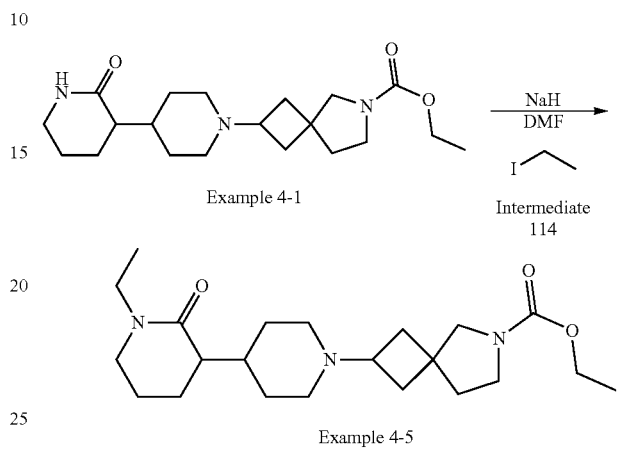

Example 4-1

Intermediate 114

Example 4-5

Ethyl 2-(2-oxo-[3,4'-bipiperidin]-1'-yl)-6-azaspiro[3.4]octane-6-carboxylate, Example 4-1, (0.2 g, 0.55 mmol), was dissolved in DMF (3 mL) and cooled to 0-5° C. Sodium hydride (0.080 g, 1.6 mmol) and iodoethane (0.139 g, 0.8 mmol), were added and the reaction mixture stirred at room temperature for 3 h. The reaction was quenched with water (50 mL), extracted with EtOAc (3×30 mL), and the combined organic layers were dried ($Na_2SO_4$), filtered and concentrated in vacuo to give crude ethyl 2-(1-ethyl-2-oxo-3,4'-bipiperidin-1'-yl)-6-azaspiro[3.4]octane-6-carboxylate as a mixture of diastereomers. The crude product was purified by prep. HPLC [X-Bridge C18 (150×19 mm, 5 um, 17 mL per min, gradient 27% to 100% (over 30 min), then 100% (4 min), 0.1% $NH_3$ in acetonitrile to give ethyl 2-(1-ethyl-2-oxo-[3,4'-bipiperidin]-1'-yl)-6-azaspiro[3.4]octane-6-carboxylate Example 4-5 Isomer-1 (0.011 g, 5.11%) as a colorless gum and ethyl 2-(1-ethyl-2-oxo-[3,4'-bipiperidin]-1'-yl)-6-azaspiro[3.4]octane-6-carboxylate Example 4-5 Isomer-2 (0.012 g, 5.80%) as a colorless gum. The data for Isomer 2 are in Table 3.

Route av

Typical Procedure for the Preparation of Piperidines Via Sodium Triacetoxyborohydride Reductive Amination as Exemplified by the Preparation of Example 4-8, ethyl 2-[4-(2-oxotetrahydropyrimdin-1(2H)-yl)piperidin-1-yl]-6-azaspiro[3.4]octane-6-carboxylate

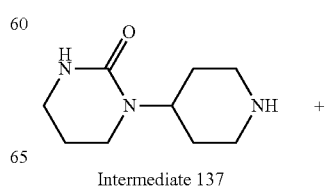

Intermediate 137

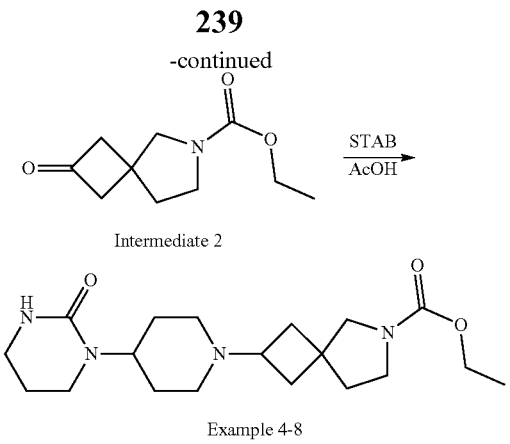

Intermediate 2

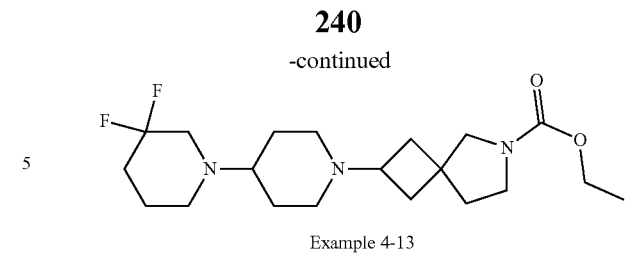

Example 4-13 tert-Butyl 3,3-difluoro-1,4'-bipiperidine-1'-carboxylate (0.347 g, 1.14 mmol) was dissolved in 4.0M HCl in dioxane (5 mL) and the reaction mixture was stirred at rt overnight. The solvents were removed in vacuo and the residue was used in the next step without further purification. The crude reaction mixture and ethyl 2-oxo-6-azaspiro[3.4]octane-6-carboxylate (0.212 g, 1.14 mmol) were dissolved in DMF (6 mL) at rt and DIPEA (0.295 g, 2.28 mmol) was added. The reaction mixture was stirred at 50° C. under nitrogen for 2 h. The reaction mixture was cooled to rt, glacial acetic acid (0.068 g, 1.14 mmol) and STAB (0.604 g, 2.85 mmol) were added and the reaction mixture was stirred overnight at 50° C. under nitrogen. Water (2 mL) was added to the cooled reaction mixture and the solvents were removed in vacuo. The residue was partitioned between DCM (15 mL) and sat. NaHCO₃ (aq) (15 mL), the aqueous layer was washed with DCM (2×15 mL). The organic layers were combined and dried by passing through a Biotage Phase Separator Cartridge. The solvents were removed in vacuo, and the residue was purified by column chromatography (normal phase, [Biotage SNAP cartridge KP-sil 10 g 40-63 μm, 60 Å, 12 mL per min, gradient 1% to 10% MeOH/DCM]). The residue was further purified by preparative reversed phase HPLC (Phenomenex Gemini-NX 5 μm C18 110A Axia column, 100×30 mm, eluting with 30 to 60% MeCN/Solvent B over 14.4 min at 30 mL/min [where solvent B is 0.2% of (28% $NH_3/H_2O$) in $H_2O$] and collecting fractions by monitoring at 210 nm) to give ethyl 2-(3,3-difluoro-1,4'-bipiperidin-1-yl)-6-azaspiro[3.4]octane-6-carboxylate, Example 4-13 Isomer 1, (0.011 g, 2.6%) as a colourless oil and ethyl 2-(3,3-difluoro-1,4'-bipiperidin-1-yl)-6-azaspiro[3.4]octane-6-carboxylate, Example 4-13 Isomer 2, (0.005 g, 1.3%) as a colourless oil. The data for Isomer 2 are in Table 3.

Example 4-8

1-(Piperidin-4-yl)tetrahydropyrimidin-2(1H)-one (0.183 g, 1.0 mmol) and ethyl 2-oxo-6-azaspiro[3.4]octane-6-carboxylate (0.197 g, 1.0 mmol) were dissolved in DCM (10 mL) under N₂ at rt, acetic acid (0.13 mL, 2.2 mmol) was added and the reaction mixture stirred at rt for 3 h. STAB (0.530 g, 2.5 mmol) was added and the reaction mixture stirred overnight. The reaction mixture was quenched with the addition of NaHCO₃ (sat aq.) (30 mL), extracted with DCM (4×25 mL) and the combined DCM layers passed through a Biotage phase separator. The solvents were removed in vacuo, and the residue was purified by column chromatography (normal phase, [Biotage SNAP cartridge KP-sil 25 g, 40-63 μm, 60 Å, 40 mL per min, gradient 0% to 10% MeOH in DCM) to give an inseparable mixture of diastereomers of ethyl 2-[4-(2-oxotetrahydropyrimidin-1(2H)-yl)piperidin-1-yl]-6-azaspiro[3.4]octane-6-carboxylate. Preparative HPLC was used to separate the diastereomers, using a Phenomenex Gemini-N C18 column, 150×21 mm, eluting with 15 to 30% MeCN in 0.2% $NH_3/H_2O$ at 18 ml/min and collecting fractions by monitoring at 210 nm to give ethyl 2-[4-(2-oxotetrahydropyrimidin-1(2H)-yl)piperidin-1-yl]-6-azaspiro[3.4]octane-6-carboxylate, Example 4-8 Isomer 1, (0.028 g, 7.7%) as a colourless solid and ethyl 2-[4-(2-oxotetrahydropyrimidin-1(2H)-yl)piperidin-1-yl]-6-azaspiro[3.4]octane-6-carboxylate Example 4-8 Isomer 2, (0.025 g, 6.9%) as a colourless solid.

The data for both isomers are in Table 3.

Route aw

Typical Procedure for the Preparation of Piperidines Via Deprotection and Sodium Triacetoxyborohydride Reductive Amination, as Exemplified by the Preparation of Example 4-13, ethyl 2-(3,3-difluoro-1,4'-bipiperidin-1'-yl)-6-azaspiro[3.4]octane-6-carboxylate Route ax Typical Procedure for the Preparation of Piperidines Via Reductive Amination as Exemplified by the Preparation of Example 4-16, ethyl 2-[(2R)-2-(methylcarbamoyl)-1,4'-bipiperidin-1'-yl]-6-azaspiro[3.4]octane-6-carboxylate

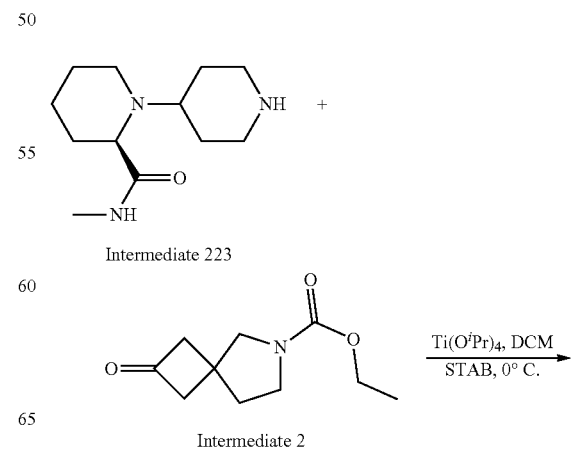

Intermediate 223

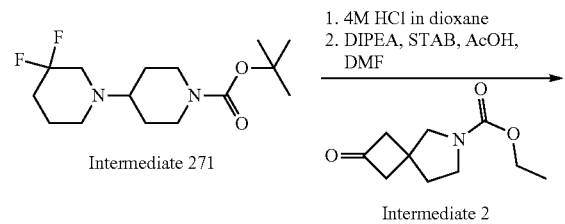

Intermediate 271          Intermediate 2

-continued

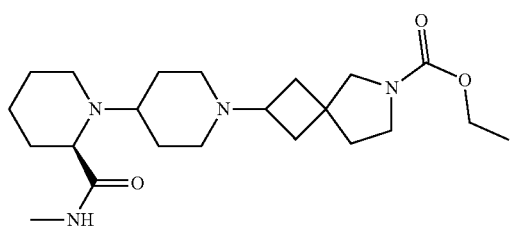

Example 4-16

To a solution of (R)-N-methyl-[1,4'-bipiperidine]-2-carboxamide (200 mg, 0.890 mmol) and ethyl 3-oxo-8-azabicyclo[3.2.1]octane-8-carboxylate (175 mg, 0.890 mmol) in DCM (7.5 mL), Ti(OiPr)$_4$ (0.80 mL, 2.67 mmol) was added at 0° C. and the reaction mixture was stirred for 1 h. Na(OAc)$_3$BH (562 mg, 2.67 mmol) was added portion wise to the reaction mixture and stirred at 0° C. for 2 h. After completion, the reaction mixture was quenched with aq sat NaHCO$_3$ and extracted with DCM (3×30 mL). The organic layers were combined and washed with brine, dried (Na$_2$SO$_4$) and concentrated in vacua. The residue was purified by prep-HPLC (reverse phase, X BRIDGE, C-18, 19×250 mm, 5μ, gradient 10% to 90% ACN in water containing 5 mM NH$_4$OAc, to give 25 mg (7%) of ethyl 2-[(2R)-2-(methylcarbamoyl)-1,4'-bipiperidin-1-yl]-6-azaspiro[3.4]octane-6-carboxylate Example 4-16 Isomer-1 and 25 mg (7%) of ethyl 2-[(2R)-2-(methylcarbamoyl)-1,4'-bipiperidin-1'-yl]-6-azaspiro[3.4]octane-6-carboxylate Example 4-16 Isomer-2 as colorless semisolids. The data for Isomer 2 are in Table 3.

Route ay

Typical Procedure for the Preparation of Piperidines Via Alkylation, Cyclisation and Sodium Triacetoxyborohydride Reductive Aminations, as Exemplified by the Preparation of Example 5-1, ethyl 2-[4-(2-oxoazepan-1-yl)piperidin-1-yl]-6-azaspiro[3.4]octane-6-carboxylate

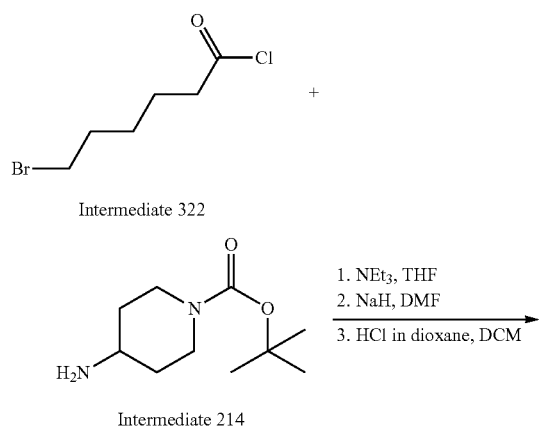

-continued

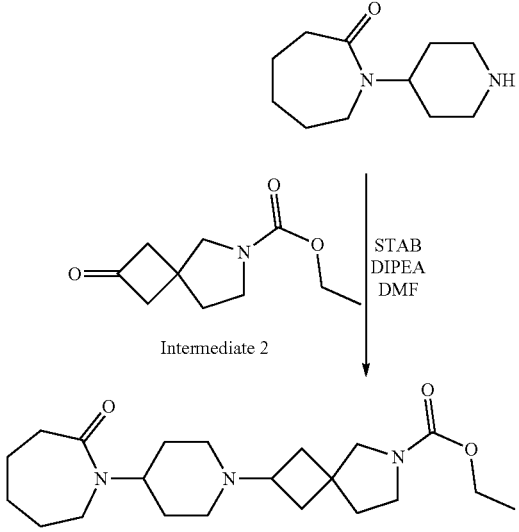

To a solution of 4-Amino-1-Boc-piperidine (200 mg, 1.0 mmol) in THF (2 mL) was added triethylamine (0.153 mL, 1.1 mmol) and 6-Bromohexanoyl chloride (0.168 mL, 1.098 mmol) and cloudy suspension was stirred at rt for 2 h. The solvents were removed in vacuo, and residue was partitioned between H$_2$O (15 mL) and EtOAc (25 mL), aqueous layer was extracted with EtOAc (2×25 mL), organic layers were combined, dried over Na$_2$SO$_4$ and solvent was removed in vacuo to give tert-butyl 4-[(6-bromohexanoyl)amino]piperidine-1-carboxylate (378 mg, >99%) as an orange oil.

tert-butyl 4-[(6-bromohexanoyl)amino]piperidine-1-carboxylate (378 mg, 1.0 mmol) was dissolved in DMF (25 mL) and sodium hydride was added (48 mg, 1.2 mmol). The reaction mixture was stirred at 80° C. for 1 h, the solvent was removed in vacuo and the residue was was purified by column chromatography (normal phase, [Biotage SNAP cartridge KP-sil 10 g, 40-63 μm, 60 Å, 25 mL per min, 1% to 10% MeOH in DCM]) to give tert-butyl 4-(2-oxoazepan-1-yl)piperidine-1-carboxylate (178 mg, 60%). The residue was dissolved in DCM (1 mL), followed by the dropwise addition of HCl in dioxane (3 mL, 4.0 M solu.). The resulting reaction mixture was stirred at rt for 1 h, the solvents were removed in vacuo and the residue was carried on to the next step without further purification. 1-(piperidin-4-yl)azepan-2-one.HCl (0.182 g, 0.738 mmol) and ethyl 2-oxo-6-azaspiro[3.4]octane-6-carboxylate (0.155 g, 0.785 mmol) were dissolved in DMF (2 mL) at rt and DIPEA (0.136 mL, 0.790 mmol) was added. The reaction mixture was stirred at rt for 3 h. STAB (0.332 g, 1.569 mmol) was then added and the reaction mixture was stirred overnight under nitrogen at rt. The solvents were removed in vacuo and the residue was purified by preparative reversed phase HPLC (Phenomenex Gemini-NX 5 μm C18 110A Axia column, 100×30 mm, eluting with 25 to 45% MeCN/Solvent B over 14.4 min at 30 mL/min [where solvent B is 0.2% of (28% NH$_3$/H$_2$O) in H$_2$O] and collecting fractions by monitoring at 210 nm) to give ethyl 2-[4-(2-oxoazepan-1-yl)piperidin-1-yl]-6-azaspiro[3.4]octane-6-carboxylate, Example 5-1 Isomer 1 (6.2 mg, 2%) as a colourless oil and ethyl 2-[4-(2-oxoazepan-1-yl)piperidin-1-yl]-6-azaspiro[3.4]octane-6-carboxylate, Example 5-1 Isomer 2 (3.9 mg, 1%) as a colourless oil. The data for Isomer 2 are in Table 3.

TABLE 2

Characterising data and commercial sources for starting materials and intermediates

| Intermediate | Route | Name | Data |
|---|---|---|---|
| 1 |  | 6-Boc-2-oxo-6-azaspiro[3.4]octane | Commercially available, CAS: 203661-71-6 |
| 2 |  | ethyl 2-oxo-6-azaspiro[3.4]octane-6-carboxylate | $^1$H NMR: (400 MHz, CDCl$_3$) δ: 1.27 (t, J = 7.0 Hz, 3H), 2.08 (t, J = 6.2 Hz, 2H), 2.94-3.17 (m, 4H), 3.49-3.59 (m, 4H), 4.15 (q, J = 7.0 Hz, 2H) |
| 3 |  | methyl 2-oxo-6-azaspiro[3.4]octane-6-carboxylate | $^1$H NMR: (400 MHz, CD$_3$OD) δ:: 2.06-2.15 (m, 2 H), 2.94-3.04 (m, 2 H), 3.05-3.17 (m, 2 H), 3.47 (td, J = 6.8, 2.5 Hz, 2 H), 3.54 (d, J = 2.5 Hz, 2 H), 3.69 (s, 3 H) |
| 4 |  | 2-fluoroethyl 2-oxo-6-azaspiro[3.4]octane-6-carboxylate | LCMS (Method F): m/z 216 (M + H)$^+$ (ES+) at 1.79 min, UV inactive |
| 5 |  | 4-(1H-imidazol-2-yl)piperidine dihydrochloride | Commercially available, CAS: 90747-46-9 |
| 6 |  | 4-(1-methylimidazol-2-yl)piperidine hydrochloride | Commercially available, CAS: 1198420-89-1 |
| 7 |  | 4-(1H-pyrazol-5-yl)piperidine | Commercially available, CAS: 278798-08-6 |
| 8 |  | 5-(piperidin-4-yl)-1H-pyrazol-3-amine | Commercially available, CAS: 1325671-21-3 |
| 9 |  | 4-(1-methyl-1H-pyrazol-5-yl)piperidine | Commercially available, CAS: 640270-01-5 |
| 10 |  | 4-(1-methyl-1H-pyrazol-3-yl)piperidine | Commercially available, CAS: 1211527-48-8 |
| 11 |  | 4-(1H-pyrrol-1-yl)piperidine | Commercially available, CAS: 169751-01-3 |
| 12 |  | 4-(1H-pyrazol-1-yl)piperidine | Commercially available, CAS: 762240-09-5 |
| 13 |  | 4-(4-methyl-1H-pyrazol-1-yl)piperidine | Commercially available, CAS: 1211520-55-6 |
| 14 |  | 4-(Pyridin-2-yl)piperidine-4-carbonitrile hydrochloride | Commercially available, CAS: 767263-33-2 |
| 15 |  | 4-(1-Methylimidazol-2-yl)piperidine hydrochloride | Commercially available, CAS: 1198420-89-1 |
| 16 |  | 4-(1H-1,2,4-Triazol-1-yl)piperidine | Commercially available, CAS: 158655-26-6 |
| 17 |  | 4-(1H-1,2,4-Triazol-3-yl)piperidine hydrochloride | Commercially available, CAS: 1417359-91-1 |
| 18 |  | 4-(1H-1,2,3-Triazol-1-yl)piperidine hydrochloride | Commercially available, CAS: 690261-88-2 |
| 19 |  | 2-(piperidin-4-yl)pyridin-3-ol dihydrochloride | Commercially available, CAS: 1260650-52-9 |
| 20 |  | 4-(5-chloro-1-methyl-1H-imidazol-2-yl)piperidine trifluoroacetate | LCMS (Method C): m/z 200/202 (M + H)$^+$ (ES+), at 1.33 min, UV active |
| 21 |  | 4-(4,5-dichloro-1-methyl-1H-imidazol-2-yl)piperidine trifluoroacetate | LCMS (Method C): m/z 234/236/238 (M + H)$^+$ (ES+), at 1.53 min, UV active |
| 22 |  | 4-(5-chloro-1H-imidazol-2-yl)piperidine dihydrobromide | LCMS (Method C): m/z 186/188 (M + H)$^+$ (ES+), at 0.92 min, UV active |
| 23 |  | 4-(5-ethyl-1H-1,2,4-triazol-3-yl)piperidine hydrochloride | Commercially available, CAS: 1432680-84-6 |
| 24 |  | 4-methyl-4-(3-methyl-1,2,4-oxadiazol-5-yl)piperidine hydrochloride | Commercially available, CAS: 1361112-08-4 |
| 25 |  | 4-(4,5-dichloro-1H-imidazol-2-yl)piperidine dihydrobromide | m/z 220/222/224 (M + H)$^+$ (ES+), at 0.54 min, UV active |
| 26 |  | 2-(piperidin-4-yl)pyrimidin-4-amine dihydrochloride | Commercially available, CAS: 1461714-43-1 |
| 27 |  | ethyl 4-(1H-imidazol-2-yl)piperidine-1-carboxylate | Commercially available, CAS: 1198420-87-9 |
| 28 |  | tert-butyl 4-(4,4,5,5-tetramethyl-1,3,2-dioxaborolan-2-yl)-3,6-dihydropyridine-1(2H)-carboxylate | Commercially available, CAS: 286961-14-6 |
| 29 |  | 2-5-bromo-1,2,4-thiadiazole | Commercially available, CAS: 43201-13-4 |
| 30 | Route 1 and intermediates 28 and 29 | 5-(piperidin-4-yl)-1,2,4-thiadiazole | LCMS (Method G): m/z 170 (M + H)$^+$ (ES+), at 3.761 min, UV active |

TABLE 2-continued

Characterising data and commercial sources for starting materials and intermediates
Table 2

| Intermediate | Route | Name | Data |
|---|---|---|---|
| 31 | | 4-(1H-tetrazol-5-yl) piperidine | Commercially available, CAS: 112626-97-8 |
| 32 | | 4-(1H-pyrazol-1-yl)piperidine | Commercially available, CAS: 762240-09-5 |
| 33 | | 4-[4-(trifluoromethyl)-1H-imidazol-2-yl]piperidine hydrochloride | LCMS (Method F): m/z 220 $(M + H)^+$ $(ES^+)$, at 2.16 min, UV active |
| 34 | | 4-(1,5-dimethyl-1H-imidazol-2-yl)-1,2,3,6-tetrahydropyridine hydrochloride | LCMS (Method G): m/z 178 $(M + H)^+$ $(ES^+)$, at 3.90 min, UV active |
| 35 | | 2-bromo-1,4-dimethyl-1H-imidazole | Commercially available, CAS: 235426-30-9 |
| 36 | Route 2 and intermediate 35 | 4-(1,4-dimethyl-1H-imidazol-2-yl)-1,2,3,6-tetrahydropyridine | LCMS (Method G): m/z 178 $(M + H)^+$ $(ES^+)$, at 3.80 min, UV active |
| 37 | | 4-[1-methyl-4-(trifluoromethyl)-1H-imidazol-2-yl]piperidine hydrochloride salt | LCMS (Method F): m/z 234 $(M + H)^+$ $(ES^+)$, at 1.48 min, UV active |
| 38 | | 4-(1-methyl-1H-pyrazol-5-yl)piperidine | Commercially available, CAS: 640270-01-5 |
| 39 | | 2-bromooxazole | Commercially available, CAS: 125533-82-6 |
| 40 | | 2-bromothiazole | Commercially available, CAS: 3034-53-5 |
| 41 | Route 1 and intermediate 39 | 4-(1,3-oxazol-2-yl)piperidine | LCMS (Method H): m/z 153 $(M + H)^+$ $(ES^+)$, at 7.92 min, UV active |
| 42 | Route 1 and intermediate 40 | 4-(1,3-thiazol-2-yl)piperidine | LCMS (Method H): m/z 169 $(M + H)^+$ $(ES^+)$, at 7.58 min, UV active |
| 43 | | 4-(1,3,4-oxadiazol-2-yl)piperidine | $^1$H NMR: (400 MHz, CDCl$_3$) δ: 1.78-1.90 (m, 2H), 1.99-2.16 (m, 2H), 2.70-2.85 (m, 2H), 3.02-3.16 (m, 1H), 3.16-3.27 (m, 2H), 8.35 (s, 1H), NH not observed |
| 44 | | 4-(3-methyl-1,2,4-oxadiazol-5-yl)piperidine | LCMS (Method H): m/z 168 $(M + H)^+$ $(ES^+)$, at 5.80 min, UV active |
| 45 | | tert-butyl 4-formylpiperidine-1-carboxylate | Commercially available, CAS: 137076-22-3 |
| 46 | | tert-butyl 4-[4-(trifluoromethyl)-1H-imidazol-2-yl]piperidine-1-carboxylate | LCMS (Method F): m/z 320 $(M + H)^+$ $(ES^+)$, at 2.16 min, UV active |
| 47 | | 4-(1H-imidazol-2-yl)piperidin-4-ol hydrochloride salt | LCMS (Method G): m/z 168 $(M + H)^+$ $(ES^+)$, at 2.46 min, UV active |
| 48 | | 4-(1H-imidazol-2-yl)-4-methoxypiperidine hydrochloride salt | LCMS (Method G): m/z 182 $(M + H)^+$ $(ES^+)$, at 2.87 min, UV active |
| 49 | | 4-(1-methyl-1H-imidazol-2-yl)piperidin-4-ol hydrochloride salt | LCMS (Method G): m/z 182 $(M + H)^+$ $(ES^+)$, at 3.09 min, UV active |
| 50 | | 4-methoxy-4-(1-methyl-1H-imidazol-2-yl)piperidine hydrochloride salt | LCMS (Method G): m/z 196 $(M + H)^+$ $(ES^+)$, at 3.35 min, UV active |
| 51 | | (S)-Tert-butyl 2-(piperidin-4-yl)pyrrolidine-1-carboxylate | Commercially available, CAS: 1449131-15-0 |
| 52 | | (R)-Tert-butyl 2-(piperidin-4-yl)pyrrolidine-1-carboxylate | Commercially available, CAS: 1451390-44-5 |
| 53 | | Tert-butyl 2-(piperidin-4-yl)pyrrolidine-1-carboxylate | Commercially available, CAS: 929974-12-9 |
| 54 | | Propionyl Chloride | Commercially available, CAS: 79-03-8 |
| 55 | | Methyl chloroformate | Commercially available, CAS: 79-22-1 |
| 56 | | Ethyl chloroformate | Commercially available, CAS: 541-41-3 |
| 57 | | Methylaminoformyl chloride | Commercially available, CAS: 6452-47-7 |
| 58 | | Dimethylaminoformyl chloride | Commercially available, CAS: 79-44-7 |
| 59 | | Cyclopropanecarbonyl chloride | Commercially available, CAS: 4023-34-1 |
| 60 | | Cyclobutanecarbonyl chloride | Commercially available, CAS: 5006-22-4 |
| 61 | | Acetyl chloride | Commercially available, CAS: 75-36-5 |

TABLE 2-continued

Characterising data and commercial sources for starting materials and intermediates
Table 2

| Intermediate | Route | Name | Data |
|---|---|---|---|
| 62 | | Ethyl 2,2,2-trifluoroacetate | Commercially available, CAS: 383-63-1 |
| 63 | | Acetic Anhydride | Commercially available, CAS: 108-24-7 |
| 64 | | 3-iodo-2-methoxypyridine | Commercially available, CAS: 112197-15-6 |
| 65 | Route 3 and intermediates 28 and 64 | 3-(piperidin-4-yl) pyridin-2-ol | $^1$H NMR: (400 MHz, DMSO-d$_6$) δ: 1.70-2.00 (m, 4H), 2.84-3.15 (m, 3H), 3.32 (d, J = 12.5 Hz, 2H), 7.00 (dd, J = 7.3 and 5.2 Hz, 1H), 7.53 (dd, J = 7.3 and 1.5 Hz, 1H), 8.06 (dd, J = 5.2 and 1.5 Hz, 1H), 8.93-9.39 (m, 2H) |
| 66 | Route 4 and intermediates 28 and 64 | 2-methoxy-3-(piperidin-4-yl)pyridine | LCMS (Method F): m/z 193 (M + H)$^+$ (ES+), at 6.19 min, UV active |
| 67 | | 5-bromo-2-methoxy-4-methylpyridine | Commercially available, CAS: 164513-39-7 |
| 68 | | 5-bromo-2-methoxy-3-methylpyridine | Commercially available, CAS: 760207-87-2 |
| 69 | Route 5 and intermediate 65 | 3,4'-bipiperidin-2-one | LCMS (Method F): m/z 183 (M + H)$^+$ (ES+), at 0.32 min, UV active |
| 70 | | 4-(piperidin-4-yl)pyrimidin-2-amine | Commercially available, CAS: 1211532-88-5 |
| 71 | Route 4 and intermediates 28 and 67 | 2-methoxy-4-methyl-5-(piperidin-4-yl)pyridine | LCMS (Method F): m/z 207 (M + H)$^+$ (ES+), at 1.44 min, UV active |
| 72 | Route 4 and intermediates 28 and 68 | 2-methoxy-3-methyl-5-(piperidin-4-yl)pyridine | LCMS (Method F): m/z 207 (M + H)$^+$ (ES+), at 1.59 min, UV active |
| 73 | | 4-(4-methyl-1H-pyrazol-1-yl)piperidine | Commercially available, CAS: 1211520-55-6 |
| 74 | | 4-Isoxazol-3-yl-piperidine | Commercially available, CAS: 1060814-32-5 |
| 75 | | N-[(benzyloxy)carbonyl]-N-methylglycine | Commercially available, CAS: 39608-31-6 |
| 76 | | Methoxyamine hydrochloride | Commercially available, CAS: 593-56-6 |
| 77 | | Isopropylamine | Commercially available, CAS: 75-31-0 |
| 78 | | 2,2,2-Trifluoroethylamine | Commercially available, CAS: 753-90-2 |
| 79 | | Azetidine | Commercially available, CAS: 503-29-7 |
| 80 | | Morpholine | Commercially available, CAS: 110-91-8 |
| 81 | | Cyclopropylamine | Commercially available, CAS: 765-30-0 |
| 82 | | Cyclobutylamine | Commercially available, CAS: 2516-34-9 |
| 83 | | 2-methoxyethylamine | Commercially available, CAS: 109-85-3 |
| 84 | | Pyrrolidine | Commercially available, CAS: 123-75-1 |
| 85 | | N,O-dimethylhydroxylamine hydrochloride | Commercially available, CAS: 6638-79-5 |
| 86 | | 1-methylcyclobutan-1-amine hydrochloride | Commercially available, CAS: 174886-05-6 |
| 87 | | 3-amino-3-methyloxetane | Commercially available, CAS: 874473-14-0 |
| 88 | | 3,3-difluoropyrrolidine hydrochloride | Commercially available, CAS: 163457-23-6 |
| 89 | | 3,3-difluorocyclobutanamine hydrochloride | Commercially available, CAS: 637031-93-7 |
| 90 | | 3,3-difluoroazetidine hydrochloride | Commercially available, CAS: 288315-03-7 |
| 91 | | tert-Butyl carbazate | Commercially available, CAS: 870-46-2 |
| 92 | | cyclobutanol | Commercially available, CAS: 2919-23-5 |
| 93 | | 2-fluoroethylamine hydrochloride | Commercially available, CAS: 460-08-2 |
| 94 | | 2,2-difluoroethylamine | Commercially available, CAS: 430-67-1 |

TABLE 2-continued

Characterising data and commercial sources for starting materials and intermediates
Table 2

| Intermediate | Route | Name | Data |
|---|---|---|---|
| 95 | | methoxyacetyl chloride | Commercially available, CAS: 38870-89-2 |
| 96 | | 2-fluoroethyl chloroformate | Commercially available, CAS: 462-27-1 |
| 97 | | 2,2,2-trifluoroethyl chloroformate | Commercially available, CAS: 27746-99-2 |
| 98 | | methyl chlorothiolformate | Commercially available, CAS: 18369-83-0 |
| 99 | | 2-methoxyethanol | Commercially available, CAS: 109-86-4 |
| 100 | | 2-dimethylaminoethanol | Commercially available, CAS: 108-01-0 |
| 101 | | acetoxy acetyl chloride | Commercially available, CAS: 13831-31-7 |
| 102 | | 3,3,3-trifluoropropionic acid | Commercially available, CAS: 2516-99-6 |
| 103 | | 2-(aminomethyl)pyridine | Commercially available, CAS: 3731-51-9 |
| 104 | | 2,2,2-Trifluoro-N-methylethanamine hydrochloride | Commercially available, CAS: 2730-52-1 |
| 105 | | oxetan-3-ylamine | Commercially available, CAS: 21635-88-1 |
| 106 | | N-methyl-3-aminooxetane | Commercially available, CAS: 952182-03-5 |
| 107 | | Lawesson Reagent | Commercially available, CAS: 19172-47-5 |
| 108 | | (2S,4R)-1-Boc-4-hydroxy pyrrolidine-2-carboxylic acid methyl ester | Commercially available, CAS: 102195-79-9 |
| 109 | | triethyl phosphono acetate | Commercially available, CAS: 867-13-0 |
| 110 | | ethyl cyanoacetate | Commercially available, CAS: 105-56-6 |
| 111 | Intermediates 108, 109 and 110 | benzyl 4-[(2S,4R)-1-(tert-butoxycarbonyl)-4-hydroxypyrrolidin-2-yl]piperidine-1-carboxylate | LCMS (Method D): m/z 405 (M + H)$^+$ (ES+), at 1.98 min, UV active |
| 112 | Intermediate 111 | tert-butyl (2S,4S)-4-fluoro-2-(piperidin-4-yl)pyrrolidine-1-carboxylate | LCMS (Method D): m/z 273 (M + H)$^+$ (ES+), at 1.80 min, UV active |
| 113 | Intermediate 111 | tert-butyl (2S)-4,4-difluoro-2-(piperidin-4-yl)pyrrolidine-1-carboxylate | LCMS (Method D): m/z 291 (M + H)$^+$ (ES+), at 1.88 min, UV active |
| 114 | | iodoethane | Commercially available, CAS: 75-03-6 |
| 115 | | D-proline methyl ester hydrochloride | Commercially available, CAS: 65365-28-8 |
| 116 | | 2-pyridine propionic acid | Commercially available, CAS: 15197-75-8 |
| 117 | | 2-[(methylamino)methyl]pyridine | Commercially available, CAS: 21035-59-6 |
| 118 | | 2-pyridinemethanol | Commercially available, CAS: 586-98-1 |
| 119 | | piperidine, 4-(3-methyl-1H-pyrazol-1-yl)- | Commercially available, CAS: 1138819-53-0 |
| 120 | | piperidine, 4-(1-ethyl-1H-pyrazol-5-yl)- | Commercially available, CAS: 442876-34-8 |
| 121 | | (R)-1-tert-Butyl 2-methyl 4-oxopyrrolidine-1,2-dicarboxylate | Commercially available, CAS: 256487-77-1 |
| 122 | Route 6 and intermediates 2 and 53 | Ethyl 2-[4-(pyrrolidin-2-yl)piperidin-1-yl]-6-azaspiro[3.4]octane-6-carboxylate•HCl | LCMS (Method D): m/z 350 (M + H)$^+$ (ES$^+$), at 2.64 min, UV inactive |
| 123 | | O-Methylhydroxylamine hydrochloride | Commercially available, CAS: 593-56-6 |
| 124 | | N,O-Dimethylhydroxylamine hydrochloride | Commercially available, CAS: 6638-79-5 |
| 125 | Intermediate 257 | tert-butyl (2S)-4,4-difluoro-2-methylpyrrolidine-1-carboxylate | LCMS (Method C): m/z 222 (M + H)$^+$ (ES+), at 1.97 min, UV inactive |
| 126 | Intermediate 121 | tert-butyl (2R)-4,4-difluoro-2-(hydroxymethyl)pyrrolidine-1-carboxylate | LCMS (Method C): m/z 238 (M + H)$^+$ (ES+), at 1.63 min, UV inactive |

TABLE 2-continued

Characterising data and commercial sources for starting materials and intermediates
Table 2

| Intermediate | Route | Name | Data |
|---|---|---|---|
| 127 | Route 6 and intermediates 2 and 51 | Ethyl 2-{4-[(2S)-pyrrolidin-2-yl]piperidin-1-yl}-6-azaspiro[3.4]octane-6-carboxylate•HCl | LCMS (Method G): m/z 336 (M + H)$^+$ (ES$^+$), at 6.23 min, UV inactive |
| 128 | | 3-bromo-2-methoxy-5-methylpyridine | Commercially available, CAS: 717843-56-6 |
| 129 | Route 4 and intermediate 28 and 127 | 2-methoxy-5-methyl-3-(piperidin-4-yl)pyridine hydrochloride | LCMS (Method C): m/z 207 (M + H)$^+$ (ES+), at 1.62 min, UV active |
| 130 | | Iodomethane | Commercially available, CAS: 79099-07-3 |
| 131 | | 3-aminopropan-1-ol | Commercially available, CAS: 156-87-6 |
| 132 | Intermediates 131 and 160 | 3-(piperidin-4-yl)-1,3-oxazinan-2-one hydrochloride | LCMS (Method D): m/z 185 (M + H)$^+$ (ES+), at 0.29 min, UV inactive |
| 133 | | 3-bromo-2-methoxy-4-methylpyridine | Commercially available, CAS: 717843-51-1 |
| 134 | Intermediates 28 and 133 | 2-methoxy-4-methyl-3-(piperidin-4-yl)pyridine hydrochloride | LCMS (Method F): m/z 207 (M + H)$^+$ (ES+), at 1.56 min, UV active |
| 135 | | benzyl 4-oxopiperidine-1-carboxylate | Commercially available, CAS: 185847-84-1 |
| 136 | | tert-butyl (3-aminopropyl)carbamate | Commercially available, CAS: 75178-96-0 |
| 137 | Route 7 and intermediates 135 and 136 | 1-(piperidin-4-yl)tetrahydropyrimidin-2(1H)-one | LCMS (Method B): m/z 184 (M + H)$^+$ (ES+), at 4.28 min, UV inactive |
| 138 | | (S)-N-methylpyrrolidine-2-carboxamide hydrochloride | Commercially available, CAS: 33208-98-9 |
| 139 | Route 8 and intermediates 138 and 160 | (S)-N-methyl-1-(piperidin-4-yl)pyrrolidine-2-carboxamide dihydrochloride | LCMS (Method G): m/z 212 (M + H)$^+$ (ES+), at 6.65 min, UV inactive |
| 140 | | 2-bromo-6-methoxypyridine | Commercially available, CAS: 40473-07-2 |
| 141 | Route 4 and intermediates 28 and 140 | 2-methoxy-6-(piperidin-4-yl)pyridine hydrochloride | LCMS (Method G): m/z 193 (M + H)$^+$ (ES+), at 0.65 min, UV active |
| 142 | | 3-bromo-2-methoxy-5-methylpyridine | Commercially available, CAS: 717843-56-6 |
| 143 | Route 3 and intermediates 28 and 142 | 5-methyl-3-(piperidin-4-yl)pyridin-2(1H)-one hydrochloride | LCMS (Method F): m/z 193 (M + H)$^+$ (ES+), at 0.276 min, UV active |
| 144 | Route 5 and intermediate 143 | 5-methyl-[3,4'-bipiperidin]-2-one | LCMS (Method J): m/z 197 (M + H)$^+$ (ES+), at 4.05 min, UV inactive |
| 145 | | 3-bromo-2-methoxy-4-methylpyridine | Commercially available, CAS: 717843-51-1 |
| 146 | Route 3 and intermediates 28 and 145 | 4-methyl-3-(piperidin-4-yl)pyridin-2(1H)-one hydrochloride | LCMS (Method I): m/z 193 (M + H)$^+$ (ES+), at 2.82 min, UV active |
| 147 | Route 5 and intermediate 146 | 4-methyl-[3,4'-bipiperidin]-2-one | LCMS (Method I): m/z 197 (M + H)$^+$ (ES+), at 3.14 min, UV inactive |
| 148 | | tert-butyl (3-amino-2,2-dimethylpropyl)carbamate | Commercially available, CAS: 292606-35-0 |
| 149 | Route 7 and intermediates 135 and 148 | 5,5-dimethyl-1-(piperidin-4-yl)tetrahydropyrimidin-2(1H)-one | LCMS (Method D): m/z 212 (M + H)$^+$ (ES+), at 0.70 min, UV inactive |
| 150 | | 1,4-dioxa-8-azaspiro[4.5]decane | Commercially available, CAS: 74-88-4 |
| 151 | Intermediates 2 and 150 | ethyl 2-(4-oxopiperidin-1-yl)-6-azaspiro[3.4]octane-6-carboxylate | LCMS (Method D): m/z 281 (M + H)$^+$ (ES+), at 0.992 min and 1.04 min, UV inactive |
| 152 | | tert-butyl (2-aminoethyl)carbamate | Commercially available, CAS: 57260-73-8 |
| 153 | | 4-bromo-2-methoxypyridine | Commercially available, CAS: 100367-39-3 |
| 154 | Route 3 and intermediates 28 and 153 | 4-(piperidin-4-yl) pyridin-2(1H)-one hydrochloride | LCMS (Method I): m/z 179 (M + H)$^+$ (ES+), at 2.57 min, UV active |
| 155 | | benzyl 4-(4,4,5,5-tetramethyl-1,3,2-dioxaborolan-2-yl)-3,6-dihydropyridine-1(2H)-carboxylate | Commercially available, CAS: 286961-15-7 |

TABLE 2-continued

Characterising data and commercial sources for starting materials and intermediates
Table 2

| Intermediate | Route | Name | Data |
|---|---|---|---|
| 156 | | isopropyl iodide | Commercially available, CAS: 75-30-9 |
| 157 | Route 6 and intermediates 3 and 51 | methyl 2-{4-[(2S)-pyrrolidin-2-yl]piperidin-1-yl}-6-azaspiro[3.4]octane-6-carboxylate•HCl | LCMS (Method J): m/z 322 (M + H)$^+$ (ES$^+$), at 4.37 min, UV inactive |
| 158 | | Diethylamine | Commercially available, CAS: 109-89-7 |
| 159 | Route 13 and intermediates 115 and 160 | tert-butyl 4-[(2R)-2-(methoxycarbonyl)pyrrolidin-1-yl]piperidine-1-carboxylate | LCMS (Method D): m/z 313 (M + H − $^t$Bu)$^+$ (ES$^+$), at 1.85 min, UV inactive |
| 160 | | tert-butyl 4-oxopiperidine-1-carboxylate | Commercially available, CAS: 79099-07-3 |
| 161 | | Ethyl 4-piperidinecarboxylate | Commercially available, CAS: 1126-09-6 |
| 162 | Route 6 and intermediates 2 and 52 | ethyl 2-{4-[(2R)-pyrrolidin-2-yl]piperidin-1-yl}-6-azaspiro[3.4]octane-6-carboxylate | LCMS (Method E): m/z 336 (M + H)$^+$ (ES+), at 5.16 min, UV inactive |
| 163 | | 4-bromo-1,3-thiazole | Commercially available, CAS: 34259-99-9 |
| 164 | Intermediates 155 and 163 | 4-(1,3-thiazol-4-yl)piperidine hydrobromide | $^1$H NMR: (400 MHz, D$_2$O) δ: 1.82-2.10 (m, 2H), 2.15-2.44 (m 2H), 3.05-3.72 (m, 5H), 7.72 (s, 1H), 9.62 (s, 1H), Two exchangeable protons not observed |
| 165 | | 2-bromoethyl methyl ether | Commercially available, CAS: 6482-24-2 |
| 166 | | bromoacetonitrile | Commercially available, CAS: 590-17-0 |
| 167 | | methyl bromoacetate | Commercially available, CAS: 96-32-2 |
| 168 | | Methylamine solution (2.0M in THF) | Commercially available CAS:74-89-5 |
| 169 | | 2-chloropyrimidine | Commercially available, CAS: 1722-12-9 |
| 170 | | (1S,3S,5S)-Cyclohexane-1,3,5-triol | Commercially available, CAS: 50409-12-6 |
| 171 | | phenylboronic acid | Commercially available, CAS 98-80-6 |
| 172 | Intermediates 170 and 171 | (1R,5S)-3-phenyl-2,4-dioxa-3-borabicyclo[3.3.1]nonan-7-one | $^1$H NMR: (400 MHz, CDCl$_3$) δ: 2.29 (d, J = 13.7 Hz, 1 H), 2.47 (d, J = 12.8 Hz, 1 H), 2.63 (d, J = 16.2 Hz, 2 H), 2.95 (d, J = 15.9 Hz, 2 H), 4.85 (br.s., 2 H), 7.30-7.48 (m, 3 H), 7.73 (d, J = 7.0 Hz, 2 H) |
| 173 | | 4-(1-propyl-1H-pyrazol-5-yl)piperidine | Commercially available, CAS: 1342846-65-4 |
| 174 | Intermediates 126 and 160 | 4-[(2R)-4,4-difluoro-2-(methoxymethyl)pyrrolidin-1-yl]piperidine trifluoroacetate | LCMS (Method C): m/z 235 (M + H)$^+$ (ES+), at 1.02 min, UV inactive |
| 175 | | 4-chloropyridine | Commercially available, CAS: 626-61-9 |
| 176 | | 2-bromopyridine | Commercially available, CAS: 109-04-6 |
| 177 | | 4-(1,4-dimethyl-1H-pyrazol-3-yl)piperidine | Commercially available, CAS: 1511937-89-5 |
| 178 | | 4-(1,4-dimethyl-1H-pyrazol-5-yl)piperidine | Commercially available, CAS: 1540203-24-4 |
| 179 | intermediates 126 and 160 | 1-[(2R)-4,4-difluoro-1-(piperidin-4-yl)pyrrolidin-2-yl]ethanol trifluoroacetate | LCMS (Method C): m/z 235 (M + H)$^+$ (ES+), at 0.79 min, UV inactive |
| 180 | | 5-(pyrrolidin-2-yl)-1H-pyrazole dihydrochloride | Commercially available, CAS: 1361114-72-8 |
| 181 | Route 9 and intermediates 180 and 160 | 4-[2-(1H-pyrazol-5-yl)pyrrolidin-1-yl]piperidine trifluoroacetate | LCMS (Method C): m/z 221 (M + H)$^+$ (ES+), at 0.87 min, UV active |
| 182 | | 5-methylpyrrolidin-2-one | Commercially available, CAS: 108-27-0 |
| 183 | | 4-iodopyridine | Commercially available, CAS: 15854-87-2 |

TABLE 2-continued

Characterising data and commercial sources for starting materials and intermediates
Table 2

| Intermediate | Route | Name | Data |
|---|---|---|---|
| 184 | Route 10 and intermediates 182 and 183 | 5-methyl-1-(piperidin-4-yl)pyrrolidin-2-one acetate | LCMS (Method C): m/z 183 (M + H)+ (ES+), at 0.53 min, UV active |
| 185 | | 5,5-dimethylpyrrolidin-2-one | Commercially available, CAS: 5165-28-6 |
| 186 | Route 10 and intermediate 185 | 5,5-dimethyl-1-(piperidin-4-yl)pyrrolidin-2-one acetate | LCMS (Method C): m/z 197 (M + H)+ (ES+), at 0.78 min, UV active |
| 187 | | (4S)-4-(propan-2-yl)-1,3-oxazolidin-2-one | Commercially available, CAS: 17016-83-0 |
| 188 | Route 10 and intermediate 187 | (4S)-3-(piperidin-4-yl)-4-(propan-2-yl)-1,3-oxazolidin-2-one acetate | LCMS (Method C): m/z 213 (M + H)+ (ES+), at 0.74 min, UV active |
| 189 | | methyl azepane-2-carboxylate | Commercially available, CAS: 5228-33-1 |
| 190 | Route 9 and intermediate 189 | methyl 1-(piperidin-4-yl)azepane-2-carboxylate trifluoroacetate | LCMS (Method C): m/z 241 (M + H)+ (ES+), at 1.20, UV inactive |
| 191 | | pyrrolidine-2,5-dione | Commercially available, CAS: 123-56-8 |
| 192 | | tert-butyl 4-hydroxypiperidine-1-carboxylate | Commercially available, CAS: 109384-19-2 |
| 193 | | 1-(piperidin-4-yl)pyrrolidine-2,5-dione trifluoroacetate | LCMS (Method C): m/z 183 (M + H)+ (ES+), at 0.29 min, UV inactive |
| 194 | | tert-butyl 4-cyanopiperidine-1-carboxylate | Commercially available, CAS: 91419-52-2 |
| 195 | Route 15 and intermediates 130 and 194 | 4-(1-methyl-1H-tetrazol-5-yl)piperidine hydrochloride | LCMS (Method K): m/z 168 (M + H)+ (ES+), at 2.41 min, UV inactive |
| 196 | | (4R)-4-(propan-2-yl)-1,3-oxazolidin-2-one | Commercially available, CAS: 95530-58-8 |
| 197 | Route 10 and intermediate 196 | (4R)-3-(piperidin-4-yl)-4-(propan-2-yl)-1,3-oxazolidin-2-one acetate | LCMS (Method C): m/z 213 (M + H)+ (ES+), at 0.78 min, UV active |
| 198 | | (5S)-5-(hydroxymethyl)pyrrolidin-2-one | Commercially available, CAS: 17342-08-4 |
| 199 | Route 11 and intermediate 198 | (5R)-5-methyl-1-(piperidin-4-yl)pyrrolidin-2-one acetate | LCMS (Method C): m/z 183 (M + H)+ (ES+), at 0.53 min, UV active |
| 200 | Route 11 and intermediate 198 | (5R)-5-ethyl-1-(piperidin-4-yl)pyrrolidin-2-one acetate | LCMS (Method C): m/z 197 (M + H)+ (ES+), at 0.69 min, UV active |
| 201 | | (5R)-5-(hydroxymethyl)pyrrolidin-2-one | Commercially available, CAS: 66673-40-3 |
| 202 | Route 11 and intermediate 201 | (5S)-5-methyl-1-(piperidin-4-yl)pyrrolidin-2-one acetate | LCMS (Method C): m/z 183 (M + H)+ (ES+), at 0.54 min, weakly UV active |
| 203 | Route 11 and intermediate 201 | (5S)-5-ethyl-1-(piperidin-4-yl)pyrrolidin-2-one acetate | LCMS (Method C): m/z 197 (M + H)+ (ES+), at 0.69 min, UV active |
| 204 | | (2R)-2-aminopropan-1-ol | Commercially available, CAS: 35320-23-1 |
| 205 | Route 12 and intermediate 204 | (4R)-4-methyl-3-(piperidin-4-yl)-1,3-oxazolidin-2-one acetate | LCMS (Method C): m/z 185 (M + H)+ (ES+), at 0.37 min, UV active |
| 206 | | (2R)-2-aminobutan-1-ol | Commercially available, CAS: 5856-63-3 |
| 207 | Route 12 and intermediate 206 | (4R)-4-ethyl-3-(piperidin-4-yl)-1,3-oxazolidin-2-one acetate | LCMS (Method C): m/z 199 (M + H)+ (ES+), at 0.59 min, UV active |
| 208 | | (2S)-2-aminopropan-1-ol | Commercially available, CAS: 2749-11-3 |
| 209 | Route 12 and intermediate 208 | (4S)-4-methyl-3-(piperidin-4-yl)-1,3-oxazolidin-2-one acetate | LCMS (Method C): m/z 185 (M + H)+ (ES+), at 0.39 min, UV active |
| 210 | | (2S)-2-aminobutan-1-ol | Commercially available, CAS: 5856-62-2 |
| 211 | Route 12 and intermediate 210 | (4S)-4-ethyl-3-(piperidin-4-yl)-1,3-oxazolidin-2-one acetate | LCMS (Method C): m/z 199 (M + H)+ (ES+), at 0.60 min, UV active |
| 212 | | 1-methylimidazolidin-2-one | Commercially available, CAS: 694-32-6 |

TABLE 2-continued

Characterising data and commercial sources for starting materials and intermediates
Table 2

| Intermediate | Route | Name | Data |
|---|---|---|---|
| 213 | Route 12 and intermediate 212 | 1-methyl-3-(piperidin-4-yl)imidazolidin-2-one acetate | LCMS (Method C): m/z 184 (M + H)+ (ES+), at 0.40 min, UV active |
| 214 | | tert-butyl 4-aminopiperidine-1-carboxylate | Commercially available, CAS: 87120-72-7 |
| 215 | Intermediate 214 | 4-(1H-tetrazol-1-yl)piperidine hydrochloride | LCMS (Method K): m/z 154 (M + H)+ (ES+), at 2.22 min, weakly UV active |
| 216 | | 1-(tert-butoxycarbonyl)piperidine-4-carboxylic acid | Commercially available, CAS: 84358-13-4 |
| 217 | | cyclopropanamine | Commercially available, CAS: 765-30-0 |
| 218 | Intermediates 216 and 217 | 4-(1-cyclopropyl-1H-tetrazol-5-yl)piperidine hydrochloride | LCMS (Method F): m/z 194 (M + H)+ (ES+), at 0.46 min, weakly UV active |
| 219 | | 1-ethyl-4-methyl-1H-pyrazol-5-amine | Commercially available, CAS: 3702-13-4 |
| 220 | Route 1 and intermediates 28 and 252 | 4-(1-ethyl-4-methyl-1H-pyrazol-5-yl)piperidine hydrochloride | LCMS (Method I): m/z 194 (M + H)+ (ES+), at 3.13 min, UV active |
| 221 | | R-pipecolinic acid | Commercially available, CAS: 1723-00-8 |
| 222 | | propylphosphonic anhydride solution ≥50 wt. % in ethyl acetate | Commercially available, CAS: 68957-94-8 |
| 223 | Route 16 and intermediates 160, 221 and 222 | (R)-N-methyl-[1,4'-bipiperidine]-2-carboxamide | $^1$H-NMR (400 MHz, DMSO) δ: 1.75-1.91 (m, 4H), 2.21-2.29 (m, 4H), 2.69 (d, J = 4.8 Hz, 3H), 2.94-3.07 (m, 3H), 3.30-3.49 (m, 4H), 3.62-3.80 (m, 2H), 4.10-4.12 (m, 1H), 9.03 (br.s., 1H), 10.01 (br.s., 1H). |
| 224 | | S-pipecolinic acid | Commercially available, CAS: 3105-95-1 |
| 225 | Route 16 and intermediates 160, 221 and 224 | (S)-N-methyl-[1,4'-bipiperidine]-2-carboxamide | $^1$H-NMR (400 MHz; CDCl$_3$) δ: 1.25-1.40 (m, 2H), 1.55-1.69 (m, 4H), 1.82-2.10 (m, 4H), 2.32-2.38 (m, 1H), 2.51-2.65 (m, 3H), 2.79-2.85 (m, 1H), 2.82 (d, J = 4.8 Hz, 3H), 3.12-3.19 (m, 3H), 6.75 (br.s., 1H). |
| 226 | | Z-β-ala-OH | Commercially available, CAS: 2304-94-1 |
| 227 | | 2-bromopyridine | Commercially available, CAS: 109-04-6 |
| 228 | | Cbz-OSu | Commercially available, CAS: 13139-17-8 |
| 229 | Intermediates 160, 227 and 228 | ethyl 2-([2,4'-bipiperidin]-1'-yl)-6-azaspiro[3.4]octane-6-carboxylate | $^1$H-NMR (400 MHz; CDCl$_3$) δ: 1.22 (t, J = 6.8 Hz, 3H), 1.32-1.49 (m, 4H), 1.60-2.90 (m, 12H), 2.08 (bs, 1H), 2.51-2.75 (m, 4H), 2.91-2.98 (m, 3H), 3.25-3.50 (m, 6H), 4.12 (q, J = 6.8 Hz, 2H). |
| 230 | | propionic acid | Commercially available, CAS: 79-09-4 |
| 231 | | 2-bromo ethyl methyl ether | Commercially available, CAS: 6482-24-2 |
| 232 | | benzyl bromide | Commercially available, CAS: 202-847-3 |
| 233 | | methyl bromoacetate | Commercially available, CAS: 96-32-2 |
| 234 | | 1,1'-carbonyldiimidazole | Commercially available, CAS: 530-62-1 |
| 235 | | tert-butyl (2-hydroxyethyl)methylcarbamate | Commercially available, CAS: 57561-39-4 |
| 236 | | 1,1,1-trifluoro-3-iodopropane | Commercially available, CAS: 460-37-7 |
| 237 | | 2,2,2-trifluoroethyl trifluoromethanesulfonate | Commercially available, CAS: 6226-25-1 |
| 238 | | 2-chloro-N,N-dimethylacetamide | Commercially available, CAS: 2675-89-0 |
| 239 | | methyl isothiocyanate | Commercially available, CAS: 556-61-6 |
| 240 | | isoindoline-1-carboxylic acid hydrochloride | Commercially available, CAS: 96016-96-5 |

TABLE 2-continued

Characterising data and commercial sources for starting materials and intermediates
Table 2

| Intermediate | Route | Name | Data |
|---|---|---|---|
| 241 | | trimethylphosphonoacetate | Commercially available, CAS: 5927-18-4 |
| 242 | | methyl cyanoacetate | Commercially available, CAS: 105-34-0 |
| 243 | Intermediates 240, 241 and 242 | tert-butyl 1-(piperidin-4-yl)isoindoline-2-carboxylate | $^1$H-NMR (400 MHz; CDCl$_3$) δ: 1.42 (s, 9H), 1.51-1.62 (m, 3H), 3.15-3.18 (m, 2 H), 3.37-3.42 (m, 4 H), 4.08-4.11 (m, 1H), 4.32-4.38 (m, 2H), 7.18-7.34 (m, 4H). |
| 244 | | 1-iodo-2-fluoroethane | Commercially available, CAS: 762-51-6 |
| 245 | | tert-butyl 4-hydroxypiperidine-1-carboxylate | Commercially available, CAS: 109384-19-2 |
| 246 | | 1H-1,2,3-triazole | Commercially available, CAS: 288-36-8 |
| 247 | Intermediates 245 and 246 | 4-(2H-1,2,3-triazol-2-yl)piperidine hydrochloride | LCMS (Method K): m/z 153 (M + H)$^+$ (ES+), at 2.94 min, UV active |
| 248 | | 1-ethyl-4-methyl-1H pyrazole amine | Commercailly available CAS: 354795-57-6 |
| 249 | | isoamyl nitrite | Commercailly available CAS: 110-46-3 |
| 250 | Route 17 and intermediates 248 and 249 | 4-ethyl-5-iodo-1-methyl-1H-pyrazole | LCMS (Method I): m/z 236 (M + H)$^+$ (ES+), at 4.36 min, UV active |
| 251 | Route 1 and intermediates 28 and 250 | 4-(1-ethyl-4-methyl-1H-pyrazol-5-yl)piperidine hydrochloride | LCMS (Method I): m/z 194 (M + H)$^+$ (ES+), at 3.37 min, UV active |
| 252 | Route 17 and intermediates 219 and 249 | 4-methyl-5-iodo-1-ethyl-1H-pyrazole | LCMS (Method I): m/z 236 (M + H)$^+$ (ES+), at 4.40 min, UV active |
| 253 | | tert-butyl 4-bromopiperidine-1-carboxylate | Commercailly available CAS: 180695-79-8 |
| 254 | | 5-methyl-2H-tetrazole | Commercailly available CAS: 4076-36-2 |
| 255 | Intermediates 253 and 254 | 4-(5-methyl-1H-tetrazol-1-yl)piperidine hydrochloride | $^1$H-NMR: (400 MHz, DMSO) δ: 2.15-2.29 (m, 4H), 2.56 (s, 3H), 3.08 (d, J = 10.2 Hz, 2H), 3.42 (d, J = 12.6 Hz, 2H), 4.74-4.87 (m, 1H), 6.33-6.38 (m, 1H). |
| 256 | | 2-bromo-1,3,4-thiadiazole | Commercailly available CAS: 61929-24-6 |
| 257 | | 1-(tert-butyl) 2-methyl (R)-4,4-difluoropyrrolidine-1,2-dicarboxylate | Commercailly available CAS: 647857-74-7 |
| 258 | Intermediates 160 and 257 | (R)-2-(4,4-difluoro-1-(piperidin-4-yl)pyrrolidin-2-yl)propan-2-ol hydrochloride | $^1$H-NMR: (400 MHz, CDCl$_3$) δ: 1.11 (s, 3H), 1.21 (s, 3H), 1.21-1.31 (m, 1H), 1.49-1.52 (m, 2H), 1.71-1.89 (m, 2H), 2.19-2.30 (m, 2H), 2.50-2.83 (m, 3H), 3.02-3.43 (m, 4H). N—H and O—H not observed. |
| 259 | | (R)-Methyl 4,4-difluoropyrrolidine-2-carboxylate•HCl | Commercially available CAS: 1408057-39-5 |
| 260 | Route 14 and intermediates 160 and 259 | tert-butyl 4-[(2R)-4,4-difluoro-2-(methoxycarbonyl)pyrrolidin-1-yl]piperidine-1-carboxylate | LCMS (Method D): m/z 349 (M + H)$^+$ (ES+) at 2.03 min, UV inactive |
| 261 | | (S)-Methyl 4,4-difluoropyrrolidine-2-carboxylate•HCl | Commercially available CAS: 156046-05-8 |
| 262 | Route 14 and intermediates 160 and 261 | tert-butyl 4-[(2S)-4,4-difluoro-2-(methoxycarbonyl)pyrrolidin-1-yl]piperidine-1-carboxylate | LCMS (Method D): m/z 349 (M + H)$^+$ (ES+) at 2.04 min, UV inactive |
| 263 | | (R)-(−)-3-Fluoropyrrolidine•HCl | Commercially available CAS: 136725-55-8 |
| 264 | | (S)-(+)-3-Fluoropyrrolidine•HCl | Commercially available CAS: 136725-53-6 |
| 265 | | 4,4-difluoropiperidine•HCl | Commercially available CAS: 144230-52-4 |
| 266 | Route 14 and intermediates 160 and 265 | tert-butyl 4,4-difluoro-1,4'-bipiperidine-1'-carboxylate | LCMS (Method D): m/z 305 (M + H)$^+$ (ES+) at 1.97 min, UV inactive |
| 267 | | Thiomorpholine | Commercially available CAS: 123-90-0 |

TABLE 2-continued

Characterising data and commercial sources for starting materials and intermediates
Table 2

| Intermediate | Route | Name | Data |
|---|---|---|---|
| 268 | Route 13 and intermediates 160 and 267 | tert-butyl 4-(thiomorpholin-4-yl)piperidine-1-carboxylate | LCMS (Method D): m/z 287 (M + H)$^+$ (ES+) at 1.86 min, UV inactive |
| 269 | | 1-piperidin-4-yl pyrolidin-2-one | Commercially available CAS: 91596-61-1 |
| 270 | | 3,3-difluoro-4-piperidine•HCl | Commercially available CAS: 496807-97-7 |
| 271 | Route 14 and intermediates 160 and 270 | tert-butyl 3,3-difluoro-1,4'-bipiperidine-1'-carboxylate | LCMS (Method D): m/z 305 (M + H)$^+$ (ES+) at 1.54 min, UV inactive |
| 272 | Route 13 and intermediates 80 and 160 | tert-butyl 4-(morpholin-4-yl)piperidine-1-carboxylate | LCMS (Method D): m/z 271 (M + H)$^+$ (ES+) at 1.54 min, UV inactive |
| 273 | | 2-(R)-2 Trifluoromethylpyrrolidine | Commercially available CAS: 1073556-31-6 |
| 274 | Route 13 and intermediates 160 and 273 | tert-butyl 4-[(2R)-2-(trifluoromethyl)pyrrolidin-1-yl]piperidine-1-carboxylate | LCMS (Method D): m/z 267 (M + H)+ (ES+) at 2.27 and 2.30 min, UV inactive |
| 275 | | piperidine | Commercially available CAS: 110-89-4 |
| 276 | Route 13 and intermediates 160 and 275 | tert-butyl 1,4'-bipiperidine-1'-carboxylate | LCMS (Method D): m/z 269 (M + H)$^+$ (ES+) at 2.06 min, UV inactive |
| 277 | | 2-(S)-2 Trifluoromethylpyrrolidine | Commercially available CAS: 119580-41-5 |
| 278 | Route 13 and intermediates 160 and 277 | terf-butyl 4-[(2S)-2-(trifluoromethyl)pyrrolidin-1-yl]piperidine-1-carboxylate | LCMS (Method D): m/z 323 (M + H)$^+$ (ES+) at 2.27 min, UV inactive |
| 279 | | 3-azabicyclo[3.1.0]hexane•HCl | Commercially available CAS: 73799-84-1 |
| 280 | Route 14 and intermediates 160 and 279 | tert-butyl 4-(3-azabicyclo[3.1.0]hex-3-yl)piperidine-1-carboxylate | LCMS (Method D): m/z 267 (M + H)$^+$ (ES+) at 2.24 min, UV inactive |
| 281 | | (R)-1-(tert-Butoxycarbonyl)piperidine-2-carboxylic acid | Commercially available CAS: 28697-17-8 |
| 282 | Intermediate 281 | tert-butyl (2R)-2-(dimethylcarbamoyl)piperidine-1-carboxylate | $^1$H NMR: (400 MHz, DMSO-d6) δ: 1.22-1.42 (m, 12 H), 1.46-1.83 (m, 4 H), 2.79 (s, 3 H), 2.95 (s, 3 H), 3.70 (d, J = 12.5 Hz, 1 H), 4.74-4.94 (m, 1 H) |
| 283 | Route 14 and intermediates 160 and 282 | tert-butyl (2R)-2-(dimethylcarbamoyl)-1,4'-bipiperidine-1'-carboxylate | LCMS (Method D): m/z 340 (M + H)$^+$ (ES+) at 1.89 min, UV inactive |
| 284 | | (S)-3-Boc-thiazolidine-4-carboxylic acid | Commercially available CAS: 63091-82-7 |
| 285 | Intermediate 284 | 3-tert-butyl 4-methyl (4S)-1,3-thiazolidine-3,4-dicarboxylate | $^1$H NMR: (400 MHz, CDCl$_3$) δ: 1.47 (s, 5 H), 1.43 (s, 4 H), 3.13-3.22 (m, 1 H), 3.22-3.37 (m, 1 H), 3.75 (s, 3 H), 4.34-4.52 (m, 1 H), 4.57-4.60 (m, 0.5 H), 4.61-4.70 (m, 1H), 4.84-4.92 (m, 0.5 H) |
| 286 | Route 14 and intermediates 160 and 284 | tert-butyl 4-[(4S)-4-(methoxycarbonyl)-1,3-thiazolidin-3-yl]piperidine-1-carboxylate | LCMS (Method D): m/z 331 (M + H)$^+$ (ES+) at 2.16 min, UV inactive |
| 287 | | 5-(Pyrrolidin-2-yl)-1H-1,2,3,4-tetrazole | Commercially available CAS: 758710-03-1 |
| 288 | Route 13 and intermediates 160 and 287 | tert-butyl 4-[2-(2H-tetrazol-5-yl)pyrrolidin-1-yl]piperidine-1-carboxylate | LCMS (Method D): m/z 323 (M + H)$^+$ (ES+) at 1.90 min, UV inactive |
| 289 | | (R)-2-Piperidinecarboxylic acid methyl ester hydrochloride | Commercially available CAS: 18650-38-9 |
| 290 | Route 14 and intermediates 160 and 289 | 1'-tert-butyl 2-methyl (2R)-1,4'-bipiperidine-1',2-dicarboxylate | LCMS (Method C): m/z 327 (M + H)$^+$ (ES+) at 1.43 min, UV inactive |
| 291 | | (2R,4R)-4-Hydroxypyrrolidine-1,2-dicarboxylic acid 1-tert-butyl ester 2-methyl ester | Commercially available CAS: 114676-69-6 |
| 292 | | D-proline, 2-methyl-, methyl ester, hydrochloride (1:1) | Commercially available CAS: 1286768-32-8 |
| 293 | Route 14 and intermediates 160 and 292 | terf-butyl 4-[(2R)-2-(methoxycarbonyl)-2-methylpyrrolidin-1-yl]piperidine-1-carboxylate | LCMS (Method D): m/z 271 (M + H)$^+$ (ES+) at 2.36 min, UV inactive |

TABLE 2-continued

Characterising data and commercial sources for starting materials and intermediates
Table 2

| Intermediate | Route | Name | Data |
|---|---|---|---|
| 294 | | (2R)-(+)-1-Boc-2-pyrrolidinemethanol | Commercially available CAS: 83435-58-9 |
| 295 | Intermediate 294 | tert-butyl (2R)-2-(fluoromethyl)pyrrolidine-1-carboxylate | $^1$H NMR: (400 MHz, CDCl$_3$) δ: 1.46 (s, 5 H), 1.57 (s, 4 H), 1.80-2.00 (m, 2 H), 2.01-2.15 (m, 2 H), 3.09-3.23 (m, 1 H), 3.65 (dt, J = 11.4, 7.8 Hz, 1 H), 3.80-3.96 (m, 1 H), 4.17 (dd, J = 8.8, 3.3 Hz, 1 H), 4.51 (t, J = 8.4 Hz, 1 H) |
| 296 | Route 14 and intermediates 160 and 295 | tert-butyl 4-[(2R)-2-(fluoromethyl)pyrrolidin-1-yl]piperidine-1-carboxylate | LCMS (Method D): m/z 287 (M + H)$^+$ (ES+) at 2.56 min, UV inactive |
| 297 | Intermediate 294 | tert-butyl (2R)-2-(difluoromethyl)pyrrolidine-1-carboxylate | $^1$H NMR: (400 MHz, CDCl$_3$) δ: 1.36-1.45 (m, 1 H), 1.47 (s, 3 H), 1.57 (s, 6 H), 3.16 (dt, J = 11.0, 6.8 Hz, 1 H), 3.22-3.32 (m, 1 H), 3.34-3.54 (m, 1 H) 3.59-3.73 (m, 2 H), 3.77-3.99 (m, 1 H), 4.12-4.29 (m, 1 H) |
| 298 | Route 14 and intermediates 160 and 297 | tert-butyl 4-[(2R)-2-(difluoromethyl)pyrrolidin-1-yl]piperidine-1-carboxylate | LCMS (Method D): m/z 305 (M + H)$^+$ (ES+) at 2.80 min, UV inactive |
| 299 | | 7-Oxa-1-azaspiro[4.4]nonan-6-one•HCl | Commercially available CAS: 1018670-73-9 |
| 300 | Route 14 and intermediates 160 and 299 | tert-butyl 4-(6-oxo-7-oxa-1-azaspiro[4.4]non-1-yl)piperidine-1-carboxylate | LCMS (Method D): m/z 325 (M + H)$^+$ (ES+) at 2.08 min, UV inactive |
| 301 | | 4-Nitrophenyl chloroformate | Commercially available CAS: 7693-46-1 |
| 302 | Route 18 and intermediates 1, 32 and 301 | 4-nitrophenyl 2-[4-(1H-pyrazol-1-yl)piperidin-1-yl]-6-azaspiro[3.4]octane-6-carboxylate | LCMS (Method D): m/z 428 (M + H)$^+$ (ES+) at 2.12 min, UV active |
| 303 | | Ethanol-1,1,2,2,2-d$_5$ | Commercially available CAS: 1859-08-1 |
| 304 | | Ethanol-1,1-d$_2$ | Commercially available CAS: 1859-09-2 |
| 305 | | Ethanol-2,2,2-d$_3$ | Commercially available CAS: 1759-87-1 |
| 306 | Route 18 and intermediates 1, 9 and 301 | 4-nitrophenyl 2-[4-(1-methyl-1H-pyrazol-5-yl)piperidin-1-yl]-6-azaspiro[3.4]octane-6-carboxylate | LCMS (Method D): m/z 440 (M + H)$^+$ (ES+) at 2.11 min, UV active |
| 307 | | Dimethylamine hydrochloride | Commercially available CAS: 506-59-2 |
| 308 | Route 15 and intermediates 130 and 288 | Mixture of tert-butyl 4-[2-(1-methyl-1H-tetrazol-5-yl)pyrrolidin-1-yl]piperidine-1-carboxylate and tert-butyl 4-[2-(2-methyl-2H-tetrazol-5-yl)pyrrolidin-1-yl]piperidine-1-carboxylate | LCMS (Method D): m/z 337 (M + H)$^+$ (ES+) at 2.43 min, UV inactive |
| 309 | | 1-tert-butyl 2-methyl (2R,4R)-4-fluoropyrrolidine-1,2-dicarboxylate | Commercially available CAS 647857-43-0 |
| 310 | | 1-tert-butyl 2-methyl (2R,4S)-4-fluoropyrrolidine-1,2-dicarboxylate | Commercially available CAS 647857-39-4 |
| 311 | Route 14 and intermediates 160 and 309 | tert-butyl 4-[(2R,4R)-4-fluoro-2-(methoxycarbonyl)pyrrolidin-1-yl]piperidine-1-carboxylate | LCMS (Method D): m/z 331 (M + H)$^+$ (ES+) at 1.96 min, UV inactive |
| 312 | Route 14 and intermediates 160 and 310 | tert-butyl 4-[(2R,4S)-4-fluoro-2-(methoxycarbonyl)pyrrolidin-1-yl]piperidine-1-carboxylate | LCMS (Method D): m/z 331 (M + H)$^+$ (ES+) at 2.04 min, UV inactive |
| 313 | | (R)-2-(pyrrolidin-2-yl)thiazole | Commercially available CAS: 1228558-20-0 |
| 314 | Route 9 and intermediates 160 and 313 | 4-[(2R)-2-(1,3-thiazol-2-yl)pyrrolidin-1-yl]piperidine dihydrochloride | LCMS (Method K): m/z 238 (M + H)$^+$ (ES+) at 7.00 min, UV active |
| 315 | | (2R)-2-(thiophen-2-yl)pyrrolidine | Commercially available CAS: 154777-22-7 |
| 316 | Route 9 and intermediates 160 and 315 | 4-[(2R)-2-(thiophen-2-yl)pyrrolidin-1-yl]piperidine dihydrochloride | LCMS (Method K): m/z 237 (M + H)$^+$ (ES+) at 7.80 min, UV active |
| 317 | | 3-[(2R)-pyrrolidin-2-yl]-1,2-oxazole | Commercially available CAS: 1255147-67-1 |

TABLE 2-continued

Characterising data and commercial sources for starting materials and intermediates
Table 2

| Intermediate | Route | Name | Data |
|---|---|---|---|
| 318 | Route 9 and intermediates 160 and 317 | 4-[2-(1,2-oxazol-3-yl)pyrrolidin-1-yl]piperidine dihydrochloride | LCMS (Method K): m/z 222 (M + H)$^+$ (ES+) at 6.24 min, UV active |
| 319 | Route 15 and intermediates 114 and 194 | 4-(2-ethyl-2H-tetrazol-5-yl)piperidine hydrochloride | LCMS (Method I): m/z (M + H)$^+$ (ES+) at 3.128 min, UV active |
| 320 | Route 15 and intermediates 114 and 194 | 4-(1-ethyl-1H-tetrazol-5-yl)piperidine hydrochloride | LCMS (Method I): m/z 182 (M + H)$^+$ (ES+) at 2.54 min, UV active |
| 321 | | 6,7-dihydro-5H-pyrrolo[3,4-b]pyridine dihydrochloride | Commercially available CAS: 147740-02-1 |
| 322 | | 6-Bromohexanoyl chloride | Commercially available CAS: 22809-37-6 |
| 323 | Route 6 and intermediates 3 and 53 | Mthyl 2-[4-(pyrrolidin-2-yl)piperidin-1-yl]-6-azaspiro[3.4]octane-6-carboxylate•HCl | LCMS (Method J): m/z 322 (M + H)$^+$ (ES$^+$), at 4.37 min, UV inactive |

TABLE 3

| Ex. No. | Name | Intermediate | Synthetic method | ¹H NMR | LCMS Method | LCMS data |
|---|---|---|---|---|---|---|
| 1-1 | Isomer 2: ethyl 2-[4-[4-(1H-imidazol-2-yl)piperidin-1-yl]-6-azaspiro[3.4]octane-6-carboxylate | 2 and 5 | a | (400 MHz, DMSO-$d_6$) δ: 1.14 (t, J = 6.6 Hz, 3H), 1.60-1.86 (m, 11H), 1.95-2.02 (m, 2H), 2.60-2.66 (m, 1H), 2.76-2.84 (m, 2H), 3.10-3.28 (m, 4H), 3.98 (q, J = 6.6 Hz, 2H), 6.78-6.83 (m, 2H), NH not observed | B | m/z 333 (M + H)⁺ (ES+), at 2.69 min, UV inactive |
| 1-2 | Isomer 2: ethyl 2-[4-(4-chloro-1H-imidazol-2-yl)piperidin-1-yl]-6-azaspiro[3.4]octane-6-carboxylate | 2 and 22 | as | (400 MHz, CDCl₃) δ: 1.24 (t, J = 7.0 Hz, 3H), 1.81-2.23 (m, 12H), 2.77-2.97 (m, 2H), 2.97-3.15 (m, 2H), 3.28-3.35 (m, 2H), 3.35-3.46 (m, 2H), 4.11 (q, J = 7.0 Hz, 2H), 6.82 (s, 1H), NH not observed | C | m/z 367/369 (M + H)⁺ (ES+), at 1.57 min, UV active |
| 1-3 | Isomer 2: ethyl 2-{4-[4-(trifluoromethyl)-1H-imidazol-2-yl]piperidin-1-yl}-6-azaspiro[3.4]octane-6-carboxylate | 2 and 33 | b | (400 MHz, DMSO-$d_6$) δ: 1.18 (t, J = 7.0 Hz, 3H), 1.60-1.73 (m, 2H), 1.73-1.93 (m, 8H), 1.97-2.06 (m, 2H), 2.61-2.73 (m, 2H), 2.78-2.87 (m, 2H), 3.14-3.20 (m, 2H), 3.26-3.33 (m, 2H), 4.01 (q, J = 7.0 Hz, 2H), 7.64 (s, 1H), NH not observed. | G | m/z 401 (M + H)⁺ (ES+), at 5.42 min, UV active |
| 1-4 | Isomer 2: ethyl 2-[4-(4-cyano-1H-imidazol-2-yl)piperidin-1-yl]-6-azaspiro[3.4]octane-6-carboxylate | Example 1-3 | c | (400 MHz, DMSO-$d_6$) δ: 1.17 (t, J = 7.0 Hz, 3H), 1.58-1.71 (m, 2H), 1.73-1.92 (m, 8H), 1.95-2.05 (m, 2H), 2.62-2.73 (m, 2H), 2.76-2.87 (m, 2H), 3.13-3.19 (m, 2H), 3.25-3.32 (m, 2H), 4.00 (q, J = 7.0 Hz, 2H), 8.02 (s, 1H), 12.66 (br, 1H). | G | m/z 358 (M + H)⁺ (ES+), at 4.71 min, UV active |
| 1-5 | Isomer 2: ethyl 2-[4-(4,5-dichloro-1H-imidazol-2-yl)piperidin-1-yl]-6-azaspiro[3.4]octane-6-carboxylate | 2 and 25 | as | (400 MHz, CD₃OD) δ: 1.20-1.31 (m, 3H), 1.67-1.82 (m, 2H), 1.87-2.02 (m, 8H), 2.10-2.18 (m, 2H), 2.61-2.72 (m, 1H), 2.76-2.88 (m, 1H), 2.90-3.04 (m, 2H), 3.25-3.29 (m, 2H), 3.36-3.46 (m, 2H), 4.10 (q, J = 7.0 Hz, 2H), NH not observed | C | m/z 401/403/405 (M + H)⁺ (ES+), at 1.57 min, UV active |
| 1-6 | Isomer 2: methyl 2-[4-(1-methyl-1H-imidazol-2-yl)piperidin-1-yl]-6-azaspiro[3.4]octane-6-carboxylate | 3 and 15 | at | (400 MHz, CDCl₃) δ: 1.81-2.10 (m, 11H), 2.17-2.53 (m, 1H), 2.57-2.79 (m, 2H), 2.87-3.05 (m, 2H), 3.19-3.47 (m, 4H), 3.59 (s, 3H), 3.68 (s, 3H), 6.77 (s, 1H), 6.93 (s, 1H). | B | m/z 333 (M + H)⁺ (ES+), at 2.78 min, UV inactive |
| 1-7 | Isomer 2: ethyl 2-[4-(1-methyl-1H-imidazol-2-yl)piperidin-1-yl]-6-azaspiro[3.4]octane-6-carboxylate | 1 and 6 | d | (300 MHz, CDCl₃) δ: 1.22 (t, J = 7.0 Hz, 3H), 1.76-2.09 (m, 12H), 2.54-2.78 (m, 1H), 2.92-2.96 (m, 2H), 3.19-3.29 (m, 2H), 3.37 (dt, J = 13.6, 6.6 Hz, 2H), 3.57 (s, 3H), 4.08 (q, J = 7.0 Hz, 2H), 6.74 (s, 1H), 6.90 (s, 1H) | B | m/z 347 (M + H)⁺ (ES+), at 3.07 min, UV inactive |
| 1-8 | Isomer 2: ethyl 2-{4-[1-(ethoxycarbonyl)-1H-imidazol-2-yl]piperidin-1-yl}-6-azaspiro[3.4]octane-6-carboxylate | 1 and 5 | d | (400 MHz, CDCl₃) δ: 1.24 (t, J = 7.5 Hz, 3H), 1.42 (t, J = 7.0 Hz, 3H), 1.74-2.15 (m, 12H), 2.70-2.76 (m, 1H), 2.93-2.99 (m, 2H), 3.19-3.49 (m, 5H), 4.11 (q, J = 7.0 Hz, 2H), 4.42 (q, J = 7.5 Hz, 2H), 6.89 (s, 1H), 7.35 (s, 1H) | B | m/z 405 (M + H)⁺ (ES+), at 3.94 min, weakly UV active |
| 1-9 | Isomer 2: methyl 2-[4-(1,5-dimethyl-1H-imidazol-1-yl)piperidin-1-yl]-6-azaspiro[3.4]octane-6-carboxylate | 3 and 34 | b and e | 400 MHz, DMSO-$d_6$) δ: 1.60-1.85 (m, 10H), 1.99-2.08 (m, 2H), 2.11 (d, J = 1 Hz, 3H), 2.60-2.71 (m, 2H), 2.79-2.88 (m, 2H), 3.21-3.28 (m, 2H), 3.28-3.32 (m, 2H), 3.41 (s, 3H), 3.58 (s, 3H), 6.49 (s, 1H) | G | m/z 347 (M + H)⁺ (ES+), at 4.83 min, UV active |

TABLE 3-continued

| Ex. No. | Name | Intermediate | Synthetic method | $^1$H NMR | LCMS Method | LCMS data |
|---|---|---|---|---|---|---|
| 1-10 | Isomer 2: ethyl 2-[4-(1,5-dimethyl-1H-imidazol-2-yl)piperidin-1-yl]-6-azaspiro[3.4]octane-6-carboxylate | 2 and 34 | b and e | (400 MHz, CD$_3$OD) δ: 1.22-1.36 (m, 3H), 1.82-2.10 (m, 10H), 2.12-2.27 (m, 2H), 2.20 (s, 3H), 2.76-2.97 (m, 2H), 2.99-3.12 (m, 2H), 3.25-3.47 (m, 4H), 3.53 (s, 3H), 4.12 (q, J = 7.1 Hz, 2H), 6.61 (s, 1H) | G | m/z 361 (M+ H)$^+$ (ES+), at 5.55 min, UV active |
| 1-11 | Isomer 2: methyl 2-[4-(1,4-dimethyl-1H-imidazol-2-yl)piperidin-1-yl]-6-azaspiro[3.4]octane-6-carboxylate | 3 and 36 | b and e | (400 MHz, DMSO-d$_6$) δ: 1.57-1.93 (m, 10H), 1.96-2.06 (m, 2H), 2.02 (s, 3H), 2.59-2.79 (m, 2H), 2.81-2.92 (m, 2H), 3.15-3.22 (m, 2H), 3.26-3.33 (m, 2H), 3.50 (s, 3H), 3.57 (s, 3H), 6.66 (s, 1H) | G | m/z 347 (M + H)$^+$ (ES+), at 4.54 min, UV active |
| 1-12 | Isomer 2: ethyl 2-[4-(1,4-dimethyl-1H-imidazol-2-yl)piperidin-1-yl]-6-azaspiro[3.4]octane-6-carboxylate | 2 and 36 | b and e | (400 MHz, DMSO-d$_6$) δ: 1.18 (t, J = 7.0 Hz, 3H), 1.59-1.91 (m, 10H), 1.98-2.05 (m, 2H), 2.02 (s, 3H), 2.67-2.75 (m, 2H), 2.82-2.90 (m, 2H), 3.16-3.22 (m, 2H), 3.27-3.32 (m, 2H), 3.49 (s, 3H), 4.01 (q, J = 7.0 Hz, 2H), 6.66 (s, 1H) | G | m/z 361 (M+H)$^+$ (ES+), at 5.34 min, UV active |
| 1-13 | Isomer 2: methyl 2-[4-(5-chloro-1-methyl-1H-imidazol-2-yl)piperidin-1-yl]-6-azaspiro[3.4]octane-6-carboxylate | 3 and 20 | as | (400 MHz, CDCl$_3$) δ: 1.81-2.01 (m, 10H), 2.01-2.11 (m, 2H), 2.55-2.66 (m, 1H), 2.66-2.79 (m, 1H), 2.91-3.00 (m, 2H), 3.25 (s, 1H), 3.32 (s, 1H), 3.34-3.47 (m, 1H), 3.41-3.46 (m, 1H), 3.52 (s, 3H), 3.68 (s, 3H), 6.86 (s, 1H) | C | m/z 367/369 (M + H)$^+$ (ES+), at 1.61 min, UV active |
| 1-14 | Isomer 2: ethyl 2-[4-(5-chloro-1-methyl-1H-imidazol-2-yl)piperidin-1-yl]-6-azaspiro[3.4]octane-6-carboxylate | 2 and 20 | as | (400 MHz, CDCl$_3$) δ: 1.25 (t, J = 7.0 Hz, 3H), 1.81-2.01 (m, 10H), 2.01-2.11 (m, 2H), 2.55-2.66 (m, 1H), 2.66-2.78 (m, 1H), 2.90-3.00 (m, 2H), 3.26 (s, 1H), 3.31 (s, 1H), 3.34-3.47 (m, 1H), 3.52 (s, 3H), 4.12 (q, J = 7.0 Hz, 2H), 6.86 (s, 1H) | C | m/z 381/383 (M + H)$^+$ (ES+), at 1.69 min, UV active |
| 1-15 | Isomer 2: ethyl 2-{4-[1-methyl-4-(trifluoromethyl)-1H-imidazol-2-yl]piperidin-1-yl}-6-azaspiro[3.4]octane-6-carboxylate | 2 and 37 | b | (400 MHz, DMSO-d$_6$) δ: 1.18 (t, J = 7.0 Hz, 3H), 1.58-1.72 (m, 2H), 1.73-1.93 (m, 8H), 1.95-2.08 (m, 2H), 2.65-2.81 (m, 2H), 2.82-2.92 (m, 2H), 3.14-3.23 (m, 2H), 3.25-3.34 (m, 2H), 3.65 (s, 3H), 4.02 (q, J = 7.0 Hz, 2H), 7.67 (s, 1H) | G | m/z 415 (M + H)$^+$ (ES+), at 4.95 min, UV active |
| 1-16 | Isomer 2: methyl 2-[4-(4,5-dichloro-1-methyl-1H-imidazol-2-yl)piperidin-1-yl]-6-azaspiro[3.4]octane-6-carboxylate | 3 and 21 | as | (400 MHz, CDCl$_3$) δ: 1.79-2.00 (m, 10H), 2.00-2.11 (m, 2H), 2.56-2.66 (m, 1H), 2.67-2.76 (m, 1H), 2.89-3.00 (m, 2H), 3.25 (s, 1H), 3.31 (s, 1H), 3.33-3.40 (m, 1H), 3.41-3.46 (m, 1H), 3.53 (s, 3H), 3.69 (s, 3H) | C | m/z 401/403/405 (M + H)$^+$ (ES+), at 1.70 min, UV active |
| 1-17 | Isomer 2: ethyl 2-[4-(4,5-dichloro-1-methyl-1H-imidazol-2-yl)piperidin-1-yl]-6-azaspiro[3.4]octane-6-carboxylate | 2 and 21 | as | (400 MHz, CDCl$_3$) δ: 1.25 (t, J = 7.0 Hz, 3H), 1.79-2.00 (m, 10H), 2.01-2.10 (m, 2H), 2.55-2.66 (m, 1H), 2.66-2.79 (m, 1H), 2.90-2.99 (m, 2H), 3.26 (s, 1H), 3.31 (s, 1H), 3.34-3.47 (m, 2H), 3.53 (s, 3H), 4.12 (q, J = 7.0 Hz, 2H) | C | m/z 415/417/419 (M + H)$^+$ (ES+), at 1.79 min, UV active |
| 1-18 | Isomer 2: ethyl 2-[4-(1H-pyrazol-5-yl)piperidin-1-yl]-6-azaspiro[3.4]octane-6-carboxylate | 2 and 7 | a | (400 MHz, CDCl$_3$) δ: 1.24 (t, J = 7.0 Hz, 3H), 1.68-2.13 (m, 12H), 2.69-2.75 (m, 2H), 2.91-2.98 (m, 2H), 3.18-3.52 (m, 4H), 4.11 (q, J = 7.0 Hz, 2H), 6.11 (s, 1H), 7.48 (s, 1H), NH not observed | B | m/z 333 (M + H)$^+$ (ES+), at 3.16 min, UV inactive |
| 1-19 | Isomer 2: ethyl 2-[4-(3-amino-1H-pyrazol-5-yl)piperidin-1-yl]-6-azaspiro[3.4]octane-6-carboxylate | 2 and 8 | a | (400 MHz, CDCl$_3$) δ: 1.25 (t, J = 6.2 Hz, 3H), 1.60-2.20 (m, 12H), 2.53-2.59 (m, 1H), 2.70-2.75 (m, 1H), 2.92-2.98 (m, 2H), 3.21-3.47 (m, 4H), 4.01-4.20 (m, 2H), 5.45 (s, 1H), 3xNH not observed | B | m/z 348 (M + H)$^+$ (ES+), at 2.75 min, UV inactive |

TABLE 3-continued

| Ex. No. | Name | Intermediate | Synthetic method | ¹H NMR | LCMS Method | LCMS data |
|---|---|---|---|---|---|---|
| 1-20 | Mixture of diastereomers: methyl 2-[4-(1-methyl-1H-pyrazol-5-yl)piperidin-1-yl]-6-azaspiro[3.4]octane-6-carboxylate | 3 and 38 | b | (400 MHz, CDCl$_3$) δ: 1.56-1.70 (m, 2H), 1.79-2.01 (m, 8H), 2.05-2.25 (m, 2H), 2.51-2.83 (m, 2H), 2.88-3.14 (m, 2H), 3.23-3.51 (m, 4H), 3.71 (s, 3H), 3.83 (s, 3H), 6.03 (br, 1H), 7.34-7.43 (m, 1H) | B | m/z 333 (M+H)$^+$ (ES+), at 2.70 min, UV inactive |
| 1-21 | Isomer 2: ethyl 2-[4-(1-methyl-1H-pyrazol-5-yl)piperidin-1-yl]-6-azaspiro[3.4]octane-6-carboxylate | 2 and 9 | a | (400 MHz, CDCl$_3$) δ: 1.18-1.30 (m, 3H), 1.67-2.30 (m, 12H), 2.57-2.63 (m, 1H), 2.70-2.84 (m, 1H), 3.00-3.15 (m, 2H), 3.22-3.61 (m, 4H), 3.81 (s, 3H), 4.11 (q, J = 6.4 Hz, 2H), 6.04 (s, 1H), 7.37 (s, 1H) | B | m/z 347 (M + H)$^+$ (ES+), at 3.18 min, UV inactive |
| 1-22 | Isomer 2: ethyl 2-[4-(1-methyl-1H-pyrazol-3-yl)piperidin-1-yl]-6-azaspiro[3.4]octane-6-carboxylate | 2 and 10 | a | (400 MHz, CDCl$_3$) δ: 1.14-1.32 (m, 3H), 1.54-1.71 (m, 2H), 1.78-2.12 (m, 10H), 2.43-2.49 (m, 1H), 2.60-2.78 (m, 1H), 2.84-2.96 (m, 2H), 3.16-3.46 (m, 4H), 3.84 (s, 3H), 4.03-4.20 (m, 2H), 7.13 (s, 1H), 7.32 (s, 1H) | B | m/z 347 (M + H)$^+$ (ES+), at 3.51 min, UV inactive |
| 1-23 | Isomer 2: ethyl 2-[4-(1,3-oxazol-2-yl)piperidin-1-yl]-6-azaspiro[3.4]octane-6-carboxylate | 2 and 41 | b | (400 MHz, DMSO-d$_6$) δ: 1.18 (t, J = 7.0 Hz, 3H), 1.57-1.73 (m, 2H), 1.73-1.91 (m, 6H), 1.92-2.05 (m, 4H), 2.63-2.72 (m, 2H), 2.73-2.85 (m, 2H), 3.13-3.21 (m, 2H), 3.25-3.34 (m, 2H), 4.01 (q, J = 7.0 Hz, 2H), 8.01 (s, 1H), 7.12 (s, 1H) | G | m/z 334 (M + H)$^+$ (ES+), at 5.37 min, UV active |
| 1-24 | Isomer 2: methyl 2-[4-(1,3-thiazol-2-yl)piperidin-1-yl]-6-azaspiro[3.4]octane-6-carboxylate | 3 and 42 | b | (400 MHz, DMSO-d$_6$) δ: 1.58-1.73 (m, 2H), 1.73-1.92 (m, 6H), 1.96-2.10 (m, 4H), 2.65-2.74 (m, 1H), 2.79-2.89 (m, 2H), 2.91-3.03 (m, 1H), 3.20-3.32 (m, 4H), 3.58 (s, 3H), 7.61 (d, J = 3.4 Hz, 1H), 7.72 (d, J = 3.4 Hz, 1H) | G | m/z 336 (M + H)$^+$ (ES+), at 5.15 min, UV active |
| 1-25 | Isomer 2: ethyl 2-[4-(1,3-thiazol-2-yl)piperidin-1-yl]-6-azaspiro[3.4]octane-6-carboxylate | 2 and 42 | b | (400 MHz, DMSO-d$_6$) δ: 1.18 (t, J = 7.0 Hz, 3H), 1.59-1.74 (m, 2H), 1.76-1.92 (m, 6H), 1.97-2.09 (m, 4H), 2.63-2.75 (m, 1H), 2.80-2.90 (m, 2H), 2.92-3.05 (m, 1H), 3.14-3.20 (m, 2H), 3.25-3.34 (m, 2H), 4.01 (q, J = 7.0 Hz, 2H), 7.60 (d, J = 3.0 Hz, 1H), 7.72 (d, J = 3.0 Hz, 1H) | F | m/z 350 (M + H)$^+$ (ES+), at 1.61 min, UV active |
| 1-26 | Isomer 2: ethyl 2-[4-(4H-1,2,4-triazol-3-yl)piperidin-1-yl]-6-azaspiro[3.4]octane-6-carboxylate | 1 and 17 | f | (400 MHz, CDCl$_3$) δ: 1.15-1.38 (m, 3H), 1.77-3.21 (m, 15H), 3.23-3.78 (m, 5H), 4.00-4.27 (m, 2H), 8.42 (s, 1H), NH not observed | E | m/z 334 (M + H)$^+$ (ES+), at 2.78 min, UV inactive |
| 1-27 | Isomer 2: ethyl 2-[4-(5-ethyl-1H-1,2,4-triazol-3-yl)piperidin-1-yl]-6-azaspiro[3.4]octane-6-carboxylate | 2 and 23 | as | (400 MHz, CDCl$_3$) δ: 1.25 (t, J = 7.0 Hz, 3H), 1.34 (t, J = 7.5 Hz, 3H), 1.73-2.35 (m, 12H), 2.79 (q, J = 7.5 Hz, 2H), 2.84-3.15 (m, 4H), 3.31-3.46 (m, 4H), 4.11 (q, J = 7.0 Hz, 2H), NH not observed | C | m/z 362 (M + H)$^+$ (ES+), at 1.43 min, UV active |
| 1-28 | Isomer 2: ethyl 2-[4-(1,3,4-oxadiazol-2-yl)piperidin-1-yl]-6-azaspiro[3.4]octane-6-carboxylate | 2 and 43 | b | (400 MHz, DMSO-d$_6$) δ: 1.18 (t, J = 7.0 Hz, 3H), 1.62-1.74 (m, 2H), 1.75-1.94 (m, 6H), 1.95-2.06 (m, 4H), 2.65-2.74 (m, 1H), 2.74-2.83 (m, 2H), 2.93-3.01 (m, 1H), 3.14-3.21 (m, 2H), 3.26-3.32 (m, 2H), 4.00 (q, J = 7.0 Hz, 2H), 9.15 (s, 1H) | G | m/z 335 (M + H)$^+$ (ES+), at 4.89 min, UV active |
| 1-29 | Isomer 2: ethyl 2-[4-(3-methyl-1,2,4-oxadiazol-5-yl)piperidin-1-yl]-6-azaspiro[3.4]octane-6-carboxylate | 2 and 44 | b | (400 MHz, DMSO-d$_6$) δ: 1.18 (t, J = 7.0 Hz, 3H), 1.62-1.74 (m, 2H), 1.75-1.95 (m, 6H), 1.95-2.05 (m, 4H), 2.33 (s, 3H), 2.65-2.72 (m, 1H), 2.72-2.81 (m, 2H), 2.93-3.03 (m, 1H), 3.14-3.20 (m, 2H), 3.25-3.33 (m, 2H), 4.01 (q, J = 7.0 Hz, 2H) | F | m/z 349 (M + H)$^+$ (ES+), at 1.63 min, UV active |

TABLE 3-continued

| Ex. No. | Name | Intermediate | Synthetic method | ¹H NMR | LCMS Method | LCMS data |
|---|---|---|---|---|---|---|
| 1-30 | Isomer 2: ethyl 2-[4-(1,2,4-thiadiazol-5-yl)piperidin-1-yl]-6-azaspiro[3.4]octane-6-carboxylate | 2, 28, 29 and 30 | b | (400 MHz, DMSO-d₆) δ: 1.17 (t, J = 7.0, 3H), 1.59-1.95 (m, 8H), 1.95-2.20 (m, 4H), 2.39-2.93 (m, 4H), 3.09-3.53 (m, 4H), 4.00 (q, J = 7.0 Hz, 2H), 8.82 (s, 1H) | G | m/z 351 (M + H)⁺ (ES+), at 5.47 min, UV active |
| 1-31 | Isomer 2: ethyl 2-[4-(1H-tetrazol-5-yl)piperidin-1-yl]-6-azaspiro[3.4]octane-6-carboxylate | 2 and 31 | b | (400 MHz, DMSO-d₆) δ: 1.03-1.27 (m, 3H), 1.88-1.92 (m, 4H), 1.92-2.26 (m, 6H), 2.39-2.63 (m, 2H), 2.66-2.87 (m, 3H), 3.00-3.40 (m, 4H), 3.99 (q, J = 7.0 Hz, 2H), 4.80-4.96 (m, 1H), 8.93 (s, 1H) | F | m/z 335 (M + H)⁺ (ES+), at 1.56 min, UV active |
| 1-32 | Isomer 2: ethyl 2-[4-(1H-pyrrol-1-yl)piperidin-1-yl]-6-azaspiro[3.4]octane-6-carboxylate | 2 and 11 | a | (400 MHz, DMSO-d₆) δ: 1.27 (t, J = 7.0 Hz, 3H), 1.91-2.06 (m, 10H), 2.13-2.18 (m, 2H), 2.81-2.87 (m, 1H), 3.00-3.04 (m, 2H), 3.30-3.43 (m, 4H), 3.95-4.00 (m, 1H), 4.12 (q, J = 7.0 Hz, 2H), 6.05 (s, 2H), 6.77 (t, J = 2.0 Hz, 2H) | B | m/z 332 (M + H)⁺ (ES+), at 3.90 min, UV inactive |
| 1-33 | Isomer 2: ethyl 2-[4-(1H-pyrazol-1-yl)piperidin-1-yl]-6-azaspiro[3.4]octane-6-carboxylate | 1 and 12 | a | (400 MHz, CDCl₃) δ: 1.18 (t, J = 7.0 Hz, 3H), 1.78-2.13 (m, 12H), 2.63-2.73 (m, 1H), 2.88-2.95 (m, 2H), 3.19-3.40 (m, 4H), 4.05 (q, J = 7.0 Hz, 2H), 4.09-4.13 (m, 1H), 6.20 (t, J = 2.0 Hz, 1H), 7.37 (d, J = 2.0 Hz, 1H), 7.44 (s, 1H) | B | m/z 333 (M + H)⁺ (ES+), at 3.14 min, UV inactive |
| 1-34 | Isomer 1: ethyl 2-[4-(4-methyl-1H-pyrazol-1-yl)piperidin-1-yl]-6-azaspiro[3.4]octane-6-carboxylate | 1 and 13 | d | (400 MHz, CDCl₃) δ: 1.25 (t, J = 7.0 Hz, 3H), 1.79-2.01 (m, 9H), 2.06 (s, 3H), 2.07-2.18 (m, 3H), 2.65-2.78 (m, 1H), 2.92-2.98 (m, 2H), 3.28-3.43 (m, 4H), 4.03-4.11 (m, 1H), 4.12 (q, J = 7.0 Hz, 2H), 7.18 (s, 1H), 7.28 (s, 1H) | B | m/z 347 (M + H)⁺ (ES+), at 3.43 min, UV active |
| 1-34 | Isomer 2: ethyl 2-[4-(4-methyl-1H-pyrazol-1-yl)piperidin-1-yl]-6-azaspiro[3.4]octane-6-carboxylate | 1 and 11 | d | (400 MHz, CDCl₃) δ: 1.25 (t, J = 7.0 Hz, 3H), 1.81-2.19 (m, 9H), 2.07 (s, 3H), 2.10-2.16 (m, 3H), 2.65-2.81 (m, 1H), 2.93-2.99 (m, 2H), 3.21-3.49 (m, 4H), 4.10-4.12 (m, 1H), 4.12 (q, J = 7.0 Hz, 2H), 7.20 (s, 1H), 7.28 (s, 1H) | B | m/z 347 (M + H)⁺ (ES+), at 3.55 min, UV inactive |
| 1-35 | Isomer 2: ethyl 2-[4-(1H-1,2,3-triazol-1-yl)piperidin-1-yl]-6-azaspiro[3.4]octane-6-carboxylate | 1 and 18 | f | (400 MHz, CDCl₃) δ: 1.19 (t, J = 7.0 Hz, 3H), 1.76-2.10 (m, 10H), 2.10-2.24 (m, 2H), 2.62-2.79 (m, 1 H), 2.84-3.02 (m, 2H), 3.17-3.28 (m, 2H), 3.28-3.42 (m, 2H), 3.98-4.12 (q, J = 7.0 Hz, 2H), 4.38-4.59 (m, 1H), 7.54 (s, 1H) 7.64 (s, 1H) | E | m/z 334 (M + H)⁺ (ES+), at 2.90 min, UV inactive |
| 1-36 | Isomer 2: ethyl 2-[4-(1H-1,2,4-triazol-1-yl)piperidin-1-yl]-6-azaspiro[3.4]octane-6-carboxylate | 1, 16 and 56 | f | (400 MHz, CDCl₃) δ: 1.21-1.81 (m, 3H), 1.84-2.12 (m, 10H), 2.13-2.30 (m, 2H), 2.62-2.88 (m, 1H), 2.88-3.08 (m, 2H), 3.22-3.33 (m, 2H), 3.34-3.47 (m, 2H), 4.06-4.15 (m, 2H), 4.16-4.25 (m, 1H), 7.93 (s, 1H), 8.10 (s, 1H). | E | m/z 334 (M + H)⁺ (ES+), at 2.88 min, UV inactive |
| 1-37 | Isomer2: ethyl 2-[4-hydroxy-4-(1H-imidazol-2-yl)piperidin-1-yl]-6-azaspiro[3.4]octane-6-carboxylate | 2 and 47 | b | (400 MHz, DMSO-d₆) δ: 1.17 (t, J = 7.0 Hz, 3 H), 1.65-1.88 (m, 6H), 1.93-2.04 (m, 4 H), 2.14-2.26 (m, 2H), 2.36-2.47 (m, 2 H), 2.62-2.72 (m, 1 H), 3.12-3.20 (m, 2 H), 3.23-3.31 (m, 2H), 4.00 (q, J = 7.0 Hz, 2H), 5.04 (s, 1 H), 6.77 (s, 1 H), 6.94 (s, 1 H), 11.71 (s, 1 H) | H | m/z 349 (M+H)+ (ES+) at 7.05 min, UV active |
| 1-38 | Isomer 2: ethyl 2-[4-(1H-imidazol-2-yl)-4-methoxypiperidin-1-yl]-6-azaspiro[3.4]octane-6-carboxylate | 2 and 48 | b | (400 MHz, DMSO-d₆) δ: 1.16 (t, J = 7.0 Hz, 3 H), 1.71-1.86 (m, 6 H), 1.89-2.08 (m, 6H), 2.53-2.58 (m, 2 H), 2.59-2.71 (m, 1 H), 2.84 (m, 3 H), 3.11-3.20 (m, 2 H), 3.22-3.29 (m, 2H), 4.00 (q, J = 7.0 Hz, 2H), 6.82 (s, 1 H), 7.09 (s, 1 H), 11.94 (s, 1 H) | F | m/z 363 (M+H)+ (ES+) at 1.41 min, UV active |
| 1-39 | Isomer 2: ethyl 2-[4-hydroxy-4-(1-methyl-1H-imidazol-2-yl)piperidin-1-yl]-6-azaspiro[3.4]octane-6-carboxylate | 2 and 49 | b | (400 MHz, DMSO-d₆) δ: 1.17 (t, J = 7.0 Hz, 3 H), 1.70-1.90 (m, 6 H), 1.93-2.04 (m, 4 H), 2.11-2.24 (m, 2H), 2.42-2.47 (m, 2 H), 2.63-2.72 (m, 1 H), 3.11-3.18 (m, 2 H), 3.24-3.30 (m, 2H), 3.77 (s, 3H), 4.00 (q, J = 7.0 Hz, 2H), 5.09 (s, 1 H), 6.70 (s, 1 H), 7.00 (s, 1 H) | G | m/z 363 (M+H)+ (ES+) at 4.05 min, UV active |

TABLE 3-continued

| Ex. No. | Name | Intermediate | Synthetic method | ¹H NMR | LCMS Method | LCMS data |
|---|---|---|---|---|---|---|
| 1-40 | Isomer 2: ethyl 2-[4-methoxy-4-(1-methyl-1H-imidazol-2-yl)piperidin-1-yl]-6-azaspiro[3.4]octane-6-carboxylate | 2 and 50 | b | (400 MHz, DMSO-d₆) δ: 1.17 (t, J = 7.0 Hz, 3 H), 1.72-2.21 (m, 12 H), 2.60-2.72 (m, 1 H), 2.87 (s, 3 H), 3.11-3.18 (m, 2 H), 3.24-3.30 (m, 4H), 3.77 (s, 3H), 4.00 (q, J = 7.0 Hz, 2H), 6.78 (s, 1 H), 7.11 (s, 1 H) | F | m/z 377 (M+H)+ (ES+) at 1.50 min, UV active |
| 1-41 | Isomer 2: ethyl 2-[4-methyl-1,2,4-oxadiazol-5-yl)piperidin-1-yl]-6-azaspiro[3.4]octane-6-carboxylate | 2 and 24 | as | (400 MHz, CDCl₃) δ: 1.24 (t, J = 7.0 Hz, 3H), 1.56-2.12 (m, 11H), 2.30-2.39 (m, 2H), 2.40 (s, 3H), 2.57-2.78 (m, 2H), 3.21-3.45 (m, 4H), 4.11 (q, J = 7.0 Hz, 2H) | C | m/z 363 (M+H)+ (ES+), at 1.70 min, UV active |
| 1-42 | Isomer 2: methyl 2-[4-(4-methyl-1H-pyrazol-1-yl)piperidin-1-yl]-6-azaspiro[3.4]octane-6-carboxylate | 3 and 73 | at | (400 MHz, CD₃OD) δ: 1.82-2.19 (m, 15 H), 2.82 (quin, J = 7.9 Hz, 1 H), 2.92-3.05 (m, 2 H), 3.27 (s, 2 H), 3.34-3.44 (m, 2 H), 3.66 (s, 3 H), 4.02-4.16 (m, 1 H), 7.27 (s, 1 H), 7.44 (s, 1 H) | E | m/z 333 (M+H)+ (ES+), at 2.77 min, UV active |
| 1-43 | Isomer 2: ethyl 2-[4-(1,2-oxazol-3-yl)piperidin-1-yl]-6-azaspiro[3.4]octane-6-carboxylate | 2 and 74 | at | (400 MHz, methanol-d₄) δ: 1.24 (t, J = 7.0 Hz, 3 H), 1.65-1.82 (m, 2 H), 1.84-2.20 (m, 10 H), 2.72-3.02 (m, 4 H), 3.27 (s, 2 H), 3.39 (q, J = 6.6 Hz, 2 H), 4.09 (q, J = 7.0 Hz, 2 H), 6.18 (s, 1 H), 8.27 (s, 1 H) | E | m/z 334 (M+H)+ (ES+), at 3.14 min, UV active |
| 1-44 | Isomer 2: ethyl 2-[4-(3-methyl-1H-pyrazol-1-yl)piperidin-1-yl]-6-azaspiro[3.4]octane-6-carboxylate | 2 and 119 | at | (400 MHz, CD₃OD) δ: 1.24 (t, J = 7.2 Hz, 3 H), 1.82-2.17 (m, 12 H), 2.22 (s, 3 H), 2.83 (quin, J = 7.9 Hz, 1 H), 3.00 (d, J = 9.4 Hz, 2 H), 3.27 (s, 2 H), 3.39 (q, J = 6.5 Hz, 2 H), 4.01-4.15 (m, 3 H), 6.04 (d, J = 2.3 Hz, 1 H), 7.52 (d, J = 2.3 Hz, 1 H) | E | m/z 347 (M+H)+ (ES+), at 3.11 min, UV active |
| 1-45 | Isomer 2: methyl 2-[4-(3-methyl-1H-pyrazol-1-yl)piperidin-1-yl]-6-azaspiro[3.4]octane-6-carboxylate | 3 and 119 | at | (400 MHz, CD₃OD) δ: 1.81-2.17 (m, 12 H), 2.22 (s, 3 H), 2.83 (quin, J = 7.9 Hz, 1 H), 2.95-3.05 (m, 2 H), 3.27 (s, 2 H), 3.39 (t, J = 6.4 Hz, 2 H), 3.66 (s, 3 H), 4.00-4.13 (m, 1 H), 6.04 (d, J = 2.3 Hz, 1 H), 7.52 (d, J = 2.3 Hz, 1 H) | E | m/z 333 (M + H)+ (ES+), at 2.84 min, UV active |
| 1-46 | Isomer 2: methyl 2-[4-(1-ethyl-1H-pyrazol-5-yl)piperidin-1-yl]-6-azaspiro[3.4]octane-6-carboxylate | 3 and 120 | at | (400 MHz, CD₃OD) δ: 1.37 (t, J = 7.2 Hz, 3 H), 1.60-1.78 (m, 2 H), 1.84-2.01 (m, 8 H), 2.07-2.18 (m, 2 H), 2.67-2.88 (m, 2 H), 2.99 (d, J = 11.7 Hz, 2 H), 3.27 (s, 2 H), 3.39 (t, J = 6.4 Hz, 2 H), 3.66 (s, 3 H), 4.12 (q, J = 7.3 Hz, 2 H), 6.09 (d, J = 2.0 Hz, 1 H), 7.38 (d, J = 2.0 Hz, 1 H) | E | m/z 347 (M + H)+ (ES+), at 2.89 min, UV active |
| 1-47 | Isomer 2: ethyl 2-[4-(1-ethyl-1H-pyrazol-5-yl)piperidin-1-yl]-6-azaspiro[3.4]octane-6-carboxylate | 2 and 120 | at | (400 MHz, CD₃OD) δ: 1.24 (t, J = 7.2 Hz, 3 H), 1.37 (t, J = 7.22 Hz, 3 H), 1.60-1.78 (m, 2 H), 1.82-2.04 (m, 8 H), 2.07-2.19 (m, 2 H), 2.67-2.87 (m, 2 H), 2.99 (d, J = 11.7 Hz, 2 H), 3.27 (s, 2 H), 3.39 (q, J = 6.6 Hz, 2 H), 4.05-4.18 (m, 4 H), 6.09 (d, J = 1.6 Hz, 1 H), 7.38 (d, J = 1.6 Hz, 1 H) | E | m/z 361 (M + H)+ (ES+), at 3.23 min, UV active |
| 1-48 | Isomer 2: methyl 2-[4-(1-propyl-1H-pyrazol-5-yl)piperidin-1-yl]-6-azaspiro[3.4]octane-6-carboxylate | 3 and 173 | as | (400 MHz, CDCl₃) δ: 0.93 (t, J = 7.4 Hz, 3 H), 1.58-2.19 (m, 13 H), 2.52-2.87 (m, 2 H), 2.93-3.12 (m, 2 H), 3.23-3.51 (m, 5 H), 3.68 (s, 3 H), 4.00 (t, J = 7.3 Hz, 2 H), 6.05 (br.s., 1 H), 7.42 (s, 1 H) | B | m/z 361 (M + H)+ (ES+), at 3.66 min, UV active |
| 1-49 | Isomer 2: ethyl 2-[4-(1-propyl-1H-pyrazol-5-yl)piperidin-1-yl]-6-azaspiro[3.4]octane-6-carboxylate | 2 and 173 | as | (400 MHz, CDCl₃) δ: 0.93 (t, J = 7.4 Hz, 3 H), 1.25 (t, J = 7.0 Hz, 3 H), 1.56-2.20 (m, 13 H), 2.51-2.83 (m, 2 H), 2.90-3.12 (m, 2 H), 3.25-3.50 (m, 5 H), 4.00 (t, J = 7.4 Hz, 2 H), 4.12 (q, J = 7.3 Hz, 2 H), 6.05 (br.s., 1 H), 7.42 (s, 1 H) | B | m/z 375 (M + H)+ (ES+), at 4.16 min, UV active |

TABLE 3-continued

| Ex. No. | Name | Intermediate | Synthetic method | $^1$H NMR | LCMS Method | LCMS data |
|---|---|---|---|---|---|---|
| 1-50 | Isomer 2: ethyl 2-[4-(1,3-thiazol-4-yl)piperidin-1-yl]-6-azaspiro[3.4]octane-6-carboxylate | 2 and 164 | as | (400 MHz, CDCl$_3$) δ: 1.25 (t, J = 7.0 Hz, 3 H), 1.51-2.31 (m, 11 H), 2.63-3.16 (m, 4 H), 3.20-3.47 (m, 5 H), 4.12 (q, J = 7.3 Hz, 2 H), 6.90-7.05 (br.s., 1 H), 8.76 (s, 1 H) | B | m/z 350 (M + H)$^+$ (ES+), at 1.39 min, weakly UV active |
| 1-51 | Isomer 2: ethyl 2-{4-[1-(2-methoxyethyl)-1H-imidazol-2-yl]piperidin-1-yl}-6-azaspiro[3.4]octane-6-carboxylate | Example 1-1 and 165 | 9 | (400 MHz, CDCl$_3$) δ: 1.25 (t, J = 7.2 Hz, 3 H), 1.74-2.15 (m, 12 H), 2.72 (br.s., 2 H), 3.01 (br.s., 2 H), 3.28-3.46 (m, 4 H), 3.32 (s, 3 H), 3.61 (t, J = 5.5 Hz, 2 H), 4.04 (t, J = 5.5 Hz, 2 H), 4.11 (q, J = 7.2 Hz, 2 H), 6.89 (s, 1 H), 6.96 (s, 1 H) | B | m/z 391 (M + H)$^+$ (ES+), at 3.56 min, weakly UV active |
| 1-52 | Isomer 2: ethyl 2-{4-[1-(cyanomethyl)-1H-imidazol-2-yl]piperidin-1-yl}-6-azaspiro[3.4]octane-6-carboxylate | Example 1-1 and 166 | h | (400 MHz, CDCl$_3$) δ: 1.25 (t, J = 7.0 Hz, 3 H), 1.47-2.32 (m, 11 H), 2.64-3.26 (m, 4 H), 3.27-3.50 (m, 5 H), 4.06-4.17 (m, 2 H), 4.90 (s, 2 H), 6.97 (br.s., 1 H), 7.02 (s, 1 H) | B | m/z 372 (M + H)$^+$ (ES+), at 3.24 min, weakly UV active |
| 1-53 | Isomer 2: (2-{1-[6-(ethoxycarbonyl)-6-azaspiro[3.4]oct-2-yl]piperidin-4-yl}-1H-imidazol-1-yl)acetic acid | Example 1-1 and 167 | i | (400 MHz, DMSO-d$_6$) δ: 1.18 (t, J = 7.2 Hz, 3 H), 1.59-1.94 (m, 10 H), 1.95-2.08 (m, 2 H), 2.80-2.93 (m, 2 H), 3.95-4.07 (q, J = 7.0 Hz, 2 H), 4.29-4.38 (br.s., 2 H), 6.70 (s, 1 H), 6.89 (s, 1 H), 7 protons obscured by water peak. | B | m/z 391 (M + H)$^+$ (ES+), at 1.57 min, UV inactive |
| 1-54 | Isomer 2: ethyl 2-{4-[1-(methylamino)-2-oxoethyl]-1H-imidazol-2-yl]piperidin-1-yl}-6-azaspiro[3.4]octane-6-carboxylate | Example 1-53 and 168 | i | (400 MHz, CDCl$_3$) δ: 1.25 (t, J = 7.2 Hz, 3 H), 1.71-2.33 (m, 11 H), 2.68-3.20 (m, 4 H), 2.81 (d, J = 4.7 Hz, 3 H), 3.27-3.48 (m, 5 H), 4.11 (q, J = 7.0 Hz, 2 H), 4.66 (s, 2 H), 6.01 (br.s., 1 H), 6.91 (d, J = 5.5 Hz, 1 H), 7.05 (s, 1 H) | B | m/z 404 (M + H)$^+$ (ES+), at 2.18 min, weakly UV active |
| 1-55 | Isomer 2: methyl 2-[4-(1,4-dimethyl-1H-pyrazol-3-yl)piperidin-1-yl]-6-azaspiro[3.4]octane-6-carboxylate | 3 and 177 | as | (300 MHz, CDCl3) δ: 1.51-2.26 (m, 15 H), 2.56-2.82 (m, 2 H), 2.92-3.14 (m, 2 H), 3.20-3.53 (m, 4 H), 3.69 (s, 3 H), 3.83 (s, 3 H), 7.18 (s, 1 H) | B | m/z 347 (M + H)$^+$ (ES+), at 4.22 min, UV active |
| 1-56 | Isomer 2: ethyl 2-[4-(1,4-dimethyl-1H-pyrazol-3-yl)piperidin-1-yl]-6-azaspiro[3.4]octane-6-carboxylate | 2 and 177 | as | (400 MHz, CDCl$_3$) δ: 1.27 (t, J = 7.0 Hz, 3 H), 1.63 (s, 5 H), 1.68-2.25 (m, 10 H), 2.43-2.75 (m, 2 H), 2.84-3.06 (m, 2 H), 3.29-3.43 (m, 4 H), 3.82 (br.s., 3 H), 4.10-4.18 (m, 2 H), 7.18 (s, 1 H) | B | m/z 361 (M + H)$^+$ (ES+), at 3.70 min, UV active |
| 1-57 | Isomer 2: methyl 2-[4-(1,4-dimethyl-1H-pyrazol-5-yl)piperidin-1-yl]-6-azaspiro[3.4]octane-6-carboxylate | 3 and 178 | as | (300 MHz, CDCl$_3$) δ: 1.53-2.20 (m, 15 H), 2.54-2.90 (m, 2 H), 2.94-3.17 (m, 2 H), 3.27-3.50 (m, 4 H), 3.68 (s, 3 H), 3.77 (s, 3 H), 7.04 (s, 1 H) | B | m/z 347 (M + H)$^+$ (ES+), at 4.74 min, UV active |
| 1-58 | Isomer 2: ethyl 2-[4-(1,4-dimethyl-1H-pyrazol-5-yl)piperidin-1-yl]-6-azaspiro[3.4]octane-6-carboxylate | 2 and 178 | as | (400 MHz, CDCl$_3$) δ: 1.25 (t, J = 7.0 Hz, 3 H), 1.67-2.19 (m, 15 H), 2.54-2.82 (m, 2 H), 2.93-3.12 (m, 2 H), 3.25-3.48 (m, 4 H), 3.77 (s, 3 H), 4.11 (q, J = 7.3 Hz, 2 H), 7.04 (s, 1 H) | B | m/z 361 (M + H)$^+$ (ES+), at 4.07 min, UV active |
| 1-59 | Isomer 2: ethyl 2-[4-(1-ethyl-4-methyl-1H-pyrazol-5-yl)piperidin-1-yl]-6-azaspiro[3.4]octane-6-carboxylate | 2 and 173 | b | (400 MHz, CD$_3$OD) δ: 1.25 (t, J = 7.2 Hz, 3 H), 1.33 (t, J =7.2 Hz, 3 H), 1.77 (d, J = 10.7 Hz, 2 H), 1.90-2.10 (m, 8 H), 2.10-2.24 (m, 2 H), 2.13 (s, 3 H), 2.79-2.96 (m, 2 H), 3.08 (d, J = 8.9 Hz, 2 H), 3.28-3.30 (m, 2 H), 3.37-3.45 (m, 2 H), 4.07-4.18 (m, 4 H), 7.18 (s, 1 H) | I | m/z 375 (M + H)$^+$ (ES+), at 4.22 min, weakly UV active |

TABLE 3-continued

| Ex. No. | Name | Intermediate | Synthetic method | $^1$H NMR | LCMS Method | LCMS data |
|---|---|---|---|---|---|---|
| 1-60 | Isomer 2: ethyl 2-[4-(4-ethyl-1-methyl-1H-pyrazol-5-yl)piperidin-1-yl]-6-azaspiro[3.4]octane-6-carboxylate | 2 and 251 | b | (400 MHz, CD$_3$OD) δ: 1.18-1.40 (m, 6 H), 1.96-2.10 (m, 3H), 2.11-2.31 (m, 5H), 2.33-2.46 (m, 2H), 2.59 (q, J = 7.5 Hz, 2H), 2.67-2.84 (m, 2H), 3.07-3.23 (m, 1H), 3.37-3.61 (m, 6H), 3.85 (s, 3H), 4.13 (q, J = 6.8 Hz, 3H), 7.28 (s, 1H). | I | m/z 375 (M + H)$^+$ (ES+), at 4.36 min, UV active |
| 1-61 | Isomer 2: ethyl 2-[4-(2H-1,2,3-triazol-2-yl)piperidin-1-yl]-6-azaspiro[3.4]octane-6-carboxylate | 2 and 247 | ak | (400 MHz, CD$_3$OD) δ: 1.27 (t, J = 7.1 Hz, 3H), 1.88-2.02 (m, 4H), 2.12-2.28 (m, 8H), 2.81-2.92 (m, 1H), 2.93-3.05 (m, 2H), 3.27-3.36 (m, 2H), 3.37-3.46 (m, 2H), 4.12 (q, J = 7.1 Hz, 2H), 4.51-4.61 (m, 1H), 7.69 (s, 2H). | I | m/z 334 (M + H)$^+$ (ES+), at 3.90 min, UV active |
| 1-62 | Isomer 2: ethyl 2-[4-(1H-tetrazol-1-yl)piperidin-1-yl]-6-azaspiro[3.4]octane-6-carboxylate | 2 and 215 | b | (400 MHz, CD$_3$OD) δ: 1.25 (t, J = 7.0 Hz, 3 H), 1.90-2.00 (m, 4 H), 2.05-2.21 (m, 6 H), 2.21-2.32 (m, 2 H), 2.81-2.91 (m, 1 H), 3.02 (d, J = 7.3 Hz, 2 H), 3.28 (s, 2 H), 3.36-3.44 (m, 2 H), 4.10 (q, J = 7.1 Hz, 2 H), 4.60-4.71 (m, 1 H), 9.26 (s, 1 H) | I | m/z 335 (M + H)$^+$ (ES+), at 3.47 min, weakly UV active |
| 1-63 | Isomer 2: ethyl 2-[4-(5-methyl-1H-tetrazol-1-yl)piperidin-1-yl]-6-azaspiro[3.4]octane-6-carboxylate | 2 and 255 | b | (400 MHz, CD$_3$OD) δ: 1.20-1.34 (m, 4H), 1.90-2.03 (m, 4H), 2.04-2.32 (m, 9H), 2.61 (s, 3H), 2.84-2.93 (m, 1H), 3.02-3.13 (m, 2H), 3.30-3.52 (m, 2H), 4.12 (q, J = 7.1 Hz, 2H), 4.42-4.54 (m, 1H). | I | m/z 349 (M+H)$^+$ (ES+), at 3.44 min, UV active |
| 1-64 | Isomer 2: ethyl 2-[4-(1-methyl-1H-tetrazol-5-yl)piperidin-1-yl]-6-azaspiro[3.4]octane-6-carboxylate | 2 and 195 | b | (400 MHz, CDCl$_3$) δ: 1.25 (t, J = 7.2 Hz, 3 H), 1.82-2.31 (m, 8 H), 2.74-3.72 (m, 12 H), 4.02-4.16 (m, 5 H) | I | m/z 349 (M + H)$^+$ (ES+), at 3.40 min, UV active |
| 1-65 | Isomer 2: ethyl 2-[4-(1-ethyl-1H-tetrazol-5-yl)piperidin-1-yl]-6-azaspiro[3.4]octane-6-carboxylate | 2 and 320 | ak | (400 MHz, DMSO-d$_6$) δ: 1.17 (t, J = 7.3 Hz, 3 H), 1.42 (t, J = 7.3 Hz, 3 H), 1.62-1.96 (m, 10 H), 1.96-2.07 (m, 2 H), 2.66-2.76 (m, 1 H), 2.82-2.91 (m, 2 H), 2.95-3.06 (m, 1 H), 3.17 (d, J = 7.0 Hz, 2 H), 3.25-3.32 (m, 2 H), 4.00 (q, J = 7.2 Hz, 2 H), 4.39 (q, J = 7.3 Hz, 2 H) | I | m/z 363 (M + H)$^+$ (ES+), at 3.75 min, UV active |
| 1-66 | Isomer 2: ethyl 2-[4-(2-ethyl-2H-tetrazol-5-yl)piperidin-1-yl]-6-azaspiro[3.4]octane-6-carboxylate | 2 and 319 | ak | (400 MHz, DMSO-d$_6$) δ: 1.17 (t, J = 7.2 Hz, 3 H), 1.49 (t, J = 7.3 Hz, 3 H), 1.61-1.75 (m, 2 H), 1.75-1.92 (m, 6 H), 1.92-2.06 (m, 4 H), 2.63-2.74 (m, 1 H), 2.79 (d, J = 11.3 Hz, 2 H), 2.88 (tt, J = 11.4, 4.0 Hz, 1 H), 3.16 (d, J = 6.7 Hz, 2 H), 3.28 (q, J = 7.0 Hz, 2 H), 4.00 (q, J = 7.0 Hz, 2 H), 4.64 (q, J = 7.3 Hz, 2 H) | I | m/z 363 (M + H)$^+$ (ES$^+$), at 4.06 min, UV active |
| 1-67 | Isomer 2: ethyl 2-[4-(1-cyclopropyl-1H-tetrazol-5-yl)piperidin-1-yl]-6-azaspiro[3.4]octane-6-carboxylate | 2 and 218 | b | (400 MHz, DMSO-d$_6$) δ: 1.12-1.26 (m, 7 H), 1.66-1.94 (m, 8 H), 1.94-2.06 (m, 4 H), 2.66-2.79 (m, 1 H), 2.89 (d, J = 11.6 Hz, 2 H), 3.03-3.14 (m, 1 H), 3.18 (d, J = 7.0 Hz, 2 H), 3.26-3.35 (m, 2 H), 3.84 (s, 1 H), 3.96-4.07 (m, 2 H) | I | m/z 375 (M + H)$^+$ (ES$^+$), at 3.88 min, weakly UV active |
| 1-68 | Isomer 2: (1,1-$^2$H$_2$)ethyl 2-[4-(1H-pyrazol-1-yl)piperidin-1-yl]-6-azaspiro[3.4]octane-6-carboxylate | 302 and 304 | j | (400 MHz, DMSO-d$_6$) δ: 1.13 (s, 3 H), 1.73-2.03 (m, 12 H), 2.61-2.74 (m, 1 H), 2.78-2.88 (m, 2 H), 3.14 (d, J = 6.2 Hz, 2 H), 3.26 (q, J = 6.6 Hz, 2 H), 4.08-4.17 (m, 1 H), 6.20 (t, J = 2.0 Hz, 1 H), 7.37-7.44 (m, 1 H), 7.71-7.81 (m, 1 H) | E | m/z 335 (M + H)$^+$ (ES$^+$), at 3.59 min, UV inactive |
| 1-69 | Isomer 2: (2,2,2-$^2$H$_3$)ethyl 2-[4-(1H-pyrazol-1-yl)piperidin-1-yl]-6-azaspiro[3.4]octane-6-carboxylate | 302 and 305 | j | (400 MHz, DMSO-d$_6$) δ: 1.73-2.03 (m, 12 H), 2.61-2.74 (m, 1 H), 2.84 (d, J = 7.8 Hz, 2 H), 3.14 (d, J = 6.2 Hz, 2 H), 3.26 (q, J = 6.6 Hz, 2 H), 3.96 (s, 2 H), 4.07-4.17 (m, 1 H), 6.20 (t, J = 2.0 Hz, 1 H), 7.35-7.45 (m, 1 H), 7.68-7.80 (m, 1 H) | E | m/z 336 (M + H)$^+$ (ES$^+$), at 3.58 min, UV inactive |

TABLE 3-continued

| Ex. No. | Name | Intermediate | Synthetic method | ¹H NMR | LCMS Method | LCMS data |
|---|---|---|---|---|---|---|
| 1-70 | Isomer 2: (²H₅)ethyl 2-[4-(1H-pyrazol-1-yl)piperidin-1-yl]-6-azaspiro[3.4]octane-6-carboxylate | 302 and 303 | j | (400 MHz, DMSO-d₆) δ: 1.73-2.03 (m, 12 H), 2.68 (t, J = 7.4 Hz, 1 H), 2.84 (d, J = 7.8 Hz, 2 H), 3.14 (d, J = 6.2 Hz, 2 H), 3.22-3.29 (m, 2 H), 4.07-4.15 (m, 1 H), 6.20 (t, J = 2.0 Hz, 1 H), 7.36-7.43 (m, 1 H), 7.75 (m, 1 H) | E | m/z 338 (M + H)⁺ (ES⁺), at 3.58 min, UV inactive |
| 1-71 | Isomer 2: (1,1-²H₂)ethyl 2-[4-(1-methyl-1H-pyrazol-5-yl)piperidin-1-yl]-6-azaspiro[3.4]octane-6-carboxylate | 306 and 304 | j | (400 MHz, DMSO-d₆) δ: 1.13 (s, 3 H), 1.47 (q, J = 11.8 Hz, 2 H), 1.65-1.94 (m, 8 H), 1.94-2.03 (m, 2 H), 2.56-2.72 (m, 2 H), 2.82 (d, J = 11.3 Hz, 2 H), 3.13 (d, J = 6.2 Hz, 2 H), 3.23-3.28 (m, 2 H), 3.68-3.74 (s, 3 H), 6.02 (s, 1 H), 7.25 (d, J = 1.6 Hz, 1 H) | E | m/z 349 (M + H)⁺ (ES⁺), at 3.59 min, UV inactive |
| 1-72 | Isomer 2: (2,2,2-²H₃)ethyl 2-[4-(1-methyl-1H-pyrazol-5-yl)piperidin-1-yl]-6-azaspiro[3.4]octane-6-carboxylate | 306 and 305 | j | (400 MHz, DMSO-d₆) δ: 1.47 (q, J = 12.0 Hz, 2 H), 1.72-1.93 (m, 8 H), 1.93-2.03 (m, 2 H), 2.56-2.71 (m, 2 H), 2.82 (d, J = 10.2 Hz, 2 H), 3.13 (d, J = 5.9 Hz, 2 H), 3.22-3.29 (m, 2 H), 3.68-3.75 (s, 3 H), 3.96 (s, 2 H), 6.02 (s, 1 H), 7.25 (d, J = 1.6 Hz, 1 H) | E | m/z 350 (M + H)⁺ (ES⁺), at 3.58 min, UV inactive |
| 1-73 | Isomer 2: (²H₅)ethyl 2-[4-(1-methyl-1H-pyrazol-5-yl)piperidin-1-yl]-6-azaspiro[3.4]octane-6-carboxylate | 306 and 303 | j | (400 MHz, DMSO-d₆) δ: 1.40-1.54 (m, 2 H), 1.67-1.93 (m, 8 H), 1.94-2.05 (m, 2 H), 2.57-2.71 (m, 2 H), 2.82 (d, J = 10.9 Hz, 2 H), 3.13 (d, J = 5.9 Hz, 2 H), 3.22-3.28 (m, 2 H), 3.72 (s, 3 H), 6.02 (s, 1 H), 7.23-7.28 (m, 1 H) | E | m/z 352 (M + H)⁺ (ES⁺), at 3.56 min, UV inactive |
| 2-1 | Isomer 2: ethyl 2-[4-(pyrrolidin-2-yl)piperidin-1-yl]-6-azaspiro[3.4]octane-6-carboxylate | 2 and 53 | m | (400 MHz, DMSO-d₆) δ: 1.16 (t, J = 7.1 Hz, 3 H), 1.49-1.87 (m, 13 H), 1.97 (t, J = 9.2 Hz, 2 H), 2.55-2.85 (m, 9 H), 3.14 (d, J = 6.1 Hz, 2 H), 3.24-3.27 (m, 1 H), 4.00 (q, J = 7.1 Hz, 2 H), NH not observed | F | m/z 336 (M + H)⁺ (ES+), at 1.70 min, UV inactive |
| 2-2 | Isomer 2: ethyl 2-[4-(1-formylpyrrolidin-2-yl)piperidin-1-yl]-6-azaspiro[3.4]octane-6-carboxylate | 122 and 63 | k | (400 MHz, CDCl₃) δ: 1.17-1.57 (m, 5 H), 1.59-2.30 (m, 14 H), 2.57-2.73 (m, 1 H), 2.84-3.01 (m, 2 H), 3.17-3.51 (m, 6 H), 3.55-3.75 (m, 2 H), 4.12 (q, J = 7.0 Hz, 2 H), 8.19-8.31 (m, 1 H) | G | m/z 364 (M + H)⁺ (ES+), at 5.07 min, UV active |
| 2-3 | Isomer 2: ethyl 2-[4-(1-acetylpyrrolidin-2-yl)piperidin-1-yl]-6-azaspiro[3.4]octane-6-carboxylate | 122 and 60 | m | (400 MHz, CDCl₃) δ: 1.22-1.31 (m, 3 H), 1.53-1.77 (m, 11 H), 1.78-1.99 (m, 6 H), 2.00-2.12 (m, 5 H), 2.58-2.69 (m, 1 H), 2.84-2.99 (m, 2 H), 3.22-3.33 (m, 2 H), 3.34-3.53 (m, 3 H), 4.13 (q, J = 7.2 Hz, 2 H) | G | m/z 378 (M + H)⁺ (ES+), at 5.22 min, UV active |
| 2-4 | Isomer 2: ethyl 2-{4-[1-(trifluoroacetyl)pyrrolidin-2-yl]piperidin-1-yl}-6-azaspiro[3.4]octane-6-carboxylate | 122 and 62 | L | (400 MHz, CD₃OD) δ: 1.27 (t, J = 7.1 Hz, 3 H), 1.30-1.68 (m, 6 H), 1.74-2.21 (m, 12 H), 2.75-2.90 (m, 1 H), 3.00 (d, J = 10.4 Hz, 2 H), 3.39-3.45 (m, 2 H), 3.51-3.61 (m, 1 H), 3.75-3.87 (m, 1 H), 4.11 (q, J = 7.1 Hz, 2 H), 4.15-4.23 (m, 1 H), 4.64 (br.s., 1 H) | G | m/z 432 (M + H)⁺ (ES+), at 6.50 min, UV active |
| 2-5 | Isomer 2: methyl 2-[4-(1-propanoylpyrrolidin-2-yl)piperidin-1-yl]-6-azaspiro[3.4]octane-6-carboxylate | 323 and 54 | m | (400 MHz, DMSO-d₆) δ: 0.97 (t, J = 7.1 Hz, 3 H), 1.11-1.27 (m, 2 H), 1.36-1.62 (m, 4 H), 1.66-1.89 (m, 9 H), 1.93-2.02 (m, 2 H), 2.24 (q, J = 7.1 Hz, 2 H), 2.56-2.65 (m, 1 H), 2.74-2.86 (m, 2 H), 3.14 (d, J = 2.8 Hz, 2 H), 3.22-3.30 (m, 3 H), 3.39-3.47 (m, 1 H), 3.56 (s, 3 H), 3.84-3.92 (m, 1 H) | G | m/z 378 (M + H)⁺ (ES+), at 5.21 min, UV active |

TABLE 3-continued

| Ex. No. | Name | Intermediate | Synthetic method | $^1$H NMR | LCMS Method | LCMS data |
|---|---|---|---|---|---|---|
| 2-6 | Isomer 2: ethyl 2-{4-(1-propanoylpiperidin-2-yl)piperidin-1-yl]-6-azaspiro[3.4]octane-6-carboxylate | 122 and 54 | m | (400 MHz, DMSO-d$_6$) δ: 0.93-0.99 (m, 3 H), 1.16 (t, J = 7.0 Hz, 3 H), 1.20-1.27 (m, 1 H), 1.35-1.44 (m, 2 H), 1.45-1.62 (m, 2 H), 1.64-1.89 (m, 7 H), 1.90-2.01 (m, 2 H), 2.19-2.29 (m, 2 H), 2.54-2.63 (m, 3 H), 2.78 (d, J = 11.3 Hz, 2 H), 3.14 (d, J = 6.1 Hz, 2 H), 3.22-3.30 (m, 2 H), 3.39-3.48 (m, 3 H), 3.76-3.91 (m, 1 H), 3.99 (q, J = 7.0 Hz, 2 H) | G | m/z 392 (M + H)$^+$ (ES+), at 5.27 min, UV active |
| 2-7 | Isomer 2: ethyl 2-{4-[(2S)-1-propanoylpyrrolidin-2-yl]piperidin-1-yl]-6-azaspiro[3.4]octane-6-carboxylate | 54 and 127 | m | (400 MHz, DMSO-d$_6$) δ: 0.92-1.00 (m, 3 H), 1.12-1.28 (m, 6 H), 1.32-1.63 (m, 4 H), 1.64-1.90 (m, 10 H), 1.92-2.03 (m, 2 H), 2.19-2.29 (m, 2 H), 2.73-2.88 (m, 2 H), 3.14 (d, J = 5.5 Hz, 2 H), 3.23-3.30 (m, 2 H), 3.38-3.47 (m, 1 H), 3.74-3.93 (m, 1 H), 4.00 (q, J = 7.0 Hz, 2 H) | F | m/z 392 (M + H)$^+$ (ES+), at 1.69 min, UV inactive |
| 2-8 | Isomer 2: ethyl 2-{4-[(2S)-1-(cyclopropylcarbonyl)pyrrolidin-2-yl]piperidin-1-yl]-6-azaspiro[3.4]octane-6-carboxylate | 59 and 127 | m | (400 MHz, CD$_3$OD) δ: 0.73-0.87 (m, 3 H), 0.88-1.03 (m, 1 H), 1.24 (t, J = 7.2 Hz, 3 H), 1.30-1.46 (m, 2 H), 1.49-2.03 (m, 15 H), 2.04-2.15 (m, 2 H), 2.67-2.82 (m, 1 H), 2.89-3.01 (m, 2 H), 3.25 (s, 2 H), 3.34-3.42 (m, 2 H), 3.63 (s, 1 H), 4.01-4.15 (m, 3 H) | E | m/z 404 (M + H)$^+$ (ES+), at 3.49 min, UV inactive |
| 2-9 | Isomer 2: ethyl 2-{4-[(2S)-1-(cyclobutylcarbonyl)pyrrolidin-2-yl]piperidin-1-yl]-6-azaspiro[3.4]octane-6-carboxylate | 60 and 127 | m | (400 MHz, CD$_3$OD) δ: 1.24 (t, J = 7.1 Hz, 3 H), 1.28-1.61 (m, 5 H), 1.66-2.28 (m, 20 H), 2.67-2.78 (m, 1 H), 2.88-2.99 (m, 2 H), 3.25 (s, 2 H), 3.35-3.52 (m, 3 H), 3.99-4.05 (m, 1 H), 4.09 (q, J = 7.1 Hz, 2 H) | E | m/z 418 (M + H)$^+$ (ES+), at 3.67 min, UV inactive |
| 2-10 | Isomer 2: methyl 2-{4-[1-(methoxycarbonyl)pyrrolidin-2-yl]piperidin-1-yl]-6-azaspiro[3.4]octane-6-carboxylate | 55 and 323 | m | (400 MHz, DMSO-d$_6$) δ: 1.07-1.26 (m, 2 H), 1.38-1.49 (m, 2 H), 1.50-1.62 (m, 2 H), 1.69-1.78 (m, 6 H), 1.78-1.88 (m, 2 H), 1.93-2.01 (m, 2 H), 2.54-2.65 (m, 2 H), 2.80 (d, J = 10.1 Hz, 2 H), 3.15 (d, J = 2.8 Hz, 2 H), 3.24-3.31 (m, 2 H), 3.37-3.43 (m, 2 H), 3.53-3.60 (m, 6 H), 3.62-3.70 (m, 1 H) | G | m/z 380 (M + H)$^+$ (ES+), at 5.62 min, UV active |
| 2-11 | Isomer 2: ethyl 2-{4-[1-(methoxycarbonyl)pyrrolidin-2-yl]piperidin-1-yl]-6-azaspiro[3.4]octane-6-carboxylate | 55 and 122 | m | (400 MHz, DMSO-d$_6$) δ: 1.09-1.28 (m, 6 H), 1.40-1.52 (m, 2 H), 1.70-1.88 (m, 8 H), 1.93-2.05 (m, 2 H), 2.53-2.59 (m, 3 H), 2.76-2.89 (m, 1 H), 3.10-3.31 (m, 7 H), 3.56 (s, 3 H), 3.63-3.70 (m, 1 H), 4.00 (q, J = 7.0 Hz, 2 H) | G | m/z 394 (M + H)$^+$ (ES+), at 5.74 min, UV active |
| 2-12 | Isomer 2: ethyl 2-{4-[(2S)-1-(methoxycarbonyl)pyrrolidin-2-yl]piperidin-1-yl]-6-azaspiro[3.4]octane-6-carboxylate | 55 and 127 | m | (400 MHz, DMSO-d$_6$) δ: 1.07-1.29 (m, 6 H), 1.38-1.50 (m, 2 H), 1.50-1.63 (m, 2 H), 1.69-1.87 (m, 8 H), 1.92-2.03 (m, 2 H), 2.57-2.66 (m, 1 H), 2.80 (d, J = 10.4 Hz, 2 H), 3.14 (d, J = 5.8 Hz, 2 H), 3.27 (q, J = 6.5 Hz, 2 H), 3.38-3.43 (m, 2 H), 3.56 (s, 3 H), 3.67 (brs., 1 H), 4.00 (q, J = 7.0 Hz, 2 H) | F | m/z 394 (M+H)$^+$ (ES+), at 1.73 min, UV active |
| 2-13 | Isomer 2: ethyl 2-{4-[(2R)-1-(methoxycarbonyl)pyrrolidin-2-yl]piperidin-1-yl]-6-azaspiro[3.4]octane-6-carboxylate | 55 and 162 | m | (400 MHz, CD$_3$OD) δ: 1.24 (t, J = 7.1 Hz, 3 H), 1.29-1.46 (m, 2 H), 1.51-1.63 (m, 2 H), 1.66-1.97 (m, 11 H), 2.04-2.15 (m, 2 H), 2.73 (quin, J = 8.0 Hz, 1 H), 2.93 (d, J = 11.4 Hz, 2 H), 3.25 (app s, 3 H), 3.33-3.43 (m, 2 H), 3.44-3.55 (m, 1 H), 3.66 (s, 3 H), 3.72-3.84 (m, 1 H), 4.09 (q, J = 7.1 Hz, 2 H) | E | m/z 394 (M + H)$^+$ (ES+), at 4.30 min, UV inactive |

TABLE 3-continued

| Ex. No. | Name | Intermediate | Synthetic method | ¹H NMR | LCMS Method | LCMS data |
|---|---|---|---|---|---|---|
| 2-14 | Isomer 2: ethyl 2-{4-[1-(ethoxycarbonyl)pyrrolidin-2-yl]piperidin-1-yl}-6-azaspiro[3.4]octane-6-carboxylate | 56 and 122 | m | (400 MHz, DMSO-d₆) δ: 1.11-1.21 (m, 6 H), 1.38-1.63 (m, 6 H), 1.67-1.87 (m, 9 H), 1.92-2.00 (m, 2 H), 2.55-2.67 (m, 2 H), 2.75-2.84 (m, 2 H), 3.09-3.22 (m, 3 H), 3.24-3.30 (m, 2 H), 3.62-3.59 (m, 1 H), 4.00 (m, 4 H) | G | m/z 408 (M + H)⁺ (ES+) at 6.01 min, UV active |
| 2-15 | Isomer 2: methyl 2-{4-[(2S)-1-(methylcarbamoyl)pyrrolidin-2-yl]piperidin-1-yl}-6-azaspiro[3.4]octane-6-carboxylate | 57 and 157 | m | (400 MHz, CD₃OD) δ: 1.24-1.42 (m, 2 H), 1.51-1.64 (m, 2 H), 1.67-1.98 (m, 12 H), 2.09 (dd, J = 11.0, 7.6 Hz, 2 H), 2.68-2.77 (m, 4 H), 2.93 (d, J = 11.0 Hz, 2 H), 3.22-3.26 (m, 2 H), 3.35-3.41 (m, 3 H), 3.66 (s, 3 H), 3.82-3.91 (m, 1 H), NH not observed | E | m/z 379 (M + H)⁺ (ES+), at 2.23 min, UV inactive |
| 2-16 | Isomer 2: ethyl 2-{4-[1-(methylcarbamoyl)pyrrolidin-2-yl]piperidin-1-yl}-6-azaspiro[3.4]octane-6-carboxylate | 57 and 122 | m | (400 MHz, DMSO-d₆) δ: 1.16 (t, J = 7.0 Hz, 3 H), 1.37-1.47 (m, 2 H), 1.49-1.63 (m, 3 H), 1.64-1.88 (m, 9 H), 1.92-2.03 (m, 2 H), 2.53-2.64 (m, 4 H), 2.73-2.85 (m, 2 H), 3.08-3.30 (m, 7 H), 3.67-3.76 (m, 1 H), 3.99 (q, J = 7.0 Hz, 2 H), 5.93-6.02 (m, 1 H) | G | m/z 393 (M + H)⁺ (ES+), at 5.46 min, UV active |
| 2-17 | Isomer 1: ethyl 2-{4-[(2S)-1-(methylcarbamoyl)pyrrolidin-2-yl]piperidin-1-yl}-6-azaspiro[3.4]octane-6-carboxylate | 57 and 127 | m | (400 MHz, CD₃OD) δ: 1.25 (t, J = 7.0 Hz, 3 H), 1.28-1.43 (m, 2 H), 1.49-1.64 (m, 2 H), 1.66-1.95 (m, 12 H), 2.06-2.15 (m, 2 H), 2.65-2.78 (m, 4 H), 2.93 (d, J = 11.3 Hz, 2 H), 3.21-3.29 (m, 2 H), 3.33-3.38 (m, 3 H), 3.82-3.89 (m, 1 H), 4.10 (q, J = 7.0 Hz, 2 H) NH not observed | E | m/z 393 (M + H)⁺ (ES+), at 2.99 min, UV inactive |
| 2-17 | Isomer 2: ethyl 2-{4-[(2S)-1-(methylcarbamoyl)pyrrolidin-2-yl]piperidin-1-yl}-6-azaspiro[3.4]octane-6-carboxylate | 57 and 127 | m | (400 MHz, CD₃OD) δ: 1.24 (t, J = 7.1 Hz, 3 H), 1.27-1.42 (m, 2 H), 1.50-1.63 (m, 2 H), 1.67-1.96 (m, 12 H), 2.04-2.13 (m, 2 H), 2.66-2.78 (m, 4 H), 2.93 (d, J = 11.3 Hz, 2 H), 3.23-3.27 (m, 2 H), 3.34-3.41 (m, 3 H), 3.83-3.89 (m, 1 H), 4.09 (q, J = 7.1 Hz, 2 H) | E | m/z 393 (M + H)⁺ (ES+), at 3.16 min, UV inactive |
| 2-18 | Isomer 2: ethyl 2-{4-[(2R)-1-(methylcarbamoyl)pyrrolidin-2-yl]piperidin-1-yl}-6-azaspiro[3.4]octane-6-carboxylate | 57 and 162 | m | (400 MHz, CD₃OD) δ: 1.24 (t, J = 7.0 Hz, 3 H), 1.29-1.43 (m, 2 H), 1.50-1.65 (m, 2 H), 1.66-1.98 (m, 11 H), 2.09 (dd, J = 11.1, 7.6 Hz, 2 H), 2.67-2.77 (m, 4 H), 2.93 (d, J = 11.0 Hz, 2 H), 3.22-3.27 (m, 2 H), 3.35-3.42 (m, 2 H), 3.82-3.89 (m, 1 H), 4.09 (q, J = 7.0 Hz, 2 H), NH not observed | E | m/z 393 (M + H)⁺ (ES+), at 2.20 min, UV inactive |
| 2-19 | Isomer 2: ethyl 2-{4-[1-(ethylcarbamoyl)pyrrolidin-2-yl]piperidin-1-yl}-6-azaspiro[3.4]octane-6-carboxylate | 122 and 158 | q | (400 MHz, CDCl₃) δ: 1.16 (t, J = 7.3 Hz, 3 H), 1.22-1.41 (m, 5 H), 1.50-1.74 (m, 4 H), 1.76-1.96 (m, 9 H), 1.99-2.10 (m, 2 H), 2.56-2.69 (m, 2 H), 2.82-2.98 (m, 2 H), 3.18-3.47 (m, 8 H), 3.86-3.97 (m, 1 H), 4.06-4.25 (m, 3 H) | G | m/z 407 (M + H)⁺ (ES+) at 5.46 min, UV active |
| 2-20 | Isomer 2: ethyl 2-{4-[1-(dimethylcarbamoyl)pyrrolidin-2-yl]piperidin-1-yl}-6-azaspiro[3.4]octane-6-carboxylate | 58 and 122 | m | (400 MHz, DMSO-d₆) δ: 1.08-1.15 (m, 2 H), 1.16 (t, J = 7.0 Hz, 3 H), 1.36-1.63 (m, 7 H), 1.70-1.88 (m, 6 H), 1.93-2.01 (m, 2 H), 2.73 (s, 6 H), 2.78-2.87 (m, 2 H), 3.12-3.30 (m, 7 H), 3.87-3.95 (m, 1 H), 4.00 (q, J = 7.0 Hz, 2 H) | G | m/z 407 (M + H)⁺ (ES+) at 5.81 min, UV active |
| 2-21 | Isomer 2: ethyl 2-{4-[(2S)-1-(dimethylcarbamoyl)pyrrolidin-2-yl]piperidin-1-yl}-6-azaspiro[3.4]octane-6-carboxylate | 58 and 127 | m | (400 MHz, DMSO-d₆) δ: 1.09-1.15 (m, 2 H), 1.16 (t, J = 7.0 Hz, 3 H), 1.38-1.69 (m, 7 H), 1.72-1.89 (m, 6 H), 1.93-2.03 (m, 2 H), 2.72 (s, 6 H), 2.78-2.82 (m, 2 H), 3.11-3.30 (m, 7 H), 3.86-3.95 (m, 1 H), 3.99 (q, J = 7.0 Hz, 2 H) | G | m/z 407 (M + H)⁺ (ES+) at 5.92 min, UV active |

TABLE 3-continued

| Ex. No. | Name | Intermediate | Synthetic method | ¹H NMR | LCMS Method | LCMS data |
|---|---|---|---|---|---|---|
| 2-22 | Isomer 2: ethyl 2-[4-(1-methylpyrrolidin-2-yl)piperidin-1-yl]-6-azaspiro[3.4]octane-6-carboxylate | 122 | o | (400 MHz, CD₃OD) δ: 1.22-1.45 (m, 7 H), 1.54-1.87 (m, 8 H), 1.88-2.01 (m, 4 H), 2.08-2.17 (m, 2 H), 2.17-2.32 (m, 1 H), 2.35 (s, 3 H), 2.72-2.84 (m, 1 H), 2.93-3.02 (m, 2 H), 3.03-3.12 (m, 1 H), 3.28 (s, 2 H), 3.37-3.46 (m, 2 H), 4.11 (q, J = 7.0 Hz, 2 H) | H | m/z 350 (M + H)⁺ (ES+), at 6.86 min, UV active at 202 nm |
| 2-23 | Isomer 2: ethyl 2-{4-[1-(N-methylglycyl)pyrrolidin-2-yl]piperidin-1-yl}-6-azaspiro[3.4]octane-6-carboxylate | 75 and 122 | n | (400 MHz, CDCl₃) δ: 1.16-1.39 (m, 4 H), 1.40-1.52 (m, 1 H), 1.54-1.75 (m, 3 H), 1.76-2.13 (m, 12 H), 2.45 (s, 3 H), 2.56-2.71 (m, 1 H), 2.82-2.97 (m, 2 H), 3.20-3.48 (m, 8 H), 4.07-4.20 (m, 3 H) NH not observed. | H | m/z 407 (M + H)⁺ (ES+), at 5.77 min, UV inactive |
| 2-24 | Isomer 2: ethyl 2-{4-[1-(methoxycarbamoyl)pyrrolidin-2-yl]piperidin-1-yl}-6-azaspiro[3.4]octane-6-carboxylate | 76 and 122 | m | (400 MHz, CDCl₃) δ: 1.17-1.47 (m, 5 H), 1.48-2.27 (m, 15 H), 2.56-2.76 (m, 1 H), 2.85-3.02 (m, 1 H), 3.14-3.53 (m, 6 H), 3.74 (s, 3 H), 3.91-4.03 (m, 1 H), 4.06-4.19 (m, 2 H) NH not observed. | H | m/z 409 (M + H)⁺ (ES+), at 5.23 min, UV active |
| 2-25 | Isomer 2: ethyl 2-{4-[(2S)-1-(propan-2-yl)carbamoyl]pyrrolidin-2-yl]piperidin-1-yl}-6-azaspiro[3.4]octane-6-carboxylate | 77 and 127 | q | (400 MHz, CD₃OD) δ: 1.09-1.17 (m, 6 H), 1.24 (t, J = 7.0 Hz, 3 H), 1.28-1.44 (m, 2 H), 1.50-1.65 (m, 2 H), 1.66-1.99 (m, 11 H), 2.04-2.15 (m, 2 H), 2.68-2.79 (m, 1 H), 2.93 (d, J = 10.9 Hz, 2 H), 3.22-3.28 (m, 4 H), 3.38 (q, J = 6.6 Hz, 2 H), 3.85-3.94 (m, 2 H), 4.08 (q, J = 7.0 Hz, 2 H) NH not observed. | E | m/z 421 (M + H)⁺ (ES+), at 4.15 min, UV inactive |
| 2-26 | Isomer 2: ethyl 2-{4-[(2S)-1-[(2,2,2-trifluoroethyl)carbamoyl]pyrrolidin-2-yl]piperidin-1-yl}-6-azaspiro[3.4]octane-6-carboxylate | 78 and 127 | q | (400 MHz, CD₃OD) δ: 1.24 (t, J = 7.0 Hz, 3 H), 1.29-1.43 (m, 2 H), 1.48-1.65 (m, 2 H), 1.66-2.00 (m, 11 H), 2.04-2.14 (m, 2 H), 2.67-2.79 (m, 1 H), 2.94 (d, J = 11.3 Hz, 2 H), 3.25 (s, 3 H), 3.33-3.42 (m, 3 H), 3.63-3.78 (m, 1 H), 3.85-3.98 (m, 2 H), 4.09 (q, J = 7.0 Hz, 2 H) NH not observed. | E | m/z 461 (M + H)⁺ (ES+), at 4.03 min, UV inactive |
| 2-27 | Isomer 2: ethyl 2-{4-[(2S)-1-(azetidin-1-ylcarbonyl)pyrrolidin-2-yl]piperidin-1-yl}-6-azaspiro[3.4]octane-6-carboxylate | 79 and 127 | q | (400 MHz, DMSO-d₆) δ: 1.08-1.22 (m, 6 H), 1.38-1.89 (m, 13 H), 1.98 (br.s., 2 H), 2.07-2.20 (m, 2 H), 3.03-3.31 (m, 7 H), 3.67 (q, J = 7.6 Hz, 2 H), 3.79-3.88 (m, 1 H), 3.91-4.07 (m, 5 H) | H | m/z 419 (M + H)⁺ (ES+), at 5.88 min, UV active at 202 nm |
| 2-28 | Isomer 2: ethyl 2-{4-[(2S)-1-(morpholin-4-ylcarbonyl)pyrrolidin-2-yl]piperidin-1-yl}-6-azaspiro[3.4]octane-6-carboxylate | 80 and 127 | q | (400 MHz, DMSO-d₆) δ: 1.02-1.19 (m, 5 H), 1.33-1.61 (m, 7 H), 1.64-1.86 (m, 6 H), 1.93 (t, J = 9.2 Hz, 2 H), 2.52-2.62 (m, 1 H), 2.75 (d, J = 9.8 Hz, 2 H), 2.96-3.06 (m, 2 H), 3.03-3.28 (m, 7 H), 3.44-3.61 (m, 4 H), 3.87-4.00 (m, 3 H), 4.05-4.13 (m, 1 H) | E | m/z 449 (M + H)⁺ (ES+), at 3.29 min, UV inactive |
| 2-29 | Isomer 2: ethyl 2-{4-[(2S)-1-(cyclopropylcarbamoyl)pyrrolidin-2-yl]piperidin-1-yl}-6-azaspiro[3.4]octane-6-carboxylate | 81 and 127 | q | (400 MHz, DMSO-d₆) δ: 0.28-0.40 (m, 2 H), 0.43-0.53 (m, 2 H), 1.02-1.24 (m, 5 H), 1.39 (t, J = 11.3 Hz, 2 H), 1.43-1.58 (m, 2 H), 1.58-1.85 (m, 6 H), 1.94 (t, J = 9.2 Hz, 2 H), 2.52-2.61 (m, 1 H), 2.76 (d, J = 11.3 Hz, 2 H), 3.07-3.19 (m, 7 H), 3.19-3.28 (m, 1 H), 3.66-3.76 (m, 1 H), 3.97 (q, J = 7.0 Hz, 2 H), 4.04-4.15 (m, 2 H), 6.09 (d, J = 2.7 Hz, 1 H) | E | m/z 419 (M + H)⁺ (ES+), at 3.24 min, UV inactive |

TABLE 3-continued

| Ex. No. | Name | Intermediate | Synthetic method | ¹H NMR | LCMS Method | LCMS data |
|---|---|---|---|---|---|---|
| 2-30 | Isomer 2: ethyl 2-{4-[(2S)-1-(cyclobutylcarbamoyl)pyrrolidin-2-yl]piperidin-1-yl}-6-azaspiro[3.4]octane-6-carboxylate | 82 and 127 | q | (400 MHz, DMSO-d₆) δ: 1.02-1.22 (m, 5 H), 1.29-1.57 (m, 6 H), 1.58-1.98 (m, 10 H), 1.99-2.12 (m, 2 H), 2.51-2.60 (m, 1 H), 2.75 (brs., 1 H), 3.07-3.27 (m, 8 H), 3.71 (brs., 1 H), 3.97 (q, J = 7.0 Hz, 2 H), 4.04-4.15 (m, 2 H), 6.13 (d, J = 8.2 Hz, 1 H) | E | m/z 433 (M + H)⁺ (ES+), at 3.65 min, UV inactive |
| 2-31 | Isomer 2: ethyl 2-(4-{(2S)-1-[(2-methoxyethyl)carbamoyl]pyrrolidin-1-yl}-1-piperidin-1-yl)-6-azaspiro[3.4]octane-6-carboxylate | 83 and 127 | q | (400 MHz, DMSO-d₆) δ: 1.01-1.26 (m, 5 H), 1.32-1.58 (m, 5 H), 1.59-1.86 (m, 8 H), 1.94 (t, J = 9.2 Hz, 2 H), 2.52-2.61 (m, 1 H), 2.76 (d, J = 10.5 Hz, 2 H), 3.02-3.28 (m, 13 H), 3.64-3.74 (m, 1 H), 3.97 (q, J = 7.0 Hz, 2 H), 6.01 (t, J = 5.5 Hz, 1 H) | E | m/z 437 (M + H)⁺ (ES+), at 3.06 min, UV inactive |
| 2-32 | Isomer 2: ethyl 2-{4-[(2S)-1-(pyrrolidin-1-ylcarbonyl)pyrrolidin-2-yl]piperidin-1-yl}-6-azaspiro[3.4]octane-6-carboxylate | 84 and 127 | q | (400 MHz, DMSO-d₆) δ: 1.01-1.18 (m, 5 H), 1.32-1.86 (m, 17 H), 1.93 (t, J = 9.2 Hz, 2 H), 2.52-2.61 (m, 1 H), 2.75 (d, J = 9.0 Hz, 2 H), 3.02-3.30 (m, 9 H), 3.84-3.92 (m, 1 H), 3.97 (q, J = 7.0 Hz, 2 H), 4.06-4.12 (m, 1 H) | E | m/z 433 (M + H)⁺ (ES+), at 3.85 min, UV inactive |
| 2-33 | Isomer 1: ethyl 2-{4-[(2S)-1-(methoxycarbamoyl)pyrrolidin-2-yl]piperidin-1-yl}-6-azaspiro[3.4]octane-6-carboxylate | 76 and 127 | q | (400 MHz, CDCl₃) δ: 1.03-1.45 (m, 5 H), 1.47-2.24 (m, 16 H), 2.56-2.77 (m, 1 H), 2.92 (brs., 2 H), 3.14-3.53 (m, 5 H), 3.75 (s, 3 H), 3.89-4.04 (m, 1 H), 4.12 (q, J = 6.8 Hz, 2 H) NH not observed. | I | m/z 409 (M + H)⁺ (ES+), at 3.50 min, UV active at 202 nm |
| 2-33 | Isomer 2: ethyl 2-{4-[(2S)-1-(methoxycarbamoyl)pyrrolidin-2-yl]piperidin-1-yl}-6-azaspiro[3.4]octane-6-carboxylate | 76 and 127 | q | (400 MHz, CDCl₃) δ: 1.27 (t, J = 6.50 Hz, 3 H), 1.36-2.22 (m, 17 H), 2.76 (brs., 1 H), 2.93-3.10 (m, 2 H), 3.16-3.26 (m, 1 H), 3.28-3.48 (m, 5 H), 3.74 (s, 3 H), 3.99 (d, J = 5.49 Hz, 1 H), 4.14 (q, J = 6.50 Hz, 2 H) NH not observed. | I | m/z 409 (M + H)⁺ (ES+), at 3.64 min, UV active at 202 nm |
| 2-34 | Isomer 1: ethyl 2-(4-{(2S)-1-[methoxy(methyl)carbamoyl]pyrrolidin-2-yl}piperidin-1-yl)-6-azaspiro[3.4]octane-6-carboxylate | 85 and 127 | q | (400 MHz, CDCl₃) δ: 1.15-1.48 (m, 8 H), 1.56-2.07 (m, 11 H), 2.09-2.39 (m, 5 H), 2.95-3.11 (m, 3 H), 3.19-3.54 (m, 6 H), 3.57-3.73 (m, 3 H), 4.04-4.20 (m, 2 H) | I | m/z 423 (M + H)⁺ (ES+), at 4.17 min, UV active at 202 nm |
| 2-34 | Isomer 2: ethyl 2-(4-{(2S)-1-[methoxy(methyl)carbamoyl]pyrrolidin-2-yl}piperidin-1-yl)-6-azaspiro[3.4]octane-6-carboxylate | 85 and 127 | q | (400 MHz, CDCl₃) δ: 1.19-1.37 (m, 7 H), 1.53-2.01 (m, 12 H), 2.10-2.27 (m, 2 H), 2.99 (s, 3 H), 3.29-3.45 (m, 6 H), 3.46-3.54 (m, 1 H), 3.59-3.67 (m, 3 H), 4.07-4.21 (m, 4 H) | I | m/z 423 (M + H)⁺ (ES+), at 4.30 min, UV active at 202 nm |
| 2-35 | Isomer 2: ethyl 2-(4-{(2S)-1-[(1-methylcyclobutyl)carbamoyl]pyrrolidin-2-yl}piperidin-1-yl)-6-azaspiro[3.4]octane-6-carboxylate | 86 and 127 | q | (400 MHz, CD₃OD) δ: 1.24 (t, J = 7.0 Hz, 3 H), 1.28-1.39 (m, 2 H), 1.43 (s, 3 H), 1.49-2.02 (m, 17 H), 2.03-2.14 (m, 2 H), 2.15-2.32 (m, 2 H), 2.73 (quin, J = 7.8 Hz, 1 H), 2.93 (d, J = 11.3 Hz, 2 H), 3.20-3.28 (m, 3 H), 3.33-3.44 (m, 3 H), 3.81-3.91 (m, 1 H), 4.09 (q, J = 7.0 Hz, 2 H) NH not observed. | E | m/z 447 (M + H)⁺ (ES+), at 4.06 min, UV inactive |

TABLE 3-continued

| Ex. No. | Intermediate | Synthetic method | Name | ¹H NMR | LCMS Method | LCMS data |
|---|---|---|---|---|---|---|
| 2-36 | 87 and 127 | q | Isomer 2: ethyl 2-(4-{(2S)-1-[(3-methyloxetan-3-yl)carbamoyl]pyrrolidin-2-yl}piperidin-1-yl)-6-azaspiro[3.4]octane-6-carboxylate | (400 MHz, CD₃OD) δ: 1.24 (t, J = 7.1 Hz, 3 H), 1.28-1.44 (m, 2 H), 1.50-1.65 (m, 5 H), 1.66-1.98 (m, 11 H), 2.04-2.14 (m, 2 H), 2.67-2.79 (m, 1 H), 2.93 (d, J = 11.3 Hz, 2 H), 3.21-3.27 (m, 3 H), 3.33-3.42 (m, 3 H), 3.81-3.89 (m, 1 H), 4.09 (q, J = 7.1 Hz, 2 H), 4.38 (d, J = 7.0 Hz, 2 H), 4.72 (dd, J = 14.8, 7.0 Hz, 2 H) NH not observed. | E | m/z 449 (M + H)⁺ (ES+), at 3.09 min, UV inactive |
| 2-37 | 88 and 127 | q | Isomer 2: ethyl 2-(4-{(2S)-1-[(3,3-difluoropyrrolidin-1-yl)carbonyl]pyrrolidin-2-yl}piperidin-1-yl)-6-azaspiro[3.4]octane-6-carboxylate | (400 MHz, CD₃OD) δ: 1.24 (t, J = 7.0 Hz, 3 H), 1.27-1.40 (m, 2 H), 1.51-1.80 (m, 7 H), 1.81-1.98 (m, 6 H), 2.05-2.14 (m, 2 H), 2.28-2.45 (m, 2 H), 2.73 (quin, J = 7.9 Hz, 1 H), 2.93 (d, J = 10.9 Hz, 2 H), 3.25 (s, 3 H), 3.34-3.43 (m, 3 H), 3.43-3.57 (m, 2 H), 3.68-3.77 (m, 1 H), 3.82-3.97 (m, 1 H), 4.00-4.13 (m, 3 H) | E | m/z 469 (M + H)⁺ (ES+), at 2.44 min, UV inactive |
| 2-38 | 89 and 127 | q | Isomer 2: ethyl 2-(4-{(2S)-1-[(3,3-difluorocyclobutyl)carbamoyl]pyrrolidin-2-yl}piperidin-1-yl)-6-azaspiro[3.4]octane-6-carboxylate | (400 MHz, CD₃OD) δ: 1.24 (t, J = 7.0 Hz, 3 H), 1.27-1.44 (m, 2 H), 1.49-1.64 (m, 2 H), 1.65-2.00 (m, 12 H), 2.02-2.14 (m, 2 H), 2.46-2.63 (m, 2 H), 2.73 (quin, J = 7.9 Hz, 1 H), 2.78-2.89 (m, 2 H), 2.93 (d, J = 11.7 Hz, 2 H), 3.22-3.28 (m, 2 H), 3.34-3.42 (m, 3 H), 3.84-3.92 (m, 1 H), 4.00-4.13 (m, 3 H) NH not observed. | E | m/z 469 (M + H)⁺ (ES+), at 2.83 min, UV inactive |
| 2-39 | 90 and 127 | q | Isomer 2: ethyl 2-(4-{(2S)-1-[(3,3-difluoroazetidin-1-yl)carbonyl]pyrrolidin-2-yl}piperidin-1-yl)-6-azaspiro[3.4]octane-6-carboxylate | (400 MHz, CD₃OD) δ: 1.24 (t, J = 7.0 Hz, 3 H), 1.27-1.40 (m, 2 H), 1.52-1.66 (m, 2 H), 1.67-1.98 (m, 11 H), 2.04-2.14 (m, 2 H), 2.74 (quin, J = 8.0 Hz, 1 H), 2.93 (d, J = 10.9 Hz, 2 H), 3.16-3.27 (m, 3 H), 3.34-3.43 (m, 3 H), 3.99 (q, J = 6.1 Hz, 1 H), 4.04-4.22 (m, 4 H), 4.36-4.49 (m, 2 H) | E | m/z 455 (M + H)⁺ (ES+), at 2.83 min, UV inactive |
| 2-40 | 78 and 127 | q | Isomer 2: methyl 2-(4-{(2S)-1-[(2,2,2-trifluoroethyl)carbamoyl]pyrrolidin-2-yl}piperidin-1-yl)-6-azaspiro[3.4]octane-6-carboxylate | (400 MHz, CD₃OD) δ: 1.26-1.44 (m, 2 H), 1.49-1.65 (m, 2 H), 1.66-1.99 (m, 12 H), 2.04-2.14 (m, 2 H), 2.67-2.82 (m, 1 H), 2.94 (d, J = 10.9 Hz, 2 H), 3.17-3.27 (m, 3 H), 3.35-3.43 (m, 2 H), 3.62-3.78 (m, 4 H), 3.86-4.00 (m, 2 H) NH not observed. | E | m/z 447 (M + H)⁺ (ES+), at 2.45 min, UV inactive |
| 2-41 | 90 and 157 | q | Isomer 2: methyl 2-(4-{(2S)-1-[(3,3-difluoroazetidin-1-yl)carbamoyl]pyrrolidin-2-yl}piperidin-1-yl)-6-azaspiro[3.4]octane-6-carboxylate | (400 MHz, CD₃OD) δ: 1.26-1.42 (m, 2 H), 1.68-1.99 (m, 11 H), 2.04-2.15 (m, 2 H), 2.73 (quin, J = 7.9 Hz, 1 H), 2.93 (d, J = 10.9 Hz, 2 H), 3.17-3.28 (m, 3 H), 3.34-3.44 (m, 3 H), 3.67 (s, 3 H), 3.94-4.04 (m, 1 H), 4.09-4.24 (m, 2 H), 4.36-4.51 (m, 2 H) | E | m/z 441 ((M + H)⁺ (ES+), at 2.22 min, UV inactive |
| 2-42 | 91 and 127 | r | Isomer 1: ethyl 2-(4-{(2S)-1-[ethyl(propan-2-yl)carbamoyl]pyrrolidin-2-yl}piperidin-1-yl)-6-azaspiro[3.4]octane-6-carboxylate | (400 MHz, CD₃OD) δ: 1.02-1.12 (m, 6 H), 1.17-1.26 (m, 6 H), 1.28-1.40 (m, 2 H), 1.49-1.98 (m, 15 H), 2.05-2.15 (m, 3 H), 2.67-2.79 (m, 2 H), 2.85-2.96 (m, 3 H), 3.33-3.41 (m, 3 H), 3.88-4.00 (m, 1 H), 4.02-4.15 (m, 3 H) | E | m/z 449 (M + H)⁺ (ES+), at 3.42 min, UV inactive |
| 2-42 | 91 and 127 | r | Isomer 2: ethyl 2-(4-{(2S)-1-[ethyl(propan-2-yl)carbamoyl]pyrrolidin-2-yl}piperidin-1-yl)-6-azaspiro[3.4]octane-6-carboxylate | (400 MHz, CD₃OD) δ: 1.00-1.12 (m, 6 H), 1.18-1.27 (m, 6 H), 1.27-1.43 (m, 2 H), 1.43-1.99 (m, 13 H), 2.04-2.14 (m, 2 H), 2.68-2.78 (m, 1 H), 2.85-2.98 (m, 3 H), 3.25 (br.s., 3 H), 3.37 (t, J = 6.8 Hz, 3 H), 3.88-4.00 (m, 1 H), 4.01-4.13 (m, 3 H) | E | m/z 449 (M + H)⁺ (ES+), at 3.61 min, UV inactive |

TABLE 3-continued

| Ex. No. | Name | Intermediate | Synthetic method | ¹H NMR | LCMS Method | LCMS data |
|---|---|---|---|---|---|---|
| 2-43 | Isomer 2: ethyl 2-(4-{(2S)-1-[(cyclobutyloxy)carbonyl]pyrrolidin-2-yl}piperidin-1-yl)-6-azaspiro[3.4]octane-6-carboxylate | 92 and 127 | m | 400 MHz, CDCl₃) δ: 0.78-0.95 (m, 5 H), 1.20-1.42 (m, 6 H), 1.49-2.17 (m, 15 H), 2.28-2.43 (m, 2 H), 2.57-2.71 (m, 1 H), 2.83-3.00 (m, 2 H), 3.19-3.61 (m, 4 H), 3.72-3.88 (m, 1 H), 4.13 (q, J = 7.02 Hz, 2 H), 4.88-5.04 (m, 1 H) | I | m/z 434 (M + H)⁺ (ES+), at 5.19 min, UV active at 202 nm |
| 2-44 | Isomer 2: ethyl 2-(4-{(2S)-1-[(2-fluoroethyl)carbamoyl]pyrrolidin-2-yl}piperidin-1-yl)-6-azaspiro[3.4]octane-6-carboxylate | 93 and 127 | q | (400 MHz, CD₃OD) δ: 1.24 (t, J = 7.0 Hz, 3 H), 1.28-1.45 (m, 2 H), 1.58 (t, J = 15.6 Hz, 2 H), 1.67-1.99 (m, 12 H), 2.04-2.15 (m, 2 H), 2.73 (quin, J = 7.9 Hz, 1 H), 2.93 (d, J = 11.3 Hz, 2 H), 3.25 (s, 2 H), 3.33-3.53 (m, 5 H), 3.84-3.92 (m, 1 H), 4.09 (q, J = 7.0 Hz, 2 H), 4.35 (t, J = 5.2 Hz, 1 H), 4.47 (t, J = 5.2 Hz, 1 H) NH not observed. | E | m/z 425 (M + H)⁺ (ES+), at 3.24 min, UV inactive |
| 2-45 | Isomer 2: ethyl 2-(4-{(2S)-1-[(2,2-difluoroethyl)carbamoyl]pyrrolidin-2-yl}piperidin-1-yl)-6-azaspiro[3.4]octane-6-carboxylate | 94 and 127 | q | (400 MHz, CD₃OD) δ: 1.24 (t, J = 7.0 Hz, 3 H), 1.28-1.44 (m, 2 H), 1.50-1.64 (m, 2 H), 1.65-2.01 (m, 12 H), 2.02-2.15 (m, 2 H), 2.73 (quin, J = 7.8 Hz, 1 H), 2.93 (d, J = 11.3 Hz, 2 H), 3.25 (s, 3 H), 3.33-3.60 (m, 4 H), 3.88 (d, J = 5.1 Hz, 1 H), 4.09 (q, J = 7.0 Hz, 2 H), 5.66-6.01 (m, 1 H) NH not observed. | E | m/z 443 (M + H)⁺ (ES+), at 3.45 min, UV inactive |
| 2-46 | Isomer 2: ethyl 2-{4-[(2S)-1-(methoxyacetyl)pyrrolidin-2-yl]piperidin-1-yl}-6-azaspiro[3.4]octane-6-carboxylate | 95 and 127 | m | (400 MHz, CDCl₃) δ: 1.15-1.29 (m, 3 H), 1.30-1.52 (m, 4 H), 1.51-1.98 (m, 12 H), 2.00-2.15 (m, 3 H), 2.56-2.74 (m, 1 H), 2.80-3.00 (m, 2 H), 3.12-3.53 (m, 8 H), 3.94-4.20 (m, 4 H) | I | m/z 408 (M + H)⁺ (ES+), at 3.58 min, UV active at 202 nm |
| 2-47 | Isomer 2: ethyl 2-(4-{(2S)-1-[(2-fluoroethoxy)carbonyl]pyrrolidin-2-yl}piperidin-1-yl)-6-azaspiro[3.4]octane-6-carboxylate | 96 and 127 | s | (400 MHz, CDCl₃) δ: 1.16-1.49 (m, 5 H), 1.50-2.17 (m, 17 H), 2.83-3.05 (m, 1 H), 3.16-3.64 (m, 6 H), 3.78-3.94 (m, 1 H), 4.13 (q, J = 6.5 Hz, 2 H), 4.24-4.48 (m, 2 H), 4.52-4.76 (m, 2 H) | I | m/z 426 (M + H)⁺ (ES+), at 4.50 min, UV active at 202 nm |
| 2-48 | Isomer 2: ethyl 2-(4-{(2S)-1-[(2,2,2-trifluoroethoxy)carbonyl]pyrrolidin-2-yl}piperidin-1-yl)-6-azaspiro[3.4]octane-6-carboxylate | 97 and 127 | s | (400 MHz, CDCl₃) δ: 1.17-1.47 (m, 5 H), 1.49-2.33 (m, 15 H), 2.66 (d, J = 7.32 Hz, 1 H), 2.84-3.09 (m, 2 H), 3.19-3.46 (m, 5 H), 3.47-3.71 (m, 1 H), 3.84 (dd, J = 18.16, 4.4 Hz, 1 H), 4.11 (q, J = 7.0 Hz, 2 H), 4.32-4.67 (m, 2 H) | I | m/z 462 (M + H)⁺ (ES+), at 5.07 min, UV active at 202 nm |
| 2-49 | Isomer 2: ethyl 2-(4-{(2S)-1-[(methylsulfanyl)carbonyl]pyrrolidin-2-yl}piperidin-1-yl)-6-azaspiro[3.4]octane-6-carboxylate | 98 and 127 | s | (400 MHz, CDCl₃) δ: 1.15-1.45 (m, 5 H), 1.46-1.76 (m, 9 H), 1.79-2.13 (m, 9 H), 2.35 (s, 3 H), 2.58-2.72 (m, 1 H), 2.85-3.02 (m, 2 H), 3.21-3.57 (m, 4 H), 4.13 (q, J = 6.8 Hz, 2 H) | I | m/z 410 (M + H)⁺ (ES+), at 4.74 min, UV active at 202 nm |
| 2-50 | Isomer 2: ethyl 2-(4-{(2S)-1-[(2-methoxyethoxy)carbonyl]pyrrolidin-2-yl}piperidin-1-yl)-6-azaspiro[3.4]octane-6-carboxylate | 99 and 127 | m | (400 MHz, CDCl₃) δ: 1.17-1.31 (m, 3 H), 1.35-1.51 (m, 2 H), 1.52-2.17 (m, 18 H), 2.90-3.14 (m, 2 H), 3.21-3.47 (m, 7 H), 3.48-3.65 (m, 2 H), 3.76-3.91 (m, 1 H), 4.13 (q, J = 6.8 Hz, 2 H), 4.18-4.33 (m, 2 H) | I | m/z 438 (M + H)⁺ (ES+), at 4.33 min, UV active at 202 nm |

TABLE 3-continued

| Ex. No. | Name | Intermediate | Synthetic method | $^1$H NMR | LCMS Method | LCMS data |
|---|---|---|---|---|---|---|
| 2-51 | Isomer 2: ethyl 2-{4-[(2S)-1-{[2-(dimethylamino)ethoxy]carbonyl}pyrrolidin-2-yl]piperidin-1-yl}-6-azaspiro[3.4]octane-6-carboxylate | 100 and 127 | m | (400 MHz, CDCl$_3$) δ: 1.15-1.49 (m, 6 H), 1.51-2.18 (m, 14 H), 2.32 (s, 6 H), 2.52-2.80 (m, 3 H), 2.85-3.05 (m, 2 H), 3.14-3.63 (m, 7 H), 4.07-4.27 (m, 4 H) | I | m/z 451 (M + H)$^+$ (ES+), at 4.22 min, UV active at 202 nm |
| 2-52 | Isomer 2: ethyl 2-{4-[(2S)-1-(hydroxyacetyl)pyrrolidin-2-yl]piperidin-1-yl}-6-azaspiro[3.4]octane-6-carboxylate | 101 and 127 | t | (400 MHz, CDCl$_3$) δ: 1.14-1.51 (m, 7 H), 1.52-1.77 (m, 3 H), 1.77-2.21 (m, 10 H), 2.62 (d, J = 10.1 Hz, 1 H), 2.90 (d, J = 10.1 Hz, 2 H), 3.16-3.69 (m, 7 H), 3.98-4.28 (m, 4 H) OH not observed. | I | m/z 394 (M + H)$^+$ (ES+), at 3.66 min, UV active at 202 nm |
| 2-53 | Isomer 2: ethyl 2-{4-[(2S)-1-(3,3,3-trifluoropropanoyl)pyrrolidin-2-yl]piperidin-1-yl}-6-azaspiro[3.4]octane-6-carboxylate | 102 and 127 | u | (400 MHz, CD$_3$OD) δ: 1.21-1.36 (m, 4 H), 1.44-1.66 (m, 2 H), 1.77 (d, J = 12.8 Hz, 2 H), 1.85-2.08 (m, 8 H), 2.10-2.23 (m, 2 H), 2.23-2.32 (m, 2 H), 2.39 (brs., 2 H), 3.25-3.31 (m, 2 H), 3.38-3.70 (m, 7 H), 4.06-4.17 (m, 3 H) | I | m/z 446 (M + H)$^+$ (ES+), at 4.42 min, UV active at 202 nm |
| 2-54 | Isomer 1: ethyl 2-(4-{(2S)-1-[(pyridin-2-ylmethyl)carbamoyl]pyrrolidin-2-yl}piperidin-1-yl)-6-azaspiro[3.4]octane-6-carboxylate | 103 and 127 | q | (400 MHz, CD$_3$OD) δ: 1.20-1.28 (m, 3 H), 1.29-1.47 (m, 2 H), 1.60 (t, J = 12.3 Hz, 2 H), 1.67-2.03 (m, 12 H), 2.04-2.18 (m, 2 H), 2.65-2.79 (m, 1 H), 2.94 (d, J = 9.0 Hz, 2 H), 3.33-3.51 (m, 5 H), 3.91 (q, J = 5.5 Hz, 1 H), 4.10 (q, J = 7.2 Hz, 2 H), 4.36-4.55 (m, 2 H), 7.28 (dd, J = 7.4, 5.1 Hz, 1 H), 7.38 (d, J = 7.4 Hz, 1 H), 7.79 (ddd, J = 7.4, 1.6 Hz, 1 H), 8.45 (d, J = 5.1 Hz, 1 H) NH not observed. | E | m/z 470 (M + H)$^+$ (ES+), at 2.99 min, UV inactive |
| 2-54 | Isomer 2: ethyl 2-(4-{(2S)-1-[(pyridin-2-ylmethyl)carbamoyl]pyrrolidin-2-yl}piperidin-1-yl)-6-azaspiro[3.4]octane-6-carboxylate | 103 and 127 | q | (400 MHz, CD$_3$OD) δ: 1.24 (t, J = 7.0 Hz, 3 H), 1.28-1.46 (m, 2 H), 1.60 (t, J = 9.6 Hz, 2 H), 1.67-2.02 (m, 11 H), 2.09 (t, J = 9.6 Hz, 2 H), 2.73 (quin, J = 7.9 Hz, 1 H), 2.94 (d, J = 8.6 Hz, 2 H), 3.25 (s, 2 H), 3.33-3.52 (m, 5 H), 3.91 (d, J = 5.5 Hz, 1 H), 4.03-4.14 (m, 2 H), 4.36-4.55 (m, 2 H), 7.28 (dd, J = 7.6, 5.27 Hz, 1 H), 7.38 (d, J = 7.6 Hz 1 H), 7.79 (ddd, J = 7.6, 1.6 Hz, 1 H), 8.45 (d, J = 5.3 Hz, 1 H) NH not observed. | E | m/z 470 (M + H)$^+$ (ES+), at 3.17 min, UV inactive |
| 2-55 | Isomer 1: ethyl 2-(4-{(2S)-1-[methyl(2,2,2-trifluoroethyl)carbamoyl]pyrrolidin-2-yl}piperidin-1-yl)-6-azaspiro[3.4]octane-6-carboxylate | 104 and 127 | q | (400 MHz, CD$_3$OD) δ: 1.16-1.28 (m, 3 H), 1.29-1.49 (m, 2 H), 1.51-1.80 (m, 6 H), 1.81-2.02 (m, 8 H), 2.10 (t, J = 8.2 Hz, 2 H), 2.65-2.79 (m, 1 H), 2.87-2.98 (m, 2 H), 3.01-3.16 (m, 3 H), 3.25 (s, 1 H), 3.33-3.51 (m, 5 H), 3.96-4.18 (m, 3 H), 4.47-4.70 (m, 1 H) | E | m/z 475 (M + H)$^+$ (ES+), at 4.02 min, UV inactive |
| 2-55 | Isomer 2: ethyl 2-(4-{(2S)-1-[methyl(2,2,2-trifluoroethyl)carbamoyl]pyrrolidin-2-yl}piperidin-1-yl)-6-azaspiro[3.4]octane-6-carboxylate | 104 and 127 | q | (400 MHz, CD$_3$OD) δ: 1.24 (t, J = 7.2 Hz, 3 H), 1.28-1.42 (m, 2 H), 1.51-1.80 (m, 6 H), 1.82-2.03 (m, 6 H), 2.09 (t, J = 9.8 Hz, 2 H), 2.66-2.79 (m, 1 H), 2.93 (d, J = 9.8 Hz, 2 H), 3.04 (s, 3 H), 3.25 (s, 2 H), 3.33-3.50 (m, 6 H), 4.01-4.15 (m, 3 H), 4.53-4.68 (m, 1 H) | E | m/z 475 (M + H)$^+$ (ES+), at 4.17 min, UV inactive |
| 2-56 | Isomer 2: ethyl 2-{4-[(2S)-1-(oxetan-3-ylcarbamoyl)pyrrolidin-2-yl]piperidin-1-yl}-6-azaspiro[3.4]octane-6-carboxylate | 105 and 127 | q | (400 MHz, CD$_3$OD) δ: 1.24 (t, J = 7.0 Hz, 3 H), 1.27-1.42 (m, 2 H), 1.48-1.64 (m, 2 H), 1.66-1.99 (m, 11 H), 2.02-2.14 (m, 2 H), 2.72 (quin, J = 7.9 Hz, 1 H), 2.93 (d, J = 11.3 Hz, 2 H), 3.25 (s, 2 H), 3.33-3.43 (m, 4 H), 3.89 (q, J = 5.3 Hz, 1 H), 4.08 (q, J = 7.0 Hz, 2 H), 4.55-4.63 (m, 2 H), 4.78-4.86 (m, 3 H) NH not observed. | E | m/z 435 (M + H)$^+$ (ES+), at 2.82 min, UV inactive |

TABLE 3-continued

| Ex. No. | Name | Intermediate | Synthetic method | ¹H NMR | LCMS Method | LCMS data |
|---|---|---|---|---|---|---|
| 2-57 | Isomer 2: ethyl 2-(4-{(2S)-1-[methyl(oxetan-3-yl)carbamoyl]pyrrolidin-2-yl}piperidin-1-yl)-6-azaspiro[3.4]octane-6-carboxylate | 106 and 127 | q | (400 MHz, CD₃OD) δ: 1.24 (t, J = 7.2 Hz, 3 H), 1.27-1.43 (m, 2 H), 1.48-1.79 (m, 7 H), 1.81-2.00 (m, 7 H), 2.03-2.15 (m, 2 H), 2.72 (quin, J = 7.8 Hz, 1 H), 2.81-2.99 (m, 4 H), 3.25 (s, 2 H), 3.33-3.45 (m, 4 H), 3.97-4.13 (m, 3 H), 4.56-4.84 (m, 5 H) NH not observed. | E | m/z 449 (M + H)⁺ (ES+), at 3.20 min, UV inactive |
| 2-58 | Isomer 2: ethyl 2-{(2S)-1-propanethioylpyrrolidin-2-yl}piperidin-1-yl)-6-azaspiro[3.4]octane-6-carboxylate | Example 2-7 and 107 | v | (400 MHz, CD₃OD) δ: 1.18-1.32 (m, 6 H), 1.36-1.62 (m, 4 H), 1.62-1.82 (m, 2 H), 1.83-2.16 (m, 10 H), 2.54 (br.s., 1 H), 2.65-2.82 (m, 3 H), 2.93 (d, J = 10.9 Hz, 2 H), 3.25 (s, 2 H), 3.38 (q, J = 6.6 Hz, 2 H), 3.56-3.67 (m, 1 H), 3.75-3.86 (m, 1 H), 4.09 (q, J = 7.0 Hz, 2 H), 4.62-4.73 (m, 1 H) | E | m/z 408 (M + H)⁺ (ES+), at 3.82 min, UV inactive |
| 2-59 | Isomer 2: ethyl 2-{4-[(2S,4S)-4-fluoro-1-propanoylpyrrolidin-2-yl]piperidin-1-yl}-6-azaspiro[3.4]octane-6-carboxylate | 2, 54 and 112 | ap and m | (400 MHz, CD₃OD) δ: 1.05-1.15 (m, 3 H), 1.24 (t, J = 7.0 Hz, 3 H), 1.27-1.51 (m, 2 H), 1.52-1.97 (m, 9 H), 1.98-2.27 (m, 4 H), 2.27-2.48 (m, 2 H), 2.66-2.79 (m, 1 H), 2.87-3.01 (m, 2 H), 3.25 (s, 2 H), 3.34-3.45 (m, 2 H), 3.61-3.75 (m, 1 H), 3.83-4.00 (m, 1 H), 4.03-4.21 (m, 3 H), 5.19-5.40 (m, 1 H) | E | m/z 410 (M + H)⁺ (ES+), at 3.32 min, UV inactive |
| 2-60 | Isomer 2: ethyl 2-{4-[(2S)-4,4-difluoro-1-propanoylpyrrolidin-2-yl]piperidin-1-yl}-6-azaspiro[3.4]octane-6-carboxylate | 2, 54 and 113 | ap and m | (400 MHz, CD₃OD) δ: 1.04-1.16 (m, 3 H), 1.24 (t, J = 7.1 Hz, 3 H), 1.27-1.43 (m, 3 H), 1.51-1.82 (m, 4 H), 1.83-2.01 (m, 5 H), 2.04-2.15 (m, 2 H), 2.23-2.54 (m, 4 H), 2.67-2.80 (m, 1 H), 2.87-3.02 (m, 2 H), 3.25 (s, 2 H), 3.38 (q, J = 6.6 Hz, 2 H), 3.71-4.05 (m, 1 H), 4.09 (q, J = 7.0 Hz, 2 H), 4.14-4.36 (m, 1 H) | E | m/z 428 (M + H)⁺ (ES+), at 3.52 min, UV inactive |
| 2-61 | Isomer 2: ethyl 2-{4-[(2S)-1-ethylpyrrolidin-2-yl]piperidin-1-yl}-6-azaspiro[3.4]octane-6-carboxylate | 114 and 127 | w | (400 MHz, DMSO-d₆) δ: 0.99 (t, J = 7.2 Hz, 3 H), 1.06-1.26 (m, 5 H), 1.30-1.41 (m, 1 H), 1.42-1.66 (m, 7 H), 1.67-1.89 (m, 4 H), 1.90-2.10 (m, 4 H), 2.13-2.22 (m, 1 H), 2.55-2.64 (m, 1 H), 2.65-2.85 (m, 3 H), 3.02 (t, J = 7.5 Hz, 1 H), 3.14 (d, J = 6.1 Hz, 2 H), 3.27 (q, J = 6.8 Hz, 2 H), 3.54-3.67 (m, 2 H), 4.00 (q, J = 7.2 Hz, 2 H) | K | m/z 364 (M + H)⁺ (ES+), at 5.60 min, UV active at 202 nm |
| 2-62 | Isomer 2: ethyl 2-(4-{(2S)-1-[3-(pyridin-2-yl)propanoyl]pyrrolidin-2-yl}piperidin-1-yl)-6-azaspiro[3.4]octane-6-carboxylate | 116 and 127 | x | (400 MHz, CD₃OD) δ: 1.17-1.42 (m, 5 H), 1.43-1.59 (m, 2 H), 1.60-1.98 (m, 11 H), 2.08 (t, J = 9.6 Hz, 2 H), 2.65-2.97 (m, 5 H), 3.01-3.17 (m, 2 H), 3.17-3.28 (m, 2 H), 3.38 (q, J = 6.6 Hz, 2 H), 3.49-3.65 (m, 1 H), 3.96-4.04 (m, 1 H), 4.09 (q, J = 7.2 Hz, 2 H), 7.21-7.28 (m, 1 H), 7.30-7.36 (m, 1 H), 7.73 (ddd, J = 7.6, 1.6 Hz, 1 H), 8.40-8.48 (m, 1 H) | E | m/z 469 (M + H)⁺ (ES+), at 3.32 min, UV inactive |
| 2-63 | Isomer 2: ethyl 2-(4-{(2S)-1-[methyl(pyridin-2-ylmethyl)carbamoyl]pyrrolidin-2-yl}piperidin-1-yl)-6-azaspiro[3.4]octane-6-carboxylate | 117 and 127 | q | (400 MHz, CD₃OD) δ: 1.24 (t, J = 7.0 Hz, 3 H), 1.27-1.42 (m, 2 H), 1.51 (d, J = 11.7 Hz, 1 H), 1.57-1.80 (m, 6 H), 1.82-2.02 (m, 7 H), 2.04-2.14 (m, 2 H), 2.73 (quin, J = 7.9 Hz, 1 H), 2.84-2.97 (m, 5 H), 3.25 (s, 2 H), 3.38 (q, J = 6.6 Hz, 2 H), 3.47 (t, J = 7.8 Hz, 1 H), 4.09 (q, J = 7.0 Hz, 3 H), 4.42 (d, J = 16.4 Hz, 1 H), 4.64 (d, J = 16.4 Hz, 1 H), 7.31 (dd, J = 7.2, 5.00 Hz, 1 H), 7.37 (d, J = 7.8 Hz, 1 H), 7.82 (dd, J = 7.8, 7.20 Hz, 1 H), 8.49 (d, J = 5.0 Hz, 1 H) | E | m/z 484 (M + H)⁺ (ES+), at 3.72 min, UV inactive |
| 2-64 | Isomer 2: ethyl 2-(4-{(2S)-1-[(pyridin-2-ylmethoxy)carbonyl]pyrrolidin-2-yl}piperidin-1-yl)-6-azaspiro[3.4]octane-6-carboxylate | 118 and 127 | q | (300 MHz, CD₃OD) δ: 1.20-1.47 (m, 5 H), 1.50-2.02 (m, 12 H), 2.04-2.19 (m, 2 H), 2.66-2.82 (m, 1 H), 2.94 (d, J = 10.4 Hz, 2 H), 3.26 (s, 2 H), 3.37-3.46 (m, 3 H), 3.51-3.68 (m, 1 H), 3.79-3.95 (m, 1 H), 3.99-4.19 (m, 3 H), 5.20 (s, 2 H), 7.31-7.41 (m, 1 H), 7.48 (d, J = 7.8 Hz, 1 H), 7.87 (dd, J = 7.7, 7.7 Hz, 1 H), 8.47-8.57 (m, 1 H) | E | m/z 471 (M + H)⁺ (ES+), at 3.69 min, UV inactive |

TABLE 3-continued

| Ex. No. | Name | Intermediate | Synthetic method | $^1$H NMR | LCMS Method | LCMS data |
|---|---|---|---|---|---|---|
| 2-65 | Isomer 2: ethyl 2-{4-[(2S)-1-{N-[(benzyloxy)carbonyl]-β-alanyl}pyrrolidin-2-yl]piperidin-1-yl}-6-azaspiro[3.4]octane-6-carboxylate | 127, 222 and 226 | y | (400 MHz, CDCl$_3$) δ: 1.25 (t, J = 8.2 Hz, 3H), 1.34-1.48 (m, 4H), 1.52-2.21 (m, 9H), 2.37-2.71 (m, 4H), 2.91-3.05 (m, 3H), 3.19-3.59 (m, 9H), 4.04-4.19 (m, 4H), 5.10 (s, 2H), 5.64 (s, 1H), 7.28-7.42 (m, 5H). | I | m/z 541 (M + H)$^+$ (ES+), at 4.51 min, UV active |
| 2-66 | Isomer 2: ethyl 2-{4-[(2S)-1-(β-alanyl)pyrrolidin-2-yl]piperidin-1-yl}-6-azaspiro[3.4]octane-6-carboxylate | 127, 222 and 226 | y | (400 MHz, DMSO-d$_6$) δ: 1.14-1.26 (m, 6H), 1.35-1.63 (m, 4H), 1.65-1.88 (m, 9H), 1.97-1.99 (m, 2H), 2.32-2.69 (m, 4H), 2.76-2.83 (m, 3H), 3.08-3.56 (m, 7H), 3.91-3.96 (m, 1H), 3.99 (q, J = 7.0 Hz, 2H). | I | m/z 407 (M + H)$^+$ (ES+), at 3.70 min, UV inactive |
| 2-67 | Isomer 2: ethyl 2-{4-[(2S)-1-{[2-(methylamino)ethoxy]carbonyl}pyrrolidin-2-yl]piperidin-1-yl}-6-azaspiro[3.4]octane-6-carboxylate | 127, 234 and 235 | n | (400 MHz, CD$_3$OD) δ: 1.31-1.34 (m, 3H), 1.41-1.47 (m, 2H), 1.85-2.01 (m, 9H), 2.34-2.36 (m, 5H), 2.77-2.79 (m, 6H), 3.32-3.34 (m, 6H), 3.33-3.37 (m, 2H), 3.41-3.43 (m, 2H), 3.62-3.73 (m, 1H), 3.86-3.90 (m, 2H), 4.12-4.14 (m, 2H). | I | m/z 437 (M + H)$^+$ (ES+), at 4.10 min, UV inactive |
| 2-68 | Isomer 2: ethyl 2-{4-[(2S)-1-(2-fluoroethyl)pyrrolidin-2-yl]piperidin-1-yl}-6-azaspiro[3.4]octane-6-carboxylate | 127 and 240 | z | (400 MHz, DMSO-d$_6$) δ: 1.03-1.22 (m, 5H), 1.30-1.41 (m, 1H), 1.42-1.68 (m, 8H), 1.69-1.78 (m, 2H), 1.78-1.88 (m, 2H), 1.92-2.01 (m, 2H), 2.09-2.20 (m, 1H), 2.24-2.43 (m, 2H), 2.44-2.69 (m, 2H), 2.74-2.85 (m, 2H), 2.88-3.17 (m, 3H), 3.23-3.31 (m, 2H), 3.99 (q, J = 7.0 Hz, 2H), 4.33-4.66 (m, 2H). | I | m/z 382 (M + H)$^+$ (ES+), at 4.71 min, UV inactive |
| 2-69 | Isomer 2: ethyl 2-{4-[(2S)-1-(2,2,2-trifluoroethyl)pyrrolidin-2-yl]piperidin-1-yl}-6-azaspiro[3.4]octane-6-carboxylate | 127 and 237 | aa | (400 MHz, CD$_3$OD) δ: 1.27 (t, J = 7.2 Hz, 3H), 1.29-1.54 (m, 2H), 1.60-1.71 (m, 4H), 1.72-1.85 (m, 5H), 1.90-2.01 (m, 4H), 2.09-2.17 (m, 2H), 2.42-2.50 (m, 1H), 2.55-2.65 (m, 1H), 2.76-2.83 (m, 1H), 2.95-3.05 (m, 3H), 3.20-3.31 (m, 3H), 3.36-3.39 (m, 2H), 3.39-3.44 (m, 2H), 4.11 (q, J = 7.2 Hz, 2H). | I | m/z 418 (M + H)$^+$ (ES+), at 5.11 min, UV inactive |
| 2-70 | Isomer 1: ethyl 2-{4-[(2S)-1-(3,3,3-trifluoropropyl)pyrrolidin-2-yl]piperidin-1-yl}-6-azaspiro[3.4]octane-6-carboxylate | 127 and 236 | ab | (400 MHz, CD$_3$OD) δ: 1.23-1.40 (m, 6H), 1.45-1.54 (m, 1H), 1.62-1.71 (m, 3H), 1.72-1.83 (m, 4H), 1.85-1.97 (m, 5H), 2.08-2.21 (m, 3H), 2.35-2.46 (m, 3H), 2.73-2.80 (m, 1H), 2.92-3.02 (m, 3H), 3.09-3.15 (m, 1H), 3.32-3.44 (m, 4H), 4.13 (q, J = 7.0 Hz, 2H). | I | m/z 432 (M + H)$^+$ (ES+), at 5.54 min, UV inactive |
| 2-70 | Isomer 2: ethyl 2-{4-[(2S)-1-(3,3,3-trifluoropropyl)pyrrolidin-2-yl]piperidin-1-yl}-6-azaspiro[3.4]octane-6-carboxylate | 127 and 236 | ab | (400 MHz, CD$_3$OD) δ: 1.27 (t, J = 7.2 Hz, 3H), 1.30-1.39 (m, 3H), 1.46-1.55 (m, 1 H), 1.61-1.69 (m, 2H), 1.74-1.84 (m, 4H), 1.90-1.99 (m, 4H), 2.09-2.23 (m, 3H), 2.31-2.47 (m, 4H), 2.73-2.82 (m, 1H), 2.95-3.03 (m, 3H), 3.09-3.16 (m, 1 H), 3.28 (s, 2H), 3.37-3.43 (m, 3H), 4.11 (q, J = 7.2 Hz, 2H). | I | m/z 432 (M + H)$^+$ (ES+), at 5.39 min, UV inactive |
| 2-71 | Isomer 2: ethyl 2-{4-[(2S)-1-(2-methoxyethyl)pyrrolidin-2-yl]piperidin-1-yl}-6-azaspiro[3.4]octane-6-carboxylate | 127 and 231 | w | (400 MHz, CD$_3$OD) δ: 1.21-1.42 (m, 9H), 1.54-1.99 (m, 12H), 2.07-2.18 (m, 2H), 2.26-2.51 (m, 2H), 2.76-2.85 (m, 1H), 2.95-3.09 (m, 2H), 3.16-3.44 (m, 7H), 3.52-3.59 (m, 2H), 4.11 (q, J = 7.0 Hz, 2H). | I | m/z 394 (M + H)$^+$ (ES+), at 4.55 min, UV inactive |
| 2-72 | Isomer 2: ethyl 2-{4-[(2S)-1-(2-methoxy-2-oxoethyl)pyrrolidin-2-yl]piperidin-1-yl}-6-azaspiro[3.4]octane-6-carboxylate | 127 and 233 | ac | (400 MHz, CD$_3$OD) δ: 1.22-1.29 (m, 4H), 1.30-1.38 (m, 2H), 1.45-1.54 (m, 2H), 1.64-1.85 (m, 7H), 1.92-2.00 (m, 3H), 2.09-2.17 (m, 2H), 2.40-2.48 (m, 2H), 2.54-2.59 (m, | I | m/z 408 (M + H)$^+$ (ES+), at 4.56 min, UV inactive |

TABLE 3-continued

| Ex. No. | Name | Intermediate | Synthetic method | ¹H NMR | LCMS Method | LCMS data |
|---|---|---|---|---|---|---|
| | yl]piperidin-1-yl)-6-azaspiro[3.4]octane-6-carboxylate | | | 2H), 2.88-3.04 (m, 3H), 3.18-3.22 (m, 2H), 3.23-3.25 (m, 2H), 3.38-3.45 (m, 1H), 3.53-3.60 (m, 2H), 3.69-3.73 (m, 1H), 4.08-4.15 (m, 2H). | | |
| 2-73 | Isomer 1: ethyl 2-(4-{(2S)-1-[2-(dimethylamino)-2-oxoethyl]pyrrolidin-2-yl}piperidin-1-yl)-6-azaspiro[3.4]octane-6-carboxylate | 127 and 238 | ad | (400 MHz, CD₃OD) δ: 1.20-1.43 (m, 9H), 1.52-1.81 (m, 7H), 1.84-1.98 (m, 5H), 2.12-2.22 (m, 1H), 2.33-2.41 (m, 1H), 2.53-2.57 (m, 1H), 2.84-2.90 (m, 1H), 2.94 (s, 2H), 3.00-3.06 (m, 2H), 3.13 (s, 1H), 3.19-3.21 (m, 2H), 3.22-3.27 (m, 1H), 3.36-3.42 (m, 4H), 3.55-3.63 (m, 1H), 4.13 (d, J = 7.1 Hz, 2H). | I | m/z 421 (M + H)⁺ (ES+), at 3.94 min, UV inactive |
| 2-73 | Isomer 2: ethyl 2-(4-{(2S)-1-[2-(dimethylamino)-2-oxoethyl]pyrrolidin-2-yl}piperidin-1-yl)-6-azaspiro[3.4]octane-6-carboxylate | 127 and 238 | ad | (400 MHz, CD₃OD) δ: 1.21-1.44 (m, 8H), 1.54-2.03 (m, 12H), 2.10-2.24 (m, 2H), 2.31-2.43 (m, 1H), 2.53-2.59 (m, 1H), 2.84-2.90 (m, 1H), 2.94 (s, 2H), 3.02-3.12 (m, 2H), 3.13 (s, 1H), 3.23-3.30 (m, 3H), 3.36-3.46 (m, 4H), 3.54-3.63 (m, 1H), 4.11 (d, J = 7.10 Hz, 2H). | I | m/z 421 (M + H)⁺ (ES+), at 4.06 min, UV inactive |
| 2-74 | Isomer 2: ethyl 2-{4-[(2S)-1-benzylpyrrolidin-2-yl]piperidin-1-yl}-6-azaspiro[3.4]octane-6-carboxylate | 127 and 232 | w | (400 MHz, DMSO-d₆) δ: 1.07-1.22 (m, 5H), 1.44-1.72 (m, 9H), 1.73-1.76 (m, 4H), 1.93-2.07 (m, 2H), 2.32-2.88 (m, 6H), 3.05-3.28 (m, 5H), 3.87-4.17 (m, 3H), 7.18-7.37 (m, 5H). | I | m/z 426 (M + H)⁺ (ES+), at 6.30 min, UV active |
| 2-75 | Isomer 2: ethyl 2-{4-[(2S)-1-(methylcarbamothioyl)pyrrolidin-2-yl]piperidin-1-yl}-6-azaspiro[3.4]octane-6-carboxylate | 127 and 239 | m | (400 MHz, DMSO-d₆) δ: 1.16 (t, J = 7.17, 3H), 1.22-1.54 (m, 5H), 1.70-1.86 (m, 9H), 1.90-2.03 (m, 3H), 2.64-2.75 (m, 6H), 3.11-3.45 (m, 6H), 4.00 (q, J = 7.0 Hz, 2H) 4.29 (s, 1H), 7.23 (s, 1H). | I | m/z 409 (M + H)⁺ (ES+), at 4.10 min, UV inactive |
| 2-76 | Isomer 1: ethyl 2-{4-[2-(methylcarbamoyl)-2,3-dihydro-1H-isoindol-1-yl]piperidin-1-yl}-6-azaspiro[3.4]octane-6-carboxylate | 2, 243 and 244 | ae | (400 MHz, DMSO-d₆) δ: 1.13 (t, J = 7.1 Hz, 3H), 1.27-1.57 (m, 5H), 1.56-1.76 (m, 4H), 1.83-2.01 (m, 3H), 2.57-2.70 (m, 5H), 2.70-2.81 (m, 1H), 3.10-3.25 (m, 4H), 3.97 (q, J = 7.1 Hz, 2H), 4.36-4.48 (m, 1H), 4.51-4.65 (m, 1H), 4.96-5.09 (m, 1H), 6.19-6.30 (m, 1H), 7.16-7.37 (m, 4H). | M | m/z 441 (M + H)⁺ (ES+), at 1.97 min, UV active |
| 2-76 | Isomer 2: ethyl 2-{4-[2-(methylcarbamoyl)-2,3-dihydro-1H-isoindol-1-yl]piperidin-1-yl}-6-azaspiro[3.4]octane-6-carboxylate | 2, 243 and 244 | ae | (400 MHz, DMSO-d₆) δ: 1.12 (t, J = 7.1 Hz, 3H), 1.28-1.57 (m, 4H), 1.57-1.72 (m, 2H), 1.72-1.83 (m, 2H), 1.83-2.01 (m, 3H), 2.27-2.34 (m, 1H), 2.57-2.69 (m, 6H), 2.71-2.80 (m, 1H), 3.01-3.12 (m, 2H), 3.16-3.28 (m, 2H), 3.95 (q, J = 7.1 Hz, 2H), 4.38-4.49 (m, 1H), 4.52-4.64 (m, 1H), 4.97-5.10 (m, 1H), 6.20-6.31 (m, 1H), 7.20-7.37 (m, 4H). | M | m/z 441 (M + H)⁺ (ES+), at 1.99 min, UV active |
| 2-77 | Isomer 2: ethyl 2-{4-[(2S)-1-phenylpyrrolidin-2-yl]piperidin-1-yl}-6-azaspiro[3.4]octane-6-carboxylate | 127 and 172 | af | (400 MHz, CD₃OD) δ: 1.24 (td, J = 7.0, 1.5 Hz, 3 H), 1.32-1.49 (m, 2 H), 1.53-1.62 (m, 1 H), 1.63-1.73 (m, 2 H), 1.75-1.85 (m, 2 H), 1.85-2.03 (m, 8 H), 2.04-2.15 (m, 2 H), 2.68-2.81 (m, 1 H), 2.89-3.02 (m, 2 H), 3.06-3.17 (m, 1 H), 3.26 (s, 2 H), 3.33-3.43 (m, 2 H), 3.45-3.54 (m, 1 H), 3.68-3.76 (m, 1 H), 4.09 (q, J = 7.0 Hz, 2 H), 6.56-6.64 (m, 3 H), 7.08-7.19 (m, 2 H) | I | m/z 412 (M + H)⁺ (ES+), at 6.19 min, UV active |

TABLE 3-continued

| Ex. No. | Name | Intermediate | Synthetic method | ¹H NMR | LCMS Method | LCMS data |
|---|---|---|---|---|---|---|
| 2-78 | Isomer 2: methyl 2-{4-[(2S)-1-(pyridin-2-yl)pyrrolidin-2-yl]piperidin-1-yl}-6-azaspiro[3.4]octane-6-carboxylate | 157 and 176 | ag | (400 MHz, CD₃OD) δ: 1.25-2.14 (m, 18 H), 2.66-2.79 (m, 1 H), 2.88-3.00 (m, 2 H), 3.25 (d, J = 1.5 Hz, 2 H), 3.33-3.45 (m, 2 H), 3.47-3.56 (m, 1 H), 3.66 (s, 3 H), 4.01-4.10 (m, 1 H), 6.51-6.58 (m, 2 H), 7.45-7.53 (m, 1 H), 7.97-8.01 (m, 1 H) | I | m/z 399 (M + H)⁺ (ES+), at 4.56 min, UV active |
| 2-79 | Isomer 2: ethyl 2-{4-[(2S)-1-(pyridin-2-yl)pyrrolidin-2-yl]piperidin-1-yl}-6-azaspiro[3.4]octane-6-carboxylate | 127 and 176 | ag | (400 MHz, CDCl₃) δ: 1.19-1.21 (m, 1H), 1.29-1.31 (m, 6H), 2.05-2.12 (m, 4H), 2.13-2.14 (m, 8H), 2.51-2.53 (m, 1H), 2.97-2.98 (m, 3H), 3.14-3.18 (m, 2H), 3.24-3.28 (m, 3H), 3.41-3.43 (m, 1H), 4.02-4.05 (m, 1H), 4.12-4.15 (m, 2H), 6.40 (d, J = 7.0 Hz, 1H), 6.54 (dd, J = 7.0 and 7.0 Hz, 1H), 7.41 (dd, J = 7.0 and 7.0 Hz, 1H), 8.17 (d, J = 7.0 Hz, 1H). | I | m/z 413 (M + H)⁺ (ES+), at 5.05 min, UV active |
| 2-80 | Isomer 1: ethyl 2-{4-[(2S)-1-(pyridin-4-yl)pyrrolidin-2-yl]piperidin-1-yl}-6-azaspiro[3.4]octane-6-carboxylate | 127 and 175 | ah | (400 MHz, CD₃OD) δ: 1.15-2.18 (m, 18 H), 1.25 (t, J = 7.2 Hz, 3 H), 2.69-2.81 (m, 1 H), 2.90-3.00 (m, 2 H), 3.32-3.41 (m, 2 H), 3.46-3.54 (m, 1 H), 3.85-3.92 (m, 1 H), 4.05-4.15 (m, 2 H), 6.60 (d, J = 6.4 Hz, 2 H), 8.04 (d, J = 4.9 Hz, 2 H). 2 protons obscured by MeOH peak. | I | m/z 413 (M + H)⁺ (ES+), at 4.49 min, UV active |
| 2-80 | Isomer 2: ethyl 2-{4-[(2S)-1-(pyridin-4-yl)pyrrolidin-2-yl]piperidin-1-yl}-6-azaspiro[3.4]octane-6-carboxylate | 127 and 175 | ah | (400 MHz, CD₃OD) δ: 1.13-2.18 (m, 21 H), 2.72-2.83 (m, 1 H), 2.93-3.02 (m, 2 H), 3.26 (s, 2 H), 3.34-3.43 (m, 2 H), 3.47-3.59 (m, 1 H), 3.88-3.96 (m, 1 H), 4.09 (q, J = 7.0 Hz, 2 H), 6.64 (d, J = 6.7 Hz, 2 H), 8.04 (d, J = 6.4 Hz, 2 H). | I | m/z 413 (M + H)⁺ (ES+), at 4.65 min, UV active |
| 2-81 | Isomer 2: ethyl 2-{4-[(2S)-1-(pyrimidin-2-yl)pyrrolidin-2-yl]piperidin-1-yl}-6-azaspiro[3.4]octane-6-carboxylate | 127 and 169 | ah | (400 MHz, CD₃OD) δ: 1.21-1.28 (m, 3 H), 1.35-1.82 (m, 6 H), 1.86-2.14 (m, 10 H), 2.68-2.79 (m, 1 H), 2.90-2.99 (m, 2 H), 3.26 (s, 2 H), 3.34-3.43 (m, 2 H), 3.46-3.67 (m, 2 H), 4.09 (q, J = 7.0 Hz, 2 H), 4.17-4.26 (m, 1 H), 4.56-4.70 (m, 1 H), 6.57 (t, J = 4.9 Hz, 1 H), 8.29 (d, J = 4.9 Hz, 2 H) | I | m/z 414 (M + H)⁺ (ES+), at 4.54 min, UV active |
| 2-82 | Isomer 2: ethyl 2-{4-[(2S)-1-(1,3-thiazol-2-yl)pyrrolidin-2-yl]piperidin-1-yl}-6-azaspiro[3.4]octane-6-carboxylate | 40 and 127 | ai | (400 MHz, DMSO-d₆) δ: 1.17 (t, 3 H), 1.21-1.36 (m, 4 H), 1.39-1.65 (m, 4 H), 1.67-1.82 (m, 4 H), 1.83-2.05 (m, 6 H), 2.76-2.86 (m, 2 H), 3.16-3.31 (m, 5 H), 3.38-3.45 (m, 1 H), 3.73-3.80 (m, 1 H), 4.00 (q, J = 7.0 Hz, 2 H), 6.70 (d, J = 3.7 Hz, 1 H), 7.13 (d, J = 3.7 Hz, 1 H) | E | m/z 419 (M + H)⁺ (ES+), at 4.67 min, UV active |
| 2-83 | Isomer 2: ethyl 2-{4-[(2S)-1-(1,3,4-thiadiazol-2-yl)pyrrolidin-2-yl]piperidin-1-yl}-6-azaspiro[3.4]octane-6-carboxylate | 127 and 256 | ai | (400 MHz, DMSO-d₆) δ: 1.39-1.41 (m, 4H), 1.42-1.43 (m, 3H), 1.60-1.71 (m, 3H), 1.80-1.83 (m, 3H), 1.97-2.02 (m, 9H), 3.11-3.13 (m, 2H), 3.21-3.23 (m, 4H), 3.31-3.36 (m, 1H), 3.91-3.93 (m, 1H), 4.12-4.13 (q, 2H, J = 6.2 Hz), 8.62 (s, 1H). | I | m/z 420 (M + H)⁺ (ES+), at 4.08 min, UV active |
| 2-84 | Isomer 2: ethyl 2-{4-[(2R)-2-(methoxycarbonyl)pyrrolidin-1-yl]piperidin-1-yl}-6-azaspiro[3.4]octane-6-carboxylate | 2 and 159 | aj | (400 MHz, CD₃OD) δ: 1.24 (t, J = 7.0 Hz, 3 H), 1.42-1.59 (m, 2H), 1.72-1.97 (m, 11 H), 2.02-2.17 (m, 3 H), 2.43 (t, J = 10.9 Hz, 1 H), 2.58-2.78 (m, 2 H), 2.82-2.92 (m, 2 H), 3.01-3.11 (m, 1 H), 3.25 (s, 2 H), 3.37 (q, J = 6.6 Hz, 2 H), 3.49 (dd, J = 9.4, 3.51 Hz, 1 H), 3.68 (s, 3 H), 4.08 (q, J = 7.0 Hz, 2 H) | E | m/z 394 (M + H)⁺ (ES+), at 3.29 min, UV inactive |
| 2-85 | Isomer 2: ethyl 2-{4-[(2S)-2-(methylcarbamoyl)pyrrolidin-1-yl]piperidin-1-yl}-6-azaspiro[3.4]octane-6-carboxylate | 2 and 139 | ak | (400 MHz, DMSO-d₆) δ: 1.16 (t, J = 7.0 Hz, 3 H), 1.28-1.44 (m, 2 H), 1.50-2.03 (m, 11 H), 2.15-2.30 (m, 1 H), 2.33-2.64 (m, 5 H), 2.68-2.81 (m, 2 H), 2.97-3.19 (m, 4 H), 3.22-3.39 (m, 5 H), 3.99 (q, J = 7.0 Hz, 2 H), 7.67 (q, J = 4.6 Hz, 1 H). | G | m/z 393 (M + H)⁺ (ES⁺) at 5.15 min, UV inactive |

TABLE 3-continued

| Ex. No. | Name | Intermediate | Synthetic method | ¹H NMR | LCMS Method | LCMS data |
|---|---|---|---|---|---|---|
| 2-86 | Mixture of diastereomers: 1-{1-[6-(ethoxycarbonyl)-6-azaspiro[3.4]oct-2-yl]piperidin-4-yl}-4,4-difluoro-D-proline | Example 2-87 | ao | (400 MHz, CD₃OD) δ: 1.18-1.30 (m, 3 H), 1.75 (br.s., 2 H), 1.85-2.04 (m, 4 H), 2.06-2.22 (m, 2 H), 2.23-2.42 (m, 3 H), 2.45-2.72 (m, 3 H), 2.79-2.91 (m, 1 H), 2.99 (dt, J = 17.4, 10.6 Hz, 1 H), 3.17-3.27 (m, 2 H), 3.33-3.55 (m, 7 H), 4.03-4.16 (m, 2 H) OH not observed. | E | m/z 416 ((M + H)⁺ (ES+), at 1.62 min, UV inactive |
| 2-87 | Isomer 2: ethyl 2-{4-[(2R)-4,4-difluoro-2-(methoxycarbonyl)pyrrolidin-1-yl]piperidin-1-yl}-6-azaspiro[3.4]octane-6-carboxylate | 2 and 260 | aL | (400 MHz, DMSO-d₆) δ: 1.13 (t, J = 7.0 Hz, 3 H), 1.20-1.33 (m, 2 H), 1.62-1.83 (m, 8 H), 1.90-1.97 (m, 3 H), 2.53-2.62 (m, 4 H), 3.11 (d, J = 6.2 Hz, 2 H), 3.19-3.26 (m, 5 H), 3.61 (s, 3 H), 3.81-3.86 (m, 1 H), 3.97 (q, J = 7.0 Hz, 2 H) | E | m/z 430 (M + H)⁺ (ES+), at 3.64 min, UV inactive |
| 2-88 | Isomer 2: ethyl 2-{4-[(2R)-4,4-difluoro-2-(methylcarbamoyl)pyrrolidin-1-yl]piperidin-1-yl}-6-azaspiro[3.4]octane-6-carboxylate | Example 2-87 and 168 | am | (400 MHz, DMSO-d₆) δ: 1.13 (t, J = 7.0 Hz, 3 H), 1.32 (q, J = 12.0 Hz, 2 H), 1.49-1.66 (m, 3 H), 1.66-1.75 (m, 3 H), 1.75-1.86 (m, 2 H), 1.94 (dd, J = 10.9, 7.4 Hz, 2 H), 2.03-2.22 (m, 1 H), 2.33-2.38 (m, 1 H), 2.52-2.63 (m, 5 H), 2.68-2.79 (m, 2 H), 2.91-3.07 (m, 1 H), 3.11 (d, J = 5.9 Hz, 2 H), 3.18-3.29 (m, 3 H), 3.48 (dd, J = 9.8, 5.5 Hz, 1 H), 3.97 (q, J = 7.0 Hz, 2 H), 7.82 (q, J = 4.7 Hz, 1 H) | E | m/z 429 (M + H)⁺ (ES+), at 2.96 min, UV inactive |
| 2-89 | Isomer 2: ethyl 2-{4-[(2R)-2-(dimethylcarbamoyl)-4,4-difluoropyrrolidin-1-yl]piperidin-1-yl}-6-azaspiro[3.4]octane-6-carboxylate | Example 2-87 and 307 | am | (400 MHz, DMSO-d₆) δ: 1.13 (t, J = 7.0 Hz, 3 H), 1.19-1.33 (m, 2 H), 1.51-1.75 (m, 6 H), 1.75-1.84 (m, 2 H), 1.88-1.99 (m, 2 H), 2.08-2.22 (m, 1 H), 2.53-2.62 (m, 3 H), 2.67-2.73 (m, 2 H), 2.77 (s, 3 H), 2.97 (s, 3 H), 3.11 (d, J = 6.2 Hz, 2 H), 3.24 (q, J = 6.8 Hz, 2 H), 3.37-3.47 (m, 2 H), 3.97 (q, J = 7.2 Hz, 2 H), 4.14 (dd, J = 9.0, 4.7 Hz, 1 H) | E | m/z 443 (M + H)⁺ (ES+), at 3.03 min, UV inactive |
| 2-90 | Isomer 2: ethyl 2-{4-[(2R)-2-carbamoyl-4,4-difluoropyrrolidin-1-yl]piperidin-1-yl}-6-azaspiro[3.4]octane-6-carboxylate | Example 2-87 | an | (400 MHz, CD₃OD) δ: 1.24 (t, J = 7.0 Hz, 3 H), 1.44-1.61 (m, 2 H), 1.74-1.98 (m, 9 H), 2.04-2.14 (m, 2 H), 2.17-2.31 (m, 1 H), 2.51 (t, J = 10.9 Hz, 1 H), 2.57-2.80 (m, 2 H), 2.91 (t, J = 9.5 Hz, 2 H), 2.98-3.15 (m, 1 H), 3.25 (s, 3 H), 3.34-3.50 (m, 3 H), 3.55 (dd, J = 9.5, 5.5 Hz, 1 H), 4.08 (q, J = 7.0 Hz, 2 H) | E | m/z 415 (M + H)⁺ (ES+), at 3.20 min, UV inactive |
| 2-91 | Isomer 2: ethyl 2-{4-[(2R)-4,4-difluoro-2-(methoxycarbamoyl)pyrrolidin-1-yl]piperidin-1-yl}-6-azaspiro[3.4]octane-6-carboxylate | Example 2-87 and 123 | ao | (400 MHz, CD₃OD) δ: 1.24 (t, J = 7.2 Hz, 3 H), 1.43-1.58 (m, 2 H), 1.75-1.98 (m, 8 H), 2.09 (t, J = 9.8 Hz, 2 H), 2.20-2.37 (m, 1 H), 2.43-2.53 (m, 1 H), 2.54-2.78 (m, 2 H), 2.84-2.96 (m, 2 H), 2.96-3.15 (m, 1 H), 3.25 (s, 2 H), 3.34-3.45 (m, 3 H), 3.61 (dd, J = 9.6, 5.3 Hz, 1 H), 3.68 (s, 3 H), 4.08 (q, J = 7.2 Hz, 2 H) NH not observed. | E | m/z 445 (M + H)⁺ (ES+), at 2.62 min, UV inactive |
| 2-92 | Isomer 2: ethyl 2-(4-{(2R)-4,4-difluoro-2-[methoxy(methyl)carbamoyl]pyrrolidin-1-yl}piperidin-1-yl)-6-azaspiro[3.4]octane-6-carboxylate | Example 2-87 and 124 | ao | (400 MHz, CD₃OD) δ: 1.24 (t, J = 7.0 Hz, 3 H), 1.51 (d, J = 10.9 Hz, 2 H), 1.72-1.97 (m, 8 H), 2.03-2.13 (m, 2 H), 2.24 (qd, J = 14.3, 6.1 Hz, 1 H), 2.56-2.78 (m, 3 H), 2.86 (d, J = 9.4 Hz, 2 H), 3.07-3.21 (m, 4 H), 3.25 (s, 2 H), 3.33-3.51 (m, 3 H), 3.73 (s, 3 H), 4.08 (q, J = 7.0 Hz, 2 H), 4.20-4.30 (m, 1 H) | E | m/z 459 (M + H)⁺ (ES+), at 3.63 min, UV inactive |
| 2-93 | Isomer 2: ethyl 2-{4-[(2S)-4,4-difluoro-2-(methylcarbamoyl)pyrrolidin-1-yl]piperidin-1-yl}-6-azaspiro[3.4]octane-6-carboxylate | 2, 167 and 262 | aL and am | (400 MHz, DMSO-d₆) δ: 1.13 (t, J = 7.0 Hz, 3 H), 1.26-1.38 (m, 2 H), 1.54-1.66 (m, 3 H), 1.66-1.75 (m, 3 H), 1.75-1.85 (m, 2 H), 1.89-1.99 (m, 2 H), 2.06-2.19 (m, 1 H), 2.33-2.38 (m, 1 H), 2.54-2.61 (m, 5 H), 2.71-2.78 (m, 2 H), 2.96-3.06 (m, 1 H), 3.11 (d, J = 5.9 Hz, 2 H), 3.21-3.27 (m, 3 H), 3.45-3.51 (m, 1 H), 3.97 (q, J = 7.0 Hz, 2 H), 4.30 (m, 1 H), 7.74-7.88 (m, 1 H) | E | m/z 429 (M + H)⁺ (ES+), at 2.97 min, UV inactive |

TABLE 3-continued

| Ex. No. | Name | Intermediate | Synthetic method | $^1$H NMR | LCMS Method | LCMS data |
|---|---|---|---|---|---|---|
| 2-94 | Isomer 2: ethyl 2-{4-[(2S)-2-(dimethylcarbamoyl)-4,4-difluoropyrrolidin-1-yl]piperidin-1-yl}-6-azaspiro[3.4]octane-6-carboxylate | 2, 262 and 307 | aL and am | (400 MHz, DMSO-d$_6$) δ: 1.13 (t, J = 7.0 Hz, 3 H), 1.20-1.32 (m, 2 H), 1.52-1.75 (m, 6 H), 1.75-1.84 (m, 2 H), 1.93 (dd, J = 10.5, 8.2 Hz, 2 H), 2.08-2.20 (m, 1 H), 2.52-2.62 (m, 3 H), 2.67-2.72 (m, 2 H), 2.77 (s, 3 H), 2.97 (s, 3 H), 3.11 (d, J = 6.2 Hz, 2 H), 3.21-3.27 (m, 2 H), 3.36-3.44 (m, 2 H), 3.93-4.01 (m, 2 H), 4.14 (dd, J = 9.0, 4.7 Hz, 1 H) | E | m/z 443 (M + H)$^+$ (ES$^+$), at 3.03 min, UV inactive |
| 2-95 | Isomer 2: ethyl 2-{4-[(2R)-2-(methoxycarbonyl)-2-methylpyrrolidin-1-yl]piperidin-1-yl}-6-azaspiro[3.4]octane-6-carboxylate | 2 and 293 | aw | (400 MHz, DMSO-d$_6$) δ: 1.13 (t, J = 7.0 Hz, 3 H), 1.19 (s, 3 H), 1.27-1.38 (m, 2 H), 1.40-1.51 (m, 3 H), 1.52-1.74 (m, 7 H), 1.75-1.85 (m, 2 H), 1.87-1.98 (m, 2 H), 1.98-2.08 (m, 1 H), 2.52-2.62 (m, 1 H), 2.67-2.85 (m, 3 H), 2.89 (q, J = 7.5 Hz, 1 H), 3.11 (d, J = 6.6 Hz, 2 H), 3.24 (q, J = 6.8 Hz, 2 H), 3.55 (s, 3 H), 3.97 (q, J = 7.0 Hz, 2 H) | E | m/z 408 (M + H)$^+$ (ES$^+$), at 4.06 min, UV inactive |
| 2-96 | Isomer 2: ethyl 2-{4-(6-oxo-7-oxa-1-azaspiro[4.4]non-1-yl)piperidin-1-yl]-6-azaspiro[3.4]octane-6-carboxylate | 2 and 300 | aw | (400 MHz, DMSO-d$_6$) δ: 1.13 (t, J = 7.0 Hz, 3 H), 1.25-1.50 (m, 3 H), 1.50-1.68 (m, 4 H), 1.68-1.86 (m, 8 H), 1.86-2.02 (m, 4 H), 2.18-2.35 (m, 1 H), 2.53-2.67 (m, 1 H), 2.67-2.85 (m, 2 H), 2.95-3.07 (m, 1 H), 3.11 (d, J = 6.6 Hz, 2 H), 3.24 (q, J = 6.6 Hz, 2 H), 3.97 (q, J = 7.0 Hz, 2 H), 4.06-4.18 (m, 1 H), 4.32 (t, J = 8.6 Hz, 1 H) | E | m/z 406 (M + H)$^+$ (ES$^+$), at 5.24 min, UV inactive |
| 2-97 | Isomer 1: ethyl 2-{4-[(4S)-4-(methoxycarbonyl)-1,3-thiazolidin-3-yl]piperidin-1-yl}-6-azaspiro[3.4]octane-6-carboxylate | 2 and 286 | aw | (400 MHz, DMSO-d$_6$) δ: 1.08-1.18 (m, 3 H), 1.32 (quin, J = 11.9 Hz, 2 H), 1.58-1.87 (m, 8 H), 1.96 (t, J = 9.4 Hz, 2 H), 2.32-2.38 (m, 1 H), 2.59 (t, J = 7.2 Hz, 1 H), 2.72 (d, J = 8.2 Hz, 2 H), 2.93-3.13 (m, 2 H), 3.14-3.26 (m, 4 H), 3.60 (s, 3 H), 3.93 (d, J = 9.8 Hz, 1 H), 3.98 (q, J = 7.0 Hz, 2 H), 4.26 (d, J = 9.4 Hz, 1 H), 4.41 (d, J = 5.5 Hz, 1 H) | E | m/z 412 (M + H)$^+$ (ES$^+$), at 3.62 min, UV inactive |
| 2-97 | Isomer 2: ethyl 2-{4-[(4S)-4-(methoxycarbonyl)-1,3-thiazolidin-3-yl]piperidin-1-yl}-6-azaspiro[3.4]octane-6-carboxylate | 2 and 286 | aw | (400 MHz, DMSO-d$_6$) δ: 1.13 (t, J = 7.0 Hz, 3 H), 1.24-1.43 (m, 2 H), 1.57-1.86 (m, 8 H), 1.88-2.01 (m, 2 H), 2.33-2.38 (m, 1 H), 2.58 (t, J = 6.8 Hz, 1 H), 2.72 (d, J = 9.0 Hz, 2 H), 2.93-3.03 (m, 1 H), 3.06 (d, J = 2.3 Hz, 1 H), 3.08-3.17 (m, 2 H), 3.24 (q, J = 6.8 Hz, 2 H), 3.60 (s, 3 H), 3.88-4.04 (m, 3 H), 4.26 (d, J = 9.4 Hz, 1 H), 4.41 (d, J = 5.9 Hz, 1 H) | E | m/z 412 (M + H)$^+$ (ES$^+$), at 3.78 min, UV inactive |
| 2-98 | Isomer 2: ethyl 2-{4-[(3R)-3-fluoropyrrolidin-1-yl]piperidin-1-yl}-6-azaspiro[3.4]octane-6-carboxylate | 151 and 262 | ap | (400 MHz, DMSO-d$_6$) δ: 1.13 (t, J = 7.2 Hz, 3 H), 1.26-1.35 (m, 2 H), 1.59-1.86 (m, 10 H), 1.88-1.99 (m, 6 H), 2.71-2.88 (m, 3 H), 3.12 (d, J = 7.0 Hz, 2 H), 3.20-3.29 (m, 3 H), 3.97 (q, J = 7.0 Hz, 2 H), 5.02-5.13 (m, 1 H) | E | m/z 354 (M + H)$^+$ (ES$^+$), at 3.06 min, UV inactive |
| 2-99 | Isomer 2: ethyl 2-{4-[(3S)-3-fluoropyrrolidin-1-yl]piperidin-1-yl}-6-azaspiro[3.4]octane-6-carboxylate | 151 and 263 | ap | (400 MHz, DMSO-d$_6$) δ: 1.13 (t, J = 7.0 Hz, 3 H), 1.25-1.37 (m, 2 H), 1.54-1.84 (m, 10 H), 1.86-1.99 (m, 6 H), 2.71-2.85 (m, 3 H), 3.12 (d, J = 7.0 Hz, 2 H), 3.20-3.26 (m, 3 H), 3.97 (q, J = 7.0 Hz, 2 H), 5.03-5.16 (m, 1 H) | E | m/z 354 (M + H)$^+$ (ES$^+$), at 3.03 min, UV inactive |
| 2-100 | Isomer 2: ethyl 2-(4-(3,3-difluoropyrrolidin-1-yl)piperidin-1-yl)-6-azaspiro[3.4]octane-6-carboxylate | 88 and 151 | ap | (400 MHz, DMSO-d$_6$) δ: 1.13 (t, J = 7.0 Hz, 3 H), 1.24-1.31 (m, 2 H), 1.57-1.87 (m, 7 H), 1.89-2.06 (m, 3 H), 2.11-2.27 (m, 1 H), 2.44 (brs., 1 H), 2.55-2.61 (m, 4 H), 2.68-2.71 (m, 3 H), 2.87 (t, J = 14.1 Hz, 2 H), 3.12 (d, J = 7.0 Hz, 2 H), 3.20-3.27 (m, 2 H), 3.97 (q, J = 7.0 Hz, 2 H) | E | m/z 372 (M + H)$^+$ (ES$^+$), at 3.38 min, UV inactive |
| 2-101 | Isomer 2: ethyl 2-{4-[(2S)-2-(trifluoromethyl)pyrrolidin-1-yl]piperidin-1-yl}-6-azaspiro[3.4]octane-6-carboxylate | 2 and 278 | aw | (400 MHz, DMSO-d$_6$) δ: 1.13 (t, J = 7.0 Hz, 3 H), 1.29-1.47 (m, 2 H), 1.55-1.85 (m, 12 H), 1.89-2.00 (m, 2 H), 2.54-2.68 (m, 2 H), 2.70-2.90 (m, 3 H), 3.11 (d, J = 5.9 Hz, 2 H), 3.19-3.27 (m, 3 H), 3.49-3.61 (m, 1 H), 3.96 (q, J = 7.0 Hz, 2 H) | E | m/z 404 (M + H)$^+$ (ES$^+$), at 4.22 min, UV inactive |

TABLE 3-continued

| Ex. No. | Name | Intermediate | Synthetic method | $^1$H NMR | LCMS Method | LCMS data |
|---|---|---|---|---|---|---|
| 2-102 | Isomer 2: ethyl 2-{4-[(2R)-2-(fluoromethyl)pyrrolidin-1-yl]piperidin-1-yl}-6-azaspiro[3.4]octane-6-carboxylate | 2 and 296 | aw | (400 MHz, DMSO-d$_6$) δ: 1.10-1.16 (m, 3 H), 1.21 (s, 2 H), 1.27-1.50 (m, 3 H), 1.50-1.56 (m, 2 H), 1.56-1.72 (m, 3 H), 1.72-1.92 (m, 5 H), 1.92-2.03 (m, 2 H), 2.09-2.21 (m, 1 H), 2.23-2.45 (m, 4 H), 2.69-2.94 (m, 1 H), 3.09-3.21 (m, 2 H), 3.21-3.29 (m, 4 H), 3.98 (q, J = 7.0 Hz, 2 H) | E | m/z 368 (M + H)$^+$ (ES$^+$), at 5.04 min, UV inactive |
| 2-103 | Isomer 2: ethyl 2-{4-[(2R)-2-(difluoromethyl)pyrrolidin-1-yl]piperidin-1-yl}-6-azaspiro[3.4]octane-6-carboxylate | 2 and 298 | aw | (400 MHz, DMSO-d$_6$) δ: 1.14 (t, J = 7.0 Hz, 3 H), 1.18-1.28 (m, 2 H), 1.32-1.49 (m, 2 H), 1.57-1.87 (m, 11 H), 1.89 (s, 1 H), 1.92-2.09 (m, 2 H), 2.10-2.23 (m, 1 H), 2.67-2.94 (m, 3 H), 3.06-3.21 (m, 3 H), 3.21-3.28 (m, 2 H), 3.98 (q, J = 7.2 Hz, 2 H), 5.63-5.78 (m, 1 H) | E | m/z 386 (M + H)$^+$ (ES$^+$), at 5.62 min, UV inactive |
| 2-104 | Isomer 2: ethyl 2-{4-[(2R)-2-(trifluoromethyl)pyrrolidin-1-yl]piperidin-1-yl}-6-azaspiro[3.4]octane-6-carboxylate | 2 and 274 | aw | (300 MHz, DMSO-d$_6$) δ: 1.16 (t, J = 7.0 Hz, 3 H), 1.31-1.54 (m, 2 H), 1.54-1.91 (m, 12 H), 1.97 (t, J = 9.2 Hz, 2 H), 2.58-2.75 (m, 2 H), 2.75-2.92 (m, 3 H), 3.14 (br.s, 2 H), 3.20-3.25 (m, 3 H), 3.49-3.66 (m, 1 H), 3.99 (q, J = 7.1 Hz, 2 H) | E | m/z 404 (M + H)$^+$ (ES$^+$), at 4.22 min, UV inactive |
| 2-105 | Isomer 2: ethyl 2-{4-(3-azabicyclo[3.1.0]hex-3-yl)piperidin-1-yl]-6-azaspiro[3.4]octane-6-carboxylate | 2 and 280 | aw | (400 MHz, DMSO-d$_6$) δ: 0.27 (br.s., 1 H), 0.45-0.54 (m, 1 H), 1.13 (t, J = 7.0 Hz, 3 H), 1.22-1.40 (m, 4 H), 1.57-1.86 (m, 8 H), 1.94 (t, J = 8.2 Hz, 2 H), 1.98-2.14 (m, 1 H), 2.19-2.36 (m, 2 H), 2.59-2.73 (m, 3 H), 2.93 (d, J = 8.2 Hz, 2 H), 3.11 (d, J = 5.5 Hz, 2 H), 3.20-3.25 (m, 2 H), 3.96 (q, J = 7.2 Hz, 2 H) | E | m/z 348 (M + H)$^+$ (ES$^+$), at 3.78 min, UV inactive |
| 2-106 | Isomer 2: ethyl 2-{(2S)-4,4-difluoro-2-methylpyrrolidin-1-yl]pyrrolidin-1-yl]piperidin-1-yl}-6-azaspiro[3.4]octane-6-carboxylate | 2 and 125 | aj | (400 MHz, CD$_3$OD) δ: 1.11 (d, J = 5.9 Hz, 3 H), 1.19-1.35 (m, 4 H), 1.41-1.63 (m, 2 H), 1.71-1.97 (m, 9 H), 2.05-2.15 (m, 2 H), 2.31-2.46 (m, 1 H), 2.63-2.82 (m, 2 H), 2.89-3.00 (m, 2 H), 3.08-3.22 (m, 1 H), 3.25 (s, 2 H), 3.34-3.42 (m, 2 H), 4.09 (q, J = 7.0 Hz, 2 H) | E | m/z 386 (M + H)$^+$ (ES$^+$), at 3.98 min, UV inactive |
| 2-107 | Isomer 2: ethyl 2-{4-[(2R)-4,4-difluoro-2-(hydroxymethyl)pyrrolidin-1-yl]piperidin-1-yl}-6-azaspiro[3.4]octane-6-carboxylate | 2 and 126 | aj | (400 MHz, CD$_3$OD) δ: 1.18-1.29 (m, 3 H), 1.43-1.60 (m, 2 H), 1.74-1.97 (m, 8 H), 2.04-2.23 (m, 3 H), 2.24-2.41 (m, 1 H), 2.66-2.81 (m, 2 H), 2.88-3.11 (m, 3 H), 3.14-3.28 (m, 5 H), 3.38 (q, J = 6.4 Hz, 2 H), 3.44-3.59 (m, 2 H), 4.09 (q, J = 7.2 Hz, 2 H) | E | m/z 402 (M + H)$^+$ (ES$^+$), at 3.23 min, UV inactive |
| 2-108 | Isomer 2: ethyl 2-{4-[(2R)-4,4-difluoro-2-(methoxymethyl)pyrrolidin-1-yl]piperidin-1-yl}-6-azaspiro[3.4]octane-6-carboxylate | 2 and 174 | as | (400 MHz, CDCl$_3$) δ: 1.25 (t, J = 7.0 Hz, 3 H), 1.41-1.99 (m, 10 H), 2.01-2.24 (m, 3 H), 2.24-2.44 (m, 1 H), 2.57-2.78 (m, 1 H), 2.83-3.11 (m, 3 H), 3.14-3.47 (m, 9 H), 3.35 (s, 3H), 4.11 (q, J = 7.2 Hz, 2 H) | B | m/z 416 (M + H)$^+$ (ES+), at 4.04 min, UV inactive |
| 2-109 | Isomer 2: ethyl 2-{4-[(2R)-4,4-difluoro-2-(1-hydroxyethyl)pyrrolidin-1-yl]piperidin-1-yl}-6-azaspiro[3.4]octane-6-carboxylate | 2 and 179 | as | (400 MHz, CDCl$_3$) δ: 1.14 (d, J = 6.2 Hz, 3 H), 1.24 (t, J = 7.0 Hz, 3 H), 1.40-2.20 (m, 13 H), 2.25-2.43 (m, 1 H), 2.58-2.83 (m, 2 H), 2.83-3.10 (m, 4 H), 3.10-3.34 (m, 4 H), 3.34-3.44 (m, 2 H), 3.49-3.57 (m, 1 H), 4.11 (q, J = 7.0 Hz, 2 H) | B | m/z 416 (M + H)$^+$ (ES+), at 4.20 min, UV inactive |

| Ex. No. | Name | Intermediate | Synthetic method | ¹H NMR | LCMS Method | LCMS data |
|---|---|---|---|---|---|---|
| 2-109 | Isomer 4: ethyl 2-{4-[(2R)-4,4-difluoro-2-(1-hydroxyethyl)pyrrolidin-1-yl]piperidin-1-yl}-6-azaspiro[3.4]octane-6-carboxylate | 2 and 179 | as | (400 MHz, CDCl₃) δ: 1.08 (d, J = 6.6 Hz, 3 H), 1.24 (t, J = 6.6 Hz, 3 H), 1.47-2.19 (m, 13 H), 2.20-2.37 (m, 1 H), 2.60-2.72 (m, 2 H), 2.89-3.02 (m, 4 H), 3.02-3.17 (m, 2 H), 3.18-3.44 (m, 4 H), 3.85-3.94 (m, 1 H), 4.11 (q, J = 6.8 Hz, 2 H) | B | m/z 416 (M + H)⁺ (ES+), at 3.99 min, UV inactive |
| 2-110 | Mixture of diasteremomers: ethyl 2-{4-[(2R)-4,4-difluoro-2-(2-hydroxypropan-2-yl)pyrrolidin-1-yl]piperidin-1-yl}-6-azaspiro[3.4]octane-6-carboxylate | 2 and 258 | ax | (400 MHz, DMSO-d₆) δ: 0.85-1.08 (m, 5H), 1.09-1.21 (m, 4H), 1.21-1.44 (m, 2H), 1.44-1.88 (m, 6H), 1.88-2.35 (m, 4H), 2.55-3.17 (m, 6H), 3.17-3.39 (m, 3H), 3.42-3.76 (m, 3H), 3.94-4.09 (m, 3H), 4.23 (s, 1H). | N | m/z 430 (M + H)⁺ (ES+), at 2.14 + 2.16 min, UV inactive |
| 2-111 | Isomer 2: ethyl 2-[4-(2-oxopyrrolidin-1-yl)piperidin-1-yl]-6-azaspiro[3.4]octane-6-carboxylate | 2 and 269 | ap | ¹H NMR (400 MHz, DMSO-d₆) δ: 1.14 (t, J = 7.2 Hz, 3 H), 1.46 (d, J = 10.2 Hz, 2 H), 1.52-1.66 (m, 2 H), 1.66-1.77 (m, 4 H), 1.77-1.91 (m, 5 H), 1.96 (t, J = 9.0 Hz, 2 H), 2.14-2.21 (m, 2 H), 2.80 (d, J = 10.2 Hz, 2 H), 3.12 (d, J = 5.5 Hz, 2 H), 3.22-3.28 (m, 4 H), 3.60-3.74 (m, 1 H), 3.97 (q, J = 7.0 Hz, 2 H) | E | m/z 350 (M + H)⁺ (ES+), at 2.33 min, UV inactive |
| 2-112 | Isomer 2: ethyl 2-[4-(2,5-dioxopyrrolidin-1-yl)piperidin-1-yl]-6-azaspiro[3.4]octane-6-carboxylate | 2 and 193 | as | (400 MHz, CDCl₃) δ: 1.25 (t, J = 7.0 Hz, 3 H), 1.47-1.63 (m, 2 H), 1.76-2.11 (m, 8 H), 2.41-2.56 (m, 2 H), 2.58-2.78 (m, 1H), 2.67 (s, 4 H), 2.90-3.03 (m, 2 H), 3.19-3.48 (m, 4 H), 3.92-4.06 (m, 1 H), 4.11 (q, J = 6.9 Hz, 2 H) | B | m/z 364 (M + H)⁺ (ES+), at 3.70 min, UV active |
| 2-113 | Isomer 2: ethyl 2-{4-[(2R)-2-methyl-5-oxopyrrolidin-1-yl]piperidin-1-yl}-6-azaspiro[3.4]octane-6-carboxylate | 2 and 199 | as | (400 MHz, CDCl₃) δ: 1.21-1.30 (m, 6 H), 1.57-1.72 (m, 2 H), 1.74-1.95 (m, 9 H), 1.96-2.07 (m, 2 H), 2.10-2.20 (m, 1 H), 2.21-2.33 (m, 1 H), 2.44-2.54 (m, 1 H), 2.59-2.76 (m, 1 H), 2.82-3.01 (m, 2 H), 3.27 (d, J = 19.9 Hz, 2 H), 3.32-3.45 (m, 2 H), 3.75-3.95 (m, 2 H), 4.10 (q, J = 6.6 Hz, 2 H) | B | m/z 364 (M + H)⁺ (ES+), at 3.53 min, UV active |
| 2-114 | Isomer 2: ethyl 2-{4-[(2R)-2-ethyl-5-oxopyrrolidin-1-yl]piperidin-1-yl}-6-azaspiro[3.4]octane-6-carboxylate | 2 and 200 | as | (400 MHz, CDCl₃) δ: 0.86 (t, J = 7.2 Hz, 3 H), 1.22 (td, J = 7.0, 3.1 Hz, 3 H), 1.40-1.53 (m, 1 H), 1.61 (d, J = 12.1 Hz, 1 H), 1.68-1.92 (m, 11 H), 2.03 (d, J = 8.2 Hz, 3 H), 2.18-2.30 (m, 1 H), 2.37-2.48 (m, 1 H), 2.58-2.71 (m, 1 H), 2.82-3.60 (m, 2 H), 3.18-3.29 (m, 2 H), 3.30-3.42 (m, 2 H), 3.76-3.92 (m, 1 H), 4.08 (q, J = 6.9 Hz, 2 H), (t, J = 8.4 Hz, 1 H) | B | m/z 378 (M + H)⁺ (ES+), at 3.73 min, UV active |
| 2-115 | Isomer 2: ethyl 2-{4-[(2S)-2-methyl-5-oxopyrrolidin-1-yl]piperidin-1-yl}-6-azaspiro[3.4]octane-6-carboxylate | 2 and 202 | as | (400 MHz, CDCl₃) δ: 1.20-1.30 (m, 6 H), 1.54-1.67 (m, 2 H), 1.72-1.96 (m, 9 H), 1.98-2.09 (m, 2 H), 2.09-2.20 (m, 1 H), 2.20-2.32 (m, 1 H), 2.43-2.54 (m, 1 H), 2.59-2.74 (m, 1 H), 2.82-3.01 (m, 2 H), 3.26 (d, J = 19.9 Hz, 2 H), 3.31-3.44 (m, 2 H), 3.75-3.95 (m, 2 H), 4.10 (q, J = 6.8 Hz, 2 H) | B | m/z 364 (M + H)⁺ (ES+), at 3.53 min, UV active |
| 2-116 | Isomer 2: ethyl 2-{4-[(2S)-2-ethyl-5-oxopyrrolidin-1-yl]piperidin-1-yl}-6-azaspiro[3.4]octane-6-carboxylate | 2 and 203 | as | (400 MHz, CDCl₃) δ: 0.86 (t, J = 7.2 Hz, 3 H), 1.22 (td, J = 11.7, 3.5 Hz, 3 H), 1.40-1.51 (m, 1 H), 1.61 (d, J = 11.7 Hz, 1 H), 1.67-1.91 (m, 11 H), 1.91-2.11 (m, 3 H), 2.19-2.29 (m, 1 H), 2.38-2.48 (m, 1 H), 2.59-2.68 (m, 1 H), 2.83-2.94 (m, 2 H), 3.18-3.29 (m, 2 H), 3.31-3.42 (m, 2 H), 3.60 (t, J = 8.2 Hz, 1 H), 3.78-3.89 (m, 1 H), 4.08 (q, J = 7.0 Hz, 2 H) | B | m/z 378 (M + H)⁺ (ES+), at 3.73 min, UV active |

TABLE 3-continued

| Ex. No. | Name | Intermediate | Synthetic method | ¹H NMR | LCMS Method | LCMS data |
|---|---|---|---|---|---|---|
| 2-117 | Isomer 2: ethyl 2-[4-(2,2-dimethyl-5-oxopyrrolidin-1-yl)piperidin-1-yl]-6-azaspiro[3.4]octane-6-carboxylate | 2 and 186 | as | (400 MHz, CDCl₃) δ: 1.18-1.32 (m, 9 H), 1.42-1.57 (m, 2 H), 1.63-2.11 (m, 10 H), 2.29-2.39 (m, 2 H), 2.50-2.82 (m, 3 H), 2.86-3.14 (m, 3 H), 3.21-3.32 (m, 2 H), 3.32-3.46 (m, 2 H), 4.11 (q, J = 6.9 Hz, 2 H) | B | m/z 378 (M + H)⁺ (ES+), at 5.41 min, UV active |
| 2-118 | Isomer 2: ethyl 2-[4-[(4R)-4-methyl-2-oxo-1,3-oxazolidin-3-yl]piperidin-1-yl]-6-azaspiro[3.4]octane-6-carboxylate | 2 and 205 | as | (400 MHz, CDCl₃) δ: 1.17-1.23 (m, 3 H), 1.30 (d, J = 6.2 Hz, 3 H), 1.66-1.88 (m, 10 H), 1.95-2.06 (m, 2 H), 2.58-2.68 (m, 1 H), 2.82-2.95 (m, 1 H), 3.17-3.27 (m, 2 H), 3.28-3.39 (m, 2 H), 3.53-3.67 (m, 1 H), 3.79 (dd, J = 8.2, 5.1 Hz, 1 H), 3.86-3.94 (m, 1 H), 4.06 (q, J = 7.0 Hz, 2 H), 4.30 (t, J = 8.2 Hz, 1 H) | B | m/z 366 (M + H)⁺ (ES+), at 3.30 min, UV active |
| 2-119 | Isomer 2: ethyl 2-[4-[(4R)-4-ethyl-2-oxo-1,3-oxazolidin-3-yl]piperidin-1-yl]-6-azaspiro[3.4]octane-6-carboxylate | 2 and 207 | as | (400 MHz, CDCl₃) δ: 0.85 (t, J = 7.4 Hz, 3 H), 1.21 (td, J = 6.9, 3.3 Hz, 3 H), 1.52-1.65 (m, 1 H), 1.67-1.90 (m, 11 H), 1.98-2.07 (m, 2 H), 2.58-2.68 (m, 1 H), 2.89 (dd, J = 18.9, 9.2 Hz, 2 H), 3.18-3.28 (m, 2 H), 3.35 (dt, J = 19.6, 6.8 Hz, 2 H), 3.55-3.66 (m, 1 H), 3.77 (dt, J = 7.6, 4.0 Hz, 1 H), 3.95 (dd, J = 8.6, 4.7 Hz, 1 H), 4.04-4.11 (m, 2 H), 4.26 (t, J = 8.4 Hz, 1 H) | B | m/z 380 (M + H)⁺ (ES+), at 3.73 min, UV active |
| 2-120 | Isomer 2: ethyl 2-[4-[(4R)-2-oxo-4-(propan-2-yl)-1,3-oxazolidin-3-yl]piperidin-1-yl]-6-azaspiro[3.4]octane-6-carboxylate | 2 and 197 | as | (300 MHz, CDCl₃) δ: 0.89 (dd, J = 10.1, 6.9 Hz, 6 H), 1.25 (t, J = 7.1 Hz, 3 H), 1.51-2.25 (m, 13 H), 2.60-2.78 (m, 1 H), 2.85-3.05 (m, 2 H), 3.21-3.49 (m, 4 H), 3.54-3.74 (m, 1 H), 3.74-3.83 (m, 1 H), 4.05-4.21 (m, 4 H) | B | m/z 394 (M + H)⁺ (ES+), at 3.93 min, UV active |
| 2-121 | Isomer 2: ethyl 2-[4-[(4S)-4-methyl-2-oxo-1,3-oxazolidin-3-yl]piperidin-1-yl]-6-azaspiro[3.4]octane-6-carboxylate | 2 and 209 | as | (400 MHz, CDCl₃) δ: 1.18-1.25 (m, 3 H), 1.32 (d, J = 5.9 Hz, 3 H), 1.65-1.93 (m, 10 H), 1.97-2.09 (m, 2 H), 2.58-2.71 (m, 1 H), 2.82-2.98 (m, 2 H), 3.18-3.29 (m, 2 H), 3.36 (dt, J = 19.7, 6.7 Hz, 2 H), 3.55-3.69 (m, 1 H), 3.80 (dd, J = 8.2, 5.5 Hz, 1 H), 3.86-3.97 (m, 1 H), 4.08 (q, J = 6.9 Hz, 2 H), 4.32 (t, J = 8.2 Hz, 1 H) | B | m/z 366 (M + H)⁺ (ES+), at 3.43 min, UV active |
| 2-122 | Isomer 2: ethyl 2-[4-[(4S)-4-ethyl-2-oxo-1,3-oxazolidin-3-yl]piperidin-1-yl]-6-azaspiro[3.4]octane-6-carboxylate | 2 and 211 | as | (300 MHz, CDCl₃) δ: 0.90 (t, J = 7.5 Hz, 3 H), 1.25 (t, J = 7.1 Hz, 3 H), 1.52-2.20 (m, 14 H), 2.62-2.78 (m, 1 H), 2.84-3.06 (m, 2 H), 3.22-3.55 (m, 4 H), 3.58-3.72 (m, 1 H), 3.72-3.88 (m, 1 H), 3.99 (dd, J = 8.6, 4.7 Hz, 1 H), 4.05-4.19 (m, 2 H), 4.29 (t, J = 8.6 Hz, 1 H) | B | m/z 380 (M + H)⁺ (ES+), at 3.72 min, UV active |
| 2-123 | Isomer 2: ethyl 2-[4-[(4S)-2-oxo-4-(propan-2-yl)-1,3-oxazolidin-3-yl]piperidin-1-yl]-6-azaspiro[3.4]octane-6-carboxylate | 2 and 188 | as | (400 MHz, CDCl₃) δ: 0.82-0.96 (m, 6 H), 1.25 (s, 3 H), 1.56-2.24 (m, 13 H), 2.61-2.78 (m, 1 H), 2.85-3.03 (m, 2 H), 3.21-3.48 (m, 4 H), 3.55-3.74 (m, 1 H), 3.74-3.83 (m, 1 H), 4.05-4.20 (m, 4 H) | B | m/z 394 (M + H)⁺ (ES+), at 5.16 min, UV active |
| 2-124 | Isomer 2: ethyl 2-[4-(2-oxoimidazolidin-1-yl)piperidin-1-yl]-6-azaspiro[3.4]octane-6-carboxylate | 151 and 152 | aq | (400 MHz, CDCl₃) δ: 1.16-1.36 (m, 3 H), 1.45-2.23 (m, 13 H), 2.56-2.80 (m, 1 H), 2.83-3.08 (m, 2 H), 3.17-3.52 (m, 7 H), 3.63-3.90 (m, 1 H), 4.10 (q, J = 7.0 Hz, 2 H), 4.24-4.42 (m, 1 H). | B | m/z 351 (M + H)⁺ (ES*), at 2.12 min, UV inactive |
| 2-125 | Isomer 2: ethyl 2-[4-(3-methyl-2-oxoimidazolidin-1-yl)piperidin-1-yl]-6-azaspiro[3.4]octane-6-carboxylate | 2 and 213 | ac | (300 MHz, CDCl₃) δ: 1.20-1.30 (m, 3 H), 1.61-1.98 (m, 10 H), 2.00-2.15 (m, 2 H), 2.62-2.73 (m, 1 H), 2.77 (s, 3 H), 2.86-2.98 (m, 2 H), 3.21-3.48 (m, 5 H), 3.26 (s, 3 H), 3.69-3.85 (m, 1 H), 4.05-4.19 (m, 2 H) | B | m/z 365 (M + H)⁺ (ES+), at 3.07 min, UV active |

TABLE 3-continued

| Ex. No. | Name | Intermediate | Synthetic method | ¹H NMR | LCMS Method | LCMS data |
|---|---|---|---|---|---|---|
| 2-126 | Isomer 2: ethyl 2-{4-[2-(1H-pyrazol-5-yl)pyrrolidin-1-yl]piperidin-1-yl}-6-azaspiro[3.4]octane-6-carboxylate | 2 and 181 | as | (400 MHz, CDCl₃) δ: 1.24 (t, J = 7.0 Hz, 3 H), 1.48-2.28 (m, 16 H), 2.38-2.73 (m, 4 H), 2.76-3.02 (m, 2 H), 3.07-3.22 (m, 1 H), 3.22-3.43 (m, 4 H), 4.10 (q, J = 7.0 Hz, 2 H), 6.15 (brs., 1 H), 7.52 (d, J = 2.0 Hz, 2 H). One exchangeable proton not observed. | B | m/z 402 (M + H)⁺ (ES⁺), at 3.62 min, UV active |
| 2-127 | Isomer 2: ethyl 2-{4-[2-(1,2-oxazol-3-yl)pyrrolidin-1-yl]piperidin-1-yl}-6-azaspiro[3.4]octane-6-carboxylate | 2 and 318 | ak | (400 MHz, DMSO-d₆) δ: 1.16 (t, J = 7.2 Hz, 3 H), 1.33 (dd, J = 12.1, 11.4 Hz, 2 H), 1.49-1.68 (m, 2 H), 1.68-1.89 (m, 9 H), 1.90-2.02 (m, 2 H), 2.03-2.17 (m, 1 H), 2.25 (t, J = 11.6 Hz, 1 H), 2.55-2.83 (m, 4 H), 2.83-3.01 (m, 1 H), 3.06-3.19 (m, 2 H), 3.26 (q, J = 7.0 Hz, 2 H), 3.99 (q, J = 7.0 Hz, 2 H), 4.11-4.24 (m, 1 H), 6.22-6.35 (m, 1 H), 8.39-8.48 (m, 1 H) | I | m/z 403 (M + H)⁺ (ES⁺), at 4.20 min, UV active |
| 2-128 | Isomer 2: ethyl 2-{4-[2-(1H-tetrazol-5-yl)pyrrolidin-1-yl]piperidin-1-yl}-6-azaspiro[3.4]octane-6-carboxylate | 2 and 288 | aw | (400 MHz, DMSO-d₆) δ: 1.13 (t, J = 7.2 Hz, 3 H), 1.25-1.50 (m, 2 H), 1.55-1.67 (m, 2 H), 1.67-1.84 (m, 5 H), 1.86-2.05 (m, 6 H), 2.15-2.26 (m, 1 H), 2.62 (brs., 1 H), 2.68-2.83 (m, 2 H), 2.94-3.05 (m, 1 H), 3.11 (d, J = 5.9 Hz, 2 H), 3.14-3.19 (m, 2 H), 3.21-3.27 (m, 3 H), 3.96 (q, J = 7.0 Hz, 2 H), 4.62 (brs., 1 H) | E | m/z 404 (M + H)⁺ (ES⁺), at 1.78 min, UV inactive |
| 2-129 | Isomer 2: ethyl 2-{4-[2-(2-methyl-2H-tetrazol-5-yl)pyrrolidin-1-yl]piperidin-1-yl}-6-azaspiro[3.4]octane-6-carboxylate | 2 and 308 | aw | (400 MHz, DMSO-d₆) δ: 1.13 (t, J = 7.0 Hz, 3 H), 1.19-1.33 (m, 2 H), 1.44 (d, J = 12.1 Hz), 1.49-1.60 (m, 2 H), 1.63-1.72 (m, 3 H), 1.73-1.94 (m, 7 H), 2.11-2.28 (m, 2 H), 2.51-2.64 (m, 3 H), 2.68 (d, J = 10.2 Hz, 1 H), 3.05-3.16 (m, 3 H), 3.23 (q, J = 6.6 Hz, 2 H), 3.96 (q, J = 7.0 Hz, 2 H), 4.10 (s, 3 H), 4.35 (dd, J = 9.2, 5.3 Hz, 1 H) | E | m/z 418 (M + H)⁺ (ES⁺), at 3.72 min, UV inactive |
| 2-130 | Isomer 1: ethyl 2-{4-[2-(1-methyl-1H-tetrazol-5-yl)pyrrolidin-1-yl]piperidin-1-yl}-6-azaspiro[3.4]octane-6-carboxylate | 2 and 308 | aw | (400 MHz, DMSO-d₆) δ: 0.43 (t, J = 6.4 Hz, 3 H), 0.60-0.82 (m, 2 H), 0.91-1.21 (m, 11 H), 1.24-1.31 (m, 3 H), 1.38-1.50 (m, 2 H), 1.79-1.95 (m, 2 H), 1.95-2.13 (m, 5 H), 2.13-2.24 (m, 1 H), 3.28 (q, J = 7.2 Hz, 2 H), 3.52 (s, 3 H), 3.57 (dd, J = 8.2, 3.9 Hz) | E | m/z 418 (M + H)⁺ (ES⁺), at 3.61 min, UV inactive |
| 2-130 | Isomer 2: ethyl 2-{4-[2-(1-methyl-1H-tetrazol-5-yl)pyrrolidin-1-yl]piperidin-1-yl}-6-azaspiro[3.4]octane-6-carboxylate | 2 and 308 | aw | (400 MHz, DMSO-d₆) δ: 0.43 (t, J = 7.0 Hz, 3 H), 0.66-0.83 (m, 2 H), 0.93-1.00 (m, 2 H), 1.02-1.31 (m, 12 H), 1.38-1.54 (m, 2 H), 1.83-2.13 (m, 7 H), 2.13-2.24 (m, 1 H), 3.27 (q, J = 7.0 Hz, 2 H), 3.52 (s, 3 H), 3.55-3.61 (m, 1 H) | E | m/z 418 (M + H)⁺ (ES⁺), at 3.80 min, UV inactive |
| 2-131 | Isomer 2: ethyl 2-{4-[(2R)-2-(thiophen-2-yl)pyrrolidin-1-yl]piperidin-1-yl}-6-azaspiro[3.4]octane-6-carboxylate | 2 and 316 | ak | (400 MHz, DMSO-d₆) δ: 1.21-1.30 (m, 3 H), 1.51-1.66 (m, 2 H), 1.69-1.81 (m, 3H), 1.81-2.03 (m, 7 H), 2.04-2.16 (m, 2 H), 2.16-2.30 (m, 1 H), 2.41-2.55 (m, 1 H), 2.64-2.75 (m, 2 H), 2.82-2.99 (m, 2 H), 3.08 (t, J = 10.1 Hz, 1 H), 3.36-3.43 (m, 3 H), 4.10 (q, J = 7.0 Hz, 2 H), 4.16-4.29 (m, 1 H), 4.66 (brs., 2 H), 6.90-6.97 (m, 2 H), 7.21-7.33 (m, 1 H) | I | m/z 418 (M + H)⁺ (ES⁺), at 5.32 min, UV active |
| 2-132 | Isomer 2: ethyl 2-{4-[(2R)-2-(1,3-thiazol-2-yl)pyrrolidin-1-yl]piperidin-1-yl}-6-azaspiro[3.4]octane-6-carboxylate | 2 and 314 | ak | (400 MHz, DMSO-d₆) δ: 1.16 (t, J = 7.2 Hz, 3 H), 1.28-1.48 (m, 2 H), 1.51-1.65 (m, 3 H), 1.65-1.88 (m, 7 H), 1.88-2.03 (m, 2 H), 2.08-2.25 (m, 1 H), 2.36-2.47 (m, 1 H), 2.55-2.63 (m, 2 H), 2.65-2.86 (m, 2 H), 3.01-3.20 (m, 3 H), 3.20-3.30 (m, 2 H), 3.99 (q, J = 7.0 Hz, 2 H), 4.16-4.31 (m, 1 H), 7.50 (d, J = 3.4 Hz, 1 H), 7.67 (d, J = 3.1 Hz, 1 H) | I | m/z 419 (M + H)⁺ (ES⁺), at 4.60 min, UV active |
| 2-133 | Isomer 1: ethyl 2-{4-[(2S)-1-(5,7-dihydro-6H-pyrrolo[3,4-b]pyridin-6-ylcarbonyl)pyrrolidin-2- | 127 and 321 | q | (400 MHz, CD₃OD) δ: 0.36-0.66 (m, 7H), 0.76-1.38 (m, 15H), 1.87-2.02 (m, 1H), 2.09-2.23 (m, 2H), 2.62-2.81 (m, 2H), 3.22-3.43 (m, 3H), 3.68-3.96 (m, 3H), 3.96-4.34 (m, 3H), 6.48-6.61 (m, 1H), 7.01 (d, J = 8.1 Hz, 1H), 7.65 | E | m/z 482 (M + H)⁺ (ES⁺), at 3.90 min, UV active |

| Ex. No. | Name | Intermediate | Synthetic method | ¹H NMR | LCMS Method | LCMS data |
|---|---|---|---|---|---|---|
| | yl]piperidin-1-yl}-6-azaspiro[3.4]octane-6-carboxylate | | | (d, J = 4.9 Hz, 1H). | | |
| 2-133 | Isomer 2: ethyl 2-{4-[(2S)-1-(5,7-dihydro-6H-pyrrolo[3,4-b]pyridin-6-ylcarbonyl)pyrrolidin-2-yl]piperidin-1-yl}-6-azaspiro[3.4]octane-6-carboxylate | 127 and 321 | q | (400 MHz, CD₃OD) δ: 1.13-1.49 (m, 7H), 1.55-2.24 (m, 14H), 2.67-2.83 (m, 1H), 2.88-3.04 (m, 2H), 3.21-3.77 (m, 3H), 4.02-4.24 (m, 3H), 4.45-5.15 (m, 6H), 7.37 (dd, J = 7.7, 5.0 Hz, 1H), 7.82 (d, J = 7.8 Hz, 1H), 8.45 (d, J = 3.4 Hz, 1H). | E | m/z 482 (M + H)⁺ (ES+), at 4.04 min, UV active |
| 2-134 | Isomer 2: ethyl 2-{4-[(2R,4R)-4-fluoro-2-(methoxycarbonyl)pyrrolidin-1-yl]piperidin-1-yl}-6-azaspiro[3.4]octane-6-carboxylate | 2 and 311 | aw | (300 MHz, DMSO-d₆) δ: 1.16 (t, J = 7.1 Hz, 3 H), 1.22-1.42 (m, 2 H), 1.56-1.89 (m, 8 H), 1.89-2.10 (m, 3 H), 2.31-2.48 (m, 2 H), 2.55-2.68 (m, 1 H), 2.68-2.94 (m, 3 H), 3.07 (d, J = 11.4 Hz, 1 H), 3.10-3.19 (m, 2 H), 3.19-3.28 (m, 2 H), 3.51 (dd, J = 9.9, 4.3 Hz, 1 H), 3.61 (s, 3 H), 3.99 (q, J = 7.1 Hz, 2 H), 5.02-5.30 (m, 1 H) | E | m/z 412 (M + H)⁺ (ES+), at 3.72 min, UV active |
| 2-135 | Isomer 2: ethyl 2-{4-[(2R,4S)-4-fluoro-2-(methoxycarbonyl)pyrrolidin-1-yl]piperidin-1-yl}-6-azaspiro[3.4]octane-6-carboxylate | 2 and 312 | aw | (300 MHz, DMSO-d₆) δ: 1.16 (t, J = 7.1 Hz, 3 H), 1.21-1.42 (m, 2 H), 1.57-1.88 (m, 8 H), 1.89-2.01 (m, 2 H), 2.02-2.31 (m, 2 H), 2.34-2.46 (m, 1 H), 2.55-2.65 (m, 1 H), 2.65-2.79 (m, 2 H), 2.85-3.05 (m, 1 H), 3.07-3.22 (m, 3 H), 3.22-3.27 (m, 2 H), 3.61 (s, 3 H), 3.76 (t, J = 7.0 Hz, 1 H), 3.99 (q, J = 7.1 Hz, 2 H), 5.08-5.40 (m, 1 H) | E | m/z 412 (M + H)⁺ (ES+), at 3.96 min, UV active |
| 2-136 | Isomer 2: ethyl 2-{4-[(2R,4R)-4-fluoro-2-(hydroxymethyl)pyrrolidin-1-yl]piperidin-1-yl}-6-azaspiro[3.4]octane-6-carboxylate | Example 2-134 | ar | (300 MHz, DMSO-d₆) δ: 1.16 (t, J = 7.1 Hz, 3 H), 1.25-1.51 (m, 2 H), 1.56-1.89 (m, 8 H), 1.89-2.06 (m, 3 H), 2.34-2.45 (m, 2 H), 2.58-2.68 (m, 2 H), 2.70-2.82 (m, 3 H), 2.82-2.94 (m, 1 H), 2.96-3.10 (m, 1 H), 3.11-3.20 (m, 3 H), 3.39-3.49 (m, 2 H), 3.99 (q, J = 7.2 Hz, 2 H), 4.39 (t, J = 5.7 Hz, 1 H), 4.95-5.24 (m, 1 H) | E | m/z 384 (M + H)⁺ (ES+), at 3.20 min, UV inactive |
| 2-137 | Isomer 2: ethyl 2-{4-[(2R,4S)-4-fluoro-2-(hydroxymethyl)pyrrolidin-1-yl]piperidin-1-yl}-6-azaspiro[3.4]octane-6-carboxylate | Example 2-135 | ar | (300 MHz, DMSO-d₆) δ: 1.16 (t, J = 7.1 Hz, 3 H), 1.26-1.45 (m, 2 H), 1.57-1.88 (m, 8 H), 1.91-2.09 (m, 3 H), 2.56-2.65 (m, 4 H), 2.69-2.84 (m, 3 H), 2.99-3.17 (m, 4 H), 3.18-3.24 (m, 1 H), 3.36-3.45 (m, 2 H), 3.99 (q, J = 7.1 Hz, 2 H), 4.35 (t, J = 5.7 Hz, 1 H), 4.98-5.25 (m, 1 H) | E | m/z 384 (M + H)⁺ (ES+), at 3.33 min, UV active |
| 2-138 | Isomer 2: ethyl 2-{4-[(2S)-1-(5-methyl-1,3,4-oxadiazol-2-yl)pyrrolidin-2-yl]piperidin-1-yl}-6-azaspiro[3.4]octane-6-carboxylate | 91 and 127 | r | (400 MHz, CD₃OD) δ: 1.24 (t, J = 7.0 Hz, 3H), 1.28-1.45 (m, 1H), 1.58-1.68 (m, 2H), 1.69-1.86 (m, 3H), 1.86-2.01 (m, 8H), 2.07-2.13 (m, 2H), 2.37 (s, 3H), 2.67-2.98 (m, 3H), 3.24-3.42 (m, 4H), 3.43-3.52 (m, 3H), 3.78-3.88 (m, 1H), 4.09 (q, J = 7.3 Hz, 2H). | E | m/z 418 (M + H)⁺ (ES+), at 2.57 min, UV active |
| 3-1 | Isomer 1: methyl 2-{4-(2-oxo-1,2-dihydropyridin-3-yl)piperidin-1-yl}-6-azaspiro[3.4]octane-6-carboxylate | 3 and 65 | b | (400 MHz, DMSO-d₆) δ: 1.35-1.51 (m, 2H), 1.66-1.83 (m, 8H), 1.98-2.09 (m, 2H), 2.40-2.72 (m, 2H), 2.81-2.91 (m, 2H), 3.15-3.48 (m, 4H), 3.57 (s, 3H), 6.12 (dd, J = 6.5 and 6.5 Hz, 1H), 7.16-7.26 (m, 2H), NH not observed | G | m/z 346 (M + H)⁺ (ES+), at 4.34 min, UV active |
| 3-1 | Isomer 2: methyl 2-{4-(2-oxo-1,2-dihydropyridin-3-yl)piperidin-1-yl}-6-azaspiro[3.4]octane-6-carboxylate | 3 and 65 | b | (400 MHz, DMSO-d₆) δ: 1.34-1.52 (m, 2H), 1.66-1.93 (m, 8H), 1.94-2.11 (m, 2H), 2.45-2.75 (m, 2H), 2.78-2.94 (m, 2H), 3.09-3.21 (m, 2H), 3.21-3.44 (m, 2H), 3.56 (s, 3H), 6.13 (dd, J = 6.5 and 6.5 Hz, 1H), 7.18-7.33 (m, 2H), NH not observed | G | m/z 346 (M + H)⁺ (ES+), at 4.43 min, UV active |

TABLE 3-continued

| Ex. No. | Name | Intermediate | Synthetic method | ¹H NMR | LCMS Method | LCMS data |
|---|---|---|---|---|---|---|
| 3-2 | Isomer 1: ethyl 2-[4-(2-oxo-1,2-dihydropyridin-3-yl)piperidin-1-yl]-6-azaspiro[3.4]octane-6-carboxylate | 2 and 65 | b | (400 MHz, DMSO-$d_6$) δ: 0.99-1.23 (m, 3H), 1.30-1.49 (m, 2H), 1.59-1.84 (m, 6H), 1.95-2.11 (m, 2H), 2.45-2.74 (m, 5H), 2.75-2.89 (m, 2H), 3.15-3.31 (m, 3H), 3.93-4.07 (m, 2H), 6.18 (dd, J = 6.5 and 6.5 Hz, 1H), 7.21 (d, J = 6.5 Hz, 1H), 7.26 (d, J = 6.5 Hz, 1H), NH not observed | F | m/z 360 (M + H)⁺ (ES+), at 1.54 min, UV active |
| 3-2 | Isomer 2: ethyl 2-[4-(2-oxo-1,2-dihydropyridin-3-yl)piperidin-1-yl]-6-azaspiro[3.4]octane-6-carboxylate | 2 and 65 | b | (400 MHz, DMSO-$d_6$) δ: 1.08-1.27 (m, 3H), 1.32-1.58 (m, 2H), 1.59-1.76 (m, 2H), 1.76 (m, 4H), 1.93-2.20 (m, 2H), 2.45-2.97 (m, 6H), 3.08-3.20 (m, 2H), 3.22-3.36 (m, 2H), 3.95-4.11 (m, 2H), 6.17 (dd, J = 6.5 and 6.5 Hz, 1H), 7.21 (d, J = 6.5 Hz, 1H), 7.25 (d, J = 6.5 Hz, 1H), NH not observed | F | m/z 360 (M + H)⁺ (ES+), at 1.58 min, UV active |
| 3-3 | Isomer 2: 2-fluoroethyl 2-[4-(2-oxo-1,2-dihydropyridin-3-yl)piperidin-1-yl]-6-azaspiro[3.4]octane-6-carboxylate | 4 and 65 | b | (400 MHz, DMSO-$d_6$) δ: 1.35-1.57 (m, 2H), 1.58-1.92 (m, 5H), 1.91-2.13 (m, 2H), 2.32-3.02 (m, 7H), 3.20-3.44 (m, 4H), 4.07-4.32 (m, 2H), 4.47-4.72 (m, 2H), 6.13 (dd, J = 6.5 and 6.5 Hz, 1H), 7.18-7.43 (m, 2H), 11.49 (s, 1H) | F | m/z 378 (M + H)⁺ (ES+), at 1.57 min, UV active |
| 3-4 | Isomer 2: ethyl 2-[4-(3-hydroxypyridin-2-yl)piperidin-1-yl]-6-azaspiro[3.4]octane-6-carboxylate | 2 and 18 | b | (400 MHz, CDCl₃) δ: 1.21-1.29 (m, 3H), 1.75-2.38 (m, 12H), 2.87-3.23 (m, 4H), 3.24-3.48 (m, 4H), 4.05-4.21 (m, 2H), 6.97-7.06 (m, 1H), 7.12-7.21 (m, 1H), 8.02-8.10 (m, 1H), OH not observed | C | m/z 360 (M + H)⁺ (ES+), at 1.29 min, UV active |
| 3-5 | Isomer 2: 2-fluoroethyl 2-[4-(2-methoxypyridin-3-yl)piperidin-1-yl]-6-azaspiro[3.4]octane-6-carboxylate | 4 and 66 | b | (400 MHz, DMSO-$d_6$) δ: 1.48-2.08 (m, 11H), 2.65-2.79 (m, 2H), 2.84-2.94 (m, 2H), 3.14-3.24 (m, 2H), 3.26-3.40 (m, 3H), 3.86 (m, 3H), 4.15-4.21 (m, 1H), 4.21-4.30 (m, 1H), 4.48-4.57 (m, 1H), 4.61-4.69 (m, 1H), 6.94 (dd, J = 7.0 & 5.0 Hz, 1H), 7.58 (d, J = 7.0 Hz, 1H), 8.01 (d, J = 5.0, 1H) | F | m/z 392 (M + H)⁺ (ES+), at 1.73 min, UV active |
| 3-6 | Isomer 2: ethyl 2-[4-(6-methoxy-4-methylpyridin-3-yl)piperidin-1-yl]-6-azaspiro[3.4]octane-6-carboxylate | 2 and 71 | b | (400 MHz, DMSO-$d_6$) δ: 1.16 (t, J = 7.0 Hz, 3H), 1.48-1.89 (m, 9H), 1.93-2.04 (m, 2H), 2.24 (s, 3H), 2.41-2.55 (m, 3H), 2.82-2.95 (m, 2H), 3.05-3.23 (m, 2H), 3.23-3.36 (m, 2H), 3.77 (m, 3H), 3.99 (q, J = 7.0 Hz, 2H), 6.60 (s, 1H), 7.94 (s, 1H) | F | m/z 388 (M + H)⁺ (ES+), at 1.73 min, UV active |
| 3-7 | Isomer 2: ethyl 2-[4-(6-methoxy-5-methylpyridin-3-yl)piperidin-1-yl]-6-azaspiro[3.4]octane-6-carboxylate | 2 and 72 | b | (400 MHz, DMSO-$d_6$) δ: 1.18 (t, J = 7.0 Hz, 3H), 1.54-2.10 (m, 12H), 2.12 (s, 3H), 2.70-3.10 (m, 2H), 3.15-3.23 (m, 2H), 3.24-3.36 (m, 2H), 3.37-3.52 (m, 2H), 3.84 (m, 3H), 4.00 (q, J = 7.0 Hz, 2H), 7.43 (s, 1H), 7.86 (s, 1H) | F | m/z 388 (M + H)⁺ (ES+), at 1.77 min, UV active |
| 3-8 | Isomer 1: ethyl 2-[4-(2-aminopyrimidin-4-yl)piperidin-1-yl]-6-azaspiro[3.4]octane-6-carboxylate | 1 and 70 | d | ¹H NMR (400 MHz, CD₃OD) δ: 1.18-1.32 (m, 3 H), 1.68-2.03 (m, 10 H), 2.07-2.18 (m, 2 H), 2.49 (t, J = 11.7 Hz, 1 H), 2.80 (quin, J = 8.0 Hz, 1 H), 3.00 (d, J = 11.3 Hz, 2 H), 3.33-3.45 (m, 4 H), 4.09 (q, J = 7.0 Hz, 2 H), 6.56 (d, J = 5.5 Hz, 1 H), 8.12 (d, J = 5.5 Hz, 1 H), two NH not observed | B | m/z 360 (M + H)⁺ (ES+), at 2.98 min, UV active |
| 3-9 | Isomer 2: ethyl 2-[4-(4-aminopyrimidin-2-yl)piperidin-1-yl]-6-azaspiro[3.4]octane-6-carboxylate | 2 and 26 | as | (400 MHz, CD₃OD) δ: 1.23-1.28 (m, 3H), 1.88-1.99 (m, 10H), 2.07-2.21 (m, 2H), 2.52-2.66 (m, 1H), 2.73-2.90 (m, 1H), 2.96-3.07 (m, 2H), 3.28 (s, 2H), 3.36-3.46 (m, 2H), 4.09-4.13 (m, 2H), 6.33 (d, J = 6.0 Hz, 1H), 7.97 (d, J = 6.0 Hz, 1H), 2 x NH not observed | C | m/z 360 (M + H)⁺ (ES+), at 1.56 min, UV active |
| 3-10 | Isomer 1: ethyl 2-[4-cyano-4-(pyridin-2-yl)piperidin-1-yl]-6-azaspiro[3.4]octane-6-carboxylate | 2 and 14 | at | (400 MHz, CDCl₃) δ: 1.17-1.37 (m, 4H), 1.45-1.72 (m, 2H), 1.75-2.02 (m, 3H), 2.06-2.51 (m, 7H), 2.72-3.15 | B | m/z 369 (M + H)⁺ (ES+), at 3.33 min, UV active |

TABLE 3-continued

| Ex. No. | Name | Intermediate | Synthetic method | ¹H NMR | LCMS Method | LCMS data |
|---|---|---|---|---|---|---|
| | yl]-6-azaspiro[3.4]octane-6-carboxylate | | | (m, 2H), 3.26-3.48 (m, 4H), 4.06-4.22 (m, 2H), 7.21-7.32 (m, 1H), 7.55 (d, J = 8.2 Hz, 1H), 7.74 (dd, J = 7.2 + 7.2 Hz, 1H), 8.56-8.68 (m, 1H). | | |
| 3-10 | Isomer 2: ethyl 2-[4-(cyano-4-(pyridin-2-yl)piperidin-1-yl]-6-azaspiro[3.4]octane-6-carboxylate | 2 and 14 | at | (400 MHz, CDCl₃) δ: 1.16-1.39 (m, 4H), 1.48-1.70 (m, 2H), 1.78-2.47 (m, 10H), 2.74-3.09 (m, 2H), 3.20-3.50 (m, 4H), 4.03-4.20 (m, 2H), 7.20-7.32 (m, 1H), 7.48-7.61 (m, 1H), 7.67-7.82 (m, 1H), 8.55-8.69 (m, 1H). | B | m/z 369 (M + H)⁺ (ES+), at 3.40 min, UV active |
| 3-11 | Isomer 2: ethyl 2-[4-(2-methoxy-4-methylpyridin-3-yl)piperidin-1-yl]-6-azaspiro[3.4]octane-6-carboxylate | 2 and 134 | b | (400 MHz, DMSO-d₆) δ: 1.17 (t, J = 7.0 Hz, 3 H), 1.40 (d, J = 12.2 Hz, 2 H), 1.67-1.94 (m, 6 H), 2.00 (ddd, J = 9.2, 7.1, 2.6 Hz, 2 H), 2.11-2.26 (m, 2 H), 2.29 (s, 3 H), 2.61-2.70 (m, 1 H), 2.73-2.81 (m, 1 H), 2.86 (d, J = 11.0 Hz, 2 H), 3.26-3.38 (m, 2 H), 3.84 (s, 3 H), 4.01 (q, J = 7.0 Hz, 2 H), 4.11 (q, J = 5.2 Hz, 2 H), 6.78 (d, J = 5.2 Hz, 1 H), 7.85 (d, J = 4.9 Hz, 1 H). | F | m/z 388 (M + H)⁺ (ES⁺) at 1.86 min, UV active |
| 3-12 | Isomer 2: ethyl 2-[4-(2-methoxy-5-methylpyridin-3-yl)piperidin-1-yl]-6-azaspiro[3.4]octane-6-carboxylate | 2 and 129 | b | (400 MHz, DMSO-d₆) δ: 1.14-1.19 (m, 4H), 1.57 (d, J = 9.6 Hz, 2H), 1.66 (s, 3H), 1.77-1.85 (m, 4H), 1.86 (s, 2H), 2.01 (d, J = 7.6 Hz, 2H), 2.19 (s, 3H), 2.88 (d, J = 10.0 Hz, 2H), 3.16 (d, J = 5.2 Hz, 2H), 3.26-3.34 (m, 2H), 3.82 (s, 3H), 4.00 (d, J = 6.8 Hz, 2H), 7.40 (s, 1H), 7.80 (s, 1H). | G | m/z 388 (M + H)⁺ (ES⁺) at 7.10 min, UV active |
| 3-13 | Isomer 2: ethyl 2-[4-(6-methoxypyridin-2-yl)piperidin-1-yl]-6-azaspiro[3.4]octane-6-carboxylate | 2 and 141 | b | (400 MHz, DMSO-d₆) δ: 1.16 (s, 3 H), 1.57-1.89 (m, 11 H), 1.93-2.07 (m, 2 H), 2.63-2.70 (m, 1 H), 2.86-2.95 (m, 2H), 3.08-3.18 (m, 2 H), 3.25-3.45 (m, 2 H), 3.83 (s, 3 H), 4.00 (d, J = 4.0 Hz, 2 H), 6.60 (d, J = 7.6 Hz, 1 H), 6.80-6.90 (m, 1 H), 7.55-7.70 (m, 1 H). | G | m/z 374 (M + H)⁺ (ES⁺) at 7.15 min, UV active |
| 3-14 | Isomer 1: ethyl 2-[4-(4-methyl-2-oxo-1,2-dihydropyridin-3-yl)piperidin-1-yl]-6-azaspiro[3.4]octane-6-carboxylate | 2 and 146 | b | (400 MHz, CD₃OD) δ: 0.91 (d, J = 7.3 Hz, 4 H), 1.04-1.65 (m, 8 H), 1.84-2.21 (m, 4 H), 2.31 (s, 3 H), 2.58 (d, J = 13.7 Hz, 2 H), 2.77-3.09 (m, 3 H), 3.25-3.47 (m, 2 H), 4.06-4.19 (m, 2 H), 6.22 (d, J = 6.7 Hz, 1 H), 7.17 (d, J = 6.4 Hz, 1 H), NH not observed. | H | m/z 374 (M + H)⁺ (ES⁺) at 3.85 min, UV active |
| 3-14 | Isomer 2: ethyl 2-[4-(4-methyl-2-oxo-1,2-dihydropyridin-3-yl)piperidin-1-yl]-6-azaspiro[3.4]octane-6-carboxylate | 2 and 146 | b | (400 MHz, CD₃OD) δ: 0.92 (d, J = 7.3 Hz, 4 H), 1.18-1.60 (m, 8 H), 1.88-2.25 (m, 4 H), 2.31 (s, 3 H), 2.50-3.20 (m, 5 H), 3.28-3.50 (m, 2 H), 4.12 (q, J = 7.0 Hz, 2 H), 6.23 (d, J = 6.7 Hz, 1 H), 7.18 (d, J = 6.4 Hz, 1 H), NH not observed. | I | m/z 374 (M + H)⁺ (ES⁺) at 4.04 min, UV active |
| 3-15 | Isomer 1: ethyl 2-[4-(5-methyl-2-oxo-1,2-dihydropyridin-3-yl)piperidin-1-yl]-6-azaspiro[3.4]octane-6-carboxylate | 2 and 143 | b | ¹H NMR (400 MHz, DMSO-d₆) δ: 1.17 (t, J = 7.0 Hz, 3H), 1.40-1.62 (m, 2H), 1.65-1.78 (m, 4H), 1.78-1.95 (m, 5H), 1.95-2.09 (m, 5H), 2.57-2.73 (m, 1H), 2.81-3.06 (m, 2H), 3.08-3.23 (m, 2H), 3.24-3.46 (m, 2H), 4.00 (q, J = 7.0 Hz, 2H), 7.00 (s, 1H), 7.10 (s, 1H), 11.30 (s, 1H). | E | m/z 374 (M + H)⁺ (ES⁺) at 3.27 min, UV active |
| 3-15 | Isomer 2: ethyl 2-[4-(5-methyl-2-oxo-1,2-dihydropyridin-3-yl)piperidin-1-yl]-6-azaspiro[3.4]octane-6-carboxylate | 2 and 143 | b | (400 MHz, DMSO-d₆) δ: 1.18 (td, J = 7.1, 2.9 Hz, 3 H), 1.38-1.96 (m, 10 H), 2.04-2.28 (m, 3 H), 2.57-2.77 (m, 1 H), 2.84-3.10 (m, 2 H), 3.12-3.45 (m, 7 H), 4.01 (q, J = 7.2 Hz, 2 H), 7.00 (s, 1 H), 7.10 (s, 1 H), 11.31 (br.s., 1 H). | E | m/z 374 (M + H)⁺ (ES⁺) at 3.33 min, UV active |

TABLE 3-continued

| Ex. No. | Name | Intermediate | Synthetic method | $^1$H NMR | LCMS Method | LCMS data |
|---|---|---|---|---|---|---|
| 3-16 | Isomer 2: ethyl2-[4-(2-oxo-1,2-dihydropyridin-4-yl)piperidin-1-yl]-6-azaspiro[3.4]octane-6-carboxylate | 2 and 154 | b | (400 MHz, DMSO-d$_6$) δ: 1.16 (t, J = 6.9 Hz, 3 H), 1.41-2.09 (m, 12 H), 2.28-2.44 (m, 1 H), 2.61-2.76 (m, 1 H), 2.86 (d, J = 10.7 Hz, 1 H), 3.03-3.44 (m, 5 H), 4.00 (q, J = 7.0 Hz, 2 H), 6.00 (d, J = 7.0 Hz, 1 H), 6.13 (d, J = 8.5 Hz, 1 H), 7.35 (dd, J = 9.2, 7.0 Hz, 1 H), 11.20-11.58 (m, 1 H). | I | m/z 360 (M + H)$^+$ (ES$^+$) at 3.26 min, UV active |
| 4-1 | Isomer 2: ethyl 2-(2-oxo-3,4'-bipiperidin-1'-yl)-6-azaspiro[3.4]octane-6-carboxylate | 2 and 69 | b | (400 MHz, DMSO-d$_6$) δ: 1.17 (t, J = 6.7 Hz, 3 H), 1.22-2.11 (m, 18 H), 2.57-2.69 (m, 1 H), 2.80 (t, J = 11.6 Hz, 2 H), 2.96-3.15 (m, 2 H), 3.16-3.30 (m, 4 H), 4.01 (q, J = 7.0 Hz, 2 H), 7.39 (br.s., 1 H). | G | m/z 364 (M + H)$^+$ (ES$^+$) at 4.86 min, UV inactive |
| 4-1 | Isomer 3: ethyl 2-(2-oxo-3,4'-bipiperidin-1'-yl)-6-azaspiro[3.4]octane-6-carboxylate | 2 and 69 | b | (400 MHz, DMSO-d$_6$) δ: 1.16 (t, J = 7.0 Hz, 3 H), 1.21-2.12 (m, 18 H), 2.55-2.70 (m, 1 H), 2.72-2.86 (m, 2 H), 3.00-3.17 (m, 4 H), 3.27 (d, J = 7.0 Hz, 2 H), 4.00 (q, J = 7.2 Hz, 2 H), 7.39 (br.s., 1 H). | G | m/z 364 (M + H)$^+$ (ES$^+$) at 4.95 min, UV inactive |
| 4-1 | Isomer 4: ethyl 2-(2-oxo-3,4'-bipiperidin-1'-yl)-6-azaspiro[3.4]octane-6-carboxylate | 2 and 69 | b | (400 MHz, DMSO-d$_6$) δ: 1.16 (t, J = 7.0 Hz, 3 H), 1.21-1.89 (m, 14 H), 1.89-2.02 (m, 3 H), 2.02-2.12 (m, 1 H), 2.55-2.64 (m, 1 H), 2.65-2.85 (m, 2 H), 2.98-3.18 (m, 4 H), 3.20-3.39 (m, 2 H), 4.00 (q, J = 7.2 Hz, 2 H), 7.39 (br.s., 1 H). | G | m/z 364 (M + H)$^+$ (ES$^+$) at 4.97 min, UV inactive |
| 4-2 | Isomer 4: methyl 2-(2-oxo-3,4'-bipiperidin-1'-yl)-6-azaspiro[3.4]octane-6-carboxylate | 3 and 69 | b | (400 MHz, DMSO-d$_6$) δ: 1.07-2.20 (m, 18 H), 2.99-3.21 (m, 4 H), 3.23-3.43 (m, 5 H), 3.56 (s, 3 H), 7.44 (br.s., 1 H). | G | m/z 350 (M + H)$^+$ (ES$^+$) at 3.23 min, UV inactive |
| 4-3 | Isomer 2: ethyl 2-(4-methyl-2-oxo-3,4'-bipiperidin-1'-yl)-6-azaspiro[3.4]octane-6-carboxylate | 2 and 147 | b | (400 MHz, CD$_3$OD) δ: 0.98 (d, J = 7.0 Hz, 3 H), 1.19-1.70 (m, 7 H), 1.71-1.84 (m, 2 H), 1.84-2.10 (m, 6 H), 2.11-2.43 (m, 4 H), 2.83-3.09 (m, 2 H), 3.23-3.46 (m, 9 H), 4.13 (q, J = 7.0 Hz, 2 H). | E | m/z 378 (M + H)$^+$ (ES$^+$) at 3.75 min, UV inactive |
| 4-4 | Isomer 1: ethyl 2-(5-methyl-2-oxo-3,4'-bipiperidin-1'-yl)-6-azaspiro[3.4]octane-6-carboxylate | 2 and 144 | b | (400 MHz, CDCl$_3$) δ: 1.02 (d, J = 6.7 Hz, 3 H), 1.24-1.35 (m, 3 H), 1.48-2.42 (m, 14 H), 2.76-3.30 (m, 10 H), 3.38 (d, J = 19.8 Hz, 3 H), 4.14 (q, J = 7.0 Hz, 2 H), 6.38 (br.s., 1 H). | I | m/z 378 (M + H)$^+$ (ES$^+$) at 3.59 min, UV inactive |
| 4-4 | Isomer 2: ethyl 2-(5-methyl-2-oxo-3,4'-bipiperidin-1'-yl)-6-azaspiro[3.4]octane-6-carboxylate | 2 and 144 | b | (400 MHz, CDCl$_3$) δ: 1.03 (d, J = 6.4 Hz, 2 H), 1.22-1.36 (m, 3 H), 1.48-2.19 (m, 14 H), 2.20-2.45 (m, 3 H), 2.79-3.67 (m, 10 H), 4.13 (q, J = 6.7 Hz, 2 H), 6.58 (br.s., 1 H). | I | m/z 378 (M + H)$^+$ (ES$^+$) at 3.67 min, UV inactive |
| 4-5 | Isomer 2: ethyl 2-(1-ethyl-2-oxo-3,4'-bipiperidin-1'-yl)-6-azaspiro[3.4]octane-6-carboxylate | Example 4-1 and 114 | au | (400 MHz, CD$_3$OD) δ: 1.13 (t, J = 7.2 Hz, 3 H), 1.19 (t, J = 7.2 Hz, 3 H), 1.23-2.39 (m, 17 H), 2.63-3.04 (m, 3 H), 3.25-3.52 (m, 9 H), 4.11 (q, J = 7.2 Hz, 2 H). | I | m/z 392 (M + H)$^+$ (ES$^+$) at 3.91 min, UV inactive |
| 4-6 | Isomer 2: ethyl 2-[2-oxo-1-(propan-2-yl)-3,4'-bipiperidin-1'-yl]-6-azaspiro[3.4]octane-6-carboxylate | Example 4-1 and 156 | au | (400 MHz, CD$_3$OD) δ: 1.14 (dd, J = 7.0, 5.2 Hz, 6 H), 1.21-1.74 (m, 8 H), 1.79-2.01 (m, 7 H), 2.08-2.22 (m, 3 H), 2.35 (ddd, J = 10.5, 6.6, 4.3 Hz, 1 H), 2.74-3.08 (m, 3 H), 3.10-3.23 (m, 1 H), 3.24-3.46 (m, 7 H), 4.12 (q, J = 7.2 Hz, 2 H), 4.78 (sept, J = 6.8 Hz, 1 H). | E | m/z 406 (M + H)$^+$ (ES$^+$) at 4.12 min, UV inactive |
| 4-7 | Isomer 2: ethyl 2-[4-(2-oxo-1,3-oxazinan-3-yl)piperidin-1-yl]-6-azaspiro[3.4]octane-6-carboxylate | 2 and 132 | at | (400 MHz, CDCl$_3$) δ: 1.22 (td, J = 7.0, 3.9 Hz, 3 H), 1.66-1.76 (m, 4 H), 1.76-1.92 (m, 4 H), 1.92-2.12 (m, 4 H), 2.58-2.76 (m, 1 H), 2.91 (d, J = 10.2 Hz, 2 H), 3.17-3.31 (m, 4 H), 3.31-3.44 (m, 2 H), 4.09 (q, J = 7.0 Hz, 2 H), 4.14-4.29 (m, 3 H). | B | m/z 366 (M + H)$^+$ (ES$^+$) at 2.35 min, UV inactive |
| 4-8 | Isomer 1: ethyl 2-[4-(2-oxotetrahydropyrimidin- | 2 and 137 | av | (400 MHz, CDCl$_3$) δ: 1.24 (td, J = 7.0, 3.1 Hz, 3 H), 1.58-1.74 (m, 4 H), 1.74-2.01 (m, 8 H), 2.02-2.21 (m, 2 H), | E | m/z 365 (M + H)$^+$ (ES$^+$) at 2.68 min, UV inactive |

TABLE 3-continued

| Ex. No. | Name | Intermediate | Synthetic method | ¹H NMR | LCMS Method | LCMS data |
|---|---|---|---|---|---|---|
| | 1(2H)-yl)piperidin-1-yl]-6-azaspiro[3.4]octane-6-carboxylate | | | 2.52-2.78 (m, 1 H), 2.78-3.03 (m, 2 H), 3.10-3.41 (m, 8 H), 4.10 (q, J = 7.3 Hz, 2 H), 4.22-4.42 (m, 1 H), 4.67-4.82 (m, 1 H). | | |
| 4-8 | Isomer 2: ethyl 2-[4-(2-oxotetrahydropyrimidin-1(2H)-yl)piperidin-1-yl]-6-azaspiro[3.4]octane-6-carboxylate | 2 and 137 | av | (400 MHz, CDCl₃) δ: 1.17-1.31 (m, 3H), 1.49-1.77 (m, 4H), 1.77-1.97 (m, 7H), 1.97-2.19 (m, 3H), 2.52-3.02 (m, 3H), 3.09-3.31 (m, 6H), 3.31-3.48 (m, 2H), 4.01-4.17 (m, 2H), 4.23-4.46 (m, 1H), 4.57-4.92 (m, 1H). | E | m/z 365 (M + H)⁺ (ES⁺), at 2.81 min, UV inactive |
| 4-9 | Mixture of diastereomers: ethyl 2-[4-(5,5-dimethyl-2-oxotetrahydropyrimidin-1(2H)-yl)piperidin-1-yl]-6-azaspiro[3.4]octane-6-carboxylate | 2 and 149 | av | (400 MHz, CDCl₃) δ: 0.96-1.12 (m, 5 H), 1.25 (td, J = 7.0, 3.9 Hz, 3 H), 1.46-1.96 (m, 8 H), 1.96-2.71 (m, 5 H), 2.79-3.00 (m, 5 H), 3.16-3.60 (m, 5 H), 4.03-4.19 (m, 2 H), 4.25-4.73 (m, 2 H). | B | m/z 393 (M + H)⁺ (ES⁺), at 2.67 min, UV inactive |
| 4-10 | Isomer 2: ethyl 2-(1,4'-bipiperidin-1'-yl)-6-azaspiro[3.4]octane-6-carboxylate | 2 and 276 | aw | (400 MHz, DMSO-d₆) δ: 1.13 (t, J = 7.0 Hz, 3 H), 1.28-1.50 (m, 8H), 1.54-1.67 (m, 4 H), 1.67-1.86 (m, 4 H), 1.86-2.01 (m, 2 H), 2.34-2.44 (m, 3 H), 2.50-2.62 (m, 2 H), 2.76 (d, J = 11.7 Hz, 2 H), 3.10 (d, J = 6.2 Hz, 2 H), 3.19-3.26 (m, 3 H), 3.96 (q, J = 7.0 Hz, 2 H) | E | m/z 350 (M + H)⁺ (ES⁺), at 3.62 min, UV inactive |
| 4-11 | Isomer 2: ethyl 2-[4-(morpholin-4-yl)piperidin-1-yl]-6-azaspiro[3.4]octane-6-carboxylate | 2 and 272 | aw | (400 MHz, DMSO-d₆) δ: 1.14 (t, J = 7.0 Hz, 3 H), 1.23-1.37 (m, 2 H), 1.52-1.83 (m, 7 H), 1.92-2.12 (m, 3 H), 2.36-2.45 (m, 6 H), 2.52-2.57 (m, 2 H), 2.76 (d, J = 10.2 Hz, 2 H), 3.13-3.26 (m, 3 H), 3.48-3.57 (m, 3 H), 3.98 (q, J = 7.0 Hz, 2 H) | E | m/z 352 (M + H)⁺ (ES⁺), at 2.70 min, UV inactive |
| 4-12 | Isomer 2: ethyl 2-[4-(thiomorpholin-4-yl)piperidin-1-yl]-6-azaspiro[3.4]octane-6-carboxylate | 2 and 268 | aw | (400 MHz, DMSO-d₆) δ: 1.13 (t, J = 7.0 Hz, 3 H), 1.39 (q, J = 10.9 Hz, 2 H), 1.49-1.66 (m, 5 H), 1.66-1.85 (m, 5 H), 1.89-2.00 (m, 3 H), 2.22 (t, J = 12.1 Hz, 2 H), 2.68-2.74 (m, 5 H), 2.78 (d, J = 10.5 Hz, 2 H), 3.11 (d, J = 5.9 Hz, 2 H), 3.20-3.27 (m, 3 H), 3.97 (q, J = 7.0 Hz, 2 H) | E | m/z 368 (M + H)⁺ (ES⁺), at 3.18 min, UV inactive |
| 4-13 | Isomer 2: ethyl 2-(3,3-difluoro-1,4'-bipiperidin-1'-yl)-6-azaspiro[3.4]octane-6-carboxylate | 2 and 280 | aw | (300 MHz, DMSO-d₆) δ: 1.16 (t, J = 7.1 Hz, 3 H), 1.29-1.48 (m, 2 H), 1.57-1.91 (m, 9 H), 1.92-2.00 (m, 2 H), 2.37-2.49 (m, 4 H), 2.53-2.71 (m, 5 H), 2.74-2.86 (m, 2 H), 3.06-3.22 (m, 4 H), 3.99 (q, J = 7.0 Hz, 2 H) | E | m/z 386 (M + H)⁺ (ES⁺), at 3.64 min, UV inactive |
| 4-14 | Isomer 2: ethyl 2-(4,4-difluoro-1,4'-bipiperidin-1'-yl)-6-azaspiro[3.4]octane-6-carboxylate | 2 and 266 | aw | (400 MHz, DMSO-d₆) δ: 1.13 (t, J = 7.0 Hz, 3 H), 1.28-1.44 (m, 2 H), 1.56-1.67 (m, 4 H), 1.67-1.75 (m, 2 H), 1.75-2.01 (m, 8 H), 2.20-2.30 (m, 1 H), 2.51-2.63 (m, 5 H), 2.77 (d, J = 11.7 Hz, 2 H), 3.11 (d, J = 6.2 Hz, 2 H), 3.24 (q, J = 6.9 Hz, 2 H), 3.97 (q, J = 7.0 Hz, 2 H) | E | m/z 386 (M + H)⁺ (ES⁺), at 3.49 min, UV inactive |
| 4-15 | Isomer 2: methyl (2R)-1'-[6-(ethoxycarbonyl)-6-azaspiro[3.4]oct-2-yl]-1,4'-bipiperidine-2-carboxylate | 2 and 290 | aw | (400 MHz, DMSO-d₆) δ: 1.13 (t, J = 7.0 Hz, 3 H), 1.23-1.50 (m, 7 H), 1.57-1.67 (m, 5 H), 1.67-1.87 (m, 5 H), 1.95 (t, J = 8.4 Hz, 2 H), 2.38-2.42 (m, 1 H), 2.70-2.94 (m, 3 H), 3.11 (d, J = 5.9 Hz, 2 H), 3.24 (q, J = 6.8 Hz, 3 H), 3.42-3.45 (m, 1 H), 3.58 (s, 3 H), 3.97 (q, J = 7.0 Hz, 2 H) | E | m/z 408 (M + H)⁺ (ES⁺), at 3.86 min, UV inactive |
| 4-16 | Isomer 2: ethyl 2-[(2R)-2-(methylcarbamoyl)-1,4'-bipiperidin-1'-yl]-6-azaspiro[3.4]octane-6-carboxylate | 2 and 223 | ax | (400 MHz, CDCl₃) δ: 1.22 (t, J = 6.8 Hz, 3H), 1.41-1.50 (m, 2H), 1.61-1.75 (m, 4H), 1.81-1.95 (m, 6H), 2.51-2.61 (m, 1H), 2.70-2.75 (m, 1H), 2.82 (d, J = 4.6 Hz, 3H), 2.95-3.45 (m, 11H), 3.10-3.27 (m, 4H), 4.12 (q, J = 6.8 Hz, 2H), 7.06 (br.s, 1H). | M | m/z 407 (M + H)⁺ (ES+), at 1.69 min, UV inactive |
| 4-17 | Isomer 2: ethyl 2-[(2R)-2-(dimethylcarbamoyl)-1,4'- | 2 and 283 | aw | (400 MHz, DMSO-d₆) δ: 1.13 (t, J = 7.0 Hz, 3 H), 1.29-1.41 (m, 2 H), 1.43-1.53 (m, 3 H), 1.53-1.66 (m, 5 H), | E | m/z 421 (M + H)⁺ (ES⁺), at 4.13 min, UV inactive |

TABLE 3-continued

| Ex. No. | Name | Intermediate | Synthetic method | ¹H NMR | LCMS Method | LCMS data |
|---|---|---|---|---|---|---|
| | bipiperidin-1'-yl]-6-azaspiro[3.4]octane-6-carboxylate | | | 1.66-1.74 (m, 2 H), 1.74-1.87 (m, 3 H), 1.87-1.99 (m, 3 H), 2.41-2.45 (m, 3 H), 2.76 (s, 6 H), 3.10 (d, J = 6.2 Hz, 4 H), 3.12-3.15 (m, 4 H), 3.97 (q, J = 7.0 Hz, 2 H) | | |
| 4-18 | Isomer 2: ethyl 2-[(2S)-2-(methylcarbamoyl)-1,4'-bipiperidin-1'-yl]-6-azaspiro[3.4]octane-6-carboxylate | 2 and 225 | ax | (400 MHz, CDCl₃) δ: 1.25 (t, J = 6.8 Hz, 3H), 1.41-1.50 (m, 2H), 1.61-1.75 (m, 4H), 1.81-1.95 (m, 6H), 2.51-2.61 (m, 1H), 2.70-2.75 (m, 1H), 2.82 (d, J = 4.6 Hz, 3H), 2.95-3.45 (m, 11H), 3.10-3.27 (m, 4H), 4.12 (q, J = 6.8 Hz, 2H), 7.22 (br.s., 1H). | M | m/z 407 (M + H)⁺ (ES+), at 1.67 min, UV inactive |
| 4-19 | Isomer 2: ethyl 2-(1-propanoyl-2,4'-bipiperidin-1'-yl)-6-azaspiro[3.4]octane-6-carboxylate | 222, 229 and 230 | y | (400 MHz, CDCl₃) δ: 1.10-1.15 (m, 3H), 1.22-1.25 (m, 3H), 1.34-1.54 (m, 4H), 1.55-1.68 (m, 4H), 1.70-1.80 (m, 3H), 1.81-1.90 (m, 4H), 1.98-2.20 (m, 6H), 2.27-2.40 (m, 2H), 2.42-3.10 (m, 4H), 3.22-3.34 (m, 2H), 3.34-3.45 (m, 2H), 4.05-4.15 (m, 2H), 4.53-4.64 (m, 1H). | O | m/z 406 (M + H)⁺ (ES+), at 4.48 min, UV inactive |
| 4-20 | Isomer 2: ethyl 2-[1-(methylcarbamoyl)-2,4'-bipiperidin-1'-yl]-6-azaspiro[3.4]octane-6-carboxylate | 57 and 229 | m | (400 MHz, CDCl₃) δ: 1.22-1.27 (m, 3H), 1.31-1.47 (m, 3H), 1.48-1.62 (m, 5H), 1.72-1.79 (m, 2H), 1.82-1.91 (m, 4H), 2.02-2.12 (m, 5H), 2.61-2.82 (m, 5H), 2.90-3.06 (m, 2H), 3.25-3.33 (m, 2H), 3.34-3.44 (m, 2H), 3.48-3.64 (m, 1H), 3.88-4.00 (m, 1H), 4.05-4.13 (m, 2H), 4.37 (br.s., 1H). | O | m/z 407 (M + H)⁺ (ES+), at 4.29 min, UV inactive |
| 5-1 | Isomer 2: ethyl 2-[4-(2-oxoazepan-1-yl)piperidin-1-yl]-6-azaspiro[3.4]octane-6-carboxylate | 2, 214 and 322 | ay | (400 MHz, CD₃OD) δ: 1.24 (t, J = 7.0 Hz, 3 H), 1.52-1.79 (m, 10 H), 1.80-1.99 (m, 6 H), 2.04-2.17 (m, 2 H), 2.48-2.61 (m, 2 H), 2.72-2.88 (m, 1 H), 2.96 (d, J = 11.7 Hz, 2 H), 3.26 (s, 2 H), 3.33-3.46 (m, 4 H), 4.09 (q, J = 7.0 Hz, 2 H), 4.40 (tt, J = 12.01, 4.20 Hz, 1 H) | E | m/z 378 (M + H)+ (ES+), at 2.85 min, UV inactive |
| 5-2 | Isomer 2: ethyl 2-[4-[2-(methoxycarbonyl)azepan-1-yl]piperidin-1-yl]-6-azaspiro[3.4]octane-6-carboxylate | 2 and 190 | as | (400 MHz, CDCl₃) δ: 1.24 (t, J = 7.0 Hz, 3 H), 1.28-2.14 (m, 20 H), 2.46-2.70 (m, 2 H), 2.73-2.92 (m, 3 H), 2.94-3.05 (m, 1 H), 3.21-3.46 (m, 4 H), 3.52-3.61 (m, 1 H), 3.67 (s, 3 H), 4.06-4.16 (m, 2 H) | B | m/z 422 (M + H)⁺ (ES+), at 5.54 min, UV active |

Biological Activity

Example A

Phospho-ERK1/2 Assays

Functional assays were performed using the Alphascreen Surefire phospho-ERK1/2 assay (Crouch & Osmond, *Comb. Chem. High Throughput Screen,* 2008). ERK1/2 phosphorylation is a downstream consequence of both Gq/11 and Gi/o protein coupled receptor activation, making it highly suitable for the assessment of $M_1$, $M_3$ (Gq/11 coupled) and $M_2$, $M_4$ receptors (Gi/o coupled), rather than using different assay formats for different receptor subtypes. CHO cells stably expressing the human muscarinic $M_1$, $M_2$, $M_3$ or $M_4$ receptor were plated (25K/well) onto 96-well tissue culture plates in MEM-alpha+10% dialysed FBS. Once adhered, cells were serum-starved overnight. Agonist stimulation was performed by the addition of 5 μL agonist to the cells for 5 min (37° C.). Media was removed and 50 μL of lysis buffer added. After 15 min, a 4 μL sample was transferred to 384-well plate and 7 μL of detection mixture added. Plates were incubated for 2 h with gentle agitation in the dark and then read on a PHERAstar plate reader.

$pEC_{50}$ and $E_{max}$ figures were calculated from the resulting data for each receptor subtype.

The results are set out in Table 4 below.

For each example two diastereomers exist which have been separated, unless stated otherwise, and assigned based on their retention time on LCMS analytical trace. In most examples, isomer 1 is not active. Analytical data for active isomers is reported in Table 3. Data for several weakly active compounds are included in Table 4 to highlight preference of absolute stereochemistry.

TABLE 4

| Ex. No. | Muscarinic Activity | | | |
|---|---|---|---|---|
| | $pEC_{50}$ $M_1$ (% Emax cf. ACh) | $pEC_{50}$ $M_2$ (% Emax cf. ACh) | $pEC_{50}$ $M_3$ (% Emax cf. ACh) | $pEC_{50}$ $M_4$ (% Emax cf. ACh) |
| ACh | 8.3 (102) | 7.8 (105) | 8.1 (115) | 8.1 (110) |
| 1-1 Isomer 2 | 7.2 (121) | <4.7 (20) | <4.7 (26) | 8.1 (112) |
| 1-2 Isomer 2 | 6.6 (93) | <4.7 (6) | <4.7 (4) | 7.6 (100) |
| 1-3 Isomer 2 | 6.3 (30) | NT | NT | 6.7 (41) |
| 1-4 Isomer 2 | 6.0 (55) | NT | NT | 6.6 (67) |
| 1-5 Isomer 2 | 6.9 (94) | <4.7 (19) | <4.7 (2) | 7.7 (81) |
| 1-6 Isomer 2 | 5.9 (128) | <4.7 (57) | *7.2 (38) | 7.2 (71) |
| 1-7 Isomer 2 | 6.8 (97) | <4.7 (15) | <4.7 (22) | 7.6 (97) |
| 1-8 Isomer 2 | 6.5 (76) | <4.7 (34) | <4.7 (0) | 7.8 (98) |
| 1-9 Isomer 2 | <4.7 (57) | NT | NT | 6.1 (48) |
| 1-10 Isomer 2 | 5.3 (62) | NT | NT | 6.6 (106) |
| 1-11 Isomer 2 | 5.8 (98) | NT | NT | 6.6 (85) |
| 1-12 Isomer 2 | 6.0 (85) | <4.7 (11) | <4.7 (15) | 6.9 (128) |
| 1-13 Isomer 2 | 5.8 (61) | NT | NT | 6.4 (86) |
| 1-14 Isomer 2 | 6.2 (66) | <4.7 (27) | <4.7 (5) | 7.3 (99) |
| 1-15 Isomer 2 | 7.0 (70) | <4.7 (4) | <4.7 (6) | NT |
| 1-16 Isomer 2 | 5.8 (80) | *5.1 (34) | <4.7 (1) | 6.8 (82) |
| 1-17 Isomer 2 | 6.2 (53) | <4.7 (14) | <4.7 (0) | 7.2 (90) |
| 1-18 Isomer 2 | 6.9 (65) | <4.7 (3) | <4.7 (56) | 7.3 (89) |
| 1-19 Isomer 2 | 6.1 (83) | NT | NT | *5.1 (48) |
| 1-20 Mixture of diastereomers | <4.7 (62) | NT | NT | 6.0 (56) |
| 1-21 Isomer 2 | <4.7 (11) | <4.7 (8) | <4.7 (0) | 7.4 (79) |
| 1-22 Isomer 2 | 6.7 (47) | NT | NT | <4.7 (20) |
| 1-23 Isomer 2 | 6.4 (55) | <4.7 (7) | <4.7 (9) | 7.5 (105) |
| 1-24 Isomer 2 | 6.6 (102) | *5.2 (32) | <4.7 (0) | 7.6 (78) |
| 1-25 Isomer 2 | 7.3 (110) | <4.7 (15) | <4.7 (13) | 8.4 (128) |
| 1-26 Isomer 2 | 5.6 (46) | <4.7 (99) | 6.1 (53) | 6.7 (76) |
| 1-27 Isomer 2 | 6.0 (27) | NT | NT | 6.4 (41) |
| 1-28 Isomer 2 | 5.7 (57) | NT | NT | 6.3 (60) |
| 1-29 Isomer 2 | 6.1 (44) | NT | NT | 6.9 (36) |
| 1-30 Isomer 2 | 6.5 (37) | <4.7 (9) | <4.7 (5) | 7.9 (101) |
| 1-31 Isomer 2 | 5.6 (34) | NT | NT | 7.0 (40) |
| 1-32 Isomer 2 | 7.1 (113) | <4.7 (56) | <4.7 (16) | 8.2 (126) |
| 1-33 Isomer 2 | 7.6 (11) | 4.7 (49) | <4.7 (7) | 8.4 (118) |
| 1-34 Isomer 1 | 6.3 (49) | <4.7 (10) | <4.7 (0) | 6.8 (48) |
| 1-34 Isomer 2 | 8.1 (130) | <4.7 (43) | <4.7 (0) | 8.6 (117) |
| 1-35 Isomer 2 | 6.4 (80) | NT | NT | 6.7 (61) |
| 1-36 Isomer 2 | 5.3 (73) | NT | NT | 6.6 (47) |
| 1-37 Isomer 2 | 5.6 (78) | NT | NT | 6.3 (126) |
| 1-38 Isomer 2 | 7.0 (31) | <4.7 (14) | <4.7 (19) | 6.1 (98) |
| 1-39 Isomer 2 | 6.0 (49) | NT | NT | 6.4 (97) |
| 1-40 Isomer 2 | <4.7 (904) | NT | NT | 6.8 (50) |
| 1-41 Isomer 2 | 6.0 (52) | NT | NT | 6.6 (35) |
| 1-42 Isomer 2 | 7.4 (123) | 6.5 (27) | <4.7 (16) | 8.2 (76) |
| 1-43 Isomer 2 | 6.8 (32) | <4.7 (7) | <4.7 (8) | 7.5 (61) |
| 1-44 Isomer 2 | 7.1 (126) | <4.7 (80) | <4.7 (7) | 8.2 (126) |
| 1-45 Isomer 2 | 6.5 (80) | 5.8 (56) | <4.7 (26) | 7.7 (80) |
| 1-46 Isomer 2 | <4.7 (35) | NT | NT | 6.7 (63) |
| 1-47 Isomer 2 | <4.7 (7) | 4.7 (82) | <4.7 (19) | 7.8 (81) |
| 1-48 Isomer 2 | <4.7 (63) | NT | NT | 6.2 (68) |
| 1-49 Isomer 2 | 5.2 (71) | <4.7 (21) | <4.7 (9) | 7.1 (92) |
| 1-50 Isomer 2 | 8.1 (124) | <4.7 (20) | <4.7 (8) | 8.7 (122) |
| 1-51 Isomer 2 | 5.9 (74) | NT | NT | 6.8 (106) |
| 1-52 Isomer 2 | 6.8 (102) | <4.7 (15) | <4.7 (20) | 7.8 (106) |
| 1-53 Isomer 2 | 5.3 (38) | NT | NT | 5.9 (80) |
| 1-54 Isomer 2 | <4.7 (51) | NT | NT | 6.1 (74) |
| 1-55 Isomer 2 | 5.3 (40) | NT | NT | 6.3 (64) |
| 1-56 Isomer 2 | 6.0 (30) | <4.7 (0) | <4.7 (3) | 6.9 (89) |
| 1-57 Isomer 2 | 5.7 (63) | <4.7 (7) | <4.7 (7) | 6.9 (69) |
| 1-58 Isomer 2 | 6.1 (55) | <4.7 (13) | <4.7 (2) | 7.5 (93) |
| 1-59 Isomer 2 | 6.4 (38) | NT | NT | 7.0 (76) |
| 1-60 Isomer 2 | 6.5 (82) | NT | NT | 7.4 (88) |
| 1-61 Isomer 2 | 6.5 (66) | <4.7 (1) | <4.7 (2) | 7.6 (97) |
| 1-62 Isomer 2 | 5.9 (73) | NT | NT | <4.7 (10) |
| 1-63 Isomer 2 | <4.7 (82) | NT | NT | 6.0 (24) |
| 1-64 Isomer 2 | 5.3 (40) | NT | NT | 6.5 (78) |
| 1-65 Isomer 2 | <4.7 (60) | NT | NT | 6.6 (73) |
| 1-66 Isomer 2 | <4.7 (14) | NT | NT | 6.6 (32) |
| 1-67 Isomer 2 | 5.5 (37) | NT | NT | 6.5 (75) |
| 1-68 Isomer 2 | 7.1 (91) | NT | NT | 8.2 (98) |
| 1-69 Isomer 2 | 7.1 (99) | NT | NT | 8.3 (104) |
| 1-70 Isomer 2 | 7.1 (92) | NT | NT | 8.3 (101) |
| 1-71 Isomer 2 | <4.7 (6) | NT | NT | 7.0 (69) |
| 1-72 Isomer 2 | <4.7 (17) | NT | NT | 6.8 (69) |
| 1-73 Isomer 2 | <4.7 (11) | NT | NT | 6.9 (72) |
| 2-1 Isomer 2 | <4.7 (6) | <4.7 | <4.7 | 6.5 (63) |
| 2-2 Isomer 2 | 6.1 (39) | <4.7 (53) | <4.7 (16) | 7.2 (79) |
| 2-3 Isomer 2 | *5.0 (32) | <4.7 (14) | <4.7 (4) | 7.3 (89) |
| 2-4 Isomer 2 | 6.5 (102) | <4.7 (2) | <4.7 (3) | 7.3 (110) |
| 2-5 Isomer 2 | *5.2 (34) | NT | NT | 6.8 (66) |
| 2-6 Isomer 2 | 5.5 (57) | <4.7 (30) | <4.7 (16) | 7.8 (132) |
| 2-7 Isomer 2 | 6.1 (41) | <4.7 (13) | *5.1 (27) | 7.9 (100) |
| 2-8 Isomer 2 | 6.2 (36) | <4.7 (3) | <4.7 (4) | 7.8 (86) |
| 2-9 Isomer 2 | 6.0 (43) | <4.7 (4) | <4.7 (6) | 8.0 (104) |
| 2-10 Isomer 2 | <4.7 (19) | NT | NT | 6.7 (50) |
| 2-11 Isomer 2 | *4.7 (39) | <4.7 (7) | <4.7 (7) | 7.6 (100) |
| 2-12 Isomer 2 | <4.7 (9) | <4.7 (9) | <4.7 (6) | 8.0 (57) |
| 2-13 Isomer 2 | *5.0 (69) | <4.7 (7) | <4.7 (24) | 6.8 (57) |
| 2-14 Isomer 2 | <4.7 (43) | <4.7 (3) | <4.7 (7) | 7.8 (91) |
| 2-15 Isomer 2 | 6.4 (72) | <4.7 (9) | <4.7 (9) | 7.8 (111) |
| 2-16 Isomer 2 | 6.6 (41) | <4.7 (53) | <4.7 (7) | 8.2 (114) |
| 2-17 Isomer 2 | 6.7 (72) | <4.7 (5) | <4.7 (4) | 8.5 (116) |
| 2-18 Isomer 2 | <4.7 (8) | <4.7 (1) | <4.7 (4) | 7.1 (56) |
| 2-19 Isomer 2 | 6.2 (44) | <4.7 (3) | <4.7 (10) | 8.1 (113) |
| 2-20 Isomer 2 | <4.7 (24) | <4.7 (1) | <4.7 (6) | 7.5 (106) |
| 2-21 Isomer 2 | 6.2 (46) | <4.7 (4) | <4.7 (2) | 8.1 (113) |
| 2-22 Isomer 2 | <4.7 (7) | NT | NT | 6.5 (31) |
| 2-23 Isomer 2 | 5.9 (65) | <4.7 (3) | <4.7 (9) | 7.3 (104) |
| 2-24 Isomer 2 | 6.2 (37) | <4.7 (5) | <4.7 (9) | 7.7 (121) |
| 2-25 Isomer 2 | 6.2 (74) | <4.7 (6) | <4.7 (2) | 8.0 (86) |
| 2-26 Isomer 2 | *7.9 (92) | <4.7 (66) | <4.7 (4) | 8.2 (99) |
| 2-27 Isomer 2 | *7.5 (24) | <4.7 (0.4) | <4.7 (15) | 8.0 (73) |
| 2-28 Isomer 2 | <4.7 (7) | <4.7 (3) | <4.7 (5) | 7.6 (63) |

TABLE 4-continued

| Ex. No. | Muscarinic Activity | | | |
|---|---|---|---|---|
| | pEC$_{50}$ M$_1$ (% Emax cf. ACh) | pEC$_{50}$ M$_2$ (% Emax cf. ACh) | pEC$_{50}$ M$_3$ (% Emax cf. ACh) | pEC$_{50}$ M$_4$ (% Emax cf. ACh) |
| 2-29 Isomer 2 | 6.3 (60) | <4.7 (5) | <4.7 (13) | 7.8 (110) |
| 2-30 Isomer 2 | 6.3 (34) | <4.7 (52) | <4.7 (13) | 7.8 (97) |
| 2-31 Isomer 2 | 6.9 (93) | <4.7 (7) | <4.7 (7) | 8.5 (108) |
| 2-32 Isomer 2 | 5.6 (69) | <4.7 (52) | <4.7 (11) | 7.9 (110) |
| 2-33 Isomer 1 | 6.4 (86) | <4.7 (8) | <4.7 (3) | 8.1 (109) |
| 2-33 Isomer 2 | <4.7 (4) | <4.7 (5) | <4.7 (5) | 7.7 (65) |
| 2-34 Isomer 1 | 5.7 (74) | <4.7 (16) | <4.7 (8) | 7.6 (89) |
| 2-34 Isomer 2 | 5.5 (56) | <4.7 (3) | <4.7 (39) | 6.6 (58) |
| 2-35 Isomer 2 | 6.4 (108) | <4.7 (1) | <4.7 (4) | 7.8 (92) |
| 2-36 Isomer 2 | 6.8 (89) | <4.7 (3) | <4.7 (5) | 8.2 (113) |
| 2-37 Isomer 2 | 5.5 (106) | <4.7 (33) | <4.7 (58) | 7.7 (83) |
| 2-38 Isomer 2 | 6.8 (110) | <4.7 (1) | <4.7 (2) | 8.3 (115) |
| 2-39 Isomer 2 | 5.6 (41) | <4.7 (1) | <4.7 (1) | 7.8 (76) |
| 2-40 Isomer 2 | 6.1 (78) | <4.7 (2) | <4.7 (1) | 7.5 (90) |
| 2-41 Isomer 2 | 5.6 (36) | NT | NT | 7.0 (91) |
| 2-43 Isomer 2 | *5.5 (19) | <4.7 (4) | <4.7 (5) | 7.3 (47) |
| 2-44 Isomer 2 | 6.5 (71) | <4.7 (4) | <4.7 (8) | 8.3 (100) |
| 2-45 Isomer 2 | 6.6 (67) | <4.7 (5) | <4.7 (5) | 8.3 (111) |
| 2-46 Isomer 2 | *5.8 (32) | <4.7 (5) | <4.7 (8) | 7.8 (85) |
| 2-47 Isomer 2 | 5.2 (45) | NT | NT | 6.0 (63) |
| 2-48 Isomer 2 | 6.5 (34) | <4.7 (3) | <4.7 (5) | 8.0 (81) |
| 2-50 Isomer 2 | 6.6 (63) | <4.7 (4) | <4.7 (2) | 7.6 (73) |
| 2-51 Isomer 2 | <4.7 (237) | <4.7 (1) | <4.7 (3) | 7.2 (53) |
| 2-52 Isomer 2 | 6.2 (49) | <4.7 (4) | <4.7 (4) | 7.7 (85) |
| 2-53 Isomer 2 | 7.1 (109) | <4.7 (10) | *5.2 (21) | 8.1 (126) |
| 2-54 Isomer 1 | <4.7 (1) | <4.7 (50) | <4.7 (0) | 7.8 (45) |
| 2-54 Isomer 2 | 7.3 (86) | <4.7 (8) | <4.7 (23) | 8.9 (134) |
| 2-55 Isomer 1 | <4.7 (15) | NT | NT | 6.8 (67) |
| 2-55 Isomer 2 | <4.7 (7) | <4.7 (22) | <4.7 (12) | 7.6 (52) |
| 2-56 Isomer 2 | 6.2 (96) | <4.7 (8) | <4.7 (0) | 8.3 (134) |
| 2-57 Isomer 2 | <4.7 (16) | <4.7 (25) | <4.7 (4) | 7.5 (117) |
| 2-58 Isomer 2 | 6.0 (66) | <4.7 (45) | <4.7 (9) | 7.5 (156) |
| 2-59 Isomer 2 | *5.5 (28) | <4.7 (11) | <4.7 (7) | 6.6 (67) |
| 2-61 Isomer 2 | <4.7 (10) | NT | NT | 6.3 (40) |
| 2-62 Isomer 2 | <4.7 (20) | <4.7 (6) | <4.7 (8) | 7.8 (65) |
| 2-63 Isomer 2 | 6.6 (34) | <4.7 (0) | <4.7 (4) | 7.2 (60) |
| 2-64 Isomer 2 | <4.7 (12) | <4.7 (6) | <4.7 (8) | 8.5 (41) |
| 2-65 Isomer 2 | 6.8 (60) | <4.7 (1) | <4.7 (1) | 8.1 (107) |
| 2-66 Isomer 2 | 7.4 (96) | <4.7 (18) | <4.7 (8) | 8.9 (115) |
| 2-67 Isomer 2 | <4.7 (19) | <4.7 (67) | <4.7 (1) | 7.7 (79) |
| 2-68 Isomer 2 | 6.0 (32) | <4.7 (4) | <4.7 (6) | 7.2 (73) |
| 2-69 Isomer 2 | 6.4 (87) | <4.7 (3) | <4.7 (2) | 7.9 (110) |
| 2-70 Isomer 1 | 5.4 (37) | NT | NT | 6.8 (52) |
| 2-70 Isomer 2 | 5.8 (93) | <4.7 (1) | <4.7 (3) | 7.5 (111) |
| 2-71 Isomer 2 | 5.3 (39) | NT | NT | 6.9 (56) |
| 2-72 Isomer 2 | 6.1 (30) | <4.7 (13) | <4.7 (10) | 7.1 (52) |
| 2-73 Isomer 2 | <4.7 (14) | NT | NT | 6.5 (43) |
| 2-74 Isomer 2 | <4.7 (18) | <4.7 (16) | <4.7 (8) | 7.1 (54) |
| 2-75 Isomer 2 | 6.5 (80) | <4.7 (6) | <4.7 (4) | 8.6 (109) |
| 2-76 Isomer 1 | 6.9 (82) | <4.7 (10) | <4.7 (35) | 7.4 (114) |
| 2-76 Isomer 2 | 7.3 (88) | <4.7 (16) | <4.7 (14) | 7.9 (107) |
| 2-77 Isomer 2 | 6.6 (51) | <4.7 (14) | <4.7 (47) | 8.2 (105) |
| 2-78 Isomer 2 | <4.7 (11) | 4.9 (27) | <4.7 (5) | 6.9 (49) |
| 2-79 Isomer 2 | 6.3 (37) | <4.7 (2) | <4.7 (19) | 7.5 (70) |
| 2-80 Isomer 2 | 6.9 (98) | <4.7 (16) | <4.7 (18) | 7.7 (107) |
| 2-81 Isomer 2 | <4.7 (12) | NT | NT | 7.2 (33) |
| 2-82 Isomer 2 | 6.3 (52) | <4.7 (1) | <4.7 (0) | 7.7 (70) |
| 2-83 Isomer 2 | 5.4 (55) | NT | NT | 8.0 (100) |
| 2-84 Isomer 2 | 6.6 (36) | <4.7 | <4.7 | 7.7 (82) |
| 2-85 Isomer 2 | 5.6 (66) | NT | NT | <4.7 (3) |
| 2-87 Isomer 2 | 6.4 (46) | <4.7 (54) | <4.7 (3) | 7.8 (100) |
| 2-88 Isomer 2 | 6.5 (25) | <4.7 (80) | <4.7 (5) | 7.4 (44) |
| 2-89 Isomer 2 | 5.2 (37) | <4.7 (68) | <4.7 (8) | 6.7 (102) |
| 2-90 Isomer 2 | 6.8 (54) | <4.7 (4) | <4.7 (1) | 7.9 (53) |
| 2-91 Isomer 2 | 6.3 (40) | <4.7 (12) | <4.7 (10) | 7.1 (67) |
| 2-92 Isomer 2 | 5.5 (50) | <4.7 (2) | <4.7 (2) | 7.5 (82) |
| 2-93 Isomer 2 | <4.7 (7) | NT | NT | <4.7 (3) |
| 2-94 Isomer 2 | <4.7 (7) | NT | NT | 5.17 (80) |
| 2-95 Isomer 2 | <4.7 (19) | <4.7 (16) | <4.7 (9) | 7.2 (49) |
| 2-96 Isomer 2 | <4.7 (2) | <4.7 (1) | <4.7 (3) | 6.9 (63) |
| 2-97 Isomer 2 | <4.7 (5) | <4.7 (3) | <4.7 (3) | 7.4 (37) |
| 2-98 Isomer 2 | <4.7 (10) | NT | NT | 6.9 (45) |
| 2-99 Isomer 2 | <4.7 (18) | NT | NT | 6.8 (54) |
| 2-100 Isomer 2 | <4.7 (16) | <4.7 (4) | <4.7 (5) | 6.7 (55) |
| 2-101 Isomer 2 | 5.0 (70) | NT | NT | 6.2 (98) |
| 2-102 Isomer 2 | 5.3 (23) | <4.7 (1) | <4.7 (11) | 6.5 (45) |
| 2-103 Isomer 2 | 6.7 (26) | <4.7 (4) | <4.7 (3) | 7.7 (100) |
| 2-104 Isomer 2 | 7.1 (102) | <4.7 (8) | <4.7 (8) | 7.8 (111) |
| 2-105 Isomer 2 | <4.7 (26) | NT | NT | 6.7 (38) |
| 2-106 Isomer 2 | 6.9 (97) | <4.7 (10) | <4.7 (5) | 7.7 (102) |
| 2-107 Isomer 2 | 7.2 (87) | <4.7 (5) | <4.7 (46) | 8.2 (92) |
| 2-109 Isomer 2 | 6.4 (50) | <4.7 (9) | 5.0 (26) | 7.8 (91) |
| 2-109 Isomer 4 | 6.5 (42) | <4.7 (15) | <4.7 (9) | 7.7 (82) |
| 2-111 Isomer 2 | 6.3 (31) | <4.7 (1) | <4.7 (0) | 7.5 (62) |
| 2-112 Isomer 2 | <4.7 (7) | NT | NT | 6.6 (63) |
| 2-113 Isomer 2 | 6.9 (100) | NT | NT | 7.8 (113) |
| 2-114 Isomer 2 | 6.9 (103) | NT | NT | 8.1 (114) |
| 2-115 Isomer 2 | 6.7 (68) | NT | NT | 7.6 (78) |
| 2-116 Isomer 2 | 7.2 (109) | NT | NT | 8.2 (103) |
| 2-117 Isomer 2 | 5.2 (99) | <4.7 (4) | <4.7 (7) | 7.2 (96) |
| 2-118 Isomer 2 | <4.7 (33) | NT | NT | 6.9 (84) |
| 2-119 Isomer 2 | 5.6 (85) | NT | NT | 6.9 (84) |
| 2-120 Isomer 2 | 6.4 (96) | NT | NT | 6.5 (87) |
| 2-121 Isomer 2 | 6.0 (31) | NT | NT | 6.7 (60) |
| 2-122 Isomer 2 | 6.0 (59) | NT | NT | 6.8 (60) |
| 2-123 Isomer 2 | 6.5 (114) | <4.7 (8) | <4.7 (29) | 6.5 (93) |
| 2-124 Isomer 2 | 6.2 (45) | <4.7 (2) | <4.7 (0) | 7.1 (77) |
| 2-125 Isomer 2 | 5.4 (32) | NT | NT | 6.5 (81) |
| 2-126 Isomer 2 | <4.7 (15) | NT | NT | 7.1 (60) |
| 2-127 Isomer 2 | <4.7 (11) | NT | NT | 8.0 (72) |
| 2-128 Isomer 2 | 5.0 (89) | NT | NT | 5.8 (104) |
| 2-129 Isomer 2 | <4.7 (12) | NT | NT | 7.0 (55) |
| 2-130 Isomer 1 | 6.5 (42) | NT | NT | 7.9 (20) |
| 2-130 Isomer 2 | <4.7 (11) | NT | NT | 7.2 (66) |
| 2-131 Isomer 2 | 6.3 (61) | NT | NT | 6.8 (108) |
| 2-132 Isomer 2 | <4.7 (18) | NT | NT | 7.9 (72) |
| 2-133 Isomer 1 | <4.7 (37) | NT | NT | 8.0 (70) |
| 2-133 Isomer 2 | 7.1 (69) | NT | NT | 9.2 (118) |
| 2-134 Isomer 2 | <4.7 (18) | NT | NT | 7.2 (95) |
| 2-135 Isomer 2 | <4.7 (15) | NT | NT | 7.9 (90) |
| 2-136 Isomer 2 | 6.2 (105) | NT | NT | 7.9 (110) |
| 2-137 Isomer 2 | 6.0 (78) | NT | NT | 7.4 (111) |
| 2-138 Isomer 2 | <4.7 (17) | NT | NT | 7.4 (44) |
| 3-2 Isomer 1 | 7.5 (97) | <4.7 (7) | <4.7 (0) | 8.2 (115) |
| 3-3 Isomer 2 | 7.6 (81) | *5.0 (50) | <4.7 (56) | 8.2 (106) |
| 3-5 Isomer 2 | <4.7 (20) | <4.7 (65) | <4.7 (11) | 7.8 (80) |
| 3-6 Isomer 2 | <4.7 (74) | <4.7 (0) | <4.7 (4) | 7.4 (58) |
| 3-7 Isomer 2 | <4.7 (40) | NT | NT | 7.0 (39) |
| 3-8 Isomer 2 | <4.7 (19) | <4.7 (2) | <4.7 (0) | 7.6 (54) |
| 3-9 Isomer 2 | 6.6 (103) | <4.7 (2) | <4.7 (4) | 7.6 (96) |
| 3-10 Isomer 1 | 5.9 (42) | <4.7 (3) | <4.7 (5) | 7.1 (71) |
| 3-10 Isomer 2 | 8.0 (90) | 7.0 (96) | <4.7 (0) | 8.9 (103) |
| 3-11 Isomer 2 | 7.4 (36) | NT | NT | 7.6 (58) |
| 3-12 Isomer 2 | 6.6 (34) | <4.7 (2) | <4.7 (5) | 8.4 (110) |
| 3-13 Isomer 2 | 7.9 (97) | <4.7 (2) | <4.7(1) | 7.9 (82) |
| 3-14 Isomer 1 | 5.5 (65) | NT | NT | 6.3 (65) |
| 3-14 Isomer 2 | 5.5 (29) | NT | NT | 6.6 (75) |
| 3-15 Isomer 2 | 6.6 (60) | NT | NT | 7.4 (36) |
| 3-16 Isomer 2 | 5.1 (39) | NT | NT | 5.6 (47) |
| 4-1 Isomer 2 | <4.7 (10) | NT | NT | 7.16 (47) |
| 4-1 Isomer 4 | 6.4 (58) | <4.7 (3) | <4.7 (5) | 7.3 (68) |
| 4-2 Isomer 4 | 6.1 (94) | NT | NT | 7.1 (42) |
| 4-3 Isomer 2 | 6.8 (103) | <4.7 (9) | <4.7 (4) | 7.9 (88) |
| 4-4 Isomer 2 | 7.5 (97) | <4.7 (19) | <4.7 (21) | 8.3 (73) |
| 4-5 Isomer 2 | 6.3 (52) | <4.7 (9) | <4.7 (9) | 7.8 (60) |
| 4-6 Isomer 2 | 6.9 (66) | <4.7 (75) | <4.7 (9) | 7.3 (77) |
| 4-7 Isomer 2 | 5.4 (73) | <4.7 (1) | <4.7 (10) | 6.6 (67) |
| 4-8 Isomer 1 | 6.3 (42) | <4.7 (3) | <4.7 (8) | 7.2 (74) |
| 4-10 Isomer 2 | <4.7 (7) | NT | NT | 6.6 (31) |
| 4-11 Isomer 2 | <4.7 (54) | NT | NT | 6.7 (55) |
| 4-12 Isomer 2 | <4.7 (19) | <4.7 (7) | <4.7 (14) | 7.4 (32) |
| 4-13 Isomer 2 | 6.2 (51) | <4.7 (10) | <4.7 (13) | 7.0 (59) |
| 4-14 Isomer 2 | 6.7 (28) | <4.7 (55) | <4.7 (0) | 7.7 (48) |
| 4-15 Isomer 2 | 6.6 (82) | <4.7 (7) | <4.7 (13) | 7.2 (113) |
| 4-16 Isomer 2 | 6.0 (94) | NT | NT | 6.8 (105) |
| 4-17 Isomer 2 | <4.7 (27) | NT | NT | 6.6 (106) |
| 4-18 Isomer 2 | 5.5 (76) | NT | NT | 6.2 (79) |
| 4-19 Isomer 2 | <4.7 (7) | NT | NT | 6.6 (38) |

TABLE 4-continued

| Ex. No. | Muscarinic Activity | | | |
|---|---|---|---|---|
| | pEC$_{50}$ M$_1$ (% Emax cf. ACh) | pEC$_{50}$ M$_2$ (% Emax cf. ACh) | pEC$_{50}$ M$_3$ (% Emax cf. ACh) | pEC$_{50}$ M$_4$ (% Emax cf. ACh) |
| 4-20 Isomer 2 | <4.7 (11) | NT | NT | 6.8 (34) |
| 5-2 Isomer 2 | 6.0 (58) | <4.7 (5) | <4.7 (4) | 7.3 (96) |

*variable results,
NT—Not tested

Example B

Passive Avoidance

Studies were carried out as described previously by Foley et al., (2004) *Neuropsychopharmacology*. In the passive avoidance task scopolamine administration (1 mg/kg, i.p.) at 6 hours following training rendered animals amnesic of the paradigm. A dose range of 3, 10, and 30 mg/kg (po) free base, administered 90 minutes prior to the training period via oral gavage, was examined.

Example 1-33 Isomer 2 was found to reverse scopolamine-induced amnesia of the paradigm in a dose-dependent manner, with an approximate ED$_{50}$ of ca. 10 mg/kg (po). The effect of 30 mg/kg was similar to that produced by the cholinesterase inhibitor donepezil (0.1 mg/kg, ip) which served as a positive control (FIG. 1).

Example C

Effect of a Novel Test Compound and Xanomeline on d-Amphetamine-Induced Hyperactivity in Rats The aim of the study is to examine the effect of a novel test compound on d-amphetamine induced hyperactivity in rats. Schizophrenia is a complex multifactorial disease that cannot be fully represented by a single experimental procedure. Antipsychotic-like behaviour was assessed in rats by the inhibition of hyperactivity (or hyperlocomotion) elicited by d-amphetamine. This procedure is sensitive to clinically relevant dopamine receptor antagonists and is therefore considered suitable for comparing muscarinic agonists that influence dopaminergic signalling. A dose of xanomeline previously observed to significantly reduce d-amphetamine induced hyperactivity was employed as a positive control. Statistical analysis typically involved three-way analysis of covariance or robust regression with treatment, day and rack as factors and activity during the 30 minutes prior to treatment as a covariate, followed by appropriate multiple comparison tests. A P value of <0.05 was considered statistically significant and is marked accordingly in all subsequent figures.

Data for Examples 1-21 Isomer 2, 1-32 Isomer 2, 1-33 Isomer 2, 2-7 Isomer 2 and 2-17 Isomer 2 is shown in FIG. 2.

Example D

Pharmaceutical Formulations (i) Tablet Formulation

A tablet composition containing a compound of the formula (1), (1a) or (1b) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1), (1a) or (1b) with 100 mg lactose and optionally 1% by weight of magnesium stearate and filling the resulting mixture into standard opaque hard gelatin capsules.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1b):

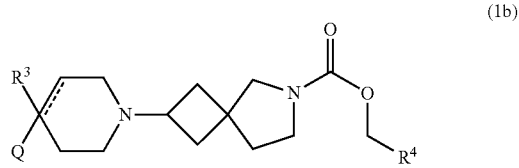

(1b)

or a salt thereof, wherein
Q is an optionally substituted five or six or seven membered heterocyclic ring containing 1, 2, 3 or 4 heteroatom ring members selected from N, O and S;
R$^3$ is selected from hydrogen; fluorine; cyano; hydroxy; amino; and a C$_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;
R$^4$ is a hydrogen or a C$_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;
and the dotted line indicates an optional second carbon-carbon bond, provided that when a second carbon-carbon bond is present, then R$^3$ is absent.

2. The compound according to claim 1 represented by formula 1

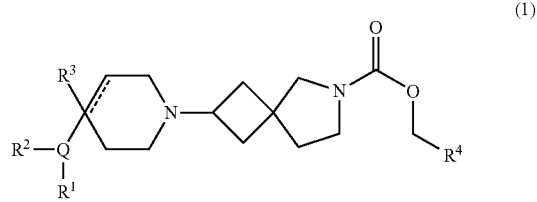

(1)

or a salt thereof, wherein

Q is a five or six membered monocyclic heterocyclic ring containing 1, 2, 3 or 4 heteroatom ring members selected from N, O and S;

$R^1$ is selected from hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$; $SO_2R^5$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

$R^2$ is selected from hydrogen; fluorine; chlorine; bromine; cyano; hydroxy; methoxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$; $SO_2R^5$; and a $C_{1-6}$ non-aromatic hydrocarbon group; or $R^1$ and $R^2$ can be joined together to form a 6 membered fused aromatic ring;

$R^3$ is selected from hydrogen; fluorine; cyano; hydroxy; amino; and a $C_{1-9}$ non-aromatic hydrocarbon group which is optionally substituted with one to six fluorine atoms and wherein one, two or three, but not all, carbon atoms of the hydrocarbon group may optionally be replaced by a heteroatom selected from O, N and S and oxidized forms thereof;

$R^4$ is a hydrogen or a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidised forms thereof;

$R^5$, $R^6$ and $R^7$ are the same or different and each is independently selected from hydrogen, a non-aromatic $C_{1-4}$ hydrocarbon group optionally substituted with one or more fluorine atoms, and a group of formula $CH_2N(R^a)COOR^b$;

$R^a$ is selected from hydrogen and a non-aromatic $C_{1-4}$ hydrocarbon group;

$R^b$ is a non-aromatic $C_{1-4}$ hydrocarbon group which is optionally substituted with one or more groups selected from fluorine; chlorine; bromine; cyano; hydroxy; methoxy; and amino; a cycloalkyl, heterocycloalkyl, aryl or heteroaryl group;

and the dotted line indicates an optional second carbon-carbon bond, provided that when a second carbon-carbon bond is present, then $R^3$ is absent.

3. The compound according to claim 1 wherein Q is an aromatic heterocyclic ring.

4. The compound according to claim 3 wherein Q is an aromatic heterocyclic ring containing one or two nitrogen atoms.

5. The compound according to claim 4 wherein Q is (i) an imidazole ring or (ii) a pyrazole ring.

6. The compound according to claim 1 wherein Q is (i) a piperidin-2-one ring or (ii) a pyrrolidine ring.

7. The compound according to claim 1 wherein Q is a 5, 6 or 7 membered unsaturated heterocyclic ring.

8. The compound according to claim 1 wherein the moiety:

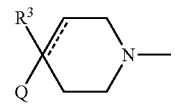

is selected from groups AAA to ACB, BAA to BCZ, CAA to CBZ, DAA to DBG and EAA to EAB:

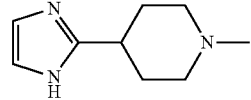
AAA

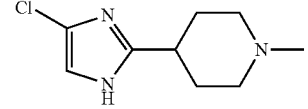
AAB

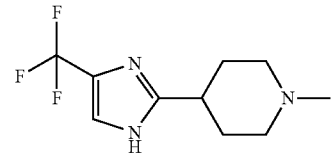
AAC

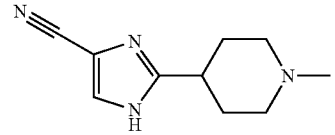
AAD

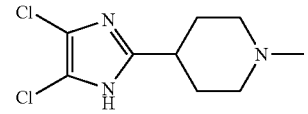
AAE

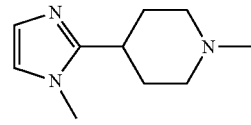
AAF

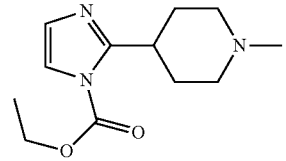
AAG

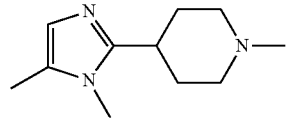
AAH

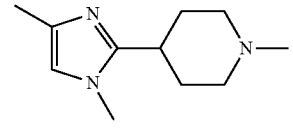
AAI

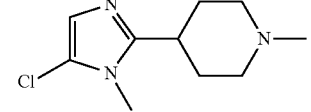
AAJ

| | |
|---|---|
| 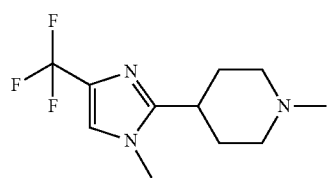 | AAK |
| 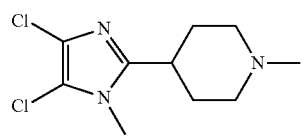 | AAL |
| 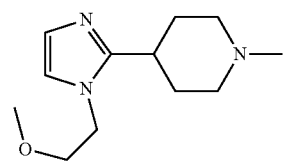 | AAM |
| 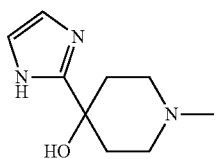 | AAN |
| 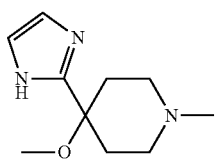 | AAO |
| 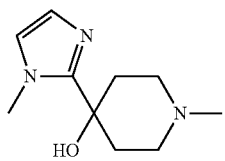 | AAP |
| 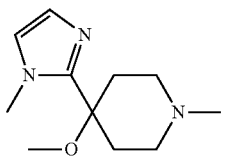 | AAQ |
| 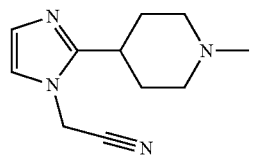 | AAR |
| 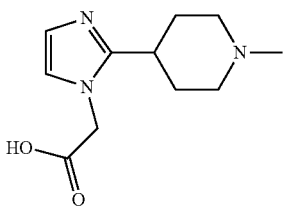 | AAS |
| | |
|---|---|
| 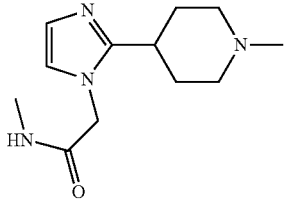 | AAT |
| 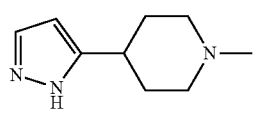 | AAU |
| 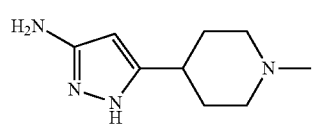 | AAV |
| 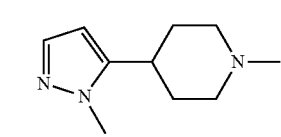 | AAW |
| 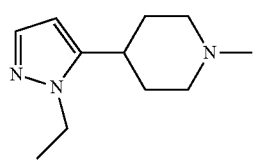 | AAX |
| 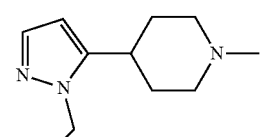 | AAY |
| 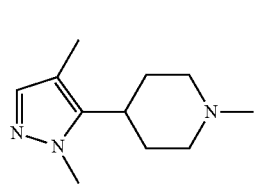 | AAZ |
| 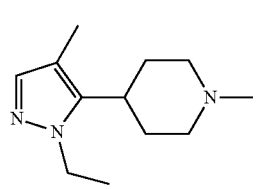 | ABA |
| 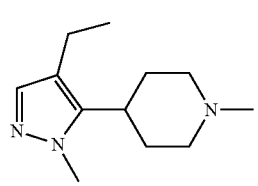 | ABB |
| 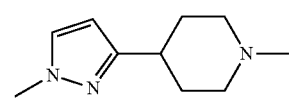 | ABC |

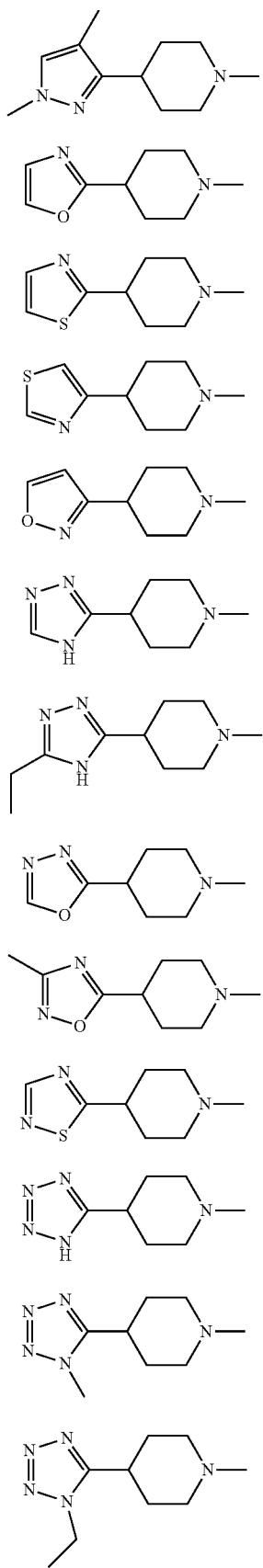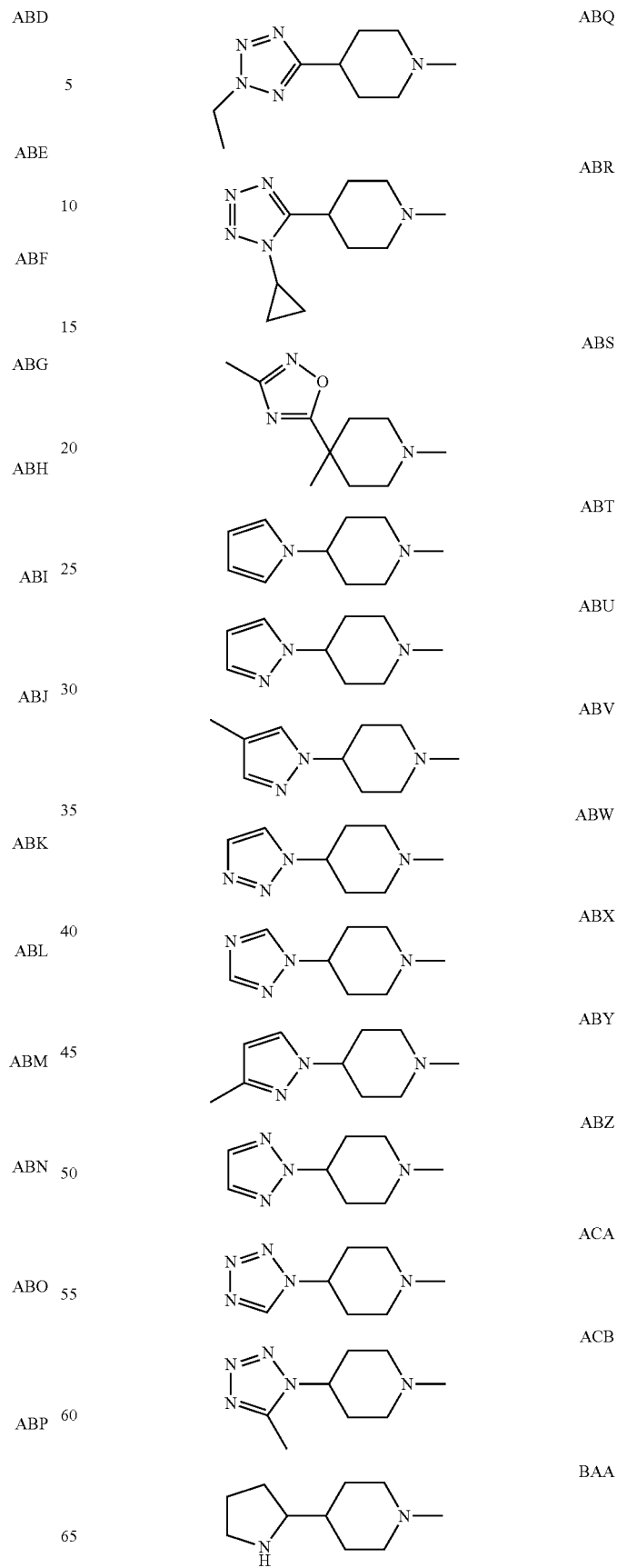

| | |
|---|---|
| BAB 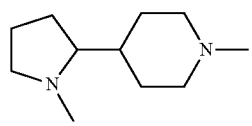 | BAJ 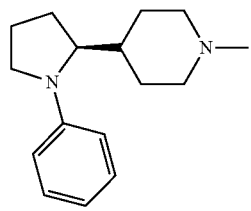 |
| BAC 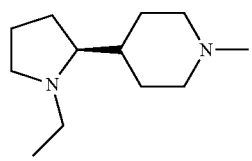 | BAK 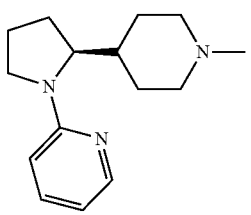 |
| BAD 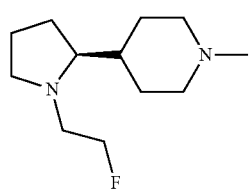 | BAL 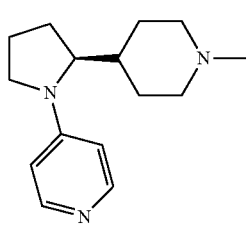 |
| BAE 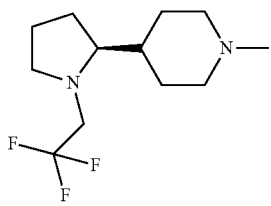 | BAM 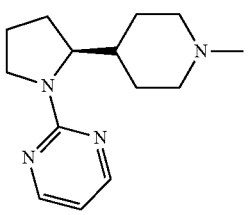 |
| BAF 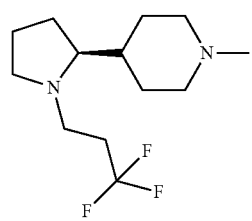 | BAN 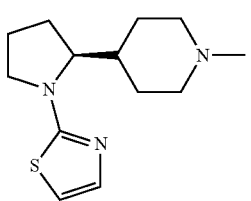 |
| BAG 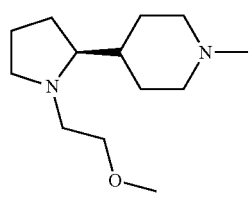 | BAO 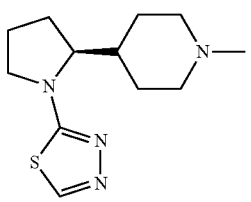 |
| BAH 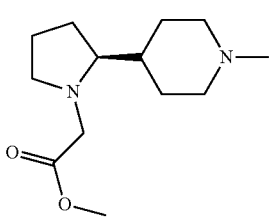 | BAP 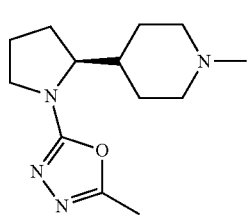 |
| BAI 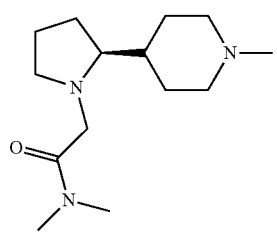 | |

343
-continued
BAQ 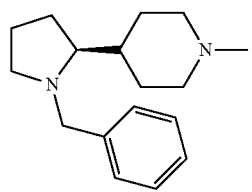
BAR 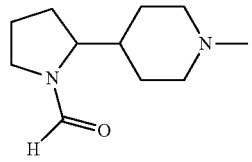
BAS 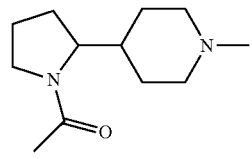
BAT 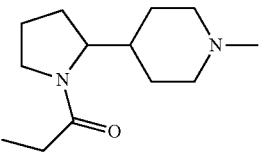
BAU 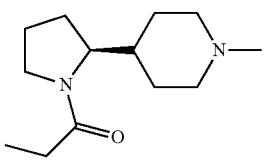
BAV 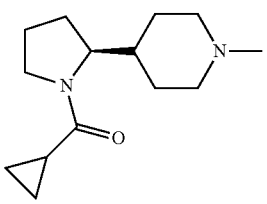
BAW 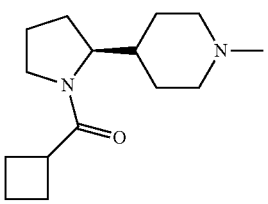
BAX 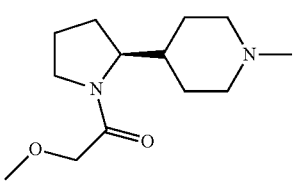
BAY 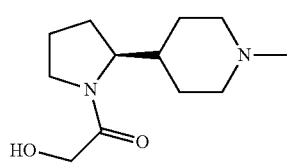
344
-continued
BAZ 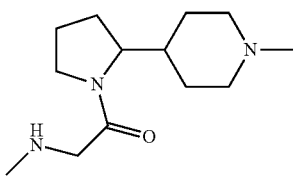
BBA 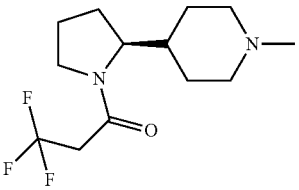
BBB 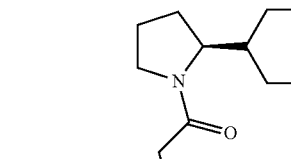
BBC 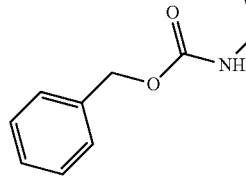
BBD 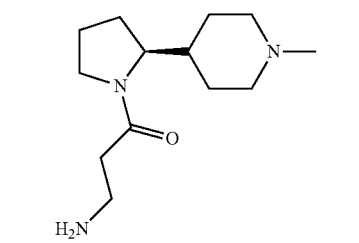
BBE 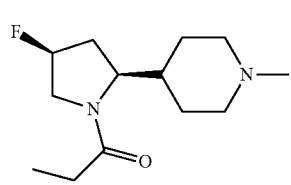
BBF 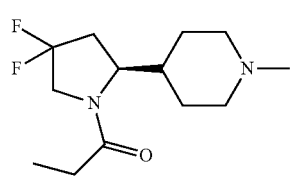

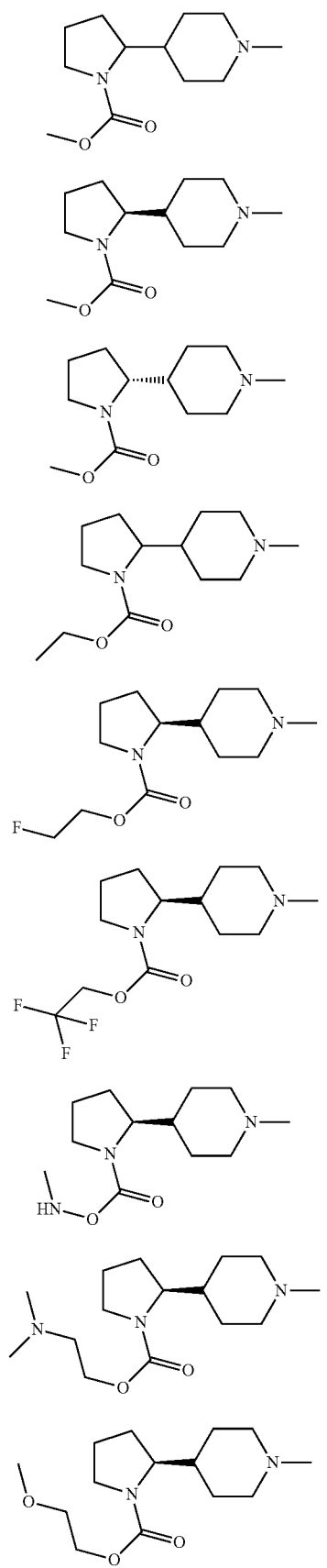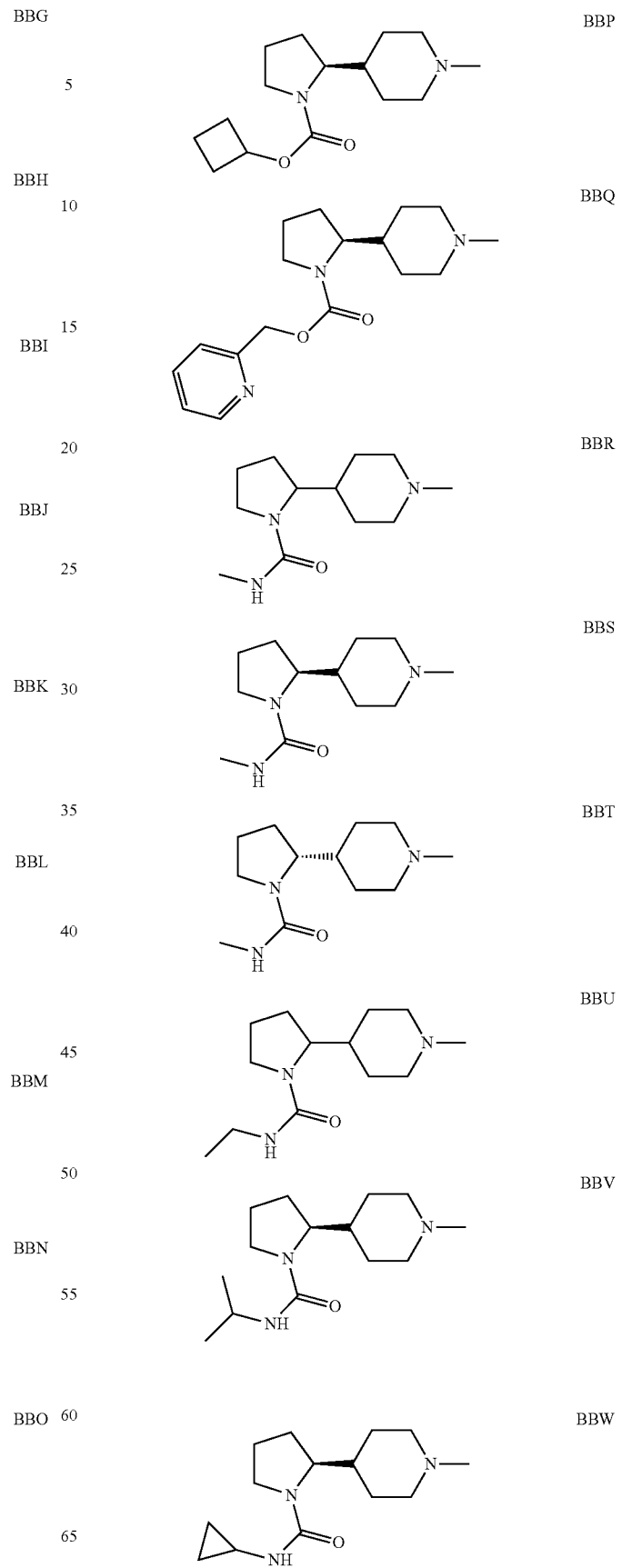

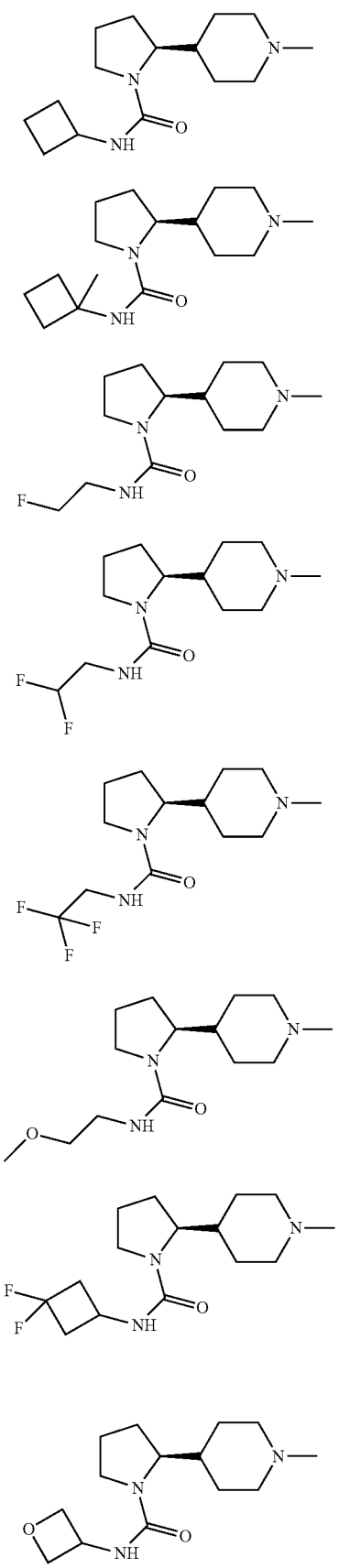
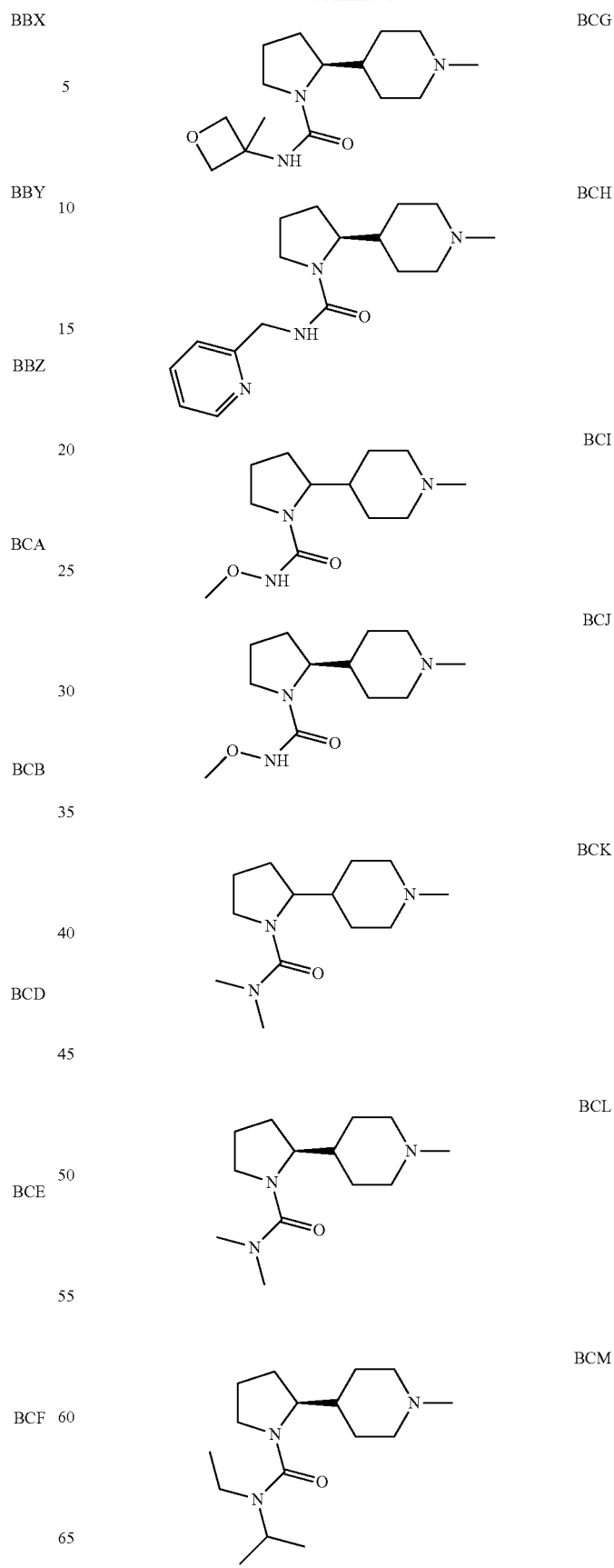

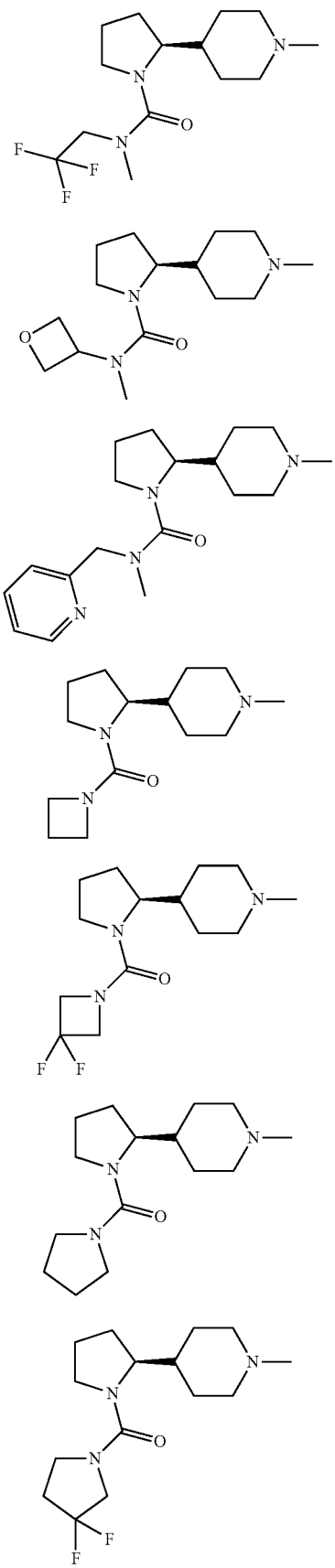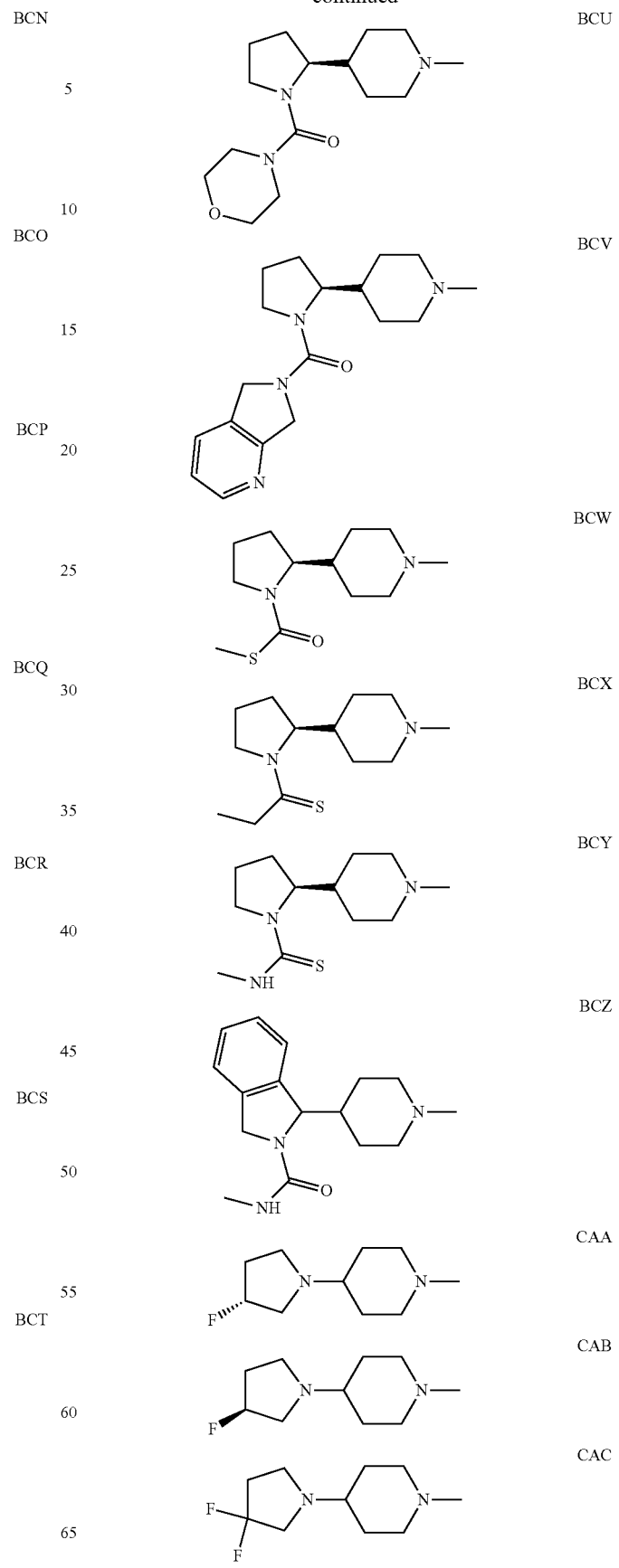

351
-continued
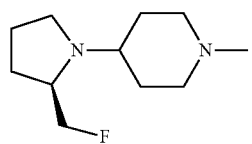 CAD
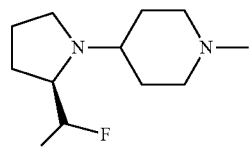 CAE
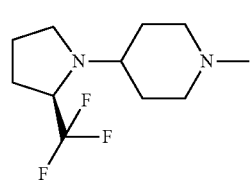 CAF
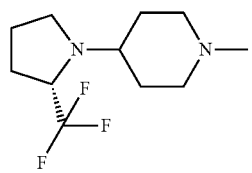 CAG
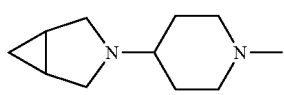 CAH
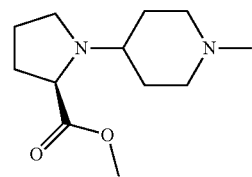 CAI
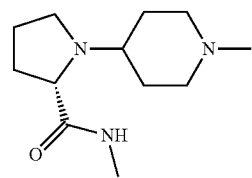 CAJ
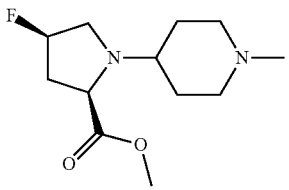 CAK
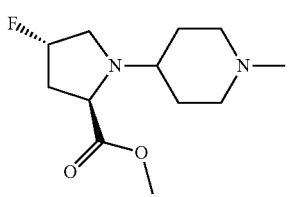 CAL
352
-continued
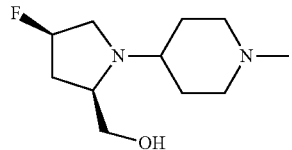 CAM
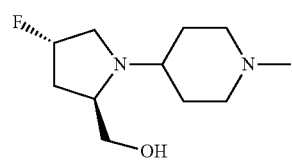 CAN
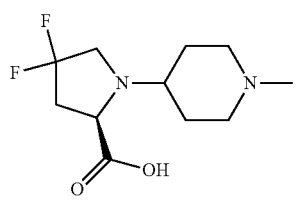 CAO
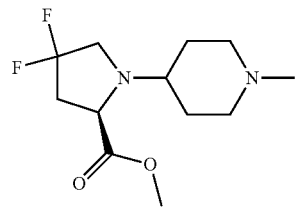 CAP
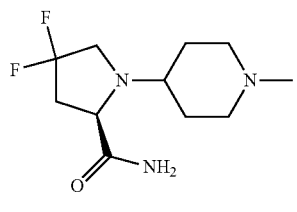 CAQ
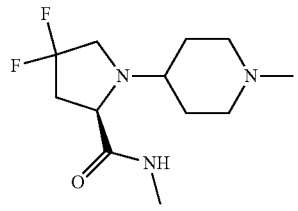 CAR
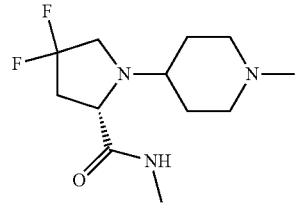 CAS
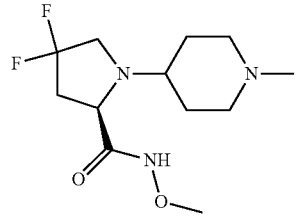 CAT

| | | |
|---|---|---|
| 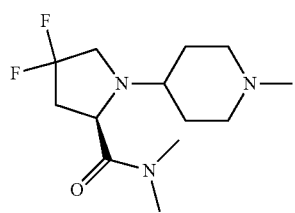 | CAU | 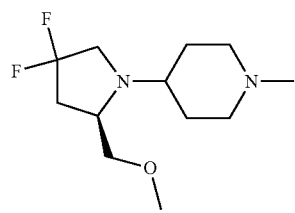 CBC |
| 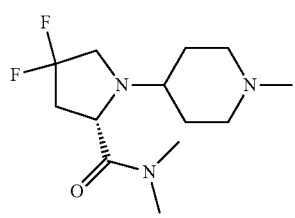 | CAV | 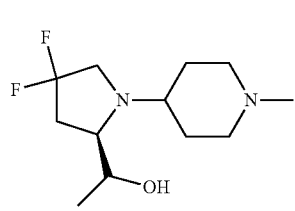 CBD |
| 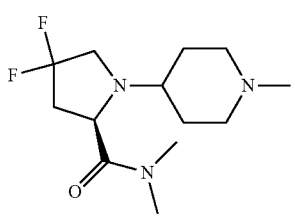 | CAW | 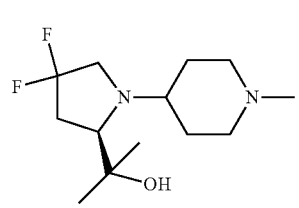 CBE |
| 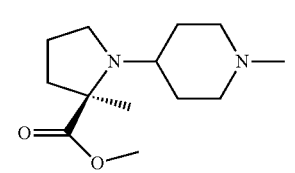 | CAX | 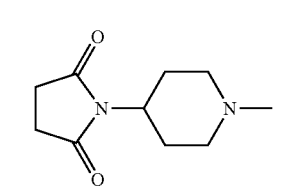 CBF |
| 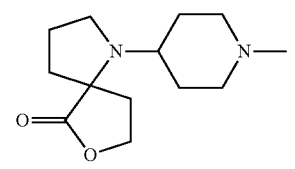 | CAY | 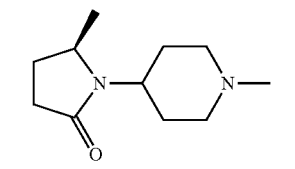 CBG |
| 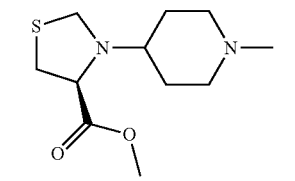 | CAZ | 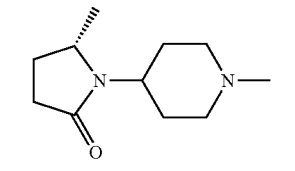 CBH |
| 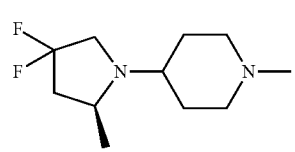 | CBA | 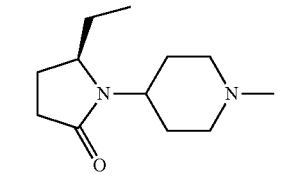 CBI |
| 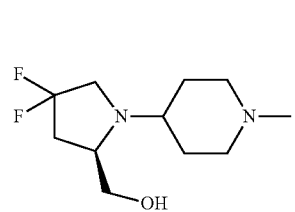 | CBB | 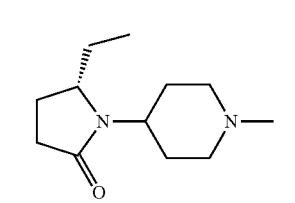 CBJ |

| | |
|---|---|
| CBK | 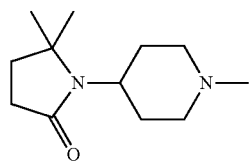 |
| CBL | 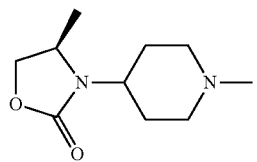 |
| CBM | 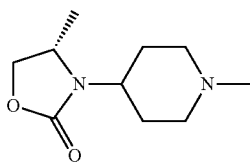 |
| CBN | 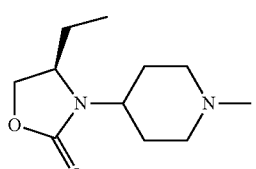 |
| CBO | 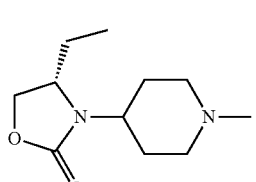 |
| CBP | 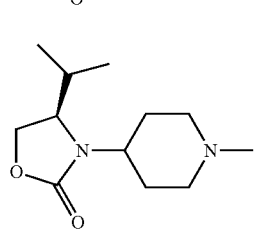 |
| CBQ | 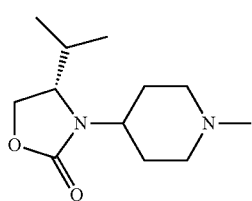 |
| CBR | 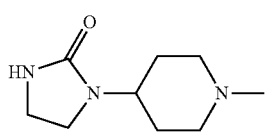 |
| CBS | 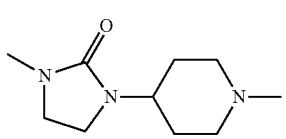 |
| CBT | 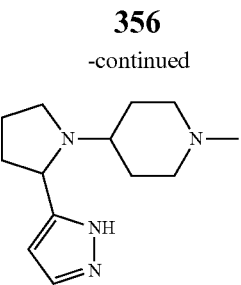 |
| CBU | 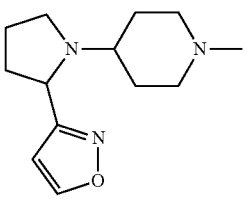 |
| CBV | 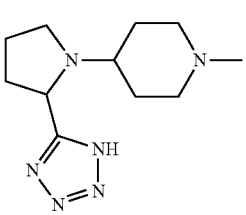 |
| CBW | 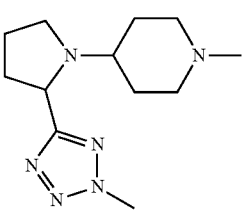 |
| CBX | 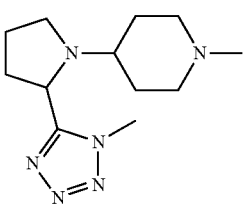 |
| CBY | 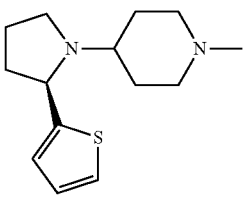 |
| CBZ | 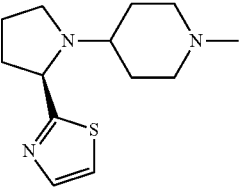 |
| DAA | 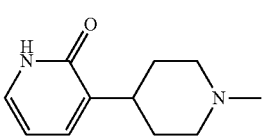 |

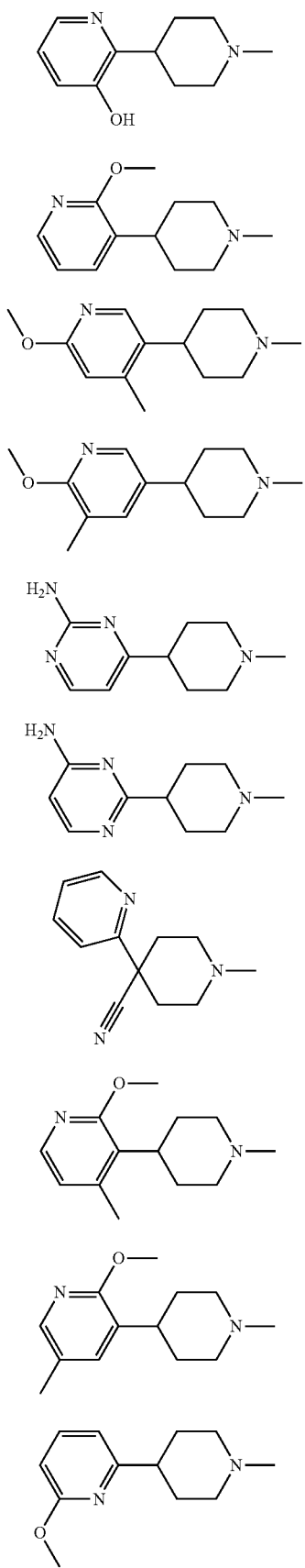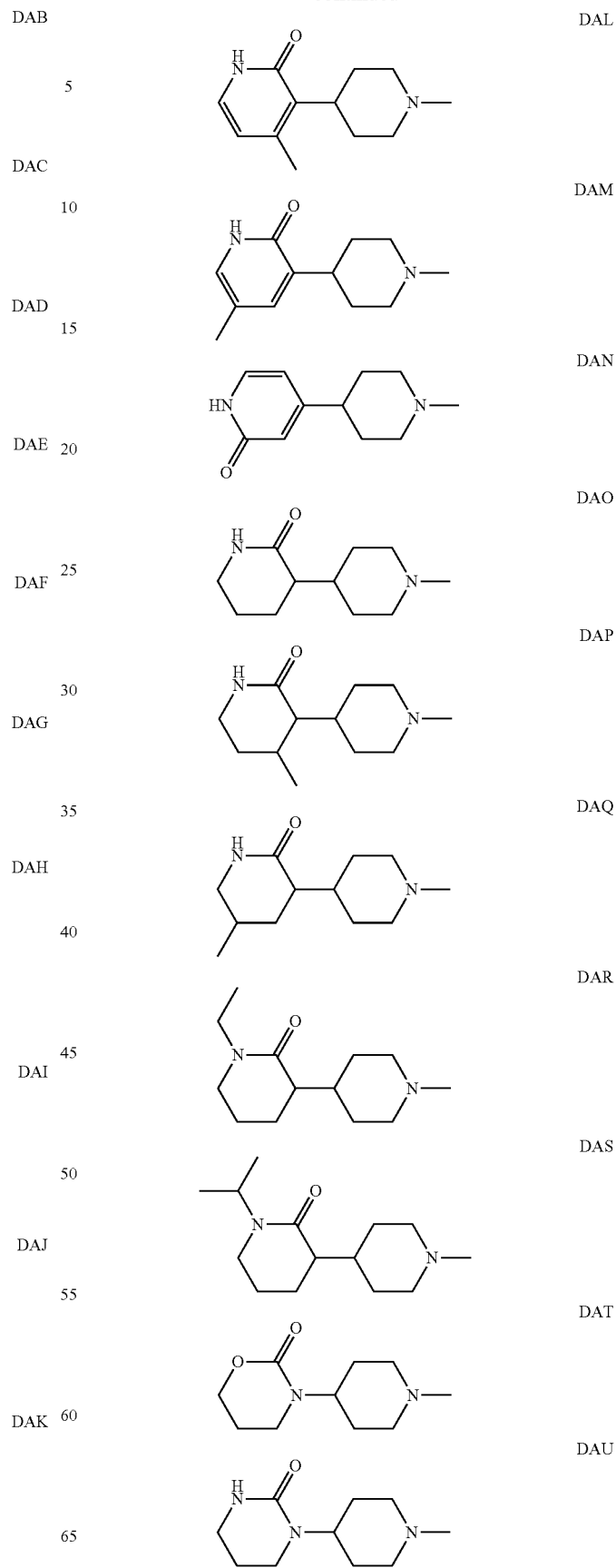

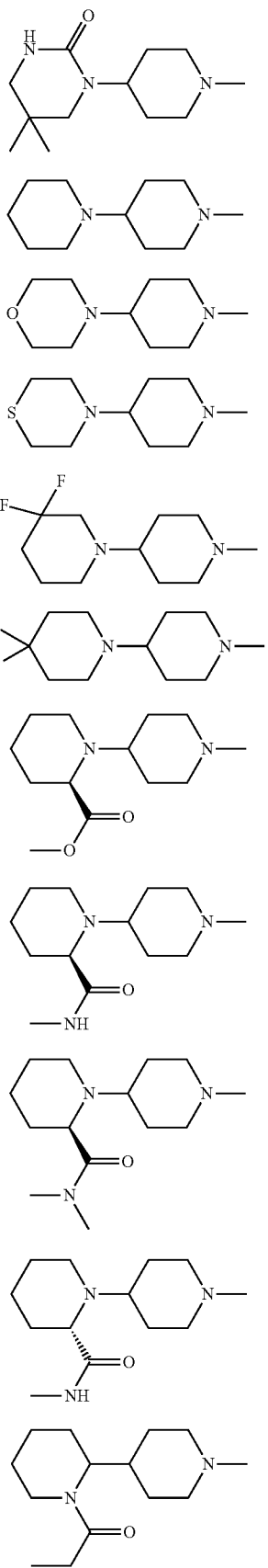

9. The compound according to claim 1 wherein Q is bicyclic or is substituted with one or more groups selected from (L)-$R^{10}$; (L)-$R^{11}$ and (L)-$R^{12}$, where L is a bond or a $CH_2$ group; $R^{10}$; $R^{11}$ and $R^{12}$ are independently selected from hydrogen; fluorine; chlorine; bromine; cyano; oxo; hydroxy; $OR^{15}$; $NR^{15}R^{16}$; $COR^{15}$; $CSR^{15}$; $COOR^{15}$; $COSR^{15}$; $OCOR^{15}$; $NR^{17}COR^{15}$; $CONR^{15}R^{16}$; $CSNR^{15}R^{16}$; $NR^{17}CONR^{15}R^{16}$; $R^{17}COOR^{15}$; $OCONR^{15}R^{16}$; $SR^{15}$; $SOR^{15}$; $SO_2R^{15}$; a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof; and an optionally substituted 5- or 6-membered ring containing 0, 1, 2 or 3 heteroatoms selected from O, N and S and oxidized forms thereof;

wherein the optional substituents for the optionally substituted 5- or 6-membered ring are selected from a group $R^8$ consisting of hydrogen; fluorine; chlorine; bromine; cyano; oxo; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $OCONR^5R^6$; $SR^5$; $SOR^5$ and $SO_2R^5$; and a $C_{1-6}$ non-aromatic hydrocarbon group which is optionally substituted with one to six fluorine atoms and wherein one or two, but not all, carbon atoms of the hydrocarbon group may optionally be replaced by a heteroatom selected from O, N and S and oxidized forms thereof;

wherein $R^{15}$, $R^{16}$ and $R^{17}$ are the same or different, or may be joined together to form a ring, and each is independently selected from hydrogen; a non-aromatic $C_{1-6}$ hydrocarbon group optionally substituted with one or more fluorine atoms and wherein one or two, but not all, carbon atoms of the hydrocarbon group may optionally be replaced by a heteroatom selected from O, N and S and oxidized forms thereof; a group of formula $CH_2N(R^a)COOR^b$; and a group of formula (L)-$R^{18}$ where L is a bond or a $CH_2$ group and $R^{18}$ is an optionally substituted 5- or 6-membered ring containing 0, 1, 2 or 3 heteroatoms selected from O, N and S and oxidized forms thereof;

$R^5$, $R^6$ and $R^7$ are the same or different and each is independently selected from hydrogen, a non-aromatic $C_{1-4}$ hydrocarbon group optionally substituted with one or more fluorine atoms, and a group of formula $CH_2N(R^a)COOR^b$;

$R^a$ is selected from hydrogen and a non-aromatic $C_{1-4}$ hydrocarbon group;

$R^b$ is a non-aromatic $C_{1-4}$ hydrocarbon group which is optionally substituted with one or more groups selected from fluorine; chlorine; bromine; cyano; hydroxy; methoxy; and amino; a cycloalkyl, heterocycloalkyl, aryl or heteroaryl group;

wherein the optional substituents for the optionally substituted 5- or 6-membered ring are selected from a group $R^8$.

10. The compound according to claim 2 wherein $R^1$ is selected from hydrogen; fluorine; cyano; hydroxy; $OR^5$; $NR^5R^6$; $COR^5$; $COOR^5$; $OCOR^5$; $NR^7COR^5$; $CONR^5R^6$; $NR^7CONR^5R^6$; $NR^7COOR^5$; $SO_2R^5$; and a $C_{1-4}$ non-aromatic hydrocarbon group which is optionally substituted with one to six fluorine atoms.

11. The compound according to claim 10 wherein $R^1$ is selected from hydrogen; $NH_2$, $COR^5$; $COOR^5$ and a $C_{1-4}$ saturated non-aromatic hydrocarbon group which is optionally substituted with one to six fluorine atoms, and wherein $R^5$ is selected from $C_{1-4}$ alkyl.

12. The compound according to claim 10 wherein $R^1$ is selected from hydrogen; methyl; ethyl; COOMe; COOEt; COMe; COEt; $CONH_2$; $CF_3$; CONHMe; $CON(Me)_2$; $COCF_3$; CO-cyclopropyl; CO-cyclobutyl; CONHEt; COH; $NH_2$ and OMe.

13. The compound according to claim 2 wherein $R^2$ is hydrogen.

14. The compound according to claim 1 wherein $R^3$ is present and the optional second carbon-carbon bond is absent.

15. The compound according to claim 14 wherein $R^3$ is selected from hydrogen; fluorine; hydroxyl, methoxy and cyano.

16. The compound according to claim 15 wherein $R^3$ is hydrogen.

17. The compound according to claim 1 wherein $R^4$ is selected from hydrogen and methyl.

18. The compound according to claim 1 which is selected from the group consisting of:
ethyl 2-[4-(1-methyl-1H-pyrazol-5-yl)piperidin-1-yl]-6-azaspiro[3.4]octane-6-carboxylate;
ethyl 2-[4-(1H-pyrrol-1-yl)piperidin-1-yl]-6-azaspiro[3.4]octane-6-carboxylate;
ethyl 2-[4-(1H-pyrazol-1-yl)piperidin-1-yl]-6-azaspiro[3.4]octane-6-carboxylate;
ethyl 2-[4-(1-ethyl-1H-pyrazol-5-yl)piperidin-1-yl]-6-azaspiro[3.4]octane-6-carboxylate;
ethyl 2-[4-(2H-1,2,3-triazol-2-yl)piperidin-1-yl]-6-azaspiro[3.4]octane-6-carboxylate;
ethyl 2-{4-[(2S)-1-propanoylpyrrolidin-2-yl]piperidin-1-yl}-6-azaspiro[3.4]octane-6-carboxylate;
ethyl 2-{4-[1-(methylcarbamoyl)pyrrolidin-2-yl]piperidin-1-yl}-6-azaspiro[3.4]octane-6-carboxylate;
ethyl 2-{4-[(2S)-1-(methoxycarbonyl)pyrrolidin-2-yl]piperidin-1-yl}-6-azaspiro[3.4]octane-6-carboxylate;
ethyl 2-{4-[(2R)-4,4-difluoro-2-(methoxycarbonyl)pyrrolidin-1-yl]piperidin-1-yl}-6-azaspiro[3.4]octane-6-carboxylate;
ethyl 2-{4-[(2R)-4,4-difluoro-2-(1-hydroxyethyl)pyrrolidin-1-yl]piperidin-1-yl}-6-azaspiro[3.4]octane-6-carboxylate;
ethyl 2-{4-[(2R)-2-methyl-5-oxopyrrolidin-1-yl]piperidin-1-yl}-6-azaspiro[3.4]octane-6-carboxylate;
ethyl 2-{4-[(2R)-2-ethyl-5-oxopyrrolidin-1-yl]piperidin-1-yl}-6-azaspiro[3.4]octane-6-carboxylate;
ethyl 2-{4-[(2S)-2-methyl-5-oxopyrrolidin-1-yl]piperidin-1-yl}-6-azaspiro[3.4]octane-6-carboxylate;
ethyl 2-{4-[(2S)-2-ethyl-5-oxopyrrolidin-1-yl]piperidin-1-yl}-6-azaspiro[3.4]octane-6-carboxylate
ethyl 2-[4-(2,2-dimethyl-5-oxopyrrolidin-1-yl)piperidin-1-yl]-6-azaspiro[3.4]octane-6-carboxylate;
ethyl 2-{4-[2-(1,2-oxazol-3-yl)pyrrolidin-1-yl]piperidin-1-yl}-6-azaspiro[3.4]octane-6-carboxylate
ethyl 2-{4-[(2R,4S)-4-fluoro-2-(methoxycarbonyl)pyrrolidin-1-yl]piperidin-1-yl}-6-azaspiro[3.4]octane-6-carboxylate;
ethyl 2-{4-[(2R,4R)-4-fluoro-2-(hydroxymethyl)pyrrolidin-1-yl]piperidin-1-yl}-6-azaspiro[3.4]octane-6-carboxylate;
ethyl 2-[4-cyano-4-(pyridin-2-yl)piperidin-1-yl]-6-azaspiro[3.4]octane-6-carboxylate;
ethyl 2-(2-oxo-3,4'-bipiperidin-1'-yl)-6-azaspiro[3.4]octane-6-carboxylate; and
ethyl 2-{4-[2-(methoxycarbonyl)azepan-1-yl]piperidin-1-yl}-6-azaspiro[3.4]octane-6-carboxylate.

19. The compound according to claim 1 which is
Ethyl 2-[4-(1H-imidazol-2-yl)piperidin-1-yl]-6-azaspiro[3.4]octane-6-carboxylate;
Ethyl 2-[4-(4-chloro-1H-imidazol-2-yl)piperidin-1-yl]-6-azaspiro[3.4]octane-6-carboxylate;
Ethyl 2-{4-[4-(trifluoromethyl)-1H-imidazol-2-yl]piperidin-1-yl}-6-azaspiro[3.4]octane-6-carboxylate;
Ethyl 2-[4-(4-cyano-1H-imidazol-2-yl)piperidin-1-yl]-6-azaspiro[3.4]octane-6-carboxylate;
Ethyl 2-[4-(4,5-dichloro-1H-imidazol-2-yl)piperidin-1-yl]-6-azaspiro[3.4]octane-6-carboxylate;
Methyl 2-[4-(1-methyl-1H-imidazol-2-yl)piperidin-1-yl]-6-azaspiro[3.4]octane-6-carboxylate;
Ethyl 2-[4-(1-methyl-1H-imidazol-2-yl)piperidin-1-yl]-6-azaspiro[3.4]octane-6-carboxylate;
Ethyl 2-{4-[1-(ethoxycarbonyl)-1H-imidazol-2-yl]piperidin-1-yl}-6-azaspiro[3.4]octane-6-carboxylate;
Methyl 2-[4-(1,5-dimethyl-1H-imidazol-2-yl)piperidin-1-yl]-6-azaspiro[3.4]octane-6-carboxylate;
Ethyl 2-[4-(1,5-dimethyl-1H-imidazol-2-yl)piperidin-1-yl]-6-azaspiro[3.4]octane-6-carboxylate;
Methyl 2-[4-(1,4-dimethyl-1H-imidazol-2-yl)piperidin-1-yl]-6-azaspiro[3.4]octane-6-carboxylate;
Ethyl 2-[4-(1,4-dimethyl-1H-imidazol-2-yl)piperidin-1-yl]-6-azaspiro[3.4]octane-6-carboxylate;
methyl 2-[4-(5-chloro-1-methyl-1H-imidazol-2-yl)piperidin-1-yl]-6-azaspiro[3.4]octane-6-carboxylate;
Ethyl 2-[4-(5-chloro-1-methyl-1H-imidazol-2-yl)piperidin-1-yl]-6-azaspiro[3.4]octane-6-carboxylate;
Ethyl 2-{4-[1-methyl-4-(trifluoromethyl)-1H-imidazol-2-yl]piperidin-1-yl}-6-azaspiro[3.4]octane-6-carboxylate;
Methyl 2-[4-(4,5-dichloro-1-methyl-1H-imidazol-2-yl)piperidin-1-yl]-6-azaspiro[3.4]octane-6-carboxylate;
Ethyl 2-[4-(4,5-dichloro-1-methyl-1H-imidazol-2-yl)piperidin-1-yl]-6-azaspiro[3.4]octane-6-carboxylate;
Ethyl 2-[4-(1H-pyrazol-5-yl)piperidin-1-yl]-6-azaspiro[3.4]octane-6-carboxylate;
Ethyl 2-[4-(3-amino-1H-pyrazol-5-yl)piperidin-1-yl]-6-azaspiro[3.4]octane-6-carboxylate;
Methyl 2-[4-(1-methyl-1H-pyrazol-5-yl)piperidin-1-yl]-6-azaspiro[3.4]octane-6-carboxylate;
Ethyl 2-[4-(1-methyl-1H-pyrazol-5-yl)piperidin-1-yl]-6-azaspiro[3.4]octane-6-carboxylate;

Ethyl 2-[4-(1-methyl-1H-pyrazol-3-yl)piperidin-1-yl]-6-azaspiro[3.4]octane-6-carboxylate;
Ethyl 2-[4-(1,3-oxazol-2-yl)piperidin-1-yl]-6-azaspiro[3.4]octane-6-carboxylate;
Methyl 2-[4-(1,3-thiazol-2-yl)piperidin-1-yl]-6-azaspiro[3.4]octane-6-carboxylate;
Ethyl 2-[4-(1,3-thiazol-2-yl)piperidin-1-yl]-6-azaspiro[3.4]octane-6-carboxylate;
Ethyl 2-[4-(4H-1,2,4-triazol-3-yl)piperidin-1-yl]-6-azaspiro[3.4]octane-6-carboxylate;
Ethyl 2-[4-(5-ethyl-1H-1,2,4-triazol-3-yl)piperidin-1-yl]-6-azaspiro[3.4]octane-6-carboxylate;
Ethyl 2-[4-(1,3,4-oxadiazol-2-yl)piperidin-1-yl]-6-azaspiro[3.4]octane-6-carboxylate;
Ethyl 2-[4-(3-methyl-1,2,4-oxadiazol-5-yl)piperidin-1-yl]-6-azaspiro[3.4]octane-6-carboxylate;
Ethyl 2-[4-(1,2,4-thiadiazol-5-yl)piperidin-1-yl]-6-azaspiro[3.4]octane-6-carboxylate;
Ethyl 2-[4-(1H-tetrazol-5-yl)piperidin-1-yl]-6-azaspiro[3.4]octane-6-carboxylate;
Ethyl 2-[4-(1H-pyrrol-1-yl)piperidin-1-yl]-6-azaspiro[3.4]octane-6-carboxylate;
Ethyl 2-[4-(1H-pyrazol-1-yl)piperidin-1-yl]-6-azaspiro[3.4]octane-6-carboxylate;
Ethyl 2-[4-(4-methyl-1H-pyrazol-1-yl)piperidin-1-yl]-6-azaspiro[3.4]octane-6-carboxylate;
Ethyl 2-[4-(1H-1,2,3-triazol-1-yl)piperidin-1-yl]-6-azaspiro[3.4]octane-6-carboxylate;
Ethyl 2-[4-(1H-1,2,4-triazol-1-yl)piperidin-1-yl]-6-azaspiro[3.4]octane-6-carboxylate;
Ethyl 2-[4-hydroxy-4-(1H-imidazol-2-yl)piperidin-1-yl]-6-azaspiro[3.4]octane-6-carboxylate;
Ethyl 2-[4-(1H-imidazol-2-yl)-4-methoxypiperidin-1-yl]-6-azaspiro[3.4]octane-6-carboxylate;
Ethyl 2-[4-hydroxy-4-(1-methyl-1H-imidazol-2-yl)piperidin-1-yl]-6-azaspiro[3.4]octane-6-carboxylate;
Ethyl 2-[4-methoxy-4-(1-methyl-1H-imidazol-2-yl)piperidin-1-yl]-6-azaspiro[3.4]octane-6-carboxylate;
Ethyl 2-[4-methyl-4-(3-methyl-1,2,4-oxadiazol-5-yl)piperidin-1-yl]-6-azaspiro[3.4]octane-6-carboxylate;
Methyl 2-[4-(4-methyl-1H-pyrazol-1-yl)piperidin-1-yl]-6-azaspiro[3.4]octane-6-carboxylate;
Ethyl 2-[4-(1,2-oxazol-3-yl)piperidin-1-yl]-6-azaspiro[3.4]octane-6-carboxylate;
Ethyl 2-[4-(3-methyl-1H-pyrazol-1-yl)piperidin-1-yl]-6-azaspiro[3.4]octane-6-carboxylate;
Methyl 2-[4-(3-methyl-1H-pyrazol-1-yl)piperidin-1-yl]-6-azaspiro[3.4]octane-6-carboxylate;
Methyl 2-[4-(1-ethyl-1H-pyrazol-5-yl)piperidin-1-yl]-6-azaspiro[3.4]octane-6-carboxylate;
Ethyl 2-[4-(1-ethyl-1H-pyrazol-5-yl)piperidin-1-yl]-6-azaspiro[3.4]octane-6-carboxylate;
Methyl 2-[4-(1-propyl-1H-pyrazol-5-yl)piperidin-1-yl]-6-azaspiro[3.4]octane-6-carboxylate;
Ethyl 2-[4-(1-propyl-1H-pyrazol-5-yl)piperidin-1-yl]-6-azaspiro[3.4]octane-6-carboxylate;
Ethyl 2-[4-(1,3-thiazol-4-yl)piperidin-1-yl]-6-azaspiro[3.4]octane-6-carboxylate;
Ethyl 2-{4-[1-(2-methoxyethyl)-1H-imidazol-2-yl]piperidin-1-yl}-6-azaspiro[3.4]octane-6-carboxylate;
Ethyl 2-{4-[1-(cyanomethyl)-1H-imidazol-2-yl]piperidin-1-yl}-6-azaspiro[3.4]octane-6-carboxylate;
(2-{1-[6-(ethoxycarbonyl)-6-azaspiro[3.4]oct-2-yl]piperidin-4-yl}-1H-imidazol-1-yl)acetic acid;
Ethyl 2-(4-{1-[2-(methylamino)-2-oxoethyl]-1H-imidazol-2-yl}piperidin-1-yl)-6-azaspiro[3.4]octane-6-carboxylate;
Methyl 2-[4-(1,4-dimethyl-1H-pyrazol-3-yl)piperidin-1-yl]-6-azaspiro[3.4]octane-6-carboxylate;
Ethyl 2-[4-(1,4-dimethyl-1H-pyrazol-3-yl)piperidin-1-yl]-6-azaspiro[3.4]octane-6-carboxylate;
Methyl 2-[4-(1,4-dimethyl-1H-pyrazol-5-yl)piperidin-1-yl]-6-azaspiro[3.4]octane-6-carboxylate;
Ethyl 2-[4-(1,4-dimethyl-1H-pyrazol-5-yl)piperidin-1-yl]-6-azaspiro[3.4]octane-6-carboxylate;
Ethyl 2-[4-(1-ethyl-4-methyl-1H-pyrazol-5-yl)piperidin-1-yl]-6-azaspiro[3.4]octane-6-carboxylate;
Ethyl 2-[4-(4-ethyl-1-methyl-1H-pyrazol-5-yl)piperidin-1-yl]-6-azaspiro[3.4]octane-6-carboxylate;
Ethyl 2-[4-(2H-1,2,3-triazol-2-yl)piperidin-1-yl]-6-azaspiro[3.4]octane-6-carboxylate;
Ethyl 2-[4-(1H-tetrazol-1-yl)piperidin-1-yl]-6-azaspiro[3.4]octane-6-carboxylate;
Ethyl 2-[4-(5-methyl-1H-tetrazol-1-yl)piperidin-1-yl]-6-azaspiro[3.4]octane-6-carboxylate;
Ethyl 2-[4-(1-methyl-1H-tetrazol-5-yl)piperidin-1-yl]-6-azaspiro[3.4]octane-6-carboxylate;
Ethyl 2-[4-(1-ethyl-1H-tetrazol-5-yl)piperidin-1-yl]-6-azaspiro[3.4]octane-6-carboxylate;
Ethyl 2-[4-(2-ethyl-2H-tetrazol-5-yl)piperidin-1-yl]-6-azaspiro[3.4]octane-6-carboxylate;
Ethyl 2-[4-(1-cyclopropyl-1H-tetrazol-5-yl)piperidin-1-yl]-6-azaspiro[3.4]octane-6-carboxylate;
(1,1-$^2$H$_2$)Ethyl 2-[4-(1H-pyrazol-1-yl)piperidin-1-yl]-6-azaspiro[3.4]octane-6-carboxylate;
(2,2,2-$^2$H$_3$)Ethyl 2-[4-(1H-pyrazol-1-yl)piperidin-1-yl]-6-azaspiro[3.4]octane-6-carboxylate;
($^2$H$_5$)Ethyl 2-[4-(1H-pyrazol-1-yl)piperidin-1-yl]-6-azaspiro[3.4]octane-6-carboxylate;
(1,1-$^2$H$_2$)Ethyl 2-[4-(1-methyl-1H-pyrazol-5-yl)piperidin-1-yl]-6-azaspiro[3.4]octane-6-carboxylate;
(2,2,2-$^2$H$_3$)Ethyl 2-[4-(1-methyl-1H-pyrazol-5-yl)piperidin-1-yl]-6-azaspiro[3.4]octane-6-carboxylate;
($^2$H$_5$)Ethyl 2-[4-(1-methyl-1H-pyrazol-5-yl)piperidin-1-yl]-6-azaspiro[3.4]octane-6-carboxylate;
Ethyl 2-[4-(pyrrolidin-2-yl)piperidin-1-yl]-6-azaspiro[3.4]octane-6-carboxylate;
Ethyl 2-[4-(1-formylpyrrolidin-2-yl)piperidin-1-yl]-6-azaspiro[3.4]octane-6-carboxylate;
Ethyl 2-[4-(1-acetylpyrrolidin-2-yl)piperidin-1-yl]-6-azaspiro[3.4]octane-6-carboxylate;
Ethyl 2-{4-[1-(trifluoroacetyl)pyrrolidin-2-yl]piperidin-1-yl}-6-azaspiro[3.4]octane-6-carboxylate;
Methyl 2-[4-(1-propanoylpyrrolidin-2-yl)piperidin-1-yl]-6-azaspiro[3.4]octane-6-carboxylate;
Ethyl 2-[4-(1-propanoylpyrrolidin-2-yl)piperidin-1-yl]-6-azaspiro[3.4]octane-6-carboxylate;
Ethyl 2-{4-[(2S)-1-propanoylpyrrolidin-2-yl]piperidin-1-yl}-6-azaspiro[3.4]octane-6-carboxylate;
Ethyl 2-{4-[(2S)-1-(cyclopropylcarbonyl)pyrrolidin-2-yl]piperidin-1-yl}-6-azaspiro[3.4]octane-6-carboxylate;
Ethyl 2-{4-[(2S)-1-(cyclobutylcarbonyl)pyrrolidin-2-yl]piperidin-1-yl}-6-azaspiro[3.4]octane-6-carboxylate;
Methyl 2-{4-[1-(methoxycarbonyl)pyrrolidin-2-yl]piperidin-1-yl}-6-azaspiro[3.4]octane-6-carboxylate;
Ethyl 2-{4-[1-(methoxycarbonyl)pyrrolidin-2-yl]piperidin-1-yl}-6-azaspiro[3.4]octane-6-carboxylate;
Ethyl 2-{4-[(2S)-1-(methoxycarbonyl)pyrrolidin-2-yl]piperidin-1-yl}-6-azaspiro[3.4]octane-6-carboxylate;
Ethyl 2-{4-[(2R)-1-(methoxycarbonyl)pyrrolidin-2-yl]piperidin-1-yl}-6-azaspiro[3.4]octane-6-carboxylate;
Ethyl 2-{4-[1-(ethoxycarbonyl)pyrrolidin-2-yl]piperidin-1-yl}-6-azaspiro[3.4]octane-6-carboxylate;

Methyl 2-{4-[(2S)-1-(methylcarbamoyl)pyrrolidin-2-yl]piperidin-1-yl}-6-azaspiro[3.4]octane-6-carboxylate;
Ethyl 2-{4-[1-(methylcarbamoyl)pyrrolidin-2-yl]piperidin-1-yl}-6-azaspiro[3.4]octane-6-carboxylate;
Ethyl 2-{4-[(2S)-1-(methylcarbamoyl)pyrrolidin-2-yl]piperidin-1-yl}-6-azaspiro[3.4]octane-6-carboxylate;
Ethyl 2-{4-[(2R)-1-(methylcarbamoyl)pyrrolidin-2-yl]piperidin-1-yl}-6-azaspiro[3.4]octane-6-carboxylate;
Ethyl 2-{4-[1-(ethylcarbamoyl)pyrrolidin-2-yl]piperidin-1-yl}-6-azaspiro[3.4]octane-6-carboxylate;
Ethyl 2-{4-[1-(dimethylcarbamoyl)pyrrolidin-2-yl]piperidin-1-yl}-6-azaspiro[3.4]octane-6-carboxylate;
Ethyl 2-{4-[(2S)-1-(dimethylcarbamoyl)pyrrolidin-2-yl]piperidin-1-yl}-6-azaspiro[3.4]octane-6-carboxylate;
Ethyl 2-[4-(1-methylpyrrolidin-2-yl)piperidin-1-yl]-6-azaspiro[3.4]octane-6-carboxylate;
Ethyl 2-{4-[1-(N-methylglycyl)pyrrolidin-2-yl]piperidin-1-yl}-6-azaspiro[3.4]octane-6-carboxylate;
Ethyl 2-{4-[1-(methoxycarbamoyl)pyrrolidin-2-yl]piperidin-1-yl}-6-azaspiro[3.4]octane-6-carboxylate;
Ethyl 2-{4-[(2S)-1-(propan-2-ylcarbamoyl)pyrrolidin-2-yl]piperidin-1-yl}-6-azaspiro[3.4]octane-6-carboxylate;
Ethyl 2-(4-{(2S)-1-[(2,2,2-trifluoroethyl)carbamoyl]pyrrolidin-2-yl}piperidin-1-yl)-6-azaspiro[3.4]octane-6-carboxylate;
Ethyl 2-{4-[(2S)-1-(azetidin-1-ylcarbonyl)pyrrolidin-2-yl]piperidin-1-yl}-6-azaspiro[3.4]octane-6-carboxylate;
Ethyl 2-{4-[(2S)-1-(morpholin-4-ylcarbonyl)pyrrolidin-2-yl]piperidin-1-yl}-6-azaspiro[3.4]octane-6-carboxylate;
Ethyl 2-{4-[(2S)-1-(cyclopropylcarbamoyl)pyrrolidin-2-yl]piperidin-1-yl}-6-azaspiro[3.4]octane-6-carboxylate;
Ethyl 2-{4-[(2S)-1-(cyclobutylcarbamoyl)pyrrolidin-2-yl]piperidin-1-yl}-6-azaspiro[3.4]octane-6-carboxylate;
Ethyl 2-(4-{(2S)-1-[(2-methoxyethyl)carbamoyl]pyrrolidin-2-yl}piperidin-1-yl)-6-azaspiro[3.4]octane-6-carboxylate;
Ethyl 2-{4-[(2S)-1-(pyrrolidin-1-ylcarbonyl)pyrrolidin-2-yl]piperidin-1-yl}-6-azaspiro[3.4]octane-6-carboxylate;
Ethyl 2-{4-[(2S)-1-(methoxycarbamoyl)pyrrolidin-2-yl]piperidin-1-yl}-6-azaspiro[3.4]octane-6-carboxylate;
Ethyl 2-(4-{(2S)-1-[methoxy(methyl)carbamoyl]pyrrolidin-2-yl}piperidin-1-yl)-6-azaspiro[3.4]octane-6-carboxylate;
Ethyl 2-(4-{(2S)-1-[(1-methylcyclobutyl)carbamoyl]pyrrolidin-2-yl}piperidin-1-yl)-6-azaspiro[3.4]octane-6-carboxylate;
Ethyl 2-(4-{(2S)-1-[(3-methyloxetan-3-yl)carbamoyl]pyrrolidin-2-yl}piperidin-1-yl)-6-azaspiro[3.4]octane-6-carboxylate;
Ethyl 2-(4-{(2S)-1-[(3,3-difluoropyrrolidin-1-yl)carbonyl]pyrrolidin-2-yl}piperidin-1-yl)-6-azaspiro[3.4]octane-6-carboxylate;
Ethyl 2-(4-{(2S)-1-[(3,3-difluorocyclobutyl)carbamoyl]pyrrolidin-2-yl}piperidin-1-yl)-6-azaspiro[3.4]octane-6-carboxylate;
Ethyl 2-(4-{(2S)-1-[(3,3-difluoroazetidin-1-yl)carbonyl]pyrrolidin-2-yl}piperidin-1-yl)-6-azaspiro[3.4]octane-6-carboxylate;
Methyl 2-(4-{(2S)-1-[(2,2,2-trifluoroethyl)carbamoyl]pyrrolidin-2-yl}piperidin-1-yl)-6-azaspiro[3.4]octane-6-carboxylate;
Methyl 2-(4-{(2S)-1-[(3,3-difluoroazetidin-1-yl)carbonyl]pyrrolidin-2-yl}piperidin-1-yl)-6-azaspiro[3.4]octane-6-carboxylate;
Ethyl 2-(4-{(2S)-1-[ethyl(propan-2-yl)carbamoyl]pyrrolidin-2-yl}piperidin-1-yl)-6-azaspiro[3.4]octane-6-carboxylate;
Ethyl 2-(4-{(2S)-1-[(cyclobutyloxy)carbonyl]pyrrolidin-2-yl}piperidin-1-yl)-6-azaspiro[3.4]octane-6-carboxylate;
Ethyl 2-(4-{(2S)-1-[(2-fluoroethyl)carbamoyl]pyrrolidin-2-yl}piperidin-1-yl)-6-azaspiro[3.4]octane-6-carboxylate;
Ethyl 2-(4-{(2S)-1-[(2,2-difluoroethyl)carbamoyl]pyrrolidin-2-yl}piperidin-1-yl)-6-azaspiro[3.4]octane-6-carboxylate;
Ethyl 2-{4-[(2S)-1-(methoxyacetyl)pyrrolidin-2-yl]piperidin-1-yl}-6-azaspiro[3.4]octane-6-carboxylate;
Ethyl 2-(4-{(2S)-1-[(2-fluoroethoxy)carbonyl]pyrrolidin-2-yl}piperidin-1-yl)-6-azaspiro[3.4]octane-6-carboxylate;
Ethyl 2-(4-{(2S)-1-[(2,2,2-trifluoroethoxy)carbonyl]pyrrolidin-2-yl}piperidin-1-yl)-6-azaspiro[3.4]octane-6-carboxylate;
Ethyl 2-(4-{(2S)-1-[(methylsulfanyl)carbonyl]pyrrolidin-2-yl}piperidin-1-yl)-6-azaspiro[3.4]octane-6-carboxylate;
Ethyl 2-(4-{(2S)-1-[(2-methoxyethoxy)carbonyl]pyrrolidin-2-yl}piperidin-1-yl)-6-azaspiro[3.4]octane-6-carboxylate;
Ethyl 2-{4-[(2S)-1-{[2-(dimethylamino)ethoxy]carbonyl}pyrrolidin-2-yl]piperidin-1-yl}-6-azaspiro[3.4]octane-6-carboxylate;
Ethyl 2-{4-[(2S)-1-(hydroxyacetyl)pyrrolidin-2-yl]piperidin-1-yl}-6-azaspiro[3.4]octane-6-carboxylate;
Ethyl 2-{4-[(2S)-1-(3,3,3-trifluoropropanoyl)pyrrolidin-2-yl]piperidin-1-yl}-6-azaspiro[3.4]octane-6-carboxylate;
ethyl 2-(4-{(2S)-1-[(pyridin-2-ylmethyl)carbamoyl]pyrrolidin-2-yl}piperidin-1-yl)-6-azaspiro[3.4]octane-6-carboxylate;
Ethyl 2-(4-{(2S)-1-[methyl(2,2,2-trifluoroethyl)carbamoyl]pyrrolidin-2-yl}piperidin-1-yl)-6-azaspiro[3.4]octane-6-carboxylate;
Ethyl 2-{4-[(2S)-1-(oxetan-3-ylcarbamoyl)pyrrolidin-2-yl]piperidin-1-yl}-6-azaspiro[3.4]octane-6-carboxylate;
Ethyl 2-(4-{(2S)-1-[methyl(oxetan-3-yl)carbamoyl]pyrrolidin-2-yl}piperidin-1-yl)-6-azaspiro[3.4]octane-6-carboxylate;
Ethyl 2-{4-[(2S)-1-propanethioylpyrrolidin-2-yl]piperidin-1-yl}-6-azaspiro[3.4]octane-6-carboxylate;
Ethyl 2-{4-[(2S,4S)-4-fluoro-1-propanoylpyrrolidin-2-yl]piperidin-1-yl}-6-azaspiro[3.4]octane-6-carboxylate;
Ethyl 2-{4-[(2S)-4,4-difluoro-1-propanoylpyrrolidin-2-yl]piperidin-1-yl}-6-azaspiro[3.4]octane-6-carboxylate;
Ethyl 2-{4-[(2S)-1-ethylpyrrolidin-2-yl]piperidin-1-yl}-6-azaspiro[3.4]octane-6-carboxylate;
Ethyl 2-(4-{(2S)-1-[3-(pyridin-2-yl)propanoyl]pyrrolidin-2-yl}piperidin-1-yl)-6-azaspiro[3.4]octane-6-carboxylate;
Ethyl 2-(4-{(2S)-1-[methyl(pyridin-2-ylmethyl)carbamoyl]pyrrolidin-2-yl}piperidin-1-yl)-6-azaspiro[3.4]octane-6-carboxylate;
Ethyl 2-(4-{(2S)-1-[(pyridin-2-ylmethoxy)carbonyl]pyrrolidin-2-yl}piperidin-1-yl)-6-azaspiro[3.4]octane-6-carboxylate;

Ethyl 2-{4-[(2S)-1-{N-[(benzyloxy)carbonyl]-β-alanyl}pyrrolidin-2-yl]piperidin-1-yl}-6-azaspiro[3.4]octane-6-carboxylate;
Ethyl 2-{4-[(2S)-1-(β-alanyl)pyrrolidin-2-yl]piperidin-1-yl}-6-azaspiro[3.4]octane-6-carboxylate;
Ethyl 2-{4-[(2S)-1-{[2-(methylamino)ethoxy]carbonyl}pyrrolidin-2-yl]piperidin-1-yl}-6-azaspiro[3.4]octane-6-carboxylate;
Ethyl 2-{4-[(2S)-1-(2-fluoroethyl)pyrrolidin-2-yl]piperidin-1-yl}-6-azaspiro[3.4]octane-6-carboxylate;
Ethyl 2-{4-[(2S)-1-(2,2,2-trifluoroethyl)pyrrolidin-2-yl]piperidin-1-yl}-6-azaspiro[3.4]octane-6-carboxylate;
Ethyl 2-{4-[(2S)-1-(3,3,3-trifluoropropyl)pyrrolidin-2-yl]piperidin-1-yl}-6-azaspiro[3.4]octane-6-carboxylate;
Ethyl 2-{4-[(2S)-1-(2-methoxyethyl)pyrrolidin-2-yl]piperidin-1-yl}-6-azaspiro[3.4]octane-6-carboxylate;
Ethyl 2-{4-[(2S)-1-(2-methoxy-2-oxoethyl)pyrrolidin-2-yl]piperidin-1-yl}-6-azaspiro[3.4]octane-6-carboxylate;
Ethyl 2-(4-{(2S)-1-[2-(dimethylamino)-2-oxoethyl]pyrrolidin-2-yl}piperidin-1-yl)-6-azaspiro[3.4]octane-6-carboxylate;
Ethyl 2-{4-[(2S)-1-benzylpyrrolidin-2-yl]piperidin-1-yl}-6-azaspiro[3.4]octane-6-carboxylate;
Ethyl 2-{4-[(2S)-1-(methylcarbamothioyl)pyrrolidin-2-yl]piperidin-1-yl}-6-azaspiro[3.4]octane-6-carboxylate;
Ethyl 2-{4-[2-(methylcarbamoyl)-2,3-dihydro-1H-isoindol-1-yl]piperidin-1-yl}-6-azaspiro[3.4]octane-6-carboxylate;
Ethyl 2-{4-[(2S)-1-phenylpyrrolidin-2-yl]piperidin-1-yl}-6-azaspiro[3.4]octane-6-carboxylate;
Methyl 2-{4-[(2S)-1-(pyridin-2-yl)pyrrolidin-2-yl]piperidin-1-yl}-6-azaspiro[3.4]octane-6-carboxylate;
Ethyl 2-{4-[(2S)-1-(pyridin-2-yl)pyrrolidin-2-yl]piperidin-1-yl}-6-azaspiro[3.4]octane-6-carboxylate;
Ethyl 2-{4-[(2S)-1-(pyridin-4-yl)pyrrolidin-2-yl]piperidin-1-yl}-6-azaspiro[3.4]octane-6-carboxylate;
Ethyl 2-{4-[(2S)-1-(pyrimidin-2-yl)pyrrolidin-2-yl]piperidin-1-yl}-6-azaspiro[3.4]octane-6-carboxylate;
Ethyl 2-{4-[(2S)-1-(1,3-thiazol-2-yl)pyrrolidin-2-yl]piperidin-1-yl}-6-azaspiro[3.4]octane-6-carboxylate;
Ethyl 2-{4-[(2S)-1-(1,3,4-thiadiazol-2-yl)pyrrolidin-2-yl]piperidin-1-yl}-6-azaspiro[3.4]octane-6-carboxylate;
Ethyl 2-{4-[(2R)-2-(methoxycarbonyl)pyrrolidin-1-yl]piperidin-1-yl}-6-azaspiro[3.4]octane-6-carboxylate;
Ethyl 2-{4-[(2S)-2-(methylcarbamoyl)pyrrolidin-1-yl]piperidin-1-yl}-6-azaspiro[3.4]octane-6-carboxylate;
1-{1-[6-(ethoxycarbonyl)-6-azaspiro[3.4]oct-2-yl]piperidin-4-yl}-4,4-difluoro-D-proline;
Ethyl 2-{4-[(2R)-4,4-difluoro-2-(methoxycarbonyl)pyrrolidin-1-yl]piperidin-1-yl}-6-azaspiro[3.4]octane-6-carboxylate;
Ethyl 2-{4-[(2R)-4,4-difluoro-2-(methylcarbamoyl)pyrrolidin-1-yl]piperidin-1-yl}-6-azaspiro[3.4]octane-6-carboxylate;
Ethyl 2-{4-[(2R)-2-(dimethylcarbamoyl)-4,4-difluoropyrrolidin-1-yl]piperidin-1-yl}-6-azaspiro[3.4]octane-6-carboxylate;
Ethyl 2-{4-[(2R)-2-carbamoyl-4,4-difluoropyrrolidin-1-yl]piperidin-1-yl}-6-azaspiro[3.4]octane-6-carboxylate;
Ethyl 2-{4-[(2R)-4,4-difluoro-2-(methoxycarbamoyl)pyrrolidin-1-yl]piperidin-1-yl}-6-azaspiro[3.4]octane-6-carboxylate;
Ethyl 2-(4-{(2R)-4,4-difluoro-2-[methoxy(methyl)carbamoyl]pyrrolidin-1-yl}piperidin-1-yl)-6-azaspiro[3.4]octane-6-carboxylate;
Ethyl 2-{4-[(2S)-4,4-difluoro-2-(methylcarbamoyl)pyrrolidin-1-yl]piperidin-1-yl}-6-azaspiro[3.4]octane-6-carboxylate;
Ethyl 2-{4-[(2S)-2-(dimethylcarbamoyl)-4,4-difluoropyrrolidin-1-yl]piperidin-1-yl}-6-azaspiro[3.4]octane-6-carboxylate;
Ethyl 2-{4-[(2R)-2-(methoxycarbonyl)-2-methylpyrrolidin-1-yl]piperidin-1-yl}-6-azaspiro[3.4]octane-6-carboxylate;
Ethyl 2-[4-(6-oxo-7-oxa-1-azaspiro[4.4]non-1-yl)piperidin-1-yl]-6-azaspiro[3.4]octane-6-carboxylate;
Ethyl 2-{4-[(4S)-4-(methoxycarbonyl)-1,3-thiazolidin-3-yl]piperidin-1-yl}-6-azaspiro[3.4]octane-6-carboxylate;
Ethyl 2-{4-[(3R)-3-fluoropyrrolidin-1-yl]piperidin-1-yl}-6-azaspiro[3.4]octane-6-carboxylate;
Ethyl 2-{4-[(3S)-3-fluoropyrrolidin-1-yl]piperidin-1-yl}-6-azaspiro[3.4]octane-6-carboxylate;
Ethyl 2-[4-(3,3-difluoropyrrolidin-1-yl)piperidin-1-yl]-6-azaspiro[3.4]octane-6-carboxylate;
Ethyl 2-{4-[(2S)-2-(trifluoromethyl)pyrrolidin-1-yl]piperidin-1-yl}-6-azaspiro[3.4]octane-6-carboxylate;
Ethyl 2-{4-[(2R)-2-(fluoromethyl)pyrrolidin-1-yl]piperidin-1-yl}-6-azaspiro[3.4]octane-6-carboxylate;
Ethyl 2-{4-[(2R)-2-(difluoromethyl)pyrrolidin-1-yl]piperidin-1-yl}-6-azaspiro[3.4]octane-6-carboxylate;
Ethyl 2-{4-[(2R)-2-(trifluoromethyl)pyrrolidin-1-yl]piperidin-1-yl}-6-azaspiro[3.4]octane-6-carboxylate;
Ethyl 2-[4-(3-azabicyclo[3.1.0]hex-3-yl)piperidin-1-yl]-6-azaspiro[3.4]octane-6-carboxylate;
Ethyl 2-{4-[(2S)-4,4-difluoro-2-methylpyrrolidin-1-yl]piperidin-1-yl}-6-azaspiro[3.4]octane-6-carboxylate;
Ethyl 2-{4-[(2R)-4,4-difluoro-2-(hydroxymethyl)pyrrolidin-1-yl]piperidin-1-yl}-6-azaspiro[3.4]octane-6-carboxylate;
Ethyl 2-{4-[(2R)-4,4-difluoro-2-(methoxymethyl)pyrrolidin-1-yl]piperidin-1-yl}-6-azaspiro[3.4]octane-6-carboxylate;
Ethyl 2-{4-[(2R)-4,4-difluoro-2-(1-hydroxyethyl)pyrrolidin-1-yl]piperidin-1-yl}-6-azaspiro[3.4]octane-6-carboxylate;
Ethyl 2-{4-[(2R)-4,4-difluoro-2-(1-hydroxyethyl)pyrrolidin-1-yl]piperidin-1-yl}-6-azaspiro[3.4]octane-6-carboxylate;
Ethyl 2-{4-[(2R)-4,4-difluoro-2-(2-hydroxypropan-2-yl)pyrrolidin-1-yl]piperidin-1-yl}-6-azaspiro[3.4]octane-6-carboxylate;
Ethyl 2-[4-(2-oxopyrrolidin-1-yl)piperidin-1-yl]-6-azaspiro[3.4]octane-6-carboxylate;
Ethyl 2-[4-(2,5-dioxopyrrolidin-1-yl)piperidin-1-yl]-6-azaspiro[3.4]octane-6-carboxylate;
Ethyl 2-{4-[(2R)-2-methyl-5-oxopyrrolidin-1-yl]piperidin-1-yl}-6-azaspiro[3.4]octane-6-carboxylate;
Ethyl 2-{4-[(2R)-2-ethyl-5-oxopyrrolidin-1-yl]piperidin-1-yl}-6-azaspiro[3.4]octane-6-carboxylate;
Ethyl 2-{4-[(2S)-2-methyl-5-oxopyrrolidin-1-yl]piperidin-1-yl}-6-azaspiro[3.4]octane-6-carboxylate;
Ethyl 2-{4-[(2S)-2-ethyl-5-oxopyrrolidin-1-yl]piperidin-1-yl}-6-azaspiro[3.4]octane-6-carboxylate;
Ethyl 2-[4-(2,2-dimethyl-5-oxopyrrolidin-1-yl)piperidin-1-yl]-6-azaspiro[3.4]octane-6-carboxylate;
Ethyl 2-{4-[(4R)-4-methyl-2-oxo-1,3-oxazolidin-3-yl]piperidin-1-yl}-6-azaspiro[3.4]octane-6-carboxylate;

Ethyl 2-{4-[(4R)-4-ethyl-2-oxo-1,3-oxazolidin-3-yl]piperidin-1-yl}-6-azaspiro[3.4]octane-6-carboxylate;
Ethyl 2-{4-[(4R)-2-oxo-4-(propan-2-yl)-1,3-oxazolidin-3-yl]piperidin-1-yl}-6-azaspiro[3.4]octane-6-carboxylate;
Ethyl 2-{4-[(4S)-4-methyl-2-oxo-1,3-oxazolidin-3-yl]piperidin-1-yl}-6-azaspiro[3.4]octane-6-carboxylate;
Ethyl 2-{4-[(4S)-4-ethyl-2-oxo-1,3-oxazolidin-3-yl]piperidin-1-yl}-6-azaspiro[3.4]octane-6-carboxylate;
Ethyl 2-{4-[(4S)-2-oxo-4-(propan-2-yl)-1,3-oxazolidin-3-yl]piperidin-1-yl}-6-azaspiro[3.4]octane-6-carboxylate;
Ethyl 2-[4-(2-oxoimidazolidin-1-yl)piperidin-1-yl]-6-azaspiro[3.4]octane-6-carboxylate;
Ethyl 2-[4-(3-methyl-2-oxoimidazolidin-1-yl)piperidin-1-yl]-6-azaspiro[3.4]octane-6-carboxylate;
Ethyl 2-{4-[2-(1H-pyrazol-5-yl)pyrrolidin-1-yl]piperidin-1-yl}-6-azaspiro[3.4]octane-6-carboxylate;
Ethyl 2-{4-[2-(1,2-oxazol-3-yl)pyrrolidin-1-yl]piperidin-1-yl}-6-azaspiro[3.4]octane-6-carboxylate;
Ethyl 2-{4-[2-(1H-tetrazol-5-yl)pyrrolidin-1-yl]piperidin-1-yl}-6-azaspiro[3.4]octane-6-carboxylate;
Ethyl 2-{4-[2-(2-methyl-2H-tetrazol-5-yl)pyrrolidin-1-yl]piperidin-1-yl}-6-azaspiro[3.4]octane-6-carboxylate;
Ethyl 2-{4-[2-(1-methyl-1H-tetrazol-5-yl)pyrrolidin-1-yl]piperidin-1-yl}-6-azaspiro[3.4]octane-6-carboxylate;
Ethyl 2-{4-[(2R)-2-(thiophen-2-yl)pyrrolidin-1-yl]piperidin-1-yl}-6-azaspiro[3.4]octane-6-carboxylate;
Ethyl 2-{4-[(2R)-2-(1,3-thiazol-2-yl)pyrrolidin-1-yl]piperidin-1-yl}-6-azaspiro[3.4]octane-6-carboxylate;
Ethyl 2-{4-[(2S)-1-(5,7-dihydro-6H-pyrrolo[3,4-b]pyridin-6-ylcarbonyl)pyrrolidin-2-yl]piperidin-1-yl}-6-azaspiro[3.4]octane-6-carboxylate;
Ethyl 2-{4-[(2R,4R)-4-fluoro-2-(methoxycarbonyl)pyrrolidin-1-yl]piperidin-1-yl}-6-azaspiro[3.4]octane-6-carboxylate;
Ethyl 2-{4-[(2R,4S)-4-fluoro-2-(methoxycarbonyl)pyrrolidin-1-yl]piperidin-1-yl}-6-azaspiro[3.4]octane-6-carboxylate;
Ethyl 2-{4-[(2R,4R)-4-fluoro-2-(hydroxymethyl)pyrrolidin-1-yl]piperidin-1-yl}-6-azaspiro[3.4]octane-6-carboxylate;
Ethyl 2-{4-[(2R,4S)-4-fluoro-2-(hydroxymethyl)pyrrolidin-1-yl]piperidin-1-yl}-6-azaspiro[3.4]octane-6-carboxylate;
Ethyl 2-{4-[(2S)-1-(5-methyl-1,3,4-oxadiazol-2-yl)pyrrolidin-2-yl]piperidin-1-yl}-6-azaspiro[3.4]octane-6-carboxylate;
Methyl 2-[4-(2-oxo-1,2-dihydropyridin-3-yl)piperidin-1-yl]-6-azaspiro[3.4]octane-6-carboxylate;
Ethyl 2-[4-(2-oxo-1,2-dihydropyridin-3-yl)piperidin-1-yl]-6-azaspiro[3.4]octane-6-carboxylate;
2-Fluoroethyl 2-[4-(2-oxo-1,2-dihydropyridin-3-yl)piperidin-1-yl]-6-azaspiro[3.4]octane-6-carboxylate;
Ethyl 2-[4-(3-hydroxypyridin-2-yl)piperidin-1-yl]-6-azaspiro[3.4]octane-6-carboxylate;
2-Fluoroethyl 2-[4-(2-methoxypyridin-3-yl)piperidin-1-yl]-6-azaspiro[3.4]octane-6-carboxylate;
Ethyl 2-[4-(6-methoxy-4-methylpyridin-3-yl)piperidin-1-yl]-6-azaspiro[3.4]octane-6-carboxylate;
Ethyl 2-[4-(6-methoxy-5-methylpyridin-3-yl)piperidin-1-yl]-6-azaspiro[3.4]octane-6-carboxylate;
ethyl 2-[4-(2-aminopyrimidin-4-yl)piperidin-1-yl]-6-azaspiro[3.4]octane-6-carboxylate;
Ethyl 2-[4-(4-aminopyrimidin-2-yl)piperidin-1-yl]-6-azaspiro[3.4]octane-6-carboxylate;
ethyl 2-[4-cyano-4-(pyridin-2-yl)piperidin-1-yl]-6-azaspiro[3.4]octane-6-carboxylate;
Ethyl 2-[4-(2-methoxy-4-methylpyridin-3-yl)piperidin-1-yl]-6-azaspiro[3.4]octane-6-carboxylate;
Ethyl 2-[4-(2-methoxy-5-methylpyridin-3-yl)piperidin-1-yl]-6-azaspiro[3.4]octane-6-carboxylate;
Ethyl 2-[4-(6-methoxypyridin-2-yl)piperidin-1-yl]-6-azaspiro[3.4]octane-6-carboxylate;
Ethyl 2-[4-(4-methyl-2-oxo-1,2-dihydropyridin-3-yl)piperidin-1-yl]-6-azaspiro[3.4]octane-6-carboxylate;
Ethyl 2-[4-(4-methyl-2-oxo-1,2-dihydropyridin-3-yl)piperidin-1-yl]-6-azaspiro[3.4]octane-6-carboxylate;
Ethyl 2-[4-(5-methyl-2-oxo-1,2-dihydropyridin-3-yl)piperidin-1-yl]-6-azaspiro[3.4]octane-6-carboxylate;
Ethyl 2-[4-(2-oxo-1,2-dihydropyridin-4-yl)piperidin-1-yl]-6-azaspiro[3.4]octane-6-carboxylate;
Ethyl 2-(2-oxo-3,4'-bipiperidin-1'-yl)-6-azaspiro[3.4]octane-6-carboxylate;
Methyl 2-(2-oxo-3,4'-bipiperidin-1'-yl)-6-azaspiro[3.4]octane-6-carboxylate;
Ethyl 2-(4-methyl-2-oxo-3,4'-bipiperidin-1'-yl)-6-azaspiro[3.4]octane-6-carboxylate;
Ethyl 2-(5-methyl-2-oxo-3,4'-bipiperidin-1'-yl)-6-azaspiro[3.4]octane-6-carboxylate;
Ethyl 2-(1-ethyl-2-oxo-3,4'-bipiperidin-1'-yl)-6-azaspiro[3.4]octane-6-carboxylate;
Ethyl 2-[2-oxo-1-(propan-2-yl)-3,4'-bipiperidin-1'-yl]-6-azaspiro[3.4]octane-6-carboxylate;
Ethyl 2-[4-(2-oxo-1,3-oxazinan-3-yl)piperidin-1-yl]-6-azaspiro[3.4]octane-6-carboxylate;
Ethyl 2-[4-(2-oxotetrahydropyrimidin-1(2H)-yl)piperidin-1-yl]-6-azaspiro[3.4]octane-6-carboxylate;
Ethyl 2-[4-(5,5-dimethyl-2-oxotetrahydropyrimidin-1(2H)-yl)piperidin-1-yl]-6-azaspiro[3.4]octane-6-carboxylate;
Ethyl 2-(1,4'-bipiperidin-1'-yl)-6-azaspiro[3.4]octane-6-carboxylate;
Ethyl 2-[4-(morpholin-4-yl)piperidin-1-yl]-6-azaspiro[3.4]octane-6-carboxylate;
Ethyl 2-[4-(thiomorpholin-4-yl)piperidin-1-yl]-6-azaspiro[3.4]octane-6-carboxylate;
Ethyl 2-(3,3-difluoro-1,4'-bipiperidin-1'-yl)-6-azaspiro[3.4]octane-6-carboxylate;
Ethyl 2-(4,4-difluoro-1,4'-bipiperidin-1'-yl)-6-azaspiro[3.4]octane-6-carboxylate;
Methyl (2R)-1'-[6-(ethoxycarbonyl)-6-azaspiro[3.4]oct-2-yl]-1,4'-bipiperidine-2-carboxylate;
Ethyl 2-[(2R)-2-(methylcarbamoyl)-1,4'-bipiperidin-1'-yl]-6-azaspiro[3.4]octane-6-carboxylate;
Ethyl 2-[(2R)-2-(dimethylcarbamoyl)-1,4'-bipiperidin-1'-yl]-6-azaspiro[3.4]octane-6-carboxylate;
Ethyl 2-[(2S)-2-(methylcarbamoyl)-1,4'-bipiperidin-1'-yl]-6-azaspiro[3.4]octane-6-carboxylate;
Ethyl 2-(1-propanoyl-2,4'-bipiperidin-1'-yl)-6-azaspiro[3.4]octane-6-carboxylate;
Ethyl 2-[1-(methylcarbamoyl)-2,4'-bipiperidin-1'-yl]-6-azaspiro[3.4]octane-6-carboxylate;
Ethyl 2-[4-(2-oxoazepan-1-yl)piperidin-1-yl]-6-azaspiro[3.4]octane-6-carboxylate; or
Ethyl 2-{4-[2-(methoxycarbonyl)azepan-1-yl]piperidin-1-yl}-6-azaspiro[3.4]octane-6-carboxylate; or a salt of any of the foregoing.

20. A pharmaceutical composition comprising a compound as defined in claim 1 and a pharmaceutically acceptable excipient.

21. The compound according to claim 1 wherein the compound has a muscarinic $M_1$ receptor and/or $M_4$ receptor agonist activity.

22. A method of treating a cognitive disorder in a subject, comprising administering an effective amount of the compound of claim 1 to the subject in need thereof.

23. A method of treating Alzheimer's Disease dementia with Lewy bodies or other cognitive disorder in a subject, comprising administering an effective amount of the compound of claim 1 to the subject in need thereof.

* * * * *

UNITED STATES PATENT AND TRADEMARK OFFICE
CERTIFICATE OF CORRECTION

| | | |
|---|---|---|
| PATENT NO. | : 9,670,183 B2 | Page 1 of 1 |
| APPLICATION NO. | : 15/117018 | |
| DATED | : June 6, 2017 | |
| INVENTOR(S) | : Giles Albert Brown et al. | |

It is certified that error appears in the above-identified patent and that said Letters Patent is hereby corrected as shown below:

In the Claims

At Column 371, Claim number 23, Line number 7, replace "Alzheimer's Disease dementia" with --Alzheimer's Disease, dementia--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*